(12) United States Patent
Ruddy et al.

(10) Patent No.: US 7,595,385 B2
(45) Date of Patent: *Sep. 29, 2009

(54) POLYMORPHISMS IN THE REGION OF THE HUMAN HEMOCHROMATOSIS GENE

(75) Inventors: David A. Ruddy, San Francisco, CA (US); Roger K. Wolff, Mill Valley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 11/157,389

(22) Filed: Jun. 20, 2005

(65) Prior Publication Data

US 2005/0266481 A1    Dec. 1, 2005

Related U.S. Application Data

(60) Continuation of application No. 10/301,844, filed on Nov. 20, 2002, now Pat. No. 7,052,845, which is a division of application No. 08/852,495, filed on May 7, 1997, now Pat. No. 7,026,116, which is a continuation-in-part of application No. 08/724,394, filed on Oct. 1, 1996, now Pat. No. 5,872,237, which is a continuation-in-part of application No. 08/652,265, filed on May 23, 1996, now Pat. No. 6,025,130, which is a continuation-in-part of application No. 08/632,673, filed on Apr. 16, 1996, now Pat. No. 5,712,098, which is a continuation-in-part of application No. 08/630,912, filed on Apr. 4, 1996, now abandoned.

(51) Int. Cl.
    *C07H 21/04* (2006.01)
    *C12Q 1/68* (2006.01)

(52) U.S. Cl. .................... 536/24.3; 536/23.1; 435/6

(58) Field of Classification Search .................. None
    See application file for complete search history.

(56) References Cited

U.S. PATENT DOCUMENTS

| | | |
|---|---|---|
| 4,399,216 A | 8/1983 | Axel et al. |
| 4,434,156 A | 2/1984 | Trowbridge |
| 4,511,503 A | 4/1985 | Olson et al. |
| 4,666,927 A | 5/1987 | Hider et al. |
| 4,683,202 A | 7/1987 | Mullis |
| 4,711,845 A | 12/1987 | Gelfand et al. |
| 4,912,118 A | 3/1990 | Hider et al. |
| 5,075,469 A | 12/1991 | Chevion |
| 5,104,865 A | 4/1992 | Hider et al. |
| 5,116,964 A | 5/1992 | Capon |
| 5,185,368 A | 2/1993 | Peter et al. |
| 5,256,676 A | 10/1993 | Hider et al. |
| 5,328,992 A | 7/1994 | Peter et al. |
| 5,385,918 A | 1/1995 | Connell et al. |
| 5,399,346 A | 3/1995 | Anderson et al. |
| 5,420,008 A | 5/1995 | Nishida et al. |
| 5,424,057 A | 6/1995 | Peter et al. |
| 5,582,979 A | 12/1996 | Weber |
| 5,705,343 A | 1/1998 | Drayna et al. |
| 5,712,098 A | 1/1998 | Tsuchihashi et al. |
| 5,719,125 A | 2/1998 | Suzuki et al. |
| 5,753,438 A | 5/1998 | Drayna et al. |
| 5,872,237 A | 2/1999 | Feder et al. |
| 6,025,130 A | 2/2000 | Thomas et al. |
| 6,140,305 A | 10/2000 | Thomas et al. |
| 6,228,594 B1 | 5/2001 | Thomas et al. |
| 6,284,732 B1 | 9/2001 | Feder et al. |
| 6,391,852 B1 | 5/2002 | Feder et al. |
| 7,026,116 B1 * | 4/2006 | Ruddy et al. ................. 435/6 |
| 7,052,845 B2 * | 5/2006 | Ruddy et al. ................. 435/6 |
| 2003/0092019 A1 | 5/2003 | Meyer et al. |
| 2003/0100057 A1 | 5/2003 | Feder et al. |

FOREIGN PATENT DOCUMENTS

| | | |
|---|---|---|
| CA | 2115221 | 8/1994 |
| CA | 2115222 | 8/1994 |
| CA | 2115224 | 8/1994 |
| DE | 208 609 | 4/1984 |
| DE | 4 327 226 | 2/1995 |
| EP | 0 315 434 | 5/1989 |
| EP | 0 346 281 | 12/1989 |
| GB | 2 293 269 | 3/1996 |
| WO | WO 92/06180 | 4/1992 |
| WO | WO 93/14188 | 7/1993 |
| WO | WO 93/15609 | 8/1993 |
| WO | WO 93/19768 | 10/1993 |
| WO | WO 93/20221 | 10/1993 |
| WO | WO 94/01463 | 1/1994 |
| WO | WO 94/04186 | 3/1994 |
| WO | WO 94/06922 | 3/1994 |
| WO | WO 94/06923 | 3/1994 |
| WO | WO 94/11367 | 5/1994 |
| WO | WO 94/21243 | 9/1994 |
| WO | WO 95/16663 | 6/1995 |
| WO | WO 96/06583 | 3/1996 |
| WO | WO 96/17870 | 6/1996 |
| WO | WO 96/35802 | 11/1996 |
| WO | WO 97/38137 | 10/1997 |

OTHER PUBLICATIONS

Peng et al. (J. Clinical Pathol. vol. 47, pp. 605-608, 1994).*
NEB catalog (1996/1997), pp. 111.*
European Search Report from 05005829.6, Apr. 16, 2007, Bio-Rad Laboratories, Inc.

(Continued)

*Primary Examiner*—Jeanine A Goldberg
(74) *Attorney, Agent, or Firm*—Jones Day

(57) ABSTRACT

Polymorphic sites in the region surrounding the HH gene are provided. These polymorphisms are useful as surrogate markers in diagnostic assays for hemochromatosis.

2 Claims, 147 Drawing Sheets

OTHER PUBLICATIONS

Gandon et al., "Linkage Disequilibrium and Extended Haplotypes in the HLA-A to D6S105 Region: Implications for Mapping the Hemochromatosis Gene (HFE)," Human Genetics, 97(1):103-113 (Jan. 1996).

Jazwinski et al., "Haemochromatosis and HLA-H," Nature Genetics, 14(3):249-251 (Nov. 1996).

Seese et al., "Localization of the Hemochromatosis Disease Gene: Linkage Disequilibrium Analysis Using an American Patient Collection," Blood Cells Molecules and Diseases, 22(1):36-46 (Feb. 1996).

Supplementary Partial European Search Report for EP 97910741, Jun. 5, 2003, Europe.

Abravaya, K., et al., "Detection of Point Mutations With a Modified Ligase Chain Reaction (Gap-LCR)," Nucl. Acids Res. (1995) 23(4):675-682 (Abbott Laboratories).

Adams, M.D., et al., "Complementary DNA Sequencing: Expressed Sequence Tags and Human Genome Project," Science (1991) 252:1651-1656 (National Institutes of Health).

Amadou, C., et al., "Localization of New Genes and Markers to the Distal Part of the Human Major Histocompatibility Complex (MHC) Region and Comparison With the Mouse: New Insights Into the Evolution of Mammalian Genomes," Genomics (1995) 26:9-20 (0888-7543/95).

Anderson, J.R., et al., "Precipitating Autoantibodies in Sjögren's Disease," Lancet (1961) 2:456-460 (Glasgow Univ.).

Bacon, B.R., "Causes of Iron Overload," N. Engl. J. Med. (1992) 326(2):126-127 (St. Louis Univ. School of Medicine).

Barany, F., "Genetic Disease Detection and DNA Amplification Using Cloned Thermostable Ligase," Proc. Natl. Acad. Sci. USA (1991) 88:189-193 (National Institutes of Health).

Balan, V., et al., "Screening fro Hemochromatosis: A Cost-Effectiveness Study Based on 12,258 Patients," Gastroenterology (1994) 107:453-459 (0016-5085/94).

Barton, J.C., et al., "Hemochromatosis: The Genetic Disorder of the Twenty-First Century," Nature Medicine (1996) 2(4):394-395 (Brookwood Medical Center).

Beaucage, S.L., et al., "Deoxynucleoside Phosphoramidites—A New Class of Key Intermediates for Deoxypolynucleotide Synthesis," Tetrahedron Letters (1981) 22(20):1859-1862 (0040-4039/81).

Beggs, J.D., "Transformation of Yeast by a Replicating Hybrid Plasmid," Nature (1978) 275:104-109 (0028-0836/78).

Benton, W.D., et al.,"Screening λgt Recombinant Clones by Hybridization to Single Plaques in situ," Science (1977) 196:180-182 (National Institutes of Health).

Beutler, E. et al., "Mutation Analysis in Hereditary Hemochromatosis" Blood Cells, Molecules, and Diseases (1996), 22(16): 187-194.

Botstein, D., et al., "Sterile Host Yeasts (SHY): A Eukaryotic System of Biological Containment for Recombinant DNA Experiments," Gene (1979) 8:17-24 (American Cancer Society).

Broach, J.R., et al., "Transformation in Yeast: Development of a Hybrid Cloning Vector and Isolation of the CAN1 Gene," Gene (1979) 8:121-133 (National Institutes of Health).

Chong, S.S., et al., "Molecular Cloning of the cDNA Encoding a Human Renal Sodium Phosphate Transport Protein and its Assignment to Chromosome 6p21.3-p23," Genomics (1993) 18:355-359 (0888-7543/93).

Cotton, R.G.H., et al., "Reactivity of Cytosine and Thymine in Single-Base-Pair Mismatches With Hydroxylamine and Osmium Tetroxide and its Application to the Study of Mutations," Proc. Natl. Acad. Sci. USA (1988) 85:4397-4401 (Nuffield Foundation).

Church, D.M., et al., "Isolation of Genes From Complex Sources of Mammalian Genomic DNA Using Exon Amplification," Nature Genetics (1994) 6:98-105 (National Institutes of Health).

Clark, G., et al., "Characterization of a Soluble Cytoplasmic Antigen Reactive With Sera From Patients With Systemic Lupus Erythmatosus," J. Immunol. (1969) 102(1):117-122 (Univ. of New York Dept. of Medicine).

Dausset, J., et al., "Centre d 'Etude du Polymorphisme Humain (CEPH): Collaborative Genetic Mapping of the Human Genome," Genomics (1990) 6:575-577 (0888-7543/90).

Edwards, C.Q., et al., "Screening for Hemochromatosis," New Engl. J. Med. (1993) 328(22):1616-1619 (Univ. of Utah College of Medicine).

Faham, M., et al., "A Novel in Vivo Method to Detect DNA Sequence Variation," Genome Res. (1995) 5:474-482 (1054-9803/95).

Fahy, E., et al., "Self-Sustained Sequence Replication (3SR): An Isothermal Transcription-Based Amplification System Alternative to PCR," PCR Methods and Applications (1991) 1:25-33 (1054-9803/91).

Feder, J.N., et al., "A Novel MHC Class I-Like Gene is Mutated in Patients With Hereditary Haemochromatosis," Nature Genet. (1996) 13:399-408 (Mercator Genetics).

Finch, C.A., "Hemochromatosis—Treatment is Easy, Diagnosis Hard," Western J. Med. (1990) 153(3):323-325 (Univ. of Washington School of Medicine).

Fischer, S.G., et al., "DNA Fragments Differing by Single Base-Pair Substitutions are Separated in Denaturing Gradient Gels: Correspondence With Melting Theory," Proc. Natl. Acad. Sci. USA (1983) 80:1579-1583 (National Institutes of Health).

Freemont, P.S., et al., "A Novel Cysteine-Rich Sequence Motif," Cell (1991) 65:483-484 (Imperial Cancer Research Fund).

Gasparini, et al, "Where does the gene for Hemochromatosis lie in relation to HLA-A", Hepatology (1994), 19: 1050-1056.

Gandon et al., "Linkage Disequilibrium and Extended Haplotypes in the HLA-A to D6S105 Region: Implications for Mapping the Hemochromatosis Gene (HFE)," J. Hum. Genet. (1996) 97 (1):103-13.

Grunstein, M., et al., "Colony Hybridization: A Method for the Isolation of Cloned DNAs That Contain a Specific Gene," Proc. Natl. Acad. Sci. USA (1975) 72(10):3961-3965 (National Science Foundation).

Gubler, U., et al., "A Simple and Very Efficient Method for Generating cDNA Libraries," Gene (1983) 25:263-269 (0888-1119/83).

Gyapay, G., et al., "The 1993-1994 Genethon Human Genetic Linkage Map," Nature Genetics (1994) 7:246-339 (Assoc. Francais conte les Myopathies).

Herskowitz, I., et al., "The Lysis-Lysogeny Decision of Phage λ• Explicit Programming and Responsiveness," Ann. Rev. Genet. (1980) 14:399-445 (0066-4197/80).

Hinnen, A., et al., "Tranformation of Yeast," Proc. Natl. Acad. Sci. USA (1978) 75(4):1929-1933 (National Science Foundation).

Ito, H., et al., "Transformation of Intact Yeast Cells Treated With Alkali Cations," J. Bacteriol. (1983) 153(1):163-168 (0021-9193/83).

Jazwinska, E.C., et al., "Localization of the Hemochromatosis Gene Close to D6S105," Am. J. Hum. Genet. (1993) 53:347-352 (0002-9297/93).

Jazwinska, E.C., et al., "Haplotype Analysis in Australian Hemochromatosis Patients: Evidence for a Predominant Ancestral Haplotype Exclusively Associated with Hemochromatosis," Am. J. Hum. Genet. (1995) 56:428-433 (0002-9297/95).

Jack, L.J.W., et al., "Cloning and Analysis of cDNA Encoding Bovine Butyrophilin, an Apical Glycoprotein Expressed in Mammary Tissue and Secreted in Association With the Milk-fat Globule Membrane During Lactation," J. Biol. Chem. (1990) 265(24):14481-14486 (National Science Foundation).

Kan, Y.W., et al., "Antenatal Diagnosis of Sickle-Cell Anœmia by D.N.A. Analysis of Amniotic-Fluid Cells," Lancet (1978) ii:910-912 (San Francisco General Hospital, CA).

Landegren, U., et al., "A Ligase-Mediated Gene Detection Technique," Science (1988) 241(4869):1077-1080 (0036-8075/88).

Levy-Lahad, E., et al., "Candidate Gene for the Chromosome 1 Familial Alzheimer's Disease Locus," Science (1995) 269:973-977 (National Institute on Aging for the Alzheimer's Diseases Research Center).

Lovett, M., et al., "Direct Selection: A Method for the Isolation of cDNAs Encoded by Large Genomic Regions," Proc. Natl. Acad. Sci. USA (1991) 88:9628-9632 (National Center for Human Genome Research).

Maskos, U., et al., "A Novel Method for the Parallel Analysis of Multiple Mutations in Multiple Samples," Nucl. Acids Res. (1993) 21(9):2269-2270 (Univ. of Oxford).

Matteucci, M.D., et al., "*Synthesis of Deoxyoligonucleotides on a Polymer Support*," J. Am. Chem. Soc. (1981) 103:3185-3191 (National Institutes of Health).

Maxam, A.M., et al., "*Sequencing End-Labeled DNA With Base-Specific Chemical Cleavages*," Methods in Enzymology (1980) 65:499-560 (ISBN 0-12-181965-5).

Miller, M.M., et al., "*Immunoglobulin Variable-Region-Like Domains of Diverse Sequence Within the Major Histocompatibility Complex of the Chicken*," Proc. Natl. Acad. Sci. USA (1991) 88:4377-4381 (National Institutes of Health).

Myers, R.M., et al., "*Detection of Single Base Substitutions by Ribonuclease Cleavage at Mismatches in RNA: DNA Duplexes*," Science (1985) 230:1242-1246 (0036-8075/85).

Needham-VanDevanter, D.R., et al., "*Characterization of an Adduct Between CC-1065 and a Defined Oligodeoxynucleotide Duplex*," Nucl. Acids Res. (1984) 12(15):6159-6168 (Welch Foundation).

Needleman, S.B., et al., "*A General Method Applicable to the Search for Similarities in the Amino Acid Sequence of Two Proteins*," J. Mol. Biol. (1970) 48:443-453 (U.S. Public Health Service).

Newton, C.R., et al., "*Analysis of Any Point Mutation in DNA. The Amplification Refractory Mutation System (ARMS)*," Nucl. Acids Res. (1989) 17(7):2503-2516 (Univ. of Wales College of Medicine).

Seese, et al.,"Localization of the Hemochromatosis Disease Gene : Linkage Disequilibrium Analysis using an American Patient Collection," *Blood Cells, Molecules & Diseases* (1996) 22:36-46.

Altman, J.D. et al., "Phenotypic Analysis of Antigen-Specific T Lymphocytes," Science 274:94-96 (1996).

Anderson, G.J. et al., "Transferrin Receptor Distribution and Regulation in the Rat Small Intestine," Gastroenterology 98:576-585 (1990).

Arteaga, C.L. et al., "Tissue-targeted Antisense c-fos Retroviral Vector Inhibits Established Breast Cancer Xenografts in Nude Mice," Canc. Res. 56:10981103 (1996).

Banerjee, D. et al., "Transferrin Receptors in the Human Gastrointestinal Tract," Gastroenterology 91:861-869 (1986).

Brent, R. et al., "A bacterial repressor protein or a yeast transcriptional terminator can block upstream activation of a yeast gene," Nature 312:612-615 (1984).

Brent, R. et al., "A Eukaryotic Transcriptional Activator Bearing the DNA Specificity of a Prokaryotic Repressor," Cell 43:729-736 (1985).

Carbognani, P. et al., "Transferrin Receptor Expression in Nonsmall Cell Lung Cancer," Cancer 78(1):178-179 (1996).

Chien, C-T. et al., "The two-hybrid system: A method to identify and clone genes for proteins that interact with a protein of interest," Proc. Natl. Acad. Sci. U.S.A. 88:9578-9582 (1991).

Cook, J.D. et al., "Serum Transferrin Receptor," Annu. Rev. Med. 44:63-74 (1993).

Cox, G.A. et al., "Overexpression of dystrophin in transgenic *mdx* mice eliminates dystrophic symptoms without toxicity," Nature 364:725-729 (1993).

Curiel, D.T. et al., "Adenovirus enhancement of transferrin-polylysine-mediated gene delivery," FXoc. Natl. Acad. Sci. U.S.A. 88:8850-8854 (1991).

Dadone, M.M. et al., "Hereditary Hemochromatosis. Analysis of Laboratory Expression of the Disease by Genotype in 18 Pedigrees," Am. J. Clin. Pathol. 78(2):196-207 (1982).

Dalesandro, J. et al., "Cardiac and Pulmonary Replacement," J. Thoracic and Cardio. Surgery 111(2):416-422 (1996).

Delahunty, C. et al., "Testing the Feasibility of DNA Typing for Human Identification by PCR and an Oligonucleotide Ligation Assay," Am. J. Hum. Genet. 58:1239-1246 (1996).

Edwards, C.Q. et al., "Prevalence of Hemochromatosis Among 11,065 Presumably Healthy Blood Donors," N. Engl. J. Med. 318(21):1355-1362 (1988).

Fahnestock, M.L. et al., "Thermal Stability Comparison of Purified Empty and Peptide-Filled Forms of a Class I MHC Molecule," Science 258:1658-1662 (1992).

Fahnestock, M.L. et al., "The MHC Class I Homolog Encoded by Human Cytomegalovirus Binds Endogenous Peptides," Immunity 3:583-590 (1995).

Feder, J.N. et al., "The Hemochromatosis Founder Mutation in HLA-H Disrupts $\beta_2$- Microglobulin Interaction and Cell Surface Expression," J. Biol. Chem. 272(22):14025-14028 (1997).

Friedman, J.M. et al., "Cellular Promoters Incorporated into the Adenovirus Genome: Cell Specificity of Albumin and Immunoglobulin Expression," Mol. Cell. Biol. 6(11):3791-3797 (1986).

Gastinel, L.N. et al., "Expression and crystallization of a soluble and functional form of an Fc receptor related to class I histocompatibility molecules," Proc. Natl. Acad. Sci. U.S.A. 89:638-642 (1992).

Hatzoglou, M. et al., "Hepatic Gene Transfer in Animals Using Retroviruses Containing the Promoter from the Gene for Phosphoenolpyruvate Carboxykinase," J. Biol. Chem. 265(28):17285-17293 (1990).

Huber, B.E. et al., "Retroviral-mediated gene therapy for the treatment of hepatocellular carcinoma: An innovative approach for cancer therapy," Proc. Natl. Acad. Sci. U.S.A. 88:8039-8043 (1991).

Jahroudi, N. et al., "Endothelial-Cell-Specific Regulation of von Willebrand Factor Gene Expression," Mol. Cell. Biol. 14(2):999-1008 (1994).

Karin, M. et al., "Receptor-mediated Endocytosis of Transferrin in Developmentally Totipotent Mouse Teratocarcinoma Stem Cells," J. Biol. Chem. 256(7):3245-3252 (1981).

Keer, H.N. et al., "Elevated Transferrin Receptor Content in Human Prostate Cancer Cell Lines Assessed In Vitro and In Vivo," J. Urol., 143:381-385 (1990).

Klausner, R.D. et al., "Receptor-mediated Endocytosis of Transferrin in K562 Cells," J. Biol. Chem. 258:4715-4724 (1983).

Koc, O.N. et al., "Transfer of Drug Resistance Genes into Hemotopoietic Progenitors to Improve Chemotherapy Tolerance," Sem. Oncol. 23(1):46-65 (1996).

Letourneur, F. et al., "A Novel Di-Leucine Motif and a Tyrosine-Based Motif Independently Mediated Lysosomal Targeting and Endocytosis of CD 3 Chains," Cell 69:1143-1157 (1992).

Makarov, S.S., "Suppression of experimental arthritis by gene transfer of interleukin 1 receptor antagonist cDNA," Proc. Natl. Acad. Sci. U.S.A. 93:402406 (1996).

Marks, M.S. et al., "A Lysosomal Targeting Signal in the Cytoplasmic Tail of the (3 Chain Directs HLA-DM to MHC Class II Compartments," J. Cell Biol. 131:351-369 (1995).

Maxwell, I.H. et al., "Expressionof the Diptheria Toxin A-Chain Coding Sequence under the Control of Promoters and Enhancers from Immunoglobulin Genes as a Means of Directing Toxicity of B-Lympoid Cells," Canc. Res. 51:4299-4304 (1991).

McClelland, A. et al., The Human Transferrin Receptor Gene: Genomic Organization, and the Complete Primary Structure of the Receptor Deduced from a cDNA Sequence, Cell 39:267-274 (1984).

McLaren, C.E. et al., "Prevalence of Heterozygotes for Hemochromatosis in the White Population of the United States," Blood 86(5):2021-2027 (1995).

Miller, N. et al., "Targeted vectors for gene therapy," FASEB J. 9:190-199 (1995).

Miyazaki, J-I. et al., "Expression vector system based on the chicken $\beta$-actin promoter directs efficient production of interleukin-5," Gene 79:269-277 (1989).

Nolta, J.A. et al., "Transduction of: pluripotent human hematopoietic stem cells demonstrated by clonal analysis after engraftment in immune-deficient mice," Proc. Natl. Acad. Sci- U.S.A. 93:2414-2419 (1996).

Octave, J-N et al., "Transferrin Uptake by Cultured Rat Embryo Fibroblasts," Eur. J. Biochem. 123:235-240 (1982).

Oliveira, H.C.F. et al., "Human Cholesteryl Ester Transfer Protein Gene Proximal Promoter Contains Dietary Cholesterol Positive Responsive Elements and Mediates Expression in Small Intestine and Periphery While Predominant Liver and Spleen Expression is Controlled by 5'-distal Sequences," J. Biol. Chem. 271(510):31831-31838 (1996).

Omary, M.B. et al., "Biosynthesis of the Human Transferrin Receptor in Cultured Cells," J. Biol. Chem. 256(24):12888-12892 (1981).

Parham, P. et al., "Arginine 45 is a Major Part of the Antigenic Determinant of Human $\beta_2$-Microglobulin Recognized by Mouse Monoclonal Antibody BBM.1," J. Biol. Chem. 258(10):6179-6186 (1983).

Parkkila, S. et al., "Immunohistochemistry of HLA-H, the protein defective in patients with hereditary hemochromatosis, reveals unique pattern of expression in gastrointestinal tract," *Proc. Natl. Acad. Sci. U.S.A.* 94:2534-2539 (1997).

Petrylak, D.P. et al., Transferrin Receptor Expression in Testis Cancer, *J. Natl. Canc. Inst.* 86(8):636-637 (1994).

Plank, C. et al., "The Influence of Endosome-disruptive Peptides on Gene Transfer Using Synthetic Virus-like Gene Transfer Systems," *J. Biol. Chem.* 269(17):12918-12924 (1994).

Raghavan, M. et al., "The Class I Major Histocompatibility Complex Related Fc Receptor Shows pH-Dependent Stability Differences Correlating with Immunoglobulin Binding and Release," *Biochemistry* 32:8654-8660 (1993).

Raper, S.E. et al., "Safety and Feasibility of Liver-Directed Ex Vivo Gene Therapy for Homozygous Familial Hyperchoesterolemia," *Annal. of Surgery 223* (2):116-126 (1996).

Rotzschke, O. et al., "Isolation and analysis of naturally processed viral peptides as recognized by cytotoxic T cells," *Nature* 348:252-254 (1990).

Ruddy, D.A. et al., "A 1.1-Mb Transcript Map of the Hereditary Hemochromatosis Locus," *Genome Res.* 7:441-456 (1997).

Schaeffer, E. et al., "Complete structure of the human transferrin gene. Comparison with analogous chicken gene and human pseudogene," *Gene* 56:109-116 (1987).

Schneider, C. et al., "Primary structure of human transferrin receptor deduced from the mRNA sequence," *Nature* 311:675-678 (1984).

Seligman, P.A. et al., "Isolation arid Characterization of the Transferrin Receptor from Human Placenta," *J. Biol. Chem.* 254(20):9943-9946 (1979).

Sugita, M. et al., "Cytoplasmic Tail-Dependent Localization of CD1b Antigen-Presenting molecules to MIICs," *Science* 273:349-352 (1996).

Uhlmann, E. et al., "Antisense Oligonucleotides: A New Therapeutic Principle," *Chem. Rev.* 90(4):543-584 (1990).

Vandewalle, B. et al., "Transferrin Receptors in Cultured Breast Cancer Cells," *J. Canc. Res. Clin. Oncol.* 110:71-76 (1985).

Voorhees, P. et al., "An acidic sequence within the cytoplasmic domain of furin functions as a determinant of *trans*-Golgi network localization and internalization from the cell surface," *FMBO J.* 14(20):4961-4975 (1995).

Wada, H.G. et al., "Transferrin Receptor in Human Placental Brush Border Membranes," *J. Biol. Chem.* 254(24):12629-12635 (1979).

Ward, J.H. et al., "Regulation of HeLa Cell Transferrin Receptors," *J. Biol. Chem.* 257(17):10317-10323 (1982).

Waugh, S.M. et al., "Isolation of a :Proteolytically Derived Domain of the Insulin Receptor Containing the Major Site of Cross-Linking/Binding," *Biochemistry* 28:3448-3455 (1989).

Weiser, P. et al., "Endosomal Targeting by the Cytoplasmic Tail of Membrane Immunoglobulin," *Science* 276:407-409 (1997).

Williams, M.A. et al., "Accumulation of Membrane Glycoproteins in Lysosomes Requires a Tyrosine Residue at a Particular Position in the Cytoplasmic Tail," *J. Cell Biol.* 111:955-966 (1990).

Wu, G.Y. et al., "Receptor-mediated Gene Delivery and Expression in Vivo," *Biol. Chem.* 263(29):14621-14624 (1988).

Zou, L. et al., "Isolation of a Liver-Specific Promoter for Human Growth Hormone Receptor Gene," *Endocrin.* 138(4):1771-1774 (1997).

Alvarez et al., "Inhibition of the Receptor-Mediated Endocytosis of Diferric Transferrin Is Assocaited with the Covalent Modification of the Transferrin Receptor with Palmitic Acid" JBC (1990) 265(27):16644-16655.

Alvarez et al., "A Point Mutation In the Cytoplasmic Domain of the Transferrin Receptor Inhibits Endocytosis", *Biochem J.* (1990): 267: 31-35.

Nikiforov, T.T., et al., "*Genetic Bit Analysis: A Solid Phase Method for Typing Single Nucleotide Polymorphisms*," Nucl. Acids Res. (1994) 22(20):4167-4175 (Molecular Tool, Inc.).

Orita, M., et al., "*Rapid and Sensitive Detection of Point Mutations and DNA Polymorphisms Using the Polymerase Chain Reaction*," Genomics (1989) 5:874-879 (0888-7543/89).

Orum, H., et al., "*Single Base Pair Mutation Analysis by PNA Directed PCR Clamping*," Nucl. Acids Res. (1993) 21(23):5332-5336 (Research Center for Medical Biotechnology).

Pearson, J.D., et al., "*High-Performance Anion-Exchange Chromatography of Oligonucleotides*," J. Chromatog. (1983) 255:137-149 (0021-9673/83).

Pearson, W.R., et al., "*Improved Tools for Biological Sequence Comparison*," Proc. Natl. Acad. Sci. USA (1988) 85:2444-2448 (National Institutes of Health).

Phatak, P.D., et al., "*Cost-Effectiveness of Screening for Hereditary Hemochromatosis*," Arch. Intern. Med. (1994) 154:769-776 (Rochester General Hospital, NY).

Queen, C., et al., "*Cell-Type Specific Regulation of a κ Immunoglobulin Gene by Promoter and Enhancer Elements*," Immunol. Rev. (1986) 89:49-68 (National Institutes of Health).

Raha-Chowdhury, R., et al., "*New Polymorphic Microsatellite Markers Place the Haemochromatosis Gene Telomeric to D6S105*," Hum. Mol. Genet. (1995) 4(10):1869-1874 (Univ. of Wales College of Medicine).

Roberts, A.G., et al., "*Increased Frequency of the Haemochromatosis Cys282Tyr Mutation in Sporadic Porphyria Cutanea Tarda*," Lancet (1997) 349:321-323 (Univ. of Wales College of Medicine).

Saiki, R.K., et al., "*Primer-Directed Enzymatic Amplification of DNA with a Thermostable DNA Polymerase*," Science (1988) 239:487-491 (Cetus Corp.).

Saiki, R.K., et al., "*Genetic Analysis of Amplified DNA With Immobilized Sequence-Specific Oligonucleotide Probes*," Proc. Natl. Acad. Sci. USA (1989) 86:6230-6234 (Cetus Corp.).

Schneider, I., "*Cell Lines Derived From Late Embryonic Stages of Drosophila Melanogaster*," J. Embryol. Exp. Morph. (1972) 27(2):353-365 (Walter Reed Army Institute of Research).

Simon M., et al., "*Association of HLA-A3 and HLA-B14 Antigens With Idiopathic Haemochromatosis*," Gut (1976) 17:332-334 (Hopital Pontchaillou, France).

Simon, M., et al., "*A Study of 609 HLA Haplotypes Marking for the Hemochromatosis Gene: (1) Mapping of the Gene Near the HLA-A Locus and Characters Required to Define a Heterozygous Population and (2) Hypothesis Concerning the Underlying Cause of Hemochromatosis-HLA Association*," Am. J. Hum. Genet. (1987) 41:89-105 (0002-9297/87).

Smith, T.F., et al., "*Comparison of Biosequences*," Adv. Appl. Math. (1981) 2:482-489 (0196-8858/81).

Sprague, J., et al., "*Expression of a Recombinant DNA Gene Coding for the Vesicular Stomatitis Virus Nucleocapsid Protein*," J. Virol. (1983) 45(2):773-781 (0022-538X/83).

Stone, C., et al., "*Isolation of CA Dinucleotide Repeats Close to D6S105; Linkage Disequilibrium With Haemochromatosis*," Hum. Molec. Genet. (1994) 3(11):2043-2046 (Queensland Institute of Medical Research).

Strathmann, M., et al., "*Transposon-Facilitated DNA Sequencing*," Proc. Natl. Acad. Sci. USA (1991) 88:1247-1250 (U.S. Public Health Service Program).

Summers, K.M., et al., "*HLA Determinants in an Australian Population of Hemochromatosis Patients and Their Families*," Am. J. Hum. Genet. (1989) 45:41-48 (0002-9297/89).

Syvänen, A.C., et al., "*A Primer-Guided Nucleotide Incorporation Assay in the Genotyping of Apolipoprotein E*," Genomics (1990) 8:684-692 (0888-7543/90).

Taylor, M.R., et al., "*Cloning and Sequence Analysis of Human Butyrophilin Reveals a Potential Receptor Function*," Biochimica et Biophysica Acta (1996) 1306:1-4 (0167-4781/96).

Thiede, C., et al., "*Simple and Sensitive Detection of Mutations in the Ras Proto-Oncogenes Using PNA-Mediated PCR Clamping*," Nucl. Acids Res. (1996) 24(5):983-984 (Wilhelm-Sander Stiftung).

Vernet, C., et al., "*Evolutionary Study of Multigenic Families Mapping Close to the Human MHC Class I Region*," J. Mol. Evol. (1993) 37:600-612 (National Science Foundation).

Wagner, R., et al., "*Mutation Detection Using Immobilized Mismatch Binding Protein (MutS)*," Nucl. Acids Res. (1995) 23(19):3944-3948 (Genecheck Inc.).

Walker, G.T., et al., "*Isothermal in vitro Amplification of DNA by a Restriction Enzyme/DNA Polymerase System*," Proc. Natl. Acad. Sci. USA (1992) 89:392-396 (Becton Dickinson Research Center).

Wallace, R.B., et al., "*Hybridization of Synthetic Oligodeoxyribonucleotides to Φ χ 174 DNA: The Effect of Single*

*Base Pair Mismatch*," Nucl. Acids Res. (1979) 6(11):3543-3557 (City of Hope National Medical Center).

Worwood, M., et al., "Alleles at D6S265 and D6S105 Define a Haemochromatosis-Specific Genotype," Brit. J. Hematol. (1994) 86:863-866 (Univ. of Wales College of Medicine).

Wu, D.Y., et al., "*The Ligation Amplification Reaction (LAR)-Amplification of Specific DNA Sequences Using Sequential Rounds of Template-Dependent Ligation*," Genomics (1989) 4:560-569 (0888-7543/89).

Yanofsky, C., et al., "*Repression is Relieved Before Attenuation in the trp Operon of Escherichia coli as Tryptophan Starvation Becomes Increasingly Severe*," J. Bacter. (1994) 158(3):1018-1024 (0021-9193/84).

Youil, R., et al., "*Screening for Mutations by Enzyme Mismatch Cleavage With T4 Endonuclease VII*," Proc. Natl. Acad. Sci. USA (1995) 92:87-91 (National Health and Medical Research Council of Australia).

Yu, C-E., et al., "*Positional Cloning of the Werner's Syndrome Gene*," Science (1996) 272:258-262 (National Institute on Aging).

Barton, J.C., et al., "Blood Lead Concentrations in Hereditary Hemochromatosis," J. Lab. Clin. Med. (1994) 124(2):193-198 (0022-2143/94).

Beutler, E., et al., "A Strategy for Cloning the Hereditary Hemochromatosis Gene," Blood Cells, Molecules, and Diseases (1995) 21(21):207-216 (1079-9796/95).

Bjorkman, P.J., et al., "Structure, Function, and Diversity of Class I Major Histocompatibility Complex Molecules," Annu. Rev. Biochem. (1990) 59:253-288 (0066-4154/90).

Calandro, L.M., et al., "Characterization of a Recombinant That Locates the Hereditary Hemochromatosis Gene Telomeric to HLA-F," Hum. Genet. (1995) 96:339-342 (Kaiser Foundation Research Institute).

Camaschella, C., et al., "Hereditary Hemochromatosis: Recent Advances in Molecular Genetics and Clinical Management," Haematologica (1997) 82:77-84 (BioMed).

Capecchi, M.R., "Altering the Genome by Homologous Recombination," Science (1989) 244:1288-1292 (Univ. of Utah Medical Center).

Cartwright, G.E., et al., "Inheritance of Hemochromatosis: Linkage to HLA," Trans. Assoc. Am. Phys. (1978) 91:273-281 (National Institutes of Health).

Chen, X., et al., "Template-Directed Dye-Terminator Incorporation (TDI) Assay: A Homogeneous DNA Diagnostic Method Based on Fluorescence Resonance Energy Transfer," Nucl. Acids Res. (1997) 25(2):347-353 (U.S. Dept. of Energy).

Crawford, D.H.G., et al., "Evidence That the Ancestral Haplotype in Australian Hemochromatosis Patients May be Associated With a Common Mutation in the Gene," Am. J. Hum. Genet. (1995) 57:362-367 (0002-9297/95).

Crystal, R.G., "Gene Therapy Strategies for Pulmonary Disease," Am. J. Med. (1992) 92(6A):6A-44S-6A-52S (National Institutes of Health).

Darnell, J., "Molecular Cell Biology," Scientific American Books (1986) pp. 227-229 (Rockefeller Univ.).

Dugast, I.J., et al., "Identification of Two Human Ferritin H Genes on the Short Arm of Chromosome 6," Genomics (1990) 6:204-211 (0888-7543/90).

Edwards, C.Q., et al., "The Locus for Hereditary Hemochromatosis Maps Between HLA-A and HLA-B," Cytogenet. Cell Genet. (1985) 40:620 (Univ. of Utah Medical Center).

El Kahloun, A., et al., "Localization of Seven New Genes Around the HLA-A Locus," Hum. Molec. Genet. (1992) 2(1):55-60 (Institut National de la Sante et de la Recherche Medicale).

Friedmann, T., "Progress Toward Human Gene Therapy," Science (1989) 244:1275-1281 (San Diego Univ. of Calif.).

Fullan, A., et al., "A Polymorphic Dinucleotide Repeat at the Human HLA-F Locus," Hum. Mol. Genet. (1994) 3(12):2266 (Mercator Genetics).

Gasparini, P., et al., "Linkage Analysis of 6p21 Polymorphic Markers and the Hereditary Hemochromatosis: Localization of the Gene Centromeric to HLA-F," Hum. Molec. Genet. (1993) 2(5):571-576 (National Research Council).

Gnirke, A., et al., "Physical Calibration of Yeast Artificial Chromosome Contig Maps by RecA-Assisted Restriction Endonuclease (RARE) Cleavage," Genomics (1994) 24:199-210 (0888-7543/94).

Goei, V.L., et al., "Isolation of Novel Non-HLA Gene Fragments From the Hemochromatosis Region (6p21.3) by cDNA Hybridization Selection," Am. J. Hum. Genet. (1994) 54:244-251 (0002-9297/94).

Gorski, J., "HLA-DR $\beta$-Chain Polymorphism: Second Domain Polymorphism Reflects Evolutionary Relatedness of Alleles and May Explain Public Serologic Epitopes," J. Immunol. (1989) 143(1):329-333 (0022-1767/89).

Gruen, J.R., et al., "Physical and Genetic Mapping of the Telomeric Major Histocompatibility Complex Region in Man and Relevance to the Primary Hemochromatosis Gene (HFE)," Genomics (1992) 14:232-240 (0378-7543/92).

Halliday, J.W., "Hemochromatosis and Iron Needs," Nutr. Rev. (1998) 56(2)S30-S37 (Queensland Institute of Medical Research).

Harlow, E., et a., "Antibodies: A Laboratory Manual," Cold Spring Harbor Laboratory (1988) Chapter 5 pp. 75-81 (ISBN 0-87969-314-2).

Hashimoto, K., et al., "Identification of a Mouse Homolog for the Human Hereditary Haemochromatosis Candidate Gene," Biochem. Biophys. Res. Comm. (1997) 230:35-39 (0006-291X/97).

Jakobovits, A., et al., "Production of Antigen-Specific Human Antibodies from Mice Engineered with Human Heavy and Light Chain YACsa ", Ann. N.Y. Acad. Sci. (1995) 764:525-535 (Cell Genesys, Inc.).

Jazwinska, E.C., et al., "Where Does the Gene for Hemochromatosis Lie in Relation to HLA-A?," Hepatology (1994) 19:1050-1051 (Queensland Institute of Medical Research).

Jazwinska, E.C., et al., "Hemochromatosis and "HLA-H": Definite!", Hepatology (1997) 25(2):495-496 (Queensland Institute of Medical Research).

Jouet, M.M.H., et al., "Isolation of YAC Clones Containing Class I HLA Genes Which Map in the Vicinity of the Hereditary Haemochromatosis Gene," J. Med. Genet. (1991) 28(8):572 (St. Mary's Hospital, Manchester).

Koller, B.H., et al., "Normal Development of Mice Deficient in $\beta$2M, MHC Class I Proteins, and CD8+ T Cells," Science (1990) 248:1227-1230 (National Institutes of Health).

Kramer, M.F., et al., "*The Polymerase Chain Reaction*," Current Protocols in Molecular Biology (1993) Chapter 15 pp. 15.0.1-15.1.14 (ISBN 0-471-30661-4).

Lemarchand, P., et al., "*Adenovirus-Mediated Transfer of a Recombinant Human $\alpha_1$-Antitrypsin cDNA to Human Endothelial Cells*," Proc. Natl. Acad. Sci. USA (1992) 89:6482-6486 (National Institutes of Health).

Lin, A.Y., et al., "*Expression of T Cell Antigen Receptor Heterodimers in a Lipid-Linked Form*," Science (1990) 249:677-679 (Stanford Univ. School of Medicine).

Lipinski, M., et al., "*Idiopathic Hemochromatosis: Linkage with HLA*," Tissue Antigens (1978) 11:471-474 (Hopital Saint-Louis, Paris).

Miyazaki, J.I., et al., "*Intracellular Transport Blockade Caused by Disruption of the Disulfide Bridge in the Third External Domain of Major Histocompatibility Complex Class I Antigen*," Proc. Natl. Acad. Sci. USA (1986) 83:757-761 (National Institutes of Health).

Morgan, J.G., et al., "*The Selective Isolation of Novel cDNAs Encoded by the Regions Surrounding the Human Interleukin 4 and 5 Genes*," Nucl. Acids Res. (1992) 20(19):5173-5179 (National Center for Human Genome Research).

Mulford, C.A., et al., "*Endocytosis of the Transferrin Receptor is Altered During Differentiation of Murine Erythroleukemic Cells*," J. Biol. Chem. (1988) 263(11):5455-5461 (National Institutes of Health).

Murray, J.C., et al., "*A Comprehensive Human Linkage Map with Centimorgan Density*," Science (1994) 265:2049-2054 (Univ. of Iowa).

Nickerson, D.A., et al., "*Automated DNA Diagnostics Using an ELISA-Based Oligonucleotide Ligation Assay*," Proc. Natl. Acad. Sci. USA (1990) 87:8923-8927 (Whittier Foundation).

Nickerson, D.A., et al., "*Genotyping by Ligation Assays*," Current Protocols in Human Genetics (1994) Chapter 2.6 pp. 2.6.1-2.6.4 (ISBN 0-471-03420-7).

Olynyk, J.K., et al., "*Hepatic Iron Concentration as a Predictor of Response to Interferon Alfa Therapy in Chronic Hepatitis C*," Gastroenterology (1995) 108:1104-1109 (0016-5085/95).

Orphanos, V., et al., "*Thirteen Dinucleotide Repeat Polymorphisms on Chromosome 6*," Hum. Mol. Genet. (1993) 2(12):2196 (Cancer Genetics).

Patterson, M., et al., "*Molecular Characterization of Cell Cycle Gene CDC7 From Saccharomyces cerevisiae*," Mol. Cell Biol. (1986) 6(5):1590-1598 (0270-7306/86).

Raha-Chowdhury, R., et al., "*Allelic Associations and Homozygosity at Loci from HLA-B to D6S299 in Genetic Haemochromatosis*," J. Med. Genet. (1995) 32:446-452 (Univ. of Wales College of Medicine).

Roth, M.P., et al., "*The Human Myelin Oligodendrocyte Glycoprotein (MOG) Gene: Complete Nucleotide Sequence and Structural Characterization*," (1995) Genomics 28:241-250 (0888-7543/95).

Rothenberg, B.E., et al., "*The Molecular Mechanisms of Iron Overload: An Animal Model for Hemochromatosis*," FASEB J. (1994) 8. Abstract No. 5217, p. A900 (Univ. of California).

Salter, R.D., "*Intracellular Transport of Class I HLA Molecules is Affected by Polymorphic Residues in the Binding Groove*," Immunogenetics (1994) 39:266-271 (American Cancer Society).

Schild, H., et al., "*The Nature of Major Histocompatiblity Complex Recognition by γδ T Cells*," Cell (1994) 76:29-37 (German Cancer Research Center).

Sevier, E.D., "*Monoclonal Antibodies in Clinical Immunology*," Clin. Chem. (1981) 27(11):1797-1806 (Hybritech, Inc.).

Sood, A. K., et al., "*Isolation and Partial Nucleotide Sequence of a cDNA Clone for Human Histocompatibility Antigen HLA-B by Use of an Oligodeoxynucleotide Primer*," Proc. Natl. Acad. Sci. USA (1981) 78(1):616-620 (National Institutes of Health).

Summers, K.M., et al., "*Fine Mapping of a Human Chromosome 6 Ferritin Heavy Chain Pseudogene: Relevance to Haemochromatosis*," Hum. Genet. (1991) 88:175-178 (Queensland Institute of Medical Research).

Totaro, A., et al., "*New Polymorphisms and Markers in the HLA Class I Region: Relevance to Hereditary Hemochromatosis (HFE)*," Hum. Genet. (1995) 95:429-434 (Italian Ministry of Health).

Totaro, A., et al., "*Hereditary Hemochromatosis: Generation of a Transcription Map Within a Refined and Extended Map of the HLA Class I Region*," Genomics (1996) 31:319-326 (0888-7543/96).

Weber, J.L., et al., "*Dinucleotide Repeat Polymorphism at the D6S105 Locus*," Nucl. Acids Res. (1991) 19(4):968 (National Institutes of Health).

Wettstein, D.A., et al., "*Expression of a Class II Major Histocompatibility Complex (MHC) Heterodimer in a Lipid-Linked Form With Enhanced Peptide/Soluble MHC Complex Formation at Low pH*," J. Exp. Med. (1991) 174:219-228 (0022-1007/91).

Zijlstra, M., et al., "*β2-Microglobulin Deficient Mice Lack CD4-8$^+$ Cytolytic T Cells*," Nature (1990) 344:742-746 (Cancer Research Institute).

Zinkernagel, R.M., et al., "*MHC-Restricted Cytotoxic T Cells: Studies on the Biological Role of Polymorphic Major Transplantation Antigens Determining T-Cell Restriction-Specificity, Function, and Responsiveness*," Adv. In Immunol. (1979) 27:51-177 (ISBN 0-12-022427-5).

Nierman, W.C., et al.,"*ATCC/NIH Repository Catalogue of Human and Mouse DNA Probes and Libraries*," Amer. Type Culture Coll. (1994) pp. 1-70 (ISBN 0-930009-56-8).

de Sousa, M., et al., "*Iron Overload in $β_2$-Microglobulin-Deficient Mice*," Immun. Lett. (1994) 39:105-111 (0165-2478/94).

Rothenberg, B.E., et al., "$β_2$ *Knockout Mice Develop Parenchymal Iron Overload: A Putative Role for Class I Genes of the Major Histomcompatibility Complex in Iron Metabolism*," Proc. Natl. Acad. Sci. USA (1996) 93:1529-1534 (National Institutes of Health).

Boretto, J., et al., "*Anonymous Markers Located on Chromosome 6 in the HLA-A Class I Region: Allelic Distribution in Genetic Haemochromatosis*," Hum. Genet. (1992) 89:33-36 (Institut National de la Sante et de la Recherche Medicale).

Campbell, A.M., "*Monoclonal Antibody Technology*," Elsevier Science Publishers (1985) Chapter 1 pp. 1-32 (ISBN 0-444-80592-3).

Cornall, R.J., et al., "*The Generation of a Library of PCR-Analyzed Microsatellite Variants for Genetic Mapping of the Mouse Genome*," Genomics (1991) 10:874-881 (0888-7543/91).

Vogel, F. et al., "*Human Chromosomes*," Springer-Verlag (1992) pp. 18-81 (ISBN 3-540-09459-8).

Hirschhorn, et al. 2002, Genetics in Medicine 4(2) 45-61.

Ioannidis, et al. 2001, Nature Genetics, 29: 306-309.

\* cited by examiner

```
   1 CACACACACA CACACACACA CACACACACA CACACAAATG AGGTATATAA AGGGTCTCCT
  61 AAAATGTCAT CTGATATTTG TTATTTCATA TTCTCAGATT TTTAATCCAT TTAGGTAGGT
 121 CTATTTTAGA TAGCCTTGTC TGAAACAGAG CTGGGACCTG ATGAGTGAAA ATGAGCTCAC
 181 CAGAAGAAAA ATCAAACAGG CATTTCAGAG ATTGAGGCCA AGAAGTTAAA TGTCTTAAAT
 241 GGGCAGAGCT TAGCTGCTTG ATGTGAAAAG AGACCAGCGT GGCTGGAACA GCAAAGGAGA
 301 ACAGCAGAAG AGGTGAACAG AGGCCAGAGA TGGTCACTGA GTGGGCCCTT AAGTCATGGT
 361 AAGGAGTATG GAGAATGAAT TATTGCATGT ATTGAATATG TAGGTGACGT GACTCACAGA
 421 TACTTTGGAT TTGTAGAGAT GAAGGAAATG TAGCAAGTGA CACTCTTAGA ATGTTGATTT
 481 GAGTAAATGG TAGTGTCAGT TATTGAACTG GGGAGAACTG GAAGGGATAA CAGGCTTAAG
 541 GAGCACGTTT ATTCCTGTGT CTTGGAAGTG TTTAGGGTGA AAGACCTATT AGAGTTCTAA
 601 ATGGAGATGT CAAGTGAAAA TGTGGCTACA CACATTTGCA TTTCAGAAAA AAGGTCAGGC
 661 TGGAGATGTA AAATTGGAAG TTTACTGCAT ATAGATAGTC TTTGGAACCG TAGTATTGAT
 721 GAAGCCATTA ATGAGACAGA ACAAAGACTA GGGACCAGAG CCAAGCTCCA AGTTTCTAAA
 781 ATTTAGAGGA TAGTATAGTC TGGTCATTTT GAGGTGAATA CTTAATAACA GAACAATTTG
 841 TTGAAGTGTA AATTTAGAGC CCTACACTTT TAGCTCTGAC TATTAACGAA TACAGGAAAG
 901 AATGGATATG GTTATCTGCC TGGTGTCTGT GAAATAATTT AAGCCAGGAA GAGATCCTCA
 961 CCAGAAACTG ACTATGCTGG CAACTTGGAT CTTAGATTTC CAGCCTGCAG AATTGTTAGA
1021 AAATAAATGT CTATCGTTTA AGCCACCAGT CTGTAGTATT TTGTTATGGC AGTCCAAGCT
1081 GACTAAGTTT TGGTACCCAG GCGTGGGATG CTGCAACAAC AAATACCTAA ACATGGGGAA
1141 GTGGCTTTGG AAATTGGTGA TGGGTAAAGG CTGGAAGAGT TTGAGGTTCA TACTAGAAAA
1201 AGCCAATTGT GAAGGGACTA TTGAAAGAAA TATGGACATT AAAGGCAATT CTGGCAAAGG
1261 CTCAGAAAGG AAGAGAGCTG GACAGAAAGC TTCCATTTTC ATAGAAACTT AGATTTATAA
1321 CGATCATGGA TAGAATATTA AATATGCTGG TTAAAATATG GACTTTAGGC CAGGCGTGGT
1381 GGCTCACGCC TGTAATCTCA GCACTTTGGG AGGCTGAGG CACAGATCAC GAGGTCGGGA
1441 GTTTGAGACC AGCCTGGCCA ATATGGCGAA ACCCTGTCTC TACTAAAAAT ACAAAAATTA
1501 GCTGGGCATG GTGATGTGCT TCTGTGGTCC CAGCTACTCG GGAGGCTGAG GCTGAAGAAT
1561 CGCTTAAACC CGGGGGGTGG AGGTTGCAGT GACCCAAGAT CACACCACTG CACTCCAGCC
1621 TGGGATACAG AGCAGGACTC CACTCCCCCC GCCACACACA CACAAAAAAT ATATATATAT
1681 GGACATTAAA GTCAACTCTT GTGAGGTCTC AGATGAAAAT GAGGGACAGG TTATTGGAAA
1741 CTGTAGAAAT CACTGTTCTT GTTACAATGT GTCAAGAACT TGGCTGAATT ACGCTGTAGT
1801 GTTTACTGGA AAGAACTTAT AAGCAGTAAA ACTGGATATT TACCAGAAGA GATGTCTAAG
1861 CAAAGTATTG AAGGTGTGAT TTAGGTCCTC CTTACTGCTT AAAGTGAAAT GTGAGAGGAA
1921 AGAGCCGAAA TAAAGAAGGA ATTTTTAAGC AAAACACAAT CAGAACTTGG AGATTTGGGA
1981 TAGATTTCTC AATCTATATT GTAAAAATTG AGAAAGTTTT TCTTGAAGAG GTATGGTTGA
2041 ACAATGTTTT CTTTTTCTTT TTTTTTCTTG GTTTTATTTT TATTTTTATG TTTTTTGAGA
2101 CAGGGTCTGG CTATGTCATC CAGGCTGGAG TGCAGTGGCA CAATCTCAGT TCAGTGCAAC
2161 CTTTGCCTTC AGGCTCAAGC AATCCTCCCA CCTCAGCCTC CTAAGTAGCT GGGACTACAT
2221 GTATGCACCA CCACACCCTG GCTAATTTTT TGTTGTTGTT TATAGAGATG GGGTTTTGAC
2281 ATGTTGCCTA GGCTGGTCTC TAACTCCTGA GCTCAAGTGA TCTGCCCTCC TCAGTCTCCC
2341 AAAGTGTTGG GATTACAGGC GTGAAACACT GAGCCTAGCC TGAACAACCA TTTGATAAAG
2401 AGATAATGGG TGTGACCCAA GGATTAATC AGCCATCTCA GCAGAAGCCA GGAAGAGAGA
2461 TGGGATTATT CCAGCAGAGA CACTGCCAAT TTAAACTAAC GTAGGCAGAG AAAACAGAAA
2521 GGAACAAAGG AAGGTTGTCG ACTTTTTGAA TTCTATAGAA CAGGATCATA GAGCTACCTG
2581 GCTGTCAATG TGTACTATTC TTTAAGAAAA GGAAAGACTG ACCCACCAAA GGCAACTTAC
2641 AAGATCACTA GGGCTGACTC TTTTGTTTTT TCTTGAGGCA GTCTCACTGT CACCCAGGCT
2701 GTAGGGCAAT GGTGTGATCT CAGCTCACTG CAATCTCCAC CTCCCAGGTT CAAGGGATTC
2761 TCTTGCCTTA GACTCCCAAG TAGCTGGGAT TACAGGCTCT AAATCTGTAC CCTCCCGAGT
2821 AGCGCTCCTG CCACCACTTG CCCAGCTAAT TTTTGTATTT TTAGTAGAGA TGGGGTTTCA
2881 CTATGTTGGC CAGGCTAGTT TGGAACTCCT GACCTCCAGT GATCCATTCT CATTGGCCTC
2941 CCAAAGTGCT GGGATTACAG GCAGGAGCCG CCAGGGCTGC CACTTTGATG TCAGACTCAG
3001 AGAGTACAGA TGGGATAGGG TGGGGGTGGG AACATGTAGT CAAGGCTGAC TCTACCTGTT
3061 TCAAAGATGC CCTGCAGAAC TGTGTGGGAG TCTCTCACAG ATGGCTGCCT GGGTGGGACC
```

Figure 1 (Page 1 of 73)

```
3121 CCACCAAACT GAAAGACCGA GACTTCAGGC AGGGCAGATG GAGTAGGCCA ACTACAGAGC
3181 CAGAGGTGAC ACTGAGACAC CACTGGGCCT GGAAATCAGG GCATCAAGCC AAAGAGGGTT
3241 TTTCTTAAGA CCTAACAGAA TTTGCCTTGC CAGGTTTTGG ACTTGATTAG GACACATTAC
3301 ACCTTCCTTC TTTCCTATTT CTCCATTTTC TAATGGGAAT GTCTATTATG CCTGTTTCAC
3361 CATTGTACCT TAGAAGCATG TAACATTTCT GGTTTCACAC GTTCAAAGCT GGAAAGGAAT
3421 TTTGTCTCTG GATGAATCAC ACATTGAGCC TCACCCGTAA CCTGATTTAG ATGATTTTTT
3481 AGATGACACT TTGAACTTTA GAATTGATGC TAGAATGAGT TAAGACTTTC AGGGGGCTGT
3541 TGGGATGGAA TAATTTTTTT TTTTTTTTTG AGACGGAGTC TAGCTCTGTC GCCCAGGCTG
3601 GAGTGCAGTG GCACCATCTT GGCTCACTGC AAGCTCTGCC TCCCGGGTTT ATGCCATTCT
3661 CATGTCTCAG CCTCCAGAGT AGCTGGGACT ACAGGCGCCC GCCACCACGC CTGGCTAATT
3721 TTTTTTTTAT TTTAGTAGAG ATGGGGTTTC ACCGTGTTAG CCAGAATGGT CTCGATCTCT
3781 TGACCTTCTG ATCCGCCTGC CTTGGCTTCC CAAAGTGCTG GGATTACACG TGTGAGCCAC
3841 CATGCCCGGC TGGGATGGAA TAAATTTATC TTGTATGGGA GAAGGACATA CATTTTGGCA
3901 GGTCAAGGAC AGAATGTTAT GGACTAAACT GTGTCCCCCA AAATTCATTT ATTAAAACCC
3961 TAAACCCCAG TGTGACTGCA TTTGGACATA GAGCCTTTAG GGGGTACATA AAACTAAAGA
4021 TCACAGGATA GGGCCCTAAT CCCATTGGGG CTGGTGTCCT TACAGAAGAT GAGACACTTA
4081 GAGCTCTCTC TCCACGCAGG CACCAAGGAA ACACCATACA AACACACAGT GAGATGGCAG
4141 CCATCTGTTA GCCAGGAACA GATTCTCACC ATAAACTATG TTGGCACCTT GATCTTAAAC
4201 TTCCAGGCTC CAAAACTGTG AGAAAATGAA TTTCTGTTCC AAGCCTCTTA GATATGGAAA
4261 AAAAGATTCT GTTGTTTAAG CCATCCAGTC TCTGGTATTT TGTTATGGCA GCCTGAGTAG
4321 GCTAAGACAA TGAAGGATGT GGTAAAACTT TACGTCCCAA CCACATACCA AAGAGGCTGG
4381 AATTTAGCAT GCTTTCTTCT TTCAACTGTA GGCAATGTGC ACAAGTTCTA AATCCTAAGA
4441 CATGTTGGCT CCTTTACTCT GCCCAAACTA CAACTCAAAC AAACAACTGT AATATAATAA
4501 CATCCAATGA AGTTCTGACA TTTCTTCAAC ATGAGTACAG TAATTCAATG CCAGAGAATT
4561 CATTTTATTT TGAAATCTAC ATGCCATATT CCAATTTCTG TTGAAGATGC AATGGTTATA
4621 TTTATTCTTT TTAATATAGA TTTATCAGAC TGGGCGCGGT GGCTCATACC TGTAATCCTA
4681 GCATTTGAGA GGCTGAGGTG GCATATCAC CTGAGGTCAG GAGTTTGAGA CCAGGCTGGC
4741 CAACATGGTG AAACCCTGTC TCTACTATAA ATATAAAAAT TAGCTGGGTG TGGTGGTGCA
4801 TGCCTGTAGT CCCAGTTACT AGGGAGGCTG AGGTAGAATT GCTTGAACCT GGGAGCAGGA
4861 GGTTGCAATG AGTGGAAATC GCACCAGTAC ACTCCAGCCT GGATGACAGA GCAAAATAAT
4921 AAATAAATAC ATAAAATAGA TTTATCAGTT TATCAATAAT ATAGTTTTCT TTTCTAGGTG
4981 TAAATATAGG TAATGACTGT CCTTTAGTAC ATTTTCTCAT GATGCTCCTC TTACTTGGTT
5041 TGGTACAATA TTAAGTATTG AAATAAAATA GAGAATCCTG TCGCTACACA TGAGCACTTA
5101 TTCCATTTGC TCATCTCCAA TATGCACGGG AAATTCTCAA ATTGCTAATA ATCTTGTAAC
5161 ACACATGCAT TATATTCAAC AGGAATATAT AAATTTATAA TTATAATTTA GGATCAACAG
5221 ATGACAAACC TTTAGAAGGT TTGTATTTAA CCTTAAAATA TAATTTTTTA AAAATTGGTT
5281 ATAAAATTTC TAATACTTTC TTTTTTGTGA CCTCAAGGGG AAAATATAAT TCTTATAAAA
5341 GTTCAAATGA TTTACAGAAT ACAAAAGTG AATAGAGATG ATGAATGAAT TAAAGGAAAG
5401 GATATTGCTA CATAGATTTG GAAATTTAAA AAGGGAAATT ACGATTGTTG ATTTTGTGTT
5461 AAACTGATCT GCTTTGTTCA AGATACCTTA TGTACCAAAA AATGATTTTA TCTCAGCCTC
5521 ATATCTCAGT AAATTCCTGA GACAAACTTT AGTCCCTGGT GCCCAGGTGC CTTTGGTAAT
5581 TGGGAGACCT CTAGGTTTAG CATCCTCATC CACTCGCCCC AATTTAAATA GTCCTCCCCA
5641 GGGCCATTCA GGCAAGGGAG ATGAAAACTT GCTCAAGAGT TGGAATCCAA CTGAAGCTAC
5701 CGAAATTCAT TGCTCAATAG ATAATTTTCC CTGGAAGTAA CTAGGGCTTT TGAATATAAT
5761 AGTGGGCATT TCAAAGTAGA AGGTAAAGTA TTTTGGAGAT GAGGAGACAG GACAGAGCTA
5821 CGAGGAATGT CCTTTGCTTA GGGACTAGGC TCTTAGCAGT ACCTCTTAGG TAAGAACTGG
5881 TTAACTGGCA CCTTCTGTGT TTCTCTGAAG CTCCCTTTGC TTAGGGACTA GGCTCTTAGC
5941 AGTACCTCTT AGGTAAGAAC TGGTTAACTG ACACCTTCTA TGTGTCTGAA GCTCCCAGAA
6001 CAAACTGCCA GTGAAATTTG GATTTTGGA ATATAGTTTC TTTTTTCTTG TTACTTTTTG
6061 TTTTGTTGTT TTTTTTGAG AGTCTCACTC TCACTGCAAC CTCCCCCTCC TATATTCAAG
6121 TGATTCTCTT GCCTCAGCCT CCCGAGTAGC TGGGACTACA GGCGTGCACT AGCATGCCCA
6181 GCTAATTTTT GTATTTTTA GTAGAGATGG GGTTGGTTTT TTTTGAGAC GGAGTTTCAC
6241 TTTGTCGCCC AGGCTGGAGT GCAGTGGCAC GATCTTGGCT CACTACAACC TCCACCTCCC
6301 GGGGTTCAAG TGATTCTTCT GCCTCAGTCT CCTGAGTAGC TGGGACTACA GGCGCCTACA
```

```
6361 GGTGAACACC GCCACACCTG ACTAATTTGT GTAGTTTTAT TAGAGATGGG GTTTCGCCAT
6421 GTTGGCCAGG CTGGTCTCAA ACTCCTGACC TCAGGTGATC TACCCACCTC AGCCTCCCCA
6481 AGTGCTGGGA TTACAGATGT GAGACACCAG ATCAGCCTCA GAAGACATTT TCTATTGGAA
6541 AGAGAAAACA CTATTAGCAA CCTATTAGTC TAATATTTAA TACTTAATGT CTTCCTTAGT
6601 AATAAACCAA CTCTCTACAA CAAAGTGCTT CCTGGCTGCC TAAGTCATTG ATTCATTCAG
6661 TTCAACATTT TCTCAATGCC CAACAGCCAA GTGTCTCTTG TATGCCAAGT TCTATGCTGA
6721 TTATCAGTAT TTGAATAAGA GGGGGTCTAC ATCTTAAGTA CTGCTTAAGA TGAAAGCCTC
6781 TAGGTTAACA AACTTAACAC AATGTATCAT TCACTACTAA ATAGACCGAA TACAAAATCT
6841 TGTTATTGGA GCCCAGAGAG AAGAATTGAA ATTCAAGTTT TCTCTCTCTC CTTTTCTCAC
6901 TCACCACAAT AAGTCAGTTG CACCAAGTCT TGTAGCTCTT TACTGAGCCA TGTTTTCACG
6961 TGTCCCTTTG TTTTATTTGC CACACCCTAA ATAAAAATTG TACTGGCTTT TTTTCCCTGG
7021 GTTTACAGTA TTAATACATT GTCAAGATTT ACCTCTTCGT GTAGATTCCC TGGGGAAAAT
7081 TACCTTTCCT CCTTCCCTTA AATTCTTCAG AGGTTAGAAA GCCATTAGTA ACATTCTGGT
7141 ATGTGGACAA AGTTTACCCA TTATGTATGG ATGTTTTACT CTTTCTATTT TTCTGACAAT
7201 AATCTCTTAA GGAGGTGTGG TTATAGAATA GTCAGCTGTT ATAAGTACTG TTTTCCTGGC
7261 CTTACAACTT AAGTTCTTTA AGCTGTTTCT TAGTTTGCTC ATCTCAAAAT TCGGAATAAG
7321 GATAAAACCT ATCTCTTAGA TTGTTGGATT AAATGAATTA ACATACTGGA AGCTCATGAA
7381 ATGTGCCTGG CACACAGTAG TGCCTAATAA ACCATCTCTC TTATTCAGCC TGTTTTCTGA
7441 TTTCAGAATC TACACTTGCT GAGCCAGGTT CTTTTCATTT CAAGGTGAGC AAAAGCATAC
7501 AAGGAAGAGA TGGAGGTAGG AAGAGATTAA GCCCTAGGCC AAGGTCACAC ACCGATTGGG
7561 AGCTGGAATC AAAGGCAATT TGGTCAGTGA ATAAAAAGGA TTCCAAGGCC CATAAGGCAA
7621 TTCTAACCTT AGGATCGAAA TTCTCGGACA TACAGGAAAT GCTGGGGGGG GAAAATCCGG
7681 TCTTCTCAGC CCAAGAGCCA TGTGAAACCA GACCTTCAAA TCTGATGATT CTCAGCCCAG
7741 CTGCCCATTA GAATCGTTGT AATTTAAAAA TACCCTCGGA AAATTCTAAT ATGTGGCTAT
7801 CAAAGGTGAT CATTTGCTTT TATGCCACTT TGTTTTCACC CAAATGGGAC ATCCAACCCT
7861 TTTCCTTTGA GAGTAGTTGT AGGGAAAGGA GGGGGTGGAG GGAGGGAAGA GCGGAAAAGG
7921 CTGGATCCGC CCTGAGCCGG TGTCAGTATC TGGGAAGTGG GAGGCGCGTC AGCAGTAAAC
7981 AGCTTCTGCT AGGATTATTA TCTCCTGCCA CACACTCGGA TTTGAAGGCT CCAAACGAAA
8041 CAATGCAAAA CGCTTCAGTG GAGTTCCAGA AGCGTTAGAC TAAACGACTG GGTCTGTTTG
8101 GCCAGTCTGA GCAGCTGGGC GCAGATGCAT AGGCAAGACT TAGCCCGCCT AGACTTTTCT
8161 GCCCACTTAA TTCCGATCAA AGCAGAAACC GGCCGGGCGC GGTGGCTCAC GCCTGTAATC
8221 CCAGCACTTT GGTAGGCAGA GGCTGGCGGA TCACCTGAGG TCAGGAGTTC GAGACCAGCC
8281 CGGCTAACCT GGTGAAACTC CGTTTCTACT GGTGGCGGGC GCTTGTAATC CCATCTACTA
8341 GGGAGGCTGA GGCCGGAGAG TCGTCTGAAC CCGGGAGGCG GAGTTTGTAT GCAGTGAGCC
8401 GAGATCGCGC CACTGCATTC CAGCTTGGGC AACAGGAGCA AAACTCCGTT TCAAAAAAGC
8461 AAGCAAACAA ACAAAAAAAT GCAGAAACCG AGATCCGGAA GAAAACCTCG GCGAGATTCA
8521 CAGAATCCAG GAAAATAGGT CTCTAGAAAT TTGTCCATGG TCCCAGATCT CCATTTCTTG
8581 TGGGTGGGGC AGCTGTTACC AGATCCCTAG AAGCAAAGGT TTTTTTGGGG GACCGTGTCT
8641 CACTGTTGCC CAGGCTGGAG GGCAGTGGCA CGATCTCGGC TTACTACAAC CTCCGCCTCC
8701 CAGGCTCAAG CGACTCTCCT GCGTCAGCTT CAAGAGTAGC TGGGATTACA AGGTATGTGC
8761 CACCACGCCC AACTTATTTT TTTATTTATT ATTTTTATTT AGTAGAGAGG TGTTTCACCA
8821 TGTTGGCCAG GTTAGTGTCG AAGTCGTGAC CTCAGGTGAT CAGCCCCCTC GGCCTCCCAA
8881 AGTGGTAGGA TTAGAGGGGT GAGCAGAAAG CAAAGGTTTT TGAGTGGCCA CAGGCCCCAC
8941 TCTATTTCCT TTTCTGCCTG TAATGGCAAC CTAGACGCTT GAGCTTCTTA AAATACAAGA
9001 GTAAGTTGCA TGTCAGGCAC CGTTCTACAT TAGGGACATT AGTCTGTTTT ACAGACACCT
9061 TTCAACTCCC TGGTTAACTT TTAGGTAATA TACTCTGCAC TTTAGCAGGA ATGGGACCTA
9121 TAACTCTCAC AGAATTAGGA AAGTGAGGCT GCCTACAGCC TAAATTGAGA AAAAAATAGA
9181 CGGGGGACTA GTCGGAGGAC CAAACAAGGT TACCAACACG TTAGAGTTTT GCCTTCAATT
9241 TACATTTTTA AAGTAATCAC AACGAAGTGT TTAGATCACG AGGCATCCCT GCATGTAAAC
9301 TGTTAGGCAC TAACTATGGT CGATCTTACA AAGCATTAAC TAGAATATTT CTTTAGAGTA
9361 TGATAGTACG TAACTGACCT ACTATTACAT ACAAACAGAC CAACCTTTAG TAACAGCGCT
9421 CCCCAAAAAC CGAAAGCAG TAATACGCTT TGCTCAAGGT TGGCATAAAA TTAACTTACC
9481 TTAGTGCCTT TTTTCCTTCT ACCTACAAGC AGTGAGGTTA GCTCTTCCTT TGAAACGGTA
9541 GGGGGGCTCT GAAAAGAGCC TTTGGGTTTG ATAGCGTTTC CGGGAGCTCA GATACCTGTC
```

Figure 1 (Page 3 of 73)

```
 9601 AAATCACTTG CCCTTGGCCT TGTGGTGACT CTCGGTCTTC TTAGGCAGAA GCACGGCCTG
 9661 GATGTTAGGA AGGACGCCGC CCTGAGCAAT GGTCACCCGG CCTAGCAGTT TGTTGAGCTC
 9721 CTCGTCGTTG CGGATGGCCA GCTGCAAGTG GCGCGGGATG ATGCGAGTCT TCTTGTTGTC
 9781 GCGAGCCGCG TTGCCGGCCA GCTCCAGGAT CTCGGCGGTC AGGTACTCTA ACACCGCCGC
 9841 CAGGTACACC GGCGCGCCTG CCCCAACCCG CTCTGCGTAG TTGCCTTTAC GGAGCAGGCG
 9901 GTGCACTCGG CCCACCGGGA ACTGGAGACC AGCGCGAGAA GAGCGGGATT TCGCTTTGGC
 9961 GCGAGCTTTG CCTCCTTGCT TACCACGTCC AGACATTGCA ATCAGACAAA AATCACCAAA
10021 ACCAGCGGCC TAAGCTCACG AGAAAACAAA CAAAATCAAG AAATATGTAA AACATGGCCG
10081 CTTTTATAGG TAGTTCCTGG GGAGTAAATC CGACTTTTTG ATTGGTCGGT AGCAAATGCT
10141 AGTCAGATAG CCAATAGAAA AGCTGTACTT TCATACCTCA TTTGCATAGC TCTGCCCACG
10201 GATGACAACT GTGCAGTTTG TCTTCCAATT AACTAAGAGG TACTCTCCAT CCCTCATTAG
10261 CATAAAAGCC CTATAAGTAG CAGAAATCCG CTCTTTACTT TCGACACATT TCTGGTGTTT
10321 TAAGATGCCT GAGCCAGCCA AGTCTGCTCC CGCCCCGAAG AAGGGCTCCA AGAAGGCAGT
10381 GACCAAAGCG CAGAAGAAAG ATGGCAAGAA GCGCAAGCGC AGCCGCAAGG AGAGTTACTC
10441 TGTGTACGTG TACAAGGTGC TGAAACAGGT CCATCCCGAC ACTGGCATCT CTTCCAAGGC
10501 CATGGGCATC ATGAATTCTT TCGTTAACGA CATATTTGAG CGCATCGCGG GCGAGGCTTC
10561 CCGCCTGGCG CATTACAACA AGCGCTCGAC CATCACCTCC AGGGAGATCC AGACGGCCGT
10621 GCGCCTGCTG CTTCCCGGAG AGCTGGCCAA GCACGCCGTG TCGGAGGGCA CCAAGGCCGT
10681 CACCAAGTAC ACCAGCTCCA AGTAAACATT CCAAGTAAGC GTCTTAACAC CTAACCCCAA
10741 AGGCTCTTTT AAGAGCCACC CAGATACCCA CTAAAAGAGC TGTGGCCAGA CGCCAAATTT
10801 TATTTGGCGG CGGAGGGGTA TTAGAATATA GGAACTGGAG AGGGGTGGGG ACAAGTGTTG
10861 CAGCTTAGAG AGGGACAAAG GGTCCTGAAC CCGAAAGAAG CCAGCCATTA AAAATGGCTT
10921 TGGGGTCAAT TCGTTGTGCT TAAATTTAAA ATGGAGACAA GCGGCCATTT TGCTAACTCG
10981 GCGTTCCCGG AAGAAACCGC AGGCTCGCTT AGGTTTCAGA CCCAGCTGTC TGTCCCTGTC
11041 TACGTCGCCA GGATCAACGG TTGCCGTAAT GTCATAATTT CGCCACCAGC TTCTAGCCAA
11101 TAGGCTGTCC TGTCATTTTA AATATTAACC AATCGAGGGA AAGCTGTTTT GAGACTCTGA
11161 TTTACATAGC GGACCGGAGT GGGAACCTGG GCAGTAACTG CCTAAGGAAG GACTCCCCCT
11221 CTGTTTTCGT GGCGCACACC TTCGTAGTAT ACTGAAGGGT GTGTCTCCTG GGTTTCCAAC
11281 TGCCCCGGTA ATAGTCTTTT AACCTAATAT GCGTCAGTTT TGATAACAAC ACTAAGGCAG
11341 TACAGAACTA AAGATGTAAG CACTGCGCCA GATGTTGCTT CATACATCTT ATTCTATTCA
11401 ACTGGTTTAT TCAAGATTCA AATCAAATCA AATTTTGCTT GAATCCCAGT GCTCAGTCAG
11461 CCATAAATGG TGTGTTGCCT GATTGAAACT TAAAATCTCC GTAGGGGCT TGTAACATGC
11521 AGACAAGTTT GAAAGTTGCT TTAGGAGAAG CCAACTCTTA ACTGCTGGGT AAATTGACAA
11581 GCCTTCGAAC ACTGAACTGA AGGCCAGTAA GGACTAGGCG CTGGGTGGGG GAGAATGAAG
11641 AGGAGACGTC ATTAAACTTA GCACATACAC TGTATCTCCT AGAGGACTCT CCCTTCCTAG
11701 ACAACTGCAG GCCGCTTTGT GGCCTGGGAA ATTCCACATT CCCTTAAGTA TTTTACTCAT
11761 GGTCTTTTCC AGGTAAAGAT TTTAAGATGA AGGGTTAGAC GTAGTCTACC TATCTTTTTA
11821 TTCAAGTCTA GAACACGTTT TTAGCACCTA GAAGTTTGCT TTCTCCATTA AAAACCGGGA
11881 ATATACAATA AATAAAATTA GTGTTAAAGC AGATTTTTAC AAACTTAAAT ACCATGTAAT
11941 TTAGGTTACA GTTATTTAAC ATAAGGACTG TGTGATCTTA AATCTGCAAT TTCTTTCACA
12001 CCTGGGAAAT AAACTAAGGC CTGTCTTTGG TGCCAGACAA GGCCTTATAC TTGAACACTG
12061 CTGTGCAATC ACAGGCTGCC TTGCCTAGAT AACTTATCTG AGAAATTCTG ATGAGAAATG
12121 AAATTTCCAG AGTCCCTCAC AAGTAAATTT TTTTTTCTTT TTTTTTTTTT TTTTTGAGAC
12181 GAAGTTTCTC TCTTGTTTCC CAGGCTGGAG TGCAATGGCG CGATCTTGGC TCACAGCAAC
12241 CTCCGCCTCC CGGGTTCAAG CCATTCTCCT GCCTCAGCCT CCGGAGTAGC TGGGATTACA
12301 GGCATGCGCC ACGACACCCT GGCTAATTTT GTATTTTTAG TAGAGACGAG GTTTCTCCAT
12361 GTCGGTCAGG CTGGTCTCGA ACTCCGGACA TCAGGTGATC TGCCCGCCTT GGCCTCCCAA
12421 AGTCCTGGAT TACAGGCTTG AGCCACCGCG CCGGGCCTAA ATGGTTTTTT TTTTTTCTAT
12481 GCCTCTAATG GACCTGGTCA CTTATTCCCA TTCAGACTGA CCGCTCTCCT ACCTGCCAAC
12541 TAACTAATCA GTGTAACCAA AATCTGCAAA CAAAATTCAG TATTCTTTCC CCGCCTTTTC
12601 CCCTTTCTCT TACATAGATT ATGTTTTTGC CTGTGTTAGA TGAAATAATT CTATTGCTTG
12661 TTCTCTCTTC TGTACAAGTA CCCAGTAAGC AAATTATTAA CTTCTTGGTC ATTTATTTCT
12721 GAATTTTCCA CCAAGACAGT GTTTATGTGA GTCATACAAT AAGAACCAAC AGAAATGTGT
12781 GTCTTGGAAA CAGGTTGTCT ATCCCTGGAC CCTTTGAGTT TTCTGTTCAC TTTCCTTTGG
```

Figure 1 (Page 4 of 73)

```
12841 CTTTTGCATG CTAAAAGTTT ATCGTCCGCG TTTGTTTGTT TTGGTTATTC TAATTGGACT
12901 TGGCTGATTG GTTGCATATT GGTGGCAGTA GTAGAATTTG AATTCTGGTT TTCTGGTCAC
12961 ATCATTAAGT GATTAGTCAG TGGAGAGGAC AGGAAATCTG GTTTATTTAT TAACCTTTTT
13021 TTGGGGTGTT TTTGTTTGAA GATGTTGATA TTCTCTGTGA GGACACAGGG TTAGAGTTGG
13081 TGTTTTTCTT TCTGACTTTA CATGGGATTT GATGTTTTGT GCTTGTATGC CTCTTTCCAC
13141 CTTCCAAAAC TTGTCTTTTT TGAGTCCAAA TAGTTGTCGA TATCTGCAAA ACCAGTATTC
13201 CTGTGTTAAG ATGATATGAA TATAAAATGG CTGCCCTGTT ATAACTTTTG ACTTTAAGAA
13261 AGTGTTAGGA CTAACAGGAG ACAAAAAGGA AATCAAGGAA ACCGAATGTC TGGTCTCAAT
13321 AACTGCTATG GCAGAGGCTC TACAGCTTAT TATTAATTTT AGTAATTTCA CATTATTGCC
13381 CCTTCACGTT CTTTAAGTAA GGTTAGAGGA CAGAAGAAAC ATAATGTTGT TACAAATTGG
13441 ACTATTGAGT CAGGGAAAAA AAAGAGTGCT TTCAATATCT GAATAAAACA AAGATTTAAT
13501 ATTTTCTAAA CCTTAACGAG TTTATTGTAA GGGATGTGAT GCTGGAAACT AGGAAACTAG
13561 AATTTTCTTC TAAACTGAGA ATCAGAATTA TTCATATTCT CAGCAGTGGT GCCACCTGAG
13621 GGACTTCTGA TCTTAATTAC ATACTTTTAT TTCTTTAACT GATCAACATG CTAAATAGAT
13681 AACCTATGGC TCTGTTTTTA CCCACTTTAA ATTCTGTTCT ATTAGCACGG TTAGCTTTCC
13741 TAATTGGCAA TAAGATTGAG ACTATCTTTT TTTTTTTTTT GAGACAGAAT TTTGCTCTGT
13801 GGCCCAGGCT GGGGTGCAGT GGCACAATCT CGGCTCACTG CAACCTCTGC CTCCAGGGTT
13861 CTAGCAATTT TCCTGCCTCA GCCTCCCCAG TAGCTGGGAT TACAGGTGCA CCACCACGCC
13921 TGGCTAATTT GTGCATTTTT AGTAGAGATG GGGTTTCGCC ATGTTGGCCA AACTGGTCTC
13981 GAACTCAGGT GATCCACCTC GGCCTCCCAA AGTGATGAGA TTACAGGCGT GAGCCACCGT
14041 GCCCAGAAAA GACTATCTTA TTTTATGAAT TTAAATAATT GTGAAATTAT CCACTTAAGG
14101 GAATTAATAA ATTATAATGT AATCTTAAAT TTTAGTTGGC TTACATAAAG ACTTAAAATA
14161 CATCAATTTA AATAAAAACT CATTTGTCTA AAAAAAAATC AAAAATTTTC CTTGTGCTTT
14221 AAATGTGCTA CCTCTTTAAG TTCTAATTAA GAGAAAAAAA GTTTAACTGT GAGTTTCATT
14281 AGTGGTCTTA GTTAACAGCT TAAAGTATTT TGTAAAAAAA ATACTTCACA ATTTTTAAAT
14341 AACTTAAAAA TATTAATACC TCTTTTATTA GGTTTTTTTA ATAAGGAAAA TATATAATAC
14401 ATCTAATCAA GATTTTTTTT GGACAAATTG GCTTAATAAT TTCATTTTAA AAATGGCTTC
14461 TTTATTCTTA TACTGTAAAA ATAATATTAG CAGAATATTA TAGTATACAC AAGTTTAGGG
14521 TTCATATTCT AAAAAACAAA AACAAAAGCT AATTTAACTT GCATTTACTA AATTTCTTCC
14581 ACTAGTTGTA CTGGTTACAT GAGTTAACAT CACTTTATTT ATTATTCTAA AATTGTAAAT
14641 TATTCATTGA ACCAAATTAA ATGATAATAG ATAATGTCAT TTTTAAAAAT GGAATTAAAT
14701 TTTATGTTAC TAATTATAAG GATTCAATGT GTGAGCTTAA GTACTGAGTT CACAGTGTAT
14761 GATAACTTTA AGAATTTAGG TGAATATTAT TAAATTGAGT AAATTAATTC TCAATCTTTG
14821 GATACCTGGA CAATTTCTAA ATTGGAGGGT ACAAAATACA AATCACAAGA AACAGTGTAG
14881 TTTTATGCAA ATAACATTTT TACACAGTTT AGAATAACCA TTGATAAACA GATAAGAGAA
14941 CATATGATTG CCTTAGAATA GATACTGTTG CTTTCGCCAC TTTAGATTTG TAAATCACGT
15001 ACTGTATACG TGTGGGCGTA GAGGACCATG CAGGTTTTGG ATGACTGCCT CTGTTTTCGT
15061 CATGCCTATG CGGGAACACA ATTGCCTGCT TTGTTTAAGG GCTATGGTTA ATCCAAACAG
15121 CTCTGACTCT ATCAAGTACT ATAGCTACAG AGAAACACAA GTAAGCATTC GAGATAATGA
15181 CTACCTTGAG CCTTTACTTA TTTAAAAAGT TGTTACTGTT TGTTAATGTG GTACATTCAA
15241 TTTACTATGG ATTGTCACTC TAAAATAAGA CTTCAATCTT TTTCTTATTT TTATATAGCC
15301 ATGATTTATA TTCATATCTT AATGTAATAA CCAATCTTCT CTGACAACAT TATAACAATG
15361 CTGGAACCTC CATTTTCAGT ACTTCAAACA ACAAATACTG CTTTTATACT TCAGAGCAGA
15421 TGGATATGTG CTTCCCAGTG TAAACACATT TGGAATCTCA CTGAGAAATA CACTATCACT
15481 AAAAATACAG TTCTGAGATT CATTAAAAGA CCTCCAGAAT TCTGGAAGTA GGAAGTTTCC
15541 TCTTCAAAGT CTACAGAGGA AGATGAGGTC TGAAATAGAC AGCTTCTTCC TTCTTTTACC
15601 TGTGGTATTA TTCTGTTTTG TCCTTTTCTC CATTATCTGT CTTTCCAGTG ATGAAATTTT
15661 GATCTGGCCC TCCCAAGTAT TAAAAAACAA GCAAATAAAC AAATCTCAGT TATATTTTAC
15721 TAAGATATTG GCATGCTAAC TTTTTGCAGG TTTGTAACAA GGACCTTTAT AACTTGACTA
15781 AAAGTTCCTA AATAAGAATA TTTACTAGAA AATTTATTTC TGCCTGTGGC CCACATTTGA
15841 GTCAAAATAA TCAATTAGGA AAAATGAACT TGTTTAACTA AAGTTGACCA AACTGATCTT
15901 TGACCAAACT GATCTTTGAG ACCTATTCAT CTAAGACAAG CCAATTAAAT TCTTGGAGAC
15961 AATTTGTACT TTAAGGAATT CTTATAATAT TTGTAATTAC CCTCATAACT TTTTTTTTTG
16021 CCCTACTTCT GTGCTTCTCT AATATGCAGA TTATTAAATG TTGTTACAAA GCCATTGTCA
```

Figure 1 (Page 5 of 73)

```
16081 AAAAAACAAA AAACAAAAAA CTAAACAAAC TCACATGGTT AGACTTGCTC CTTTATGAGA
16141 TATTTTTACC AAAAATGGAG GAGTTGAAAA ACTCTGGTGC CAGAAATCGT GAAGACATGG
16201 CCTACCTAAC ATGGAAATGT TGGTTGTCAG TGGAAAATAC TACACAGAGA TAGCCATAGT
16261 GCTGCACAGC CAATCTTAAG TGTTTCTAGA GAATCACTAA TTGTTTCTAG AGAATCACTA
16321 ATTGTTTTCT TTTAACATTC TTGGTTTATA CAAGAAGAGA GTATCCTAC TAAACTCTTT
16381 TCTACTGAAA ATAATGTGCA AACATAACAT CCTATTCCTA GACAGTTTGT AGTTTTTTTC
16441 TCCCATTTCT ATTTTATAAA TCATCTTTTT AAAATACTTT GTTGAGTGAA ATCAGTCCAT
16501 TGCTTGATAT ACCTTGAGCA CAAGTAAATA GTATGCCAAA AATTAAATGT CTTTCAGTCA
16561 CAGTTTGACA AACTCAACTA CCCTGAGCCT ATAGAGTGGT AATAATTGCC CTACTCATAA
16621 AGATGGGGTG AAGATTAAAT GAAATAGCAC CTATAGAACA CTAGTTCCAG ACGTGGTATC
16681 ATGCTAGTAA AATGGCTGCA CAGCACTGCT CAATGATGAC AAAAGTGAA GCTTCTGGAG
16741 ACAGACTCCA AGTTTGACTC CCAGATCACC ACATATAAGA TGTGGGACTC TGAGGCAGGT
16801 CATTTAATCT CTCTGTGCAT TAGTATCCTT CTCTATACCT TTACAGTGAT GGTAATAGCA
16861 CCTACCTTCT AGAAGTATGT GAAGATTAAA GATCCTTAAT GCATATAAAC CACTGTGTTT
16921 ACTGCTGTTT GACAAATTTT ATTTATAACC ATCTTTACGC TCCTAAAAGG ACTTGAAGCA
16981 GCTTATGACT GAAGACTTTG GTAGGAGTTG GCCTTCTATA AATTATAAGA ATTTCATAAA
17041 TTATTTGATA TGAAAATGCC AGTTGATCAT AGTATGTTTA CCGGGGTCCA ACAGGTTGAG
17101 AAAAAATACA CTTTTTTTCC CTGAACATAT GAAATTAGCT CTCTAGGCAT ATTCCTAAGG
17161 ACTTAAAGAA TGATAACTAT CATTTCTCTT AAATCTTCCA GATTTGGAAG GATATATATA
17221 TTCAGCACAT TGACAGACAA TCCCAGTAGT CCTAAATTAA AAGACATTAA AAATTAGTGA
17281 AACTTTTCCT ACCTTTAGCC TGTGTAATCC TGGATGACCA AGCATAAAAT TAAATTGAGT
17341 AGAGTATACC ACTGTAACAT TTCCTGAAAG GTATTCTAGG CTCTGAGTAA TTTCTTTGGG
17401 GTCTGAAGAT CAGTTTGACA TATCCTCAAG TATCATGAGT TCATTATAAT TAAGAAAAAG
17461 AGAGTAAATC TGGAGAATGA GCCACTTTCT TACTACTCCT TGACCTCAGT TCTTTTTTTC
17521 AGAGACAGGG TCTCACTTTG TTGCCCAGGC TGCCAGGCTG GAGTGTAGTG GCGCAATCGC
17581 ATCTCATTGT AACCTCCACC TTCTGGGCTG AAGCCATCCT CCTGCCTCAG CATCCTGAGT
17641 ATCTGGAACC ACAGCAGGTG CACACCACCA TGCCAAGCTA ATTTTTTAAA AAGTTTTTTG
17701 TAGAGATGGG GTCTTACTAT GTTGCCCAGG CTGGTCTCAA ACTCCTGGGC TTAAGTGATC
17761 CTCCTGCCTC AGCCTCCCAA ATTGTTGGGA TTACTAGTGT GAGTCACTGT ACCCCGCCCC
17821 ACTTCAGTTC TGAGGAGGAA AAAATATGTA ATAATAATGG GACTTTGGTT TGCTGATTTA
17881 AAGATTCATG TAACCTTATC ATCCAATGCG CAATTTGTAG AATAATTAAT AGAGACATCT
17941 GGTCTCATGT TTCTACAGTT GCTCATGCCT TGATAGTAGA TCTCCTTGCT GCTGGCTCAG
18001 AAGGGTAAAA GAGCAGAAAT GATGGGCTT CTCTCATTCT ATGAGGAAAT AGACCTATGT
18061 AGAGGAGGCT ACCTGTGGTA AAACCTTATC CTCATCACTT AAAATTCTAG GCTTATTCTC
18121 TGACCATATC AAGTTTTCAA ATGGTAAAAG AATTGGATTC AAGAGAAATA TGAATAAACT
18181 TTTGTTTTCA CTTTTCTCCC TCCTCTCCCC CCATTCTCCC TTCCTTTATT TTCTTGTCCT
18241 TAGTTTTCTT TTCACTTTTT TGTCTACTAT TATTTGCCCA AACTCAACTG TAGGCTAGAA
18301 CAAAAAAAAA TTGAAAATTA AAATGTGCCC CTTTTGTTGT TAGACTTGCT TAAACAATTG
18361 GGGTAATGAA CCTTGGACAC TAGATTTTAA AACACACACA TTTGAGCTTC AGTGCACTGA
18421 AATAAATATA TTTTTAACAA TTAAAAAATA AAATTGCATG TTTAAAAAAT CTGCAGAGAA
18481 CAATACACGT TGTGAGATCT TGAATGGAAG GAAAACTGCT AGCCTCAAGA GTGGATCAAA
18541 GATGCTCAGC AGGCAACAGA GTAAGAGCAT GTTGGAGGGT TTAGAGAGTG TGCTCAGGGT
18601 TCTAGGCTCT AAAAATCAGA CAGTCCCCAC GGCCTGGCCT TCGTCGCTGT ATCTTCTTTA
18661 TGAAAACAC TAAGTCTTTT TCCTCACTGG ATAAATTTTT ATCCTTCAAG TTTAGATCAA
18721 ATGGAACTTT AGGACACTGA CTAGGTTACA TTCATCTTTT AAGAGCGTAC AGACATTCAA
18781 GGGCTAGAGG ATGTGGGTTT ACTGCACAGG CTCATTATCC AACAGCTGTG CTACCTGGGA
18841 AACTTAACCT CTCTGTGCCT TAATTTCCTC ATCTATAACG CAGGGAGAAT GACAGTAGGT
18901 ATCTCATAAG GTTGTTGGAA CAACTAAATG CATTGGTATC TATTGTGTAA AGTGCTTAAA
18961 ACACTGCCTG GCACAGAGCA AACATCCAGT GAACTTTAGC CATCATCATT ATCATTGTTC
19021 TCAGAGTCAA ATACAATATC TCATATCTGA TAAATTACAG AAGTGAATCA ATCACTCTCT
19081 CTCTTTTCTC CAGGGGGAGA CAACAGCTTT TAGACATATC TTTTCCAACA GTCGTCACTG
19141 CTGGACACTG TTTCATCTTG CAAATAAACC AATGAAAATG AGTGATCCTA AAGAAGATA
19201 AATGGAGGTA TTTTGAACAA TCAAAGAAGG ACAAATGAAC ACCTGGCTGA GAAAAATTAG
19261 CTCTTTTTTC TATGCATAAA ACTATTAAAA TATTCTTCAT AGAAATTTAT GACACAGGAA
```

```
19321 ACATAAAGAC AAAATTAAAA TAACTCCTAG TATCTCCTAT TCTTTTTATA TGTATATTAT
19381 ATATACTCAT ATTCATATAT ACATATATCT CACATCATGT ATCATATATA AAATAAATTT
19441 AGGTGTCATG ATATATATTT AGATAAATAT ACTTAGAAAC TTTTTTATGG ATGTATAATT
19501 TATGGATATA TTGATAATTA TGTATTTGTT ATTGACTACT TCAATTGATT CCCATTTTTA
19561 TGCATTATAT TATAGATTAT ATAGCTCACA CATCTTTGTA CATAAATCTT TGTTCAAATA
19621 TTATTTCCTA AGGATAGACT TCATGAAGTG GAAATACTAA ATCAAAGTG AAAAACATTT
19681 TCTAAGGTTC TTAACATATA CATTGCCAAA TTGCTATTCA GGATCATACC AATTTATAAT
19741 CCCAAAATAA TATGGAAATT CCTGTTTTAT AGCACTCATA TTTACAATAA ATTTTAAAAA
19801 TCACTGTTAA CCTAATAGTC CTTCAAAAGA AAAAAAAATT GAAATTACAT TATTTTAATG
19861 ACTCTATTAG TGAGGGTCAT TCTTCCCATG TTTCTTGTTA GCCATGACCC TATAAGAAAT
19921 AAACTGCACT GCAAAATGAT AAACATGACA TCAATCATTA CATGGGAAGG CACTATATAA
19981 AGAATAATAC CTTAGGTTAA GGCCACATAA ATATTTATCA GGTGCCTTTT CTGCGGAGGA
20041 CTCTGAAGGG ATACTAAACT GCATTTAGCT GCATGCAACT GAAACTACTT TTACCTACAT
20101 TGTCTCTTAT AAACATTATA ACTACTCTTT GAGAAAGTGT TTACTATGGA CTGAATTGTC
20161 TCCCCATCCC CCCAAATTCA TATATTGAAG CCATAAACCC AATATGACT CTATTCCTAG
20221 ACAGGACTTA TAAGAGGTAA TTAAGGTTAA ATGAGGTCAT TAGGATGGGT TCCTAACTGG
20281 ATAGGATTGG TGGCCTTATA AGAAGAGGAA GATTCTGCAC TTGGTCTTCC AAATTAAATA
20341 ATTTATTTAA AAGAAAAAAA AAAAAGAGGA AGAGAGGGAG CTCTGCACAT ATACTGAGGA
20401 AAGGCTATGT GAGCTCTCAC AGTGAGAAGG TAGCACTCTA CAAGCCAGCA AGAGAGCCCT
20461 CAACAGAATC CAGCCATGCT ATACCCTGCT CTGAGACTTC CAGCCTCCAG AACTGTGATA
20521 AAATTTTGTT GTTTAAACCA CACAATCTAT GGTATTTTT TATGGCAGCC CAAGCCAACA
20581 AAGACAGCAT CATTGCTGTC ACTTACAGAC AAGAAAACTA AGACTAGGAG AGAGAAAAGT
20641 TAAACTTGTC CAAGGTCACA AAAGCCAGAA ACAAGTGAGG TGAGAAGTTG ACCTTGTTCT
20701 CCTCAATCCA AGGCCAGGAC TCCTCCACTC CACATGTAGA TAGCCACCTC ACAGTCAACA
20761 GCCAAATGTC CACACCCCAG AGTCAGCATT AGACCAAGAT GTCTTACCAG GAGACAAATG
20821 CCTCATCTTG AATAAATATG ATCTAACAAC TTACCCATGT AAAACATTGA ATCTCATGAG
20881 AAACAAAAAT GCAAAGTATG TAGAAAACTA TGTTTACCAC TTAACTGACA GTGATAAAAA
20941 GCTTAATGAT ATCCTTATAG TCTTGGAGGG GTTTGTATAT GTGGTGAAAC AGGTGCTCAC
21001 GCACTGCTGA TAGACTGTAA ATTGGTCCTA GAGAGAAAAA TAAATAAACT GGAAGGAGAT
21061 ATGCTGTATG TTTACTTTTT TTATGGAAAC ATATGATATA CCTGGAAATT CGATTGACCA
21121 TGCATCTATT TCTTCAATGG GTATGCACAG TTGAGCTGTT CCCATGCACC AGGCACTGTA
21181 ATGGACAAC TGCACATGAC AGTCAAAAAT CTCAGTCTCA TGAAGTCGAC ATGCTCATGG
21241 AGAGGTGCTA CCCACTAAAC TAATATTTGT ATATCAATTA TGGATACATT GGGCCACATT
21301 TACAGAAATT CACTTACAGT GGGTTACCAG AAGGGATTTT TTTTCTTGAT TGGCAAGAAG
21361 GCTAGGCTGT TTTGTTGGGG GCTGGCAGGA GCTGTCTAGG CTGCCCAAGT ATGCAGGTCT
21421 CTTCTATCAT CCTGTGTTAA CCATCTTCCA TGTATCTTTC AACCTCATGG TCATCTGCAG
21481 CATGTCTAGG GGTCATATCT ATGTTCCATG CAGGAAAAAA GGGTAAAGGG AAAGGGAAGT
21541 AGGCATGTAC CATTTTAATG CACACCTTGG TTTTCAGAAA ATTTAAGAAG AAAGACTTTC
21601 TGCTTTTCTC TGACTATTCT GTATTCTGGA TTACAACGCA ACAGAAACGT CACCTTAAAT
21661 TCTAATGTTT TTCTCTCCTT GCTTCAAAA ACTGACTCAT TAACCTCCAC GTGGCTTGGA
21721 AAAATTATTT CAGTCATCCA GTAATGAGCT GTTCATAGAA ATGTTTGGA CATCAAGTCT
21781 GTGTTGTTAG CATTATACAT GTTAAGCATT GAATAAAAAA CAACATGATG TGGGTAAATT
21841 TCTTTACTTA CATATAAGTA CTTATATACT TATAGCTGAA AAGAGAGGTT GAAATGTCAG
21901 GTGGAACAGA AATAAGATTA CCTAGATGTT TCTCCTATGG GTGATTTTCA GCTATGCTGA
21961 TCTTTCTTCT GGGTCAGGTA CTCCCAGAAC TTCCTAATTA AATGGTGGCC CTGATCTTAG
22021 TTCCTCTCTC CTCTTAGACA TTTTCCAGGA CTACAGAAGA TGTGCAGTTT ATAAATGAGT
22081 AGCAGAAACC TACTGAACAA ATTATTCAGG CTCATCTGAA CAGAGAGGAC ACCTTCTCTG
22141 CTATACTCTC TCAGTGATTT CCCTGCCTTG GGGTCAATTA TTGTCTTGGA CATTGATTTA
22201 AGCACATAAT AATTGTGTC ATTGCTTATG TTTGGATTTC ATCTCCCAAA ATAGATGGTA
22261 AATTCTTTAG TTTAGAGACC AAGTAATACT TAAAAAAAAA TTTTGTGTGT GTGTGTGTGT
22321 TTTTTCTGTG TCTCTCAGCC CTGTAATAGC ATCGTACTTA CACTTGTTAG ATTTTTAGAG
22381 ACAACTTTTA CAAAACATGG AATTATCTAC ATACCCTTTC TACAAAACAG ACAAATTAAA
22441 TACTCAGTAG TTGAACCAAA AAAAGCAGTT CAAATAAAAT ACTTGAAAAT GAAGAAATCA
22501 TTTGAACAGA GTTAAAGTTA ATCGTAAAAT AATGTCTGTA AAAATTATTG CCAATCAAAT
```

Figure 1 (Page 7 of 73)

```
22561 ATAAAGTTCA AAAATAGTGC TTGAAAAAGG AAGAATCATA TGAAAAGGGA CTACTCATTT
22621 TAAAAATGTT AGATATCAGG AAAAGCCAAG AAGTGAGTAT GGTAAGAGTG CTGTCAAGTG
22681 AAACCCTGCT AATCTCACTG AACATGTAAA AATCTGTAGA TGCCTTTATT TTATTCACTC
22741 ACACACATAT GTAGAAAGAG AAATATATGG TAAACATTAA AAAAACCAAA TTAGAATGTA
22801 AAATTAATAC TTTAAAAAAT GGGCTGTATA CTTTTCTTAT CACCGGAGAT AAGAATTTAT
22861 TATTTTTAAA ATAAAGTTAT TTTCTCTGTG ACTGTTTCCA TGACTTTGCT ACTTAGAAGT
22921 TAGAGATGCC AAAGTTTATC TAAGAAAATG TTTATGGAAA TATTATTTCA ATAATGAATG
22981 TTTAGAAGAC TGAATTTCCT GACTGGGCGC AGTGGCTCAT GCCTGTAATC CCAGCACTTT
23041 GAGAGGCTGA AGAAGGAGGA TCGCTTGAGT CCGGGAGTTC AAGAGCATCC TGGGCAACAC
23101 AGCGAGACCC TGCAGCAAAG TAAAAAGAAA AAGAATTGA AAAAGGAAGA CTGAATTTCC
23161 TTTGGGCAAG TCATGTGACA TTCCTGTGCC TCAGTTTCTT CATCTATAAA GTTAATTCCT
23221 ACATTTTTGG GGAAGGGAGA GAAAAACTTA GGATAGTGAC TGGCACAGAA GAAGCACTAT
23281 ATACTATATA TATGTGGATA TCATTTGTTT TTATGGTACC ATTTTAGCTA TCTAATGCAA
23341 AATATGAATC TTTTTTTTCT GGGTCTTAAA TTATGGAATG TAAGAATTTT CTAAATTCTC
23401 TAATTCTGTG TTAGTTTTAA AGCAATGGAG TAACGTATCT GTCAACTTGT AAATATAAGG
23461 ATCAACCTGA TCCACAATTT GACCCCTAGC CACTAATATT TAATAGTACA ACACTCAGAA
23521 ATTATCAAAG GTCAGAGAAG CCAAACAAAT GTAAAAACAT ACAGGTGCTC AGAAAGATGC
23581 ACCTGTAATC TCTCTAAGGA GAAATATTTT CCAAACTGAG TGACACGGTG CTTTAGTGAG
23641 TTGTGGAATC AATCTCATGA TTTCCAACCT AGTGTTCTTT TAAAAATGAA CTAGTCCACA
23701 GTAGAATATA CTAAAGTGCT GGTGCTTAAG ATAGTATTGT TTTCTGGAAA AAAAAAAAAA
23761 ATTTTTTTTT TTTGAGACAG GGTCTCGCTC TTGCCCAGGC TGAAGTGCAG TGGCACAATC
23821 ATGCTCACTG CAGCCTTGAC CTCCTGGGCC CAAGTGATTC TCCCACCTCA GCCTTTTGAG
23881 TAACTGGGAC CACAGGTACG TGCCACCACA CCCGGGTAAT TTTTTAATTG TAGAGACAGG
23941 GTCTTGCTAT GTGCTTAGGC TGGCCTTGTG AACTCCTGGG CTCTAGTGAT CCACTAGCCT
24001 CAGCCTCCCA AATTTATGGG ATTATAGGCA TGAGCCACCC TACCTGGCCT GTTCCCTGAA
24061 TTTTTTTTTC TTTCAGGTGT TTGTGCATAT GTGTGTGTGT ATGGGTATAA CAGAGAGACA
24121 GAGAGAAAGA AACTTTTCTA TCTCACTTTG CAATCAGAAG TTTGAAGTCT TATCTTTTGG
24181 CTTTTGTTTC AGAAATATTT CAAATGTAGA CTCTCTCCTT TACCACACTG TCCCCTTAGG
24241 CAAGGTCTTT GCCATTCTTC TGAGACTATT GCAACAGACT CCCAACTTCT GACTGTGGGC
24301 CCTTCTCAAA AATGATTGTT TATGCAATAA ATCTAAACCC AAGACAACTA CAACAATACA
24361 ACAAATTCTC TGCTTAAAAA CTTCCAATGT CTGCCGGGCG CGGCGGCTCA CGCATGTATT
24421 CCCAGCACTT TGGAGGCAGA GGCGGGCAGA TCACTTGAGG TGGGGAGTTC GAGACTAGCC
24481 TGGCCAACAT GATGAAACCC CATCTCTACT AAAAATACAA AAAATTAGCC AGGCATGGTG
24541 GTGGGCGCCT ATAATCCCAG CTAATTGGGA GGCTGAGGCA GGAGAATTGC CTGAACCTGG
24601 GAGGTGGAGG TTGCACTGAG CCAAGATCAC ACCATTGCAC TCCAGCCTGG GCAACAAGAG
24661 CAAAACTCTG TCTCAAACCA AACCAAAACA AAACTTCTAA TATCTACCAA ATGTTTCACA
24721 CAAGTATTTG GGGATCTTCA CAAATGGCCC TTATGGAGTT TTCCTTTGCT GAGACCCTAT
24781 GCTCTGGCCA CACTAAACTC ATTCAGCATC CCAGAAAGGC CTCAGCCTTT GTGAGCAAGC
24841 TCTTATCTCC AGGCCTCTCA CAAAGACCTG TTCCAGTAGA AGCTCAGGGG AGCACACTGG
24901 ACATTATTCC AACAACCCTT TCCCCACAGC TATGCAGCCA AATCTGCCAG CTCAGTTAAT
24961 TAATTAAGCA ATTCAGAGAT GAGGGTCTGC CCAGGCTGGA GTGCAGTAGC TGCGACCTCA
25021 AGCTCCTGGG CTCTAAGTGA TCCTCTTCAG TCTACCCAGA AGCTGGGACT GCAGGCATGT
25081 GCCACCACAC CCAGCTAATT TTTTTTTTTT TCAGTAGGGA CCAGGCCAAC CTAGTCTTGA
25141 ACTCCTGGCC TCCAGCCTTC CGAAGTGCTG TAATTACAGG CATGAATCAC TGCGCCCAGC
25201 CAACCCGCCC AGTCTTGTTA GACATGGGGT CTGTAGTTTC TAGTAGGTTC TTGAGTCTAG
25261 GGTTCCTACC TCATGTTTTA TAGTTAATTT AGGGGAGGGA CTGTGTCTGT TTATCTGGGG
25321 ATGTAGGGGT GGGCAGGGGG ATAGAGGGGA CTTCAATTAA TGAAACCAGA AGCAAAACTC
25381 AGTTGAGGAC ACCGGTCATG AGAGTGGCCT GATTATGGCC AATCTTACAT AATGTGTGAG
25441 ATCTTGATAT TACCCCATCC TTGAGAGTCC TCTATAAAGC TACAGGGACT TGGGAGCACC
25501 TTTAATTACA GACAACCCAT GTTCCTGTGG ATTATGATTT ATTAGATTGC ACATGCCTAA
25561 ATAAAGACAT CCTCTGCAGT CTTTTGACAA TTCTATAAGC ATCTTCTGAC TCCGCAATTA
25621 GACAGCTAAG AGATCTGTGT TACTTCCCTC ACATATATAA ATAATTTTAA ATAAAAATCA
25681 TGGCGTGAAT AATTTCTTTC CTCTACCGAT TTGAAGCTAT CCATTTGGAA GACCACTCTG
25741 AAGAGATGAA ATAAGTCTTC TGCCAAAGAT TACTTATTAA TTTACAAGGA AAAGGGGAAG
```

Figure 1 (Page 8 of 73)

```
25801 TTTTGTTCCT CTCCGTGAAT TTGATTGAAA ATCGAGGGCT TTCTCGAATA GTTTTGGCAT
25861 CCAGGGTCAT TTTTCATTAA AAAGAGAAAA GTCATGTCAA ATATGAATTT CCGCAGATTA
25921 TTCAGCACTA GACCCTGGGA GATTCTGTAA AGAGGGGTTT TGTTATACTC AACTTTTCCG
25981 GGTAAAACAA ACACAAATAC TCCTCCTCCA AGGGGCGGGG GCGGTGCCTA GGTGATGCAC
26041 CAATCACAGC GCGCCCTACC CTATATAAGG CCCCGAGGCC GCCCGGGTGT TTCATGCTTT
26101 TCGCTGGTTA TTACATCTTG CGTTTCTCTG TTGTTATGTC TGAAACCGTG CCTGCAGCTT
26161 CTGCCAGTGC TGGTGTAGCC GCTATGGAGA AACTTCCAAC CAAGAAGCGA GGGAGGAAGC
26221 CGGCTGGCTT GATAAGTGCA AGTCGCAAAG TGCCGAACCT CTCTGTGTCC AAGTTGATCA
26281 CCGAGGCCCT TTCAGTGTCA CAGGAACGAG TAGGTATGTC TTTGGTTGCG CTCAAGAAGG
26341 CATTGGCCGC TGCTGGCTAC GACGTAGAGA AGAATAACAG CCGCATCAAA CTGTCCCTCA
26401 AGAGCTTAGT GAACAAGGGA ATCCTGGTGC AAACCAGGGG TACTGGTGCT TCCGGTTCCT
26461 TTAAGCTTAG TAAGAAGGTG ATTCCTAAAT CTACCAGAAG CAAGGCTAAA AAGTCAGTTT
26521 CTGCCAAGAC CAAGAAGCTG GTTTTATCCA GGGACTCCAA GTCACCAAAG ACTGCTAAAA
26581 CCAATAAGAG AGCCAAGAAG CCGAGAGCGA CAACTCCTAA AACTGTTAGG AGCGGGAGAA
26641 AGGCTAAAGG AGCCAAGGGT AAGCAACAGC AGAAGAGCCC AGTGAAGGCA AGGGCTTCGA
26701 AGTCAAAATT GACCCAACAT CATGAAGTTA ATGTTAGAAA GGCCACATCT AAGAAGTAAA
26761 GAGCTTTCCG GGAGGCCAAT TTGGAAAGAA CCCAAAGGCT CTTTTAAGAG CCACCCACAT
26821 TATTTTAAGA TGGCGTAACA CTGGAAACAA GTTTCTGTGA CAGTTATCTA TAGGTTTAAG
26881 TTGTGATGCA GCTGAGTTGA AAAGGCTTGA GATTGGAGAA TTAATTCAGG CCAGGCTTCA
26941 AGACCATCCT GGGCAACATA GCCAGACTAC CATCTATACC AGGGGTCCTC ATTTCCCCGG
27001 CCACCGACCG GTAACCGGTC CCTGTCCATG GCACGTTATG AATTGAGCCG CACAGCTGAG
27061 GGGTGAGCGA ACATTAACCA ACTGAGCTCC ACCGCCTGTC AGGTTAGCTG CAGCATTAGA
27121 TAGATTCTCA TAAGCTCAAA CTGTATTGTG AATGGCACAT GCAAGGGATC TAGGTTTCAG
27181 GCTCCTTGTG ACAATCTAAT GCCTGATGAT CTGAGGTTGG AGCAGTTTTA GTCCGGAAAT
27241 CATTGCTCCC AGCCCTGCA CCCCCTGGTC CGTGGTATAA TTGTCTTACA CAAAACGGTC
27301 TCTTGTGTCA AAAAGGTTGG AGACTACTGG TTTTACAAAA AAGTAAATTA GTCAAGCATG
27361 GTTGGCACGC TCCCTTAGTC CCTGCACCCA GGCGTTTAAG GATACAGTGA GCTATGATGG
27421 TGCTACCTCA CTCCAGCCTG GGTGACAGCG AGTCAGACGT TGTCTCAAAA CTTAAAAAAA
27481 AAAAAAGTTA AAACAGAAAA AGGGCTTCTT GTCAGAGACT GCCGTATATC TAGAGGTCCA
27541 GGAACTAAAA AGTCTGATGT CCAATCCTGA AAAGCTCGAT GGTGCACTAG AGGAGGCTTT
27601 TACATGTAAG AGCATCTAAG TTCTGGAAAT GCCAGTGTCA GGGAAGGGAA GTGGAGAGCA
27661 ATTTGGCATC CAAACATAAC TTGCTGATAC TTTTTTTTTT TTTAACACAA GTACTACATT
27721 CTAGTCTTTC TGTGGTGTCA TTGTAACTAT TGTTTCTTAA TATGCTATCC ACTGACTTCA
27781 AGGGATCAAT AAATAGGAAT CAAGGTGTCC CAGAATATGG ATTAGGGGAG TTTTTTTGTT
27841 GTTGTTGTTG TTGTTGTTTT TCATCTATTC ATTATCCTGT AGCTGAAATT TAGAATTTTC
27901 TTCCATTGTG TGTGACTGAT AGAAATAACA AATTTGTAGG TTATAGTTGT TGCAAGAATC
27961 TGGAAATCGT GCTTGCTTAT TTCCGAAGTA CTATTAGGTA TATCAACAAA AACACACATA
28021 TTACGGTCAA GTGGTTTGAT AATTATTTTA ATATTATTGG TCTAATACAA TTGTAACCCT
28081 ATGAATTACT TTAAGTATCT TATTTATGAA AAGAATCTGT AAGTTTCATC AGACTACCAG
28141 AGCATACCGA AGACTGAAAA ATTTTAAGAA TCCAAACCTT AATGGAAATG TTGGAGGCTG
28201 CCCAATTAGG TTCTGAATTC CACCTTCCTG AATCACAAAC TTGTTTTAAC TCTCAGTCTG
28261 AGGTAAACTA CGTTTCTCTT TAAACAGACA TAGTTTAATT TTCCTTTGAT TTTTGATTTA
28321 GTATTCTTAC TGATCATCAT AAATAACCAA TGCTAATGTT AGTCTACTTT GGACCATGGT
28381 ATTTCGAGAA ACTTTGAACA AAGTCCCTG CAAAACTATG CATTGCATTA TTTCACATAC
28441 ATTTATGTTT TCCAGACGGT TCAATAGTAC CTCACTTTTC TGAACTTATT TGTATAGTTT
28501 GGCATCTTTT TAAAAATTGT GTCCTATAAT GAAAGGTTGT AAACATTATG TTTTAAATTT
28561 GTATAGATAA AATCAACCAC AGACCTTTCC TTGCTTGGAT GTAATTGCCA TTGTTTCCCA
28621 ATGAGTTCGG AATTACTAGG ATTGTGCAAA AATATGCCTC ACTTGCCTGA CATAGCAGAG
28681 AGCCATTTTG CCTAAATGCT GTGCCCAGCA ATGGACTGTC ACCAGATTCT CATCACATAC
28741 AGTGAGGATG AACAACTAGC CTCTCCCAGC AGCTGGCCGG TCTCTCAATA ATATGGGACT
28801 CCCTCAAGAT GGCTTCCTGC ACCTTTGCTC CTCTAGCCTT GTATGTATAC AAGGCTAGCA
28861 TGCCTGGCAT ACATAAGGTT AAAAACAAAA TCAATAAGTT ATGGTTCTTC CTCCAGTTCT
28921 GGGGATTATT AGACCACTTT TTTGTTTTGT TTTGTTTTGG ATGGAGCCTC GCTCTGTCAC
28981 CCAGGCTAGA GTGCAGTGGC ACAATCTCGG TTCACTGCAA CCTCTGCCTC CTGGGTTCAA
```

```
29041 GCAGTTCTCT GGCTCAGCCT CCCACGTAGC TGGGATTACA GGTGCCCGCC ACCACGCCCG
29101 GCTAATTTTT GTATTTTTAG TAGACGGGGT TTCACCATCT TGGCCAGGCT GGTCTTGAAC
29161 GCCAGACCTC GTGATCCACC CACCTTGGCC TACCAAACTG CTGGGAATAC AGGCGTGAGC
29221 CACCGCGCCC GGACTTAGAC CACTTTGTTT TGGCCAATAG GACAACAGCC ATAGAACCCT
29281 CCGCAAATGA GAGCTTGTCC CTAAAGATGC TTTATTTACA TAGCTGTGTG CCGCATGAGC
29341 CAAAAGGTGA TAACCTTTGT TCAACACGCG CCTCCAGCCC TTCGGTTAAG TCCAAAGTAC
29401 CATTCTTAGA ATGCTCTAAA ATACATAATT TTTTTTTTTT TTTTTTTTTT TTTTTTTGAG
29461 GAGTCTCTCT CTGTCTCCCA GGCTGGAGGG GAGTGGCGCG ATCTCGGCTC ACTGCAATCT
29521 CTGCTTCCGG GCTAGCTGGG CCTACAGGTG CAGACCACCA CGCCCGGCTA AGTTTTGTAT
29581 TTTTTTTGGT AGAGGGGGTT TCACCATTTT GGCCAGGCTG GTCTCGGATT CTTGATCTCA
29641 AGTGATACAC TAGCTTTGGC CTCCCAAAGT GCTGGGATTA CAGTCGTGAG CCACTGCGCC
29701 CAGCAAAATG CTTTTTGTGG AGCCAATCAC TTTATTAGCG CTTACCTCTC TATGCCTACT
29761 TTATGCTTTG AAATTTTGTC ACAGTGTGGC CGGTCATGGC AAACACAATT CATTCTTATG
29821 CAGGATGTCA CGGTTATTTC TGTCATCCAA ACTCATTCTC GCAACGCATT TCAGCTCTTT
29881 AAACGACTTT GTGAGCGGCC CTGAAAAGGG CCTTTGGGTT TTTTGTTTT TGTTTTTTGA
29941 AGTTCTCAGG AGACCGCGTA TTCTTAGATT CAGCCGCCGA AGCCATACAG AGTGCGCCCC
30001 TGACGTTTTA GGGCATATAC TACATCCATG GCTGTGACAG TTTTGCGCTT GGCGTGCTCC
30061 GTATAGGTGA CGGCGTCTCG AATAACGTTC TCTAAGAAAA CCTTAAGCAC ACCTCGAGTC
30121 TCCTCATAGA TAAGACCGGA AATGCGCTTG ACGCCACCGC GCCGAGCCAA ACGGCGAATA
30181 GCCGGTTTTG TAATGCCCTG GATGTTATCC CGGAGCACCT TACGATGGCG CTTAGCACCA
30241 CCCTTCCCCA AGCCTTTTCC GCCTTTGCCG CGACCAGACA TGATTCCTAT CGCAGTGGAA
30301 GGTATGAACT GAAACAGTTC CTTAAATACA AACTTGGCGG ACCTGATTGA AAACAACATG
30361 AGTTGGCGCG GTTTTTTTTT TTTTTCAAAT TTGGTCACCA AGTGGGTGGA GCAAGAAAAA
30421 CTGTTTCATT ATGGTTCATT GTTTTGATTG GCCAGTGACA GCTTGCTCTT TGTGGGAGTG
30481 GAAGGGTGTT TGCAAGTTGA ATGCGCTGTA TTCCTGTCAG CTTAATGACG CTAAGCATAG
30541 CCCCATTCCA CATTTCTTTT TATTTCCACT TGCTAACTAA TAAATTACGG AATAGTTTAT
30601 TGGGGAACAT ACAAATAATG TTTAAAGGAG GTCAGATTTA TAGGTCAAGG GATTTACCCT
30661 CCCAATCATT TTAATATTTT TATTTAAACC AGGCATTTTG ATGGCCTTCT CTGTGCTGGA
30721 CAAGGTATAA GTTTGGCTAT GAAGTTTCAC TCCTAAAGAC CCTATGTTTT GGGAAGGCAA
30781 AAAGGTAGCC AAATAATTGC AAATTAAAAC CTCATAAGTG CAAACTTCTT CCTCGTCACT
30841 TTCCCTATCT CGATTCAAAT ATTTGTTGAA TGACTCATTT TTCTGCAAAA GTCTGAGAGA
30901 GACAGGGAAT ATAAACTTAA GTCTGGATAA TATGTTTTCC CGGGACGCTC TTCCTGGTCT
30961 GCTGTGCCTG TTTGCTGTGC CTGAAATTCC AAACACTCTT CCCTTCCCTC CGTTTTTAAT
31021 CCCCTTTCAA CTTGCTACAG CTTTAGAGAA AAGAACATTC GTTTGTACA GTTGGGGATT
31081 AATTGAAGTG TAGGGCTAAT ACTTGATTAA GGTCATTACA AAATCTACAG GGTCTTCCTC
31141 TGGGAGGTTT TTGTGATAAG ATTATTGGTG TTAAAATAAG GCTAATCCCC TTGAAAAATA
31201 AATAGAATAG CAGAATTGGG TCTGAATGTG GTTTGAAGAA AGGGACTTCT CAATTCAAAA
31261 TTTTATTCTT AGCTTCCTGC GGGAGCTTTC CAGAATGCCC ATAAGATCCA CTTTTGTTTA
31321 AAAAACAAAA ACAACCCCAC CCACCACTCT CTGGTTAATA AATGAATTTC TATTGGGAAT
31381 ATTTAGAATG GGGCTGTGGC CTGTGAGAGA CATTATATAG TAACCTCAGA CTTGCTCACA
31441 TGAAGAGAAG AAATCCAGGA ATGGAGAAAA AAGACCCAGG AAAGGCCAGA ATGCTCTACA
31501 TGTCATATTG TTTGTATCAC TTCTGAAATA ATTGATTACA TTCTTCTGCC CCAAATTGAG
31561 TTCTTAGGTT CTTCCACTCA CTGTCCACAT GCCACAACAC AGACCTTATA ACTAGAGACT
31621 TAGCTAGGAA GAAATGTCAA ACATTACAGA GAAAAAATGC AGAGTCTGAG ATCATAAGTA
31681 AAACTCTGAA ATCTCAACAT GCCTTTTAAT TCATGAAAAT AAAAAATATA GCAGCATATG
31741 CAATATGACA ATTCTCTGAA AACATACATC ATGTGAACTA CCCTGGAACA CATCTCGCCA
31801 AGTGCCATCT TCATTTTAAC CAGAGGTCTA GGATGCCTTT CCTTTATTTT GCCTATTATA
31861 TCATTTATAA AACCCCATTT TTATTTTGAT ATTTTATTTA CTTTCTATTT CCTGCTCCTA
31921 ATATCTCCTT TCTAAACTTT TCTCAATGAC AGTGACTCAA AAACAATGAA TGTCAGAACA
31981 AATATTTAAA GGATCTGTAC ATGTAGATAT ATATATTTAA AATGGATTCT TCCACTCTGC
32041 GAAGAATTCA GGCATACTCA ATCTTATGGT TAGGGAGAGA TTAGGCTCAC TCGCCTAATC
32101 TGTATGGCTT CTCGTTCGCT TTCCATTTCA CCTTCCTCTC ACCCATCAGA TCAAACTCAT
32161 TCATTGAACA AGAGACCTAA GCCCTTCAGA TTAAAACTCT GCAAACAAGT TGTGGTTGAG
32221 AGGATACATG AAGCATTCAA ACAAATAAAT CTATGATATT AATCAGAGGT TAATCTATGA
```

```
32281 TATTAATCAG AGGTTAATGC AGTGGCTCAC GGCTGTAATC CCAGCACTTC AGGAGGCTGA
32341 GTTGGGAGAA TCGCTTGAGC TCAGGAGTTC AAGACCATTT TGGGCAACAT AGCAAGTCTT
32401 CATCTCTACT TAAAAAAAAA TAACCAGAGG TGTTATGAAA ATATAAATTG TCCAGAACTA
32461 CCCTCCACAA ACTAACTCTC TCAGAATATT CGATATGAGG AATGAAATAT GGTGTGTGTG
32521 TGTGTGTGTG TGTGTGTATG TGTGTGTGTG TGTGTGTGTA TGCACCTATA TATGGCACCT
32581 ATATATTCAA CAAACAATTC TGATAATTGG CCAGGGTTGA GAATGACTAG CAGCCCAGCA
32641 TACACTATCA GTTTTAAGTA TATAATTGCG CTTTAGTAAA ATGTAAAGAA ATCCCAGAGT
32701 AGAAATACTT TTAAGCTATA TTACAGGTGA GAAAATGCAT AAGTATAGTC TCACCCAACT
32761 TAGACTATGG GGGCTTTATA ATGTCACAAC AGTTGTTTCC AGGCATTTGG GGACATCACC
32821 ACTGGTCTTG GGCAAGAAAC TCCTCTAGCC AATGGCTGAT TTATCTCACT CCCATCTAAG
32881 GCTTCACTGC ATTTCTCTTT TTCAGCAACC TAACTTATTT AAAAATATCC ATTTTCTGAT
32941 TCATTTTTTT CTGAATTAAA CTGTCAGTAC CATTGGCACA CCTTTGGTTC CGTAGCATAC
33001 CTGTGTCTCT GCTGTGTTTT TTTTTACCT CCACTCCTTA CTTTTCTAGA AAAAAATCTC
33061 TGCTTTTTCT TTTCAGTTTA AATTATTTCA CAAAAAGTTT TCTTGACTTG CACTTCCTAG
33121 GCTTGCTGTC CTTGTGTGGG CACGCTCCCA TAAACACTAT TAATACACTT CGATTTGTTA
33181 AAAATAAAGA TATCTGGACA GAAAATTTCT TTTCTTTTTT TAAGATTTTA AAATTTTTAA
33241 TGTTTATTTT TTTCCTAGAC TGGAGTACAG TGGCACCATG ATGGCTCATG GTAGCCTACA
33301 CTTCCCCGGG CTCAAGTGAT CCTCCCACCT CAGCCTCCCA AGTAGCTGGG ACTACAGGTG
33361 TGCACAACCA CACCTGACTA ATTTTGTTTA TTTGTTTGTT TTGTTTTTTG AGATGGAGTT
33421 TCGCTCTTGT TGCCCAGGCT GGAGTGCAAT GGCGGGATCT CGGCTCACCG CAACCTCTAC
33481 CTCCAGGTT CAAGCAATTC TCCTGCCTCA GCCTCCCGAG TAGCTGGGAT TACAGGCATG
33541 CATCACCACG CCCAGCTAAT TTTGTATTTT TAGTAGAGAC GGGGTTTCTC CATGTTGAGG
33601 CTGGTCTGA ACTCCTGACC TCAGGTGATC TGCCCGCCTC GGCCTCCCAA AGTGCTGGGA
33661 TTACAGGCGT GAGCCACCAC GCTCGGCCAC TAATTTTGTA TATTTTGTAG AGATGGGCTT
33721 TCCCTGTGTT GTCCAGGCTG GTCTTGAATT CCTGGGCTTA AGTGATCTGC CCACCTTGTC
33781 CTCCCAAAAT GCTAGGATTA CTGGCGTGAG CCACCAGGTC TGGCTGGAAA GATAATTTCT
33841 AACATTATCC TCTCTTAAAC ATTTGTTTCA AAAATTTTAC AAACATGAGA GTAATTAAAT
33901 TTGATTTTCA AAATTCCCTT GAATACTTTC TTAATAGCAC ACAGAAAGCA CAAAGTATTT
33961 TACATTTGTT TTAATGATGA AATTGTGAAC CCAAACTTAC ACAAAGAAAA ACCCGTAACA
34021 TTATACCCAT ACTTAAAACA GATGCCCTCA TATACATAGT AAAACTCTTG GGGGCAGTAG
34081 TGAAGTTGGT TATTTACTGT TTTATGAAAG TGCCATTCAG CCGGGTGCAG TGGCTCATGA
34141 CTGTAATCCC AGCACTTTGG GAGGTCGAGG CAGGCTGATC ACGAGGTCAG GAGTTCAAGA
34201 CCAGCCTGAC CAAAATGATG AAACCCTGTC TCTACTAAAA ATACAAACAT TAGCTGGGCG
34261 TGGTGGTGTG TGCCTGTAGT CCCAGCTACT CAGGAGGCTG GGGCAGGAGA ATCGCTTGAA
34321 CCTGGGAGGC GGAGATTGCA GTGAGCCGAG ATCGCACCAC CGCACTCCAG CCTGGGAGAC
34381 AGGGCGAGCT CCGTCTCGAA AAAAAAAAAC AAAAAAGTGC CGTCATAGTG ACTCAGTTTT
34441 AAGGAATAAA TCAAGGATAT TTAACTCAAT AGACTACAGT TAGCTAACGT GACTTGCACT
34501 GAAAGTTATA CGAATATTGG TACTTATTCC CCTGCCCCTG AAGTATGAAT TAAAGACTCC
34561 AAAATTCTTT TTAGAATCTT CAGAGTAAAA GCTAGAATTT GATTTTTTTA AATAATAAAA
34621 AAATACTTTG TATCTAAATC TGGTGTATAA AATAACTTGG TGGATGATGC TTCAAGGCTA
34681 TCCATCCCCA AATTTCTCCC TGAATGATAA AGAGAATAAA TGAATATGTC AATTCAAAAG
34741 TTAGAAATTT GGCCGGGCAC GGTGGCTCAC TCCTGATAAT CCTTTCGGAC GCTGAGGTGG
34801 GTGGATCGCA TGAGCTCCGG AGTTCAAGAC CAACCTGGGC AACATAGCCA GAACCCGTTT
34861 CAATAAATAA TAGAAAAAAA TGAGCCAGGC GTGGTGGTCC CAGCTACTCA GTAGGCTGAG
34921 GTGGGAGGAT CACTTGAGCT CAGGAGGTCG AGACTGCAGT GAGCCGTGAT CGCAGTACTG
34981 CACACCAGCC TTGGTGTCAG ACTGAGACCC TGTCTCAACA ACAACAAAAC AAGTTAGAAA
35041 TTTGGCTGGG CGCGGTAGCT CACGCCTGTA ATCCCAGCAC TTTGGGAGGC CAAAAAGGGC
35101 GGATCATTTG AGGTCAGGAG TTCGAGACCA GCCTGGCCAA CATGGTGAAA CTCCATCTCT
35161 ACTAAAAATA CAAAAAAAAT TAGCCGTGCA TGGTGGCATG CGCCTGTAGT CTCAGCCACT
35221 TGGGAGGCTG AGGCAGGAAA ATTGCTTGAA CCCAGGAGGC AGAGGTTGCA GTGAGCCGAG
35281 ATCATGCCAC TGCATTCCAG CCTGGGTGAT AGAGTGAGAC TCCATCTCGA GAAAAAAAAA
35341 AAAATTCTGT ATGAACTGAA CAAAATATCC TTAAATTTTA AAATACATCT GAAAGATATT
35401 TCAAAATATT TAGGAAAAAA ATTATAGGGA TCAGGCAAAT TCTGAGATTC CTTTTTCCCT
35461 GCAGCAAACA TTAGGAGTGC TGCTGTTCCT AAAAACATGG TAACTGTTGC CACACCGTAT
```

Figure 1 (Page 11 of 73)

```
35521 GTTTCCTTGG CTCAGACATA AGGTTGTGTA GTTGTTATTC CAGAATAGCT AGAATAAAAA
35581 TCCAGCACAT CATTTTCTTC AGCAAGTTAA CTAACCTCTC TGTGCCTTGG TTTCATAACA
35641 GCAACATAAG CATAACAGAA TAGCAGCAAT AGCTCCTACC TACCTCATAA GATTCTTTGG
35701 AGGAATTAAA TTAAGATTCA GAACACAGCC TAATATCTAG TAAGTAATAA TAATTGGCTA
35761 AAAAAATTTT CTTAAGATTA TATATATTCA TGGGGTACAA GTACAATTTT GCTACATTAA
35821 TATATTGCAT TGTGGTGAAA TCAGGGCCTT CAATCCATCC CGGAAAAAAA AAGTTTTTGA
35881 AAAGATTTCT GCCATGGAAA ACTTTTAATG TACAAATTCA TCCATCCAAG AAATAGAAAA
35941 TATATAAGTA TCAACTCCAA ATCCACCATA TCTATCTCTT CTACACCTTA AACAATTACT
36001 CAGAAATAGA ATGCTTGAGA TACCAGAATG CATGCATATC AAGTAATAAA TGCATGCAGG
36061 ATGTCAACGC ATCCTAGGCT TTCAAATAAA ATTGTCATAC AAAATACTTT AATATTGTAG
36121 TAACATTCTA CATGTTAGAG TGTAGAAGTT AATCGCTGAT GCAAAAAAGG AAAAGAACAC
36181 ATTATACCCA AAGCCTACAG AGAGAATCAC AATTACAAAT ATCAGCCTGC ATGTGAAAAT
36241 CTTTAATTTG AAAGTCAGAA ATATTTAAAT GATAGTCATT GTTAAATCAG ATTGTGGTTT
36301 GAAAAAAAGT TAGTTTAAAA CTGAGTTTAT GAAAAATTTG GGGATTTTAG AGACAGTGTT
36361 TTGTTTTTAA ATGTGTGTGA GTTTGTGAAG AATGTTTTAT AAAATACTGA CAGTATTATA
36421 AGATGACATT ATTATAATAC AACATAAGAA TTTTGGCCTG TACCTCTCAG CAGTCCTCAA
36481 TCACCTGCTG TACTTGACTC AATGATTATC AGAGTGGTTT GTTTTCCTTC TGTTGTGTTC
36541 CCAGTTCAGG CAGCTCAGCA ATGGCCTGTG ATTCCAGCAA TTCAAATAGC TGGTAAGTAG
36601 TTTCTTGTTT GTTTTCTCAA ATTTTCAGGG GCTTTTCTCT ACAAGTGATT TCCAGTGCAC
36661 GCCCCTCCAC CCATTCTTTA TTCCTTTACC TTCAGGAAAA CCCTCAGCGC TGCATCTCTG
36721 GTCACCGGAC CACCGTGGTA CATTTACCTA TGGCCACCAG GTGTCACCCT TCTCTTTACT
36781 ACCATGGTTT GTGAATGGTT TTGCCAGAGG TGAATAAGAA TTTAAAATGC AGGTCTTTGA
36841 TTTTTCAAAT GTAGTTGACC TTAAGAATTT ATGAATAAAG CCAGAAAAAT TAAGCTTAAA
36901 AAACACCGAA AGAAAATGAG GACTTAAAAT TTCTATTAAA AAAATTAACA GGCCACAGTT
36961 GCTGATGTTT AGTAAATGTG TTAGTGAAAT GTGTTACTGT GAAGACTGGG GTGTTTCTTG
37021 AAATCTCAGC CCAGGTGAAA TAAAACCAAT ATAAAACAAA TGCTTACCTA ATAAATTAAT
37081 TGTAACATAT TCCTTATGAG GTAGAAGAGT AAGTGAAGCC TTATAGCAGT CTGCTTTCAG
37141 TATAGTAAGA TATTAAGAGA GAAATAATTT GTCATATGCT TTCAGAATGG TTTGCTGGTA
37201 AAATAACCAA TGTCTTACAA CTTAGACGAC AATGTCCCTA GAGTGAAGAA ACACGATTAA
37261 TTCGGCTACC ACAGTTGAAT GAAAATATTC CGTAAGACAA AATGTAAAGA AATTAGAAGC
37321 AAAATAAATG TCTCCAAAAT GACAAAGCGA TTAAGTATAT ACACAAGATG AACAAGAACT
37381 TCAATAAAAT CATGCAGTAT ACAATACAAT ATACATTTAT TAAAGTATAT GCATTTTTAA
37441 TGCAACAATA ATACTAACAG GTAATAGACA AGTTGTTAAT AGTTTTTCAC TGGCTAATTA
37501 AATAACAGCT TTAATTGTAT TCATTTTATA GCTTTTCTAC AATGAGCGTA ATCACATTTT
37561 ACTTTTTTCT ACATAACTTT TCTAACCACA AAAAAAGAAA ATGGTTTAAA AGAAGAGATG
37621 AGATATCTTT GCTAAAATTT AATGCCTAAA GAAGAAACTT CTGAGCTGTA TATGGTATCC
37681 TGAAGCACCT GCCCTTCAAG ACAGAATGCT TGTACCACAT TTATGCAGCC AAGTGCATGT
37741 AGTAACATAA AGTAAACACA TGCCATCTGG ATATATATAT TAAGACTCTT TTGACGGCTG
37801 GGCAGGGTGG CTCACACCTG TAATCTCAGC ACTTTGGGAG GCCGAGGCAG GCGGATCACG
37861 AGGTCAGGAG AGTTCGAGAC CAGCCTGGCC AACATGGTGA AACCCTGTCT CTACTAAAAA
37921 TACAAAAATT AGCCGGGCAT GGTGGTGCAC GCCTGTAATC CCAGCTACTT GGGAGGCTGA
37981 GACAGGAGAA TCGCTTGAAC CTGGGAGGCA GAGGTTACAG TGAGCCGAGA TCATGCCATT
38041 GCACTCCAGC CTGGGCAATA GAGTCTCAAA AAAAAAAAAA AGACTCTTTT GAACATGGTG
38101 AACTGATTTC CCAGAATCTA GCAATTCCTG AATGTCCTGG TTAGATTTTT TTTTAATGT
38161 GCACCGGAAC CCCAGTGGCT CCATGGAAGG ACCTGGGCAT CCTCTAAGCC ACTTGGTGGC
38221 TTCCATTATA CCATCTCAAA ATGAGAGAGC TTACTCCACT TCATTGAGGG AAATACCACC
38281 AGAGTTCTGA CTCCAGAGGC ACTGGCCTAG GGAGGACACC GTGTGTGAAG CCCAGCAGGG
38341 CCACTAGCTG TCCCCACCAA TTACAGTCCT TGCGTAGGGT CCAAAGAAAT GAATGCCAAA
38401 GAGAGCAACA GAGGAGCAAG GGAGTCACAT TCCAGGACCT TCCTTCAGGG ACTTTTAAAG
38461 GAAACATGAC AGCTGAGGAT CAGTTGGTTG TTTTCTGCTG TTCCCCTTCA TGTGATTCAA
38521 GCTCACTCAG AAGAAACACA ATGAGACAAG AGAAGAGCCA TCTCCTTCCT TCTCTATTTA
38581 TTCTAGGCAT CTAAACTACT GAATGTAGTG GTGTCTGAGA TGTATCAAAC GGTCAGATTG
38641 ACTGAGTTTG AAACCTGTTT CTATCACTGA CAAACTATGA GATACTCTAT ACTTCACTTT
38701 CTTTTTTTTT TCATTTTTTT ATTTTTATTT TTATTTTTTT GAGATGGAGT CTCACTCTGT
```

Figure 1 (Page 12 of 73)

```
38761 CACCTAGGCT GGAGTGCAGT GGCGCAAACT CGGCTCACTG CAAGCTCTGC CTCCTGGGTT
38821 CATGCCATTC TCCTGCCTCA GCCTTCCGAG TAGCTGGGAC TACAGGCGTC TGCCACCACG
38881 CCCAGCTAAT TTTTTGTATT TTTATTAGAG ATGGGGTTTC ACCATGTTAG CCAGGATGGT
38941 CTCGATCTCC TGACCTCGTG ATCCACCCGC TTTGGCCTCC CAAAGTGCTG GGATTACAGG
39001 CGTGAGCCAC CGTGCCCGGC CTACTTCACT TTCTTCATTT AAAAAAGAAA TGGGGATAAT
39061 AGTACCTATC TCATAGAATT ATTGTAAGAA GTGCATGCAG TAATGCATGT AAGTAGGTGC
39121 TCAGAAGAGT CGGACACGAA GTAAGTGCTT TTATCATCCT TATCATAATT TTCATTATCA
39181 GAACAAGGAG AGACCAGGTA GAAAATTATT GTGATTCTTC AGGTCTGGAA TACTAGAGTA
39241 GCATCCCAAA TGAAGGCACC ATTAAACTTT GCAAATCTGT ATGACACCTT CATGCCAATT
39301 AGAAAAAACA CCTCTTCACA ACCCCTTTCA AGATATTTGC CTCCTACCTG CTAAAAACAC
39361 CCATCATACT ACCCACAGAT AGCCATGATG CTTTTTCTGG GACAGGTGCC TCTTCCATTC
39421 GTGCAGTGTA CAGCCTTCAT AGCTGTGCAA CTCACATCAC AATCAGATGG AAGAATCCCC
39481 AAGGCTTGGT GACAGATGAG TTACTGGGTA ACACAGAGAG AGGATTCAAA GGAAAAGTTG
39541 AACGGGTCCA GAAAATGCAT AGATACATGT GTAAAAATCT GGTAAGGTTA TGACTAGCCA
39601 CGTCCCAGGG TTCAAAGCTT TTCTCAGATG TTAAAATGAA TCATGTAAGT CCCCCAAATT
39661 TAAGGAGTCC TCTTCCAAAA ATAGGAAATG AAATGACATA GGTGTATGTC TCTGAGGTGA
39721 CGGAGGAAAT GAAGGAAGCC TCTAGATGCA GCTTGAGGTT CATGAGAGAC AGTTCCAGGG
39781 GAGAGGTCAC AGCTAGGGAT CACCGGCATG CAGGAACTCA GAAACCTAAA TGGGGAAATC
39841 TTTTTGAGGA AATGAACAGA GAAGGCTAAA ATCAAGGAGT TCGTCAGGCA ATTTCTATGT
39901 TTAGGTTCAA CTCTCTCCTG AAACATGAAG AGCTCATAAA TGCACTCCCT CTTTGAGTCT
39961 CTAGTTTTGT CTCCTTCCCA CAGTGAGTCT GCAGGCTGCG TGTCACTCAC GTTCAGCTAA
40021 GACGTAGTGC CCCATGGCTC CTCCTGTGGA GACAAGAGAC CCAGGAAAGA GGCATCACAA
40081 ACCTAGGCAC CATCTTGCCT CTTCTCTCTT CCTTATTTTC CTCATTCACC CATCTCAATT
40141 TAGACCTGGG CACTATTGGA TTTCAAGAAC CATTATCTCT CATCTGGAAA TGCTTATTGG
40201 CTTTCTAACT GGTCTCCTCA CCTCTCATCT AACTTCTTAA CAACACATTC ACCATATAAG
40261 GGAGATCGTG GTCCTCCTTT CTTAGGATCC TTCAATGACA CCCCAGTGAT CATAACCCAA
40321 TATCCCAAAA GACCCTTGGA CTCTGTATGA GCTGGCTTCT TTCTGATTCT CTTTTCCCTA
40381 CACCACAGAT GTTCAGGGGG TAGAAATGCA TAATTGGTGA GTGATAGCTA CGCAAACTCA
40441 GGGTTAAGGT ACAGTAATTA TTTCTAATCT CCCAGTATGC CTTATACTCT CCTACTTGGC
40501 ATGGTTGCTC CGTCTGTGTA GACCTCCCAT CATCTTCAAC CTCACCTAAT GGAATCCAGC
40561 TTCTCCTTCA AGATCCAGAA GGCTATCTTG ATCCCCAGCT GAATGTGATC ATTCTTTCCT
40621 TTGACACCCT AAGCATTTGC TTCCTGCCTG CTTTAGGACC TCATGGGGTC TTCTTTAACT
40681 ACATTTACTT GCTATCAATT TCATTCCCTA CCAGATTTGG GTTCTGAGAA TAGCCACAGT
40741 GACTTCTCAA CCTCAAAGCC CCTGTACTAC CTTAAACAGC TCTTGCAAAA TAGTAGGTGC
40801 TCTGAAGATG TTTGTTGAAT TAGAGACTTT CATTCTGGGG AGAACCATTA TTTTCTGTCT
40861 CCCAGGGAGC TGCTGGTGTC CCCAAAGAAT ATAAATGAGA AAAATGCTTC CCATGGATGC
40921 CAGATCCCCT CTGCCCCTCT TCCCACTGTG CCCTGGGGCA GAGGTACTAA GAGACTTCCC
40981 CCTTGTTCCT ACTCACTTGA ACCCTGCCTC TTCCTTAATA TTATGAACAA AATTCCAATG
41041 AACAAGATGA CGACAAAAAC AGCAATTCCA CTGATGACTC CAATGACTAG GGTGCCAGAC
41101 GGTGAGGGCT CTAAAACAGA AAAAGCAAGT TAAAGCCTTT GATTGCCACC CTCAGCCCAC
41161 CCCCTAACAA AGAGCAGATC CTCATCTCAC TGCCATAATT ACCTCCTCAG GCACTCCTCT
41221 CAACCCCCAA TAGATTTTCT CAGCTCCTGG CTCTCATCAG TCACATACCC CAGATCACAA
41281 TGAGGGGCTG ATCCAGGCCT GGGTGCTCCA CCTGGCACGT ATATCTCTGC TCTTCCCCAG
41341 GGGGTACAGC CAAGGTTATC CAGCCCTGGT AGGTCCCATC CCCATTGGGC AATACGTCTT
41401 TAGGTTCGAA CTCCTTGGCA TCCATTGGCT GCTTATCCTT CAGCCACTTC ATGGTGATGT
41461 TCTGGGGGTA GTAGTTCAAG GCCCGACACC GTAGAGTGGT CACTGAAGAG GTCACATGAT
41521 GTGTCACCTT CACCAAAGGA GGCACTTGAC AGGAAAGAGG AAGGATGAGG AGAGGGGATC
41581 TGTTTACCCT TGCCAGGAAG ACTGGAACTT TCACTTCCTT CTATAGGTTG GAGGAAGGAA
41641 ATACCCTTTT CAGAAAAAAA CAAGCTACAG GAGAGACACC ATTTTGTGTC CTAAGATTGG
41701 ACTCTAACAC AGTGTCACTT GGAGAGCAGT CAGATCAGCT TGTTCTCCTC ACATGTAAAT
41761 ATACATATCT GTTACCCATG TTCTTTGTTC TGATAGATAA AATTGCCCTT TATGTGCATT
41821 GAAAATGATT GAATACAGAT GGTCAGTTTC ACCTGGGTCA ACCTAGGAGG CATTGTTATA
41881 AGAAGCGGAC TTGTAAGATA GGTAGCTTCA GTGATTATTG CTATGTTCTA TGAAAGAAAC
41941 TTTTAACCTA AAGGATTCTT CTACTCTGAT AAGTGGCCTC ACTTGATATT TGTCCTGGT
```

Figure 1 (Page 13 of 73)

```
42001 ATTCATATGA TAGCTGAGAT CTCTGAATTC TCTTTTTTTT TTTTTTTTTT TTTTTAAGAT
42061 GGAGTCTCAC TCTGCTGCCT AGGCTGGAGT GCAGTGGCGC GATCTTGGCT CAGTGCAACT
42121 TCCGCTTCCC AGGTTCAAGC GATGCTCCTG CCTCAGCCTT CCAATTAGCT GGGACTACAG
42181 GTGCGCATGA CTGTGACCAG CTAATTTTTG TATTTTTTTA GAGACGGGTT TCACCATGTT
42241 GGTCAGGCTG GTCTCAAACT CCTGACCTTG TGACCACCCG CCTCGGCCTC CCAAAGTGCT
42301 GGGATTACAG GGGTGAGCCA CCGTGCCCGG CCTTGACATT TCTGAATTTT TAACAGGTAT
42361 AAATATACAA AAGATTATTG GTTAAATAAA AAGCAAGGGC CATAGACACT TCCCTTTGAG
42421 CCATATGCAT GGAGAAAAGA AATTAAACCC ATGACTTGTG GCTGTCTCAT ACATCTCAAT
42481 TATAAGGTAG AGACTCTAGG ATTGAGAAAG TCCCTTCCCA GAATTTGGAG AGGCACACAG
42541 CCTCAGCCAC CTCTGAAACT CCAACCAGGG ATTCCGTGCC CTGCAACCTC CTCCACTCTG
42601 CCACTAGAGT ATAGGGGCAG AAGTGTGTTT CCACCATACC TTGTTGGTCC AAAACACCTC
42661 TCCCCAGCTC CAGCAACTGC TGCAGCTGTG CAGGGCAGTC CCTCTCCAGG TAGGCCCTGT
42721 TCTGCCTGGC CCGAATCTTG TGCCTTTCCC ACTCCAGCTT GGTGGGCCAG GCCCTGGGTT
42781 CTGCTGCTCT CCAATCCAGT GTGTCAGGGC AGAATTCAAG GTGGTCCTGC CCATCATACC
42841 CGTACTTCCA GTAGCCCTCG GTACTGTTGT CTTCTTGCAT TTCACAGCCC AGGATGACCT
42901 GCAGGGTGTG GGACTCTGGA AAAATCCCCA GCCTTGTTAA CTGCAACCAA AGGAATAGGT
42961 CCCTATTTCC ACCATCCCCA AGGACCAAAT GATCTCAGGA AGCAAATTCC TTCCCTCTTC
43021 CCTGCTCCCA CAAGACCTCA GACTTCCAGC TGTTTCCTTC AAGATGCATG AAAAGATGAA
43081 AAGCTCTGAC AACCTCAGGA AGGTGAGGCC CCCTCTCCAC ATACCCTTGC TGTGGTTGTG
43141 ATTTTCCATA ATAGTCCAGA AGTCAACAGT GAACATGTGA TCCCACCCTT TCAGACTCTG
43201 ACTCAGCTGC AGCCACATCT GGCTTGAAAT TCTACTGGAA ACCCATGGAG TTCGGGCTC
43261 CACACGGCGA CTCTCATGAT CATAGAACAC GAACAGCTGG TCATCCACGT AGCCCAAAGC
43321 TTCAAACAAG GAAAGACCAA GGTCCTGCTC TGAGGCACCC ATGAAGAGGT AGTGCAGAGA
43381 GTGTGAACCT GGAGACAGAG CAACAGGCCT TAACCATGTG TAGTAGGAGG GGAGCAGGAT
43441 GTTGAGGCTC CACACACCTG CATCAACTCA TACCATCAGC TGTGTCTGGT CCTCATTTTG
43501 TGAAGGGTGA GTTGCAGTCC TGTCTTTCTT CCATATGACA GTCCTGGGTG CTCTTTCCTT
43561 GTGTGCTTTT CTCTGCCACA CGTGGCTGCC ACCCCTCAC TGCCCCAGA TCCTATTCCA
43621 ATACTCATGA TTAGACAGAC TCCACTAAAG CTGGTGGATT CTAGAAAATG TTAAGGTGTG
43681 TCTAGCCATG GTAGTTGAAC TCAGGAGTTG GTGCTCAGGG CAAATTAGAC CCAAATCCTG
43741 AGGAATAATT CCTTCAGTTT TTTTTTTTTT TTTTTTTTTT TTTTTGAGA CAGAGTCTCA
43801 CTCTATCACC CAGGCTGGAG TGCAGTGGCA CAATCTCAGC TCACTGCAAC CTGCACCTCC
43861 TGGGTTCAAG GGATTCTCCT ACCTAAGCCT CCTGAAAACC TGGGACTATA GGCGTGCGCC
43921 ACCACACCAG GCTAATTTTT GTATTTTTAG TAGACATGGG GTTTCACCAT GTTGGCCAAG
43981 CTTGTCTCAA ACTCCTGACC TCAAATGATC TACCTGCCTC AGCCACCAAA GTGCTGGGAT
44041 TACAGAAGTG AGCCACCGTG CCCAGCCTTG GTCCTGAATT CTTACACTGA ACTGCCTATG
44101 TGGCCTCACC ACTTGGAAGC CTGACTGGAA TCTCAAACTT AACATGTCCA AATGCAGATC
44161 CTTGATTTAC CCCAAACTGC TCTTTCCTCT GCCTTCACCA TCTCAGAAAT GGCATTGCCA
44221 ATTACCCCAC TGCTCAGGCC AATAAAATTA AAATAAAGAA CAAAGTCAAC TTTAACTCTT
44281 CTCTTTTTCA GGGGGTCAGG GGAGACAGGG TCTTGCTCTG TCACCTAGGC TGAAGTACAG
44341 TGGCACAGTC ATGGCTCACT GCAGCCTCAA CTTCCTGGGC TCAAGCAATA CCCTCCACCT
44401 CAGCCTCCCG AGTAGCTAGG ATCACAGGTG CATGCCACCA CACCCAGCTA ATTTTTGTAT
44461 TTTTTGTAGA GAAGGGGTTT TGCTGTGTTG CCCAGGCTGG TCTTGAACTC CTGAGCTCAG
44521 GAATCTGCTC TCCTTGGCCT CCTCCTTGGC ATGAGCTACT ACACCCAGCC AATTCTTCTC
44581 TTTCTCTCAC ACAACATAGA ATCCTTCAGC AACTTCCTTC AGAATATATT CAGGAGACAA
44641 TGGTTTGTCA CTCCCTTTTC TGTTCCCACC CAGCCCACTC CACTACCTCT TGCCTGGACT
44701 GTGTAACAGC TTCCTGGCTG GGCTCCCTGC TTTTACTGTT GCTCCCTTCA TTCTGCTTTC
44761 CACATAGCAG CCAGAGCAAT CTTTTAAAAG CCTGTGACAG ATCACTGTTA CTCCTTGGCT
44821 AGAATTCACA CCACAGCCTA CAGGCGCCTG CACAACCTTG TTTGTGGETC CTCTTCTGAG
44881 CCCATTACCT ACTTCTTGGC CTCTACTCCC CAGCACTACT TGTTTATTTT TTTCAACCCG
44941 AGCTTCTTAA CCAGGAGTTT GTCTACTAGG TGACATGTGG CAAAGTTTAG AGACATTTTT
45001 GGTTGTCAAG ACTGGGGGAG TGCTCCTAGC ACCTAGTGAG TAGGGAGGAC AGGATACTGC
45061 TAGACATCCT ACATGCAGAT GGTAGTCCCC CTTCCCACCC CACGCCGCC CCCCCCCCC
45121 ACACACACAC ACATGAGTAG TGCTGAGAAA ACCCGCTTTT TAATCCAACT TGCCAGGCCC
45181 ACTCAGTTTG CCTGGGAAAT ACTGCTCCCA GTCAATATCA TTCTTATTTC CTTCATGTCT
```

Figure 1 (Page 14 of 73)

```
45241 CTGCTCAAGT GTCAGCCCCA GAGTGACTTG CCCTGACTTC TCTGCTTCTC ACAACACCCA
45301 TGATTTCCTG ATGTTGTATA TCTTTCTGCT CATTTGCTTA TTGTCATCTC TCCCACTAGA
45361 ATGCAAAATA TCAAAGGGTA AAGACTTGTT TCCCTGCTCT CTCCCTTGGG GCTTGAACAG
45421 TGCAACACAT GGCTGGGACT CATTTACACT TGTAAACAAT GAATATTTCT GCTCAACATG
45481 AAATTTTATT ATTCAACCTC TAATGCAGTG TGATGTTTAA GAATCATAGC TATGAAGTGG
45541 AGACATGAGC TCTGCCACCA AAGCCCAGTG TACCATTGAA TAAATTTGCC AGGAAGCAGG
45601 CCGTGCCATG CCTCATTCTT GTCATGTGTA AAATGTGGAT ACACGTAGTA CCAAAACTCA
45661 AAGTGCTGTG CTGAGGCCGG CGTGTGACCC ACAGAACACT GTGCTACACT ACAGGGCAAA
45721 ATCACTGTCA ACTAAGATTA GAAGCAGCTG TAGTACTTGA AATAACATCA GAAAACCAGA
45781 TTATTTATGT TCTTTGTAAC CTGAAAAGAG TTATATAATC TGAATTCCAG TTAACTTCTA
45841 GTAAAATAAA CGTATTATTA GCTCCTACCT CCCTATGCCT AGTGAAAATC AAATAAGATC
45901 AGATATGAAT GTAACTTAGA AGTGAGTGCA TTGCTTACAT GTTCATTATC AGTACTTTGT
45961 AGAGAGGCCT CTTAATTACA CAGCACATTG CAAATCAATA AAGCCTAGCC GAAAAGAGAA
46021 TTGTTCAGTT CAAACGTTCA AAACTAACAT ATACTTAATT TTCCAGGCAA AAGAACAATT
46081 GCCAAGAGTG GGGAAAGGCC CGAGGTAGGC CTCTCTCAGG AGCCTCCAC CCTAGAGACC
46141 TCCACCCCAG GTCTCACCAA AAGTGGGTGG AATGGTGAAG AATTCAGATC CCCAACGCCA
46201 CTCTTTCGCG CCCCCACCGC CCAACGCATT CGTTCTGAGG TGGAAACCCC GTGCGGATCC
46261 TGCTGTGGGT TTGCTCAGCC TTCTCGGCAA GCACTCAGGG AAGAACTTCC TGTTTGGAGA
46321 TGACTGGGGA AAAAACTGCA CAGCTGACAT TGGAAATAAA CCCGAGTTCC AGGTTCAAGG
46381 AGCCCCAGGC TTAGCTCAGC TCAAGTGAGG AACTACGAGA TTTATTTAAA AGCATTCTAG
46441 TTGGGGGAAG GGAGTGGGCG GTTCCAAAAG TCACTCCGCA GAGCCGGGAC AGCCGGGGGA
46501 GGGGGCAGGT CCTGGGGCGA GGGACCCCTA TCTGCAGTTC AGTGGTAGGC ACTCCCTCAC
46561 GGGGTCTGGA CGCAGAAAGT AGGGAGAGGG GCTTGCGGAT AGGGTTGAGC AGGTCCTCCA
46621 AAGTTAGCAA ACTCCCAAGC GCAAAGAAAA AGCTAGTTTC GATTTTTCCA CCCCCGCCGC
46681 GCCCCTAGTT CGCCCGCAGC CCTCGGACTC ACGCAGCAAG CGCCCCTGCA GGACCGCGGT
46741 CTGCAAAAGC ATCAGGAGGA GAAGCGCCGG CCTGGCTCGC GGGCCCATTT CCCCAGCTCT
46801 GGCCGCACGT CCCCGTTAAA TCTCCGCTTC TTTTGGGGGG CGGGGAAACG GGGATGGCTC
46861 CAGAAGTCAC CCTACAGCTA TTGCCTAGGC TCAGGAGATG CCCAGTAAAA CTTCCTGGTG
46921 AAAAGCAACA GGTCTTTCAG AACTTTAGTT CTCTCTCTCC TACAGCAGAA GGTACCTGCT
46981 TGTGAAACAC TAGGTGATCC AGTGTCCCCC TTGGTTTTTA AATCCTGAAG GGGTGTTGTT
47041 GATTGGGGAA AGTAGCTTCG CAATGTTCTG ATCTGAACTT TAGATATTTA AATATTTATG
47101 ATTTTCAAAA TTCAATCATA CATTTAAAAA TTTTATCTCA ACCTTAGACC AACTTATGTC
47161 TTATTTGACT TAGAAATATA AAGCTTTTTC ATTTTGTTTT TTGATTCAAA TTAATTAAGT
47221 CATAACATTA ACCAATTAGA TCCTACTGAA ACACCTTCCA CAGCCTTCAT AATTGAATTA
47281 TCTGACAAGT GTTTCACAAA CTTTACAGTA TTGGGATTAT CTGGAGAATG ATTAAACATA
47341 TTGAGGCCTG CTCCTAACCC CAGACACACT GATTTAATGG GTAATTGTTA GGTAGTTAGA
47401 CATTAGCAGT TGGGAGGGGA TGACAGAAGA GAGCGGAAAG GCTGTCACTA AGACAGCCAC
47461 TGGCCCACCT AAATTCAGGC CCAAGACTAC CCTAATGCCA CCCTAAGGGA TGGAGTTTAT
47521 GATAAAGTCT GTGGCCAAAA TATCCTGGAG AAAGAGAAAG GAGGGTACAG GTGGAAATTC
47581 CCTAAGGTGG CACATGCCCA ACAACACAAA AGCCTGTCTT CAAGTTCACC CCAAGTTCAT
47641 CATGCCATCA TTATAATAGA ATTTACATAC AGTTTTGCCC CCCCATCCCT GGGAGGCTTT
47701 TCTTAACAAA TTATAGGTAA GACCATGCAC AGTTTAATTT TAGATTGTAT AGCTATACAC
47761 TTCAATCAAA TAACATCATC CTGTCACTCA GATACAGCCC AAACCTCAAC TCCTCCCCAC
47821 AAACCCCATA AAAGCACCTT GAGCTCTGTA AAGAAGTGCT GAGTTCACTT CGCAGAAATA
47881 AGCCCGCTGT CCCTCAGAGT GTATTATTGT GCTTCAATAA ACTTTGCTTT AAGCTTGCAT
47941 TTTGGTGTTA GTTTGTAGTT CTTTGCTCAC TATCACAAGA ACTGAGATTG CTGGTTCAGA
48001 GCTCCGGCTA TAATAATCTC CTCGGTTAAA GGATCCATCC CAATGCATAA TTCCCAGTAA
48061 CAGTATGGGA TGCCACCTGG GCAATGGGAT TTTAAAAGCT TTCCTTCTCC CTCAACGAAG
48121 TTTGGGAATT ATTGCCTTAG ACATTTCAAA CAATATTAAT AAATTTAATA CACCTGATTT
48181 GCTCCAAACC TTTACATATC TAGCAAATTC AACAGGCATT ATTTTTGTAA GCATGTATGC
48241 AAATTTTGGC AATTCAAGAA AATCAAACAG GATATCAGGG CCTCGACTGT AGGCAAACAG
48301 ATACAATAAC ATTGGAAACA TGTAGAATAT TGATGATGGG CACATTGGGG CTGATAGTAC
48361 TATTCCTTTT TTTCAATTTT TGGTAAGATA TAATTAGCAT ACCATATAAT TCATCTATGT
48421 AAAATGCAAA AATTGGCCCG GCTCAGTGGC TCACGCTTGT AATCCCAGCA CTTTGGGCGG
```

```
48481 CCGAGGAAGG CAGATCACCT GAGATCAGGG GTTCGAGACC AGCCTGGCCA ACATGGTGAA
48541 ACCCCGTCTT TACTAAAAAT ACAAAAATTA GCCGGGCGTG ATAGCAGGCA ACTGTAATCC
48601 CAGCTACATT AGAGGCTGAG GCAGGAGAAT CGCTTGAACC CGGGAGGCGT AGGTTGCAGT
48661 GAGCTAAGAT CGTGCCATCA CACTCCAGCA TGGGAGACAA GAGCAAGACT TCATCTCAAA
48721 AAAAAAAAAT TAGCTGGGTG TGGTGGCATG CACCTGTAAT TCCAGCTACT CGGGAAGCTG
48781 AGACAGGAGA ATCGCTTGAA CCTGGGAGGC GGAGGTTGTG GTGAGCCGAG ATCATGCCAT
48841 TGCACTCCAG CCTGGGCAAC AAGAGCGAAA CTCCGTCTCA AAAATAAAAT AAATAAAATA
48901 AAATGCAAAA ATTAATGGAT TTTAGTATAT TTACAGAGAT GTGCAACCAT TACCAAAATT
48961 TTACATTTCT ATCTCCCCAA AAAGAAACCA TGTTCCCCTA ATTCAGTACC CTTAATTCAT
49021 CGCCTCCCAG ATTCCTCCAT TCTCCTCCTC CTCCCCTCCC AGCCCTAGAC AATCTTTAAT
49081 CTACTTTCTT TCTATTTGGA ACATTTAGTA TACATAGAGG CATATAATAT ATTGCTTTGC
49141 CGTGACTGGC TTCTTTCATT TAGCATAATG TTTTTATGTA TGTTTTTCAT GGACCAATAA
49201 TATCTATTAT AAGGACATAC CACAACATAT TTTATTTATT CATTCATCAG CCGATGGACA
49261 TTGGTTTGTT TCTACTTTAT GGCTATTGGG AATAGTGCTG TTATAAACAT TTATGTACAA
49321 GTTTTTTTGT AGACTTATGT TTTGATTTCT TTTGGTTATA TATCTAGAAG TGGGTTTGCT
49381 GGGTCATATG GTAACACTGT TTAACCTTTT GAGGAATTGC CACATTCTTT TCCAAAGTAA
49441 GCATTTTATC CTCCTATCAG CAGTGTATGA GAGTTCTGAT TTCTCTCCAT CTTTGCCTGG
49501 GTTTTTGAAT CAGGGCCCCA GATAGAACAA AAATGTGGTT ATTCAGTTGT TCCACCATCA
49561 CTTGTTGAGA AGACTCTTTT TTCATTGAAG TGTTTTGGCA CCCTTATCAA AAATCAATCT
49621 ACCATAAATG TGAGAGTTTA TTTCTGGAGT CTCAATTTTA TCCCATTATG CTATAATCTA
49681 TAATCCTATC TTTTTTTTTT TTTGACAGAG CCTCACTCTA TTGCCCAGGT TGGAGTGCAG
49741 TGGCCCAATC CCGGCCACTG GCTCCTCCTC CCAGGTTCAA GCAATTCTCC TGCCTCAGCC
49801 TCCCAAGCAG CTGGGATTAC AGGTACCTGC CACCATGCCT GGTTAATTTT TGTATTTTTA
49861 GTAGAGACGG GGTTTCACCA TGTTGGTCAG GCTGGTCTGG AACTCCTGAC CTCAGGTGAT
49921 CTGCCCACCT CAGCCTCCCA AAGTGCTGGG ATTACAGGCA TGAGCCACCA CACCCAGACT
49981 ATAATCCTAT CTTTATGTCA GGACTACACT GTCTTGATTA CTATAGCTTT TTAGTAAATT
50041 GAATTCAAGA AGTTTCTCAA CTTCAAATTT GATCTTTTTT TGGAAGACTA TATTAGCTAT
50101 TCTCAGTCTG CTGAATTTCC CTAGGAATTT TAGGATCTAT TATCAATGTC TATTCTATTT
50161 TTGTATATGT TTTAATATTT TCATAAGAAA CTTTTTTCAT TTAAACTTTT TTTTTTAAGA
50221 AAAATAGTGA AAATCAGAAC ACTGGGGGTC AGGCGCATTT AACAGGCAGA AGAAGAATAA
50281 AAACTTGTCA TATAAACAAA AAAGAAATGA CCAATCACAT TGTGGAAGCC ATGGAGTGGT
50341 TATAGGTGCC AAAGGCTGCA GAGAAATGGT GTCAGATATA CCTGAAAATT GTCCATTGTA
50401 TTTGGCCATT AAGAGACTTA GAAGACTTAA GCCATAGATT GCTCAGTGAG ACCCCGAGGG
50461 CAAATGGTCT GAAGGTGAAT AGATCATTTC ACCTTTAAGA GAGCAGGTAG GAAGCTATAA
50521 ATCCAAGATT AAAAAGTTGA CTGAACTGTT AAGGAAGAAA CTCTAATCTT GAGCCACCCT
50581 ATCCTGGCTC CACCTTCTGC TGCAAGCAAA CAGAAATGCT GAAATTCAAC ACTCACAAAG
50641 GCTGGTAAGC TGGAAATGAC AAAAATTACT CCTGGGAAAG TCAGATTTAG AATTAGGCCA
50701 TATTTGTTGG GGTTCAGATT TTCATGTACA CTTGGGAAAG GGTTTAGCTT ATAGGCACAT
50761 GCATGAAGGG AACTGGTATA GGGCTGTGTT CATAAGGTCA AGAGTTGAAG GCCAGGCATG
50821 GAGGCTCTTG CCTGTAATCC CAGCACTTTG GGAGGCCGAG GCAGGAGGAT GGCTTGAGCC
50881 CAGGAATTCA AGACCAGCCT GGGAAACATA GGGAGATGCT GTCTTCACAA AACAATTAAA
50941 AAATAAAATT AGTCAGGTGT GGTGGCACAC ACTTGTGGTC CCAGCCACTC AGGAGGTTGG
51001 GAAGATCACT TAAGCCTGGG ACATTGAGGC TGTAGTCAGC CATGATAGTG CTACTGCACA
51061 CCAGTCTAGG TGACAGAATG AGACCCTGTC TCCAAAAAAA GAGCTGTATC CACATCCCAG
51121 GAAAGTGGTT GAAGATCTAC TTTTCTCTGT AAACCTAATA AAGAATAGAG TGACAAATGT
51181 GTGTTGTGGA AAGAAATGGG GTGAGAGCTA CGTAGATGCA AAACAATACA TCCCCACATA
51241 CCACTTGTTA ATCATCCTTT TCCACCCACT TATGGGATGA ATTGCATCTC CCCAAAAGAT
51301 ACTCTGTCCT AACCCTCAGT AGCTGTGAAC CTGACCTTAT CTGGAATACG GTGAGTTCAC
51361 TGGTTAAGAA GAGATTATAG TGGAATAGGG TGAGTCCTCC AACCAATGAC TGGGGTCCTC
51421 ACAGACACAG AGGGATGATG GCCAGGTAGA GATGGAGGCA GAGATTGGAG TTATGCTGCC
51481 ACAAACCAAA CACAGGAAGC TGCTAGAAGT GGAAACAGGC AAGAAAGAAT CCTTCCCCAG
51541 AGGCTACAGA GGGATCTTGG CCCTGATAAT ACCTTGATCT CAACTGGCCT ACGTAACTGT
51601 GAGAGAATAA ATTTCTTTTG TTCTAAGCCA CCCAGTTGAT AGTACTTTGT TACGGCAGCC
51661 CTAAGGAACT TGATATACAT TTCTTTTACT GTCATAGAAG TTTTGAATCT TTTAAGTAGG
```

```
51721 TCTGTACCCT TCCTCCCAGT GTCAACACAT GGAATTCCTC TCCTTGTGCC TTGAAAAGTG
51781 AAAGGTGTTT GAACTGGTAA TGAAAGAAAT CTCAGCATGA GGCCAGATGC TGTACCTCAC
51841 ACCTGTAATC TCAGCACTTC GGGAGGATGA GGCGGGCAGA TCACTTGAGG TCAGGAGTTC
51901 TAGACTACTC TGGCCAACAT GGTGAAACCC CATCTCTACT AAAAACAAAA AATGTTATCC
51961 TAGCCGGGCA TGGTGCCTGT AGTCCCAGCT ACTCAGGAGG CTGAGGCAGG AGAATTGCTT
52021 GAACCCGGGA GGTGGAGGTT GCAGTGAACT GAGATCACGC CACTGCACTC TAGCCTTGGT
52081 GAGAGAGCAA GACTTGGTCT TAAAAAGAG AAAAGAAAAA TGAAATTTCA GCATTATAGA
52141 ATAAAAATGT TTCCCCTTCC CCCCAAACTT TAAAAAAGCA GAAGTCTGCA TCATAAAATG
52201 GTCTTTGCCA ATGTTATTTT TATTATAACA AAGGAATCTT GCAAGGCTAC CAGATCTCAG
52261 CAATTGTCAC TATGTTCTGT AAAAATCACT TCCTAAAATG TCTGAATTGA CTGCTTGTCT
52321 CATTTATTTG TTTCTCGTGT CATACTGCAA TGGATATCTG TCTTGTTAGT ATAAATATTT
52381 GTGCATTTTG TTGTTGTTAA AACAGCTTTT TTGGCCTGTC TTCTTCCACC TATGAGGTAA
52441 TATAAAACTC ATGTTTAACA CTTATTTTTG TAGCAGGACA AGCTACAGAC AAAACCCCTC
52501 AGACACTGAG TTAAAGAAGG AAGGGCTTTA TTCAGCTGGG AGCTTTGGCA AGACTCACAT
52561 CTCCAAAAAC CGAGCTCCCT GAGTGAGCAA TTCCTGTCCC TTTTAAGGGC TTGCAACTCT
52621 AAGGGGGTCT GTGTGAGAGG GTCATGATCG ACTGAGCAAG TGGGGGTATG TGACTGGCAG
52681 CTGCATGCAC CAGTAATCAG AACAGAACAG GGATTTTCAC AGTGTTTTTC CACACAATGT
52741 CTGGAATCTA TAGATAACAT AACCGGTTAG GTCGGGGGTC AATCTTTAAC CAGACCCAGG
52801 GTGCAACACC AGGCTGTCTG CCTGTGGATT TCATTTCTGC CTTTTAGCTT TTACTTTTTC
52861 TTTCTTTGGA GGCAGAAATT GGGCATAAGA CAATATGAGG GGTGGTCGCC TCACTTATTC
52921 ACCCCCTTTG AGAATCTCAC TCATTAGTGG GAGTTCTCAC TTTTATTCTC ACTACCTATG
52981 TCTTCTTGAA AGACAGATTG ATAATGATTC ATATAGTACA CTTGTGCTGA AGCATTTTGG
53041 TGAGCTAAGG TAGTGATGAA GCTTTTTATC ATTTGGAGAA GTACAGGTAG CAAACAAGGA
53101 AGCAGTAAGC AGGTTTCTAT TAATATTATA ACTCCTATTA TAAGAGTTTT AAATCTTCTT
53161 AGCACTCGGA ACCATTTTTC AAACATGGCC CCAGAAACAA ATCCATACCA CACCTACATG
53221 GGCACATGTG CCACTTTTGT CATATTTCTA ACTATGTCTT CAACTACTTG CCCTTAATCA
53281 TCTATGTGTA GACAGCAATT AGTAAGGTTA AATTTCCTAC AGACCCCTCC TTCAGTTGCT
53341 AGCAAGTAGT CGAGAGCCAA TCCATTTTGA TAGATAGCAT TTTGCATCTG AGTTTCTTGC
53401 CAGGCCACAG TAGTCAGGGC TCTGCTGGTC TTATTAGTAA TTATTTCTAA GACAGCTTGT
53461 AACCGTATGA TTCAGTTGAG CATGTAAATG GGGGTCCCAT ATCCCCACAA GCCGTCTTGT
53521 GCCCAAGTAG CAGGCCCATA ATATTGTATG ATTCTCTCAG GGGGCCATTC ATTATTTTTC
53581 CAATTTTCTA TAGCTATGCT TTTTTTTTTT TTTTTTTTTT TTTTTTTTTT TTTTTGCGG
53641 GAAGCATATA CAGGGAAGCC CAGGAGTTTG CCTGTCTTTA TGGGCAGTAG GAAGAAAGAT
53701 GGTTTAGTAG TGTCAATAAC ACAACTACCT GCCCACTGGT CAGGTAATTT GGCATAAGCT
53761 GTATGCCCAC ATATCCAGTA TAATCCAGTG GGGGCTGTCC AGTCCCGGTG GGACTCTGGG
53821 TGGGTCCACA CAGTTTGCAA CTTTGGGAAT TTACTAAATA GATTTTTCTT AGTGTGGTTT
53881 GAACTCCACT AGGTGGCTGT TTTTATAGTA CTATTATACA GTTTTGCCC AAGGCAGCTG
53941 AGTCTTCCCA CAGGAAGGGT GAAGTCCTTC CCCACTTTTG CTATACAGTA TTGTCTAATG
54001 ATTGAGGCTT TTAGGACCCA GAAGTTATCA GGGTGAGTCT TTTGAGCTGG GAATTTATCA
54061 GGAACTGGGT CTGTAGGTAC TAATTCTCGT GCTTCCCATG GCCATTGATC TCCCATTACA
54121 GTTCCTCCAC ATACATACAT AACATGAAGT GACATTGAGA GACTGGGCTA CATGCTCAGC
54181 TAATTGCAAA AACAAATTTC TTGTTTTCC TGGAATTTCT AGTACTGGCA CATTCAGTTC
54241 ATCATAAGAA GGTTTGAAAT ACTGGCTCAG GGGAGCATTT ATAAACTTCT CCTCAAACCA
54301 CCATATTTAC TCAAGGATCC AGTCCAGCCC CAACTATTTC TAAGGTTACA CGATCCCCTT
54361 TTTTCAGTG AGAATCAAGG GGGTTGGTTA TTACTAGTTC TAAGGGGTTA CACTGACCAC
54421 TGGTACAGGA AGGGCCACTT TTCCCTTTCT GAAGGTGGAC AGGATTCTTT TTATTTTTA
54481 ACCAAGTTGC CTAAATGACA CAAGACCAGT ATCTACATTT ATTTCCACGC AGTCTTAATT
54541 CATGACAAGC GTACTTATTT TCTGCCATAT AGCCTCTTTC CTAATGAACA GAACCACATC
54601 CTATTTCTAA CTTATTACTA TTAATGACAG CACAGGCATC AAATTTCAAG GTGACTTGTT
54661 TGGGCATTCC TTTTTCTTCT GTTTGGCTA ACACTTTACT CGTATCGTTT ATGAACCCCC
54721 ACCAGTCCTC AGTCCTCAAT CTTATTTCAA AAACTGTGGT CGTGGGAGGC TCAGATGGGT
54781 CATAACACAC ATCAGGTTGG TCATTTCTTG GGCTACCTAC CTTGTATAGA ATAGCATTAT
54841 ACAAACAAGT TATTTTTAGA GTCTTTGTAC ACTTATAATA ACCATAAAAT AATAAGACTG
54901 TAGCAACTTT TTGTCCTACC TCAGTGACTT GATGTATACA CTGGGAACAG CCCTCAGTCT
```

Figure 1 (Page 17 of 73)

```
54961 GAGGAAGGTT AGTTGAAGTC TTTACTGTGC AAGTCCAAAT TTTAAGGAAA ATGAGTCCCT
55021 TGATGAGTTT TCTCATGTTT CGGCCATGCA TGGACCAGTC AGCTTCCGGG TGTGACTGGA
55081 GCAGGGCTTG TTGTCTTCTT CAGTCACTTT GCAGGCGTTG GCGAAGCTGC CACGTACAGC
55141 TCACAGTCTA CTGATGTTCA AGGATGGTCT TGGAAGTTGG GCCCACTAGA ATTAACTGAG
55201 TCCAATACCT CTACTCAGTC ACTTTCAACT GGGCTTTCTG ATACCAGGAG CAAGGTGGCA
55261 GGTTTTAGGG TGTTGCAAAT TTCAATGGTT ATGCAGGGAT TTTCACATAG CAAACTTTGG
55321 TACTTGGTTA ATCTAGCATT TGTTAGCCAA TGATGTATTT ATTAAAGTCA CCACAGCATG
55381 GAGGGCCTTT AAGTTTAGGT TTTGTCCAAG AGTTAGCTTA TCTGCCTCTT GTGCTAGCAG
55441 GGCTGTTGCT GCCAAGGCTC TTAAGCATGG AGGCCAACCC TTAGAAACTC CATCTAGTTG
55501 TTTGGAGGCC CAGCCTCGGC CAGGGCCCCA CAGTCTGGGT CAAAACTCCA ACCGCCATTT
55561 TTTCTCTTTC TGACACATAG AGTGTAAAGG GTTTTGTCAG GTCAGGTAGC CCCAGGGCTG
55621 GGGCCGACAT GAGTTTTTCT TTTAACTCAT GAAAAACTCA TTGCTGTTGG TTGTAATAGA
55681 TGTAGTTTAT CCAATCTACA TTTTTATTAA CTGTCACCCA CCAAAATATT GACTCAAATC
55741 CTGCAGCTAT TTGATTTTGG GATTTAAATT GATCTGCTAT TCCCTGTGGG ACTCCAATTG
55801 CATCTAAATA GATGTGAGAG TTGAAAGACA CATAAGGGTC TTCTCTTGCT TTACGATGTC
55861 TTATTTTTCC TCCCTCTGGT TGATGAAATG CTAGGGTGAA AGGGATAGCC AATTGGACTA
55921 AAGTACAAGT GCCGCTCCAG TTATTTGGCA GAGTGCCCAG TAAAGGTCCA CCACAATACC
55981 ACCACACATC CGCTTGGGA TGAACAAAGG CTGACTGATT GAGAAGCTCC TGAAAATTCT
56041 TAAGCTCACT GCATCCCTTC AGGTCTCCAA GGAATGCTAA GTTTCCTCCC TGTCATGAGA
56101 GACAAGAAGT GAACTTAGTT TTGGGAGATG GAAGCTGGAT GGCCCTCAGG GGTTGACCTG
56161 CAGGGTGCTG GACTTTGGGA TATAGCAGAG AGAGCTTGGC ACGACTTATT ACTCCAGGCT
56221 GTAGAATCCT GGAAAACAGT TACCATGCAG CCCATGCCTG GTCAACAGGA GGACCACCTT
56281 AGTGGAAAGG GGATAATCTG GCCCTCTGGC CTGCCATGTG CACAAGCATA ACAATTGGTT
56341 TTGTTTAATG TGTGGACAGA ATATTTGATC CATTCCAACT GGGCATTTGC ATCTTGGTAT
56401 CCTGCTTAAT TATCAAAGTT TGTTTTAAGT CTTTAACTTC TATGACCCTC TAGTAAAATG
56461 AATGTATGAT TTTAGGAAAT TACAAAAACC GGTTGGGGCA GTCCATCCTT GCTCTTTAGT
56521 GGTCCACACA ACATTCGACC AACTATGGCA TAAAAGCTCT ACATCGGGGG GCAAGACTCC
56581 TCGTTGACAC TGGGGTCTTT ATTGAAATCT CTCTGGAATA AATGGTCTCA GTTACTAAG
56641 GCTCAGTCTG AGGAGAGTCA GGAGGGACAG AGGTACTTTT CTGAAGTACA GAGATGTCTT
56701 CGACTTGGCA AGTCCCCACA GGGTATAACA AGGCAAGCAT TAAATTCAAT AGTTTGAGGC
56761 AAAATTGACT TGGTTATGTT AATAACTAGA TGGTCAGAAA TAGAGTGAGG GAAGAAGAAA
56821 GAGTAATAGA ATAGATGAAG GAGTTAAATT TTTCTTAGCT TTAGTTTGGT AGGGTTTTCC
56881 CCTGGGACTA TGGCCCATGA CTCTGGAGGG GGTGGCACTT TCTTGACTCG GGTGTGATGA
56941 GTCCATCCCT TTTTCACCGT ATGAACAACA GTCTCGGTGG TTAGCAGCAC AAGGTAGGGT
57001 CCTTCCTAGG CTGGCTCAAG TTTTCCTTCT TTCCACCCTT TGATGAGAAC ATGATCTTCA
57061 GGCTGGTGCT GGTTTACAGA AAATTCTAGG GGTGGTACAT GTGCTAAAAG ACTTTTAGTT
57121 TTGAGGGAAA GGAAAGTGGA AGATAAACCA AGTATATAAC TTTTAAGAAG TTGACCTTTT
57181 GTTTTAAATG TGGGGACATC AGCAGTGGAC TTTATAGTCC TTGGTGCCTT CTTACTGAGA
57241 AATTTCCTTT AGCACCTATT TTTATTAGTT TTTAGACCAA AGAAAGTCAA ATGCCATTTT
57301 ATATTTGACA ACGCTTCTTG TATGTTTATA CCAGATAAGC TAGATTTCAC CTTTATATTG
57361 GTGTGTTATT AATGTTAAAC TTAGTTTTAA TAAAACTCTG TAGACATATT TATTTGATTT
57421 TTAATGTCTG ACCATAAGGT AAGATTTTTA TAGACTTTTC TTTAACCTTT TATAATTTTT
57481 GTTAAAGAAC AGGTTAGTGC TTTAAGAAAA ACCCGTTGTG TTTTTATTTT AATGTTCAGT
57541 TCACAGAAAA ACTGTATGAT ACCCCTTAAC TTTAGCCAAT ATGTTTAGAC ACAGAATTTT
57601 CTTTACAATT AAGGTTTCAA AACTTGCTTA AACCTTCAAA ACAATTTTTG TAACCTTTTA
57661 ATGTAGGTAA AAATCCACAT TCTTATGCAT CCTCATAATC CTTTTACCAA AGGTATATTT
57721 TACTTTCCTT ACATACCTTG CACATAAACT GTTTATTCAA TAGTTTTACA TTTAGAAGGA
57781 GGCCTAATTA CTTTTAAATT ATACAACATT TCTTACATAA ATTTATTTTT CTAACACACA
57841 TTTTTTTCAT GACTTTCACA GACAATTCTT CGACATGCCT CAACTTTCTG ACTTATTGCA
57901 AACATCCCTT TCTTTAAACA ACTAGTTAAT TTATCTCAGG ACAAGGATTT TCCATACAAC
57961 ATTCTTTTTT ATATAAATTC TGCCTCCTCT TTATTTCCTT TTTTTTTTTT CCGAGGATGA
58021 TAACCATTCT TTTCCAAAGC GAACTTCTTT TATGTCTGTG GACTAGACTG TCTAAGGCCA
58081 CAAGATTAGA AGTTACTATA ATACATGTTA CACTGTTAAC TTTTAGCAAA CTTTACTTTT
58141 GTTGAAAACC TTGTAAGTTT GGGATTTCAA TTATCCTTTG CTATTAATAA GACCTTATTT
```

Figure 1 (Page 18 of 73)

```
58201 AGTCCAAATT AACTTAGAAT TGGTATAGAT GGCTTTTTTT TTTTTTTAAT TACCTGGGAG
58261 GAACCATCTA TCCTCCTGTC CTGAAGGGAG TTCCTCCTAG GTCTGGTCAG AGCTTTGTAT
58321 GGTAATTAAG ATTTAGATCC CCTGTTAGGA AACCTGCCGG GTTAAGAGAA TTTTCAGTGG
58381 TTAATGTTAA ATCATCTTCT TTTTTCTTTT TTCCTTAGGA TACTTCTGAA CCGGTGAGGT
58441 GTGCTCACAA TGAGGTTTCC TGTAAAAGTT ATTTTTTTAC TTTCTTCTGT TAGCAAAGCA
58501 GTTGCCGCTA CAGATTGAAT GCATTTGGGC CATCCGCGGG TTACTGGGTT AAGGATTTTT
58561 GATAGGAAGG CCTTAATGCT TTTGGAATAT GCCCTGACAA CAAAGTGCCA GTTCCTTCCC
58621 GGTGTTCAGC CACTGCGTTG ATCCTCCACG AGGGCCTGCC ACGTGCTGCT CTGGTGAGGC
58681 GTTCCACCGG GGCAATTGCC TACCTGGGAG CGCTCTCCAG ATCTGTGTCG CTCAAACTGG
58741 CTGGAGTTCC CCGTAGGGAT GCTCCACAGG GCAGGCCTAA GTCGCCTAAG GGGCTGCCTT
58801 GACCGTCCGT TAATCACCTC TGTCTCCAAA AACCAGCTCC CTGAGTGAGC AATTCCTGTC
58861 CCTTTTAAGG GCTTACAACT CTAAGGGGGT CTGCATGAGA GGGTCGTGAT TGATTGAGCA
58921 AGCAGCGGGT ACGTGACTGG GGCTGCATGC ATCAGTAATC AGAACAGAAC AGAACAGCAC
58981 AGGGATTTTC ACAATGCTTT TCCATACAAT GTCTGGAATC TATAGATAAC ATAACCTGTT
59041 AGGTCAAAGG TCGATCTTTA ACCAGACCCA GGGTGCGGTG CCGGGCTGTT TGCCTGTGGA
59101 TTTCATTTCT CCCTTTTAAT TTTTACTTTT TCTTTCTTTG GAGGCAGAAA TTGGGCATAA
59161 GACAATATGA GGGGTGGTCT CCTCCCTTAA TTTAAACAAA ATTTTCAAAG TCCTACCCCA
59221 AGTAAATTGG CAAATATTAA TAAAGTTATG GCATAGAAAA TAAAAATGAT TGTAAAAGGC
59281 GTAAAGATAT TTCTGTGGGG AAAACATTTG TTCATTAGTT ATCAGTTAAA ATTCTGTGAA
59341 AAATAACCAC TAGAGACCCT AAAGTACCCA GGGGCTAATA ATAAGAAGGG AGGAACACCC
59401 TCTCACTCCC CACCGTTACC TGCCCAGAAG GGAAGAGGAA GAGGGTGACT CCAGGAGAGC
59461 TGTGGTCTCC CCTCCCCATA TGTCCACATA TACCTGACCT CCCCTCCCCA AAATATATAC
59521 CCAATATCTC TCCCATATAT ACATATTTAT CTGACCTCTC CACATATGTA TACCTAAACT
59581 TTCTCTATAT ATCCACATAT ACCTAACCCT CTCACACACA TATAGCTGAC CTCCAGTGGA
59641 GGAAAATGGG GAAGAGAGAA GAAGTTATCA AAGGATAAAT CTAGGTCATA CTCAGAAATG
59701 TGAAAACAA AAACCACACA CAGAAAAAAA AAACACACAC AAAAAGAAA TTGATAAATT
59761 TGTTTGTGTC AAAATTAAGA ATTCCGGTTC AATGAAGGAT CCCATGGATA AAGTTAAGAC
59821 ACTGCTGTAA GGATGGTAGA GAATTAAATG TCTGAATCAG ACGAAAGGAT GAGTAATTAG
59881 AATGCACAAG GCCAAGAAGA ACAAAACAGA AACTCCACAT AAAAAATGTA TGAGGCCGGG
59941 CGCGGTGGCT CATGCCAGTA ATCCCAGCGC TTTGGGAGGC CAGGGCGGGC CGATCAGGAG
60001 TTTGAGACCA GGCTGGCCAA CATTGTGAAA CCCCATCTCT ACAAAAAATA CAAAAAATTA
60061 GCCGGGCGTG GTGGTGGGTG CCTATAATCC CAGCTACTTG GGAGGCTGAG GCAGGAGAAT
60121 CACTTAAACT CAGGAGGCAG AGGTTGCAGT GAGCTGAGAT CACACCATTG CACTCCAGCC
60181 TGGGTGACAG TGTGAGACTC TGTCTCAAAA AAAAAAAAAA TTATATATAT ATATATATAT
60241 ATATATATAT ATATATATAT ATATGAAATA AATGAACAAG AAATTTAGAT ACAGGAAAAT
60301 CCAAAGCACT TGGTAATGAA AGAAAGGTAA AGTGATGTGT CCTTTTGCAT TTAAAAGAGA
60361 GCATTAACAA ATTAGAGAGC TGAATAATGC TCAGTATTGG TGTGGATATG GAGACTCAGG
60421 AATCCTCATA CACTGCTGAT GGGAGTGCCC ACTCCCTGGG AATATTTTCC AAATATCATC
60481 TCAAACATAT CCCATAAAGG TGACAGGAAA GTGTGGGCTG ACTGATATCC TTCACTGAGA
60541 GAGGTGGAGG TAAAATGAAG TCACTGCACA ATATAGAGTT GGAAGCAATG GATTAGATGT
60601 CCACATAGTT ACGTGGAAGA ATCCGTAAGA TACACACACA CACACACACA CACACACACC
60661 TTTGTGTATA TTGTTCCTGG CAGGTAGGCA TGGAGGTTTA GAGGCTTTCT ACATCACACC
60721 TACTGCACAC AGTAAATGGC CAGGCTGAGC ACTGACTTCC ATGAAGGGAG ATTGAAGGTA
60781 AGAGATTGAA GATTGTTCCC TGGTCTGGGA CCCTGCAACT GAATATGCAG AAAAAAGTAC
60841 ACCCCGCCAC CCCGCTTCCC ATCTTTCCTA CCTGATTAGA ATAGCTTTTT CAGAAAACGT
60901 TGGCCAGGGG TTGTGGCTCA CACCTGTAAT CCCAGCACTT TGGGAGGCTG AGGCGGGCAG
60961 ATCATCTGAG GTCAGAAGTT CCAGACCAGC CTGGCCAACA TGGCGAAACC CCATCTCTAC
61021 TAAAAATATA AAAAATTAGC AGGGCATGGT GGCACACACC TGTCATCCCA GCTACTCGGG
61081 AGCCTGAGGC AGGAGACTCA CTTGAAGCAC AGTGATGGAG GTTGAAGTTA GCTGAGATCT
61141 TGCCACTGCA CTCCAGCCTG GCAACAGAG TGACACTTTG TCTCAACAAC AACAACAAAA
61201 CCCACCAAAA CTTTAAATCT ACCTATGGCC AAATGCCTGC TAAAATGAGC ACCCAAGAAG
61261 CAGTGTTCAG GAAAGTCAGA TGAATACCCT AAAATTAGAT GCAATGTTGG CTGGTCACAG
61321 TGGCTCAGGC CCTGTAATCC CAATCCTTCT TGGGAGGCCG AGGCGACAGA TCGCTTAAGC
61381 TCAGGAGATC GAGACCAGTC TGGACAACAT GGTGAGACCG TGTCTCTACA AAAACGTACA
```

Figure 1 (Page 19 of 73)

```
61441 AAAATGAGCT GGGAGTGGTG GCGCGCACCT GTAGTCCCAG CTACTCAGGA AGCTGAGGTG
61501 GGAGGATCTC TTGAACCCAG AAGGCGGAGA CTGCAGTGAG CAGAGATCAT GCCACTACAC
61561 CCCAGCCTGG ATGATAGAGC CAGACCCCCA TCTCCAGAAA AAAAAAATAA AGAGAGAGAG
61621 AGATGCAATA TTTAGGGTTC AACAAGACTG AATTTCTGAC TCCTTTCCCT ACCTCTCCAG
61681 CATGTTAGAT TCTGGGTCCT TCATCCTAAC CCCCTGTTCA TGCCATAGCC ACCCTGTGGT
61741 ACCAACTTTG GAAGCCTGGA TCTTCATCCC CTCATGATAA TGAGTGTCCC ATCAGGTCTC
61801 CATGCTCAGC TTGGCAAGAG TATCTGTCTT CTCCTCATGG GACGGTCACA TTCACCCAGC
61861 ACTGACAGGT TCCATTCCCA CTAGGGTGGC ACCCTATATG GTCTGAGTCC AGGCCTTCCT
61921 GGTCCCTCAG TAATCTCAGC ATGGTAGCAC AATCGAAAAG GGCTAGGCAC GGCAGCACCA
61981 TTTCCCACCA AGAGGTCTGA TGGCTCATCA CATAGACTGA AGGAGATTCT GAAGAGCAGA
62041 GGTGGAATGA AGAATGAATC GTGGGCTCTG CTCTTCCTAG GCCTGTCTTC CTCTCTCCCG
62101 AGATGTTAGC TAACTCATGA GAGCCAGAAA CCAACTGCAG GCTGGCCTCA GGCACTTAGG
62161 TAGTGCTTCA GCCTCAGCAG TCCACATTCT AGGAACCCTC ATAATATGGG TTGAAGTATG
62221 CATTCCCACA AAAATAAAGT TGTTGAAGTC CTAACCACCA GTACTGAAAT GGGAAAAGTT
62281 CCCTTGTCCC GCTCGCATGG CATGTGATAG GAGTGTGGCT AATTTCTTCA GTGCCTGGCT
62341 GCTCAAACCT CTAGGGGAAC ATTAAGACGG GCAGGTTGTG GGTCTCCAAC CCCATGACCC
62401 CACCACAGTG TCTAGGGTTG AATGTTTACA GCTCCTGAAG CCACAGTGGG TGTGTGTTAC
62461 AGGGTGCTCT TTTAGTTTTG CCATTTATAG GCAGCTGGTG TTAACCAACT CAATTAGACC
62521 GTCTACCTTG TCCCAAGGAC AGAAGAAGGC TTTCTGTATC CCAGGTTCTT GCCTTGGTGT
62581 ACCGGAATAA ATCAGACCAC ACCTGGGCTT AGAGAAAGAG TGCAAGGTTT TATTAAGTGG
62641 AGGTAGCTCT CAGCAGTTGG GCAAAGCCAA AAGTGGATGG AGTGGGAAAG TTTTCCCTTG
62701 GAGTCAGCCA CTCAGTGGCC CAGGCTCTCC TCCAACCACC CCAGTCAAAT TCCGCCTCAT
62761 TTTGCCAGGC AAACGTTTGT TGTGTGCTCT TCTGCCAGTG TGCTCCCCTG GACGTCCAGC
62821 TATTCGTGTC TTGTGGCAGG CCAGGGGAGG TCTTGGGAAA TGCAACATTT GGGCAGGAAA
62881 ACAAAAATGC CTGTCCTCAC CGTGGTCCCT GGGCACAGGC CTGGGGGTGG AGCCCTAGCC
62941 GGGGACCACG CCCTTCCCTT CCCCACTTCC ATATCATTTA AAGGGACCAT GCCCTTCCCT
63001 TCCCAGCACT TTCCCCCTCC TGTATCAGGA CCTGTGAATG TGGCCTTATT TGGAAATAGG
63061 GTCTTTGCAC TTCATCAGTT AAGATAAGAG TGGGCTCTAA CCCAACATAA AGGGTGTCCT
63121 TATAAAAAGG AGAAATGTCA TACACAGAGA CTGACACCTA TAGAGAGAAA ATGTGGTGAG
63181 TAGACACAGG GAGAATCACC ATTCAAGTCA AGCAATGAGT CTGGGGATAC CAGAAGCTGG
63241 GAGAGAAACC TGGAACAGAT TATCCCTCAT TGCCTTCAGA AGGAATCAAA CCTGATGATA
63301 CTTTGATTTC AGACTTCCAG CTTCCAGGAC TGTGTGACGA TAAATATCTG TTGTTAAGCC
63361 AACGAGTTTG AGGTACTTTG TTACTGCAGC CCCAGAAAAC TAATACAGTA GGTACTATGG
63421 ACTGAATTGA CTCCCCGTCG CAAAATTCAT ATGTTGAAAC CCTAACCCCC AGTGTGATGG
63481 TACTTGGAGC TGGGGCGTTT GGGAAGTCAT TATATTTAGA CAAACTCATC AGGATGTGTC
63541 TCTCATGATG AAATTCATGC CCTTATTAAA AGAGACAACA GGCCAGGTGC AGTGGCTCAT
63601 GCCTGTAATC CCAGCACTTT GGGAGGCTGA GGTGGATGGA TCACCTGAGG TTGGGAGTTT
63661 GAGACCAGCC TGGCCAACAT GGTAAAACCC CATGTCTACT AAAAATACAA AAATTGGCCA
63721 GGTGTGGTGG TGCACGCTTG TACTCCCAGC TACCTGGGAG GCTGAGGCAG GAGAATCCCT
63781 TGAAACCAGG AGGTGGAAGT TGCAGTGAGA TCACACCACT GTACTCTAGC CTGGGTGATA
63841 GAGACTCCAT CTCAAAAAAA AAAAAAAAA AGACAATAGA GCCAGGTGCT GCAGCTGATG
63901 CCTGTAATTC CAACACTATG AGAGGCTGAA GCAGGAGGCT CGCTTTAGCC CAGGAGTTCA
63961 AGACCAGCTT GGACAAAATA GTGAGACCCC CAACTTCTAA AAATTTAAAA AATGAACTGG
64021 GTGTGGTGGT ACACATCTGA GGCTCCAGCT ACTCTGGAGG CTGAGGTGGG AGGATTGCTT
64081 GAGCCCAGGA GGAGGCTGCA GTGAGCCATT GCTGTCCAGC CTGGGCTACA CGAGAACCTG
64141 TCTCGGGAAA AGGAGAAAAC AGTGAGACCT CTTTTTCTCT CCTCCTTCTC TCCACTGCCT
64201 AAGCCCTACA AGCACAAAAA GGACACCACA TGAGCACATA GTGAGAATGC TGCTGCCACC
64261 AACAAGTCAG GAAGAGAGCG TTCACCTAGA AACTGAATTG GCCAGCACCT GGATCTTGGA
64321 CTTCTGAGCT TCCAGAACTG TGAGAAAGTT ATTTTTTTTT TAGCGACTAA GTCTATAGTA
64381 TTTTATTACA GCAGCTCAAG GTAACTAACA TAGTAGAAGG GATGAATTAT GGAGATCACA
64441 AGTCCACGCC TCCAGAAAAA GACTTCCCTA AAAATTAGTC TGAGCAAAAT TCGAATGATG
64501 AATTATTTTT AAGAACTTTT AAGGGATCTG ACAAGTTTGC AAGAGCTAGA GAATGCTTTA
64561 CAACGTGATA ATAGAATGCT CTGTGATGAC AGAAATCTTT CCACACTGTT CAAAACTAGC
64621 TACTGGCCAC TTGTGACTAT TGTGCACTTG AAATGTGACT GGTGTCTGAG GAGCAGAATG
```

Figure 1 (Page 20 of 73)

```
64681 TTTAATTTTA CTTAATTTTA ATTCATTACA ATAGCTACAT GTAGCTAGGG GCTACTGGAT
64741 TGAACAGCAC AGCTCGAGTC TTTTAGAGGG AGACAGGACT CACCAAGATG GATGCTGGTG
64801 GCCAAGCAGC AATGGCAGGT AGTACACACA CAAGAGGCAG ATGATACAAC ACATCCTTCC
64861 CAAACCTGGA GATAAGCTCA CCCCACAATC CCGCCGCTGA AATAGAGTTG ATGTTACCAA
64921 TGTGCATTTT TATGTCCTTT TCCATACAGA AAGATCATTC AGCAAGTACT ATGGTACTTA
64981 AAAAACAACA TTCAATTCAT TATTATGACA AAATTAAATT AATAGCTCTT CCTTAAACTT
65041 TTAAATTCAA TTTACAATGC TTACTATTGG CATTTATTAA TCTACCAATT TTTTCCCATA
65101 GAACCCATAG AACAAATAAT CTACCAAATT TTTAACATTC ATTTTTGGCA AGGCTTTTGC
65161 AATTTGACGA ACTTTAAGAA GAAAACTTAT AAATTGCAAT TTTTAAATCT GACATACTGG
65221 ACTTTTAAAG TATCCAATTG ACTAATGAAC AAAACTGCTC CAAATTTTTC AATTCTTAAA
65281 AATCTTAAGA CAATACTTAA TATGGCAAAT CTTAACTTCT TAAACTTTGT AAGAATGCTA
65341 ATCAACTTAG ATTGGTATAA AGTTGAGTTA AAAATCACAG GATACATCAT CTCAGCTATA
65401 AGTTTTCATG AGTTGAGTTT TTACAATCAC TTGAAATGCT TAGAATAGGA AATACGTATA
65461 AATTATTTAA CATAAAATAT TGTTACAAAA CCTCTGGAGT GTCAGTTTCT CTGGCCAGAC
65521 TTTATGCTGC AGCACCTTTG CCTGAGTTCT TGTCCTGCAT CCAGGAAGAA TTAGGTACAG
65581 AGGCAAGAGT CAAGAAGATT AGTTTTCCAA TAGTTCAGCT CACCTAGTTA ACTCCTGTTC
65641 ACAATCTTCA AAGTTATCAG AAACCTGCAA TTGAGGGTTA TAATCCATTC TTTGCAGAGT
65701 TTCAAAACAA GACAACATTT GTCTATGAAT GTTAAAATGT CCTAGGGTAG TCACAGTCAA
65761 AAACACAATT GACAAAGAAA TTTAGTCACC TCTGTGATTT ACAATAGCCT AACACAATAA
65821 CTCTAATTAT AACTGATGAC ACAAACTCAG ATATCAGAAC TCTAGAAATC CCCTATAATT
65881 TTGGAACACA CATTCACAGT TTTCACTGAA ATATGACCTG AAGATCAAAT ATCACCTTAT
65941 TTCAACAATC CTATATAACT AAACGTGTCA AATGATCCTG TTTACCTCTC CTTTGGATAC
66001 TCCAGGGGCC CTCTGTAGCA TCCAAAAGTT AGGGGTTAGC AAAGACAATT TTGAAGCTGT
66061 AAAGGCTCAA AACACTTAAT GAACCTCTAG TCATATCTGT TCTCTACTCA CTAAATGCTA
66121 GTAGCACCTC TCAGTTGTGG CTAAGCTGGG AGGATCTCTT GAGCCTAGAA GTTTGGGGAC
66181 GCAGTGAGCT ATGATTATGC CACTGCACTC CAGCCTGGGC AACAATGCAA AATCCTGTCT
66241 CAAAAACAAA AACAAAAAAC AAATTGCCTA TGCTGTGGTT ATCTCACAAT TAATAAAAAG
66301 GAAAAAAAAA GTATGCAGTC TTTGTAGGTC CTTGGGGTTT GTTGGAACTC AGAAAACAAT
66361 ACCCCAAAAT AAAGACCGCA GAAGCCAAAG TTTTTCTCTG ATCTTCTCCT GCCCTCCTGT
66421 CTCTGAGTCC CATTCTCCCC GGAGTCTAGC CATAGAAATG AGAATTCCTC TTCCTCAAGT
66481 TAGGTCATAG AAATCAAAAC ACCTTTTCCC CAGAGCCCAG CCATAAAACC TAAAAATATT
66541 ACTCTAACTT TCCCTCTGTT TTTCTGTGTA AAAACTGGCC ATAAAGAAAT TATCTGAACT
66601 ACCTTATTTG ATCATAGATC ACCAGACCGC ATTCCAGAGA GGATCCAGAA GGAAGGAATG
66661 CTGCACAGAG AGGCGAAGAA GAATCTAGAC AGACAGGCCT TGCTGGGTTT CCCTACTCTG
66721 TTTATTAGCA ATCCTATTTC TACACGGCGG CCCATACTTT GTTGAATCTA AAAAATAAAA
66781 ATGGACAATT TCCCCTGTAC ATGTTAATAC ACATTAATAA ATTGGATATA AATTGGATAA
66841 TTTATTAATA TACACATTAA TAAATTGGAT GCAGCCGGGT GCAATGGCTC ACGCCTGTAA
66901 TCCCAGCACT TTGGGAGCTG AGGCGGGCAG ACCACGAGGT CAAGACCACC CTAGCCGAAA
66961 TGGTGAAACC CCGTCTCTAT TAAAAATACA AAAGTTAGCT GGGCGTGGTG GCACATGCCT
67021 GTAGTCCCAG CTACTGGGGA GGCTGAGGCA GGAGAATTGC TTGAACTCGG GAGGCGGAGG
67081 TTGCAGTGAG CCGAGATTGC GCCACTGCAC TCCAGCCTGG TGACAGAGTG AGACTCCGTC
67141 TAAAAATAAT AATAATAATA ATAATAATAA TAATAATAAT AATAAATTGG ATGCATTTTA
67201 TCCTATTAAT CTTCCTCTTG TCGGTGGTTT TCAGCGACTC TTCAGAGGCC AAAGAGTAAG
67261 TTTTCCCTTA GCCCTACAG GTTCTTATGT TTAATTTGTT ACTCTCATTT AAGACATAAT
67321 TAAAGTGGCT TCTCCATGAA GATTATTTCT GCATCCATTA TTTGGTAAGA TTGGCCGTTT
67381 TCTCCTTTGA TCTCTACTTC ACACTGACCC ACATAAAACA TCACTGCCTG TTTTTTTGTT
67441 GTTGTTGTTT GGAGACGGAG TCTTGCTCTG TTGCCCAGGC TGGAGTGCAG TGGTGTGATC
67501 TCCGCTCACT GCAAGCTCCG CCTCCCGGAT TCACGCCATT CTCCTGCCTC AGCCTCCTGA
67561 GCAGCTGGGA CTACAGGCAC CCACCACCAA GCCCGGCTAA TTTTTGTATT TTTAGTAGAT
67621 ACGGGGTTTC ACTTTGTTAA CCAGGATGGT CTCGATCTCC TGACCTCGTG ATCGGCCCGC
67681 CTCAGCCTCC CAAAGTGCTG GGATTACAGG AGTGAGCCAC TGCGCCCGGC CCCGTTTTTT
67741 TTTTTGGTTT TTGCATGTCT TCTCCCTTTT ACTGTAAACT ATTTCCACTA CCAGCGTAGT
67801 TATCATTTCT ACTGCTTAAT AATTGTTTTG GGGAAGTGAA TGCATCAACC CACATGAATT
67861 TCTTGTCTAT TTGACAATTT ATTCTCTTTA GGAATAGTAT TAACTCCTAA GGTCCTGGGA
```

```
67921 GCCAGTCTCT GTACTTGGCT GCTCCAGGGT CCTACTTCAG TTTCCCAGCT TCTCAGTACT
67981 GTCACTGTCA ATTGTGGGTA ATAATTATTT TTGTCCACCA AAAGACTCTG TATGTGAATG
68041 AGTTTTGAAA TCTGCTGAGT AATACAGTGT CAACCCAGTT AATGATTTGC CGGGCGGCTT
68101 GATCAGGGGC TGTCCAACTA CCGGCATTTT GATTTGGAGC GTCATCTAGT GTCTGAAAGC
68161 ACAAACAACA TCCTACATTG TAAATGCCTT TGGCTACAGA GATTGAAACC AAAGCAAACC
68221 TATGTTTTGA ATTGTTATTC TTCAGCAGTT CTGCTAGCTT TGAAAAATCT AAAAGTTAAA
68281 AAAAAGCTTT ATATTTCATT TTCTGCCTAA ACTCTTTAAA ATTGCTAGTT GACAATTAGA
68341 TATTTTCAAT TTAATGAAAT TTTTTTTTAG TTCACAGATT AATACACAAT GGGGGAGGGT
68401 TCTTATTCTG TTGGACTTTT ACATAACCTC CACTTTAGTG CAGTCTGCTT TATGGGTCT
68461 TGTTTGAGGT GTGTGTGTGT TTAAGGGAAT GTGGTTTACA ATCAAAATAT TGGGTTGCTC
68521 TTAGGCACAT TGTAAAGTCA CACACCTGTA TTCTTATTGA TACATAATGA TTAATAACAT
68581 TATTATTACA GCCTGATCAC CATCATTATT GATATATCTA AATAATGAAT TTTATAATTT
68641 TGCTTCCTGT CAGGCAAGAG CCAATTTCAG TGCTACCATG TTTGTATAGC AGTATTTATG
68701 TCTGTCATCC TCAGTCATTT TACTTCACTT GTTCTTAGCC AAACGGCCGA GAAGCGATGG
68761 TCATTTTACT TCAAAAATGA AAAGAATTAA TATTTTTACG TTTCCCTTAA AGACCCTATG
68821 TTTAACCTCC ACTCCTGGGT AAAATGGTCT AGTCCCTCCT TTTCATATCA TCTCTGATAT
68881 CTTTTGCACA GCCACTATTA CCTACCGTTT TCTAGATCCC TATTCTTCAA ACACCACCAT
68941 GAAGGTAGAG CCTGTCTGAA TTATTTTCTT GTCCCCTGAA CTCAGTACAT TGTTAGGCTT
69001 CTTGAAGATG TTGATCAGTT GTTTGTGGAG TGAATGAATC AGCTAGCATG ATTTTTCTAG
69061 ACCACTGAGA CAAGTGTCTA AGACACTTGT TCCTTCCCAT GTTCTTGCCT GCCTGTGCAA
69121 TCCATGCAGT CTCATGGCTT CCCAGTGCCT CAGAATTATC CCCTGTCAAA CAGGCATTAT
69181 AATTTCTGTC CACTGAAAAG GACAAAAAAC TAAGTGTATA GCTAGAAGTT AAAAATTACC
69241 GGCCAGGTAC TGTGGCTCAC TCCTGTTATT CCAACATTTT GGGAGGCTGA GGCGGGCAGA
69301 TCACCTGAGG TCAGGAATTC GATACCAGGC TGGCTAACAT GGCGACCCCG TCTCTATCAA
69361 AAATGTAAAA GTTAGCCAGG TGTGGTGGCT CGCACCTGTG GCCCAGCTA CTCAGGAGGC
69421 TGAGGCAGGA GGATCGTTTG AGCCCTGGAG GTTGAGGCTG CAGAAAAATA GGAATATACT
69481 CTCTTTCAAG AGTTCGTGGT TTTGACTGCC ACCTAGCGTA CATCAGAAAA ACCGCATGAC
69541 ATAGGAAATG CCTGTGACAG AGGGGTAAGG TGAGAGAGGT TGATGAAGAA TGTATTGAAG
69601 GAGTGAAAAC GCTTCCATCC CTCTACTTAC TAAATATATT AGTTAAGTAG TTGGGGCATA
69661 TTTTAATTCA TGCATTTTGT AGATAGAAAA ACAAAAGTTT TATTCTGTTT GATTTAGTTG
69721 ATACTTTAAT ATGTGTGTGT TTAGGATGCA TGATTTATAA TCAGTCTGCA GCACTTCTTG
69781 GAGAAGTCTG AATTCTCATT CTCCATTTCC TTATTGGCAA CGTGAGAATG ATTACAATGG
69841 TGGTTGTCTC ATAGAATGCA GGGAGTCAGA ATGAAAATAG TCCATATAAT GCCTGGTGCA
69901 GAGGAAGGGT TCAGTTAACT GTCTGTATTA ATATTACTGA TAACAGTCAT GACAAACAAA
69961 AGCTTAACAA CAACACCACC AACAACAGTT GCAGAATTGA GCCACCAATT TGCACACAAG
70021 ATTGTAGGTA GGATGTTTTA GAAAAGTTAT TATTTAATAT ATGTATATAT TTTTGTACTT
70081 AAAATATGTC AGAGGTTGTT CTAAGAACTA TTTAAATGTT AACTCCTTAA TCCTCATAAT
70141 GACCCATGAA ACAGGTAGGC TTATTATTGT CTCTTTACAT GTGAGAACAC TGAGACACGA
70201 AAAGGTTTAT TAACTCACCC AAAGTCACAC AGCTGGTAAA ACGGCAAAAT TGAATTTGAA
70261 CTCAGACATT CCAGGTTCCA AGACAGTCTA ATTATTCTTT TGACTAATAT ACTAAGCTGC
70321 CTCTGTATTT TTCCTTGATT ACTTTGTAAA AGTATGAGGA AAATATAAGT GCTTCAAGTA
70381 ACCATGAAAA ATATAAACAA TCTATGTATC AACTGAAGCA TAATTACAAA TCCTTTGATA
70441 AGCAAACATA ATAAAAATTT GATATCAATC AAAACTTTCA TGTAATGTAA GCAGGTTGAG
70501 ATGAATTCTA TAGTAAAAAA GTGCAGAGTG CTGGAATACC ATGCTCCTAA TATATTGGCT
70561 AGGCACACCT GCCTGCTATC AAAGGTATGC ACACACCTTG GATACAGAAA GTTGGGACTG
70621 GGTAGTTATG TGAGTGTCAT CAGAATTCTT TCCCACTTGG GAAAGAATTG TCCATCATAA
70681 GCTTGGATGA TGGACAAGGA GTGAGCTCCC AGAACAGTGA TGTGGGGATA CATCCTCACA
70741 TCACAGTGAG AATGAGTGTT CTAGACTGTT TACACACCTA CCACTCCTAA ATGCACACAT
70801 ATAATTGCTT GCACACACAC ACATACACAC TCATCTCTTC TCTGGTGGTC CAGCTCTATC
70861 TCTTATCATT AGGCTTCTTG GGCTAGTAC CTAGGGCCTG TATCCTTTCA GAGGCAGCTA
70921 AGGGAAGCAC ACATAATTAG AAAGAATGAA CCAGCTTGTT GGATTTGGTC TCTTCGCATC
70981 CAGCCCTCCA AGTTAAGGAG AGTACCATCT TTCTTAGGGT CACCAAAGGA AAAAAAAAA
71041 AAAGAAAGAA ACAGAAGGAT ATCATACAGC AAGGATCTAA TGCAAATATG CCTCAAATGA
71101 GAGGCTACTG TGTGCTGATC CCAATCCCAG GAACTGTATG CACATTATCT AATTTAATCC
```

```
71161  TCACTGTATT TCTGGGAGTA TTATTCCCAT TTTACAGAGA AGGAACTTGG CAGGGTAACC
71221  AAGCTCATGA ATGGAGAAAC TGGGATTAAA TATAAAGCTT CCTTGCTCCA GAACTGCTGT
71281  CTTTCTGCTC TTCCACACTA CCAGCTCAGC TGTGCTCTCT ACATGCAGGC AGTTTTACAA
71341  GTTTCAGATT AGCCTGGGAC TTCCAGGGTT TTGAATGGGT TAGGGAATGG GGAACTTTTG
71401  GGTTTACTTT CCATTTTTTC TTCATACATA TGTAATATAT AACATAAATC TATGGTATAT
71461  ATGATAAATA TATGGCTACA TATGAACTAT ATAATCACAT ATATGCATTA TAAATAAATA
71521  TTAATTTTAT AATATTTTAA AGGTTATCAA ATAAATATTA ATATAAATAA TTAAATAATT
71581  AATACTCAGC TTTGTTTTCC AAAGTGATAA ATGCCTATAT TTAGCAAAAT ATTTTTTGGA
71641  GGCCTGATAG TTTTTAGGAG TGTAAAGAAG TCCTGATATC TAAATGTTTA AGAACCACTA
71701  TTTTAGGCTG TTGTCTTCTG TCTTATTTTC CCAGCTAGAC TGGTAAATAC TTGAAGGCAA
71761  ACGTTTAGCC AGCACATTAA CATTTTATGT TTTTATTCTT TTGTGCTCTC AGTGGCTGTG
71821  TCTTTTCTAT CGATTTCTCA CACTGTATGA TGGTTATATT TGTCTGTATC TGTCCCACCA
71881  GGTATAAGTT CTTGAGAGGA CACACTGCTA GGCTGATCTT AGTTTTTATT ATTTCTCCTG
71941  GTGTCCTGTG CTTAACAAGT GCTCATTAAG TGTGTAAAAA CACAGCACAG TAAAAAACTA
72001  GACATTAAAA AATAATGTCA ACCAATCTAT TGAAATTTGC ATTTCCATGT TTCTTCCAAT
72061  ATAGTCATTG TGTCAGGTTA TGTACTTATT CTGATGAAGA CTATTGCCTA ATATACGTTT
72121  GCATCTTGTG CTTTATAACT GCCTTCATAT AGACACAGAT TGAGAAGGTG TAAAAATGTG
72181  CATATCCTCA CAATTGACAA ATTCTTATCC TTTGAGGGTA GGTTTGACTT TCTGAAATGC
72241  TTTGACATCA TTTGAAAGAA GCTTGAAGAA TAAGATAGCT GTTAATGACC CAGTTTCCTA
72301  TGTCACTTAT ACAATTATAA TGGCAATTTC AAAATGTTAG GTAAATATAT TTGCAATAT
72361  ATTGTTCCTT TTGTAATACT CTCTATGTAT TTATTTATAT TTTTAAATTT TATATTTATG
72421  TATTTATTTT TCTGGACAGA GTCTTGCTCT GTTGCCCAGG TTAGAGTGAA GTGTTGTGAT
72481  CATAGCTCTC TGCAACTTCA AACTGCTTGG CAAAAGTGAT CCTCCTGCCT CAGCCTCATG
72541  AGTAGAGTAG CGGGAACTAC AGGCGCATGC CACTGCACCC AGCTAATCAC TATTTATTAT
72601  GCTCCTACTG TGTGCTTTAG TATATTTTCT GTTGTTTTCT GCAACCCATT TTGAGGGCGT
72661  GTTAGGGAAT ACAGATGCAG TAACTTTCGT CTCAGCCCTT GAGGTGAGGA AATATTTAGC
72721  CTCAGGTTTA ATCTAATTGT TGGCCATTTG CCTTCAAAGA TTGAAATATG AGCAAAACTG
72781  TGGCTCTGGG TTATATGTTA AAAAAAAGTT TATGGGGCTG AAGCCAGGCA ACAGACAAGA
72841  GCCCCTACAA TCTTATTTAG GCTGAAAATA TCCTGGAGTC CCTGTATTGT TGGTCTCAAG
72901  CAGATAGCAA CACTAACACT TACTCTTTGA GGCAGGCACT GCCAGTGGGG TGGCTGTTAT
72961  TATTAGCTTC ATTAATTGGT GAGTCAGGAA AAAACAGCTT TAAATCATTC AAAGTTCTGG
73021  CCTATACAGG ATTTAGTAAT ATTAGGTTAG CTACATCCAA AAGATGACAG AACCCTACTC
73081  TAAGGCTGGG CTTGGTGGTT CACACCTATA ATCTCAAAAC TTTGGGAGGC TGAGGCAGGA
73141  GGATCACTTG GTGCCAAGAG TTTGAGACCA GCCTGAGCAA CATAGTGAGA CCCCTGTCTC
73201  TATCAAAAAC AAAGAACTCT AATTGGCATA GTAGAAGGAA AAAGTGAAAG AAAAACCAGC
73261  TGTCACCCTC ATTCCTTACA CCTGTCCTAA CAACTCCTCT CACTATCCTT TGAATATATC
73321  TTGGCTGTTT GAGTCTCTCT CTAGCCCCAT TACTGCTGTT TGGACTTGAC ATTTTGCTCT
73381  GCATTTTTAA CTTTTCTACC AGGGTTTCCA GACCCTGAAG AGTGTGGCAT GAAACAAAAC
73441  TAGTCAACCT ATAATATTTA TGATGTGTGT GTAAATAAAA GAATACACAA TATATTGCAT
73501  TACAATATTT TAACTGTGTC CTCAATTTGT TTGTGGCTTT CTTGAGGACA TCAGTTTTGG
73561  GTGGGACGAC CACATCCTTA ATCTGAACTT TCCCTTGGAG GTCATTCTTT TTTTTTTGAA
73621  ATAGAGTCTC GCTCTGTCAC CCAGGCTGGA GTGCAGTGGC GCAATCTCAG CTCACTGCAA
73681  CGTCCGCCTC CTGGGTTCAA GTGATTCTCC TGCCTCAGCC TTCCAAGTAG CTGGGATTAC
73741  AGATGCACGC CACCATGCCC AGCTAATTTT TGTATTTTTA GAAGAGACGG AATTTCACCA
73801  TGTTGGTCAG GCTGGTCTTA AACTCCTGAC CTCATGATCT GCCCACCTCA GCCTCCTAAA
73861  GTGCTGGGAT TACAGGCGTG AGCCACCCCG CCCGGCCAGA GGTCATTCTA ATAGACTTTT
73921  TTTTTGTTGT TGCTCACAGG CTTGTTCAAT CTTATTTCAA AATTTGAGAA ATACAGTTTC
73981  CATGGAACAC CAACCAGATA TCAGGTTGCT ATGGAGTTGA TAGTCAAAAG CTTTGTATCT
74041  TCCAGTTTTT CAGAATGGCT TCTAAAGGTT CTGATTCAGA GCTCTTAGGC GAAATTGAAC
74101  AACCAAGTGT CAAAGTACAA CATTCAGGAA GTTAAAAACA TGACTGACAT ATATGTACTA
74161  TATATAGTGA GCTTGTGTAT GTGTCAATGA ATGATTTAAT TCATTAATGA AGGAGGAAGC
74221  AGAATCACAA TTAGGTCAAA GGAAGATACG GGAGAATAAA ATATGTATTT GGTCAGGGAA
74281  AGGATGTATA CTGGAAGAGG AAGGGAAAAT CAGATATAAA GTTGTTTAAT GACTTATTAG
74341  GCAATACAAT AATAACTTTT AGGGTCATTT TTTCTATATT AAGAATTCAT TTCCATCTCT
```

Figure 1

```
74401 ATGACAAAAT CCTTATTAAT TTATTAAACT TCTACAAGTG AATGTTTACT TTTAGATAGT
74461 CTGGACCCAA TAAAATGTAA ACATTAAGTC AGAGTTACTT TCACGTAGGA CAGTGTTGTC
74521 CAATAAGGTA CCACTAGCTA CACGTGATCA TTGACCATTT GGACTATAGC TAGACTGATT
74581 TAAAATGTTC TAAAAGTGTA AAATACACAC CAGGTTCTGA AGATTTATCA TTTAAAAAAG
74641 AATGTCAACT GTCTTTTTTT TTAGCTTATT TATTATATGT TGAAGTGATA ATAGTTTAGA
74701 TATATTAAGT TAAATAAAAT ATCTTAAAAT TAATTTTACT TGTTTCTTTT CATTCTTTCA
74761 ATGTGACCAC TAGAAATCTG GAAAGTATTT ATGTGATTCA CATTCTATTT TACTGTCTAG
74821 TATTGCCTTA CATCATCAGG TACCCCATAA GTAGGCTTTT TAGATAATTC TCTAATATAG
74881 CTTGGAAGGA TATGGAGAAA TATTTTTGCG TTGCTTTTAA GTTTGCATA ACTTTTTCAA
74941 CACACTTTAT AAAGGATCTA GAAAAGGGTT GGTTACATGT TTCTCTGTCT TCTGGCCTCC
75001 ACCATGTTGC CAGGAGGTTG GGGACAAGAT TCTGGGTGGC TGGATGTCCT AATGGCTTGA
75061 GGTCTGGACT TGAGATTTGC ATATAAAGAG ATGTGATTAG ATTGAGTCGA CTAGAAAAAT
75121 CATATTAGAG AACTGAATCA CAGCGATTAA ATTTACATGT CGATTTATAA ACCAGGACAC
75181 CAATTTATAG TGAAAGAAGG TCCAGTTACC TGGTAATCAA GACGTTTCAT AGCTATTTTC
75241 ATGATGGATA TACTTAGCTG AGTTTTAAAT GAGAAGGGGG TTCATTGCAC ATAGAATAAG
75301 ATCTAAGTGA AATGTTTATT TTATTTTTTT TTTTTTGACA TGGAGTCTTG CTCTGTTGCC
75361 CAGGCTGGAG TGCAATGAGG CAATCTCGGC TTCTGGAGTG CAATGAGGCA ATCTCGGCTT
75421 CTGGAGTGCA ACGAGGCAAT CTCGGCTCAC TGCAACCTCC ACCTCCCGGG TTCAAATGAT
75481 TCTCCTGCCT CAGTTTCCTG AGTAGCTGGG ATTAGAGTTG CCTGCCACCA CGCCAGGCTA
75541 ATTTTTGTAT TTTTTTTAGT AGAGATGGGG TTTCACCATG CTGGCCAGGC TGGTCTCGAA
75601 CTCCTGACCT CAGGCGATCT GCCCGCCTCA GCCTCCCAAA GTGCTAGGAT TACAGGCGTG
75661 AGCCACCAAG CCTGGCCTAA GTGACATGTT CTTATATTGT TCCTTTCTTT CTTTTTTTTT
75721 CGACTGAGTC TCACCCTGTT GCACAGGCTG GAGTGCAGTG GCGTCATTTC GGCTCATTGC
75781 AACCTCTGCT TCCCGGGTTC AAGCGATTCC CTTGCCTCAG CCTCCTGAGT GCCACCACCC
75841 CCAGCTAATT TTTGTACTTT TAGTAGAGAT GGTGTTTCAC CATGTCGGCT AGGCTGATCT
75901 CAAACTCCTG GCCTCAGGTG ATCCGCCCCC GAGTCTCCCA AAGTGCTAGG ATTACAGGCG
75961 TGGGCCACGG GGCCCAGCCT TATATTATTT CTTTTACTAC AATATATTAG TATGATGCAG
76021 GTGCTTCAAT TGTTTATACA CTTTCCATAA TTTTGTATAA TTCTTATACC CTGTCACTCT
76081 GAGGAATAGC CGGTCTAAGT GTTTTTCCAC CACTGCTAAT TCATCCATCA CTAATCTCAT
76141 TAGACTGTTA ATTCCCAGAG GACATAAGCA CACAAGCAGA CAATGTTTAC AAATGTTGGA
76201 CAAATGTTAT TTAATAAAAC AATGGGGTCA CCCTTAGTCT AAAAGATGTT TCACTTTTCA
76261 TTTGTCATTG AACTCTTATT TGTAGGTTCC CTTTTGACTT TCCCACAATC TAAGGCTGTT
76321 CTCTTTAACA CATATTTTCA TGAAAACATA TATTTGAGCA GAAATTGTTG GGGAGTTGTA
76381 ATATTACCTT TGTCCCTAAA TATGAATCTA TAATTATATC AAATATATGG GCAGACAATT
76441 TACTTTGCCT TTAATCTCAA GAAAAAAATA GCAATTACTT GGGGTCGGAG AGTAAAATAA
76501 GAAGTAGTGA ACCTTAAAGT AGCAAACTTT AGAACAGAAT AGTTTCAGAG GGGATGAGAA
76561 GAGGTGATTT TTCAGCTCAT CAACAACAGA TCTTATAATA AATTACATGT TCTGGTACTT
76621 TTCTTGTCTT TCTGTGTTAA ATTTTGCTAT TTAAAAAAAT AAATTTCAAA TACATTGTTC
76681 ATCTTAAAAG TCAAGAGTGT GTTTTATTAA AGTCAGTTGC TTTATTTGCA ACTCAAAAGA
76741 TATATTTGAG TTCCCAACTG GAGATTGTCC TATATGGTAA CTTGCGTAAG GTATGGTTAC
76801 TGAAAGTAAC CTACAATTTT CATGGGCTGA AATTCATTTC TATATTGCAG CGTACAAAAA
76861 TAAATAAATA AAAAATGCTT GTTTTCTTTG AAAACATATT ATCTCAGTGC CTCTAACTGC
76921 CAAATCTATT GGCTTTTTTG CAGGCTTAAG GGCTCTCCCT TGTTCCTTTA TGATCTCTAT
76981 CTTGAGGGCC AGACCTCCTG CCTTACACAA CTCAGAGGGG GACCTCAGAG CTCTTTAAAA
77041 AGAGCCCAAT TTCTCGCCTG TAGAGAAGTG AAAAGGATGC CCCACCCCCA TCTATGAAAA
77101 GAGGGATTTG ATAGTTTCAA TGTCTTCAAA TCAAAGATTT AAGTCTGTAG CCCCCCACCA
77161 CCCCGGACCC TAGCAAGGCT CATGAACCCC CTCCCATCCC GCCCTAATTG CTTTGGACTG
77221 GCCGTGGAAT CCTTGTCCCA GTCCACAGTT CCTGTGCGAC TGCACGAAGA ATTCACAGAG
77281 GACCTGTGTT ACTTCCCTTG TGAAGAAACA GAATTATCAT GAAAATTTAG GTGGAAACCA
77341 TTTCGCTTTT TTCTTCAAAA ATAAGGGAAG CATGTGCCCA ACCACCCCTG GAAAAAGAA
77401 CCTTCAGGGG CAAAGGAGCG AACAGGTAAT TTATAAGAAA AACAGAAAGT GGTCTCTGAC
77461 TGCCCCAGAC TTCCTTCGGA GTTGGGGGAA TTGGGGACGC CTGGACGCGT TGTTTTGTG
77521 TTTGTGGAAA AAATAAATGA AGAGCATGAA GCCCGAGGCT TCTGAGATCC TTTCCTGACC
77581 AAACCCAAGT GATTTGGTGC GGGGAATTTT AATATTTTTC CCCTTTTGTG AGGTGGAACA
```

Figure 1 (Page 24 of 73)

```
77641 AACACAACTT GGGAGCAGCG CAGCGGCTCA GAGCCTGCCA GCCAGGCGGG CGACCAGAGC
77701 ACCAATCAGA GCGCGCCTGC GCTCTATATA TACAGCGGCC CTGCCCAGGC GCTGCTTCAT
77761 CGGCGCTTTG CCACTTGTAC CCGAGTTTTT GATTCTCAAC ATGTCCGAGA CTGCTCCTGC
77821 CGCTCCCGCT GCCGCGCCTC CTGCGGAGAA GGCCCCTGTA AAGAAGAAGG CGGCCAAAAA
77881 GGCTGGGGGT ACGCCTCGTA AGGCGTCTGG TCCCCCGGTG TCAGAGCTCA TCACCAAGGC
77941 TGTGGCCGCC TCTAAAGAGC GTAGCGGAGT TTCTCTGGCT GCTCTGAAAA AAGCGTTGGC
78001 TGCCGCCGGC TATGATGTGG AGAAAAACAA CAGCCGTATC AAACTTGGTC TCAAGAGCCT
78061 GGTGAGCAAG GGCACTCTGG TGCAAACGAA AGGCACCGGT GCTTCTGGCT CCTTTAAACT
78121 CAACAAGAAG GCAGCCTCCG GGAAGCCAA GCCCAAGGTT AAAAAGGCGG GCGGAACCAA
78181 ACCTAAGAAG CCAGTTGGGG CAGCCAAGAA GCCCAAGAAG GCGGCTGGCG GCGCAACTCC
78241 GAAGAAGAGC GCTAAGAAAA CACCGAAGAA AGCGAAGAAG CCGGCCGCGG CCACTGTAAC
78301 CAAGAAAGTG GCTAAGAGCC CAAAGAAGGC CAAGGTTGCG AAGCCCAAGA AAGCTGCCAA
78361 AAGTGCTGCT AAGGCTGTGA AGCCCAAGGC CGCTAAGCCC AAGGTTGTCA AGCCTAAGAA
78421 GGCGGCGCCC AAGAAGAAAT AGGCGAACGC CTACTTCTAA AACCCAAAAG GCTCTTTTCA
78481 GAGCCACCAC TGATCTCAAT AAAAGAGCTG GATAATTTCT TTACTATCTG CCTTTTCTTG
78541 TTCTGCCCTG TTACTTAAGG TTAGTCGTAT GGGAGTTACT GAGGTATCAG ACGAATTGGG
78601 TGACGGGGTT GGAGAGTGGC CGTGGTGAGG TTACAGCATT TAAACCTTTA TTGCGGCTTC
78661 TAGGTCCCTG ACCGGAGGCT TTTCTCGCTG GCGGATGGTT TTGGGATGGC AGTCCCGCCC
78721 CAGGCCTGTG AACGGCAGAA AAGACCGCAA AACAAGAGCC AGTTTCTTAG TCTAAAGGGA
78781 TGTCCGGATT GGACTAAAAA ATTTTCAAAA GTCCCGCCCT GCTCCCGGGT TGGTCCGTTC
78841 TTCTAGTACA TGACTTTCAT TCTGTATTTA ATTGGATGGT GGAAGACGTT GCTTATTCTG
78901 TGTTTTTTGC TTTACTGTGA CTTAAAAGTT TTGCCTCTTT TCTCTTTATA TTAATGTCTG
78961 GGATTTCGGA CGCTTTCCAT GTTGTTGGTA GTCAAGTTGA TGTCTCCTGG AGGTAGTGGC
79021 AACATCCAGC CCTGGGAGGA GAGTGCGTGC AGGTACCTTT GTCCTACATT CCTCTGCTGT
79081 TAATTTCTCA TTCCTGTGGC AACGAAGGAA TGCATTTAAA AAACAGCCAC AACAGCGGCA
79141 ATAGCCCTTC CTCCACCCAA GGCAATCGTG GACCTAGGGA GTTTTTTGTG CCACATAACA
79201 TGTAGCCTTC CGCTAAACTG ACAGGTTTGA GCGTATCGAT TTTGAGCGTA TCGAAAGCAC
79261 AACTTTTAGC CAGCCATTTT GTCCTCGCAT GACTACGGTT GCTTATCCTG TTTAGACAGA
79321 CAGCAACATT TAAAAATCGA AGTTCCTTTA AACGTATTTT GTTTGGCAGT CCAAATGTTT
79381 CTATGCAGAA AACAGTATTT GTACTATTAA CTATGAAGAG TGTATGGATA AATGGGAGAC
79441 ATTTCTAATA AAGGCCTTCG TTAATGGTTC CCTCTGTTTG ACATCCATGG TGCTTCTGAA
79501 TACAGAAAGC CTAGCGTCTT ATATTCGCTT CTTTTAAAAT CTGGTGGGCA CATTTTGGTG
79561 AGACCTAAAT TATGGGGACT GGGGCTTCTG GAGATAAGCT GCTCAATTAT TCTACCATCT
79621 CCACAATGAT TAATATAGTG AGTTGATTTG TTAGTGATAG TGACCACGGA TTCATCCCAA
79681 GAAAGAGAAA GGGGAGGGAG GCAAGCAGAG AGACAGGAAG ACAGAGGCAG GGAAGAAGGA
79741 GAAAACATTC TCCCATGGTT TAAGTAATTT TGTGTTGTTA ATTTTACATT ACAACACGGT
79801 TTAACATGGT GAACCCTCTA TTTTGGTGTA AGGTTTAACA TATGGACATA TTTTTCCCAA
79861 GACCATTTAT GAACTTTCAT TTCTGCTTCC CCCTTCTTCC TCCCGTGCCA CCCTCCACGC
79921 TCCTATCAAT TTTGGCTGTT TTGTCATAGG CTAATACGCT ATAATTTCAT GGACAGTTGG
79981 ACTGTCTTAG GTTTCTCAGG TTTCTATTTT GTTCCTTTAG TCATTCCCAC AATTCTTAAG
80041 GTAGAATTGT ATTGTTTTAA ACATTGTGTT GTGTGCTATC CTCAATGCTG AGATGATTAT
80101 GTGACAAATG GCAAGTGTTC AACTAATACC TAAATCTGTA GTATCTTATC AAGCCTAATG
80161 CTACTTCACA ATGCCTACTC CATTCACCTC ACTTTATCTC ATTACTGGCA TTCTGTCATC
80221 TCACATCATC ACAAGTAAAA CGGTAAGCTA TTTTGAGAGA GATCACAGTC ATATAATTTA
80281 TATTTATATT TATTTATTTA TTTATGAGAC GGAGTTTCCC TCTGTCACCC AGGCTGGAGT
80341 GCTGTGGCAC GTTCTCGGCT CACTGCAACC TCCGCCTCAC GGGTTCAAGC GATTCTCCTG
80401 CCTCCGCCTC CCGAGTAGCT GAGATTACAG GGCCTGCCA CCATGCCCGG CTAATTTTTG
80461 TATTTTTAGT AGAGACGGGG TTTCACTAAG TTGGCCAGGC TGGTCTCGAA CTCCTGACCT
80521 CAGGTTATCC GCCCACCTCA TCCTGCCAAA GTGCTAGAT TACAGGCGTG AACCACCGTT
80581 CACAGACTCA AATCATTTTT ATTACAGTAT ATTGTTATAA TTGTTGTTTT ATTATCAGTT
80641 ATTGCTAATC TCTTACAGTG CCTGATTTAT AAATTAAATT CATCATTGCC ATGTGTATAT
80701 AGAAAAAAAC AGTGTATATA CGGTTCAGTA CTATCTGTGG TTTCAGGCAT CCACTGGGGG
80761 TGCAGTTTAT TAAACATGCA TTTACATTAG TCTCCCCTTT GGGAGACTAA TTAACTGAGA
80821 TGTTGTAACG TGACTTTAAT AGCAGATAGA GCTAATTTTC TCTCATTACT CTTCTTTTTC
```

Figure 1 (Page 25 of 73)

```
80881 AGAATTTTCC TGGTTATTCC ATTTTTTATT TTTCCATATG TATATTAAGA TCTCTTCCAC
80941 CTCCTCCTGT TTCTCCATCT CAACATCAAA CAATTAAAAA AAAAAAAAAG GCTGGGCGCG
81001 GTGGCTCACG CCTATAATCC CAGCTCTTTG GGAGGCCTAG GCGGGTGGAT CACGAGGTCA
81061 GGAGTTCAAG ACCAGCCTCG CCAAGATGGT GAAATCCCGT CTCTACTAAA AGTATAAAAA
81121 TTAGCCAACC ATGGTGGCAG GCGCCTGTAA TCCCGGCTAC TCGGGAGGCT GAGGCAGAGA
81181 ATTGCTTGAA CCTGGGAGGC GGAGGTTGCA GTGAGGCGAG ACCTTGCACT CCAGCCTGGG
81241 TGACACAGCG AGACTCCGTC ATAAAAAAAA AAAGCCGGAA GCAGTGGCTC ACGCCTGTAA
81301 TTCCAGCACT TTGGGAGGCT GAGTCAGGCA GATTACCTGA GGTCAGGAGT TCAGGACCAG
81361 CCTGGCCATG AAAATACAGC CTGGCCATGA AAACACACAA TAAATTAGCT GGGCGTGGTG
81421 TCACACACCT GTAATCCTAG CTACTCGGGA GGCTGAGACA GGAGAATCAC TTGAACCCAG
81481 GAGGCAGAGG TTGCAGTGAG TTAAGATGAC GCCACTGCAC TCCATCTGGG CGACAGAGCC
81541 AGACTCTCTC TCAAAAAACT AAATAAATAA AAATAAAGTT ATGGTACATT GAACTTCTGT
81601 GTTCCTTTCT CCCTTAGATA CTTTCATGGC TACCCATTTA ATTGATGTTC TTATCATCTC
81661 CAAGAGTTAG TCAGGAGAGG AATCAACCCA AGCAAAAATA GCTGATTTTC TAATTTTCCT
81721 TCAATGCCCT TTGGGGTCTT AATCCATTTG ATTTATGTAC TTTCAATTAA TCCTAACCTC
81781 GAATGTCTTC TGCAAACATG TTTCCACAGA TGAAACTCGT CAAATGAAAC ACATTCCTTT
81841 AATTTATAGA GTTAAAAATT AGAAAAATTT TCAATTCTAT TTGGCCTTTA GATTCAGTCT
81901 TGCATATGTT TTCTCAATTT TGTTCATGCT CTTTAGTTTT GTTTTATTCC ATCACAATTG
81961 TTCACATAGC TTACTGGCTT AGGTCTAATG AACCATTCAT TTGGAAATTA AAATTGGCCA
82021 TTTTAAGATG AAAAAGATTC TTGCCTCAAT TTTACTTAGT TTTTGAAACT GTCAATGAGG
82081 ACACATGTTT TTCTGTACTC TTAGATTCAC TAAGTAGTGT CTTGCAAATT TAACTGACAA
82141 AGGACAGATT AACATGCGAA AAAAAGAGCA TGCAATTTTA TTAGTATATT ACATGCACAG
82201 AGTTCCCAAA GAAAAAAAAA TTGAAACCTT AAAAACGCGG TTAGACTCAC AGACTTATAC
82261 ACCATTCCAA CAAAGGAAAG GGAGTTTGCA CTTCATGGGA TGACGAATTT GGGAATGTGA
82321 CAAGGAAATA AATACATGGG CAATAAAAAC CATGGAAGAT AAAATGAAAG ATAGAAATAA
82381 TTGTAGTAAG GTTTGTTTTT GCAGAGTCAT CTCAGTGCCA ACCTTCCATA TCTAGTGATA
82441 AGAATTGCTC TCTTTTTCCT GGTATAGCAG TTGGGGACAC TTTTACAAGG GAAATTTCTG
82501 TCACCTTCAC AAAGGGAAAT TTGGGTAAAG AGAAGACAGA GACCTCTTCC TACACCTGTT
82561 GATTTTCAAT TGCCTTCAGC TGAAAATAAC TTTTATGCCA AAGTAGAATA ATTTGGGGGT
82621 GACATCCTGA TATTCTTCAA AACTTATATT TAATTTCACA TTAGTAATTA TATCATTTTT
82681 GATTTTTAAA TTAGTTTTAT AAAATAATTT TGAAAACGG TAATAATATT CAAATAATTC
82741 CAGAAACACT GCTGATAAGC CAAAAACATC AATGAATATT GCATAAACAA CTGATAATTC
82801 AACCATGAAA ATTTATGACA TTGTTCTTGT GTGATAAAAC TATGAGTAAC ATAAAAACTA
82861 GAGGCTACTT GTAATGCATT ATTCCAAACT TTCTGTTTTT TATTTATTTA TTTATTTATT
82921 TTGAGACATA GTCTCTCTCT GTCACCCAGG TTGGAGTGCA ATGGCGTGAT CTTGGTTCAC
82981 TGCAGCCTCC ACTTCCCCGG TTCAAGCAAT TCTCCTGCCT CAGCCTCCTG AGTAACTGGG
83041 ATTACAGGCA CCTGACACCA AACCCGGCTA ATTTTTTGT ATTTTTAGTA GAGACGGGGT
83101 TTCGCCATGT TTGCCAGGCT AGTCTCGAAC TCCTGACCTC AGTGATCCAC CTACCTCGGC
83161 CTCCCAAAGT GCTAGGATTA CAGGCGTGAG CCACCATGCC CGGCGCATTA TTCCAAACTT
83221 TCATACACAG TGCTATCATG GCTACAAATT GAAGTATCAT ATTATACACT CCTAGGCAAA
83281 GCTCTGGATA TTTTGGCTAT ATAAGCCTGA GGGAAATGTA GTAAGGACAT TGTGGTTGAA
83341 ATTCATACCA GAGATGAACA GGCCCAGTGC AAGACAGAAT TACATCACTA AAGGATATCA
83401 GAAGAGAATA GGGATTTAGG GTACAGTGGC AACAACAGTT TTGGGAACTA GCATTTTTG
83461 AGCACTTATT TACAATATGC CAAGCACTGT TGCTGATTAC TCTATATTTA TTTTCAAACA
83521 CATTCTTGTC ACAGCACTTT GAAGTAAGTG CCATTGTCAT TCCCACTTCA GGGTGAAGGA
83581 CTAAAGCTTG GTGTCATTAA GGATGTAGCT AGTTAGCTGT GTGTGTGTGT GTGTGTGTGT
83641 GTGCATTTTT TTTTAAATTT AAAGTCAATA AATTTTTATT TGAAGAATTT CACATCAAGG
83701 TAAACTTTGT TCCTCTAAAG AGCTGGAGTC AAAATGTATC TTCAAAAGAT TCATCTTCAA
83761 GTTAGCCCTT CTTAATAGAA CTGATGCTTA ATCCACAGTT GTCAGCCCAC AGTTCTTTTA
83821 TTTTGACTTT TTTTTTTTT TTTTTTGAG ACGGAGTCTC TCACTGTCAC CCAGGCTGCT
83881 GGGCAGTGGC GTGATCTCGG CTCGCTGCAA CCTCTGCCTC CCGGGTTCAA GTGATTCTCC
83941 TGCCTCAGCC TCCTTAGTAG CTGGGACCAC AGGCGCATGC CATCGTGCTC GGCTAATTTT
84001 TGTATTTTTA TTAGAGACAG GGTTTCACTA TGTTGGCCAG GCTGATCTCA AACTCCTGAC
84061 CTCATGATCC GCCTGCCTTG GCCTCTCAAA GTGCTGGGAT TACAGGTGTG AGCCACTGCA
```

Figure 1 (Page 26 of 73)

```
84121 CCCGGCCTTA TTTTGCCTTC TTTAATCTCC ATTTGAACAT ACACATACTG ATGAAAACTA
84181 CAACATTCTT CACCAAAAAT CTTTGGGATT TAATTTCTTC AACCACTTTA CTTTGGGGTC
84241 ATTTTAAGAT TAGGTGTATC TGCCTGGTTC TCAATTTGAC ACCCTTTCTC TCTAAACATG
84301 AATGAGTTCC AATCATATTT ATTCCTAAGC TATCACACTC AAATATACTA CAGATCTGTG
84361 GAATATGCCA AAAGTTAAGG TGAAAAATTA AATTATTAGG TATTTCATAG TTTTGCTAGT
84421 TTTTGATCTG TGAGTGAATA TAACTATCCT CTATGTCCTG GCACTGTTCC TCAGAAACAT
84481 AGGGTCCACA TATGTAATTT TAAATTTTTT AATAGGCACA TTTTAAAAAG TGAAAAAAGA
84541 AATCTATTTT AATGATTTGA ATCCAGTGTA ACCAAAAATT GTTTCAACAA GGTATCTAAT
84601 ATTAAAATAT TGAGTTTTTA CTTTGTTATT TTACTAGTTC TTTGAAATCT GGTGTGTATT
84661 TTACACTTAA AGCACATCAC AGTTTGGAGT AGCCACATTT CCAATGCTTA ATACTCACAT
84721 ATGGTTAGTG GCAACTATCT TGGACAGGAC AGCTTTTATA CTCTGGGAAG ACACAAGCAA
84781 ATACTTGCTC TGCAGCAGAA TCCAGATGTT TTCCAAGAAA ACACTTTTTC TGACCTGTTC
84841 CTGAAACCCA GGTAGTGTCT CTAATACTTT ATATTTATT GGTTTGTCCT ATTGTAACCA
84901 CCCAACGGGC TCTCCTTGTC CACTTCCTAG ACAGAGCTGA TTTATCAAGA CAGGGGAATT
84961 GCAATAAGGA GCCAGCGCTA CAGGAGACTA GAGTTTTATT ATTACTCAAA TCAGTCTCCT
85021 TGAGAATTTG GGGACCAAAG TTTTTAAGGA TAATTTGATT GTAGGGACC AGTGAGTCGG
85081 GAGTGCTGCT TGGTTGGGTC AGAGATGAAA TTATAGGGAG CCTAAGCTGT CCTCTTGTGC
85141 TAAATCAGTT CCTGGGAGTG GTGGGTGGG GGACTCAAGA CCAGATAATC CAGTTTATCT
85201 ATATGGGTGG TGCCAGCTAA TCCATTGTGT TCAGGGTCTG CAAAATAGCT CAAGCATTGA
85261 TCTTAGGTTT TAAAATAGTG ATTTTATCCC CAGGAGCAAT TTGAGGTTTA GAATCTTGTA
85321 GCTTCCAGCT GCATGACTCC TAAACCATAA TTTATAATCT TGTGGCTAAT TTGTTAGTCC
85381 TGCAAAAGCA GTCTGGTCCC CAGGCAGGAA AGGGGTTTGT TTCTGAAAGG GCTGTTATTG
85441 TTTTTGTTTA AAAGCAAAAG TATAAACTAA GCTCCTCCCA AAGTTAGTTA ATCCCAAACT
85501 CAGGAATGAA AAGGACAGCT TGGAGTTTAG ACGTTAGATG GAGTCGGTTA GGTAAGATCT
85561 CTTTCACTGT AATAATTTC TCAGTTATGA TTTTTGCAAA GGCAGTTTCA CTGTCCACTT
85621 CACCTCACAT CAGGCCTCTG ACTAGAGGAT TCCAACAATA CTTAGGCCAG GACACCACCA
85681 TGTCTCCTTA TCCACCCTGA GGGAGTCCAA TTTCTGAAAC AAAGGAAACT ATATATGATA
85741 GTATGAAACT ATATATGAGA AGGAAATTAT ATATGATAAT CAATTTTAGG GTTATCTTAT
85801 TGATTAGAAG ATATTAAAGT GTGACACTGC CTGGCAATGA TATCTGCTGG TAGTAAGAAT
85861 TTGGCGAATT TAGTGAAATT CCTGAGGCTG AACCTCCACT TCTGTAAAAT GGAGACAGTG
85921 AGATAATTTG CCTTACAATG CTGAAGTAAG AATTTTACAC AATAATTCAG ACCAACCACT
85981 TCATGTGGTA CTTGGCCCGT GGAAGACTAT CAATGACAGT TAGTTTATAG TTTATACTAT
86041 TAATGAATCC TTTGTTTCAT TGTTATTTCC TTCTACACGT TGGCCTCTCT AAAAGAAGGT
86101 AATATTCAAT ACAAATAAAG TTAAAACAGC TTGCAGAGTT GTCCCAGGGA ACTCACTTAA
86161 CCACTGAAGT GTTCAAATTG CTTAAGGTTG ACTTTATATT CTCCTGACTA ACCTTTCTCC
86221 TTCTGGTATT TCTTCTGAGA ACAGCACCAC CATCCAAAGC ATCATGCAAA CAGTGGTCAT
86281 CCCAGACCAG TAATTCTCAA CTCACAGGGT GCTCCTGCAG AGATGTATTT GAATAGAGTG
86341 GTAGGATGCT GAAGAAGGCC ACGTAAAATT TGGCCAGTGA TCTGGGGCAG ATTTATCCTG
86401 AAGCTAATGA AACACAAGTG TAAGGGCCTG TACTTCCAAG GTGCAGAGAG GGGCCCTACA
86461 AATGTGTTAG TTTGTCTCTC TCTCTCTCTC TGATTTTAAA ATTTGCAGTA TTAAGGTACT
86521 TTAATCACGG ATGGTTCAGG CTGCTATTTT CACTCAATCC TCCTTTTTAT TAAAATCACC
86581 ATTGTCTGAT TATGTTAGAA TCCTGATGAA AATATTTGGA ATTTGAGTAA GAGAAAGTTT
86641 AGTTGAAGAT GTATCTAGTA TGGGGATAAT AAGTTACGTG ATTTGCATAT GTGATCATGT
86701 GTACTTCATT CGTTGCCAGC CAATCTGACG TAAGAATGGC TTCAAGGAGG CCGGGCGCGG
86761 TGGCTCACGC CTGTAATCCT AGCACTTTGG GAGGCCGAGA CGGGCGGATC ACGAGGTCAG
86821 GAGATCGAGA CCATCTTGGC TAACACGGTG AAACCCCGTT TCTACTAAAA ATACAAAAAA
86881 TTAGCCGGGC GTGTTGGCGG CGCCTGTAG TCCCAGCTAC TTGGGAGGCT GAGGCAGGAG
86941 AATGGCATGA ACCTGGGAGG CGGAGCTTGC AGTGAGCCGA GATTGCGCCA CTGCACTCCA
87001 ACCTGGGAGA CACAGCGAGA CTCCGTCTCA AAAAAAAAAA AAAAAGAATG GCTTCAAGGA
87061 ATGTTCCTAC TGCTCACTGG AATAACTCAC CTAAATTCCT GGCAAGATGC AGGTCTAGAT
87121 AAAATGTTAT GACATCTAAG TATTCAAAAC ACATTCCCAG CACTGAGAGT GAGTGTCTAG
87181 TGGAGAGTAG AAACGTATAG AGCCAGAAGC TAGTCTGGAA AGAATTCTTA CAAAGTTTAC
87241 AACTTACATG TGAAAGGAGC TTAACAGAGG ATTTTCCAAA TTTGAAAACA ATCCTAAAAA
87301 CTTACTTGAC ATTACCAATA ATGTGTTTTG AAACTGAAAT ACTTCTAAGT TATGAAGAAA
```

```
87361 ACATATTATC ATCAGCCACC CTGGAGGAAA GATTGAATTC TATTTCCATT ACCTATAGAC
87421 AACATTACAA AATAATTTCG ATCTGAAGAT GGAATCAGAG TATTCAGTCA AAACTACAGG
87481 AAAATATACT TGGTAGTGTC ATATTCAGAA GTTAATAAAA TATGCTATTT TCTGAATTTT
87541 GTGATGGCTG TTGTTTTGTC AGCTTTTATA AAATTGGAAT TTGATTTTAT TTTCCCATTA
87601 TAAATTTATA TTTACAGTCT GCAGTACTTT TGCATTTTTA ATTTTACATT ATAGTTTTTA
87661 ATAGTTAACA AGTTGTAAAA GGTTTGATCC CCAGAAAACC TTGATCTACC CCATCAGTTA
87721 AGTATACTAA TATATTTAGA AAATGGATGA AATCAGCATT TGAATATTTT TAAATATTTA
87781 TTAAAAGAGG ACATGGGTAA AAGAGCTTTG CAGTTGCCAC CCTTCATTCT CAAATTCCCT
87841 GGATAAGGAT GACCGCATAA TCTTTGGATG GTCATACGCA AGTCTTGTGT ACTTGTTACA
87901 TAAATCTATT TAGTGGACTT TTGGCAGTGT GTACTGAGGC CAGTTTCTTC CACCTGAGCT
87961 CTGACTCCAC CTCCAGCAGC CCAAAACCAA TACTGAATTT TGGGGTCAGC TATTGTTTTT
88021 GTGGACTTAG GTAACTACAC ACACATTGTC TTTATGATAG CTTTAATAAT ACTGCCATCA
88081 GAACTAAAAT TGTCACGTGG ATTAAAAGGA GTGACGGTGG TGTCCCCAGG AGCCTTTCAA
88141 TATGTAAGTA TTTACACATA TACATGCTAA AAAGACCCCT AGGAATTTTT TAACAAGGGC
88201 AAAACAGTAA CTCAGCTTGT TTTCTCGCAG TAAAACCGGT TGAAAAGGCC TGATAGACTT
88261 GTCTGCAGTT ACAAAACTTG TGTGTAGTTA TCACCTTTAT ATCTCCTGGA AACTAACATA
88321 GACAACCGAA TGGGTTACAA CTGTTTTTAA GTGAAATTGT GAGTGGCTCT GAAAAGAGCC
88381 TTTTCAATGA GGAAGAAACG GGCAGACTTA TGCCCTTTCC CCACGGATGC GACGTGCCAG
88441 CTGGATATCT TTGGGCATGA TGGTGACGCG TTTAGCGTGA ATAGCGCACA GATTGGTGTC
88501 TTCGAAGAGT CCCACCAGGT AGGCCTCACA AGCCTCCTGC AGCGCCATCA CCGCAGAGCT
88561 CTGGAAACGC AGGTCGGTTT TGAAGTCCTG GGCGATTTCT CGCACCAGGC GCTGGAACGG
88621 CAGCTTCCGG ATCAGCAGCT CGGTGGACTT CTGGTAGCGA CGGATTTCGC GCAAGGCCAC
88681 GGTGCCCGGG CGGTAGCGAT GAGGTTTCTT CACGCCACCG GTGGCCGGAG CGCTCTTACG
88741 GGCTGCTTTA GTAGCAAGCT GCTTGCGCGG AGCTTTGCCG CCGGTAGACT TGCGAGCTGT
88801 TTGCTTCGTA CGAGCCATTT GCAATGAGAG CACACACAAA AGTGTAGTGA ACTGAGAGCA
88861 AGTGGCCTTT AAATATAGTG AGAACATTC TGATTGGTCC TGTAATATTT CAAAAGTCCC
88921 GCGCGATAAA ATCATTGGCT GAAGAGTGAC CAGACTGATT GGTTCATTAC TAGACAATCT
88981 TATTGGATGA GTTGCCCCAC CGCCCATCCT GTCCTTTTCG TTTCAGTTAT CTGCAGCGAC
89041 AAATTGTCTA AAATTCTAGT TCATCCAGTC CCAAAGAACA GAGTGTATAA CAAGGTATCT
89101 AAGGATTTTT AAAATGTAAA TTCCGATTCA GTAAGTTTGA GTGGGACTTG AAATTCTGCA
89161 TTCCTGACAG TCTCGCAAGT TATCAATGCT GGTGAACACT CACTAAACCA CCAGAAACGT
89221 TCAGACTCAT GTCGGGAAAT AACGCTTATA TTCAGAGAAT GAGATTCCAT GCTATTTTGT
89281 TACTGGCGAA CAGCAAGTTT CCTTGCCCTT TGTTTTCTAA GTCCAAGTCA CATTCCCACC
89341 CTGCCTGTTC TCAAAATGTC TTATTTTGGT TGGCCTTAAG TTTCACTTTG TATACTCTAA
89401 AATGTACTTT CTAAAGGAAG GTGTTATTTT CTCGAAACTT AACTTTTTAA CACCATTAGG
89461 CTAGGGGGGC GGTGGCTCAC GCCTGTAATC CAGCATTTT GGGAGGGCGA GATGGGACGA
89521 TCACTAGAGG CCAGGAGTTC AAGACAACCC TGGCTAAAAT GGTGAAACCC CGTCTCGCAT
89581 AAAAATACAA AAACTAGCTG GGCGCGGTAG CAGACGCCTG TAATCCCAAG TACACAGGAG
89641 GCTGAGGCAT GAGAACCGCG TGAAGCGGCG GGGTGGAGGT TGCAGTAAGC CGATATCGCG
89701 CCGCTGCACT CCAGCCTGGG TGACAGAACT AGACTGTCTC AAAACAAACC AATCCAAACG
89761 AAAAGCAAAA AATACCCTAA CAGAAGCAAG TTATCATCCT TTCTTGTGTA ACTATGGACG
89821 GCTCTGAAAA ATGCCGTTTC AAGTGTAAGC TACGTTTTCT GATTTGAGTG TTTACTTGAC
89881 CTTGGCCTTA TCGTGGCTCT GTTATTTTGG CAACAGGACG GCCTGAATAT TGGACAGGAC
89941 GCCTCCCTGA GCAATAGTGA CGTTGCCCAG CTGCTTGTTG ACCTCCTCGT CGTTTCGGAT
90001 GGCCAGCTGC AGGTGGCGGG GGATGATGCT GCGGGTCTTG TCACGTATGG CGCTGCCCAC
90061 CAGTTCTAAG ATCTCGGCGG CCAGGTATTG TAAGTACACT GGCGCACCGG CTCCGACCGG
90121 CTCAAAATAA TTGCCCTTTC GAAAAGATG ACGGACTCTG CCCTATTGGG AACTGCAAGC
90181 CCGGTAGCGA CGAACAAGTT TTTGCTTTAG CTCCATTTTC CACGTCCGCA AATAGCGACC
90241 TATGAAAGCA GCGGAAAACT GTGAAAGACA AGCAAGCTGG AATGGCGCCT GAACAAATCC
90301 TTTTATACAA ACTGCAAGGC TGCAATAGGA AGCTATCCTA TTGGTCAATT ATGTTTGGTG
90361 CTTTATCCAA TAGAAAAGA TAACATAAAT TCCATATTTG CATAAACCCC ACCCCTCAGT
90421 GAAACCGTGT TTCTTTTGTC CAATCAGAAG TGAGGAATCT TAAACCGTCA TTTGAATCTC
90481 AGGACTATAA ATACATGGGC TCTGAACTGT TCTCTGTACT ACTCTGTAGT GGAGAGTGTT
90541 AGTAGCTTTT CTATTCTGTT TAGGAATAGC AATGCCTGAA CCCTCTAAGT CTGCTCCAGC
```

Figure 1 (Page 28 of 73)

```
90601 CCCTAAAAAG GGTTCTAAGA AGGCTATCAC TAAGGCGCAG AAGAAGGATG GTAAGAAGCG
90661 TAAGCGCAGC CGCAAGGAGA GCTATTCTAT CTATGTGTAC AAGGTTCTGA AGCAGGTCCA
90721 CCCCGACACC GGCATCTCAT CCAAGGCCAT GGGGATCATG AATTCCTTCG TCAACGACAT
90781 CTTCGAGCGC ATCGCGGGCG AGGCTTCTCG CCTGGCTCAC TACAATAAGC GCTCGACCAT
90841 CACCTCCAGG GAGATTCAGA CGGCTGTGCG CCTGCTGCTG CCTGGGGAGC TGGCTAAGCA
90901 TGCTGTGTCC GAGGGCACTA AGGCAGTTAC CAAGTACACT AGCTCTAAAT AAGTGCTTAT
90961 GTAAGCACTT CCAAACCCAA AGGCTCTTTT CAGAGCCACC TACTTTGTCA CAAGGAGAGC
91021 TATAACCACA ATTTCTTAAG GTGGTGCTGC TGCTATTCTG TTTCAGTTCT AGAGGATCAA
91081 CTGGAATGTT AGCGAAGACA AGTTTTAGAG CCAAGGTTAA CTTGGACGGG GCCGTGCGCG
91141 GTGCCTCTTG CCTTTAATCC CGGCAATTTG GGAGGCCGAG GCGGGCGGAT CACGAGGTCA
91201 GGAGATGGAG ACCATCCTGC TTAACACGAT GAAACCCCGT CTCTACTAAA AATACAAAAT
91261 AATTAGCTGG GCGTGATGGT GGGCGCCTGT AGTCCCAGCT ACTCGGGAGG CTGAGGCAGG
91321 AGAATGGCGT GAACGCGGGA GGCGGAGCTT GCAGTGAGCC GAGATCGCGC CATGGCACTC
91381 CAGCCTGGGT GACAGAGCGA GACTCCGTCT CAAAAAAAAA AAAAAAAAAA AATTAAAAAA
91441 ATATGAAGTT TTGAAGCAGA AATTATTTTG TCGTATGTTC TTTCATAAAT TTTTTGCCTG
91501 CCTGCCTTCT TCCTTTGTTA CAGAACTCCA ACACTTACCC AAAGGTAGCT GTTGGGTCAG
91561 GGTTTCTGTA CTATAGTCCC TTCTGTGGTG GCCAGAAATA TGTTACAGGA AAGAGGTCCC
91621 CATCCAGACC CCAAGAGAGG GTTCTTGGAT CCCGCGCAAG AAAGAGTTCA GGGTGAGTCC
91681 GCAGTGCAAA GTAAATGCAA GTTACTAAG AAAGTAAAGT GGTGAAACGA CAACTACTCC
91741 ATAGACGGAG CAGGACATTC CCGAAAGTAA GAGGAGGAAG GCATCCACCC TAGGTACAAT
91801 ACTTGTATAT ATGGGGAGAT GTGCTCTGCT ACAAGTTTGT GATAAAGGAT TAATTTTCTT
91861 AGTTACTATA TTTTGCAAGA ATCAACATTA TTATCTTTAA ACAAAATTAA GAATGCCTTT
91921 GTTCTCCAGA TATAGGGATA TCTGGACACT CCTAAGTCTG AGTCTGTTTA GTAAACATTA
91981 TTTATTTGTT CCCTTAACCG TAAACATCTA GAAGCTAGGA ATGACTGACT TTCTGGGAAT
92041 GCAGCCCAGA AAGTCTCAGC CTCATTTTCC TAGCCCTCAC TCAAAATGGA GTTACTCTGG
92101 TTCAAGTAAC TCTGACACTT TTCTTCTCTT TTTTTCTTCT TTTTTCCTTC CTTTATTTTT
92161 TATTTTTTAT TTTTGAAATA AGAAATCAAG AATACTTGAT GTTTCATCTA AAACAATACC
92221 CATAATTGAT AAGCCAAAAC AAAAACCTAG GTCTTCTAAC TCAAAACTAG GATGTTTTGC
92281 TGTCTCTGCT GATACTCGGC TGATCGTTAA TAGGTAATTA ACAAACAAGC CTTGCTATGT
92341 CCCCCTCAGT TTATTACCAT TAGATCATAT GCCTACTGTC AATCATATTA ATCCACAACT
92401 ATGCATTTCA CAAAACTTGC CATAAAAATT CACAGGTTTC CCGCTTCCCT CGAGTTTTCA
92461 TTTCCGAAGG GTCCCATGTA ATATAAAACT TATATTAAAT ACATTTGTAT GCTTTTCTCT
92521 TGCTAATCTT TTTTTTTGTT TTTTGAGACT GAGCCTTGCT CTGTCACCCA GGCTGGAGTG
92581 CAATGGCGCG ATCTCGGCTC ACTGCAACCT CCGCTTCCCA GGTTCAAGCG ATTCTACTGC
92641 CTCGCCCTCC CGAGTAGCTG GGACCACAGA TACGTGCCAC CATGCCCCGC TAATTTTTGT
92701 ATTTTTAGTA GAGACAGGGT TTCACCGTGT TGGCCAGGAT GTTCTCAATC TCCTTACCTC
92761 GTGATCCGCC CGCCTCGTCC TGCCAAAGTG CTCGGATTAC AGACGTGAGC CACTGCACCC
92821 GACCAATCTG TCTTTTGTA GAGGGGCCTC AAGCATGAAC TTACTGATGG GTGAGAAAAA
92881 CAGAATTTTC TTTTCCCCTA CAATATAAAC ATTAATTGTA ATGTTATCAT TCAGGACATT
92941 TTGGTGACCA ATCTTACAGA AATTTTATCT TGTGCAAGTC TATGCAAACC AATATGTAAA
93001 TCTTCTATAA GTGAGATTGT ATTTCACTTT TCTAGTATCC TTTTAAATTA ATAAAAGAGA
93061 TTCTAATGAT TATTTTCATT ACTGCATTTC ATTGTAGGGA AGTAGATAAT TGCCCTTTAT
93121 TCACTGACCT TCGCTTTTTA AAAATTTAAA CCATGTTACC ATGAAAATGC TTTTCAGTAT
93181 TTCTCTACAC ACAAGATTGC TGTAAGGGCA AAAATAGAGA TAGGAATCAT GCATCCATTG
93241 ATATACATAT TTTGATTTTT AATACATGTT ACCAAGTTGC CTCCTGAAGG TCTGTTTACA
93301 CTCTCACCAA CAGGGTGTTT TTTCCTGACT TCCACAAATG CTCTTGAACA GTGGGTGTGT
93361 TAGTCTGTTC AAATTGCCGA CATGAACAAT TAAATCTCAT TGTTGTTTTT ATTTTAAGA
93421 CAATTATTGT TTGAGACTGC ACATTTGAT AATAACATTT CTTCTATTAT GGTTTGATTA
93481 CTCATGATTC TTGCCCATTT TCTTTTGGGA TGTTGCCTTA TGTACATTAT TTTAAATAGA
93541 TAGCTCCATG TATTAAAAGA TTATTAAGTT TGAGGGCTTA TGATATGTCA GTTACATTTC
93601 TAAGATTTTT TTTTTTTTTT TTTTGAGAC GGAGTTTCAC ACTTGTTGCC CAGGCTGGAG
93661 TGCAATGGTG CGATCTCGGC TCACCGCAAC CTCCGCCTCC AGGGTTCAAG CAATTCTCCT
93721 GCCTCAGCCT CCCCAGTAAT TGGGACTACT GGCAAGCGCC ACCACGCCTG CTAATTTTG
93781 TATTTTTATT AGAGATGAGG TTTCTCCATG TTGGTCAGAC TGGTCTCGAA CTGCCGACCT
```

Figure 1 (Page 29 of 73)

```
93841 CAGGTGATCC ACCCGCCTCG GCCTCCCAAA GTGCTGGGAT TACAGGTATG AGCCACTGGG
93901 CCCGGCCACA TTTCTAAATT CTTTATAAGT ATAAATTCAT TCAATCTTCA CCAAAACTCA
93961 ATGAAGTGTG AGTACTATTA TTATCATTGT TTTACAGATC AAAACAAGTA ATACAGTCAC
94021 TTACTGAGTT CTATACACCT GGTAATTTTT TTGTTTCGTT GTTCTATCAA TTATTGGGGA
94081 AGGGGTGTTG AAATCTCTAC CTTTAAATCA TGTATGTGTC TATTTCTCCT TTCGGTTCTA
94141 TCAGGTTTTG CTACACATAT TTTGCAGTTC TGTTATTTGG TGCATATACA TTTAGAATTG
94201 CTTGTTTTTC GTATTGGATT GACCCTGTTA TCATTATGTA ATATCCCTGT CTGTTCCTAG
94261 TAATTTTCTT TGCTCTGAAA TATACTTATC TGATATATCA TCCAAAAGAC CACCAGGATG
94321 GCTAAAGAGT AGAAAGGAGA GATTTACTGG CAATACTAAT TTGCAAGCCA GGAAGAGATG
94381 GTCCCAGAAC CTGCCAAAAT TACTCTCTCT TTGGGGAGAA GGAGCAGGTT GGTTATTTTT
94441 ATGCCTCATA GGCTATATAT TACACAATAG AGTCATACAT ATTTAGCACG TTTGGGGGGA
94501 CAGCTATATA TATTATGAGG GGTGCCAAGT GCATTCACAA TGGATAAACA CGTGTAATAT
94561 ACCTCCCATG TTCACTTCGA GGTTAAATTT TGGTTAAAAT GAGGTAGAAT TTAGGTCTTT
94621 ACATCACAAG GTGAACTATA GGAACAAAGT TTACGTGCTG CCTCTAGCAG CTGGCTGAAA
94681 ATGGCTTAAG GTCTACAATT ACGTGTAAGA ATAGAATGTG TGTCAAGGCG GTCCTCTGTC
94741 CAATCAGAGT TGTAGTGGAC TGGACTGTAA ATCAGAGTTA GGAGGGCTTC TGATAGCTCC
94801 TATAGTTAAG GAATTTAGCA AGTGTGAGTT TTTTGGTAGT CTTTGGAATT TAGGAATTTG
94861 CCATGCCAGC CAAGCCATGA ATGCTCTACC AGTAGGTAAC TTTGTTTGCT TAATCTTAGA
94921 GTCTGTCTTA GTTGGTATAG GGCATCTAT TTTGGTCTTT CAGATCCCAG ATATTATTAA
94981 TACAGATACT CTTGCAGTTT TGGGCTGATG TTTATATGGC TTATCTTTTT TGCAGCCTTT
95041 AATTTCAACC TGCGTTATGT TTATATTTGA AGTGAGATTC TTGCAGACAG TGTACAGTTG
95101 TTGTTTTTTT TTTTTGAGA TGGAATTTCA CTCTTGTTGT CCAGGCTGGG GTGCAGTGGC
95161 ACAGTCTCAG CTCACTGCAA CCTCCGCCTC CTGGGTTCAA GGGATTCTCC TGCCTCAGCC
95221 TCTTGAGCAG CTGGGATTGC AGCCATGCGC CACCACACCC GGCTAATTTT TGTATTTTTA
95281 GTAGAGACAG GATTCACCAT GTTGCCCAGG CTGGTCTCGA ACTCCTGACC TCAAGTGATC
95341 CGCCAGCCTC GGCCTACCAA AGTGCTGGGA TTACAGGTGT GAGACCTCGC GCCCAGCCAA
95401 ACTGTTTTTT TATGGGTGTA TTTATACCAC ACACATTTAA TGCAATTATT GATATCTTAG
95461 GGCTTAAGTT CATGAAGGGT AGTGTGGGAA CCATAGTCTC TTGGCCCACT AAATGTTTGC
95521 CAGAAATCAC TGACAAGGCA GATTGATTAA TAGGTGAAAA GGCATTTTAC CTATTGTTTA
95581 ACGTGTCTAT GTGGGAGCAT TCAGAATTAA TTACCTAACT TCCCAATGAG TTATAGATGC
95641 TTATATACCA TTTTTAGATC ACAGAAAGAA TTGGGGCTTA GATTCTGGTA AAACAGGTTA
95701 TGGGAGGCAA AAGAGGTTTG GCTTGCAAAG GTGGCCTTGT TAGGTAGGTG AAGCCTCCCT
95761 CAGAAAGAAC AGATGGTAAA TGTTTCTTTT ATGATTTTTA AGTGTCAGAC TCTCAGTCTC
95821 TCCTGGATCT GGGGAAAGGT ATAGAAAGGT GAGGAGGCAT GGCTGCATTA ATGGAGATTC
95881 TCTACAGATG TAAAATTTTT CCCATTTAAG GCAGCTTTGC AAGCCCATTT CTGCCTGCTG
95941 GCCAAGCAGC AGCCATTTCA AAATATGTCA AAGAAATATA TTTTGGGGTA AAATATTTTG
96001 ATTTCCTTTA GACTGGTGGC CTTATAAGAA AAGGAAGAGA CACCTGAGCT GACACACATA
96061 CCCTTGCTCT CTCAACATGT TATGATGCAG TAAGAAGGCC CTCACCAGAT ACTAATTCCA
96121 TGCCCTTAGC TTCCCAGGTT CTAGAACAGT AGGAAATAAA TTTCTTTTCT TTAAAAGTTA
96181 GCCAGTCTGT GGTATTCTGT TATAGTATCA CAAAATGGAC TAAGTAACTA TATTATGATC
96241 ATCTTACATG ACTGATCCCT CCTACATCAT ACACATACAC AGGCCACATT TGGAACATTG
96301 TTAGAGGTTC CTCTGCCCAG TACAAATGTA CTACAAATTA TATATGTATT TTTAAATTTT
96361 TGAGTATCTT CAATAGTATA TTTTCGTTAA CTTTTGTAGT CAAAATGTCA TTATAACATG
96421 TATTCAATAT GCATAATTAT TAGTCAGATG TTTTACATTC TTTCTTCATA CTAAGTGATA
96481 TGGTTTGGAT ATTTGTCCCC TCTAAATCTC ATGTTGAAAT GTAATCTCCA ATGTTGGAAG
96541 TGAAGCCTGG TGAAAGGTTT TTGGATCGTG AGGGTGAACC CCTCATGAAG CGCACTCTTC
96601 AGGGTAATCA ATGGGTTCTC ACTTTGAGTT CACAAGAGAT CTGGTTCTTT AAAAGAGTGT
96661 GACACCTCCC CCATCTCTCT CGCTCAGCTC TCACCATATG ATATGCCTAC TCCCTCTTCA
96721 CCTTCCACCA TGATTGGAAG TTTCCTGAGG ACTTGCCAGT AGCAGATGCC TGCACCACAC
96781 CTCCTGTACA GCCTGCACAA CCGTGAGCCA AAAAAAATTA CTTTTCTTTA TAAATTAGTC
96841 AGTTCAGGG ATTCCCTTAT AGTAATGCAA GAACGAACTA ACACACTAAG TCTATTTCAT
96901 ATTTACAGAA TAGCTCAATC TGAAGTACCC TTTTCAACT TCACAGTAGC TACTTGTAGC
96961 TAGTGGGCAC TGATTTGGAG CGTGTTCAAG GGTGAATTGT ATTATGCAAT TAACAGATTT
97021 TTTTTATTGT TTTCGCAAAC CACGAGGCAT AGATTGTCTT ACTTTCTCTG CTCCTGGTGT
```

Figure 1 (Page 30 of 73)

```
97081  TGGAGTTGTT ATTGGGAAAC AACTTATTTT CCTCTTATAT TTATATGGAA TAAATAACCC
97141  CCAATATTTC CCTCCCCAAT ATCTGCCTTT TGTATGTTTT TTGAAGGCAA GTGCCTAGAA
97201  TTTACTGTTT TTGAAGCACT TACTGAAAGG ATTGCCATCA AGTTGTTTTG CTAATAGTAC
97261  ATGCCAGGCG CTTGTTGGTT TGCTTAATTC AAGGTAACTT GGATGAGAAG AAGAGTTTTT
97321  CTCATCCATG GCTCAGTGGA GTATAGATTA CTGATATTGT GACTGGATGT ACTCCTGCTT
97381  TCTAGTCTGA GTTTTTGAAG CTACCCTTAA TCTTGGTTTC AATTTTATCT AGCCCTGTAC
97441  ATATCCAAGG CTCTTTCCAA AATGGTCTAC GATTTGTTTA GGAAGTTAGA ATAGCTGTAC
97501  TTTCTGAACC ACGGTTCCTG ACATTTTCTG GACTTCAAAC ACATCCAGCA TTTTATCGAA
97561  GTATTTATCC TTCCTACTTG GCTGGCTTCT TCCTTGCCTT CAGGTCTGAA TTCAAATGAC
97621  ATTCTCCTGA TGAAACTTTC CATCCTTATT TCTATTCTTT TTTCTTATCC CCTTTCTTTA
97681  TTTTTCTCCA CAGCACTCAT CACTTATCTC TACATTTTCA TTATGTATTT ACCTTATTGT
97741  GCACCTCCCA CTACAAGACA AGTAGCACCG TAAGGAAACA GGTTGTCTGC TTTTTCACTG
97801  CTATGCTCCC TGCACCTAGA ACACTCTCTG GCACTTAGCA GGTTTTCAGT AAATATATGC
97861  TGAACTAATA ATGCTGGATA TACATCTCCC TCATGAACTC TCTAAATCCT TCTAATTTAC
97921  ATTGATCAAT CTTCTTTTCC ATGTGCTTTT GTATGATTTA TTGCTCAAAA TCTTTATTTT
97981  ATATGCAGAA CGTGCACTGC TATTTAATCT TCATGTACGT AAGTCCTCCC TTCTCTGAGT
98041  ATAATCTCTT CAGGGCACTA TCTGAGATAA CTTTTTAACA TCTCCATCAT GAATCTTGTA
98101  CCTTTTCAAA GAAAATGAGC CAGTGATTAC TGATGTTTAC GGCTATTGTT GAGGGTGAAG
98161  ATCATTATAA TTTTGAAAAG GGAAGTTGAA TATTGTGAAG GGAAAGATAA CACTAGAGTC
98221  AGAAGACTTG GGAGAAGGCA AAAACAAAC TAAAAATGAG CACTTTTAGT CTCCTGACAG
98281  TTTCTCTGAA TCAAATCCAT AGTTCTGTGA CAGCGTTGGC TTAGAAGCAG ATTTTTTTTT
98341  TTTTTTTTTT TGAAATGGAG TTTCGCTCTT GCCCAGGCTG GAGTGCAGTG GCACGATCTC
98401  GGCTCACTGC AACCTCTGTC TCCAGGGTTC AAGCGATTCT CCTGCTTCAG CCTATGGAGT
98461  AGCTGGGATT ACAGGCTCCC ACAACCACGC CCAGCTAATT TTTTGTATTT TTAGTGAAGA
98521  CTGGGGTTTC ACCATGTTGG CCAGGCTGGT TACGAACTCC TGTTCTCAAG TGATCTGCCC
98581  GCCTTGGCCT CCCAAAGTGT TGGGATTACA GGCATCAGCC ACCGTGCCCA GCCAGGAGCA
98641  GATTTTTTTA CACTCATGTT TCTTTTTCCT TCTGTCATCC TGTTTCAGTA TAAGCAGACC
98701  ACAGATAGAA GTAGTAGATA CCTCAGAAAT TCCTGGAATA ATTAATCCAC GTTCATCTGT
98761  ACTCCATCTG CTCCTATCTC ATGGAATATA AAAGGAAAAA CACCAAGATT TCCCTAGGCA
98821  ATCTGTCTTG ATTTTAGGTT CCTCAACAGG AGAGCCAGAC AATGGCTGTA ATAATATTGT
98881  CCCGGCCAAG GAAAAACTTC CCCTTTGCCC TCCAAGGTT TATGGAAAAT TACTGGCAAA
98941  ACACAGATTA ACTGGAGAAA AGGCATATAT ATTTATTTCA TCACAATTTT ACAGGAGATT
99001  TTAGAATTAA GACTGAAAGA TACAGGGGAA ATTGCCCATT TTTATGCTTA GGTTCAACAA
99061  GATAAACAGC TGTATAGGGT ACGATCTAAT GCTAACAGAC TGAGTGGGGA AGCCCCGCAA
99121  GGCTTGTCTG TCAAGATTCT TCTTGACCTC TCAGTGCAGC ATTTCTTCCT TCTGGTTATA
99181  GGACAAGACT CTCTTTTAGA ATGGGGGTC TTATGACCTA CAGGCAAACA AGGTAGGTTA
99241  GAGTAATACT TTTAGGTTTT ATGGCTGGTT CTAGGGAAAA GGAGTTCTGG TTTGTATGGC
99301  CTACCTTGAG GAGGAATTCT GGTTTCTATG GCTAGACTTT GGGGAGAATG GGACTTACAG
99361  ACAGGAAGGC AGAAGGTGGT CAGTGAAACA CTTTTATAAT CATAATCCCA TTTTGAGTAT
99421  TTCTGTGTTA TGGAATGTTT GTTCTCTCAT TTCCTGAAAG ATTCCAGAGA CTCCTCATTC
99481  AGTGTTGTGA AAAAGTTCAG GAAATGCAAC TCAAAAATGT GCCACTTTGT TACGCTGATT
99541  TCTTTGAACT GAGGGCACCT AGGAAACAGT AAATTCAAGG AAGGGCTTTC GCTGAACTCT
99601  AATCAAAAAT TTGAAAATTA AAAAAAATT CAAAAAGGAA TTTAGTTGTT AAGATTCACT
99661  TCCCTGGGGA ATCTCATCAA CCAGAGAAGA TTAACTGTAT CACAGGAGAG GAGACTGGTG
99721  GTTAACACCA TCTAAACAGA CTTTGTCACA GCTGTCACCT ATTCTTTGAA ACACCCATTT
99781  ATTTTTCTCC AAAATCATAT ACTCTCCCCT AAGTTGCCTA CATCCCCCTT CTTTCTCCCT
99841  TATGAATCAA GAGAGCTTAT AAGCTTCTAC AGTTCACTGG GATTTGGGGT ATTCGCTTTT
99901  CTTCCCTCCC ACTCCCCCTC CCCTTTTTTT GTCTTTGAGA CACAGTCTTC TGGCTCTGTC
99961  GCCCACGCTG GAGTGTGGTG GCTCTATGTG AACTCACTGC AACCTCCTCC TCTCGGGTTC
100021 AAGCGATCCT CCCACCTCAG CTTCTCGAGT AACTGGAACT ACAGGCGTGC ACTACCAAGC
100081 CCGGCTTTTT TTTTTCTTTT TCTCCCCCGT TTCTTTTTTG GTTATTTTAC TGGAGACAGG
100141 GTTTCTCCAT GTTGTCCACG CTGGTCTCGA ACGCCTGACC CGCCGTCCTC GGCCTCCCAA
100201 AGTGCTGGTA TTACGGGCAT GAGCCACTGC GCCCGATTTG AAGGACCTCT TAAATATCTA
100261 TTTAGAAATT GGTCGGAGTC CACTCCTTTC CAAAAACATG AGTCACAATC CGGGAAAAGC
```

Figure 1 (Page 31 of 73)

```
100321 ACGAGCGGCT GAAAGTCAAA ATAACCAGAA CAAAACCTCC ACTCATGCTT AAAAAAGGTA
100381 TTTTGACAAA ATCCTAATTC GGCCAATTAT TATTAGTATT CAAGTCGAAG GCTCGTCAAG
100441 CCAGACTGGG GATTGGGTCA AACATAAACC TTACACCAGA CGGAAGGATT ACATGCAAAT
100501 GAAGGATGCA GATTCTGATT TCCCATTGGG TATTTGACAT TAGCCAATGG GAGAATTCCT
100561 CACAGCCTAC CTCCAGTCAG TATAAATACT TCTCTGCCTT GCGTTCTAAT GTAGTTTCAT
100621 TACATTTTCT TGTGGCGATT TTCCCTTATC AGAAGTAGTT ATGTCTGGTC GCGGCAAACA
100681 AGGCGGTAAA GCTCGCGCCA AGGCTAAGAC TCGGTCTTCT CGTGCAGGTT TGCAGTTTCC
100741 TGTGGGCCGA GTGCACCGCC TGCTCCGCAA AGGCAACTAC TCCGAGCGCG TCGGGGCTGG
100801 CGCGCCGGTG TATCTCGCGG CGGTGCTTGA GTACCTGACC GCCGAGATCC TGGAGCTGGC
100861 GGGCAATGCG GCCCGCGACA ACAAGAAGAC CCGCATCATC CCGCGCCACC TGCAATTGGC
100921 CATCCGCAAT GACGAGGAGC TTAATAAACT CTTGGGGCGT GTGACCATCG CGCAGGGTGG
100981 CGTTTTGCCT AATATTCAGG CGGTGCTGCT GCCTAAGAAA ACTGAGAGCC ATCATAAGGC
101041 CAAGGGAAAG TGAAGAGTTA ACGCTTCATG CACTGCTGTT TTTCTGTCAG CAGACAAAAT
101101 CAGCCTAACA GCAAAGGCTC TTTTCAGAGC CACCTACGAC TTCCATTAAA TGAGCTGTTG
101161 TGCTTTGGAT TATGCCGCCC ATAAAGATGT TTTTGAGGTG TTTTTAATGG CTTTGAGTGT
101221 GGCACTTTTA GTAATTTGTC CTGCAGAAAT TAGATCCATA GAAACCTCAG GAATTCTAGG
101281 TATGTGGGAG AAGTGCCATG CAGCACAAAA CATGTTTACA GGGGTGATTC GCGTTAAGTT
101341 TCACACACAG CAGTTACTAC ATTTTAGAGG AAGGAAATTA TACCCATGAG TGCATTCCTA
101401 ACTATCTTGA ATGGAAGTGT TAAAACCCGC ATGCCCCACA CAAGTTTGAA TATGTCATAC
101461 CATTTGCTGT AGCAATTAAT GGCATACACA ATTGAGAGCA CACACATTAC CACTGAACAT
101521 TTGAGTATGT ATTTCCCAAA ATGAGCTTTT TTCCAGTTTG GGGATGTTTT GCTTTGTTTT
101581 GGGGTGGAGT CTCCCTCTCG CCCAAGCTGC AGTGCAGCGG CGTGATAACA GCTCACTGTA
101641 ACCTCGAACT CGGGCTCAAG CGATCCTCTT GACAGCCTTC TGAGTAGCTG GGATTACAGG
101701 CGAGAGCCGC CACGCCCGGC TAAGAGCATT TTTCTAATTG CCCACACTTC TTATGCGACA
101761 CCCAGAAAAA TACAATTTTA AATAAAGCGC ATATGCAAAT TTCCCTAATC GTCTCCAATA
101821 TTCTCTGATT TCTTTTTTAT ATTTTAACTA GAAACAATTG GAGGTTTCCG CGTTGCTTTG
101881 TGTGGTTGTA AATTTTAAGA CTTCAGGAAA CTTTTCCAGT ACAAGACTTG TCCACAGTGG
101941 ATATAGCAGC TAAGGGGTTA ACAAAATGAC GTCAGAGTAG CTACGGTAAT GGGCAGGAGC
102001 CTCTCTTAAT CTGCAACCAG GCACAGAGAT GGACCAATCC AAGAAGGGCG CGGGGATTTT
102061 TGAATTTTCT TGGGTCCAAT AGTTGGTGGT CTGACTCTAT AAAAGAAGAG TAGCTCTTTC
102121 CTTTCCTCCA CAGACGTCTC TGCAGGCAAG CTTTTCTGTG GTTTTGCCAT GGCTCGTACT
102181 AAACAGACAG CTCGGAAATC CACCGGCGGT AAAGCGCCAC GCAAGCAGCT GGCTACCAAG
102241 GCTGCTCGCA AGAGCGCGCC GGCTACCGGC GGCGTGAAAA AGCCTCACCG TTACCGCCCG
102301 GGCACTGTGG CTCTGCGCGA GATCCGCCGC TACCAAAAGT CGACCGAGTT GCTGATTCGG
102361 AAGCTGCCGT TCCAGCGCCT GGTGCGAGAA ATCGCCCAAG ACTTCAAGAC CGATCTTCGC
102421 TTCCAGAGCT CTGCGGTGAT GGCGCTGCAG GAGGCTTGTG AGGCCTACTT GGTAGGGCTC
102481 TTTGAGGACA CAAACCTTTG CGCCATCCAT GCTAAGCGAG TGACTATTAT GCCCAAAGAC
102541 ATCCAGCTCG CTCGCCGCAT TCGCGGAGAA AGAGCGTAAA TGTAAAGTCA CTTTTTCATC
102601 AGTCTTAAAA CCCAAAGGCT CTTTTCAGAG CCACCCACTT ATTCCAACGA AAGTAGCTGT
102661 GATAATTTTT TGTTGTCTTA ACAGAACAAA TTTCTAAGGA CCCCCCCGGA AAGCATTAGA
102721 CTATGGTCTT AAAGTTGATT AACAGAAATA ACGGTTTGGT CAGTCTTGCA GTGTAGGTTA
102781 TTTCTGACCT TATTAAGGTG CTATTTGGAG AGAAGCTGTG TAAGTCCACT ATCATTCAGG
102841 CCTCTAGCTT GCTATGATTA GCATTTGTTT AAACAACTTT GTAAGAGTAA GGGAAAAATC
102901 TGGTAAGTAG TTAACTGGCG CTTACTAGGC ATTTTTGCAA AGCTTTGAAA AGATTAGAAA
102961 ATTGTGTCTT GCGAGTTCCA GTGTCTTCCT CAAAATGCTT AGGAAGATTT TCTCAGCTCA
103021 ATACATAGTC CCCTAGGTTT TCTCATATAT TATATATATA TATATATATA TATATACTGT
103081 TAAATTCATT TGGCTGTTAA CATTAACCTG AAATTTATTC TGGTGCAAAA TGTGAGGCAG
103141 GGATCTAACT GGCTCTCATT TTATCCATAG CTAGCTACCC ACTTAAATC TGTCAGTCTG
103201 TCGACCAAGC ATAATTTAAT CCCTTATATA TGAATTTTA TATGTGTGGC TTTGCTTGTA
103261 AATAGTCTAT CTGGTTGCAT TGCTTTGTCT CCTCTAGGAC TATGCACCAT GACATGCCAC
103321 ATTCTTTTTT TCAGTACTTC TTGCCTGTAG TTATTAAAAT CTAGAATTTA CAAGTTTTAA
103381 CCATTTTCTT TCTGTTGATC TTGCTTTCG GTTTTGGAGG TTGGGGATTG AGTACTGGAA
103441 GAAAATTTAG AGGGATGGGA ATACTGTACG CAAACAAAAG TAATATTTAC TTTAAAATTT
103501 TTATATTTTG TATTTTTTTA TCATATAGCT TTTACATCAC ATTTTACAGA CTAACTTTAG
```

Figure 1 (Page 32 of 73)

```
103561  AACAACCACA  GAATGTCCAA  CATTAAAACT  ACTAATTCCA  AAGACCTTGC  CTCACATTCT
103621  TTTTTACAAT  AAATATTTTT  TACACCTAAC  ATTCTTTCTT  GGCCTACATC  TAGAATGTAA
103681  ACTGATGTAC  CATACTAAAA  TCGCCTGACC  AACTGTCAAC  AACAACAAAT  CACACACACA
103741  AAAGATTAAA  TTTGAATTGC  ATCGTTTACT  TAAATTCATT  TGTGTTCCAG  CTTTTAATAA
103801  GGCAGTTTTT  GGTTTATAAA  GTAATATTTG  CATTTTAAAA  ATTATGAAAA  TGAATATGTC
103861  AGTTTGTTTT  ATGATTCGTT  TTTCTTGACT  CTTATACAAG  CGACTCTAAC  TGGCATAGAC
103921  ATTTGTTATC  CACAGACAGT  ATAGATATGT  TAGAGATGCC  AATGGACTTG  GTCTATGCCA
103981  AGGTGACTAC  TCACAAGCTC  TGGGCCCAGC  TGAAGGTCAA  GTATTTTTTT  TCCAGTTATA
104041  GATGTGCTGG  ATCTGATGTA  TAGCGCTTGA  CTTTTTATAT  TTTCTTTATC  TGTAGGAAAC
104101  AAATGTGTTG  GAGGTACTGG  GTCTGACGAA  TAGCATAAAA  GAATAAAGTT  ACATTACTGT
104161  CTGAGGATCA  GATGGACAGG  GGGTGGTAGC  TCAGTCCAGC  TATTTTCCAC  TCCCTCACTT
104221  ACATTCTTTG  CCCCCTCCTC  AACAGAACAA  GGATTCTGCT  GTAACTCTTC  ATTGACAGTT
104281  GATATTTAAA  AATTAACGAA  TGGATGAAAT  TCTCATTTGT  GAAAGAAAAT  TTATTGAGCA
104341  TTTTGTATTT  GTGAGTAGTG  CAAACATTTT  AATATTATAT  TAAGAATCTA  TTGTTTTGTA
104401  TTAGAGGAGT  AATTAAGGAG  AGATTGGAGA  CAAAAAGGGG  GTGTTGTTTG  CAGAATATAC
104461  CATCCAAAAA  TAGACCACTG  TGGGATCAGG  ATTCTTTTGA  GCTAAAGGCA  CTTCAAAAAC
104521  AGCATTCAAG  AAGGGAATTC  TTCTAAACTT  TTCTTTCTGA  AAACAGGAGA  TAAAAGTTCC
104581  AATGTGAAAA  ATGCTCTGCT  TGTACCAGGT  GAAAAGACAT  ATTCTTCAGC  CCAGAGGCAT
104641  AGATGAGATA  ATTCTGCACA  AACACAGCAG  GGAGTCATAG  CCGAGAGACT  TCTATACACA
104701  AACAAACCTT  GTTAAAATAA  TCATATATTC  CTTTAATCTC  CTCATATGGT  TTACTTTCCC
104761  ACAATTGCCT  CTCTTTAACT  TAATGTGAAA  GCATTTAGCT  TTTGCCATTT  CTTTGGGGCT
104821  TCACTTTTTT  ATGAGGGTTC  TCCTGTCCCA  TAAAATTTAC  ATTAAATACA  TTTGTATGCT
104881  TTCATTCTGC  TAATCTGTTT  TATGGCAAAT  GAATTATCAG  GTCCAGCTGG  AGACCCTAAC
104941  AGAGTAGAGG  TAAAATTTTG  CCTCCCTACA  AGATAGAGAT  TGTGTGCATT  AAATGTTGTT
105001  TGTTCCCAGT  TGTTCAGTTT  GTCAGGCCTC  TGAGCCGAAG  CTAAGCCATC  ATATCCCTG
105061  TGAACTGCAC  GTATGCCTCT  AGATGGCCTG  AAGTAACTGA  AGAAACACAA  AGAAGTGAA
105121  AATGCCCTGT  TCCTGCCTTA  ACTGATGACA  TTACCTTGTG  AAATTCCTTC  TCCTGGCTCA
105181  TCCTGACTCA  AAAGCTCCCC  CACTGAGCAC  CTTGTGACCC  CCACCCCTGC  CAGCCAGAGA
105241 .ACAACCCCCT  TTGACTGTAA  TTTTCCACTA  TCTACCCAAA  TCTTATAAAA  CGGACCCACC
105301  CCATCTCCCT  TCGCTGACTC  TTTTCGGACT  CAGCCCGCCT  GCACCCAGGT  AGAATAAACA
105361  GCCTTGTTGC  TCACACAAAC  CCTGTTTGAT  GGTCTCTTCA  CACGGACGCG  CCTGAAACAG
105421  TTTAACAGGG  TTTTTCCTGC  CCAGTCACAA  CAAAGTGATG  TTATGCTGCA  GGCTGAAGTT
105481  TACAGCTAAT  GCTGTTGAAG  TCTAAAATCA  GTTTTGGTTT  GTTAGATTTG  GGTGAGATGG
105541  CTAAGATTCT  CAGAGAAAGA  AGTCAAGTTT  GGGGTGCATT  TTTCAGACTT  AAAAATTTAG
105601  CAGTAGCCCT  TGCAGTTTTT  CCAATAGAAG  TGATTTAAGA  ATGTTTTCAG  GAAATTTAAA
105661  ACAACAGTGA  GAAGCGTGTA  TGGAGAGTTG  AACTACACTC  CAGACTTGGC  TATAGGAAAG
105721  CACGAATGCT  GCTATTGTAT  TGCACCTTGG  AAAAGAGAAC  AAAGGAATAT  TTTCGGACAA
105781  TTTTAACATG  TCACATATGA  AAAGCTAAAC  GGAATCTGTC  AACACCTTGT  ACGTTATTAC
105841  AGGCTGTGAT  TTTAAAAAAA  CAATCCTTAC  TAATACATAC  ATAGTTGCTG  CTAGCAATAT
105901  AGTGTTGGGA  GTAAAAACAC  GAAAATGAGA  GTTCAGGACA  ATATCCCAAC  TCTGAGCAGA
105961  TTTTTTTAAG  TAGTAACATC  TAAAATTAAA  CCATATTATG  TAATATTTAT  TTCTTTTCCA
106021  CAGTCTCTTC  TCATGCCTCG  TTCACATTAG  CTAATTAAAA  GTCCCCTGAG  TATCATCATA
106081  ACCCGATTTA  CAGATGAAGG  CACGGTTGCA  ATGAGCTATC  ACCCTCTTCT  GAATGAGACA
106141  GTACAGTGTG  AAGGATAGCA  AAACTCCACT  CCCATCCTCT  TAGGGCTCTG  GCTGGACCAG
106201  CAAATTAAAT  TAATGTAAAA  TGGATTAACA  GGAGAAAGGT  ATATGCATTT  ATTTAACACA
106261  GGTTTTACGT  GACACAGGTG  CTCTCATAAG  GTAATGAAAG  CCCAAAAAAA  GCAGTTAGCT
106321  ACTTATATAA  TGAATTGGAC  AATTAGTAAA  ATGTAAAAAT  GCGCTAAAGC  AAAGGGATTT
106381  AGGCTAGAAT  ATATAACTGT  GTAGAGAAGC  GCCCAGCAAG  GGCTAGTGCA  AGGTTTGTAC
106441  AGAATTCTCT  TGGCCTCAGC  CTCCTATCCT  TGAAGAGAAT  GTTGCTTTTT  TTAAACTACA
106501  GTGAGAACAT  CTTTCATATG  AGAATTTCAC  CTACTGCTTC  TAAGAAACAG  GTCAGCTTTC
106561  AAGAAAACAT  AAGGCCAGAG  TGATCTTTTC  ACGCCTGCTC  TTTTAAGTAC  CTTTGAATAG
106621  TCAATATGTC  TTCAAGCACT  TGAAAGACTT  AAAAAGTTTA  CCACTCCGGC  ATATTAGTGA
106681  AAGCCCTTAA  TATAAGCCCT  TATTAAAATT  CTCAGTCGAG  GGTATAAATT  CAGATTCAAA
106741  TAGTAGTGTC  GTAAACGGGA  GGGAAAAACT  AAAGGGATTA  AAAAGTGAAA  CTATTGTGTT
```

Figure 1 (Page 33 of 73)

```
106801  CTCCCTCGCA GTCCTTAGGT CACTGCCCCT CGAGGGGCGG AGCAAAAAGT GAGGCAGCAA
106861  CGCCTCCTTA TCCTCGCTCC CGCTTTCAGT TCTAATAAG GTCCGATGTT CGTGTATAAA
106921  TGCTCGTGGC TTGCTTTCTT TTCGCGTACC TGGTTTTTGT TGTCAGCTGG TTAGACATGT
106981  CTGGTCGCGG CAAAGGCGGT AAAGGTTTGG GTAAGGGAGG TGCCAAGCGT CACCGAAAAG
107041  TGCTGCGGGA TAACATCCAA GGCATCACCA AACCGGCCAT TCGGCGCCTT GCTAGGCGTG
107101  GTGGGGTTAA GCGAATTTCC GGTTTGATTT ATGAGGAGAC TCGTGGCGTT CTCAAGGTGT
107161  TTCTGGAGAA CGTGATCCGG GACGCCGTGA CCTACACGGA GCACGCCAAG CGCAAGACTG
107221  TCACTGCCAT GGATGTGGTT TACGCGCTCA AGCGTCAAGG ACGCACTCTG TACGGCTTCG
107281  GCGGTTAATC TTTTCGTCAG TTTTCTTCCA ATGGCCCTTT TCAGGGCCGC CCACTCCCTC
107341  TCAGAAAGAG CTGTGATTGT ATTCTTTCGG ATGGTAACAT CTCAATGGCC TTACTCGGCT
107401  ATTCTGCCTA GTATGTAGAA CTATTATAAA CCAGTTGGGA GAGACCAGGT TGTTTGGTCT
107461  GAGTGGCTGC TAAAGCAGAA ATCAGCTAAG TAAACGAGGT CTCCGAGATA AGTGAGCTAT
107521  AAACTTCAAT GCTATAGTTT TGACATGTCA AGCAACTTAA CGTGCAGCGC GAGTCCGATA
107581  AATGAGTAGC TCAGCTTTTT AGTTTTAAAA ACGAGTTGTG CGTTATTTGT ACGAGAGCCT
107641  AAGATGCTAG CTGCCTGGAA CTGAGTAGGT GGATTAAAAT GGGTGTCAGG TCTGTTTTCC
107701  CAGGCGTATC TGACTTAACG TCAGCAAAAG CTGTACTTTT AGCTTCCCTG GTAACACCTG
107761  CCGTCCTTAA CCGCCCCCTG CCGGTAGCGC CAGAAGCCTT TACTTCCATT TCTAGTTGAG
107821  CTTGGCGTCC TGCTGAGTGA CGTCACCTCC CCCTTCTCTG GAGTAGGACT GGCGGTTAAA
107881  GCTGCTTTGC TATTTTCAGT CCTCAGGCTG GAGGCTCCCC TAAGCAGGCT GCCTACGCAG
107941  TTCGTAAATT CCCACTTAGT AGACTAAGGG AGTCTGTTTT ATAAATAAGG ACTCAAATTT
108001  CTTCTGACTC CGAGGTCCGT GGCAGCAGCT ATAAGATGGA AGCCCCTCT GATGTAAGAT
108061  TCTCAGATGA CTTGCATCTT CACTGTACCT GTCAACCCAA TAGTCTTCTA TTCCTGCCTT
108121  AAATTGTAAA TTCCAAAACT GATTTAATTG TGAAAGTTTC AAACTGTACG ACCTAGGAAG
108181  TGTCAAAGTT AGGTGACCAG ATTTTTAGAA GTCAGCCAAA TATTCAGCAT CTTTGATTTA
108241  GTAACAAATA TATTGATGGC TACTTCAGCA AAAAAAATCA ACTTTGTTTT CTGGTTACTT
108301  TGCTAACAAG CTTCTCCTGA CAGGAGGATA TAGTGAATAG GCAGTTGAAT AAGTGAGTTC
108361  GGGTGAGAGG TCTGAGCTGG AGATAAAAAT GTGTGAGTCA TCAGCAGATA AATAAATGCT
108421  GAGACCAGAT GAGATGGCTA AAAACTGAAA CATAATGTAG TGCAGCATTG TTTGTAATAG
108481  TAAATGAGTG GCAACTGTAA AGTTTTCATC AGAAAGGACT AGAGTGATCT ATACATCCAT
108541  AAAATAGAGT ATTTCTCTAC ACAGCCCTAC TAAAGAATGA GAAAGCTGTA CTCCACTACA
108601  TACTCTGGTG TACTCTGGCT CAGTTCTTGG ACTCCTCTTT TCTTGGCTAA CTCAACTGGC
108661  CTCACCACTT ACATGCTCTG TGCTCTGTCA AATAGTTTGT TCAACAGAAC ACCACGGCCT
108721  AGCTGTAAGT GCCACGTTAA CTTCTAGCAA TGCCAAAGCC TGTGATAGTG GCAGCTTCGG
108781  GCTGTTTCTC ATTCCCGGGA TGCCTAACCA CCTCTCCAAA TTCTATCAGT TTGCTTCCAC
108841  CCACTTCAAG CTTCAGAACG AAACATAGAG CTTAAGAAAT ATAGGCCCGG CAAGGTGGCT
108901  CACGCCTGTA ATCCCGGCAC TTTGGAAAGC TGAGCCTGGT GGATCACCTG GGTCAGGGG
108961  TTCGAGACCA GCCTGGCCAA TATTGTGAAA CCCCGTCTCT ACTAAAAAAA AAAAAAAAAT
109021  TAGCTGGGCA TGGTTGCGGG CGACTGTAAT CCAAGCTACT CGGGAGGGTG AGACAGGAGA
109081  ATAGCTTGAA CTCGGGAGGC AGAAGTTGCA GTGAGTTGAG ATCGCGCTAT TACACTTAGG
109141  CCTGGGAGAC AAGAGTGAAA CTGTGTCTCT AAATAAGTGT TTGCAATTAT AAACCATCTC
109201  CCTGACCTTA AATCTCTAGA CTCATATACA ACTGCATATT TGATGTATCT AATTGAATAA
109261  TGGGCATCTC GAACTTGTCC AAAATATGTT TATACGTAAA CACCAAGTCT GTTCTTCCTC
109321  TGATATTTGT CATGTCAATC AATAGAACTC CATTCTTCAA GCAGCTTGGG CCAGGAATTG
109381  TGCAATATTG TTTGTCCTGA GCTTCTTACA ACTTTCACCC AATGCAGTCA GCTCTGTTGA
109441  AAATCAATCA GAATACCTTT CATTGTTTTC TTTGCTGCTT CTCTAGGAGC AAGCTGCCAT
109501  GGCGGTTTGT CTGAATGACC ACAGTGACCC CAAACTGGTC TTTGTTTTCA CTTTTAATCC
109561  CCCTGTCATA CAGTTTTTTC TCTATCCAGC ATCAACAGTG ATCCTTTTG AAGGTATTAT
109621  GTCCACTGTC TGCTGAAAAG ATTCCACTGG CTTTCCATCA CCTTCATAAT AAAAACCAGC
109681  ATCCTTATCA TAGCCTACAA GTAAGATGAC CAACCATTAC AGTTTGCCTG ACTCTCAGGG
109741  GTTTCTCAGG GTGTAAGACT TACAGTGCTG AAACTTAGAA AGTTCCAAGC AAACTAGGAT
109801  GAGCTGCTCA ACCTACTAGA TCTGTACTCT GGCTACCCTC TGACCTCATT CTCTTCGCAG
109861  TTCTTTCTCT TCACTGACCT TGCTGTTTCT GGAATGGACC AAGCATTTCC AGCATCAGCA
109921  CCTTTATATC TATTCTTTCT CCCTAGAAGG GTCTTGTCCT GGATATCTGA ATGGCTCTAG
109981  ATCTCATTTC ATTCAAGCCT CTCCTCAAAT ACCAACCTTA CGAAAGAGAC CTCCCATAAT
```

Figure 1 (Page 34 of 73)

```
110041 CATCCCTTGT AAAATAAGCT TTTCTGCTCA TTTAGCATAT ATATATATAG TTGACTATCC
110101 TCAATAGCAT ATATATATAA CATTTCCCCA CCTAGAATTA TATATGTAAT AATATATTTA
110161 ACAAAAAATA CATATAACTA GATATATTTT ATTTTGTGTT TGTTCTCTCT CCCCCAACTG
110221 GAATATATTT TTTGAAGGTA GGGACTTTGT TTTGTCCCAG AAGTATCCCT AGCACCTTGA
110281 ACAGGGCTGA CGTTTAACAG GTAGTTTATG GAGGTTTGTT GAATGAAAGG ATGTGTGAAT
110341 TTTCTATGTA AGTCTCCAGG CTCTCCACTA AGCCCACCAG AATGCTAACA CAATCAATTC
110401 CCCATCTCAT TCCTTGACCT GCCACTGCCT GAAGCAATCA GCGTGCAGTT TCTCTTTAGA
110461 AAATCTGGGG GATAGTCTAG GGGTTGCAAA TTAAGCAACA TTATCTTTGT TCTGAACAAG
110521 GACTGCATGA GTGTTAGGAC TGAAGAAGGC CCAAGGTGGT GGTGGGTATG CCTAAGATGA
110581 GTATGACATA TCAGCAATGC TATGAACATA GCAATGCTAT GAAAGGCCAG GCAAAACGTA
110641 ACAGGAGCTA GTCGTGGCTT ATTGTTACAA CGACTATACC TCCCATATGG GTAATCGATA
110701 TCCACACACC CCTCTACATT GACTCTGGAA TTCAGGAAAG GGAATTAAAA TTTTCTAACT
110761 TATGTACCCC AATGATTTCA ACAATATCTG GCATATGAGA TCAATAAATA TCTTTAAAAT
110821 ACCAACTAAG AAAGACATAA AATGACCCAC CCTCCATACC AGGCTCATTT TTGCTCCTCT
110881 GATTCCTGAA ACTATCCAGA ATGCAGCTAT GAATTCTCTC CATTGTCAGT TTTAAATTAA
110941 GCCAAGCTGG GTACTTGTGT AATTCCTCAA GAAATCCTGG ATGAAAACTG TCAGGTGGAA
111001 AACAGGACCT CAAAATAAAG AGACATCCAT CACTGAAGCT AACATCGTGA GGCTGAAATC
111061 AGTCCTATAA CAATGGTACC AAAAAGAGCA CAATGAGAGG CATTTGTGAA TATTTACTCA
111121 GATGAGAGTA AGATATTTCC CTATCAGCTA ACCTGAAGTT CACATCCCTT TTCCAGCTGA
111181 GTTCTGAAGC TAGATGTACT TAACTGGAAC ACATAACTGC ATCAGGAACA TCCTTTAAAA
111241 CTATGGCTAC CATGGCTTGA CTGGACAAAC CCCAGGCTTC CAGGTTTAGC ACAGGTGGCC
111301 CTTCACAGAC CAACATTGCC TATGCTACCA ACCTCATGTC CTACCACCCT GCTTGCATCA
111361 TTTCTCTCTC TGCATATATA AAAATATATG TGTATGTATA TAATCAGCTT TATTGATATT
111421 TAATGTACCA CAAAATTTGC CCACTTTAGG TACAGTTCAA TGAATTTTAC CGTGTTTTCT
111481 TAGTTGTACA ACCATCATCA CAATTTAATT TCGGAATATT TCTATCACCC AAATTTCCAT
111541 TTCTGCGTAA AGGGGGAAAA AAAAAGGTTA ACTGCTGAAG GCCGCGGTAA CACTGAAAAA
111601 GGTGCCTTTT CTCTCTAAAA CAGATTTTAA TCTCCCCTGA ATTTAGTGTC CTGGGTATTC
111661 CAGGAGTCTG AATAGGGTTT CAATTTTCAG GGTCTTTTTA ATAGAGTAAA ACTGTATTGG
111721 TGGCGATAAA TTTAGTATTG CTCTCAGTAC ATGATTGAGG GATACTTAAA TGTCTCTGTG
111781 ATTTTATTTC ATAATCGCTA AAAGATGGTT TTTTTTTTTC CTAAAACAGG GTTTTTGTTT
111841 TTTCTCAATA AGCTTCTTAG CTTCCCCTCC GGCTCCCTGG CTTGCCTCAG GAAATATTAG
111901 CTCATCAGTT CTGATTGGTT GACAGCTACG AATGGCCCTC ATTGATTGGG CAGCGCTTCT
111961 TTGTCCCTTG GAAACTAATA CAAATTTTTA ACACTACTTT TTTTCCACTC TTTCTTCAGA
112021 GTTGGAATAT CGTTGCTCCC CTACCCATAT GTAGTGAGTG GAGGGCAAAC TTGGAGTTCC
112081 CCTAATCTTT CCTTTTTAGG ATGTCAGCTC AGTATCATTC ATCTTAATTA CACATTGAGC
112141 TTCTTGACTT AATGGATACA GCTCTTCTTT TGTTTAGTTG GGCGGCCCTG AAAAGGGCCT
112201 TTGGTTCAGA AATGCAAGCT GTGGAGAAAT CAGCAACCTT AACCGCCAAA GCCATAAAGG
112261 GTGCGTCCCT GGCGCTTAAG CGCGTAGACC ACGTCCATGG CAGTGACTGT CTTGCGCTTG
112321 GCGTGCTCCG TATAGGTGAC AGCGTCACGG ATCACGTTCT CCAAAAACAC CTTGAGCACC
112381 CCGCGAGTCT CCTCGTAGAT CAGACCAGAG ATCCGCTTCA CACCGCCACG CCGGGCCAGA
112441 CGCCGGATGG CCGGCTTGGT GATGCCCTGG ATGTTGTCAC GCAACACCTT GCGGTGGCGC
112501 TTGGCACCCC CCTTACCCAA ACCCTTCCCG CCCTTACCAC GTCCAGACAT GACTTCCCAA
112561 GAAGTGAACC AAGAGCAAGT GAGAGAATAG GAAACCGATC TTTATATATC TACGTTACCC
112621 CTGCCCCCAC CTCCAGCGGA CACTGAGACT GAAAAGCGCG CAGGCGGGAA ATGTGACGCC
112681 TACAGTCCGC TCCTTTAACC CCTCCTCCAA GCCCCAGGAA ATGGCGGGAG CAGCGATTGG
112741 GGGAGGGTGG GGAGATGAGG GTGGGACCAA GCAGGCTTGA CCAATGGCCT TTATTTTCTT
112801 AACAGAGCTA CAGGCTTTGA GGAACTGGGT TAAGAATTAA ATGTAAACCC ATTCTGACTC
112861 CAGAATTATT TTAAGTCGAA CTTTTTTTTT AACCGAATCT CTCTGTCGCC CAGACTGGAG
112921 TACATTAGAG CCATCTCGAT TCACTGAAAC CTCTGCCTCT CAGGTTCAAG TGTTTCTCCT
112981 GCCTCAGCCT TCAGAGTGTA GCTGGATTA CAAGCGCTCG CCGTCGCGCC CGGCGTGTTT
113041 TTGTATTTTT CGTAGAGACG GGATTCGGCC ATGTTGGCCA GGCTGATCCC GAACTCCTGA
113101 TTTCTGGTAA TCCGCCCGCC TCAGCCTCTC AAAGTGCTTG AATTACAGGC GTGAGTCACC
113161 GCGACCGGCC GAAATCGATT GGTTTGAAG CCTTCAGTAG CATTAAAACG AAAAGTGCTC
113221 CCAATGCATT CCCTTTTGTC TTAAATTGGT TTCTTACAGC TACTTTACTT GAAAAGGTGG
```

```
113281 TGGCTCTGAA AAGAGCCTTT GCTTGGACCG TCAGAGAGAC CACAGTAATC ACGCCCTCTC
113341 TCCGCGGATG CGGCGGGCGA GCTGGATGTC CTTGGGCATG ATAGTGACGC GCTTGGCGTG
113401 GATGGCGCAC AGGTTAGTGT CCTCAAATAG CCCTACCAAG TAGGCCTCGC ACGCCTCCTG
113461 CAGAGCCATC ACAGCGGAGC TCTGGAAACG CAGGTCTGTT TTAAAGTCCT GCGCAATCTC
113521 GCGCACCAGG CGCTGGAAAG GTAGTTTACG AATAAGCAGT TCAGTGGACT TCTGATAACG
113581 GCGGATCTCG CGCAGAGCCA CGGTGCCCGG CCGGTAGCGG TGGGGCTTTT TCACGCCGCC
113641 GGTGGCCGGA GCGCTTTTGC GGGCTGCCTT AGTGGCCAAC TGTTTGCGTG GCGCCTTGCC
113701 ACCAGTAGAC TTCCGAGCAG TTTGCTTAGT GCGAGCCATG ACGGAAAAAC AGCACAGCGG
113761 AACACCCAAC ACTAGCGCAA ATACGCCCAT GAGCTGCTCT ATTTATAGTG TGTAAAGTGC
113821 AGTGATTGGA TGATAGAAGA CGCTAAATAT GACGTTACAC ACTCTGATTG GTCTATCTTT
113881 AAGCCAGCAA CAATCGTGCA GTTTCACCGG CTACTATATT CTATTCCAAC TCTACAGATG
113941 ATTATTTAAG TGGTATTTTA TTACTACTAT TATTTTATTT TACTTTTGCT TTGTTCCCCA
114001 AGCTGGTCTT AAACTTGGGC TCAAGGATC TTCCCGCCTC AGCATCCAGA GTAGCTGGGA
114061 TTACAGGGGA GCCCCACTGC GCCGGCTTGG ACTTTAATTT TTTAAACTTG TCCTCTTCTA
114121 CATCTGGTTT TCATAACCTG AAGGCTGTGT TTATTTTCCA TAAAACAAGG CATTGATTCC
114181 AAAGGTATTA TAATTCCCCA ATTCCGTATA ACCTTCAGCT CTTTAGGAAA AAAAAAAAAA
114241 AAAAAAAAAA GAGGGAATAC TGCTCACCTC CTCTCCGGAA ATGTACCCTT TACGGGAATT
114301 TCTGAAACCT TTCACAAGAA TTGGATTCCT TTGTAATGCT TTAATTGACT TAGGAGTGTT
114361 ATTGAAATCT ACAAAGCATC TCAAACATAG TAGGATTACA CTATTACTCA GAAACATTTT
114421 CTATGAGACG TCTTTCTCTT GATTATGCTC TTTGAATCCT AAACTTGCAG CGTTCTGCAG
114481 CTTTTGTTTT CTAAAGCCTA GGTGTACTCT GCCAGTCACA AAATGGCGTT TCTCCAGCAC
114541 TGCCGCCAGG TACCACCAGC TGGGAGTTGT TCCTCTTGCG GAGCAGGAGG TGGACTTGGC
114601 CCAAGAGAAA CTGGATAGTG GTTCGCAAGG AACATAATTT AGCATTGCCA AGAGCTAATG
114661 CAATCATTTT GAAAATCTCA AAACACTGAA AAGTGGATTG TGACCTTTTT AAATTCACAA
114721 GAGACAGGCC ACATTCTATC TTTTGATTGG TTTAGGCTAT TTTCTTGAAC AGCCATTTAG
114781 AAAGCAGATC TATCATCCTT CATTTGCATG GAGCGTTCCC ATTTTATTTG AAACCAGTTT
114841 AACCCAATAG AAAAAAGGGA GGCAGAACCC ATTATTTAAA GTGGAAACTC CTGAATCAGA
114901 TAATTAGGAG TATTTCCTTT TCAAAAGTTG CGTTTTTTCA GATACCTCGC TTATTACACT
114961 AAGAAAGGTT TATATCTTTC ACAAAGGGTT TACTTACAAA AATCTTCCAA TTTTGTATAC
115021 CTGTGTTTCA TAACTGACTA GCCGTCAAAC CAAGATGTAG AGTTTCCAAC CGTTATTTTC
115081 CAAATTTTTA GAAATTACGT GAAATATTTG AATGCATGCC TTCTCAATAA AATGGGACGT
115141 AGGAAGCACT GGTGCAGAAG ATGGGTACAA TACTTATCTG GGACCACTCC ATTATTTGGT
115201 TGGCACGTTG TTTGAACAAA AAGGGGAAAA GCTCAGGTTA CTTAGCATGG TTCGGACTTA
115261 TTTGAAAACT ACCACAGCAG GAGCGGAAAT AAGACCGCAT TACCTCACTC TCTGCTGTGC
115321 TGTGCTAGGG GGTTATCCAG AATAGGATTG TAGAAGTGGA TGTCGATTTA ATAGTTTTTT
115381 ATTCTCCCAT TAGCTGAGTC TCTGATTGGC AATGTGAGAT CGTTTTAGCT TATTGATACT
115441 TTGAAATGCA CTTAACAGCC ACAAACAAGT TAAAGGGTTG TTACCATAAA ATCTTATCCC
115501 CAGGGTGTGC TTGCATTTAT CACCCGTGTT TGCTTTCACA CTAAGTGGAC TTAACTCCCC
115561 AGCAGAATGC CTGTCAGGGA ACCGGTTTCG TGGACCCAGC ATTTAACGCC TTTCGCAGGC
115621 TTGTGAGGCC CATAAATATT TGTTGAATAA AAGAATGAGT TGACCATGTC ATGGTGCGCT
115681 GATTGCGTGT GCTGACATGG AACACAGGTT GTAAACCTTA ATACCAATTT GGGGCATGTT
115741 GTATGGATGA AAAGGGCATT GGAAATTCCT GAAGTGCATC CCACATTGGA CTGTGGAAAT
115801 AAGTTGCAAG TGCAGAAACG TTTCCACACT TGCAGTTTGA GTATTAATTG CAGCGTTTGT
115861 GAATTCTGGT GTTGTCTACG ATTCATTCTT GTTTGACGTG AAAGGTATTC GCGAGACACA
115921 TCGCTCTAAA ACATTGCCAG AAAATGTAAT AGAGTTGATG ACAACTGGCC CTAACACGGC
115981 CTAAAACTCG CACTTTTCTC TCCCTCCGCA ACTATTCAAA ACACTGTATT TTACATTTCT
116041 TGCAAATTAA AAACTAACAT CTCTGGCAAC GGACCTCTAA AAATTTCTAA TAAAACTCCT
116101 CGGATGCTTG TGGCACTGCA TTTGTAAACC GCCCCTCTC AACCTACTCC CTAAAAAAGA
116161 GCTGCTTTTT GAGAGAGAAG CGGTACCCTC TGATGTTACT GGGCGGCAGT CTGCCTACAA
116221 TTTCCTTCAC AATGAGGCAA CCAGAGCGGC TTTTTCTGTG TGTTTGCTTG CGTTGAGGGG
116281 AGCAGGACCA TAGGCCCTAG AGGCCCCCAG CTGCCTTCTG AGACTGGGCG AAACCCTCGG
116341 CAGCGCGCAG GGGGCGCTAG GGCGCGAGGG GCGGGCACTG ACGGGCACCA ATCACGGCGC
116401 AGTCCCACCC TATAAATAGG CTGCGTTGGG GCCTTTTTTT CGCATCCTGC TTCGTCAGGT
116461 TTATACCACT TTATTTGGTG TGCTGTGTTA GTACCATGTT CTGAAACAGT GCCTCCCGCC
```

Figure 1 (Page 36 of 73)

```
116521 CCCGCCGCTT CTGCTGCTCC TGAGAAACCT TTAGCTGGCA AGAAGGCAAA GAAACCTGCT
116581 AAGGCTGCAG CAGCCTCCAA GAAAAAACCC GCTGGCCCTT CCGTGTCAGA GCTGATCGTG
116641 CAGGCTGCTT CCTCCTCTAA GGAGCGTGGT GGTGTGTCGT TGGCAGCTCT TAAAAAGGCG
116701 CTGGCGGCCG CAGGCTACGA CGTGGAGAAG AACAACAGCC GCATTAAGCT GGGCATTAAG
116761 AGCCTGGTAA GCAAGGGAAC GTTGGTGCAG ACAAAGGGTA CCGGAGCCTC GGGTTCCTTC
116821 AAGCTCAACA AGAAGGCGTC CTCCGTGGAA ACCAAGCCCG GCGCCTCAAA GGTGGCTACA
116881 AAAACTAAGG CAACGGGTGC ATCTAAAAAG CTCAAAAAGG CCACGGGGGC TAGCAAAAAG
116941 AGCGTCAAGA CTCCGAAAAA GGCTAAAAAG CCTGCGGCAA CAAGGAAATC CTCCAAGAAT
117001 CCAAAAAAAC CCAAAACTGT AAAGCCCAAG AAAGTAGCTA AAAGCCCTGC TAAAGCTAAG
117061 GCTGTAAAAC CCAAGGCGGC CAAGGCTAGG GTGACGAAGC CAAAGACTGC CAAACCCAAG
117121 AAAGCGGCAC CCAAGAAAAA GTAAATTCAG TTAGAAGTTT CTTCTAGTAA CCCAACGGCT
117181 CTTTTAAGAG CCACCTACGC ATTTCAGGAA AAGAGCTGTA GTACACAGAT GAAATCCCCC
117241 AAGCAAATGC AACACGCCCT CAATTATATT AGAATCACTT GGAGAGTCGA TAGAACTTTA
117301 ACATAGCCTC ATCTAGTAAG AATTTACTAC TCAATCTATC AAAGATAGCA AGGTGAATTC
117361 AAATGCACCG AGTTAAAATC GAGTTTTAAA GTCACCTGGG TTTCGGTAGC CGGAAGTCCC
117421 GCGTCTCACG ACTCCAAGCT AATTAGTCAT AACCGTATTG AACCAAGGTT GAAGCCCAGT
117481 CCCAGGCTTG AGGCTTTTTA TTATACAAGG TTAAAGTGGG GATATTGCGT TTTGGGGTCA
117541 ATATTGCTAA AGTAGCATTT TCCGAAATTG GGTGGTCCTA AGAAATGCTT CTGGGATAGT
117601 TGGCAAAATA TATGGCTTAA CCACGCCCTC TCCACAGGAG TGGCTAGCGA GCTGTCTGTC
117661 CTTGGGAAGG ACGGTGACCC TGCTGGCGTG GCTGGCGCCC ACGTTGGCGT CCTCTGAAAG
117721 CCCCGCCAGG TAGGCCTAGC TCGCTTGCTT TCTGCAGCGC CATCATGACA AAGCTTTGAA
117781 ACGCAAAATG CTTTCTTTGT GCAGCGCCTT ACCATGGGTG CACTTACGGG CTGTCGACTT
117841 GGTTTAGGCC CTTGTCAGGA CAAAGGAGCT TAGTTTGTTG GAGTTTTAGA GCTGCAACCC
117901 AAAATCCCTT GCTCGGTTTC TCTGTTTTTA GAAACGGAAG CGCCCTGATT GGATATTTGA
117961 AAATTACTGT GCTTAACTGG ATCGTGTTTC ATCAGTCGTG CAGGATTTTC AACCCTGGTG
118021 GAGCCCACAC ATTCAAAACT GAAGATCCTT TTCTCAGAAC TGCCCCTTTA AGCTTTTGCA
118081 ATTTTAATTC TGGGGGTCAG ATTTTAATAA TTGGACTTTT TTGTTTACAT CTGACAAGAG
118141 TATATGATGA GCCAAGTTTA CTCACTTTTA CTTAGTGCAG TTCAATTCTA AAAGTTTATT
118201 TTTGCGTGTG TGCATATGAG TTAATAATCA GTTGTATTTT TCAAACGGTC TTTTTTCAAT
118261 TGTTTTGCTT AGCTCCTTCC ATCGTCTAAA GTCAGGGATA CAGGCACATC ACATCCCTGT
118321 TCCCCCTTCC TCAAACTAAT ATGTAGCTAC CTAGGTTTAT CCTTTAAAAC AAAAATTCTC
118381 ACCTATTTTT GTGAGAAATA TACATGTTTT TCTTTGAACT AAGTATTTTA CATACACCTA
118441 TCTATATACA TGCATACTTG TGGTTTTGTT TTTTTAAAAA AAAAAAAAAA AAAACACGTT
118501 ATCTTTTGAG ACTGGGTCTC AGTCTGTTGC CCAGACTGGA CTGCAGTGGC ATAATCACAG
118561 CACACTGTAA CCTCCAACTC CTGGGCTCAG GCTATCCTGC AGCCTCAGCA TCCGGAGTAG
118621 CTGGGATTGC ATGCACGCAC CACCAAGCCG GCTTTTTGT TTTTATTTTT TGTGGAGACA
118681 GTCACACCAT GTTGTCCAAG CTGGTCTAGA AATGGCCTCA AGTGATCATC GACCTCCCAA
118741 AGTGTTGGGA TTACGGTCAC TGTGCCTGGC CTTGTATGCA TAATTGTTTT GTCTTTTGAT
118801 TAGGGTTATT AATTTAAAAA ACAAAGCCTG GACGCAGTGG CTCACATCTG TAATCCCAGC
118861 ACTTTAGGAA GCCAGATGGG CAGATTACTT GAGCTCAGGA GTTCAAGACC AGCCTGGGCA
118921 ACATGGTGAA ATCCATCTT GACAAAAAAT ACAAAAAATT AGCAAGGCCC AGTGGCACGC
118981 ACTTATAGTC CCAGCTACTT GGGAGGCTGG GGTGGGAAGA TGACTGGAAC CTGGGAGGTA
119041 GAGGCTGCAG TGAGCAGAGA TCGTGCCACT GCACTCAAGC CTAGGTGACA GAATGAGACC
119101 CAGTCTCAAA ACAAAAATAA TAAAAATTTT TTACAACGAT GTTATATACA CTTCTGCATG
119161 TTGCTTTTCT CTTAACCAAA CTTTTCTAAA ACCCTGTCAT GAAAAAAGAA ATCCTTCACA
119221 TGGAATAGCA TAAGTTATTC ATCCATTTCT TATTGATAAG CATTGATGTT TCCAGTTACC
119281 ACTGCTGAAC ATGGTGCAAT TGAATAGAAT TCCAGGGCTG AGATTGCTAG GTTTTAGGTT
119341 GTATTTTATT ATTTTATTTA TTTATTTATT TATTTAGACA GAGTCTTACT CTGTCACCCA
119401 TGGTGGAGTA CAGTGCCATG ACCTCAGTTG CAACCTTTGC CTCCTGAGTT CAAGCGATTC
119461 TCATGCCTCT GGTCTCCCGA GTAGCTGGGA TTACAGGCAC CTGCCACCAG GCCTGGCTAA
119521 TTTTTGTATT TTTAGGAGAG ATGGGGTTTC ACCATGTTGG CCAGACTGGT CTCAAACTCC
119581 TGGCCTCAAG TGATCTGGCC ACCTCGGCCT CCCGAAGTGC TGGGATTACA GGTGTGAGCC
119641 ATGGCGCCAG ACCTGGACTT TGTCTTCTGT TTCATCAGTC CTTCTGTTGG TTCAAGCACA
119701 GTATCACACT GAAGACTGAT GATTCTATAT AAATATGGTA AAGACTGTAC ACCCTAACTG
```

```
119761  TTCTTATTTT  TTAATTTTAA  GGCAATTTTA  GATTCCAGCT  TTCCAAAGAA  TTGTGGAATG
119821  CTTAGAGCTA  GAGAAGCCTT  GGAAGTCATT  TAGTTTTTGT  TTTGTCAGAG  AAAATTCTGT
119881  AGAGACTCTG  TCCTGCTCTC  ACTGAATACC  ATCCCATAGT  ACCCCCCAAC  AGCTTTAAAG
119941  GGCAATAATA  CCTTATGGAC  AGTATGCTTT  TCCTCAAATA  TATTCTAAGC  CATGGTCAAT
120001  GCAAAGAGT   GAGAAGGAAA  GTAGAATAAG  TTATCTAAGA  ATCAGTGGGT  GCTCTCTTTA
120061  AACTGATTTA  TCACTCCCCC  TTCCAAACTC  TCTTGAAGGT  CACTCTGCCT  CCCTTTCTAC
120121  ATAAGAACTC  CTAACTCCAA  GGGAGGAAGG  TAAGTTATTC  TTATTCCTTG  CTTAGAAAAA
120181  GAGAAAATAG  GTTTGGTAAG  CATCCGCTTT  CTGCTACCAT  TCTCTGTGTT  TCTGTGTTTT
120241  TTATAGGATC  ATTCAATTAT  TGGTTGGCTC  TTGAGAGGGA  ATGCAAGGTT  CAAGGACACA
120301  AGCCTAGATC  TTGCCTGTAT  AGAACCTCAT  GATGTTATGC  TTCTCTAAAA  TGAGGCCTGG
120361  AGGAGACATG  TTGAAAGTGA  CCCATAAATC  TGCAGTATCT  CATGTCTCTC  AATGGGGACA
120421  AGGAGTACCA  TGGGAAATAG  CATTAGGTCA  ATGACAGTAA  CAACTCCCAG  GTGAGTTGAT
120481  TTATTCTTTT  ATTTATAAAG  TTGTTAATAT  GCTACATAGT  CCCTAATTTT  GCCACAAATA
120541  GTCATTATTT  TAATTTCATA  TTTCACTATT  GATAAATGAA  GGAAAAAATG  AGTAGCAGTT
120601  AAGCAGTCCA  TAAACCTACA  TATAAAGCAA  ATTGGAGATT  TTAAAATTGA  TTCTGGATGC
120661  TTAAAATCCT  TCTCATTGAA  AAAAAATTTC  GTATTAGAAG  ATTTCAACAT  TCTTTAAACT
120721  GAGAAGCATA  ACATATAAAC  AGAAACCAC   AGCAAAACAA  AAATGCAAAG  CTCAATAAAT
120781  GAACACAAAG  TGAACACCAT  AATAATTGCC  ACACAAGTAA  AAAAACAGAA  AATCAGCCAA
120841  CCCTCCCAGA  GCCGCCTGAT  GCTTGCTTCC  AGTCACATTA  TCACTCCATC  TGCCCTAAAC
120901  ATAACCCCTA  TTTTGATTTC  CAATGCTGTA  ATTTAGTATG  CCTGTTTTTG  AAACATATAA
120961  AATGAAATA   AAACAAATGT  AATCCTATGT  ACCTGACATA  TTTCACTCCA  GAACATTAGG
121021  TTTGAATAGA  TTCATCTGTG  TTGCTGTGTA  TAACTTTAAT  TCATTTTTAT  TGTTATGTAA
121081  TATTCCATGT  TATGAGTGCA  ACAATTTAGG  TGTCTACTGT  TGATGCATAT  TTGCTTCCCT
121141  TTTTCAGCTA  ATATAAACAA  TACCGTGAAT  ATTCCTGTGT  ATGTGTCTTG  GTATATATAG
121201  GAATACATAT  TTTGTTTGTA  TACCTAGGAG  AGGAATTGTT  GGGTCAAATG  CTAAACTCTT
121261  TTTGAAAGTG  GTGATATTAG  GTTTACATGC  GATGAAATGA  AAATTAAAAC  CACAGTTATA
121321  AACAGCATGG  ATGAACCTCA  CAAACCTAAT  GTTGATGGAA  TCTAGCTGGG  AATTCCTGTT
121381  CTTCCATATA  CTTCCCAATA  TTTTTTTCCA  ATTAAAATTG  TTAATCTTTT  GAAGATGTTA
121441  TCCATTGTGG  CAGATGTGCA  GTATTATCTC  ATTATGGTTT  TATTTTACAT  CTTTTGCCCA
121501  TTTTTTCTTA  ATTGGATTGT  ATATCAGTCG  ACTTGGGCTG  CCATAACAAA  AATACTAGAC
121561  TAGGTAGCTT  GAACAAAAGG  AGTTTATTAC  CTCACAGTTC  TAAAGGCCAG  GCCAGAAATC
121621  CTAAATTGAG  GTGCCAAGAG  ATTCAGTTTC  TAGTGAGGGC  TCTCTTATTG  ACCTGAAGAT
121681  AGTTGCTGTC  TTAGATTGTT  TGGTGCTGAA  CAGAATACCA  GAGACCAAAT  AATTTATAAA
121741  GAATACAGAT  TTATTTCTTA  CAATTCTGGT  GGCTATAAAG  CCTATGGTCG  AGGGGCCCAC
121801  CTCTGGCAAG  GGCCTTCTTA  CTGTTATGGC  AGATGTGAGA  TGTCATCTCA  TATTCAAACC
121861  ACAGCAGTCG  CCTTTTGTGT  CCTCATGTGG  CCTCTTCATA  TGCCCATAAA  ATGACCTCAT
121921  GTCTCTTCCT  TTTCTTATAA  GGACACCAGA  TCTATCAGAC  TACTGGCCTA  CTCTTATGAC
121981  CTCATTTAAC  CTTAAATATC  TCCATAAAGT  CCCAAAATCC  CTATCTCCAA  ATATAGGCAC
122041  ATTGGGTGTT  AGAGTTTCAA  CATCAATTTT  GGGGAACAC   AATTTAGGCC  AAAAAGATTG
122101  TGTTTTTTCT  TGTTGGTTTA  AGATAGCTGT  CTTTTTGTCC  TTTTTGTCCT  TTCTTTTTTT
122161  TTGAGGTGGA  CTCTTGCTGT  GTCACCCGGG  TTGGAGTGCA  GTGGCGCTGT  CTCAGCTCAC
122221  TGCAACCTCC  ACCTCCTGGG  TTCAAGAAAT  TCTCCTCCTC  CCAAGTAGCT  GGGACTACAG
122281  GTGCATACCA  CCGCGCCCTG  CTAATTTTTG  TATTTTTGAT  AGAGACGGGG  TTTCACCATG
122341  TTGGCCAGGC  TGGTCTCAAA  CTCCTGACCT  CAGGTGATCC  ACCTGCCTCG  GCCTCCCAAA
122401  ATGCTGAGAT  TACAGGTGTG  AGCCACCAAA  CCTGGCCTGT  CTTTTCTGTT  TTAAGTTTTT
122461  AAATTTTGCT  CACGAACCCT  TTATCCATTT  TATGTGTTGC  AGGTATTTCC  TCTGTAACTT
122521  GTCTTCACTC  TGTCAGAGGC  TGGAGTGCAG  TGGCACAATC  ACAGCTCACT  GCAGCCTCCA
122581  CCTCCCAGGA  TCAAGCGATC  CTCCCATCTT  ATCCTCCTTA  GTAGGTGGGA  CTACATGTGC
122641  AGGCCACCAT  GCCCAGCTAA  TCTTTGTATT  TTTTTGTAGA  GATGGTGCTG  TTGCCCAAGT
122701  TGGTCTCAAA  CTCCTGAGCT  CAAGCAATCC  ATCAACCTTG  GCCTCCCAAA  GTGTTGGGAC
122761  TAGAGGTGTG  AGCCACCACT  GCACCCAGCC  AATGATATCT  CATGATGCAT  TAAAGTCATT
122821  AATTTAGTGT  ACTCAAATTA  AGCACACTGC  CCTTTTATGC  ACAACCTTTT  TTGTATCTTA
122881  TTTAAAAAAT  CATTTTCTAT  TTCAAGGTCA  TGAAGATCTT  ATTTTATAAT  ACCTTCTTGT
122941  GAAATTAGTT  CTCAAGACTA  CCCTCACTTC  TAACACCAAT  TATAAGTTGG  GAGGTCTGTG
```

Figure 1 (Page 38 of 73)

```
123001 GTTCCCAATC AACCTTAGGT TAGTAATTTG CTAAAAGGAC TCACAGAACT TGCTGAAGCT
123061 GTTAGCCTCA TGGTTACAAT TTATTATAGG ATATATAGCT TATTATGTCA TTCCAATGCA
123121 ATGTAAAATT ATACAACTAC TTTTAAAAAG ATTTTAGCAT TTGACCCAAC AATTTCACTC
123181 TGAGGTATAC AAACAGCAGA TATGTGTGCA CATATATACC AAGACACATA CACAGCAAAA
123241 TTCATTGTTT GTAATAGTTG AAAAGGGGAA ACAACTCAAG GAATAAAGAT TAAAATCAGC
123301 TGAGAAAAGA AACACACAAG GCAGTATTAT GGATCGAATT GTATGCAGAT CTCCCTTGCC
123361 CCCAGAAGAT ATGTTTAAAG TCCCAACTCC CAGTACCTCA GAATTGTGGC CTTATTTGGA
123421 AATAGGATAG TTGCAGATAT AATTAGTTAA GATGAGGTTA TAGTACAGTA TGATGGGCTG
123481 GTGACTTAGA AGAAGTAGTA TATATATATT TTTTAATAGA ACTAGTATTC TTCTAAGGTG
123541 GTCACGTGAA GACAGACACA CACAGGCAGA GACTGAGGTT ATGCAGCTGC AGGTCAAGGA
123601 ATGTCAAAGG TTGCCAGCAA GTACGAGAAG CTAGGAAGAG TCAAGGAAGG ATTTTCCTAC
123661 AGGCTTCAGT GGAAGCATAG ATCTAATGAT ACCTTCATGT CAGATTTCTA GCTTCCAGAA
123721 CTACAAGAGA ATATATTTGT TGTTTTAAGC CACCCTAGCT TCTAGCTCTT TGTTACAGCA
123781 GCCCTAGGAA ACTAATATAG GCACAATCCA GGCAAGTTCC AAATATGAGC TTCCAGTTGT
123841 CCTCTCCCAG TAATATGAAC AGTATTACTT TCCCAGCATT AATGTGTGAC AATACACATG
123901 ACGTACAGAG CAGTCCCCAC TTATGCACAA AACATATGTT CCAGGACCTC CAGTGGATGT
123961 CTGAAACCAT GGATAGTACT GAACTCTATA TAGCTGTTTT TTCCTATACA GACACAGCTA
124021 TGATAAGGCT TAATTTATAA ATTAGGCACA GTAAGAGATT AATAACAATA AATTAGAATA
124081 ATTGTTAAGA ATATACTGTA TAAAAGTTAG GTGAATGTTT ATTTCTGAAA TTTACCGTTT
124141 ATTATTTTTG GACTGCAGTA GACCACAGGA ACTAAAACCA TGTAGAAACC GTATACAAGA
124201 GAACTGTATT TCACCCGAGC CTCAGTGTGC AGTTTTAATG GCCTGCCATG GTTGACTGCT
124261 CACATGGCCG ATCTTTTAGT CTACCTCCAC AGGTAGAGCT GATACTGTGT GGCTCAAAGT
124321 TCCTATTATA AATCACATTG TTGACTGTGT GGTGGTCAAA ACCTCCAGGT AAACAAAGAC
124381 ACACTTATCA GTGAGAACAT TTCAAGGGTC TAAAATTCAT CTCCCAGTAG CTGAGGGCAA
124441 AGGCTAGACC TCTTTTTGGG TAAGATAAAT TTTTTACCAT ATACTTTATT TTGCTTTTCA
124501 TGTTTAACTT TATTTTGCTT TTCATGTTAG TTCCCCTGGA ATTGTTTTTT GTGTATAGTG
124561 TGAAGTAGGG GGTCAAGTTT CTTTTTTTT CCTTTTTGTT CTTTTTCTGT TTAAAAGGCT
124621 ATACAATTGT CCCATGCCAT TTATTTACAA GAGTCCTTTC ACCATTGTTG TATGGTGCCA
124681 CTTTAGATGT AAATCAATGT CCATATTTGT TTGAGCCTGT TCCATTCGTT TGTCTATTTT
124741 TGGACAACAC TGCCCTGATT ATTGTCATTT TATCAGTTTT GATATTTAAT AAAGCAACAG
124801 ATTTGTTTAT TTTGGGCCCT TGGATTTGTG TATTAAATTT GAACCCTGTT TGTCAATTTC
124861 TATAATAAAG CTTATTGGGA ATCGATTAG GATTACAATG GTTTTGTAGA TCAGTTTGGG
124921 GACAATTAAT ACCTTTAAAA TATTGACCGC TTCAACTGTA AATATACTCC TCCATTATTT
124981 AGTTTTCCTG TTTAATTTAT CTGAGTAATA CATTATAGTT TTCTTCGTAG AAGTCAGATA
125041 CGTAGAAAAT TCAAAGCCCA AGTGCAATAG CTCATGTCTG TAATACCAGC ACTTTGGGAG
125101 GCCGATGTGG GTGGATCACC TGAGGTCAGG AGTTTGAGAC CAGACTGGCC AACATGGTGA
125161 AACCTCATCT CTAGTAAAAA TACAAAAATT AGCTGGGTGT GGTGGCGGGC ACCTGTAATC
125221 CCAGCTAATC AGGAGACTGA GGCAGGAGAA TCGCTTGAAC CCAGGAGGCA GAGGTTGCAG
125281 TGAGCCAAGT TCCTGTCACT GCACCCACC CTGGGCGACA GAGCGAGACT TCGTCTCAAA
125341 AAAACAAAAA AAAGAACATT CAAATAATCA ATGTAGATAA TTCAAATAAC TAAAAAATGA
125401 ACAGTTATTA AAATATCAGG ATATAAAAGC AAAAAAATCA ATAACCTCCA TATATACAAA
125461 ATGGCCAGTT AGAGAAAAAA AAAAGAATAG GCGAGACTTA AAAAGGCTGG GAATCTCCCT
125521 GAAAATCTTT GAGAGCCTTG GCCCTGCCCT CAGGGATTTC TCTGGCTTCA TGCCCAGATA
125581 CGGGTACAGT TCCTTGTTTA AAAAAATTTT GCTCCATCAA TCAACAAGGG GCTCCTTCCT
125641 CAGAGCACAA GGACCTCCAT AACACCGGAC ACTAGATGTC TAAGGGACAC CTCTTAAGGA
125701 AGTTAGACTT CCAAAGAATG GTGTTTCCTC TGTCCCCAAA CTCTGGAACT CACAGCACAA
125761 CTGCTCCTTG GAGTTCGGTT TCAAATCTAC AAGGCTGTCA TGGAGGTTGC AGACCAAGTC
125821 CGTGGCCTCA GTGTCCGGAT GTACGGTGGC CTTGGCACCT GAATGTGAGA ACATGACCTC
125881 CCTGAAACCA CCACAAGTAT TGTTTCATGT TATGTATGTT TTTTCTTATC TGAAATTCCT
125941 TTTCTTTAAA AATTCAAATT ACATATTTTG CAAGCCCCTG AACAAGCTTC ATGAGCATTT
126001 ATTGAACCCA CAGCTTTTAA AACCTACTGA ACACTTTGCT CTATGTTGTC ATTCACTATC
126061 CACCAATTAT TTAATTATTG ATCAATATTG TTTCCTTAGT GTTGGGATCA TTTATGCATG
126121 TATTTCTTTT ATATTGCATA TTTTATATTT CTGCATTACA GTTATTACAT ATTACTTTTG
126181 CTACAGTAAT AGTTCAAAAG TGTACATCCA AAATTTAGCT GTGAAGTGGA TGGACTGAGG
```

Figure 1 (Page 39 of 73)

```
126241 CAGAACTGGA GGCAAGAAAA TGTCACAGTA ATTCTAAAAA AGATGATGTA CAATTAGAGC
126301 AAGAGAGTAG CACTGAAATT GAAGAAAAAT AGATGCGTTT GAGAGAAAAT TAGGAGGTAG
126361 AATCAACAGA TTAGATGTAG GGATGAGAAG GGTCAAAGAT GACACTAGGG TTTTTAACTG
126421 GAGCAAGTAG GTAGACAGAA CATTTCTTCC TGAAAGGGCA GGTCAGATCA TGTGTTGTCT
126481 CAAAGGGCAT GAAGAGTAGA AAGCCTGGGA CAGATCCTGA GATGACCAAT ACCCATGGTG
126541 CAGGGAGAGG GAGGGAGATC TGCTAAAAAG ACTGCAAATG TCAGGATAGT AGAAAATCAT
126601 GAGTGTGTGA TGTCCTGGAA GTTGAGACAG TATCACATTT GAGAACATTT AAATTGGTAA
126661 CTCTGACAAA AAGCTGGAGG CCAACTGTGA ATGCCCATGA GAGTGAGAAG CTCCCACACT
126721 TTTGTGGGCA TCAGAAAGCC CACCAGGTTC CTGCAGTGAA GATCTGAGAA GGATCCTCTT
126781 GTGGCTTTGG CAGGGAGAGA AGAATTATTA TGAAATACAC CCCAGAACCT TCTTCAAAAC
126841 AAAGGCCTAC TCTCAAGGGG AAAACATTTT GCCAGAGTCT TATCCCAGCT GGGAGAAGGT
126901 AATTCTTCCC ACTGCAGCCT CATCTAGGCT TTCTGTCTCA CTTAAGGGAA GAAAATTAGT
126961 CAACAGGGAT CAGAGCTTCA TGAAAATAAA TTGGAAATGG TGCAGCCAGG AAAGGAGCAA
127021 AGGTCTGAGG AGGAGGAGAA GGAGGAAGAG GAGTTGTATC ATTATAAATA CTTGAGGAAG
127081 AGGAGGAGAA GGAGGAGGAG GAGGAGTTGT ATCATTATAA ACACTTGAGG AAGAGGAGGA
127141 GGAGAAGGAG GAGGAGGAGT TGTATCATTA TAAACACTTG AGGAAGAGGA GGAGGAGAAG
127201 GAGGAGGAGG AGGAGTTGTA TCATTATAAA CACTTGTGAC GGTCCCAGCC CCAAGATATA
127261 GGCATGCTAA TAAACTGAGG CTTAACACTT TGACTACAGA ATGCTGCTTC TCCCTAACAC
127321 CATCAAGGCT CCAACTGAAT AACAATGAAT TATGAATGAA AGAGCTGTAA GGAGAGACAA
127381 AAGTTAGAAT GAGACAAGTA TTGTTATCTA GAGATGCCAA GAAGGCAAGG AAGATAACTA
127441 AAAAGGCACT CTGGATTTAG AAATAGGAAG TCATTAGTGA CCTTGTAAAT AATGGAGCCA
127501 GAGGAATACC AAGGGCAGAA GCCTCACTAT AGTGTGTTGC ACCTGTCAGA GGTCAGGAGG
127561 TGTAACTGAC TCTCCCACAG TGTGGCTTTG GAAGAGAGAA GTCAGCAGCT GCATGGAGAT
127621 TTGGGAGAGG GAAAGCTTTT TTTTTTTTTT TTTAATTGGA AAAGACTGAG CTATGTGTAA
127681 ATAGAATAAG ACAGGAAGAG TGTAGACACA GGAAAGAGGG CAGACAAAAA CAAGTGCACA
127741 GTTATCTAAG GGAAACAATG GGATCAAGCT GCAAGTATAT AAACTTGTCT TGATAGAAGA
127801 ATCCTTGATC TGGTTTATTC AGTGTTTGGT CCAAACCCAC ATCCCTGTTC TGCCTGTCTC
127861 TGACTTGCTC TGTGCCCCAG AAGCCCAGCT TCTACAGATA GCATTAGCTG GGCAGCCCTG
127921 CCCTCTTGCA ACAGCTGGAT TTGGCCAGTG ATCAGCCCAG CAGGAATGTA GATGGCAAAG
127981 GAGAGAGAGG TTAGTGTACT TATTCCCTGC ATCACCCCCC TGCTTGGTGG GCAGCTCTTC
128041 CTCCACAGTC CCAGCTCTGG CCTAGCTCTG GTTACAGGTT CCCTCCCATT GCCTCTTCAG
128101 ATTTAAAGGT GTGTCTGTCA GGGTATAACT GGGAGCTAGA AATTGCACTG AAATTGAACA
128161 AAGAATTTTA TGGGAATGGT TGTTAACTAG TTATAAGAGG ACTGAAAATG GAAAAGTGGA
128221 CAAACGTATC AGAGATAGTA ATGACAGAAA GCAACTACCA CCTCCAGGTT TAGGAGAACA
128281 AGGAAAAGAT TCTTTGAAGA GATCCCCAGA ACTGGGACCT CTGAGGAGTG TATGCTGGAC
128341 CACTGATGAT GATATGTCTG TAGATAGAGG CATGATGAGG CTGATTTTAG GAGCATGGAA
128401 GATCTCCAAA CTGAAGCCAA CTGCTGTTAC TGGATTCAAC TGCCACTGCC AGGTTGAAGA
128461 ACCCATTCTG TGAGGATGTC AACAAACAAA GTGGGAAATC TTTTCACATC CTTCCAGCCC
128521 TCTAGTCTTC CTCCAGTGCT TTCTATTGGT AGGGTTTGGG GAGGTGGCTA GCAAAGCGGT
128581 ATTGGAAAAG ATAGAAGAGA CTAAATCTTC ATAACCAGCA CAGGGTGACA CTGGATCACT
128641 ACTGTTGCTG ATCTTGGGCT GCCTCATATC CCCTGTTCTT CCCATTAGCC CTGTCACAAC
128701 TTTGTAGATA TCCCTTCATT ATATGCCCTT CATATATTCT TTTGGTTTAA CTTTTTCTGT
128761 TGGAATCCTA ATATGGCACT CCTCCATTTT TCAGGACCAA AAGAGTATAA AAGATTATCT
128821 TTTACCAAAA AAAAGACAAA AAACTGATCT AATTCCTGAT TTGATCATTA CACAATCTAT
128881 ACATGTATCA AAATATCACA TAGTACCCCA TAAATATATA CAACTGTGTC CATTAAAAAT
128941 AAAAATTAAA GAAAAGATGG TAAATATAGC TCTGTCAGGC AGTGGAGGTT TTACCACGAT
129001 GGCTGTTATT TCCCCCATGA AGGGGGGAGT GAGGGAGCAG CTGAAAGTAG GTGCTTATAG
129061 GGGTATAGAG GGGCTCAAAG CTTTGAGAGA GGAGAATGTC TGAAAGAGCT GCCAAATAGC
129121 ATGCAGGTCC CATGGGGGCA GAGCCTCTGC TCATTCACCA GTGCCTCTTC AATATCTACA
129181 CTTAAGCCTA ACACAAAGTG TGTGCTTAAT AAGTATTTGC TGAGTATGTA AAGTGGAAAC
129241 AGAACCAATC TGGCAAACTT TGTAGGACTG GTGGGCAATG AAGATCAGTC AGGTAAAATC
129301 TGTGGATATA AATTTATATT GATCAAAAAA TTCAAGGTTA GGTGTTTTTC TTCAGTCATG
129361 CTCAACGATG CTTCAGCCAT GCTCAACTCT TCTGTAGCCA CAGAAAAAAG TTTACCCATA
129421 ATCGAGCTGT GTCTGTCTCT GAATAATGAA AAGACCATGA TGCAAGGGAG TTGGAGACAC
```

Figure 1 (Page 40 of 73)

```
129481  AGAAACAGTG TTTGAAGTAA TGGGTAATGG AAGCATGCTA CCAGGGAAAG GAAAGAAGTG
129541  GCAATAGGAA GGAACAGAGA TCTGTGGTCC TATGTCCCCT GAGCATATTC ACATGTTAAA
129601  GCTAATTCAG TTTTCAATCA TCATTAAAAT TTTGTTCCTA AATATATGGC CATTATTTTC
129661  CACAACCACA CTAAAACTTT ATTACCTCTG GCAAGTGACT ATGCAAGTAA CTAAGAGCAA
129721  AAATATCCAC AACTACCATT TGAGCTATCA ATTTAGGGAA AGTCATCTGG CTATAATCTA
129781  AGTGACCCTC CACTGAATGT CAGTATCTTT GCATATGTGA TTTAAATCTG GGCCTTCGCA
129841  ACACCATGAA CTGTTCTTGT CTTGAATATC CAGATTGAAG GAAATAATCT GAGTAGTTAC
129901  GAGTCCTGAA GCTAGAAAGA TGGAAACCCC ATTTGCTCAT CAGAAAGCCT TAGAGCTTGG
129961  GCGCTGGCGG GTCCTGTCTC ACCGGGACAG AGGGGCTCTT TCCTCCCCAT CTGATAGTCT
130021  GATAACTAGA GAAGCCGGCC AACTTATTCT CCAAGAAGGA GCCATCTTAG TTCCTCCTGA
130081  AATGTTCATA TTTAGAAATT ATTGTTTGTC AGTAATTTAA CCCCTTAATG GGCTTGCCTT
130141  GTGGTCCATA CCACTGAGTG CAGAGCTTGC CTGGAAGAAT TGTGAGGGCC ATTCCATCTT
130201  CCAGGCAGTA GAGTTCAGTA CTTCTTTAAA ATTGCTGCTG AACTCTGTAT TTGAAAAGAA
130261  AGAATCATTT GGGTGTGGTA GCTCACACCT GTAATCCTAG CGCTTTGGGA GGCTGAGGTG
130321  GGAGGATCAT TTGATGCCAG GAGGACCACT TGAGACCACC CTGGGTAACA TAGCAAGACC
130381  CTGTCTTTAG AAAAAAAAAA TACAATAAAA TAAATACAAT AAAAATAAAA GCAAAAAGAA
130441  AGAGTCCATC TTAGGGACAG ACTGTAACTA CTCACTGGAG CTTACCTTTA CATAGTTCAG
130501  GATCAATTAT AATAAAACAC TTTTGTGCAG ATTCAATAGG ATTATTTTAA TCCCCATCAT
130561  CTCTCTGAGT TTCCAGTCAG TTTCTCTGCA TGTAGACACC CTTCTCCAGC CCACCATTGT
130621  CTCTCCTCCT ATAGCTCCAC CAACAAATCA GAACTTTTTC TAACTGCACC TAGTGCACCT
130681  AGAGTCTACT CCAGAATGCT CATGGAGAAA GTTTCTGAAA GGTAAAACTC TGAATGATAT
130741  TTGTAGCTAA AGGGAGACTT GCTAGAGACA ATAAGCTAAT AGTTGTAGAC TTCAGTAGAA
130801  GAGGAATGAC ACTGCAATGT CAGGGTGCAG GACTTCAAGA GGGCAGAGTA TGGAAACCCA
130861  ATGGGAAAAA TGCTCACCAG GAACATGAAG AGAAGGAATT ACGTGTAAGG ATTTCTCAAT
130921  GTGTTCCCAA ATTTGCCCAG CAGAGGGAGG CCTCGGGTTG ATGGCAGGCT GACCACACAA
130981  TTAAAGAAGG CTGAACCTGG GGGCTTTTAA CAACCATCGT GGGCTCTACT GTAAGCATTT
131041  AGAAAAAGAA AGTTATCCAT TCAAAAATAT ATATATTTTT AAACTTCAGA ACAAAATTAT
131101  GAAGAGCTAT ATTTACTTTT CTACATTCTA ATTTTTATAA ATCTGAGTAT ATTTTGCATA
131161  TATTGTTATA GTACATATTC AATTTGTAT TTGCTGTTT TCACTTAACC ATTTTTACTA
131221  GATTACTCTG TGTTCATAAT AATCACTTTT TTAAAACTTT TATTTTTATT TATTTATTTT
131281  TTTTTTGAGT CAGAGTCACA CTCTGTCGCC CAGGCTGGAG TGCAGTGGCG TGATCTTGGC
131341  TTACTGCAAC TTCCACCTCC TGGATTCAAG CAGTTCTCCT GCCTTAGCCT CCTGAGCAGC
131401  TGGGATTACA GGTGTGCACC ACCAAGCCCG CTAATTTTT GTATTTTTAG TAAAGACGGG
131461  GTTTCACCAT GTTGGTCAGG CTGGTCTCCA ACTCCTGACC TCATGATCTG CCCACCTTGG
131521  CCTCCCAAAG TGCTGGGATA ATCACTTTTT ATGCTGCATA ATTCTTCAGA TTTGTCAGTA
131581  CGACTGTATT TACACTCATT TGTTTATTA GAAAGAATTC CAGAATATTT TGGCTGCCCT
131641  AATTAATTTT ACAATTAATA TGATTTTGAA ATTGGGTATT GGCTCCTTCT GAATTGGTTT
131701  ATTAAAATAT ATTCTAATGT AATTTATGAC ATTTTCATCA TATTAGCATA TTTATTCTGT
131761  TAGAATTTCA TAATTTATAA AGCTACAAAC TGTATGTGAT ATAGCTTGTA ACTTTATCTC
131821  ATAACTTTAT GCAGTTACAA GTAGAAATAA AATGTTCCCC TCAAGATTGC TTAAAATTTT
131881  ATTATAAACA AGTGTAAAAA ACAAAATCAC TAAAACACTC CCTCTTTTTT CCCCCAAAAT
131941  GCATGTTTCC ATTTTAACAG AACCCGTATT TAATCAGCAG ATTTCTATGG TGGCTAGATT
132001  TGTAGACTAA ATATTAAAAG TCCCAAAGCA AATGCATTTT TCTCTTAAAT TTTACTGACT
132061  TTTTTTTTTT TTCTTTTTCT GAGACGGAGT CTTGCTCTGT CGCCCAGGCT GGAATGCAGT
132121  GGCACAATCT CGGCTCACTG CAACCTCCGC CTCCCGGATT CACGCCATTC TCCTGCCTCA
132181  ACCTCCCGAG TAGCTGGGAC CACAGGCGCC CGCCACCACG CCCAGCTAAT TTTTTGTATT
132241  TTTAGTAGAG ACAGGGTTTC ACCGTGTTAG CCGGGATGGT CTCGATCTCC TGACCTCATG
132301  ATCTGCCCAC CTCAGCCTCC CAAAGTGCTA GGATCACAGG CATGAGCCAC CGCGCCCGC
132361  CTACTGACTT TTATCCAAAG AAAATATAAG AGCTCTTCAT CATAACGTAT GTTTCTTGCT
132421  CTTGTTATTA AATATGACAC ATTTAGACTT AAACTGATTT GAAGGTTTAT GACATTGTTT
132481  AAGTTATTAC ATAATTAATT CATAAAGATA ATGACTAGTT TGAACTACTG ACAGCTCACA
132541  CATCATCAGT TGAACAGCAG AAAGCTTACT AAGCTACTTT CTTATGTTTC TGTCTCCCAG
132601  CTACTAAAAG AAACGAAACC CTTCCAGGTG TTAAGGCAAA ACTTTCCTCC CCCTTTCTTC
132661  TATAAATCTG ATTCCATGTT AGTGAAATTT CTACTGATGG CTTTGGTTTC CTCTATAGTA
```

```
132721  GAATAGAGAT  CCTATGGCAA  AAGTCATGTC  TGACATGGTA  GCAAATAGAA  ATGGGGAAAA
132781  GGAAGGTCTG  CAAGAGCCAA  TGTGGGAAAT  GGGGAGAGGA  CTGACTACAA  AAACCCAGCA
132841  GGAATTCCAG  AAGAAAACTC  CTCAGGACGG  GCACATTGGC  TCATGCCTGT  AATCCCAGTA
132901  CTTTGGGAGG  CCGAGGTGGG  CAGATCACTT  GAGTCCAGGA  GTTTGAGACC  AGCCTGGTCA
132961  ACATGGCGAA  ACCTCATCTC  TACAAAAAAT  AAAAAAATTT  GTCAGGCGTG  GTGGCATGCA
133021  CCTGTAGTCC  CAGCTACTCA  AGAGACTTAA  GTGGGAGAAT  CACTCGAGCC  TTGGAGGTGG
133081  AGGTTGGTGA  GCCGAGATCA  CGCCACTGCA  TTCCAGCCTG  GGCGACAAAG  TGAGACGCCA
133141  TCTCAATCAA  TCAGTCTCCT  CGAAAAGCAA  CATTATGGAG  AGACAGGATT  CCGTCAAGGC
133201  CTGGGGCACA  CAGGAAAATA  TTAAGGCAGA  AGAGAGTTTC  CTCCCCACAC  CACACCGTAT
133261  CCCACAGGCA  CTGCGGATGT  GCATATGCAA  GAGGGGTTGA  TCCTAAGAAT  TTAGAGTCAC
133321  AGAGGAGGAG  GCACCAAGCA  GACTGTGGAG  AAAGTCATGA  CCAGAAAGGG  ACAGAATGTA
133381  AAGCTTCAGC  TGATTATCTG  GCCTCAGGGA  TTCCAGAGGA  ACTGGTCCCA  ATGGTCTCCT
133441  GGTGATGTAG  GTTCTTAGGT  TTCTTTTACA  GGGGTTTTCT  GGGAGATCGT  TGACCCAGTT
133501  AGCATTCAAG  CAACTTCCAC  CCTGCACTTT  TATTCTTTCC  CCTTCACCTG  CTTAGGTTTT
133561  ATCTGTCCAG  GAAATAATAA  TAAAATTATT  GAGCCCTGGA  CATGTACCTG  TAAAGCTCCT
133621  TAAAGATGAT  GCCTTCTAAC  TCCTCATTCA  ACAGATACAA  AAACATTACA  ATAAAATGAC
133681  TCATGCAAGA  CACCCAGGTA  GTTTATAGCA  GCTAATAAAA  ACAGAATAAC  TATAAAATAT
133741  GGTAAGTTTA  TAAAAGTTAC  ATTGAGTATA  CTTTATAAGA  ACTGCTTATT  GAGTTTGCCT
133801  AATAACCACA  CAGCACAATA  ATAATATGTA  TATATTTTTA  AATATGTGTA  AATATGTGTA
133861  ACACAAACTT  GTAGAAGGTA  TATCTGAGTA  CAACCCTATT  CTGTTTGGTT  ACCTTTTCTA
133921  GTTCATTATG  TAAGTGGCAT  AGCTACCTAA  GGACTTATGC  TTATAAATGT  TACTCAAAAA
133981  AATACAGAGG  ACATATGTGG  ATAGATAATG  GAAGAGATAA  GATAGGTAGG  TTGAAGGGTT
134041  GGGCTGCCCC  TCCACACCTG  TGGTTGTTTC  TCGTTAGGTG  GAATGAGAGA  CTTGGAAAAG
134101  AAAGAGACAC  AGAGACAAAG  TATAGAGAAA  GAAAAAAAGG  GGTCCAGGGG  ACCGGTGTTC
134161  AGCATACGGA  GGATCCCACC  GGCCTCTGAG  TTCCCTTAGT  ATTTATTGAT  CATTATTGGG
134221  TGTTTCTCGG  AGAGGGGGAT  GTGGCAGGGT  CAAAGGATAA  TAGTGGAGAG  AAGGTCAGCA
134281  GGTAAACACG  TGAACAAAGG  TCTCTGCATC  ATAAACAAGG  TAAAGAATTA  AGTGCTGTGC
134341  TTTAGATATG  CATACACATA  AACATCTCAA  TGACTTGAAG  AGCAGTATTG  CTGCCAGCAT
134401  GTCCCACCTC  CAGCCCTAAG  GCAGTTTTCC  CCTATCTCAG  TAGATGGAAT  ATACAATCGG
134461  GTTTTACACT  GAGACATTCC  ATTGCCCAGG  GACGAGCAGG  AGACAGATGC  CTTCCTCTTG
134521  TCTCAACTGC  AAAGAGGCGT  TCCTTCCTCT  TTTACTAATC  CTCCTCAGCA  CAGACCCTTT
134581  ACGGGTGTCG  GGCTGGGGGA  CGGTCAGGTC  TTTCCCTTCC  CACGAGGCCA  CATTTCAGAC
134641  TATCACATGG  GGAGAAACCT  TGGACAATAC  CTGGCTTTCC  TAGGCAGAGG  TCCCTGTGGC
134701  CTTCCTCAGT  GTTTTGTGTC  CCTGAGTACT  TGAGATTAGG  GAGTGGAGAT  GACTCTTAAC
134761  GAGCATGCTG  CCTTCAAGCA  TTTCTTTAAC  AAAGCACATC  TTGCACAGCC  CTTAATCCAT
134821  TTAACCCTGA  GTTGACACAG  CATATGTCTC  AGGGAGCACA  GGGTTGGGGC  TAGGGTTAGA
134881  TTAACAGCAT  CTCAAGGCAG  AAGAATTTTT  CTTAGTACAG  AACAAAATGG  AGTCTCCTAT
134941  GTCTACTTCT  TTCTACACAG  ACACAGTAAC  AATGTGATCT  CTCTCTCTTT  TCCCCACAGG
135001  AGGTGATGGC  CGGAAGAACA  TGGCAGAGGG  CAAAACAAAA  CAGCATTGGG  AACAAGCTCT
135061  GTTTAAAAGG  AGACTTGTGA  ACAGCAAAGA  GTAGAAAGGG  TTCTCTTACA  ACTGAAGCCC
135121  ATGGAAGACA  AATGTGTACT  GCGTGAGTTT  TAAGGCAATA  GGAGTAGTGG  GACCTAGGGC
135181  ACACCAGAGA  GCATATTAAC  TCTCAAACTT  TTAAAAACAT  TATATCTGCT  GGACACAGTG
135241  GCTCACACCT  TAATCCTACA  ACTTTGGGAG  GCCGAGGCGG  GCGGGTGTAG  CTTGAGCCCA
135301  GGAGTTCGAG  ACCAACCTGG  GCAACATGGC  AAAATCCCGT  CCCTACAAAA  CAAACAAACA
135361  AAAAACAAAA  TTAGCCAGGC  ACGGTGATGC  GTACCTGTGG  TCCCAGCTAC  TCAGAGGCTG
135421  AGGTGGGAGG  ATCGCTTGAG  CCCCGGGAGG  TTAAGGCTGC  AGTGAGCCAT  GATAATGCCA
135481  CTGCATCTCA  GCCTGGGCAA  CAGAGGGAGA  ACCTGTCTCA  AAACAAAAAC  AAAAACACAC
135541  CATACCCAAC  CACAATGCAT  CTGTCTTAAG  TACCAGTACC  ACACCCTCT   ACTCACTACT
135601  AAATAGGTGA  GTTCCCAATC  CCTGGTAGCA  GGTTTAAGCA  TGTTATATTA  AAGGTCTTAG
135661  GCTAGTGACT  CATTCACTCA  TTAAACAAAT  ACTTATTGTG  CATCTACTAT  AAACTAAGTA
135721  CTGTGCTAGG  TACAAAAGCA  AATAATCTAA  GCTCTATAAA  CTTTACTTTC  TTCATCAACA
135781  AAATGGAGAT  GTTTTAGGCA  TCTACTCATC  ATTCTGAGCT  CCATCTTTTG  TGACTGTAGT
135841  TGGCAGAGCT  TTTTATCAGT  TTCTCTAAAT  AGCTCTACCA  GTCCCTGGTG  GATGCTGGCA
135901  TGCCCAAAGG  ATCCATCCTG  ATGGCCCTGT  CTGCTTACCT  TACCTGCCTG  CCTTTGCAGC
```

```
135961 ACCGCTCTGC TCTTCTGCAG GACTTCCCTT ATCCTTTGGG GTCTTGCTGC TCTTAGGCTG
136021 CTCTGCTTGT TTTGATCTGC TTTGCATCAC ATGTATGTAA AGGTCCTTTC CTTATTTACC
136081 CATGACCAAG GTATTATGAG ATTCTGGAAT TTCCCCAAAC CACATTGATT GCTGGGAGAA
136141 TAGAAGAAGT GGATTACAAG TGGAACTTAG AAGGGGAGTA TTCGAGAAGA CGTCTCTGCA
136201 AATCCATTTA GAGAGACCTT TCTCCAGTGG TGACTCAAAG ATGCAGCTCC TTTCATCCTG
136261 TGGCTTGGCC ATCTTCAGCA CATGGCTCCC AAGGATGTCC TCAGGATGGT CTCTAATCCA
136321 AGGAGCCTGA AGAGAAAAAA AGGCATGGAG TATTGTGAGT GGTAGGTGGT TATGGACCAG
136381 TTATGGAAGA ATACACATCA CTTTTGCCCA CCTTCTACTA ACCAGAACTC ACACAGCCAT
136441 AGACACTGAC AAGTAGGACT TAACAAGAAT CTAATTTTGA GTCTAGGAAT ACGACTGTAG
136501 CAAATATTTA ACAGCTTCAA ACACAGGTGC ATTGCTATCA CTATGCTTGG CCCAGGCCTG
136561 TCTCCCTTTC CTGCCATGTC ACAGGGGCCA GCATTTATGT CTAGATTGGG TTGGTTGGGA
136621 TATTAAGACA ATAATGAACC AATACAACAT CTTGAGCATA AAACCAACTG ATACAATGAT
136681 GTACAAGTCA GATGATTCTG ATGATTATGA ATTATGTCAA TAAAAGAAAT GTGATAACTA
136741 AGGTAATTTT TGTTTTGGCA AATTTTTGTT TGTTCATGAC AGGATGAAAT CCTGTCATTT
136801 GTAGCAACAT GGATGGAATT GCAGGATACT ACATTAAGTG AAATAAGCCA GAAACAGAAA
136861 GTTAAACACC ACATGTTCTC ACTTATATGC AGAAGCTAGC TAACTAAGTA AATAAGTTTA
136921 TCTCATTGAA GTAAAAAGTA CAACAGAGAT TACTAGAGGC TGGGAATGGT AGGGGAAAGA
136981 GATGATAAAG AGAGATTCGT TAAAATAAGT TACAGCTAGA TAAGAGCAAT CAGTTCTAGT
137041 GTTCTATTTG TACTACAGAA TGGCAATAGT TAACAGTAAT AAATAATTTC AAAGAGCTAG
137101 AAAAGAGGAC ATTGAATGTT TCCAACACAA AGAAATGAGA AATGCTTGAA ATAATGGATA
137161 TTCTAATTAA TTACCCTGAT CTGATCACTA TACACAGTAT GTATAAAAAT AACACTATGG
137221 GCTGGGCGCA GTGGCTCACA CCTGTAATCC CAGCACTTTG GGAGGCCAAG GTAAGCAGAT
137281 CACTTGAGGT CAGGAGTTAG AGACCAGTCT GGCCAACATA GTGAAACTCC ATCCCTACTA
137341 AAAATACAAA AATCAGCCAG GCGTGGTGGC ATGTGCCTGT AATCCCAGCT ACTCAGGAGG
137401 CTGAGGCAAG AGAATTGCTT GAACCCAGGA GGCGGAGGTT GCAGTGAGCC GAAATCGCGC
137461 CACTGCACTC CAGCCTGGGT AACAGAGCAA GGCTCTGTTT CAAAAATAAA TAAATACATA
137521 AATAAATATT TTTTAAAAAA AGAACATCAC TATGCACCCC ATATATACAT ATAATTATTA
137581 TGTCAATTTG AAACATAATT TTGAAAAATG AAAAAATGAA ACACAAATAT GAATCAATCC
137641 TCTCCAAGTT GATATACTTA AAAGGAAAAA AGTCCGAGGG CTTAAACTAT TCAATCAAAA
137701 TTTTATTAAA ATGCTATAGT AATCTGGAAA GTATTTCAGA ATGAATTGGT ATAAGGTTAG
137761 ACACAAAGAT CAGTGAAACA AAACAGAGAA CCCAGAAATA GATTCACACA TCTATGGACA
137821 ACTGGTTTTG ACAAAGGTGT CAAGGCTATT TAATAAGTAA AAAAATCGTC TTTTCAGTAA
137881 ATGTTTCTTG AACAAGTAGA CATCCGGTGT GGGGGAGAGG AGCAGGAGCC TTACCTCAAA
137941 CTTTATGCAA AAATTAACTC AAAATAGACC ATAGACTTAA ATGTAAAAGC TAAAATTATA
138001 AAACTTCTTT AAAAAATAGG AGAAAATCAT CAACACCCTA GGATTAGCAA AGATTTCTTT
138061 AAAACAAAAC AACAGGTTTA TAGTTTATAA AACATAAATA ACAAAATGAT AAATTTCATC
138121 AAAAGTGAAA ATTTGCTTTT CAAAAAACAT TATAAAATGA AAAGCAGGAG GCTGAGGCAT
138181 GAGAATCACT GGAACCCGGG AGCTACAGGT TGCAGTGAGC CAAGATGGTG CCACTGCACT
138241 CCAGCCTGGG TGACAAAGTG AGACTCTTCC TAAAAAATAA ATAAATAAAT AAATAAATAG
138301 AAAAGAAAAA GAAAAATCAC AGGCTGAGAG AAAATATTTA TAATACATGT ATCTGACAAA
138361 GGACTCGCAC CTGGAAAATA TAAGGAACCT TATAACTTAG TAAGATGACA AGCCAAAACA
138421 AAGAGTAAAA GTTTTCAACA GACATTTCAC AAAAGAAAAC ATACAAATGG CCAGTATGCA
138481 CATGAAAAGA TTTTAAACAT CATTAGTTAC TAGGGAAATG CAAGTCAAAA CCACAATGAG
138541 ATACTTCACA TTCAACAGAA TAGCTAATGT TAAAAGGACT GACAATCCCC AGGGTGAGCA
138601 AGGGTGTGGA GGAAACTACT CTCATATATT GTGAATGTAA GAGGACAATG TTACAACTAC
138661 TTTGAAAAAA GTTTGGCTGT TTCAACATA AAATTAAACA CTTATACAGC CCAGCAATAT
138721 TTCTGGGTCA TTTCTCCCAG ATAAATGAAC ACATGTCCAT ACTATGACAT GTACAAATGT
138781 TCATACTGGC TTTGTTCAC AATGCTATAA ACTGGAAACA ACCCACGTGT CCATCAACAG
138841 GTGAATGGGT AAATAAATTG TAATATATCG GCCAGACGCA GTGGTTCATG CCTGTAATCC
138901 CAGAACTTTG GGAGGCCAAG ATGTACGGAT CACCTGAGAT CAGGAGTTTG AGACCAGCCC
138961 ATCCAACATG GTGAAACCCC ATCTCTACTA AAAAATTAGC TGGGCATGGT CACGGGCGCC
139021 TGTAATCCCA GCTACTCGGA AGGCTGAGGC AAGAGAATCA CTTGAACCGA AGAGGCGGAG
139081 GTTGCAGTGA GCCAAGACCA TGCCATTGCA CTTCAGCCTG GGCAACAAGA TGGAAACTCC
139141 ATCTCAAAAA AAAAAAAAAT TGCAATATAT CTATATCTTG GAATATTATA AAGCAATAAA
```

139201 AGGGAATAAA CTACTGATAT ATACACAAAA TGGATGAATC TCAAAAATGT GAAGGAAAAT
139261 AAAAAATACA TATGATATAA ATTCCATTCA TATGAAATTT TAGGAATGGG AAAACTAAGC
139321 TGTAATTATG GAAAGTACAT CAGTGGCTGC CTGGGGCCAA GAGGATGGAA GAGGCGGCAC
139381 AGGTGATACT ACAAATGGAA ACTATCTAGG TTGACGAAG TGTTCTGTAA CTTGATTACA
139441 GTAGTAACTG TTTGGGTATA TAAAACGCAT CAAATTGTAT AATTAATACA GGTGTATTTT
139501 ACTGTGTATA AATTATTCCT CAATAAAGTT GATTTTTCAT TAAATATATT ATTTGCTAAA
139561 ATGAGGAGAG ACAACTATTA TCTTAAAATA GTTAAGCACA ATAAAAATAC TACAATCAAC
139621 TCATTATATA TGGAAATTAA AGGAGAAAAA TAGTGGTATG ATTAATTAAA ATAAAAAGAA
139681 AACCTTCTAA ATTTTATCTT AGCTCATAGT TGTAAAAGCT GCCATCCCTA ACCAAGGCCA
139741 CCCTTGACCC TTTCTCATGT TCCATCTTTC TGTTTGTTTC ATAGTTTATG TCTCACCAAA
139801 ATCTATCAGA TAAACGTATT CATATGAAGA TTTAAATATA TTACATGTTA AGCCTTAGCG
139861 AATACTTCAA TATCTAAAGA AGGTACAAAC AAAACAAAAA TCAACACTTA GTTATAAGAG
139921 ATTACATACT CTCCAGGGAA GACCTGAAGA CTAGCCCCTT TCTGGATCCC ACTAGCCCCT
139981 CATCCCACTC CAAGCCCTCC CCTCCAATCC CATATGCACT GGGCATTCAT ACAAATAAGA
140041 CCATCAGCTC TGGATATCTG TACTGATTGA TGCTCCTGCT AACTACCTGA ATGATTGCGA
140101 TGTAAGGACA GCACTGCCTG AATCCTATTT ATCTCTCGCT ATGCCATAGC GGCCTTCCAT
140161 GCTGATGGCG TGTTTGAGGA TCCAGAGGGG TCTTTGGTTG GCAGGATTGT TTTATTTCCC
140221 CAAGAGGAGA GCCTTGATGC AAAAATAGGT GAAGAAATCA GTACAACAAA ACAGAAAGCC
140281 TAGAAACTAC TATGAACACA ATAGAGCAGA AGTAGCCTTA AGAGTTGGTG GAGAAAGGAT
140341 GGTCTATTCA ATTACCTGGG CTGAGAAACT GGCTTTCATA TGGAATAAAA ATAAAATTAT
140401 AGCTATACCC CATATCATAC ACAAAAGTTT CTACATCTAA CAAAGACACA GATAGAAAAT
140461 GTTTTAAAAT TTTAGAAGAA AATAGTGCAG AATTTTAGTG CAGAATTTCT TAGACTAGAT
140521 GCAAAAACAA AAATGATTAA AGTGGCCAGG CACGGTGGCT TATGCCTGTA ATCTCAGCAC
140581 TCTGGGAGGC CGAGGTAGGT GGATTAGTGG AGGTCATGAT TCGAGACCA GCCTGGACAA
140641 CATAGTGAAA CCCCATCTCT ACTAAAATAC AAAAATTGGT AGGGTGTGGT GGCTCACGCT
140701 TTTAATCCCA GCTACTTGGG AGTCTGAGGC AGGAGAATCA CTTGAACCTG GGAGGCAGAG
140761 GTTGCAGTGA GGGGAGATGG CGCCACTGCA CTCCAGCCTG AGCAACACAG CGAGACTCTG
140821 TCTCAAAAAA ATCTAAAAAT AAAAAGATTA TTTTTAAAAG ACTATTTTAA ACAAAAAAAA
140881 TCGTTTAAAT GATATGACAC ACTACATCTA ATATTTGGAA AAGTACTTCT TAATACTTTT
140941 AATAAAAAGA GGCGCTGAGA GCATACAACC TATCCTCAGA AGAGTGTTTG ACCTCTAGGA
141001 GGGACGCAAG CGCGTTCTTC CTTCATTTTA ACTGGTCATT TTCATTTATT TCAGGAACAT
141061 CTGAAGTAAA CACAGTCACA CGTTAACCTT TAAAAATCTA GGAGGTGCGT ACGCATAGTT
141121 CCATTACTTC AATTTTTGTA CTTTTGCATT TTAAAATATC ACAGGGAAGC TCGGTACAGC
141181 TTCAAGGCTA GGAGGGGTGG CTCTCTCTTA AGCCCTGTCC CCGCCAGCCC CAGACCTCTC
141241 GTCCCGCCCC CATTGCCCAG TCCCCACCCT CACTTCCCCA TTTCCCCACT CCCGCGGTCT
141301 CTTAACGCAC CTCGTTTTTC GTCCAGTGGA CTCAGACCTG TAGTCTTCCA CCAGGATCGG
141361 CTCCTTTCCC GGAGCTCTCG CTCTTAGAGG AAATTGAGAG AAGCATCAGC GGAGACCCAT
141421 CTGTGGCTCT CCAGAGGGCG CGGCATTCAG ACCCCAGATC CAGCTGTGAG AACGGACCCC
141481 AGGCTCACAC CAGGCCTGCG GGAGGCGGCC CACCAGAGGC GCTAGAAAAC AAGCCTCGCG
141541 GGGAGGCGCG CAGGGCGACT GCAAGCTGTA GGGGCGCTG GCGCCCTCAC AGGCCAGGGG
141601 CAGGGCCGGC GCTGCGGGCG GGCTCCTGC GGCGTGAGGG GCGGCCCCAG GCCAGCAGCT
141661 GCGCCCTGGC TGGGAGCCGG GGAGCATTTG CTGCTCTGCT GGACCCTGAG TCTGGCGGCG
141721 GGCGGCCTCC TCTCCGCTCC CCGCCCGCCA TCCCCAACT CCCGATCTCT CTGCTGCGTC
141781 TGGCCTCAGG CTGAGACCCC AACGAATCAT TCCCCGCATG GAACATTTT ATGATATAAC
141841 TGAATTCAGT TTTATGTATA ACTGAATTAC GGATATGAGA ATCTCAAATG AGGACGAATG
141901 GTTTTTACGC ACAAAACATG AGACACAAAT CTGTAAGAAA TATAAAGTCG TGACCACGTC
141961 CTTTCAGAAC TTTAACCTGT TTGCTGAAGT ACGTCAGTAA CAATGGCAGG GAAAGGGTAT
142021 CTTAAATTTC ACCACAGCCT CAAAGAGGCC ATTTCGTGGA TCCGCTGAGG CTTGGAGTCG
142081 GCCTTCTGAC CACGAGTCCT GCGGCTATGA AAGAGGAAGC CGCGGTTCAG GGCGTCCTCG
142141 CGAGTCGTGC AGCCCGCCCT GCTCCAGCTG GGACACCGG TGGTCACGGC GCTTTCCAGC
142201 TGCAGATCCA GGCGGCAGCC CAAGATTTGG TCCAGCCGCC AAGGGGTGGC TCGAGTGACT
142261 GACGGGCCTT GAACGCTCCC AGGACCCACA TCTGGAGAGG GAGGTGGGG TGGGGTGCTG
142321 AAGTCATTCT TGGGGCCCCT GGGGCGGGC ATGGACCTGG GTAAGGCCAG AGAAATTGAC
142381 ACCTCGTGAC ATCCCTGGAA GAGAAGTACG TTCAGTGTCA CTCCAGAGCT GAAACCGCCT

Figure 1 (Page 44 of 73)

```
142441 TCTGGCTGGT CCCTCCTCAC CTACATACTT TTCTAATTTG TCTGGAGCAG GCCGGGCATC
142501 TGTATTATCT GGTTATTTAA ATATCTGGTT ATTTAAAAGC TCTCCATTAA ATTCACATAC
142561 ACGAAAATAA AAATTAAAAA AAATTTTAAA AAAAAGAAAC AAAAGCTCTC TAATGACCAA
142621 GTCCTACACG ATAGTGAATA AATTTTTTTG TGTGGTCCCT AAAATTGAGT TCATGCCTTT
142681 TCTGAAGTAA TAGACGCCCA GAGAAGGGAT CGACTTACCC ATCATGCCAC AGAGATTAAT
142741 TGGCCCCAGA ATTCTTTAGC AGACCGTGTA TATGAACGTC CTTTGCAATC ATATAAATTA
142801 ACTGGGAAAA CCTCATTTAG TATGTTACAT GCCTAGCGTT TTGTGCCTGA ACACCTTACA
142861 AGAACCAGGG ACTATTGCCC CAATATTATA TTTCAGGAAA GGAAGGCCCA GACAAATGGT
142921 GTCACTGGTC CACTTTCACC CAGTTGGTAA ATGAAACCAG AAATTATAGC TGTACCACAG
142981 AAAGGTGAAA ACGTTTCTTT TATAATTTCA CATACAATCT TTAATGGACC CAGTGTCCAA
143041 CACATTAAAG CAAGTGCTCA GGAGTGACAT CAAGATGTAA AAAATAGTCC TGTCCTCAGG
143101 GAGTTTAGGT CTTGGAGAAA AGAGACCCAA GGAGACACAA GACAAAGGGG AAAGAGAAGG
143161 AGCGCTGAAG ACTGAGGACC CTGCCTGTGG ACTGAAGTGA GGATGGGGAC ACCCGATGCC
143221 CGGAATATGA CAGTTTGGAG GGGCCTGAAG GACTCTTCTA TTCTCTATCA GAAAAACAGA
143281 ATTACTCTCC TAACCAGAAA AGGTATTTCA ATTTATATTT TCCATCACAG CACTTTTCTG
143341 GTGATAATTT AATGTGTTTT AAAAAATGTA TCACAGTGAT GGCCTGGTGT GAAATAAATA
143401 ATAAAATTTT AAGAATTAAA AAATATAAAA ATCTTTTATA TAGACATTAG GAGTTACAAG
143461 GATAACTGTG AATTATAATT AGTAATTAAA TTGAAATACT GATTATTTTC ATTTTTATTT
143521 AATTATTTAA TAAAACCTAT TTAACATTTA ATATTTATCA GTAATTAAAT CTAATTGTTA
143581 ATATTTATTA TTATAAATTA TTTTAGAATT AAAAATAAGT GTAGAAGCGA GGCATGGTGG
143641 CTCAAGCCTG TAATCCCAAC ACTTTGGGAG GCTAAGGTGG GAGGATTGCT TGAGCCCAGT
143701 AGTTCAAGAC CAGCCTGGGC AACATGGAGA AACCCTGTCT CAATACAAAA AAATGAGCCA
143761 TGTGTGGTGG TGCGTGCCTG TAGTCCCAGC CATTCTGGAG GCTGAGGTGG GAGGATGACT
143821 TGAGCCTAGG CAGTCAAGGC TGCAGTGAGC CCTGATCTTG CCACTGCACT CCAGTCTGGG
143881 CAACAGAGCA AGACCCTGTG TCAATATACA TATGGACAAA CTTAAAATTT AAAATGAAAG
143941 CATACTACTG ATACAGAATT GAGTAGAGAT GCAAAGCTAG TCCTATAACC AGAACAATAA
144001 AGATAAAAAG GAGAGTGGAA GAAGGTATGT CATGAATTTC ATGATAAATG GCAATTGCAA
144061 ATATCCTGTA GCAGAACAAA ACAACAAAAC TGTAGATAAA ACATATCCAA CCCTTTGGAA
144121 GGCCAAGGAG GGAGGATTGT TTGAGCCCAG AAGTTGGAGA CCAGCCTGGG CAACATAGTG
144181 AGACCCTGTA TCTAAAAAGG AAGAAAGAAA AAAAAAAAA GGATGATAAA GTAGACAATA
144241 TTGAAAGCCA TTTTCTGCAA ATACATAGTG AATTTGATCA GTAATTTTCT TCCAACAGTG
144301 CAAAAATGAA TAGATATTAG TTGCCTGAAA TAAAAATCAA ATATCCAACA AAAAATATTG
144361 ACTATCTAAT AGTATCTAAG CTAGTAAATT TGGCCAGTTA TAAAATGTCT TAAATTTTTA
144421 TTTAAAAAAA GAAAACCATA TTTATAAGAA GAGGTGATAA AGAGAAATTA TTTCAGTTAT
144481 GAAGATTTTG TTAGAAAACT ATGAGAAAAA AACTATTTTT TGTTTTCAAA AAGTGAAAGA
144541 TTAAGTTACC AAACAGTTGC TAAAGAATAC CAGATGGCTG AGCGTGGTGA CTTATGCCTG
144601 TAATCCCAGT ACTTTGGAAG GCCAAGGCAG GAGGATCATT TTAGGCCTGG AGTTCGAGAC
144661 CAGCCTGGGC ACTGTAGCAA GACCCGTCTC TATTAAAAAA AAAAAAAAAA AAAAAAAGA
144721 ATACAAGACC TTGCTAACAA TAGCAAAGAT CAATTAATTC AAAATTTGAA AAACTGTAAT
144781 TTATTTAGCT TTAGAGTACT CTCGTGATAT GAGATTGCCA AATTAATACT TTGGGTGCAT
144841 TTCTTTTCTC AAAGGACTTG CAAATTTACA AGAAGTGTT GAAGAAAAGC CACACATTGG
144901 CAGGTAATGT TTGCAAAAGA CAGATCTGAT GAAGAACAAT ATTTTTAGAA TATACAAAGA
144961 ATACTTAAAA CTCAACAGTA AGAAAATAAC CTGATTTAAA GCAGGCCAAT GACCTGAACA
145021 TCTGTTCACC AAAGAAGATA CACAGATGCA AGTATGCATA TGAAAAGATG CTTGACATCA
145081 TGTCATTAGG GAACTGCAAA TTAAAACAAG TAGATACCAC TGCATACCTA GTAGAATGAC
145141 CAAAATTTAG AACACTGTCA GCACCAAAGG TTGCAAAGAT ATGTAGCAAT AGTAACTTGT
145201 TCATTACTGG TGAGAATGCA AAATGTGCAA TCACTTTGGA AGACAGTTTG GTGGTTTCTT
145261 ACAAAAGTAA CCATACTTTT ACCATAAGAT TCACCAATCA CACTCCTTAG TATTTATCCA
145321 AAGGAATTGA AAACTTATCT CCACACAAAA ACCTGCACAT AGATGTTTAT AGCAGCTTTA
145381 TTCATAATTT ATCCAAAACT TGGAAACAAG ATGTCTTCA GTAGGTAAGT GGATAACTGT
145441 GGTACTTCTG AATAATGGAA TGTTATTTAG AGTTAAAAAG AAATGCATTC ACTTTGGGAG
145501 GCCGAAGTGG GTGGATTGCT TGAGGCCAGG AGTTTGAGAC CAGCCTGGTC AACATGGGAA
145561 AACCCCAATT AGCCGGGCAT AGTGGCGTGA GCCTGTAATC CCAGCTACTC GGGAGGCTGA
145621 GATATGAGAA TCGTTTGAAC CTGGGAGATG GAGGTTGCAG TGAGCCAGTG CCACTGCACT
```

Figure 1 (Page 45 of 73)

```
145681 TCAGCCTGGG CAACAGAGCA AGACTCCTCT GTCTCAAAAA AAAAAAAAAA AAGAAAGAAA
145741 AGAAAAAAGA AAAAGAAAAA GAAAAGAAAC GATCAAGCCA TGAAAACACA TGAAGGAAAC
145801 TTAAATGTAT GTTACTAAAA AGCCAACCTG AAAAGACTGC ATACTATATG ACTCCAACTG
145861 ATGCAGGGCA AGCAAGCCAA AAATTAGGGC TTAGCCCGGG AAGAATTCAA GGGTGAAGTG
145921 GTGGTGTTAG CAACTTTTAC TGAAGCAGCA GTGTACAACA GCAGAACAGG TACTGCTCCT
145981 TGCTGAGCAG GGCTAACCCA TAAGTAATGT GCCCAGAGTA GCAGCTCAGG GGCAGTTCTG
146041 CAGTAATATA CCTGCTTTTA GTTAAGTGCA TGTTAAGGGG GATTATGCAG AAATTTCTAG
146101 AAAAAGAGTG GTAACTTCGG AGTAGGTACA GAGGAAAGAA GTCGATAATG TCCTGTTGTT
146161 GCCATGGCAA CGAAAAACTG ACATGGCGCT GGTGGGCGTG TCTTATGGAG AGGTGCTTTA
146221 ACCTCGTCCC TGTTTCGGCT AGTCTTCAAT CTGGTCCGGA GTAAAGTCCC TGCCTCCGGA
146281 GTTCACTCCT GCTTCCTGCT TCACAACTGT ATGACACTCT AGAAAAGACA GTAACTATGG
146341 ACACAGTCAA AAGATTAGTT GATAGAAATT GGGTGACAGG AAGTGTTGAA AAGGCAGAAC
146401 ACAGGATTTT TAGGGCAGTG AAACTTCTGT GATACTATAA TGGTGAATAC ATGACATTAT
146461 ACATTTGTCA AAACCCATAG AAAGCACAAC ACCAAGAATA AACCCTAATG TAAATTACAG
146521 ACTTTCGTTG ATAATGACGT GTCAATGTAA GTTCAATTGT AATAAATGTA CTACTGTGGT
146581 GCTGGATGTC TATGGTGGGG GGACATTTTT GCTTCAATAG TTACAGTTGA AGTAAATGTT
146641 TGTGTTTCCC ACAATGCATA TGTAGAAACT CTCACATTCA ATGTGATGGT CTTTGGAGGT
146701 GGGCTCTTTG GGTGATAGTT AGGTTTAGTT GAGATCCTAG CAGATCGAGT CTTCATGATG
146761 GGCATGATGG GACTGGTCCC TTATAAGAAA AGACCAGAAA GCTAGCTCTC TCTTTGCCAT
146821 GTGAAGACAT AGCAGGAAGG TAGCCATCTG CAAGCTAGGA AAGGGCCTTC ACAAAGAATC
146881 AACTCAGACC TCAGAACAGT GAGAGATAAA TTGTCGTTGT TTAAGTCACT CAGGCTGTGG
146941 TATTTTGTTT CAGCAGCCCA ACCTAAGACT GTTAATTGGA TTAGAAATTT CCTTTTGGGG
147001 ATGGTGTGTG GCGGGCGGGG GGCGGGGAGT ACCTTTGTTA AGCTTTTATA TCAATGAGTT
147061 TGTAGGCTTT TCTTTTTTGG TCATTGACTA GGACAGTTTA AATAGTATGA GTGTGAAGGA
147121 GATTGTTGGT CATCTATTCG ATGTCCCTTC TCTGTTTTTT AATATGAGAA CTCCTGATTT
147181 TCAGCCAACT ACCCTGGAAA AAAGCTAAT CTTTCTGACT TCTTAAGTGT GGCCATGTAC
147241 TAAATTCTGG CTAATGCAAG GCAAGCCAAA GGTTTTATGA TAGGTTTTAG GACACTAGAG
147301 TAAAAGAGAG CTGTTGCACA CATGCTCTTC ACCCTACTTT TGTGTCCTTT TTTCCATCCT
147361 ACAACTTGGG TTGTGAGTAT GATGGCTGGA ACTTTAGTGG CTCTCTTGGA TCCCAGGGGT
147421 AATTGAGGGG TGGCTGGAAG GAATCTGTGA TTTTCTGGAG TTTCCATACA CAAACAAGAC
147481 CTGGATTTTC TGGGCTTCCC AGACTTCCAC ATCTAGACTT GCTTTAAATG GGAGATAAAT
147541 AAACTTGTTT CAGCCACTGT CATTTTGGGC TATTTTATAG AACTTAATCT AATCTTCAAG
147601 GGTACATGAA TTGCTTTTCC TTAAAAAAAA AATCAGCCAT AAAATCATCT TCTTTTTTCT
147661 TTTGTTCCCC ACATTATTTA GTTGGAGCTC TGTAACTTTT TTTTTTTTTT TTTTTGAGAC
147721 AAGGTCTTGC TCTGTCACTT AGGCTGGAAT TCAGTGGCAT GACCATGGCT CACTGCAGCC
147781 TTGCCCTCCT AGGCTCAAGC AATCCTCGTC TCAGCCTCCT GAGTAGCTGA AACTAAGGCA
147841 CATGCCACCA TGCCCAGCTA ATTTCTTTTC TTTTAGAGAT GGGAGCCTTG CCCAGGCTAG
147901 TCTCAAACTC CTAGCCTCAA GTGATCCTCC CATCTCAGCC TCCCAAAGTG ACAGGATTAC
147961 AGGTGTGAGC CACCATGCCT GGCTGCTCTG TAAGTGTCTG AATTTCATTT TGTATTTATC
148021 AGTCTGTTTA GATTTTCTTT CCCTTCTTGG GTCAGTTAGG CCATTGGTTT CTTTTTAAAG
148081 GTTTTCAAAT TTATTTGCAT CTAATTCTTC AAATTACTCT CAAAATTATT CCAGTATATA
148141 TTCTTTTGTT CCTATTTTCT TCTGTATTCT TTATTAAAAT AGCTAATGAT TTATCTAGCA
148201 GGACTTATAT TCTTTCCATA ACTTTCCTGC ACCCCAATTA ATCTCCAATT TTATATTTCT
148261 TCTGGCCTTC CTTATAGTTT CCACAGGTTT ATTTTATTCA TTTTTTAAAA CTTTTATTTA
148321 ATTGTTTATT TTATTATCAT TCTTTCTTAT TCAGCAATCT AAGTGCTTAG GGATATAGAA
148381 TTTCCTCTAA GCAGCATATG CTAGGCTTTA ACAATGTTAG GGAGGCCTCC CCTTTCTGGG
148441 GAAGACCACA CTTACATTAA CACAGGACTG TGGGATGCCA AGAGGTAGAG AAGAGCTTAT
148501 GAATATCCAG ATTACATCTT CACTGATCCT GCACAAAGGT GGGGTTCCTC GGTTACCCAC
148561 TGGGTCCTAT TACCCAAGTC TGGGTCAGCA TACCGAGACT ACGGGTATAT AGAACAAGTG
148621 CAACTGGCGA TAATCCTTCT GTTGGGGAGA AAAATCTTTT TTTTCTATTC ATCTTAGGTT
148681 CTCCATCTGT GGCCCTATCA AGTAGACTAA CAAAAGACAG ATTGACAAGA CAGAAACAAA
148741 GCATGTGCAT TGTACAAACA CAGGGGAGTA CTGAGATGAA TACTCAAAAG AGGATTTAGA
148801 ACTTGGGCTT ATATAGCATT TTAAGAAAAG AATACATTTT TTAAGTGACA AGGAAGACGA
148861 AAAGGACTTT GAGTTTCTAG TGCAGTAAAT TGTGGGAAGG CAACTTTTTC TTTCCCTTTT
```

Figure 1 (Page 46 of 73)

```
148921 TTTTTTTTTT TTTTTAAAAA AAAAGACTTC TCTGGTGCTA TGTCCAGGCT GATAAGAGTC
148981 TAAAGTCTCT GGTGACTAAC TTTTGTTCTT CCCCGAGTAA GAAGACACCT TCACAATTTC
149041 ATATCCTGCT TTTAGGCAAA TAGGGAGAGG GCAGAGGTGT TTGTTTGTTT TTAATCTATT
149101 TTTTTTCTCA ATTGTCTTCA ACTCAAAATA CTTCTTATGC CAAAGATGGC ATATTCTGCT
149161 ACCCTTCACT TACTACTTAC AACCCAGCCT CTATCATCAT AATTAGAACT TCTGACCCTG
149221 GGGAACATGG GCAATAGTTT GAACTCTTTT ATATCTCCCT TAGGCAGAGA TGGAGGCCCA
149281 GCCATGCCTC TGACATCTAG ACACAACTGT TGCTTCATTT CTCCTATTCT CAGAGGTGAT
149341 GTTGTAGGAC TTCAACAAAT ATCAGTAAAC ATTAATTTTT TTTTTCCTTG AGGCACAGCA
149401 TGATCTTGGC TTACTGCAGC TGCTGCAGGC TCAAGCAATT CTCCTGCCTT GGCCTCACGA
149461 GTAGCTGGGT TACAGGCCCC TACCACCATG CCCGGCTAAT TTTTGTATTT TTAGTAGAGA
149521 CAGGGTTTCA CCATGTTGGC CAGGCTGGTG TTGAACTCCT GACCTCAAGT GATCCACCTG
149581 CCTCAGCCTC ACATAGTTCT GGGATTACAG GCGTGAGCCA CCATGCCTGG CCATCAATTT
149641 TTATGTCAAC TCTAAATTAT AACATTTAGC AATTTTGTGA CTTTTTATGG TCATCATTAA
149701 TGTTGTTTAT GTTTTAGTTG TAGTCCTGTC ATTACTCACT CGGGTATGGT AATTTGGTCT
149761 TTTTCAAAAT GAAGTTAAGG TCTATTTGCT CTTCTCTGAA TCATAATAAG AACTGCCAAC
149821 AGCCATTTCA GCAATAACTA TTTACTGAGA TTTTAAAATA TTTCAAGGTA ATTGGTCCTA
149881 GCAGACTGGA AAATACCAAA TTCTTTTCCA GAACTGAATC CCCCATCAAA GTTCAATTTT
149941 ACTCATAATT CCCTTTTCAT TTGAAGCATC TCATTGTAAG CCAGTCTTAA CCCTTCTCTC
150001 ACACTTTGCT TGGCTGTTTC TCAGGTAGAA CTCAGTAAGT CTGGTAGCCT CCAGGACTGC
150061 CGCTTAGATT ATTAAACAAC ATGTCAGTGG TTGGAAGAGT CAATGTTATT TTGATTTTTC
150121 TGTTTTGTTT TGTTTTAAAT GCAGTTGGCG GATAATTGCA GCTTTCTTTC ATTCCCTACA
150181 TGAGTTCAAA TGGCAGCAAA CAAACTAGGA GAACGCAGAC CTTCTGACTT GTGGGTACCC
150241 CTACTCATCA CCTGAAGACC CTTGGAAATC AAAGCCCTGA CCCATTAAAG ACGGATGGAG
150301 ACAGCAACAT ACGATCATCA CTATTATCTT GCTTTGCCCC AGTCCAGGTT AACCATCTGT
150361 GGTATTTTTA GTTGCTAAGT CCATATATTC AACATAAATC AATTATATAT CCACTAAAAT
150421 CTCAGCACTA GTCTAACTAC TAAGGAAATG ACAGCGAAGA AAACAGACCA AACGTCTGCC
150481 CTTATGGGAT TTATATTATT TTCTCTGTGC TGGTTAAACC AAGGAGCTTC TGCTCTTTTC
150541 CTTAGTCACC TGGGGGAGGC AGAAACAAAG GAGAATATTG ATAAACCTGG AAATAGGGCC
150601 GGAGAGTATC AGAGAAGGAA GCCTTCGGGA AAGTAAAGAT GTGGCAGCCA GTATTCCCGT
150661 TATAAAAGGA TACAACTCCG GCCTCATAGT CCAGAAAAAT TCCCACAAGC AGGGGCTGCT
150721 CATGCAGATG AAGGGAAGTT GGGGGAGAAG TAAGTGCTAC ATAGCCTTTC TTTTTGCACA
150781 GCCTGAGGGT CCAGAATCCA GACTGAGGCT CTTGCTTCAT GCCAGTGCCC CTCTGCACAT
150841 TTTCCATACA AACTCCTAAA TCCCATCCGG TTCCTTCGCC AACATCCACT TCAAAGTAAC
150901 GTCTTCCTGA GGTGAAGCCT TCACAACCCA AGACACAGGG GAAGGCAGTA AATCTCCTGG
150961 AAGATGTGTC CTGATTCTCC TGGGTGTATC CACGAGTCAC TTGTCTCCGA TCCTCAGAGA
151021 GAATTAGTTC GTGATGAGCT GTATCTGGAT CCAGAGTCAC ACTAACTGCA AAACAAAACA
151081 AAACAAACAA AAATAATTTT GTTGCTGTGA AGAACACAGG TTATTTTATT TTATTTTATT
151141 TTGAGATGGA GTGTTGCTGT CACCCAGGCT GGAGTGCACT GGCACTATCT CAACTCACTG
151201 CAACCTCCAC CTCCTGGATT CAGGCAATTC TCCTGCCTCA GCCTCCGGAG TAACTGCGAC
151261 TACAGGTGCG CACCACCACA AGTGGCTAAT TTTTTTAAAT TTTCTGTAGA GATGGGGTTT
151321 CGCCATGTTG GCCAGGCTGG TCTCAAACTC CTGACCTGAA GTGTTCCACC CACCTCGGCC
151381 TCCCAAAGTG CTGGATTACA CAGGTGTGAG CCACCATGCC CAGCCACAAG TTATTTTCAA
151441 TAAAACCAGC CTGTGTTCAA ACCAACTAT TGTTTCTTAT AAACTGGGTG AGCTTAGGCA
151501 AATCATTTAA CTTTCTGAGC CTCAGTTTGT TAACTATAAA GTGGAAATTA CCGTATTTGT
151561 TGCAGAGAAT GGTGGGTAGG ATTGAATAAG CTTATGTTTG CTTAATGCTT GGTAAAATTC
151621 CTGGTACATG GTAACCACCT AATAAGTGGT AGTTGTTGGG GTGATCAGGC CAACACCAG
151681 GCCGTGGGGG CTACAAAGTC CGGCGGGTC AAAGGAATGA GAAAGACAA GTTAAGAGTG
151741 CATAAAGTGG GTCCAGGGTG CCAGCACTAG ATTGGAGGCT GCAAAGGCCC TAAGCTCTGG
151801 GAGCCCACAC TATTTATTGG TGATCAAACA AAGAAGCAGG TGGTGAGGAC GTGAGGGTAA
151861 ACAGGTGAGG GCATGAGGAC ATGGGGTAG AAAGGTAGTG GTGCATTAAG CGTAGCTGTG
151921 ACAGTTTAGC ATTTCTTTG ACACATGTAG AATATACTCT GCTGCTTGAG ATAGTAGAGG
151981 ACACGTTTAT GAGTGAAAAG CAAGGAACCA ACAAGTCTGT GCACTTTCCA GAGGCTATGA
152041 GGGGTTTTAT GCCCTGAGCC CTGGGTTCCA TCCAAGCCAC AAGGGGTTTT ATGCCCTAGG
152101 CTTAGATTTG TGGTGCGGCA GGGCAGCCTT CCACCATTTG GCACAGAGCT TGGTGTTCCA
```

Figure 1 (Page 47 of 73)

```
152161 AAGGCCACGA GGGGTTTTGG ACCCTGGACC CCGGACATCT TCCAAGACTC TTTTACATTA
152221 TGACAGACAA GCCAGTCCTG CTTCAGCTCT TCTAACAACA TGTAGTAATA ATGATATCAT
152281 CAACATCATC TTCGTCTTAA TTATTCAAGG ATGCCAAGGT ACAGAACTAA CCTGTTAATA
152341 TGGTTACCAT CCTGTCCAAA GTTCTTCTCC CATGCAGGAC TTCCAGGAAT CATGAGACAG
152401 TTGAGCAGAA AGATACCTTT TCCCTTCTCT ACTGAATAAC CACCAACATT GAGAATCAGA
152461 GAGGGAAAAT GACTCAGCTA ATGTCTTAGC TTGTTATTGG AAGACCCAGG TCTCATGACA
152521 CATGCCTAGT CCCATGACTT TTAATTGTAA GCTCTTCTCT TTCCCCTCAG ATAATGTTCC
152581 ATAAGCATTA GTATGAGATA ATAATACACT GAGGACCAAT ATACATGAAA AATATCAGAC
152641 TAGAATCAAA CAAGACAGAA AAAAGATCTG ATAACCTAAA GTGAGATACT GAACAGTATG
152701 CAGTTTTAAA AATAAAAAAT GGTAATAGGA TGTTCTAACA AGAGAGTTAA GAAACCACTG
152761 TGCTACTGAG TTAAATGTTG ATCAGTTGGT CTGTGACAAT TAAGGAATTC AAGTATTCAG
152821 AAACACTTCC TGTGCTGGAT GCTCTCTGTT TGTTCTTCCA AATAATCCCT CACTTTTCCC
152881 TGTCTTGCTC TGTGCCCAGG AAGGCTGACA TGGACAGATT AACCAGGCTT TCCGCCCTCT
152941 GGCTTGGTTC AGCCAATGGG AAGCACCAGA GGAGACCATA GGGCACAAAG AAGCAGCCTT
153001 GGGAGTATTC AGTACCCCAG TCCCACGCTA TGATTTGGAG GGTCTGCATT CCTCTGCCTC
153061 TGGGCACACT CTAGTATAGT TACAGCTCCC TACACCTGCC ACTTGAGGCC CAGAGGAGGT
153121 GATGGCTCTC TAACTGTTCC TAGTTCTGGG TGCTTCCTGT TCCTTGTGGA TTTCCCAACT
153181 CCTCACCTTT GTAAATACCC TCCTTTTTCA AACTCTATTC AGTTAGCTTT TATCAGCCTG
153241 ACTCACAGAA GTTTGGGGTT TCAATTCATA TTACCTGAAT GACCCAGGAA AACCCATGTT
153301 GAGAAATTAA AATGTTTACG GGGTGGTAAT ACCACTTAAG AGAAAAAATA TCAATTGGAT
153361 TTTTAAAATT CCACCTATCT ATTGGTGTGA CACATCAACA AAAACATATA GAAAGATTGG
153421 AAGCTAAAAG ATAGATAATA TAGTCATATA CTGTTATAGT ATTATATCAA AAGATATTAA
153481 GTCAGAGCAT TATTAAGAAT GGAAGAAGGG CCAGGTGTGG TGGCTCATGC CTGTAATCCC
153541 AGCACTTTGG GAGGCCAAGG CAGGCGGATC ACTTGAAGCC AGGAGTTCAA GACCAGCCTG
153601 CCCAACATGG CAAAACCCTG GCTCTACCAA AAATACAACA ATTAGCTGGG CATTGTGGCA
153661 CATGCCTGTA ATCCCAGCTA CTTGGGAGGC TGAAGCACAA GAATCACTTG AACCGGGGAG
153721 GCAGAGGTTG CAGTGAGCTG AGATTTCGCC ACTACACTAC AGCCTGGGTG ACAGAGAGAG
153781 ATTCTGTCTC AAAAAAAAAA AAAAAGAAAG AATGAAAGGA GTCACCTAAA AAAGATAACA
153841 CAATTTTAAA CATAAATGTA CTACATTATT AGTGAATTCA TGTTTAGAAT TGTGTTAATA
153901 TACAAAGCAA AAATTGTAGA ATTATAGGAG AAATGGACAA ATCTACAATC ATCATGGGAT
153961 GTTTTAACAT TCTTCTTTCC ATAATTGATA GATCAGGCAG ACCAAAAGAA AGAAATAAGG
154021 GAAGATACGG AAGGTCTGAA CAATCTAAGA AGCGCAATCT CATAGTCAAT ACATAAAGCT
154081 CAGCAATTGT TTAATAATAG TAAGCAGAGA ATATGCAGTT TTCTCAGGTA TAGATGGAAC
154141 ATGCACTAAC TGAGTAAATA CTAGGCAGAA AACAGTCTGA ACAAGTTTCA ATAAATCTGT
154201 ATTACACAGA TCATTTTCTC TAGCCTCAAT ATAAGATTAT AAACCAATAA TAAAAAGATG
154261 ACTAAAAAGA TTCTAAATAT TAGGAAATGT AAACTACTAA TAAGTCATTA GAAGATGTAT
154321 AGAATGGAAC AATAATAAAA AGTTATTTAT AAAAATATAC AATGAAGCTA AAGCAGAATT
154381 TTAAGGAAAA TTTGTAGGCT TTAAATGCTT ATCTTAGAAA AATTAAAAAG CTGAACATTA
154441 ATGAGCCAAG CATCTAATTT AAATTTTAAA AAGAACATAG AAAGCCAAAT ATAATTTTTT
154501 AAAAAGAAAA AATAGATATT AAACAATATA ACAGTGAAGT TAAAGAAAAC AAGAATGCAA
154561 TAAAGAGGAA AAACAAACAA AAAAAAAGGT AGCTTCTTTT AAAAGAAATT TAATAAAATA
154621 GACATACCTC CAATGAGATT TATCAAAGTA AGACAGAAGG CACAAATGGA ATGAATACAG
154681 AAACTTTTTA AATATTACAG AACTTTATAA TAAATCTTAT GCTACTAATA AAATTGAAAG
154741 TACTGATAAA ATTATTACTT CCTAGAAAAA ATATTTCTGA GTAAAACTCA CTCAAAAAAC
154801 AAATAAAGCA TGGGCAGACC TAACATTAAA GAAATGAAAT CACTACTTTA AATTTTACCG
154861 ACAGATAATA AAACGTGCAT CTTTATCAAG CAAAAATGGA ACTTGTCAGT TTTATAGGAA
154921 ATTTAGAAGT CAAGGCATGA GTAATGCCAA TCTCATACCA AATCCTACAA AGAATAGAAA
154981 ATTATGGCTC CCGCTTATAG ACATAGATAT AGAACTCCTG CACAAAATAA TATAAATAAC
155041 AAACCAAATT TTATATTTGC AACTATACAT ATTATATGTG TATGTATTAT ATATGTTAAC
155101 ATATACATAT ATAATATGTA TAGCATATGT TCTACATATT ATATATGTAT AGTGTATGTA
155161 TTTTACAATA TATAAATGAA AACCCAATCT TTAATATATT CATCTAGATT GTCATATATG
155221 ACATATATAA TACATTACAT CAAAAATGTG TACAATAATC AGGCCAGGCA CAGTGACTCA
155281 TGCCTGTAAT CCCAGCACGT GGGAGGCTG AGGCGGGTCA ATCACTTGAG TCCAAGAGTT
155341 TGAGACCAGC CTGGTCAATA TGGCCAAATT CCATCTCTAC AAAAAATATG AAAAATTATC
```

```
155401 CAGGCATTGT GGTGCACACC AATAGTCCCA GCTACTCGGG AAGCTGAGGT GAGAGGATCA
155461 CTTGAGCCTG GGAGGTGGAG ATTGCAGTGA GTCGAGATTG CGCCAGTGCA CTCCAGCCTG
155521 GGTGGCAAAG GGAGACCCTG TCTCAAAAAA AAATTAAAAA ATTAGCCAGG TATGGTGGCC
155581 TGTTCCTGTA GTCCCAGCAA CTGGGGAGGC TGAGGTGAGA AGATCACTTT AGCTCAGGTG
155641 GTGGAGCCAT GATCGCACCA CTGTACCACT CGGCTTGGGC AACAGAGTGA GAGCCTGTCT
155701 CGAAAAAACA AATATATACA CACAGTAATC AATATATATA TTATATGTAC CAATCAATGC
155761 TTCACTTTTA TATATAATAT AGATTACATC TTATTAGATA TATAGTATTC CTTCTCCATA
155821 GATAGATAGA TACAGATATA GACATAGTAT CCTCTATCCA TATTAGAGAG AGGATACTAT
155881 ATATATCTAT AGCATATAGA GATGCTGTCT CAAAAAAATT TAAACATCAG CCAGATGTGG
155941 TGGCCCATGC CTGTAGTCCC AGCTACTGGG GAGGCTGAAA TGAGAGGATT GCCATTGATC
156001 CTCTCATTGG TTGAGCCATA ATCGCACTAC TGCACCACTC AGCCTGGGAG ACAGAGGGAG
156061 ACCTGAGGTG GAAGGATATA GATAGATA TATAAATAAA TATGTATAGA GAGAATATAA
156121 TATATGTGTG TATGTGTATA TATATATATT ATGAAGCAC TGGGAGAGAA TACTATATAT
156181 ATATGTGTGT GTGTATATAT ATATTATGAA GACACTGGTG GGATGGTTTC ATTACCAATT
156241 GGACCAAGAG TCCAGGTATG GAGCCAACAT GCAATGTTGT TGTTGACTGA GCTGGCAGAG
156301 CACTGGTCAT AGTTACGGGA AAAGAAGGTC TCCAATGAGA CATACTTAAC AAAATATATG
156361 AACTTGCCAT ATACGTGGAG AGTTCTGGTG TGTATATAGC CTTCTCTCAC CAACCTAGCA
156421 ATTGTCTTCA TCATCATTAT AATGCTATCA GAGCAAAGAT GACAGCTAAA TTTTTTTGTC
156481 CCTTTCTTCT TCTTTCTCTT CCTTCCCCTC CCCACCTCT TTCTCTTCCT CCTCCTCCTT
156541 CATCTCTCTT CTTTTTTTTT TTGAGATGGA GTCTTACTCT GTCGCTCAAG CTGGAGTGCA
156601 GTGGCACAAT CTCAGCTCAC TGCAACCTCT GCCTTCTGGG TTCAAGCAAT TCTGCCTAAG
156661 CCTCCAGAGT AGCTAGGACT GCAAGTGCAC ACCACCACAC CTGGCTAATT TTTGTATTTT
156721 TAGTAGAGAT AGGGTTTCAC AATGCTGGCC AGGCTGGTCT CAAACTCCTG CCCTCAAGTG
156781 ATCCTCCTGC CTCGGCCTCC CAATGTGCTG GGATTACAGG CGTAAGCCAC TGTACCCGGC
156841 CTCCTCCTTT AATAGACAGG GTCTAGCTCT GTTGCCCAGG CTGGGTACAG TGGCGTGATC
156901 ATAGCTTACT GCAGCCTCGA ACTCCTGGGC TCAGGAGATC CTCCTGCCCT AGTCTCCCCA
156961 GTAGCTGGAA CTACAGGCAT AGCACACGGG GCTAATAAAA TTAATTAGGT GATAAAATTC
157021 ACTGCCCACT GATGACTAAG CTCTTTGGAC ATAAAAGACA CAGACCTTGA AGGAAAATGT
157081 GTCTACTTAA TTTTGAAACC CTATTTATCA AAAAACAGGA TGAAAATGCA AAATGCCATC
157141 CACATGCCAG AAGATATCAG CTATAATAAG TTCCCATAAA TCAATAAGGA AAAGAACCCA
157201 ATAAAAATTA TTAAACCACA GTAAATCATG GGTAAATCAC AGAGGCCTGA AGGGCTAATG
157261 GACATACAAA AAGAATCTCA ATCTCACTAG TGAAATCAGA AAAGCACAAA TTAAGTACAC
157321 AATTAGGTAC CATTTTAAAT CTGTAAGACT GTCAAAATCA TAAATTATAT AAGTAAAGAC
157381 TCAGGGAGTT TTGGAGGAGT GAGAGCTCTT ATATTGCTTG TGGGGTAGAA TTGGAACAAT
157441 TTCAAGATCT GTAGTATCTG GTAAAATTAT GATATGCATC CCTCACACCA GCATGTCACT
157501 CCAAGGTATC TCCCTGGAGG GAACATTTAC GGGACACAAG GAAGCATGGA TAAGAATGTT
157561 CACAGTAGTA TTGTCTGCAA CAGCAACAAC AACAAAAAAA CCCAACTACA CACAACTTCA
157621 ATGCCCAGTC CACAAGGCAA TGGATTAAAT AAACTTCAGG CCGGAGATGG TGGTTCATGC
157681 CTGTAATCCC AACACTTTAG AAGGCCGAGG CGAGAGGACT GCTTGAGCCC AGGAGTTCAA
157741 GACCAGCCTG AACAAAATAA AGAGATAGTG TTTCTACAAA AAATTTTTAA AAAATTAGCC
157801 AGACGTGGCA GTGCTTGCCT GTGGTCCCAG CTACTGGGGA AGCTGACGTG GGAGGATTGC
157861 TTAAGCCCAG GAATTTAAGG CTGCAGGGAG CCATGATGGG GCCATTGCAC TCCAGCCTGG
157921 GTGACAGAGT GAGACCCTGT CTAAAAGAGA TAAGTAAATA ACAACTTTGC ATTTTCTGCC
157981 ACATTGCAAA ATGGTGAGAG AGTGGTTTCT AGACTCTAGA CTCTTTCTAT GACTACCTTC
158041 TAGTTATGAG ATCCTACAAC ACTCACCTAA CCTCTCTGTG TCATATTTCC TCCTCTATAA
158101 AGCAAAAATG CCCCATATAG AGAGGACTGT GATATAAAAC AAGAACCAAG AAAAGTAAAG
158161 CTTTTCTAAT CTGTCACAGA CTAAAGAGTG CTCAGTATAT GTGAGTCATT ATTCCTGGTG
158221 CTGGTAGGAG TGTATGTTAC AACTTTGAGT CAAGTAATAT GGTACCATAT ATTAAGATTA
158281 ACAACAACCT CGGCAATCCC AGTTTGGGGT ATGTTCCCAA AAGAAATGAA AGCACCAGGA
158341 TATAAGGATG CATGGACTAG AAAGTTATTG TAGCAACATT GTAATAACTA AGTTCTAAAA
158401 ACAGCCTGAA GCTCCATCAG TAGGGATATG GTTACATATA TTTATTATAT TCTTATGGAA
158461 TATTAGACAT AAAAAGTAAC GAGTAACATA GAAGAGACAG TGTATATATG TTACGTTTGT
158521 ACAAACTTAG GGAAAGATAT AGATCACCCT ACCTAGAGAA GTCAGATTGG AGACGGGTGG
158581 GAAAAACCTT GAACTTTCTC CTTATATCCT TTATATTGTT TGACTGATTA AAATGTATTT
```

Figure 1 (Page 49 of 73)

```
158641 GTTGCATCTG CTTGAAGGCA ATGTAAAATA AAATAAACAT ACATTTAAAA ATAAAAATAA
158701 AATTTATTCC TATCACTTTT GTAATAAAGC TGGGCACAGT GACTAACACT TGTAATCCTA
158761 GCACTTTGGG AGGCAGAGAC AGGCAGATCA CCTGAGGTCA GGGGTTTGAG ACCAGCCTGG
158821 CCAACATTGT GAAACCCCAT CTCTACTAAA AATACAAAAA TCAGCCAGGC ATAGTGGTGC
158881 GTACCTGTAA TCCCACGCTA CCCGGGAGGC TGAGGCGCTG GAACCCAGGA GGCAGAGGCT
158941 GCAGTGAGCT GAGATTGCGG CACTGCAAGC CAGCCTGGGT AACAGCGAGA CTCCATCTCA
159001 AAAAAAAATT TGAAAAAAGA AAAATTTTAA TAAACAGTGT TTAAGAGGGG AGAAATATTT
159061 AGTTAAAAGA TAAGCCCATT TAAGAAATAG TTTCACTTGA CCCGGAAGGC GGAGCTTGCA
159121 GTGAGCCGAG ATCGCACCAC TGCACTCCAG CCTGGGCGAC AGAGCGAGAC TCTGTCTCAA
159181 AAAAAAAAAA AAAGAAAGAA AGAAAGAAAG AAATAGTTTC ACTTGAACCA TATTATGATT
159241 CCTTCTGTAA AAGATGAGAG TAGGCAAATT GACTCAGTGA AATCCCAGCA AAACTTACAC
159301 AAAGTCTTGT TCTTCCTTCC TGTCATCTGT ATAGGATGAA ATACAGAGTG CTTTTGGGTT
159361 TTGTTGTTGT TTGTTGTTGT GTATTTGAGG GGAACACAGG TCTATAATTC CTTTTCTGAA
159421 ATCCCTGGAA CAAAATGGGC TTTGCCATTC AAATTAGTTT AGAAGTTATA AAGGCAAAAA
159481 AATGCATATA CTCTAAAGTT CAACCCCATC ATGGCCTAAG GCAGAGCCCT GTAATCAAAT
159541 TCATCAATAT ATCTGCAGCA AAACATTTAT TCAAATTAAG TGGGATAAAT AAAGACTTTT
159601 AAATAGTCTC ATCTCAGTGC CGTTCAGGGT TGGCCACTGT GGAAGACAGA CTCAAGGGTG
159661 GCCTTCTATG ATTCCTGCCT CTTGGTGTTC ACACCCTCGT AAAATTCCTT GTCTTTGAGT
159721 GTGAGCAGGG CTTATGAATT GCTTCTGACC AATAGGATAT GGCAAAGATG ATGGATATA
159781 ATTTCTATGA TTACGTTTCA TTATGTAAGA CTCCATCTTG CTGGCAGATT TTCTCTAAAG
159841 AGTCTGTCTC CTGAGCTCTC TCTGAAGAAA TAACTGGCCA TGTTAGAAGC CCATGTGCAA
159901 AGAGCTGAGG GGTGGCCTGT AGAAGCTGTG GGCAACCTCC AGCCAACAGC CAGAAATAAC
159961 CAGGGCCAAA GTCCTGCAAC CATCAGGAAA GAAATTCTGC CTGCTACCTC AGTGAGCTTG
160021 GAAGTGGATT CTTCCTTAGC CTAGCCTCCA GATAAGAACA CAGCCTGACC AACACCTTAA
160081 CTGCAGCCTT ATCAGACCCT AAGCAGCAGG CCCAACTAAG CTGTGCCCAG ATTCCTGAAC
160141 CACAAAAATT GAGATAACAT ATCAGTGTTG TATTAAGGTT CTAAATTATG GTAATTTGTT
160201 TGTACTAATA GATAACTAAT ATAACCACCA AATCATTTCA GGTTAGGCCA GATTTTTGTA
160261 GCCAAATGAA TCATGATAAA ACTTTCCATT TTCAGGGGTT TTTTTGATTT TGTACTTACG
160321 GATACAAATT TGTGAAAGTA TAGTCAGCAC TGATTTAAAA AATCAAGGGA GCAGGAAACT
160381 CAGTAAATGG TTCTAACATT TTGGAATCTG TAAATTGGTT GTAACATTTG TCATCTGTGT
160441 TATCTAAGTC AAGTTCCTAA AATATGTGAA TGATAGGTTA TCATACTCAC CTACTTTTCT
160501 TGCATTGCTC TAAGAGTTGG CTGAGCTATT GATAATAAAC ACTATGATCA GATCTAATAC
160561 CATGATGTGC TATTATGATC ATGTGTCAGT CACAGGGCTA AGCACTTTGT ACATGTTGAT
160621 GCATTTAATT TTGATGATAA CTCAATGAAG TAGGAGCTGT TAATATTTTC ATTTTTCAGA
160681 GGGGGAAACC AAGTCACTTG GAGTAACATG GCTAATAAGT GAAAGAATAA GAATTTGAAA
160741 GGTTTGCACA GATAACCAGA ATGCAATGCT CATCACATTC ACTGAGCAGT GAATCATACT
160801 AACTAGAGAA AGTATGAAAG CTCTACTGAA ATTAACTAAA CAACCTCTCT GGCTGTGAGC
160861 CTGCCAAGGG ACAGGTGGTA AACTTGGTTA CTGCATAAGG CCCCTTCTAT CCACAGTATT
160921 CAGGAATTCT TTAGTGAACA TACCTTGATG ACTCCTTAAC ATTTTCTTCA CATCGAAGTA
160981 AAGCTTGGAA ACATTGCACA TAGTATGAAG TTCCAAGGAG ACAGCCTCTG ATGTTTCCAG
161041 CTTCACAGCC CAACTCCTAG AATAAGCAGA GGCGAGAGAT TTCTTCAGAG GTGCATTCCA
161101 TTCATTTCTA TATACGCACA CCCCTCCCCT CCTGCATTCA AACAGGACTT ACCTGCTCAA
161161 AGTGTCATTC ACATTCTATA AAGAAACAAA AAGAAAAGGT GAGCATGGGA ACATCGGTAT
161221 TTCATGGGGC TTGTCATGCA GGGCTATTCT TCTTTGCTTT ACCCGAAGAA GTAAAGAGAG
161281 TTACCCTAGT CTTAGTCTTA GATATTGATG GATACTCAAA CAAAGTAATT CCCACCAGTC
161341 TTAGGTATTG ATGGATACCC AGATGGAATA ATTCCTACCA GCTTCTGGGA GATTCAGCAT
161401 GGCAGGATGT TTATCAACAT TTGCATCTAT TCTCATCCTT GCTGAAGTCT GAGGGCCAGG
161461 AGCTTTGTCC ATGCTCCCTC TGTAAGGACT AGCTTTTGGT GATCGGATTT CCTTCACAGT
161521 GAGCCCAGAT TAGAGAACAC TTATCATAAA GGTCCTTAGT GGTGAATCTG TGCACAGCCC
161581 TGAGACTGGG CCACTGCCAC TAAGATGGTG GTAGCAGGTA TCACACAGTG GTAAAGCAAT
161641 CATGCTATAC ACTCAGCCTT ACAGTATAGT CACCAATCCT GTTAGTTAGA ACCAGAATTA
161701 ATGGCTCCAG ATGTTTATCT TCCTACAGAT AAAGCTGTAG ATTGTACCAT AACAGCTCTG
161761 GAGCAAGGGT TCTACAAGCA AATCAGGGAA AAGGTTATCA CTCATTTTGG CTGCCCCACT
161821 TCATCACCCA TCAGTCACCT AGTGGAGTAT TTCAGGAGAG AGTCAACAAC CAGGGTTCTC
```

Figure 1 (Page 50 of 73)

```
161881 TGCACATGGG CCAAGGAGGC AAACAGTGGT AAATGTTATC CCGTGGTTTC ATTTGGCCAA
161941 GCTGTGTTCC CTCAGAAGTT TATTTTTCTA ATTGACATAA AGGTACCCTA TAAATTAGTG
162001 AAGGCCAGCC TGATGGCACT GATGTACATC TAAAAGAAAC ATTACTTTAT CTTCCCATGC
162061 TTCCTTACCA TTCTCCTTTA ATAGCACTAT AACATACCTT TTTTCCCTAC TCCAAGTACA
162121 CAGCCTCACC TGCAGCAATT TCTGGGCTGA GCCCTGACAT TTTTCCTCCA GTTCCAGGAT
162181 GTGGCTCTTG AGTTCATTGC TCTTCAGCCC CAGACCAGCC TCATAGTCCC TCAGTCTACT
162241 CAGAGTCTGT TGTTCTTCTT TCTCCAGCCT CCAGAGATAA GACTTCTCTT CCTCATGTAG
162301 GAAACACTGG AGATTCTTAA AGTCAGACCG GATTTTTGT CTCTGAATCT GTACCTTCTC
162361 CTGGAGTCAA GAAAGTATGG TCAAAAGGTG AAGTAAACC AAATGTCCAT CTATGGATGA
162421 ATGGATAAAC AAGAATGAAA GTCTGACACA CGCTACTACA TGACAAGCCT TGAAGACATT
162481 CAAGCAAAAT AAGCCAGAAA CAAAAGGGCA AATATTGTAA GACTTTGCTT ATACAAGGCA
162541 TCTGGAGTAG TTAAGTTCAT AGAGACAGAA AGTAAAATAG TGGTTACAAG GTGTTGGCAA
162601 GACCAGAAAA TGGACAGTTA TTGTTTAATG GGTAGTGAGT TTCAGTTTAG AAGATGAAAG
162661 ATGAAACTGA GTTGCAGTTT GGAGATGGGA ATGGTGATGG TTGCACAACA ATGTAACAAT
162721 GTAAAAGCAC TTAATTCTAC TGAACTATAT ACTTAAAAGT GGTTAAATGC TTAAGTGTTA
162781 TATATATTTT CACACAAACA CACACACACA CACAATCAGC CACTGGGACA TTATTTTCTC
162841 ATGAGTCACT GAAGCTGGAA GAATGTCCCC AGTTTCCTGC TGCAGAGTCA TGTGTGGGAG
162901 GCAGGCACTC AGATGTGGAA GAGGTTGCCT CAGATTCCTT ATAGTCACCC AATTAATTTT
162961 CTTGTTCTTC AGCCAAGACA CAGGAGAAAG CTGGGTTAGG AGTGCTAGAT AATTTAATTG
163021 TGAAACTAGG GCCAAGTTCA AACACTTTAT CAGTTACAAG GATAAAAGA GGTTTTTACT
163081 TATGATTTAA GAAGTTAGAT TTCTGAGTTG GAGCGATTTT CTTGAAGTAA AAGCTTATAA
163141 TGAACATCAC CCAGACTGGA TTTTAAGACA ACCAGGCTGG TAAGAGGGTC CATAATTCTT
163201 GGCAGGGGGA GCTTTGAGTG TGACAGGCAT TTATTATGGT TAACTGAGAA ATACTGTTCT
163261 ACTACCCTAG GGTCATCTTA AGCATTCCTA TGTGTAAGAC TGACAGAAAT CAAGTGAAAC
163321 TCTCATCTGA GGAGATGTAA AGTTGCAATT TCCATTAGTG CTGTCTAAAT TAATGCAGTG
163381 GGAGTGTGTA TTCAGGGCAA TTTGAATCTA TGTTCTTGGA TTGCAGTCTT CAAACTTGGC
163441 CCAAATAAAC TCTCTACTTA TCTTAAAAAA ATAAAAATTA AAAAATAAAA ATAAATTCAT
163501 ACAGTGTTTT GATGACTATG ATATAGAAGA AGGGTCTTTG ACTTAGGATG AGGTGGAATT
163561 TTTGTGTAGG AGACAGGTGC AGCTTTAACT CTTGTATAGA CGGGTTTTCA TATATGTTAG
163621 TTACAATCAA GGTCTTCCCC ATTGCCCAAG ATCCTAGAAA TGGGGAAGT AAGAGTGTAC
163681 TCAGGAGCTC AAGAGCAACA TCCACAAACA AAGATCAGGG TAGAGGTTAG AGAGGACTCC
163741 TGAAAGAGAG AAAATTGGTA ATCAGCTTGT GGGATTTTAC TGCAAGCTAG TGAATTATAT
163801 AAATATAAAG ATTGGTGCAA AAGTAATTGT GGTTTTTGCC TTTACTTTAA TGGCAAAGAC
163861 CGCAATTACT TTTGCACAAA CCTAAATATT TCCATAAAAG AATGTGGCTC TGATAATGTG
163921 GAGGTTAGTC AGCCACGGAA ATAATCTGAA AGTTTGTAGT TGCAAGTGTG TAGGTTGTTG
163981 CATTACTTGT GATGTACTTA TAAATCAAGT ATAGGCCGGG TGCAGTGGCT CACGCCTGTA
164041 ATCCCAGCAC TTTGGGAGGC TGAGGTGGGT GAATCACGAG GTCAGGAGAT CAAGACCATC
164101 CTGGCCAACA TGGTGAAACC CCGTCTCTAC TAAAATACAA AAAATTAGCC AGGCATGGTA
164161 GCACATGCCT GTAATCCCAG CTACTCAAGA GGCTGAGGCA GGGGAATTGC TTGAACCCGG
164221 GAGGTGGACA TTGCAGTGAG CTGAGATCGC ACCACTACAC TCCAGCAAGA CTCCATCTCA
164281 AAAAATAGTA ATAATTTAAA AATAAATAAA TAAATAAAGT ATATTTCTTT CATCAGCTTC
164341 ATGAGCTAGA GTAGTATGAA TTTCAATCTG GAGTGATCCT GTTTTCTAAG TGTTCACAAA
164401 GCTTGGTTTC TGTACCTGTA AAGTTGAGAG CCAGATGCTC CACTGTGGTA AAAGTGCCAG
164461 GGTAATGAGT TGAGGCCTGC AAACCAGGTT TATTTTGACG TATTTAAAGT TTGAGACCCA
164521 CTCGATGCTT TTTCTAGGTA AATAGTCATA CTAATTCTGC TTCTTCTGAC TGAAGTATCA
164581 GGAATCCCAG CCAACTACAG TTTAAAGATG GAAAGATTGG TGCTAAATAC TCATGGATGT
164641 AAACCTGGAA CCAGGGGCAT AAGTACAAAT AATGGTTTCT TCCTTGGGTT TCATTTTTTC
164701 AATCTGGTTT AGTGAGAATA AATCCTCATT GTGCTTTTCC TCAATCATCC CCTATGCCTA
164761 AGCTCTAGAA TGGAAAATAG CTTGAGATCA ATGAAGTCAG ATTCTTACTT TCCATTTAGT
164821 TATTCGCATT GCTGTGGACA GCTTCTGCTC CGTACATCTG TCTTCAAGTT GCTTCAGTTT
164881 TGTCACAGCT TTCTGGAGCT TTTCCTGAAG GAAAAATTTG ATAAGTGAAG CCTATTCAAT
164941 TTGACTCTTC ATTAGGGACC TAGGGGAAT CCCAATCTTC TAAGATATAT TTGAATAATA
165001 GTGAATATTT ATAGAGTCCT CATTGTTTTT TGCTAGAGAG CATGCTAAAG GCTATATGTG
165061 CAGGAACATA CTGATCCCCT TGCAACCCT GAATAGTTGG TAGGATTTTA AACTTCATTT
```

Figure 1 (Page 51 of 73)

```
165121 CTGTGCTGTA GAAAATGAGA CTAAGAAAGG GGTAAAATAA CTTGCCCAAA GGGCTATGAC
165181 TGCCAGGTGG TGGAGCAACA ATTGCAATCT CATCTGCTGA CCCAGAGCCT GAGCTATGTC
165241 CACCACTAGA GTCCTGCCAG GAAAAAGTTG GATATAGAAC AAGGTAATCA TCATCTAAAA
165301 GATTTTGTAA AACAACATGC TGAACCAAGC AAAACCAATA CCAGTGTTTG CACACATGA
165361 AATTTTGTGT CTTATGAGTC AGGAAAAATC AGGATGCCAG CTGGTTATTA GAAACAGTTC
165421 ATGGAAGAGG GGAATTCTGG TATCTTTTGA ACAATGGTAT CATGAATCCA ATTTAAAATG
165481 ATTTAGTATT CATGTCAAGC TTTTAGCTTA TTCTTCAAAA CAGTTTCTCA TATTTCTATT
165541 GAAAGTGATT TGAAGCTGAC CCAAATTGCT AATTGTAGTC AATGCTGAAA GAATTGTCTC
165601 CTGTCCTCTG TAAACCCAAC AAGTATACTC ATTCATTCTC GAGTGTTCTC AGGAAAAGGT
165661 TCTATGTAAC TGTTTTAGCA AAAGATGACA TTGTCCTTAC TATATGCCAA GTGCTATTCT
165721 ATGCATTCTA TATTTTAATG TCCTCAAAGC TTATAACCAC CTCCTGTGTA TGTGTTTTAG
165781 GGAGGGAGGA CACTGCTATT ATCCCCATTT ACAGATGGAG AAACCAAGGT GTGAAGACAT
165841 TAAGTAACGT GCCCAAAATT GCCCATCTAG TAAGTGACAA AACTCAATTT CAACATAAGC
165901 TGGTTCCTTT TCTTACTACT TGGTGGAAAA GTAATTCAAA TGGGAATATG ATCATCGCAG
165961 TTATTAGCTG CTCCATGGAG TTTAAGGAAG AGCTGCCATG AGCTGAGTGG TGGTCATGAT
166021 TGACATGTCC TTAGAAGGAC TTAGAGCCTT CATACAAGAC CACCTCTGCC TCATGGAGGA
166081 CAGAATAAGG AGCCTGACAC TGGAGACAAC ATTTTCCTCA AATTTAGGCA GGACAGAGAA
166141 GGAAAAAGGA CATCAGGACT ATGCCCATTC CTCCATGCTG CCAACAGCAA AGTCCCACCT
166201 TCCTTAATAT GCTTTCTGGC AAGAAATCTG GATGGTACAC AAAACCTCTC CCTCTGCTTC
166261 ACCTTCCACA ACCAAGCATT TCCAAATCTT TGACTCTTCT TCCTGAATCG TGCTTAAAAT
166321 CTGCCCTCTC CTCCCTTTCT TATACGGATA GTTTGAATTT TACTCCTTGA TATTCCTTTT
166381 ATCATAGACA TGCCACAGTA GCTGGGCACA GTGGTTCATG CCTCTAATCC CAGCATTTTG
166441 GGAGGCTGAG ATGGGAGGGA GACCAGGGGT TTGAGGCCAG TATAAGCAAG AAAGGCAGAC
166501 CATGTCTCTA CAAAAAATAA AAAAATTATC CAGGTATGGT GGGGCATCCC TGTAGTCCTA
166561 GCTACTTGGG AGGCTGAGGT GGAGGATTG CTTGAGCCCC AGAAGGTTGA GGCTGCAGTG
166621 AGCCGAGATT GCACCATTGT ACTCCAACCT GGGATACAGA GCAAGACCCT ACCTCAGGAA
166681 AAAAAAAAAA AAAAAAAAAA AAAAGTAGAG GTACCAGAGT GATATTTTCA ATGTCACTGA
166741 CCCTTCATTC CCCAAATGAA AATCCCCCAA TAGGTGTTCA ATTTTTACGT GTCCTTCAGG
166801 AGTTACTTCT AAGATGAACC ACTCTCTACC CTAAATGTCC CTCCCCACCA CCAAAACCAG
166861 GGACCTCCAG GCAGACATTT TTGATGGTTT GTTTCTTTA CTAGACTGTA GATACCTAAA
166921 AGGTGATGGG TCTTTCTTCC CTGTTTTCAG GCCCTACTGC ATGGCTTTAC ATATTGTGGT
166981 TTTTCAAATG ATATTCATGG TGTGAAACAA GAAAAAATGC GGGTGTTTGG TTTGAGAACA
167041 ACCTGTTCTA AAGCAAAAAG AAATTCATCA TAACACAAAT GGATAGAGAT AAGAGTCCAA
167101 CCATCCCATT GAAGGTCAGG ATGGACAGTC TAGATAATTG AGCAAGAAAT CATCATAAAC
167161 TATTTTTCAG AAGAATGACA TGATGAAAGC TGTATTTCCA AGTCATAATG TTAGGTTTCA
167221 AGTTAAATCA TCTCAGCTCC TGGGGAGCAG GATAAGACTT GGTACTTACC AAAGCTCCCG
167281 GGCCCACACA CTCACCTTGT AGCCCTGGCA TACGTCTTCA ACAAGAGCTG TGGTGTGCCC
167341 TTTGTGCTGT GGTGCCCGCT CACAGCGCCA GCAGATGAGC TGCCCCTCGT CTTCGCAGAA
167401 CAGGTGGAAC TGCTCTCCGT GTTCCTCACA TGACATTTCT TGATCCGTCT CTTTGAGGGC
167461 TTCAATGAGG CTTCCCAGCT GCTTGTTGGG TCGGAGGCTA TCCATATGAA ATGGAGCCCG
167521 ACACTGGGGA CAGCAGAATG TCTCCTGCCT CAGTTGCTTT TGGCTTGGGT TTTTAAAGAA
167581 GTCTGTTATA CACAAGTGGC AGTAGCTGTG TCCACAGTTG ATGCTTACTG GGTTCGTCAT
167641 CAGGCTCAGG CAGATGGAGC AGGTGGCTTC CTCCATCATC TTCTTGGTGC TGGTGGTTGA
167701 GGCCATAGCT TTTATTGAAA AGCTCCAATA TTGGCTCTAG AGATGGAGAT GAAGCAGCCA
167761 GAATTTTCCA CCGTGATGAA AATACACCTC ACCTGCACCT CTATGTGATG AGCTGGCTGC
167821 AACTGACTTC CATAGGTCTT GAAGGTTTTC CTTCCAACCC CTATTATCTC ATTTTGTATT
167881 GAAGAAAGA GGACCTAAAA GGAAGAAGTT GAGGCTGAGG TTGTTTGGGC CACGTTTGAG
167941 AACTGCAACC CAAGTGCAGA GTTTCAAGTT GCCCTCATTA GCAAGCAGTT ACAAGTGGTT
168001 GTTTAGAGGA AAAAAGCAG TTTTAAAGCA GTTTTAAAGT TGTTTGCCAA GAATTTACAT
168061 TAAAATAGCA TAAGCTTTTG ACTGGCTATA CATTGTTCTT TGTATTACAA ATCTCGGGAA
168121 TATGTAGGTA ATAGATGAGG CAGCCAGTCA GGAACAAAAT GCTTTTAAAC ATGGGGTCTT
168181 AACTGAAGAC CTATACTCCT GCCTCACTTG TCCTGATAAA TTTTGCATAC CTCACATAGC
168241 TCAGACTGCT CTAAATTATT TCATTATTTT TCTTTTCTCA GTCTTCTAAC TTTTTTTTTT
168301 TTTTTAATG AGACGGAGTC TCACTCTGTC ACCCAGGCTG GAGTGCAGTG ACGCTATCTC
```

```
168361 GGCTCACTGC ACCTCCGCCT CCCGGGTTCA AGCGATTCTC CTGCCTCAGC CTCCCGAGTA
168421 GTAGCTGGGT CTACAGGTGT GCACCACTAC GCCCAGCTAA TTTTTGTATT TTTAGTAGAG
168481 ATGGGGTTTC ACCATGTTGG TTGGCTCGAT CTCTTGACCT TGTGATCCAC CCGCCTCAGC
168541 CTCCCAAAGT GCCAGGATTA CAGGCATGAG CCACCGTGCC CAGCCTCTTT TTCTTTTCTT
168601 ATAAGACAAG TTCTCGCTCT CTTGCCCAGG CTGTAGTGGA GGGCAGTGGC ATGACCACAG
168661 CTCACTGCAG CCTCGACCTC CTGGGTTTAA GCAATCCTCC TGCCTCACCC TGGCAGAGTG
168721 GCTGGGACTA CAGGTATGTG CCACCATGTC CAGCTAAAGT CTTCTCTCCA GAAAGAAGAA
168781 ATGCATTGGA ATTTAGAGGA TACACAAACA TCTAGCTGTA TAGCTAATAC AGTAGCCACT
168841 ATCATGAGTA GGAATTTAAA TTTAACTTAA TAAAAATTAA AATGAAAAAA TTCAGTTTTT
168901 CTGTTCCAGT TGCCACATTT TGATTGCTTA ATAGTTGCAT GTGACTAGTG GCTACATAAC
168961 AGCCTCAATA TACAACATTC TGTTATCACA GAAAGTTACC TTGGACCAAG TGCTGGGAGA
169021 AGCAATGCAG GCTTCCTCAC AAAAGCTGTA AAAGAGAGAA CTCAGGGAGT GTGAAACTCT
169081 TTCCTATTCT AGTTAACTTC AAGAATAATT GTTACCAGGC CAGCACGGTG GCTCACGCCT
169141 GTAATCCTAG CACTTTGGGA AGCCGAGGCG GGCAGATCAC CTGAGGTCAG GAGTTTGAGA
169201 CCAGCCTGAC CAACATGGCA AAACCTCATC TCTACTAAAA ATACAAAAAG TTAGCTAGAT
169261 GTGGTGGTGC ACACCTGTAA TCCCAGCTGC TCAGGAGGCT GAGGAAGGAG AATGACTTGA
169321 GCTCCGGAGG GGGAGGTTGC AGTGAGCCCA GATTACACCA CTGCACTCCA GCCTGGGTGA
169381 AAGAGCGAGA ATCTGTCTTA AAAAAAAAAA AAAGAATAAT TGGTACCAGA ATTACTCTTT
169441 GTAATTAGTA GTAACACTTA TGCAATTGGG TGATCTGTGA CAGATTCCAT TGAAGGAGTA
169501 TGGGGAGCTT CACCCCAATA TATGACTCCC TGGTATAATG AGTATTTTGA ATTAAAGGCC
169561 CTTAGAGATC AGCAGATGCT GGAAGAGACT TTTCCCCTAT CTACATAAAG ACCAGTCACA
169621 CTAGACAAGA AGAACAATTG TTTTTCCTTC CAACCCCTAT TATCTCATTT TGTACTGAAG
169681 AAAAGAGGAC TAAGAATGTA ACCAGACCTA ATCAGACACT TTCACAAAAT AATGTCTGTC
169741 TCTCAGGCTC ATTCATTTTC CAAAGAGAAC CATTTACAAG TTAAACTCTG TTCCTCCATT
169801 CATTCATCCT CCCAAATATT CATTTATTCT CCCTAGTAAT CATTTACTGC CCCTCAAAGA
169861 ATTACCTATA TTCTCCTGAT ATCACCCTTC CCCTCTGAAA TAAATATGTA TACATGTATA
169921 AACGTTATAC ATACATATTT ATACAGTATA CATACATATT TATACATACA TACATATGCA
169981 TACATATTTA TATTTATGTA TTTATACATA AGTATTTATA AATAAGGCTA TATAAGTATC
170041 TACCCCCATT GGCAGAGGGG GTAATCACTC TGTGATTCTA GCCCATGTAC TTGTTAATAA
170101 ATTTGTATGC CTTTTCTCCA ATTAGCCTGC CTTTTGTGAG TCGATTTTTC AGTGAACTTC
170161 AGAAGGCAAA GGGGAAGTGT TCCCTTGGCT CCTACACCAT CATGACAATA AAATTTGACT
170221 CCACCTCGAC CCCCCCCATC CCCCACAAAG AACAACAACC AACACTGGTT AATAAGGTCG
170281 GTTGTTTTTT GTTTGTGTTT TTGTTGTTGT TGTTTTTGCT TTCAGGAGCA GAGGTATAAT
170341 AGGCAAAAGA AAGAGAAAGG AGAATAGTGA ATACCTCTTC TGCAGAGAGG GGTGCCTAAG
170401 TGGGACTTCC CTGGCTAATA ACGTCTTGCT AGAGACCCAA CCAGGAGGAT AATGGAAGCA
170461 ATCAAGGCAA CCAGAACAAC CAGAAGAACC GGTTTATCCT TTTTGTGCCC TCTCCCTAAA
170521 CTGAGGGAAT AAGAATTGGA AAGAAGGCTG CAGAGCAGAG GGTTTGCTCC TGAGGAGCAG
170581 TTATTTCTAT GGGATCAGAG CTCCTGCAGA ACTGGGGAGT TTACTTTTAC TATCTCTTCT
170641 CCAGGACAGG ACCTATCTCA AGAGACATGT TCAGAGTGAT TGCAACATAA AGAGTTTGCA
170701 GACCCAAGGA GGTAGGGAAG GCAGAAAGAA GATGGGGGAG GCCAGGGATA GGCAACAGAG
170761 GAGTGACCAG GAGCGAAAAA GCCTGCCTCT TCTGAGAACC TAGCTGGGCT CTCCCTGTAC
170821 CCCCGATCCC TCCCCCCCGC CCGCCCCCAC ACCCCTACTC CTGGGAGCTC CTCTAGGACA
170881 GGGGCAGAGT CAGGAGGAAG TTTGAAGAGT GCCTAGAATA AAAAACAGTA ATTTAACTAC
170941 AATTACCGGG TAGGCTGTTT TCCTCTCACA ATTTGATCAG TCTCTTGAAG CCACACAGAA
171001 TTTCTTCTGA AGACGTGTAT TCCTTGGCAG GCTATTTCCT CCAGTGATAC ACCAGGCCCC
171061 TCTCTGCTGG GGTCACTGCT CTTCTGGGGA GATGGGGCTC CCCTCCTTCC AAGGCTCCAG
171121 GGTTCCTGTC CTGGGCCCCA CTCATCTAAG TTCTGAATCT TCTGAGATTT GGTGTAAAGT
171181 CTGGTGAAAG AAAGAGCAGG AAAGAGGTGA GAGCTGTAAA ACAAAGAAAG TCCTGACCAT
171241 TTTCAGAGTT GGAGGGGCCC TGCTGTCACG AAATATATTC CCCACCCCAC TTGCCATCAG
171301 TACACACTCA CATATCCACT GAGAAAACCT TAGCCTGGAC CTTTTCCGTA ACCTTCACTG
171361 CTCAGACACT TACATATTCG CTGCTAGTCC CCTCTGTTGC TGCCACTTCC TGGGTCAGGA
171421 AGTTAACTCA GACCGGATTA AACTGAGAAG TGAAACTACT GTGGGAGGCG GGGCTCATAA
171481 GATTTAGGAG AAAACTAGTG ACGTTGTTCA TATCATTTGC ACTCCGCCTC TCCGGTAAAG
171541 GAGGGGGAAA CGTAGGAAGA AAATATCCTT CTTTTACAGC AATAAAAAGA AGGAACCAAT
```

Figure 1 (Page 53 of 73)

```
171601 TAATAACCCT GTAAACTATC ATGTGACCCC AACACAGAGT ATCTAAAAAC AGGAAGCCTG
171661 CAGAGGTTCA GTTCACAGAC TCTGATTTGA GATCTTTCTA CTTTTGCCAC CAACTCCCTT
171721 GGGAGTCCTT AAGCCTTCCT AGCTGATGTT ACTTCTTTTG CTATTTATGG GTTGCTTGTG
171781 GTTCTATAAC TGCTCTGAAG GGTGTGGTGG AAAAAGGGGT GGTAACAGCA GTAGGACTCA
171841 TTGGCATCAC AAAATTCATC TGAGTCAGCT TTCTATTCTT CTCTGTCCCG TTCTGTGTCT
171901 TGTTTTTCTC CTTGCTGTCC TTCTGCAGGA CTCAGATCTT CTTCAATAGC GAGGGTCAGC
171961 CAGGATAGAA AATGGGAGTC ACTAGTGGCC CAGCAGTGAG TGCCCCCAGC TTAGAGCTGT
172021 GTGGGATCCC TGGGACCATC ACTCTGCTTT GTGCTTTGTG GAGAAAAGGC TGTGGGGTCC
172081 AGGGTCAAGT CCTTAATGAC TTAGCTCCAG CTTCTCCACT TCAAAATGAA AGGAAAAGTA
172141 CTATCACCAC CCGTTAGAAT TATTATTTCA TGGGGAAAAA AGATGGATTA CTATCTCACA
172201 ATAAGAGCTT GTCACATTTA TAAGTCTCAG GTGTAAGAGG CATTTATGAT AACAACATAA
172261 TAAATGCTGG CTTAAGTAGA TGCAGTGGTC CAAGGGAACC AGTAAGGGGA GCTCAGGACA
172321 CAGGTGGGAG GAGAAATTAA ACTTGAATTC TGGGAGCCAC TGGCCTGTCT GGGCCCCTGG
172381 CCTGCCTGCT GACCCTGATA GCCAATGGAA CATGGAGTTT GGCCCAGCTG CAATCCCTCT
172441 GGTCCAACTA CTCAAAATAA AGGCAAGATT GGGAAACACG TTCCTTTCTT CCTATACCAA
172501 GCAGAAGACT CTTCAGCACT GCACCCTCCT GGGTGCTCAC AGAGCCTTCT GTTGTTTTGC
172561 CACCTACGAT TCATCATGCC CTGGCATGAT GGTTGCAGAC CCCATGCATA GCATGGGACA
172621 TTCTACTCCT GAGGCAACCA GCACACAGAG AGAGGAGAAA GAATGAGCCC CTGAATCCTT
172681 GGTCCCACGA TGAGTCCTTG CAGATATCTA CAACTTTCAT TGTTGTGGAT GTGACTCTGT
172741 ACCCAGGCAT GGCTCATTCC AGATCTGTCC TATTGTCAGA GGTGTTCAAA CCAGAATGAC
172801 TCCATTTTGA ATGGGGGCTA GGTAAAATAA GGCTGAGACC TACTGGGCTG CATTCCCAGG
172861 AAGTTAGGCA TTGTAAGTCA CAGGATGAAA TAGGCAGTTG GCACAAGACA CAGGTCATAA
172921 AGATCTTGCT GATAAAACAG GTTGCAGTAA AGAAGCTGAC CAAAACCCAC CAAAATCAAG
172981 ATGCAACAA GAGTGGCCTC TAGTCATTCT CATTGCTCAT TATACACGAA TTATAATGTG
173041 TTAGCAAGTT AGAAGGCATT CCCACCAGCT CCATAGTGGG TTATAAATAC CATGGCGATG
173101 TCAGGAAGCT ACCCTATATA GTCTAAAAAG GGGAGGAACG CTTGGTTCTG GGAATTGCCC
173161 ACATCTTTCC CAGAAAACAT ATGAATAATC CACTCCTTGT TTAGTACATA ATCAAGAAAT
173221 AACTGTAAGT ATCTGTATTA GTCCATTTTC ACACTGCTGA TCCAGACATA CCTGAGACTG
173281 AGTAATTTAT ACCAGGAAAA AATGTTTCAT GCTCTTACAG TCCCACGTGT CTGGGGAGAC
173341 CTCACAACCA CAGCAGAAGG CAAGGAGGAG CAAGTCAGGT CTTACATGGA TGGCAGCAGG
173401 CAAAGAGCTT GTGCAGGGAA ATTCCTTTCT ATAAAACCAT CAGGTCTCAT GAAACTTATT
173461 GACTATCATG AGAACAGCAG TATAAATTAC TCAGGGAAAG ACCTGCCCCC ATGATTCAAT
173521 TACCTCCCAC CAGGTCCCTC CCACAATATG TGGGAATTTA AGATGAGAGT TAGGTGGGGA
173581 CACAGCCAAA CCATATCAGT ATCCTTAGTC CAGAAGCTGA TGCTCTGCCT GTAGAGTAGC
173641 CGTTCTTTTA TTCCTTTACT TTCTTGCTTT CACTTTACTG TGTAGACTTG CCCCAAATTC
173701 TTTCTCACAC GAGATCTAAG AACCTTCTCT TAGGGTCTGG GTTGGGACCC CCTTTCTGGT
173761 AACACTATCA AAGGATCAGG AAAAGGAAGC TAGTGAATGC TAAAAAGGAA ACAAACTACC
173821 ATTACCAATA ATAACAGCAA GACAAAAGCA AAACGGATTG TGACAGCTGT CCCATCTCAC
173881 ACCTGTTTCC CATTGCAGGA AGGAGGGGCT GGTTCATGCA CAGAGTGGCC AATATTAGAA
173941 GCAGAGATGG GGTGCAGATG AGACTTCAGG AATATGTTGA CAAAGGCAGG CCTAGGGAGA
174001 AATCAACCTG AACTATCCCC AAGGAGGAAT GCATTATCTC TAATATGTAA AGTTAGGCTT
174061 GATCCTGTGA TTATGGGATA TAGGAGTCCA AAGACTCACA ATGGGAAGTA GGTCACTAGA
174121 GTCTCCTTCA GAAGCTCTGT ACTGTGTGTT CCCACTGTGG GCAAGAGTCA GCACTCAGCT
174181 ATTCCTAGAA TGCCTTTCCT CAACTCCTTC AGATTTTGCC TCTCAACTAA CCCTATCCTG
174241 ACCACTTGTT AGCAAGTGTA CCCCTCTCTC CCTCCCAAAC ATTTTCAAAT CTATTTTGTT
174301 CCCATGGCAC TTATCACTGA ATATTTTACT AATTTATTTT GTTTAGTGTT TGCTTCCCTC
174361 ATGAGAATGC AAAGGGATGG ATTTTTTTCA ATATTGTTCA CTGATGAATC CCAGTAACTA
174421 GAATATTTCT AAGCATAGTG ATGTGCATTA AATCAAAGAG TAACTTTCTG AATTGCACTA
174481 AACACACATC ACAAGAGGTG TGTGCACATA TGTGCATGAT GCACGTAGTG TGGTGTGGGT
174541 GTTGTGTGGG GTATGTGGTA CTGTGTGTGC TGTGTGTGG ATGTGATACA TAGTTTGTGT
174601 TAGTGTGATG CATGTGATGT GGTATGTGTG TGCGTGTCCA TACATATTAG GGGTGGCGGG
174661 GATGTTAATA TGTCAAATGG TACTAGAAAG TATCAGAACT CATGGTGCTT ACTGGTTTCC
174721 CAGAGAGCTG CTTCTCTCCC ACCTGTAGGA TATACTGATG GTTTGGACAG AGAAGAAATA
174781 AAAAGAAGGC TGTGACCTAC TGGGCTGAGG AAATAAAAAC GAAAGTAAAA GAAGAGCTGG
```

```
174841 GAAAAGAGAG TGGAGGGGCC AAGGGAAATT TCCCCTTTGG CTTCTGGGGA AACTTTGCTG
174901 AAAAATCAAC TCACAAATTT ATTAACATGT ACACAGGGAG AACCATAGAA TGATTATCCA
174961 CTTCCCAAGA GGGCTTAAAA GCTTATATAT TATCCTGGCA AAACAGATTA TGGGAGGGGA
175021 AGAAGAGAAA CTCTGTTGAT GGGATTACTG TTGCGGATTT TTGCTCCTTC GCTCAGCTAG
175081 GTCCGGGTTT TTGTCTCACA GCCAGGAAGA ATTAGGCATG CAGCCATCAA AGAATGAGTG
175141 GAGTAGAATT TATTAAGTGA AAGGAAAGCT CTCAGCAAAG ACAAGGGTCC TGAAAGCAGA
175201 TTTCTGGTTT GCTCTTCACA GTTGAATACT AGGGCTTAAG ACTCAAATTC CTGACAACTC
175261 CACCCTGTCC TACCAGTGCA TGCAGGCCTT TAGACTGAGC TACTCCATAT TGATTAATTT
175321 CCTGAACTGT GCATGTGTTA AGGAAAGGAA TCATCCACTG CAGGCATGTT TAGGCAAGCC
175381 CCCTGTGCAA GTTCCCTTAT CTGCACAAAA CATCCGGTGT AAGCACTTGT GGGGCAGGTC
175441 AGAGGTTCTC TGGGTACCAT TCCCTTACTG TCTGCCTAAA GCAAGCTGGC CAACTCCTTT
175501 CATTACTAGG GAGAGTAAGT AGATCAGGGA ACAGAGATTA ACTTGAACAT TATCTTGTGA
175561 AAGTCCGTTC GGGCATGGTT ACATTCTTGG TCTTACAGGA AGGGTAAATA AAAATAATTG
175621 CTCTTTTTGG TGGGTCTGGA TCTTAGGTAG ATAAAGAAAC TTTAATTCCA CGATGTGTTT
175681 TGGTAGGGAT AGTTGGTGGC AGGGATGTCA GAGAGACTTT GAGGCTTCTT CAGTTCAATA
175741 TGACCAAGGG CCATATATTA GGGTATCAAT TTCTGAGCCC AACAAGAGC TTAGGAGAGA
175801 TGTGATAGCA TCACAGTGTG AAAGCAATTT TTTGTTTGTT TTTAGAGACA GGCTCTTGCA
175861 CTGTCACCCT GGCTGAAGTA CAATGGTACG ATCACAGCTC ACTGTAATCT TGAACTGGGT
175921 TCAAATGATC CTCCCATCTA AGCATTTCAA AGTGTTGGGA TTACAGGCAT GAGCCACGGT
175981 ACCCAGCCTG AAACTGCACC CACTTTCTGA TAAACTTTTC AAATGACTAA AGGGGAGAGA
176041 GTAAGCACTA CTCAGAGGTA GGAAGAAAGG ACACAGGATT ATAGGATTAA AACAACAACC
176101 ACCAAAAAAA ACCAGACCGG TGTGGTGGCT CACACCTGTA ATCACAGCAC TTGGGGAGGC
176161 TGAGGTGGGG GGAGTCACTG GAGGCCAGGA GTTCGAGACG AGCCTGGCCA ACATAGCAAG
176221 ATGCTGTCTC TATTAAAAAA AAAAAATACC TGCCTTGAGC TAATCAGAAT CATGGACCCT
176281 GACAAAGGAT GTCCCAAAGT AAGTCTTAGC ATTTTTTTTT TTTTTTTGAG ACAGTCTCGC
176341 TGTGTTGCCC AGGCTGAAGT TCAGTGGCGT GATCTCGGCT CACTGCAACA GCTGCCTCCC
176401 AGGCTCAAGC AATTCTCCCT GCCTTCAGCC TCCCAAGTAG CTGGGATTAC AGATGCCCAC
176461 CACCACGCCT GGCTAATTTT TGTTTTTTTT AATAGAGATG GGGTTTTGCC ATGTTAACCA
176521 GGCAGGTCTT GAACTCCTGA CCTCAAGTGA TCTGCCCACC TTGGCCCCTC CATAGTGCTG
176581 GGATTACAGG CGTGAGTCAC TGCACCCGGC AAAGTCTTAG CATTCTTTAC AAACAGTTTG
176641 TACCCGTATC TCTAAAAGGG AGTAGTGAAT TCACCCCAA AATGTGGCTT CCTGATATAA
176701 TGAGTATTTT GAATGAAAAA CTCTTAGAGA TCAACAGACA CTAAAGAGAC TTTTCCCTAG
176761 GTACATAAAA ATAGGATGGC CCCACCAGCG AGAACAATTG TTCTTTTCTC CCTCTCTGTT
176821 ATCTCATTGT GCATTATAGG AAAGACCAAG AATGTAACCA CACCTGAACA GACCCTTTTA
176881 TAAGATAATC AGTCTCTAAG CATCATTTAA ATTCCAAGGA GAACTATTTA CAAATTTATC
176941 TGTTCTTTGA TCCAATTAGT CTCTCCTGGT AGTTACATAT TGCCCCTCAA CAGAATTCCT
177001 CTTCTTCTGT TTCCCATAAC CTATTTTGCA AGGATCAAGC CCCTGTTATT TCTTCAACTT
177061 CAAGGTGGCA TATAAGCTTC TAAATTCCAC TGGGATATTG GTACTATGTG CATGAGGAGA
177121 ACCACAGAGT AATTAAATTG TAAAGCCTTT TATCTTATGA ATCTGCCTTT TTTTGTGTTC
177181 ATTTTTCAGC AAAACTTCCA AGGGCAAAGG TATAAAACAA AAATAAAATT CTAAAGCCCC
177241 CCAACCATCT GAATAGACTT TCTCTTCAGT CAGGCTTCTT AAAATGTAAC CTGAAAGACT
177301 GGCTCAGGCC ATTAAGGGAA GTGGGGGTTG AACATGCCTC ATTATTCCTC TCTGGCATTA
177361 ACATCAACAC AGCTTTTAAG TCTGATAAGA AACATTTTAC AACCTATTCT CTCTGAAGCC
177421 TGCTAGCTAA AAACTTCATC CCATAGTACA ACTTTGGTCT TCACAACCTG TTATCACAAC
177481 CTAGTGCTCC TTTCTATTAA TCCCAAATCT TTATACAAAC TCAACCAATT GTCATCACCT
177541 CCACCCCACT CCTCCGCTGC TTCAGTTGT CCCGCCTCTC TGGACCAAAC CAGTGTACAT
177601 TTCTTAAACG TATTTGATTG ATGTCCCATG CCTCCCTAAA ATGTATAAAG CCAAGGTGCA
177661 TCCCAACCAC CTTGAGCGCT TGTTCTCAGG ACCTCCTGAG GGCTGTGTCA TGGGCCATGG
177721 TCACTCAAAT TTGGCTCAGA ATAAATCTCT TCAAATGTTT TACAGAGTTT GGCTCTTGTC
177781 ATGACACAGA TGACTGCTTC ACTGAAGCCT GCTCTGGAAG TGAGTGGGGG TTTTGCAAGG
177841 ATAATTTTCC CCGGATAGCC CCAGAAGCAG CTAGTAATAA TACACTTAAA GGTAGCTAAA
177901 ATGCATTGAA CACTTGTTTT GTGCCAGACC TATGTCAACA TTTGCTTTGT GCCAGGCTTA
177961 TGCCAGTACT CCTGATTTGT TAATACATTC TAAATAAAAA TTCTGGAGTT TCAAATATAA
178021 TAACTGAAAA ACAGAAAATA AATAAAAATA TATAATAACT GAAATAAAAA TTTACTAAGG
```

Figure 1 (Page 55 of 73)

```
178081  CTGGGGATGG  TGGCTCACTC  ACACCTGTAA  TCCTGTTACC  GGAAAGGGGT  CCGTCCAGAT
178141  CCAGACCCCA  AGAGAGGGTT  CTTGGATCTC  ACACAAGAAA  GAATTCGGGC  GAGTCTGTAA
178201  AGTGAAAGCA  AGTTTATTAA  GAAAGTAGAG  GAATAAAAGA  ACGGCTACTC  CATAGGCAGA
178261  GCAGCTCTGA  GGGCTGCTGG  TCGCTCATTT  TTATGGTTAT  TTCTTGATTA  TGTGCTAAAC
178321  AAGGGGTGGA  TAATTCATGC  CTCCATTTTT  TAGACCATAT  AAAGTAACTT  CCTGACGTTG
178381  CCATGGCATT  CGTAAACTGT  CGTGGCGCTG  GTATGAGCAT  AGCAGTGAGG  ACGACCAGAG
178441  GTCACTCTCA  TCGCCATCTT  GGATTTGGTG  GGGAGCAGTG  AGGATGACCA  GAGGTCACTC
178501  TCATCGCCAT  CTTGGATTTG  GTGGGGTTTA  GCCAGCTTCT  TTACTTTTTT  CTTTTTTTTT
178561  TTTGCCCAGG  CTGGAGTGCA  GTGGCACGAT  CTCAGCTCAC  TGAAACCTCC  AATTTCTGAG
178621  TTCAAGCGAT  TCTCGTGCCT  CAGCCTCCCA  AGTAGCTGGG  ATTACAGGCA  TGTGCCACCA
178681  CACCCAGCTA  ATTTTTTATA  TTTTTAATAG  AGACCGGGTT  TCGCCATGTT  GCCTACGCTG
178741  ATCTCCAACT  CCTGCGCTCA  AGCCATCCAG  CCACCTTAGC  CTCCCAAAGT  GCTGGGCTTA
178801  TAGGTGTGAG  CCACCCCACC  TGGCCTAGCC  GGCTTCTTTA  CTGCAACCTG  TTTTATCAGC
178861  AAGGTCTTTA  TGACCTGTAT  TTTGTGCCCA  CTGCCTGCCT  CATCCTGTGG  CTTACAATGC
178921  CTAACTTACA  GGGAATGCAG  CCCAGCAGGA  CTCAGCCTTA  TTTCACCCAG  CTCCTATTCA
178981  AGATGGAGTC  TTTCTTGTTC  AAATACCTCT  GACAAGCCCA  ACACTTTGGG  AGGATGACAC
179041  AGGAGGATTG  CTTTAGCCTA  GGAGCTCAAG  ACCAGCCTGG  GCAACACAGT  GAGACCCCAT
179101  CTCTAAAAAA  AAAAATACAA  AAAAATTAGC  CAGGCATGAT  GGTGTGTGCC  TGTAGTCCCT
179161  GCTACTCAGG  AGGCTGAAGT  GGGAAGATGG  CTTCAGCCCA  GGAATTCAAG  CTGCATTGT
179221  CAGAGGCATT  TGAACCAGAA  TGACTCTATC  TTGAATAGGC  GCTGGATAAA  ATAAGGCTGA
179281  CACCTGCTAG  GCTGCATTTC  CAGTATGTTA  GGCATTCTTA  GTCACAGGAT  GAGATAGGAA
179341  GTCAGCACAA  GGTACACATC  ACAAAGACCT  TGCTGATAAA  ATAGGTTGTG  GTAAAGAAGT
179401  TGGCCAAAAC  CCATCAAAAC  CAACATGGCC  ACCAAAGGGA  CCTCTGGTTG  TCTTCACTGC
179461  TCATTATATG  TTAATTATAA  TGTATTAACA  TGCTAAAAGA  CACTCCTACC  AGCATCATGA
179521  CAGCTTACAA  ATACTGCGGC  AATATCTGGA  CTTTACCTTA  TATGGTCTAA  AAGGTGGAGG
179581  AACCCTCAAT  TTTGGGAATT  GTCCACCCCT  TTTTTGGAAT  GCTCATGAAT  AATCCACCCC
179641  TTGTTTAGCA  CATAATCCAG  AAATAACTAT  AAGTATGCTT  ATTTGAGCAG  ACCACGCTGC
179701  TGTTCTGCCT  ACAGAGTAGC  CATTCTTTTA  TTTCCTTACT  TTCTTAATAA  ACCTGCTTTC
179761  ACTTTACTGT  ATGGACTTGC  CCTAAATTCT  TTCTTGTGTG  AGATCCAAGA  ACCCTCTCTT
179821  GGGGTCTGGA  TCAAGACCCC  TTTCTGGTAA  CATCTTTCTG  GTGACCACGA  AGGGACAATA
179881  CTGAGGAGAC  TCTGAAGCCA  AAGGAAACAG  ACTACAGCAC  CAACTGGCTG  ACTTTGGGTA
179941  AGTGGTGGAG  TCCCCGGGTA  AAGGATAGGA  TTGGGTTAGA  GGTGCAACTT  AGGGGAGATA
180001  GGGTCTCTCC  TAAGACAGAG  AGGGTTTCAG  TCCGCTCTTA  ATAAAGGGCA  AGAATGCTTG
180061  ACCGAACTTG  GGTTTGAGAC  CCAACTTAGG  AAGGCTACAG  TCCTTAAGAT  TTAAGGGGTT
180121  AGAGGCCCCT  CTCAGTAAAG  TCTCTCTTGG  TTAAAAACGG  ATTTAGCATT  AGGGGATGTT
180181  AACTGCTATT  CTGTTTGTAT  TAATCTTCCC  TGTGCTCTTT  GCTGACAGCT  ATGGGTGACA
180241  GGATTAGGCA  TGTACAGGAT  CACGGGACAT  TGGGAACTTT  TCTTCTCTCC  AAAAGGGGAA
180301  GCTTGACAGC  TGATAGGACT  GTTGGAAAAG  ATCCCTTTGC  TATGACAAGC  AGCCGCCTGA
180361  ACTTTTGATT  CAGTGTTGCT  GCAATGGGTG  GGTCTTTCTC  TGGCCTCTGT  GAACTCCTCA
180421  CCTTCCCCAT  CTCACCACAG  GCAATGCTTT  TCTCCCTTTC  TCTCTTTTCT  CTTTTCTGTC
180481  TTTTCTGTTA  CTTGAGACAA  CCATCTTGCC  CAGAGACCAT  ATGTTGAAAC  TCCTGGTCAG
180541  AAGTTTGATT  AAAGATGAAA  GGGCCTATCT  GGGGCAAGT   TTGAGCCTTC  CCAGTTAGAT
180601  ATTGGGTGCT  AAGTGGAGTG  GCCAATGTCT  ATGTTTTGTC  ACATGTATAT  TGCTCTGGCT
180661  GAAATGGAAA  ACGTTAATTT  GGTTACTTTA  TGTGGCCATT  GGGCAGCATC  TTACAAAAGT
180721  GAGAGACATT  TATTTGCCTG  TGGTTCCATG  AAACAGAAAA  AAGTTGGTTT  TCTTTTGTGT
180781  CGTAGCTTGG  ACCCAAGGGC  TTTGCAGTGA  GCAAGGTTGC  TAGTGCTGCT  CAGTGAAAGA
180841  GAACCCAGAA  ACCTGGCATG  CCAGCAAAAG  GGTAAAGATT  TCTTACCAGT  CAGGCTTCTG
180901  GCCTCTCTCT  CTTAGTGAAA  ACTGAATGAA  TGGTAAAAAT  CACTGTTTAT  CACCTCTGTA
180961  AAGTTTTGAT  TAATGGGAAC  AAGGATTTGT  GGGGCTAGTC  TTAAGCTGTA  ATGAATCTGG
181021  TATACTTTGT  GATATCAATT  TGTCTTTCTG  TATTACTCTG  TCATAAAGAG  GAATATGGTA
181081  GGATAGAACA  TGGGCTCAGG  ACTCCATAAG  CCTGCTGTTC  AAGCCAGCCC  AGTAAACTGG
181141  TCCGTTGCAA  AGTTTATTAC  AGGTCCCTGG  AAAAAAAAAA  AAATAAAAAC  TGGATGAAGT
181201  TTCCTTCTCA  TCTTGTTTTA  TGTCCTTTGG  AGCTTCACCT  TGTAACCACG  TGGCGGTACT
181261  TTCTCTTGGT  CTCTGCCATC  CAGGGAACAG  GAATTTGGG   GTTTATGTAA  TAGTTAACTC
```

Figure 1 (Page 56 of 73)

```
181321 TAAAAATTAT CTCAAGCCAT TGCAAGCTCA AAATTGGCTG CTCTGGACCC CTTCTGGGAA
181381 GGGCAATGGA AACTAACCAG TGTTGTAGCT CAGCAGCTAA GGATTTGTCA TTTTATAATG
181441 GCGGCCAAGG TTCAATCCTG GCTTAGGGAA TGAGTACTTT CTGATTGATA TCTGTGTGAC
181501 CTTTACCATT TGTTGATTCT GTTCTCTTCC CCTCCACACA CTGTCTTGAG TTTTCCTCTC
181561 TCTGAGAACC TGGGAGATTA TCTTTGGTAA AGTTCAAAAG CCAGAAATAA TGGCCGTGTG
181621 GGATGGCTAA AGTTGAGTAA TAAGAAACTT AAAAGGACTC CTTTTTTTTT TGCTTTAGAG
181681 TGCTATGGTT TATGGTTAAA AGCTTAATTA AAAGTGGATA TTCAATCTCT AAAAGCCTGG
181741 GACTCCTTGG GAAAAGCAGA GGAGGCACCA CAGACCCCAT TTTGGGAAAA CCTCTGTTTT
181801 CCTCATGAAA CCCCAGGAAC TGGAAGTGGA TAGATCCTTC GCAAAATCTA AGGCTCTGTT
181861 TGGCTTTGCA TTATGTTATC TGATGTTTTT GACTTTTGGG GGTATCAGAA ATTACTTTGC
181921 ATTATGAGGG AGATCTGGTG TGTAATAACC AGGTAGGAAA TATACTTCTG GGGATAGCTA
181981 AAGGCAAATA TAGGTGAATA CTTGGCTATT TGCACTTTTG GATCACAAGA AGCATTCTCT
182041 TGACTACCTA GAAGGTATGG AAATGTCTCC ATCCCCACCG AGAGATAAGA TTCCCAGGGG
182101 AGATGGCTGA TCCCCAAAA GAGGGCTGAT TCCCTCTTTT GGGATCCAGG ATCTGGTATA
182161 AAAATGGGAC CCTGGCCAGG CACAGTGGCT CACGCCTGTA ATCTCAACAC TTTGGGAAGC
182221 CTCAGAGTTA TGAATGTCTC ACCATACTGA CACTTTGTGA CTGAGCTCCT CTCTACCCTG
182281 GACACAAGAG ACCCTAATAA TTAGACAGGA ATATCATTGC CCCTATTTAG TCTGAAGAAG
182341 TTATAGAAGA CGGATCTTTA TCCCACTGCA ATCCTTAGGA TTAAGGGTTC CCTGGTAAAA
182401 GGGAGTGGGA AAATATGTCA GAGGCATTTG AATCAGAGTG ACTCCATCTT GAATAGGGGC
182461 TGGGTAAAAT AAGGCTGAGG CCTGCTGGGT TAGGTTAGGC ATTCTAACCA GGAGTTTAGT
182521 CACAGGATGA GATAGAAGGT TGCACAAGGT ACCCGTCACA AAGACCTTGC TGATAAAATA
182581 GGTAACGGTA AAGAAGCCAG CTAAAGCCCA CCAAAACCAA CATGGCCACA AAAGTGACCT
182641 CTTGTCATCC TCACTGCTCA TATACACTAA TTATACTGCA TTAGCATGCT ACAAGACACT
182701 CCCACCAGTG CCACGACAGT TTACAAATAC CATGACAACA TCTGGACGTT ACCTTATATG
182761 GTCTAAAACG GGGAAGAACC CTTAGTTCTG GGAATTGTCC ACCTCTTTCC TGAAAAATTC
182821 TTGAATAATC CATTAGTTTA GCACATAATC CAGAAATAAC TATACGTCTG CTTATTTGAG
182881 CAGTCCATAC TGCTGCTCTG CCTATGGAGT AGCCATTCTT TTCTTTTATT TTTATTTTTT
182941 AGATAAAGAC TCGCTCTGTC ACTCAGGCTG GAGTCTGGAG TGCAGTGACG TGTTTTGGCT
183001 CACTGCAACC TTCACCTCCC GGGTTCAAGC AATTCTCCTG CCTCAGCCTC CCAACTAGCT
183061 GGGACCACAG GTGGGTGCCA CCATGCCTGG CTAATTTTTG TATTATTAGT AGAGATGGGG
183121 TTTCGCCATG TTGGCCAGGC TGGTCTCGAA CTCCTGGCCT CAAGCGATCC ACTTGCCTTG
183181 GCCTCCCAAA GTGCTAGGAT TACAGGCATT ACCCACTATG CATGACCCAT TCTTTTATTT
183241 CTTAACTTTT TTTTGTTTTT TTGAGACAGA GTCTCACTCT GTCACCCAGG CTAGAGGCTG
183301 GAGTGCAGTG GTGCGATCTT GGTTCACTGC AACCTCTGCC TCCTGGGTTC AAGCGATTCT
183361 TCTGCCTCAG TCTCCTGAGG AGCTGGGACT ACAGACATGT GCCACTACAC CCAGCTAATT
183421 TTGTATTTTT AGTAGAGACA GTGTCTTGCC ATGTTTGTCA GGCTTGTCTC GAACTCCTAA
183481 CCTCAAGTGG TCTGCCTGCC TCAGCCTCCC AAAGTGCTGT GATTACAGGC ATAAATCACT
183541 GCGCTCGGCC CTTCTTTACT TTCTTAATAA ACTTGTTTTC ACTTTACTGT ATGGACTAGC
183601 CCCAAATTCC TTCTTGTGTG AGATCCAATA ACCCTTTTGT GTGTGAAAGA ATGTATTGCT
183661 GCTGTTCAGG CTGGAGCAAG CTGGAGCTCA TGCTGCTGCT CAGACTGGAG CATGCGTGAT
183721 CTGTGATCCC AGTAAGAGGA TCATGGTCAC TCCAGCCTGA ACGACAGCAT GATATCTCAT
183781 CTGTAAGAAA AAAAAATTAC TAGAGGGCTT TAACAGCAAA TTTGAGCAGC AAAAAGAAGT
183841 AATCAGTGAA CTCAAAGATA GGTCAATTGA AATGATCTAC TCTGAAAAAC AGAAAGAAGA
183901 CAGAATGAAG AAAAAGAAAT AGAGCCTTAG AGACAGGGGA TACCATCAAG CATACTAATA
183961 TATGCATAAT GGGACTCCTA GAAGGAGAAA AGTGAGAGGA CAGGGAGAGA GAATGTTTGG
184021 AGAAATAATT TCTCAAAGCT TCCCATGTTT GGCAAAAAAG CATTAACTTG CATACATATT
184081 TTAGGAGCTC AATGAATTCC AAGTAGGATA CACTCAAAGA GATCCATACC TAGACACATC
184141 ATAATCAGAT TATCAAAAGA TGAAGAAGAT GAATCTTGAG AGCAGAAAGA AAGGAACAAT
184201 TCATCACATA CAAATAGTAC TCAAAGATG TCTGGAGTAG GTATACTAAT ATCAGACAAA
184261 ATAAACTTTA AGATAAGCAT TGTTATAATA AATAAAGAAA GGTATTTTGT AATGATAAAA
184321 GTGTCAATTC ATCAAGAAAA CATAACATTA TAAACATACA TGCACCTAAC AACAGAGCCC
184381 TAATATTCAT GAAACAAAAC TGACAGAATT GAAGGGAGAA ATAGAAAATT CGACAATAAT
184441 AGTTGGAGAC ATCAATACCT CACTAGTTAG ACAAGATCAA CAAAAAAATA GAAGACTTAA
184501 CACTTGAAAA CACCTAACCT GACCCTAACA TAAATCTATA GGTCACTACA CCCCAAAACA
```

```
184561 GCAGAATAAA CATCCTTCTG AAGCTCACAT GAAACATTTT TCAGGATAGA CTGTATATTA
184621 CTTCATGAAA TAAGTCTCAA TAAATGTAAA AGGACTATAA TAATAGAGTA TATATTCTCT
184681 GACCAAAGTG GAATGAAGAT AGAAATCAAT AACTAGGCTG GGCGTGATGG CTCACGCCTG
184741 TAATCCCAGC ACTTTGGGAG GCCAAGGCGG ACAGATCACG AGGTCAGGAG TTTGAGACCA
184801 GCCTGACCAA CATGGTGAAA CCCTGTCTCT ACTAACAAAA TACAAAAATT AGCCAGGCCT
184861 GGTGGCATCT GCCTGTAGTC CCAGCTACTC GGGACACTGA GGCAGGAGAA TCACTTGAAC
184921 CCAGGAGGCA GAGATTGCAG TGAGCTGAGA TCGCGCCACT GCATTCCAGC CTGGGAGACA
184981 GAGCGAGACT CCGTCTCAAA ATTAAAAAAA AAAAAGAAAC TAGAAAAATA AGAACAAATC
185041 AAACCCAAAG CAAGCAAGAG GAAAATGAAA AATTTCAAAG CAGCCAAGAA CAAAAGGCAC
185101 ATTATGTACA GAAGAACAAG TGTATAGATC ACATATTTCT CATAGACACA ATATAAGCAA
185161 AAAGACAGTG GAGCAAAATT TTTTAGATTA ATGAAAGACC TACAATTCTG TACCAAGCAA
185221 AAAAACTCCC CCCAAATGAG GGTGAAATAA GACAATTTAA TACAGAGAAA AGAGGAAGGA
185281 ATTTATCTAG TCATATGTGA GAGTTTTATG ATACATTTTG TACTGTATAT GTGGATGTTT
185341 TCTATTTCAT TTAAAAAATC AACCGTGCAA TTAAATGGTA GATTGTCTTG CTTCTTTTTG
185401 ATTGACACAG TCATTAACTA AAATATTGTA GTATTTTTTT ATCTCCCTGC CTAAAGGCAA
185461 TAAACATCTA ATCAGCAGAC TAGAACAATA AAAAATATTT TTTAAAAGTC CTTTAGGCAG
185521 AATGATAAAA GTCCCTTAGG CATATTGAAA TTCCTATTTA TACAAAGGAA TAAACAGTAC
185581 TAGAAATTGT AACTATGTGA GTAAACAGAT AATATTTTTT CTCCATAAAA TGTGGTTGAC
185641 TATTTTCACA AAAATAGTTA ACAATGTAAT GTGTGATTTA TAGCATTTAA AAGTAAAACA
185701 GGCCGGGCAC AAAGGTTCGT GCCTGTAATC CCAGCACTTT TGGAGGCCGA GGCGTGCAGA
185761 TCACTTGAGG ACAGGAGTTC AAGACCAGCC TGGCTAACAT GGCAAAACCC CATCTCTACT
185821 AAAAATACAA AAATTAACCA GGCGTGGTGG TGCACGCCTG TAATCCCAGC TACTCTGGAG
185881 GCTGAGGCAC AAGAATCACT TGAATCCAGG AGGTGGAAGT TGCAGTGAGG CAAAATTATA
185941 CCACTGTGCT CCAGCCTAGG CAACAGAGCT AGACTCTGTC ACACACACAC ACACACACAA
186001 AAGAAAGTG TATGACAACA ACAGTGCAAA AGAAGTGGAA ATGAAATAA TGTTATTTTA
186061 TATAAGTGG ATACTTTTAG ATGAACTACG ATAAATTAAT GATGTATACT ATAAACTCTA
186121 AGGCAACCAC TGAAATAATG AAACGAAGAA TTATGGCTAA CAAGCCACAA AAAGAAATAA
186181 AATAGAATGA GAAAAAATAT TTAAGTTGTT CAACAGATGG GAAAAAAAAG AGGAAAAAGA
186241 GAACAAAGAA CAGATGGGAC AAATGGGAAA GTAATAGCAA GATGATAGAC TTAACTCTAC
186301 CCATATAGAT TATCACACTT AAGGTAAATG ATCTAAATAC TCTAATACAA AAGCAGAGGT
186361 TGTCAGATTG AATTAAAAAA ACAGACAACA ACAAAAAAAA GCAAAAAAAG AGCCACAACA
186421 TGCTGCCTAC AAAAAATTCA CTTTAATATA AAGACACAAA TAGTCTAGAA CACCATCACT
186481 TTTAACCTTA TTTACTCAAA CCTCCTGATC CCTATTTATT TATTTATTTA TTTATTTATT
186541 TATTTATTTA TTTATTTATT TTTGAGACAG AGTCTGACTC TGTTGCCCAG GCTGGAGTGC
186601 AGTGGCACCA TCTAGGCTCA CTGCAGCCTC TACCTCTCGG GTTCAAGCGA TTCTCCTGCC
186661 TCAGGCCTCC CAAGTAGCTG GGACTATAGG CACATGCCAC CATGCCCAGC TAATTATTAT
186721 ATTTTAGTA GAGACGGGGT TTTGCCATGT TGGCCAGGTT GGTCTCAAAC GCCTGACCTC
186781 AGCCTCCCAA AGTGCTGGGA TTACAGGCGT GAGCCACAGC ACCCAGCTCC TCTTCATTTA
186841 TTCTTGCTAC GCTTCCTCCA ATCCATTTTG TGCATTTGAT GATTTTGCCA GTAACTTCTT
186901 TATTTTTCTG GTAAAATTAC TTATGGGTCA CTGAGGACTG GGATGTTCTT TCTTCTAGAG
186961 GGGGTTTGTG TCTGCTTTTG CCAGGAAGCT GGGGTACCAC CAGTCAAGTA TTACTTTAAA
187021 CTCAATTCAT GAATTGAGAC TTTTTTTTTT TTTTTTTTTT TTACGCAGAG TCCTACTCTG
187081 TCACCCAGGC TGGAGTGCAG CGGTGTGAAC ATGGCTCACT GCAGCCTCAA CCTACTGAGC
187141 TCAAGCAATC CTTCTGCCTC ACCATTCTGT ATAGCTAGGA CTACAGGTGT GTGCCACCAT
187201 GCCTGACTAA TTTTTTAAAT ATTTTTTTA GAGATGGGGC TCACTTTGTT GCCCAGGCCA
187261 GTCTCGAGCT CCTGGGCTCA AGTGATCCTC CCACCTTGGT CTCCCAAAGT GCTGGGGTTA
187321 CAGGCATGAG CCTCTGTGGC TAGCCAAGAC TTTTTATTTT TTAGCCTAAA TGTGTATAAA
187381 AGTTGGCTTG TGGTTACAAC TTATCAGGAT TGATGATCTC TCTCTCTCTC TCTCTCTCTC
187441 TCTGTCTCTC CCCACCTCTC TCACATCCCT TGCTCTGCTG AGAAGCAGAG CAAACATTCT
187501 AGCAGTTTCC AGAGAGTAGG ATGGGATTAC TTCTAGTTTA CTTTTATCAT CCTTTGGGAT
187561 CGCAGTATTA CTGGGAGAAC ACAAGTATCT CTTATTAGAC ATACCACCTT TGTAGAATCT
187621 GGACTTTCAT TTTAGACTTT ATTTGTTTTC TACTATAAGC AATTTAAGTT ACAGATCTCT
187681 CTACACACTG TTTAAGTTGC ATCCCATGAA TTTTGATGTG CTTTATTGTC ATTATTTAT
187741 AGTACAATGT ATTTTGTAAT TTTTTGTGAT TTGTTTGGAG AGATTGATTA ATTAGAATGA
```

Figure 1 (Page 58 of 73)

```
187801 TGTTTAATTT CCAAATATGT GTGTTTTTTT CTACATTTCT TATTTTTATT GATTTCAAAT
187861 TTATTTCTAC TGTAGTCAGA TTTAATAATT CATTTATTTT TATTATTTTC ATTTTTTTAG
187921 AGACAGGGCC TTTCTGTGTT GCCCAGGTTT GTCCCAAACT CCTAGTCCCA AGCAGTTCTC
187981 CTGCCTCAGC CACCCAAAGT GCTGGGATTA TAGGCACGAG CCACCCGTGC ACAACCAACA
188041 ATTCATTTAA AAAGTGGGCA AGTGAACTGA ACAGACATTT CTCAAAAGAA GGCATACAAT
188101 TGGCCAACAA ATATATGAAA GAATGCTCAA CATCACTGTA TTAGTCTGTT TTCATGCTGC
188161 TAATAAAGAC TTAACCTGAG ACTGGGGAAT TTACAAGAGA AAGAGGTTTA ATGGACTTAC
188221 AGTTCCACAT GGCTGGAGAG ATCTCACAAT CATGGTGGAA GGCAAGGAGG AGCAAGTCAC
188281 ATCTTACATG GATGGCAGCA GGCAAAGAGA GAGCTTGTGC AGGGAAACTC CCGTTTTTAA
188341 AACCATCAGA TCTCGTGAGA CTCATTCACT ATCATAAGAA CAGCATAGGA AAGACCCGGC
188401 CCATAATTCA GTCACCTCCC ACTGGGTTCC TCCCAGGACA CATGGGAATT GTGGGAGTTA
188461 CAATTCAAGA TGAGATTTGG GTAGGGACAC AGCCAAACCA TATAAATAAC TAATCATCAG
188521 GGAAATGCAA ATCAAAACCA CAATAAGGTA TCATCTCACC CCAGTTAGAA TGGCTATTGT
188581 CAAAAAAACA AAAAATAACA AATGCTGGTG AGGATGTACA GAAGAGGGGA CTCTTATGTC
188641 CCACTGGTGG AAATGTCAAT TAGCATAGCC ATTATGCAAA ATAGTATGGA AGTGAGGTAG
188701 GTTACATAGG GTGGTCACAG CCTCCCTTGA AAGGAAACAA GAAACTTGTC AAATTGATGG
188761 AGAGAACAAA TCTCTTGACA TTACACAAAC TGCATCTGGG GCTAGTGGTT AGAATATCCT
188821 CAGTCAAGGA GGTAGAAGAG CAGGAGGGAA AATCCCTAAG TTCGTGCAAG TGCAGAAACC
188881 CACAAGCTGT GTTCTCAGGT TGACATATAC TCATTTTAAT AGTAAGAAAC ACACCCTTGG
188941 GTAGAGAATT AAAATGCTAA TAATACATGT GATGTATGTA CTAGCGTGTA TGGCAATATT
189001 GCATGCACAT TCAAGAGACC ACCCAAAACA TATTTAACAA CAATGCCCAT TCCCACCCCC
189061 TCATGGATAA TCACGTAGGA CTCCCATAAC GGGAGTTTCT TCAGTGTCAA TTGGTGCTGA
189121 AGTAGCCGAC CCTGACTCTG CTATCAGCGT GTACTTTCAC CTTGCAATAA ACTCCTTTGC
189181 CTACTTTTAC TTTGGACTGG CTTTCAAATT CTTTTGTGCA GGGAATTCAA GAATCTGAAC
189241 CAGCCTACTG ACAACAGAGG TTTCTCAGAA ACCTAAAAAT AGATCTACCA GATGAGGCTG
189301 AAAATCTGCT ACTGGCTATT TATCCAAAGG GAAGGAAATC AGTATACAAA GAGACACCTA
189361 CATCCCCATG TTTATTGCGT CACTCTTCAC AAGAGCTGAT ATATAGAGTC AACCCTAAAT
189421 GTTCATTAAC AGACAAATGG ATAGAAAATG TGGCATATAT ACACAATGAA ATACTATTTG
189481 GCCATGAGAA GAATGCAATC TTGTCATTTG TGGCAACGTA GATGAAACTG GAGAACATTA
189541 TGTTAAGTAA GATAAGCTAG GATTGGAAAG ATAAATACTA CATGTTATCA CTCATATGTG
189601 AAAGTAGAGA AAAATTTTTA GCTCATGGAT TTAGAGAACA GAACTGTGGG TACCGGAAGC
189661 TGGGAAGGGT AGCAAGGAGG GGAGGATAGG GAGAGGTTGG TTAATGGTGA CAAAATTACA
189721 GCTAGATTGT AGAAATGAGT TCCGGTGTTC TGCACCATTG TAGGGTGCAT ATGGTTAACT
189781 CTCATTTATT GTATATTTTC AAAAAGCTAG AAAAGAATTT TGAATACTCA CAACAAAATA
189841 AATGATAAAT GTTTAAGGTG ATGGATATAC TAATTACTCT GATTTGATTA TTACACATTG
189901 TGTACACATA TAAAAATATC ACTCTTTATC CCGTATATAT GTACAGTTAT TATATGTCAA
189961 CTAAAAATAA AAGAAAAAAA GAATATGATC TATCATGATG TATATATCAT GTGTACTTGA
190021 GCAAAATGTG CATGCAGATA TTGTGTATAA TGTTCTATAA ATCAATTAGC TCAAGATAAT
190081 AGATAGGATT GTTCAGATCT TCTGTGTCTT TACTGATATT TTGTCTAGTT ATTGCATCAT
190141 TACCAAAAAA AGGGTGTTAA ACTCTCCAAA TGTGATTGTA GAATTGTCTA TTTTGTCTTT
190201 TCTTTTCCAT TTTTACTTTA TGTATTTTGA AACTCTGTTA TGACATTTTG CTATGTATTT
190261 TAAAACTTCG TTATGTATTT TGAAACTCTG TTGTTAGAAT CATACATTTA TGATTATTAT
190321 GTTTTCTTGA TGAAATGACA CTTTTCTATT GTCATTGTTT TTGTTTTTTC TGAAATGGAG
190381 TCTCACTCTG TTGCCCAGGC TGGAGTACAG TGGCACAATC TTGGTTCACT GCAACCTCCA
190441 CCTCCTGGGT TCAAGCGAGT CTCCTGACTC AGCCTCCAAG TAGCTGGGAT TACAGGCATG
190501 TGCCAGCATG CCAAACTAAT TTTGTATTTT TATTAGAGAC AGAGTTTCAC CACGTTGGCC
190561 AGGCTGGTCT CGAACCTCTG ACCTCAGGTG ATCCGCCCAC CTCGGCATTT TTATTTTATT
190621 TTATTTTTTT GAGACAGAGT CTCACTCTGT CACCCAGGGT AGAATGCGGT GGTGTGATCT
190681 TGGCTCACTG CAACCTCCGC CTCCTGGGTT CAAGCAATTC CCATGCCTCA GCCTCCCGAG
190741 TAGCTGGGAT TACAGGCACA TACCACCATG ACTGGCTAAT TTTTGTATTT TTAGTAGAGA
190801 TGGGGTTTTT CTATGTTGGC CAGGCTGGCA ACTGACTCCT TTAACAATAC AAAAATATCAC
190861 TCTGTCTCTG GTAACACTCT CTGTCTTAAA CTCTATTTTA GCTGTTATTA TTATAGCCAT
190921 TTAGTCTTT TTATGCTTTC TGTTTGCATA GTGTATATAT TTTAATATGT TTATTCTCAA
190981 GTTATCTGTG TTTTTATATT TAAGATGTTT CTCTTCTAGC CAACGTGTTT GGTTCTTGCA
```

```
191041 TTTTTAAGTC GATTCTAACA ATCTTTGCCT TTCAATTGAA ATATTTACAC CATTAACATC
191101 TAACATTAAC ATTTATTTTT CTTTCCACAG TACACTGGCT AGCATCTCCC ATATAATATT
191161 GAACATAAAG TGTGATAACT GACATCCTTA TTTCATTCCT ACTCTGAGTG GAAAGGGCAG
191221 GGGTGGAGAA AGCATTCAAC AATTTGCCAT AATTATAATG CTTTTTGTTA CACTGTTTTC
191281 TTCTGCATTA AAAAATATCA TTACATTTTG CATGAATTAT TAGGAGAAAA TATTTTCCAA
191341 TTTTCCTGGA AAATGCCATA ACCACGTCTC TCAATTTTGT TTCCATCTTT CTTCCACATT
191401 TTACATAACC TACATAAGAG ACACATTATC AAGTATATTT TACATGGCTT CTCAGTGTCT
191461 TCTCTGTCTG CTAACAGGTT TACCAAGAGA TGGCACTCTT GTATTTCTGG TGGCTATGTC
191521 CATATCGTTT TGCCTTTAAG ACAGCGTAAC TACTTCTTTC ACCAGTATTA AAGACATGTA
191581 CATTTGATCT GGTTCTTGTG GATGATTTTA AATGACTCAA GCTAATAATC CTAATTTTAC
191641 CTAAACACTC CATTATTTTA AAATGTATTC CTTTATGCCC ACAATAAACA TTTATTGACA
191701 TTAGGCTGGA CATTAGGCTT CTCTATGGCA GACATTAGGC TGGACCCTAG CCATATATCT
191761 ATTGAGGGAA AAAAAATTAT TTTCTATATA AGTTTCCAGA AAGCCAAGAT GTGTTTAAA
191821 AACAAAACAA AACATTACAT TCTAAATGCT GTAACAAGAT AAGAAAAAGT GTTGAGGCTG
191881 AGAGAAGAAC AAAGCAGCAA GCAACTCCTG GAAGGACCAC TGCTGCAGAG GTAATAACTG
191941 GTGAACCATG TTTTGGAGAA GGAAAAGGTC ACCAAGAGAA GGAGGGGGTC CAGGGTGTTC
192001 AGAAAGATTG CATGCATAAA GATCAAGGGT AATAAAAAAA ATTCCGTATT ATGTAAATGT
192061 GAAGTTCCAG GACCATGAGC TTGGAGAGCA TGAAGTACAG GAGGAGGGTT GGTTTCAAAT
192121 AAATCTGGGA ATGAAACAGT GAAGCCTCTG GCAGAACTCA CATCTCTTTC CTCCCCTCTT
192181 CCTTGCACAT TCCCTTTATG GAGTAATTGC AGGGATGGGA AAAGTTCAAA ACCACCACTG
192241 AGCCTAGGAA GTGCTAGGGT AAAGTGGAGA ATGAACCTGC GTGATTGCT CATCCTAAAC
192301 TAGGTTCTTC TAGGAGAGCC CTTCCCCATA AAATCTGCCC TCCTCGAAGG GGCCCAGACA
192361 GCCTAAGCTC ACCTCCCAAA GACCCCTTAC TTGCTGACTG AATCTGATTC CACCCAGACA
192421 TGGCCTAAAA CCCTTCCATA ACTCTATAGC CAAATTCAAT TTTAGACAGG CCTCATACCA
192481 ACCTTTCTTC CTCTAAGTCT GCCACCCTAG GCAATTCTCA ACATTCTCTA CACACTTTGG
192541 GGCCATAGAC GTGCTACCAA GTCTCCAGAC CTAGACCTGA TGGAGCAGTG CTGTAATGAG
192601 ACGACCACTG GCCTTTGAAC CAGACCCTTC TCTGTGGCTC CTATGCATCT CCAACCTGTT
192661 TTGAGCACTG CTGCCAAGAC ATCTTTGGCA CTTTGTTGTG AAGTTTTAAA ACTGAACTAA
192721 TCTACAAAAC ACCTAACCTT TAAAAATTCA TTGTCATTTC ATATCATGAA AGATAAAGAA
192781 AGGCCAGGAA ACTGTTCCAG GTTAATAGAG ACTAAAGAGA TAGCAACCAA ATGCAATTTG
192841 TGATCCTGGA TTGAGGGGAA AAAGTGTTGT CAGAGACATG ATTGGGACAG CTGGTAAAAT
192901 TTGAATTTGA ATTTAAAGAT AAAGTATTGA GTAATATAGG AAGATGATTA TCTGCAACTT
192961 TCAAATGTTT CAGTAAGTAT ATATATATAT AAAGAGATAT AAAGACATAT AAATAAATGG
193021 ATAGGTAGAG AAAAAGCAAA TGTATAATAT TAACAATCTA GGTAAAAAGT ATATGAGTGT
193081 TCTTTGTACT GTTTTTCTGA TTTTTCTATA TGTTTGAAAT CATTTTAAAA TAAGAAGGTT
193141 TTTGGGTTTT TTTTGTTTGT TTTTTGTTTT TAGAGACAGC ATCTTATTCT GTCACCAGGC
193201 TGTAGCTCAG TGGCCCAATC ATTGCTCACT GCAGCCTCAA CTTCCTGGGC TCCAGTAATT
193261 CCCCCTACCT CAGGCTCATG AGTAGCTGGT ACTTCAGGTG TGCACCACTG CACTCAGCTA
193321 ATTTTTATTT TTTAAATTTT TGTAGAGATG GCATGTTGCT ATGTCACCCA GGCTAGTCTC
193381 AAACTCCTGC CCCCAAGTGA TCCTCCCACT TTGGCCTCCC AAAGTGCTAG AATTATAGGC
193441 ATGAGCCACT GCACCCAGCC CCAAATAAAA AAGTATTTTA TTTTAATTAA CTAATTAACT
193501 TTGAGTCAGA GTTTCACCCT TGTCACCCAG GCTGGAGTGC AATGGCATGA TGTTGGCTCA
193561 CTGCAAACTC TGCCTCCTGT GTTTAAGCGA TTCTCTTGCC TCAGACTCCT GAGTAGCTGA
193621 GATTACAGGT GCCTGCCACC ATGCCCAGCT AATTTTTATA TTTTTAGTAG AGACGGGGTT
193681 TCAGCATGTT GGTCAAGCTT GTCTCAAACT CCTGACCTCA GGTGATCCAC CCACCTCCGC
193741 CTCCGAAAGT GTTGATGAGC CACCACACCC GGTCTAAAAA GTATTTAAA ACCACAGTCC
193801 CACTCTACCT TGTCCTACAC TACCAGGGGC TAGGATCACC CCATGTCTTC TAGGCTATGA
193861 GATAGAGGAA TCCAAGGAAG AAGATAAGCT ACTTGGTTCC TCTATAGGGT CTTGTGTGTG
193921 CTCTCATGTG CTCTCTCTCT CTCTCTCT CTCACACACA CACACACACA CACACACACA
193981 CACATGAATA CCAGAGCTAT CACTTTCCCA GTCTAGTACT CATCTCATCC CAAGGGTTTT
194041 GTGTTGTAGT GGTTTGCTCA TTTCTTTGTT TTGTTTGTTT GCTTGGATTA TTCTTTTTCT
194101 CTTTTTGCAG CTGAAGGGAG AATTTCCAGG CCAGCCCTTT GGCCATTAGA GTTACAGTGC
194161 CTCTATTCAG GCTTCATAGA GAGACCTGGG ATTCAGTAGT GGGGGGCTTT TATCCAGTTC
194221 AAAATAATGC ATTCTCACCA AGATGTACTT TGAAATAAAA CAATACTAAA ACACAAAATT
```

Figure 1 (Page 60 of 73)

```
194281 TTATTTATGC TGAACATTGA ATCACTTTTT TCTGTATTTT GTGTAGAAAG TTATACACAC
194341 ACAAACACAT TTGCTCCTGC TTTGTTTATT GGCCCAGGGG TATGTTTGGT AATACTTCAT
194401 CAGGCATGAG TAGTACGTCT TGGAAGGTGT GGTCTAAAGC CTAGACTCCT ATCTGCTTCC
194461 TTCAGCATTC TCCAGTGTAT CTGTCATCTG TCTACCTTAG GATAGGGGTC TCCAGAACTT
194521 CCATTCACAT TTAGAAGAGG GCAGCGGCTT TCTATGGAAA ATATGAACTC TCATTCATCT
194581 CTATTCCTTC TTCTAGCTAT GGTCCAGCTC AGCTGTTTGG AATAAAGTAT CTATATGAAG
194641 TCTGCGAATG GTTCTCAGAC TGGTTGAACA TTAGAATCAC CTGAGTACCT TCTAAAATTC
194701 TTATTACCCA GGGCATATCT CAGAATGAGT ACCGCAGGGT AGGGATAGGA TTAGGGATCA
194761 TGATCTCTGG AGTCTGGTTT AGGCACTAGT GCTGTTTAAA ACTACGTTCA TGAGGTGGAG
194821 GTTGCAGTGA GCCGAGATGG CGCCACTGCA CTCCAACCTG GGCGACAGAG TGAGAGTCTG
194881 TCTCAACAAA ACAAAACAAA AAAAACCAAC TACCCTTGTG ATTTGAATGT CCATCCAAAA
194941 TTGAGAACCA TTAGGTAAGG CCAAGCTGTA TAATTAAAGA GCAGTTTTCA TTTGTCTGGT
195001 GTGGTGGCAG CTTTTTGATA AGGGAAGTAT TGTTGCCATC CACATACCTG AGCCTCACTC
195061 CTGAGAACAC TGGTGTGTAT GTTGCTAAAA TTCCCCAGGT GATTCTGAGG TTCCTTCCTG
195121 GATAAAAACC ACTGACCCTG GAATGTACC CACTGCCAAT CTCCTGCGTA AACCTTGGAT
195181 ACTGGGAAGC CTACAGTTGA AAATATTGGG CTTGAGATCC TGAAACAAAT CTTGTATTTC
195241 ATTAAGACTA ATATTTGGTA CAGTGCAGCA AATCAAGGGA ATTTTGGTGG CTGAGTTCTT
195301 TTAGAACTTT TGCATTGAAA TAGGTTCAAG CAGCAATAAG TTAAAACTAC AACCTCAGCT
195361 AAAGGATTAA AAGACACGTG AGCTGGGTAG GATGAGGTCT AAGGTTGGGT GTGGCGGCTC
195421 ATACCTGTAA TCCCAGCACT TTGGGAGACT GAGGTGGGTG GATCACTTGA GGTCAGGAGT
195481 TCAAACCAG CCTGGCCAAC ATGGTGAAAA CCCATCTCTA CTAAGAATAC AAAAAAATTA
195541 GCTGGGCGAG GTGCCAGGCA CCTGTAATCC CAGCTACTGG GGAGGCTGAG GGAGGACAAT
195601 CACTTGAACT CAGGAGGCAG AGGTTGTAGT GAGCTGAGAT CGCACCACTG CACTCCAGCC
195661 TGGGTGACAG AGCAAGACTC CATTTAAAAA AAAAATAATA ATAATAACAA TAATAATAAT
195721 TCAGACATAT CCAGGCATCA AACAGATACC TGGGGCAGAT GAATAGTCTT GAGATTCAAG
195781 TCACACATGA AATTTAGGTG GAAAATGACA TTGGAGAAAT TTGAGATTAT GATGAATGGA
195841 AATTTTTCAA AGAGGAATTT CAGGCTCTGT TCTTGAGGGG ATAGATGGAC TTCCAACAGC
195901 AATAACACAG GATTAATGAG GACTTGGGAT GTTACATAAA TTAGAGATGT TAGATGGATA
195961 AAGAGATAAA AGTACTCTCT CTAAGAACAT GGGACCAGAG ATAGGCTCAC TTCTAACCAT
196021 CAGATATAAC TAGCAGACTA AACGGTCTAA AAATAAAAAT CATGCCCCAC TCCTGCTTAA
196081 GACATTTTAA TTACTCTCAG TAACTCTTCA GTTTTTCTAC TGTGTTATCT TTAACTACAG
196141 GGTTGGTCTG GGTGTGCAAC ACAAGAAAGC CTGGCATATA CATGGATTCA AGTGTATGCC
196201 ATGTGCAGGT ATTCTTTCAT GTACTATTTC ATGTATTCTT TTTCACATCT GTTTTTTCCT
196261 TCATTGAAGT CAATGGCTGA TATTAGATTC TACTATTCAT GTGTACTAGT TATATATAAT
196321 TGTTACAAAA CAAATTAGCA AAAACTTAGT GGCTTAAAGC AACACACATT TATTATTACC
196381 TAAGGTCTGT GGATAGAAGT TCTGACATGG CTTAACTGGG TTCCCTGCTT CAAGCCTCAT
196441 GTGGCTGCAA TCCAGGTGTT GGCTGAGTCT GAATTCTCAT CAGAGGCTTG ATTGTGGAAA
196501 TTTCCACTTC CAAGCTCCCT CAGGTTTGTT GAAAAATTCA GTTCTTTGCA CCGGTAGAAG
196561 CTTCTTGGTA GAGGCTGATT CAACTTCTAG AGGCTGTCTG CAGTTCCTGT CACCCAGGGT
196621 GGAGTGCAGT GGAGCAATCA TAGCTCACTG CAGCCTTGAC CTCCCAGAAT CAATCTGTTC
196681 TCCCACCTCA GCATCCTGAG TAGCTGGGAC CACAAGTGTG TGCCATCACA CCTGCCTAAA
196741 AAACAAACAA ACGAAAAAAA ACCCCAGAG AACTTTGTAG AGACAAGCTG GTCTGGAACT
196801 CCTGCGCTCA AGCAATTCTC CTGCCTTAGC CTAAAAGTTC TGGGATTATA GGTATAAGCC
196861 ACCATACCTG GCATATGGCA AGTCTTGAGC AGGACAAATA CAGATGATTT ATGTCTGTCT
196921 TCCATGGTAT TCTAGGTTAT TGTTGAGATG GTCCTCTATT GTCTTGTTCC ATCTATTGAT
196981 TAGATAAAAC GTTGTTCCTT CTGTTATTTT TCAACAGTAG CTTTTATGTG TCTCTCTTTA
197041 TCTTAAAATT CTAACCAAAG AGCTGCTCTT TTCTTGGTGT ACTTTACCTT TGGTTGATCC
197101 TTCTTAACCT CTTCTTGCCC TCTGGGGCCT AAGATGAGGG CTGTTATCAG ATGTGAGTCT
197161 ATGGGAAAGC AAGCAAGAGG TTCTTCAGCC TCCGTTCAGC CTTAAATGTC TAGGTAGAAA
197221 TCAGTCATGG CCCTTCCAAT GTGGTACAGA CCAGATCACA GAGACAGGGG TCTCAGCCAA
197281 GGTCTTGTGG CCTAAGCCTT ATAGAAATAA TGAGTGTTTA CTTACTTGGA GAACTCCCTT
197341 GGAATATCTT TTTTTGTGAA CCTGAGGCAA CTTTTGGTGA TTTCTTGATG TCTTGGGAAT
197401 CTTGGTCTAG AGCCATTTCA ACCCGATTTC TTTTCATGTC AGTGGCATTT TGTGACCAGA
197461 TAGTAAATAA GTTCTATGAT GTTCACTCAG AGAAATACAA TGACTTATGA TGCGAAGCTT
```

Figure 1 (Page 61 of 73)

```
197521 CTGTGGTTCA GCCCTTACTT CATCTTCATT CCCTCTTATC TGCATCTGTC TCCTGCTTGG
197581 GAACAAAAGT CTGGCTTCAT TCTATGACCC CCACGTTGAG TTTCTTAGTA GCACTTACTT
197641 TTCAATTAGG AGTGTCCTCA CTTCTATCCG TCAGACATAA CTAGCCGACT AAACAGTCTA
197701 AATATAAAAA TCATGTCCTA CTCCTGCTGA AAACATTTTA ATTACTCCCC ATCATTTAAT
197761 TTTTTCTACT GGGTTATCTT TAACTTCAGA GTTGGTCTTG TGTGCAACAC AAGAAAACCT
197821 GGCATATACA TGGATTCAAG TGTATGCCAC GTGCATGTAT TCCTTCATGT ACTATTTCAT
197881 GTATTCTTTT TCACATCTGT TTTTTCCTCT AAAATTTATT TCCTTTTAAA AATGAAAATT
197941 TTGCATTTGA CTAAATTTGT CAAATTTAGT CAAATTTGTT TAAAACCATT TTTAAAATGT
198001 TTCCCGAAGT TTTGAGTGAA GTTAGTACTT CAGAAAAACT GTTTTGTATT TTTCCTGTGA
198061 CCTCAGTGCA CTGCTGTGCA TTTCCATTTC TGCGTCCACA CACATTTGTT TTGAGGAAAT
198121 ATAGGAACGA CAAGATAAAG TTCAAGCTCC TGGACATTGC ATAAAAGACC GTCATGACCT
198181 GGTCCTGTTG ACTTCCCTAG ATTTCCCGCT ATTTCCTAAG TTGAGATTTT TGGTTTGGAT
198241 GCTTTGTGTT TTCCTAAAAT CAAAATAGGT TTTTGCCTTT TATGATTATA CAGTAAATAA
198301 ATGCTATTTG TGTGAAACTT TAAACAATAC AAAAAAAACC TAAGGAAGAA AGTCAGATTC
198361 ATCTAAAAAT CCTTGTGGCC AGAATTAACT ACCTTAGTTA CTATTTTCTC TATCTCTCTC
198421 TCTCAATGTA TATTTGGTGT AGGTATAGGG GTGTGTGTAG TGTGTGTGTA TGTATATATC
198481 TGTTTCTATT CCTGTATGTG GATGTGCACA ACGCATCCTG CTTTGTACAC TACAGTACTA
198541 GCATTTTTCT AATGTAATTC AATATTGTTG AAAACATTTT AAAAAAGCTT GTATATATAC
198601 ACACACATAC ACATACATGC ATGTATGTAC ATATACACAT ACAGACAAAA ATGTATCCTA
198661 TGTATATTCA CACATGTATA CACACTCACA CATACATAGA GTTTTACATC CATAGTTTAT
198721 AAATGTTGCT TTTTTTTGGT CACCTTTTTG CTAAGTCTTA CACTTTTTTT TTTTTTTTTT
198781 GAGACGGAGT TTTGTTGTCA TTGCCCAGGC TTAGTGCAGT AGCGCGATCT CACCTCACTG
198841 CAACCTCGAC CTCCCGGGTT CAAGCGGTTC TCCTGCCTTA GCCTCCTGAG TAGCTGGTAC
198901 TACAGGTGTG CGCCACCATG CCTGGCTAAT TTTTGTAGTT TTTTTATAGA GACGAGGTTT
198961 CACCATGTTG GCCAAGCTGG TCTGAACTC CTGACCTCAA GTGATCTGCC TGCCTCAGAT
199021 TCCCAAAGTT CTGGGATTAC AGATGTGAGC CACTGCACCC GGCCAAGTCT TACACATCTT
199081 TTTTTTACCA CTAAACTGTT TACCCAAACC TGATAACCCA AGTCAACAGC TATTATGGCT
199141 CACACAATCT TATGTAAACA AAGATACAGA TATATAGAAT TTTCTTGATT AATATTCAGA
199201 AAAAAATGGA GTCCCTTTAT ACGTCCTTAG TATCTGCTTT ACTCATTTAA AAATGTATTA
199261 CATTATATGA AAGTATTCAG GTCAAATGTT ATAGATGTGA TTCATTCTTT TTAACTGTGT
199321 TATTTTTCTG CAATGACTAT GTATCACAAA GTACTCAGTC TTCCACTGAT GAAAATTTGG
199381 GCTATTTCCA GTTTGTCTTC CATTTTTCTT TCTTCCTCTT GGATTTTCAC TCAATGTGTT
199441 TACTAATTTA GGAAGAATCA ATAGTTTTTA TGGTATTACT TCTCCCATTC AAGAATATAG
199501 CATATGGTAT AGTATAGTAG AGTACTTAGT TTAATTTAGC CAGATCCTGT TTTCTGCCCT
199561 TTAATAAAAT TCTATCATTT TCTGCCTTTG AGTCACATTT TCCTTGTTCA TATAATTCTT
199621 AAAAAATGTA TAGTTTTCAT TCTAAGGGAA CATAAAAACT TCTTTCCATT TCTATTCCTG
199681 TCTAGTTAAT TCTACTATTG GGAAAAGTAA CTGTTAAAAA AAATTCTTAT CTTTCCAGTC
199741 AGTTCACCAC ATTTCCTTTA TACCTTTGTA CTTTAATCCC CAGTCATGTT GAACACTTCT
199801 TATTCCTCAC ACCAAGCCTC AACGGGTTTG CTCTTTCTGG AAGGTGCTTC CCCTGTATTA
199861 CTGACTTATT CATACCACAC ATGGAGACTG GCGCAGCCCT GTTCTGCCTG GAAGCCTTC
199921 CCCTGATACC CCCAGTTGGC AGGAGTCTTC ATTTGTTCTT TTCTAGTCAC CTGTGCAAGT
199981 TTGTATTGTT CATGTTTATC ATCCTTCATT CTAGTTGTCT GTCTCTGTGT GTGGTCTCAT
200041 TCAGTGGACT CTGAACTCTT ATGAAGTCAT GTCATGGGTC AGATCTTAAT AAATTAATAT
200101 TGTCGGAAGC TAATGTCATG TCTAGAATAC AGAAATTTA TCAAAAAAAA ATATAGTATG
200161 TTGGCTGGGC GCAGTGGATC AAGCCCGTAA TCCCAGCACT TTGGGAGGCC GAGGCAGGAG
200221 GATCACATGA GGTCAGAAAT TCAAGACCAG CCTGGCCAAA ATGGTGAAAC CTCATCTCTA
200281 CTAAAAATAC AAAAAGTAGC CAGGCGTGGT GGTGCCCACC TGTAATCCCA GCTACTCAGG
200341 AGGCTGAAGC GGGAGGATCA CTTGAACCTG GGAGGCAGAG ATTGCAATGA GCTGAGATCA
200401 TGCCACTGCA CTCCAGCCTG GGCGACAGTG AGACTCCATC TCAAAATAAT AATAATAATA
200461 ATAATAATAA TAATAATAAT AATTGTATGG AATTGAACTG CTCTGATTGG AAATAGCTGT
200521 TTTTTAAAAA ATTATTATTT TTTAAGTTCC TGGGTACAAG TACAGGATGT GCAGGTTTGT
200581 TACATAGGTA AACGTGTGCC ATGGTGATTT GCTGCACCTA TCAACCCATC ACCTAGGTAT
200641 TAAGTACAGC ATGCATTAGC TCTTTTACCT AATGTTCTCC CACACCCCCA CCCCATCCTC
200701 CCCCAACAGG CCCCAGTGAG TGTTGTTCCC CTCCCTGTGT CCACATGTTC TCATTGTTCA
```

Figure 1 (Page 62 of 73)

```
200761 GCTCCCACTC ATAAGTGAGA ACATGAGGTG TTTGGTTTTC TGTTCCTGCC TTAGCTGTTA
200821 ATGTCAGGCC AGAGAGGCTT AAATTTTTAA GGATCTCTGG ACTTTTCTTC TACATTACTC
200881 TTGATGTTTA TAAATGTTAC AACTTCTTTA ATTTCATTTA ATGTATACCT TATTGAGTTG
200941 ATTTAACTGA GTTAACTTTG TTATATGAAA ATCATGATTG GGAGTGAGGG GGTTAAACCA
201001 GCTACAGAGA TCTTGATTGT TGGTGGTGAA GCAATGCAAG AATTCATTCA TTCAGTAAAC
201061 TAATGTTTAT TAAGCGTGTA CTGTCTTAGT CTGTTCAGAC TGCTGTAACA AAATATCATA
201121 AACTGGGTGA CTTATAAACA ACAAAAAATT TATTTCTTAC AGTTCTGGAG GTGGGAAGTC
201181 TAAGATTAAG GCCCTGGCAA ATTTAGTGTC TGGTGAGGAC AGGTAGCCAT CTTTTTGCTG
201241 AGTCCTAACA TGGCAGAAGG GTTGAATAAA CTTCCTTGGG TTTCTTTTAT AAGGACACTA
201301 ATCCTAGTGA TGAGGTTTCT GCCCTCATGG TATAACTACT GCCCAAAGAC CCCTCCTTCT
201361 AATATTATCA CTTTGTGGGT TAGGATTTCA ACATGAGTTT TGAGAGGATA CAGACATTTG
201421 GATCATAGCA CACACCATAG GACAGACACT GTGCCAAGAA TTGTGGATAT AGTGATTCTC
201481 AAAATGAACA AGATCCCCTC AGAGAGCTTG CAAAATCCAG CTATAAAATT ATGCTTTTTA
201541 AACAAATTAT GCAGTTTGAA AAATCTACTC TGAATCTTAC TTGTGGCATT GAATACTTTC
201601 GGCCACTCTT TCCTTATTAT ATTAAATATT TACTCTTGTT TGGGGATCC AGTCTCACCT
201661 ACTTTTTCTA CCAGAACTGG TATCAGCTCA TGCTCTGCCT TATGCAAATT AAGAAAATAT
201721 CATACCTTTT GGGTAAATTA AGCCAAGAAA GTTCTCCTTT CTTCTCTTTC TCTCTTTCTT
201781 TCTTTCTCTC TTTCTCTTTC TTTCTTTCTC TCTCTCTCTT TCTTTCTTTC TTTCTTTCTT
201841 TCTTTCTTTC TTTCTTTCTT TTTCTTTCTG ACAGGGTCTT GCTCTATTGC CTAGGCTGGA
201901 GTGCAGTGGT GCAATCTCAG CTCACTGCAG CCTTGAACTC CAGGGCTCAA GCAATCCTCC
201961 TGAGTAGCTG GGACTATAGG CATGTGCCAC AACATCAAGC TAATTTTTGC ATTTTTTTGT
202021 GGAGACGGGA TCTCCCTATG TTGCTAAGGC TGGTCTTGGA TTCCTGGGCT TATGCGATTC
202081 TCCTGCCTCA GCCTCCCAAA GTCCTGGGAT TACAGGCATG AGCCACTGCC CTGGCCATT
202141 ATAACTATTT TCATTGGCTT ATCAGGCACA TGATAACTAT AATAAATCAA TAACCAGAAT
202201 TTTTAAATAA AGAAAGGAAG GAATTGTTTC AACTCTTCCT GCTACCCTC TATCCCTCAA
202261 AAGGGTAGGC TGAATGTTGT CCTCCAAAGA TATCCATGTC CTAATCCCCA GAACCTGTAA
202321 ATATATTACC TTATATGACA AAAGGGACTT TACATGTTTA ATAAGTTAAG AATTTTGAGA
202381 TGGGCAGATT TTCCTGAATT TTGCAGATGG GCCCTAGTGT AATCACAAGG GTCCTTATAA
202441 GAGACAGGCA GAAGAGTCAG AATAAGAGAA AAATACTTCA AGATGTTACA CTGCTGGCTT
202501 TAAGGTGGAG GAAAGGCCAA GAGCCAAAAA ATGCAGTGGT CACTACAAGC TGAAAAGAAA
202561 AAGAAATGGA TTTTCCCCTA AAGCCTCTGG AGGGGGCACA ACCTTGCCAA TACCTTGATT
202621 TTGGCTCAGT GAAACCCATT TTGGACTTCT GACCTTTAGA ATTGTAAATA AATAAATAAT
202681 TTTGTGTTGT TTCAAGCCAT CACAGTTGTG GTAATTTACT ACAACAGCAA TAAAATAGAA
202741 TTAAATACAG AGATCTGAGG AGTTGAGTAG GATAAGCCTA CTCCAGCAGG TTATTTCGGG
202801 AGTATGGTGA GACTCACTAG GATGGCGGAA CTCAATTAAG GAAGTCTGAA GCTGATAAGC
202861 CAGAGAGGGA AGGCTCTCAT TTCATTTTAT AAGGGTTGCG TCACACTAGG AAGATCCAAT
202921 AGCAACCACA GTCTCAAAAT TAATGATTAC AAATAGGACA CAATTCCAAG AGTCGGGAGC
202981 CAAGCAGAAA ATGGATTAGG GAAGACATGG ATGATATGAA ACAGGAAGGA GGGGTACAAG
203041 GCAGCTTCCT GGGAAGTTGC CAGGGCAGTC ACAGTTCACA TTCATTAGGC TGTGGGCACC
203101 AAATGCATAT GGAAAATCTA GCTGACTTAA CTGAACTCCT GAAGAGGAAT GAACACCTCA
203161 TTTATTGAGG AGCTACTACC AATTAGAATA TGTATTTCAT TTGTTCAATA ACCCCATGAG
203221 TACAGTAACA CAATCCTTGC TTTACTAAAG CGGAAGCCAA TTCAAAGAGG TTCAGTGACT
203281 TGTCCAAGCT CAGGGAAAAC ACTAGGAAGT GAATATGGGT CTGACTCCAT CACTGATTTC
203341 AGGAGCCCTG CCCTTTCCTC CACACCATGC CCCCTTGCTT TCAGAAAAAA AGGCTTGTTG
203401 ACTGAATGGT TGTATGCACA GTTCAAAGCA GAAACACACG ATGACATCTT TGAGATACT
203461 CTAACAGTGA GAACTTGAAA ATGAAGTTAA AAATTAAGCG GCAAAACCAA GCCGAGGCTT
203521 TCTGAGAAAG TGGGGCCAAA CCTGTTGCCG TCTGACTGCC ACGTGGCTCA CTATTTATCC
203581 CTGTAAAAAT CTGCAAAAGT ATTTGAAAGG GAAGAAGGGA CAGAAAACTC CCTCCTTTTC
203641 CAAGTTAGCC TTATAGTCTA GGGCTTAAAA TACTGGTTTA ATGGTGAAGG TAAGTGCTTT
203701 TCTTCTTTTT GGGTAGAAGG ATTATTACTA ACTTACCAAA GGTCCATTAA GGGGAGGGAA
203761 CAGTTTTAGG AGAAGTCAGA GAAAAGACAT TAACAGCAAC ATAAGGATCT CCATCTGGTA
203821 ATATTGCCTA ATTCCAAAAT GAAGAGACTC TCTGAAAAAG ATAACTGATT CAATGAAGAC
203881 CCTAGGGCAA GGCTTGAGAA GCCACTGGTA CCAATGGACA CTGTGGACAA TGGTCATTTC
203941 TCCAAGGACG CTGTGAGTAT TAACTGTGAT GCTGTGATTA GTCAGACTGG GATTGGCTGT
```

Figure 1 (Page 63 of 73)

```
204001  GGAATGAAAT ACTGATCAGA ACTGACAAGA TTTGTGTTTG GGACTGTGGC TAACGAGTCT
204061  TTTCAGACTT CTATATGAAT TTGAAATGGT CTCTCAGGAA AAGGAGAACA TGGCCGGGCC
204121  TGGTGGCTCA CGCCTGTAAT CCCAGCACTT TGGCAGGCTG AGGCGGGCAG ATCACTTGAG
204181  GTCAGGAGTT TGAGACCAGC CTGGCCAACA TGGTGAAACC CTGTCTCCAC TAAAAATACA
204241  AAAATTAGCA GGGCGTAGCG GCGCGTGCAC CTATGCGCAT GCATAGTGCG CGTGCCAGCT
204301  ATTCAGAAGG CTGAGGCAGG AGAATTGCTT GAACCCAGGA CGTAGAGGTT GCAGTAGTTG
204361  AGATCATACC ACTGCACTCC AGCCTAGGTG ACAGAGTAAG ACTCTGTCTC AAAAAAATAA
204421  TAATAATAAA AGAAAAGGAG AACATGACCA AAGTTATGAA TAAGACTGAA GGCAAGAAAA
204481  TTGTACGCTT GTAGAGATCA CCTAGCTTGT TGCCCTCATT GTACAGCTAA GAAAAGGCAC
204541  CCAGGGACAT TGTGGTCAGC ACCAATTTCT CAGAAAGATA GGCAGATGAT GAGAGGGCCC
204601  TCAGTTTTTC TAACACTGAA GGAATTGCTT CTATGTTTTC TGGTGAACTC CTCCCCACTC
204661  ATCTTGAGGA TTCCAGGCCA GAAGAATCCA CTTTAAAAAA GAAACATTTA AAACCAATTT
204721  AACAACCAAT CAAAGGCACT TTTATAGAAA TACATTTCAT TTGCTGTAGG CCTGTATTTA
204781  TGGATCTGAG AGGGCTAGAC TGCCAATATT GTGACTGTTT ATTATTATTG CTGTTGCTAG
204841  TATCTAGAAT ATTATACAAC ATATAACACT TTGCAATTTA CGAGGCATGT CTCATACTTT
204901  TGTTTTCACT CCAAACTGCC CAGTGAAGTA ACATTATCCC AATTCTTCCT ATGAAACAGT
204961  GAAAGCCCTA AGAGTTTTTG AAACTTTACC TGGTTTACTC AATTTGGGAA TGGCAGAGCA
205021  GAATTCAGTC CTTGAATATC CTCCCACTGC AGGTTCATGC TCTTTGATCT AGGTGTAACA
205081  TTTACTCTGA GTAAACTAGG ACTCTGGGCT AACAGAGATG AAGCAAGACA GGCTGGATAT
205141  TAGGAGAATC TAAGAGCAAT CTAACGACCA TTATAATAAA ATCATGAGTT CTAGACTTAA
205201  AAAAAGGGAA AAACCTGTTT TTTTGCTTAT GCGTATACCA TAATATTTAC ATTATTTATT
205261  TTTTTCTCAA ATTCAACCTA TACTGTGTCA AGTAATTTTT TTTAATATAA CATTTTCCTT
205321  TAACTTAATT TCAATTCATT TTTCTGTGTC TACTTACAAC TTTGGCACTA GAATTCACAA
205381  TTTTTTTTTA GAGGTATATC TCCTTAAAGG GAAGGGTTCT GACACTGTTA CATGTTCTCA
205441  ATTGTTTGCA AATAGGTTAA TAATTATTCC AGTGTCTCTA AGTACATATC AACCATGCCA
205501  GTGTTCAGCC TCCATAATTT TATTAGCTTC TGTGCTTATT TTGGAAAAAC ATTTCCCATT
205561  ACCATGAAAG ACCTCAGTTT AGGATGGTTT GGTATGTTAG CCTGATTTCT GCATTCGTCT
205621  CATGCAAAGG AAAATAGGAA ACGAAGAACT GAAATTACCT ATTGATACAA AATCAAAGTA
205681  GCATTTGAAA CCATAAAACT TAAGTAGGGC TTTTCATCCT TTCTCGTTAG ACAGCAACAG
205741  AGAATGGGAA GAAAAACTAA AGTGATGGGT TTGTGATACA ATTCCAGTAA CATAAAGAGC
205801  AAGGAGAAGT AGTTTTGTTG TGTTTATGTT TAATATTCAA AGCTCAACCT AAAAGTATTT
205861  TTCATTATCA AACTTCCTTC TAGAATAAAT GATTAAAACT TGATTTAAAA TATACAAATT
205921  CTCCTTTATA ATACCTCAAA ATGGAGCTAC CCCATTGAGT TTTAAGCTTG TGATTAAAAT
205981  ATTACGAAAA CAAAGGGGAA GTTGTAATAG GTAGAACAAG CAGTAGTCTA GGCATTAGGG
206041  GATCTGGTGC TGGCTCTGTG CATCATGTGG TTTCAGGCAA CTTTTCAAAT TTTCTACGCA
206101  AATTTTCTTA TCAATAAAAT AAACAGTTGG GCCAGAGGAT CTCTGAGTCT CTTTCAGCTT
206161  TCAGTGTTTA TAAGATTGGA GAAGTTGGTG GGAAAGCTTT AAGTGGAGTG TAAGTAATTG
206221  CAGCTGCATG TACAGTTAAA GAGTTGCCTT CAGCCAAGCC ACGGGATCTT GCATAAAAAG
206281  TGAAATCAAA TAGAAAATGG TCCAAACTCT GGGTTTGACC ACAGATGACT TCAGCTAGGA
206341  TCTGAGTGTA GAGCAATGAG CTGAACTCCT GATATCCAGA TGTTAGCAAG ACTTGGAGGC
206401  CTTCTAAGGC AGAGCAACAA CCAGTATCTG TCCTGGTGCT GACCTGATCT TACTAGCAAT
206461  TGGGCCTCCA TTTGGGTCCA TTGTACAAAA CAACAACAAC AACAACAATA AAATCTCCAA
206521  ACACCCAAAA TTCAAAATTT AGATGGAGAG ATACTATTCC CAGAATTCTA GAGATATTTG
206581  GAAAGCAGAA AACTATACTT GCCATGCTGA TGAAGTCCAA TTATTGCTCT TTTAAATACA
206641  TTTAGCTACT TCTGAATATA AAATGAGTAT CTACTAATTA TTTACAAAAT CACTTGGTAA
206701  ATATAGAAAG TCACAAAGAA TGAAGTGATC ATCCTGTTTT GTAACCCAGA AATAGTCATT
206761  ACTGGCACTT GTGTGAATCA GTTCTATTC CTGTATGTGG ATGTGCACAG CGTATCCTGC
206821  TTTGTACACT AGAGTACTAG CATTTTTCTA ATGTAATTCA ATATTGTCGA AAACATTTTA
206881  AAATAGCTTC CATCACAATA ATCTATCAAA TTGACTTGCC AGACTCTCAT TATTAGGTTA
206941  ATTTATCTCT AACATTATGC AGTCATGAGT AATACTACAA AGGATATTTT TGGACACAAT
207001  TTTTCATCTA TGCCTTTCTT TATAATCCTT CATCCTAAGG TCACAGATTA TGAATATCTT
207061  TAAAGTACGG ACAAGTCTTT TAAATTTGT GTGCAAAAAC AGTGCAAAGC CTTGAATGAT
207121  AAAATAGAGG TTTGATATAT GTGTTTTTTT GTTTGTTTGT TTTGAGACGG ATTCCTGCTC
207181  TGTCCCCCAA GCTGTAGTGC AGTGGCACGA TCTTGGCTCA CTGCAACCTT TGCCTCTTGG
```

Figure 1 (Page 64 of 73)

```
207241 GTTCAAGCAA TTATCCTGCC TCAGCCTCCT TAGTAGCAGG GTCTACAGGC ATGTGCCACC
207301 ACACCCGGCT GTTTTTGTAT TTTTAGTAGA GATGGGGTTT CACCATGTTG GCCAGGATGA
207361 TCTCGAACAC CTGACCTCAA GTGATCCACC CACCTCAGTC TCCCAAAGTG CTGGGATTAC
207421 AGGTGTGAGC CACTGCACCC GGCCGATACA TGTGTTTTTA AAGTCACAGA AATTTCAGAT
207481 GTCTTGAAGG ATTTTAAGCA ATTTAAAAAA TAAAGTCATA GAAGCTTCAA TTTAGGAATG
207541 AATGGAAAAT TGATGATATT CTTAGGATAT GGATTTTTCC TAAAAGAAAC AAATGTATGC
207601 ATCCCCAAAG ATAATTTGAT TAGTATACAA ATATTAAATT AAACATGTCC ATATTTAGAG
207661 CCATGAATTC TCTTTGCCTG TCACAATAGC TGGATTTATT CACAATTGTA GTAATTAGTC
207721 CCTGTTCATT ATAATTTTCT AGGTGATATG AAGACTTTGT CAGTCCAAGC AAGTGTCCAC
207781 ATTGTGTGTA GCAAACATGA GAATAAACAT TTTAAACTTT TAAATGTAAT ACATATTAGT
207841 GTTATGTAAT GTCATCCTTC ATGTTCGAAG GCACATGGAA CATTGTTCTG GTGGTACAGA
207901 GGGGAGAGAA ACACCATCAG AATGAAAGGA AAGACCGCTC TGGAACCTTC CTCCTTAGCT
207961 CTTGAGCTTA GTTTAATTGT CCTGTCTTAT GGTCTGCTAC AAGCAATACC ACTCTTCACC
208021 TTCGCATGCT TCTCTGTGGT TTGATAAAGT ACATGCAATT TTTCATTTAA TTCTTCCAGC
208081 TGCACTAAGA AAGGAGCCTT ATCTTTATTG AACAGATGAG GAAATGAATG ATTAGAGAAT
208141 TTAAATGACT AGCTCTAGGT CACACAGCTG GAACTTACAG CCAGATTTCC TTTTAACAAT
208201 CCTGTAACCA AAAGCATACC AGTAGTGCCC CATAAAATGT AAGTTATAGA GCTGTGTTGG
208261 GTCAAAACTT TTACTGATGC TAAGAGGAGG CAACATTAAC AAGGGGAAAT TATTTGTGTA
208321 TTATGTTTTG GATTATGTTC TCTCCATAGA TAAAAGACTG TCGTAGTAAA AGAGATTCAG
208381 GGCACAGGGA AACTCCACCA CAAAGCGTGG TACCATTTCC CACAGAAGCT AAATGGACGG
208441 GAAGCCTGCC ACCAGGAAAG GTAAAGCCAC TGCTCTTGTT TGCAGGCTAT GTTAATAAGC
208501 TGAAGCTTAT TCCGACACAT TTACACATCT CTGCATCACA CTGACCCTTC GTAAAGATAC
208561 TCCCAGTGTA ACATTGGAGC CAGCTCCAGC CCCTGATCCT GTTGCTTTTT CCTTAGCCCC
208621 ATGAAATCAT CTGTGAGAAA TTAAGCCAAA TAAGCAATAA ATCCTGGGAT CTAGGGAGTG
208681 GAATAAGTTT TGGGAAAGTC TTTTTTTTTT TTTTTTTTGA CTGAGTCTTG CTCTGTCTCA
208741 CAGGCTGGAG TGCAGTGGTG CGATCTCGGC TCACTGCAAC CTCTGCCTCC CGGGTTCAAG
208801 TGATTCTCCT GCCTCAGCCT CCCGAGTAGC TTGGACTACA GGCACACACC ACCATGCCCA
208861 GATGAATTTT TGTATTTTTA GTAGAGATGG AGTTTCGCCG TGTTAGCCAG GATGGTCTCG
208921 ATCTCCTGAC CTCGTGATCC ACCGGCCTCG GCCTCCCAAA GTGCTGGGAT TACAGGCATG
208981 GGCCACCACG CCTGGCCCGG GAAAGTCATT TTAAACCAAC CTATGTATGA ATCCCTACTA
209041 TAATATTCTC ACCAAGCGGC TGGCTCTTTC TCCTGAGCTT GGAAACCTCC AGTAAAATGG
209101 AAATAATTAT TTCCAGACC ACCACTCTTA TCTGTGAGCT TTTTTGGCCA TTAAAAATTA
209161 TTTCTTCCAT TATATTTTTA TCTGTGTCTT CACAGGTTTT CTCTTTCTTT CACTTTAGTG
209221 CTTTTCTTCA AATAAGCAGG AAAAATCCAA TCTATCATGC ACATGGGAAC CCTTTCAATA
209281 TTGGTCTGTG GTTGTTCCAT TTTATGGGGA TGCTTTTAAA GAAAAAATTT GTCCTTTCAA
209341 TATATTGAAT ATCTTCCAGC ACCACATCAC CTGCAAGCTT TGTAAAAATA GTTCTACATA
209401 TTAATTTTTT TTTTTTTTTT GAGATTGAGT CTCATTCTGT CACCCAGGCT GGAGTACAGT
209461 GACATGATCT TGGCTCATTG CAACCTCTGC CTCCTGGGTT CAAGTGATTC TCCTGACTCA
209521 GCCTCCCGAG TAGCTGGGAT TACAGGCATG CATCACCATG CCTGGGTAAT TTTTGTATTT
209581 TTAGTAGAGA TGGGGTTTCA CCATGTTGAC CAGGCTGGTC TCAAACTCCT GACCTCAAGT
209641 GATCCACCTG CCTTAGCCTC CCAAAATGCT GGGACTACAG GCGTGAGCCA CTGCACCCCA
209701 CGTAGTTTTT TTTTTTTTTT AAGTTGAACA TATGTGAAGG CAGGACCTAG TGACACATAG
209761 CAATAACATT TCCAAGTAGA CATTACACTA GGGAATTAGT CGAAGTGCTC ATTTAAAGTA
209821 CCATCTCTCA AATGTATTAA AAGAGAATCC TTGGATGTGC AATACCTTAA TTCAAAGGCA
209881 GCTCGTTATG TATAAACTCT CAAGCTTTGT GATAAACAAA TGTGCATAAC AGATGGGACT
209941 ATTCACTTAC AGCCCAGGGA ATTTTATTGA CGCTGAGAAG GTTATGTGAC TGGCTCTGCC
210001 ACTGTCATCC CCATTCACTT CATTTTGGAG CAATATGACA TAAATGCCTT ACATGTGGGT
210061 TTTCTCTATT TATCATGTGT TTCCTATCCC CTTGAAAGAT GGCCATATTT GCTTTACTTG
210121 GTTATAAGAT CCCATATTCG CTGTCTTGAA GCCAACCAAA TAATTTGACA AAGTGGGTTT
210181 GTAGTGCTGG CTATTTTGGT GAAAAAAGA CAATGAGACT TCATGTGTCA TCCAAAGTTC
210241 TATCAGATCG AGCTGTGAGA GAAAGGAAAA GAAAGGGGTC TCAGTCAGGA TGCTCACTAC
210301 ATACATCTGT GTTGTTGTCT AGGTCCAGAT TTCTGTTCAT TACGCTATGG GCTGGCTCTT
210361 ATCATGCACT TCTCAAACTT CACCATGATA ACGCAGCGTG TGAGTCTGAG CATTGCGATC
210421 ATCGCCATGG TGAACACCAC TCAGCAGCAA GGTCTATCTA ATGCCTCCAC TGAGGGGCCT
```

Figure 1 (Page 65 of 73)

```
210481 GTTGCAGATG CCTTCAATAA CTCCAGCATA TCCATCAAGG AATTTGATAC AAAGGTAAGT
210541 ATGATGGAAA ATAGGGCTCT TTGTTGAGAG AAAAAACTTT GAAAGGAAGG CATAGATCTT
210601 GATTCTGTGG AGTATGGAAG TATACATTTC CAATGACAAA TTAAAACTGA CTGGAACTAT
210661 TTTTCTTTGA GACATTGCTT ACTTCAATAA TAAAAATAAG ATTTCATTGA GGTTATTATG
210721 ATTATAAGGT GGGGGAACTG TAGAGTTAAA TGTGAAAAAT TTAAAAATGG AACAGTTTAT
210781 GTGATGTCTT CAATGAAAAA CTAGGTATTA CCTGGGCACA TTCTTATAGG TTACTCAATC
210841 CTATTCAGTT CTCTGCCTGT TTTATTGTTT CTGAGCAATT TTATATCCCT GTAAATTCTA
210901 TATAACCAAT AGAAATGCAA ACGATTCTTG TCCATAGCTT TGCAAATAAA TTTTGCCAAG
210961 AGAAAAATCA GTTAAAACTT TTCTCCACTC ACCTCCCAGT TGAATTAGCC AATTTTGCTG
211021 TTTGTTTGTT TGTTTGTTTT TTGAGATAGA GTCTTCCTCT GTCATTCAGG CTGGAGTGCA
211081 GTGGCATGAT CTCAGCTCAC TGCAGCCTCC GCCTCCCGGG TTCAAGAGAT TTTCCTGTCT
211141 CGGCCTCCCA AGTAGCTGGG AGTAAGGGGG CATGCCACCG CGGCTGGCTA ATTTTTGTAT
211201 TTTTAGTAGA GACAGGGTTT CACTAGGCTG GTCTCGAACT CCTGACCTCA GGTGATCCAC
211261 CCGCCTCGGC CTCCCAAAGT GTTGGGATTA CAGGTGTGAG CCACTGTGCC AGGCTCTGCT
211321 GTATATTTAA AGTCTATTTC AGCATTGCTT CCTGCTTGTG TTATGCGTGA TTCTTTGAGT
211381 TTTCCTTTGA ACCAGTTATA ACATCTTACT TACTTCCTCC ATTAATCAAT GAGTTAAATA
211441 AAATCTTTGT TGTATGTTTA TTTTACATTT ATATGAAAAC CATGAATTTA CCCAATTAAA
211501 AAAATTATCC TTTAAATTAT CTTGTACTGT ACATTTCCCA TGTCATCCCT ATAATTCATG
211561 ATTAATGATT TTATTACATT GGACCTAGCT TATTTACAAT GAGTACATAA ATTTATTGTC
211621 TCCAGTCTTT CCTCCATTAT CCCGTCTACA TATCCACACT GAGTAGATTC ACTACTCAGG
211681 AATCTTGGAC ACCTTCAAGT TGCCAAACAT GCAGTGTTCA CTGGACATGC TGTGTTCCTT
211741 CAGAATTTGG GCCTGCTTCT CAGCACACTC ACATCTGCTA TCAATGACCC ATGGAAAGTT
211801 TTTGCCCTGA GCAAGCCAGA GTCCCTGTTA GTTCTTCCA AATGCTACAA GTTCACTTTT
211861 GCTATTTTTT CCGATGAGAT AAAATTTTCC TTTTTGACTT TCTACAAATC ATAGTCATTT
211921 TTCAAGGGAT AGTTCAAGTA TTGCTTCCTT TCTGGGACCT TCCCAAATTA TTATTTTCTC
211981 CTCTCAAAGT CTCTGTTTTA TTTATGTTCA TCCTCAAATC TTGATTCTCA CATGAATCAT
212041 ATACCTTGTA TTATTTATAG TTTTTTTGAG TGGGTAAAAT ATTTCATATT TTATATTCTT
212101 TGGCTCTCTA CTTTATAGCA TGATGCCAGA TATTTAGGGG CCTTATTGCA TTTATTTTTT
212161 ATTTTATTTT AAAATCTATT TTATTTTTTA TTTATTTATT TTAAAATCTA TTTATTTTTA
212221 GGTAAATATT CAGGTAATAT AATTTATGTA ATTATTTAGG AATTTTAGGT AGTTATTTTA
212281 AAATAATTCA AATTATTTAT TGAGTTATAT CAGAAGAATG TGATCTTATT CATTTGTAAT
212341 ATGTGTTTTA GGAACTCAGT TCAGCCAGGG CAGACCATGA TTCCCAAACT TGACTTTTCT
212401 TTTTAATTAG GCACTGATTT TGGTTAAGAG TTCAGTAAAG TTTTGTGTGT GTGTTTTAAA
212461 AAATTCTTTG ATATAAGAGT CAAGATGTTA CTCAACTTTT ACTAGAAGCA AAATAGAGGA
212521 AGTGCTTTCA CAGATGAAAT ATCTCTCAAT GTTTTCTTCC ATTTACTTCT TCCTATTATT
212581 CATCTATATA ATCATTTTCT TTACCTCTTT TCTTCATTTC TTCTGTTTTT CTCTCCTTCT
212641 ACTAAGACAA GCAAATTAGG GGTATAATTG GTTATTTGGG AAGGTAGGAA GAATATAGAG
212701 AGAAACAAAA ATCAATATTT TATACTAGGG TCTCACTAAC CTCAAGCAAC TCTGACTGTA
212761 AAGTAGATTT TCATAATAGG ACTTCTTGAC AAAGAGTTTT CCTATTTTTC CCCCAGGCCT
212821 CTGTGTATCA ATGGAGCCCA GAAACTCAGG GTATCATCTT TAGCTCCATC AACTATGGGA
212881 TAATACTGAC TCTGATCCCA AGTGGATATT TAGCAGGGAT ATTTGGAGCA AAAAAAATGC
212941 TTGGTGCTGG TTTGCTGATC TCTTCCCTTC TCACCCTCTT TACACCACTG GCTGCTGACT
213001 TCGGAGTGAT TTTGGTCATC ATGGTTCGGA CAGTCCAGGG CTTGGCCCAG GTATCCAGAT
213061 ACTTTCTCAT TCTTGGTGGG ATCCAGATTT CTGAATTCTA CAAAATATCA AAGGTCTTAA
213121 TGATTTCAT TTCAGGGAAT GGCATGGACA GGTCAGTTTA CTATTTGGGC AAAGTGGGCT
213181 CCTCCACTTG AACGAAGCAA GCTCACCACC ATTGCAGGAT CAGGTAAGTG TGCACAGATG
213241 GGTCATAGCT TTGTCATCTG TTCCATCCCA CTGTGTCTTA TCTTCTATGA ATCAAATGGT
213301 TTGGGGAAGA GAGAGAAAAA GTACTGCTGA AAAATTCAAC AATATAAGAC ACTTGCATCA
213361 CAAATAGGAA AGATGCATCT GTGCAGTAAA GACATTGAAG CTTAGAAGTA GAAAAAACCA
213421 TTGTGAGCTA GGTTTCAGCT CAGAAAAGCC TTAGTAGTCA GAAAGCCTTT AGTAGTCAGA
213481 AAAGCCTTGT CGGAAAAAGT TTAAACCTTT AAGAATTGCA CACATGGAAA AAGATCAAGT
213541 AAGCTATATA TACACCATCT TAGCAATGAT TTTGAAGTGA GAATTAAGGC TACCACAGCT
213601 CCAGGTGGTA AGGAGAGAAA TCAGGCTGGA AGAGTTTGAA GTTTCTGTAT TATTCTAAGC
213661 TCTTTACTAT TCTATTATGA GCTCATTAAT TCTCACAACA ACCCTCTCAT ATAAGTACCA
```

Figure 1 (Page 66 of 73)

```
213721 TTTTAAATTC TTATTTTACA GAGAAGGGAG TTAAGGAAGG TGGAGATTAA GAAAATTGCC
213781 CAAATACAAA TAGCCAGCAG GTGGTAGGTC TGAGATTTAA GCCCATGCAG ATTTTAGCCC
213841 CAGAGCAGAC ATTCTCAATC ACTATGCTAG ACTGCCTTTC CATGGTATGT GATCCTACTC
213901 AGGCCTCTAC AGCTTTATCA TTGCTGTTCT CCCCAGCCTG TCGTGCTGAG AGTATATACT
213961 CGAAGAGCAG AACTAAAATT CCATCCAGCT TCTCACTCCT AGGTCCACTA CACAGCTGCA
214021 TCCTGCAGAC TTTTACCTCA AGCAACCCTC CTGCGTTCTT GCTTCCTTCC ATCATAGTTG
214081 TAACCATCTC CTCTATTTGC AAATACTATC TGCTGATCTC TCTCTTCTAG ACTGGTTTCT
214141 TTCAACCTTC TTCCCACCAA AACCAAGTTA GCTTGCTAAA ATAAAGATGG CACATTTTTA
214201 CTCACCCGCT TGAGAATTTT CAATGTGTTC CTTCATGCTT ACAGAGTAAA GCCTGACCTC
214261 TTTATTGCAT GAATACAAAA GTTCTTAGCC ATCTGGCCCC AACCTTGTTC CACTCAACTC
214321 CCCTGTGCAA GCATGGCTCC AGTGGCACTG GACATTGGCT GCTCTCCACA TAGATCTGCA
214381 CTGCACTTCC CTCTGGCTCT GCTCCCGTTA GTTTATATGC CTGGAAAGTT CTTTGCCCCT
214441 GTTCCTTGTG CCAAAATTCC ATCTATCCTA TTGCATAGCT TATGTAAAAA CTTCCTAAAC
214501 CTTTTTTTTT TTTTTTTTTT TTTTTTTTTG AGACGGTGTC TCACTCTTTC GCCCAGGCCG
214561 GACTGCAGTA GCGCTATCTC GGCTCACTGC AAGCTCCGCC TCCCGGGTTC ACGCCATTTT
214621 CCTGCCTCAG CCTCCCGAGT AGCTGGGACT ACAGGCGCCT GCCACCATGA CCGGCTAATT
214681 TTTTGTATTT TTAGTAGAGA CGGGGTTTCA AGCCAGGATG GTCTCAATCT CCTGACCTCG
214741 TGATCCGCCC GCCTCGGCCT CCCAAAGTGC TGGGATTACA GGCGTGAGCC ACCGCGCCCG
214801 GCCAAAACTT CCTAAATCTT ATAATTATTA TCAATTTATC CTCAGATATA CTTCCACGTA
214861 CATTGTAGTT TTATTTATATT TATATTTTAC ATCTTTTTTT TCAAATTTCA GTTTGGGACC
214921 CATTAGTGAG TCATAAAATC CATTGAGCGG GTTAAAATCA TTATTTAAA AAATGAATAG
214981 AATAGAATAG AAATTGTTGG AGTGCATTGG ACATGGTAAA GTTAAATATC GATTCATGAA
215041 ACCATCGTTT GAGGCATATG TGTGTGGTTG TATGTACAAG TGTTTATGCA TATTGGTGTG
215101 TGTGTTATGT TACCCTGTAA AATGCATTTC TTACTATAGG TCTCTGTGAA ATATGTGTCT
215161 TGTTGTTTTT TAATGTAGAC TTCCAAAGCC TACATGGCAT TTCACTAGTG ACAATCAATT
215221 TTATTCACAT TTTTCTCTCC AATTGGACCA GAAGCTCTTT GAGGGCAGGG GCTGTATCTT
215281 ACCGATTTTT GTAAGTCTTT CATTTCCTGC CCCTAGCCTC ATATTAGATC ATGCAAGAAT
215341 GCAACTGTAA TCACAAGAAA ATGCTAATGG CTGTGATAG CAGAGAGTTA CTGTGACAAA
215401 CTAAGGGATT TAGATTTGGT CACATTGGTG TTGAGGAGCC ATTGAAGAAT CAGAGAGTGT
215461 GTTACTATTA TTTGTTAATT TTAATTATAT CATATTACTT TACTGGGGAA AATCTGTGAG
215521 CTATTTTAGA AATAAATACT CTCATTGCCC AATAATTCTA AGTCTGCCAC CTCACTGTTG
215581 GGACATTGTT TAGGGAGGCC ACGAAGTCTC AGCCTTTGAT ATTTTCATAA GTGTTTTTCT
215641 CCCTTTTTCC TTTAGGGTCA GCATTTGGAT CCTTCATCAT CCTCTGTGTG GGGGACTAA
215701 TCTCACAGGC CTTGAGCTGG CCTTTTATCT TCTACATCTT TGGTGAGTCA CTTTCTCTTA
215761 AATCCTAACG CCTCCATTTC CTGAGCATCC ATTTTGGCAC CTACACCACC CACATTCTTC
215821 CTATATGAAA GAAAATGTCC TTTATCAAAT GGAAGATGAT AAAAAATGTC AACGGTTGGT
215881 ATCATTTTTA ATCTAGTCAC ACAACCTGAT TAACACCTTC CTGGTGGTTC TGGGAAGCCA
215941 CACGCACAAG GTAGAGGAGT TGACTATTCA CATGGCACCC ACCGACTTGT GATGCAGTCT
216001 TGTCCTTCCA TATCAAGCAC CTTCTGCAGA ATCTCTACCA CCACATCTGA AGTGCCTGCT
216061 ATATGCAGTT AAGATGTCAA AGATAGTGAA GTACATTTTC AATGTGTCTT CATATTTCAT
216121 TATAATTATT ATTTCTGTCC AAGATGCCTT TCACCTGTTC TCTACCAAGT TAATCTTGCA
216181 AAGTTCAATT CAAATGTTCC CTTCCCCATG GGCCCTTCCA GGGCTTACCC TATCAGATTC
216241 TGGCATTCTC TCCTTTATGA TATTTCCTCT CTAGGTTATG TTGGTGTGTA ATTATTTATT
216301 TCTCCTTTTC TTTCCACTAG ACTGTGAAAT GCTTGAGGCA AGGAATCCAT TCTATGTTTT
216361 CATCACTTGG GTGTCATCAT GGTGCCTGAT TTTTAGCTTT AAAATAAAAG AATCAGTGAA
216421 TCCAGTAATT AGAGGGGATT TAAAGAAAAC TAGTCCTCAG AATCTTTTAA CATAGAATGT
216481 TCTTCAAATA AGGAATTCCA ATAATAAGAC AATTTTCTAC ACTTGATTTT GTTTTATAG
216541 CCAAATGGTG TCATTAAATA TAGTCCTGGC CTGAATGGCT TTCTCATTAA TGATGCTAAT
216601 TATTTTGGTT TGTACATGTT AACCAGGTAT TGTACAAAAA TATTTCTTTT GGGAATCCAT
216661 AATGGATGTA TGGCTTGAAT ACAAATAATA CTGTCTCTTG TAAGTGCATT GGAAATTTTT
216721 CCCTGCCACA TGATTTCATG GAAGGTTGTT TCGTGTATGT ATGACTGCAA ACCTGACTAT
216781 TCAGATCTTC CGCAACAAGA CAACTTATGT GTGCATTAAG AAGTTGCTGC CTAAAATACA
216841 TAACACTGTA ATCATTGGAG ACTTTAAAGT AATTAATCAG CTATGCAATG CCACGCTCCT
216901 GTTATCTCCA GAGGGCTCTG ACATTGACAA ATGGTGGCTT TCTATTTGAG ACGTAATATC
```

Figure 1 (Page 67 of 73)

```
216961 TAAAAAGCTT TAACAGGTTT GTAGAAGGAT TGAAAGAAAG AATGGGAACA TTTAGGTCCT
217021 TATGGTAGAA TAAGCATTAA TTGATTAGTG TGTAGAAGGG AGAGGCATGC CACTTCAGAG
217081 GAAACTTCCT TCCCCCAGTA AACAAATCTA CCTAAAAACT AATTTTATCC CTTCTTCCCA
217141 GGTAGCACTG GCTGTGTCTG CTGTCTCCTA TGGTTCACAG TGATTTATGA TGACCCCATG
217201 CATCACCCGT GCATAAGTGT TAGGGAAAAG GAGCACATCC TGTCCTCACT GGCTCAACAG
217261 GTACAGTGCA CACCTTGTAC CTGTGGCCCA TGCAGAGGTC TCTAGGGCAG GGTGTGGATC
217321 TCCTCTGAGA GGCACCATCT TGGCTGCTCT AATACTCATG CTGATTAGAT CTTTCTTTTC
217381 AGCCCAGTTC TCCTGGACGA GCTGTCCCCA TAAAGGCGAT GGTCACATGC CTACCACTTT
217441 GGGCCATTTT CCTGGGTTTT TTCAGCCATT TCTGGTTGTG CACCATCATC CTAACATACC
217501 TACCAACGTA TATCAGTACT CTGCTCCATG TTAACATCAG AGATGTGAGT TTACTTCCTA
217561 TACTTCTACG AAAATGATAA TGGTAATAAG GAGAAACAGT TCTGTGTTAC CTATTACATT
217621 CTGGCTTTAC ATATAACCAT TAATTTAACC TTCACAATGA CCTTGAGAGA GGCATTGTTA
217681 TAATTCCCTT TTCACAGATG TGGAAACAGG ACACTTAGAG GTGAGATAAC TTGCCCCAGG
217741 TTGCACAATA CTAAGTGATA GAGCTGCTGC AGCATCCATA TTCTTAACCA CTATGCTATA
217801 CTACCACACC AGCTGATTCC AAAGCTTCTT TTAGAAATAA TATTGCTGGG CCAGGCATGG
217861 TGGCTCATGC CTGTAATTCC AGCACTTTGG GAGGCCGAGG CAGGCAGATC ATGAGGTCAG
217921 GAATGCAAGA CCAGCCTGAC CAATATGGTT TACTAAATAT CATCTACTAA AAATACAAAA
217981 ATTAGCCAGG TGTGGTGGCA GGCACCTGTA ATCCCAGCTA TTCAGGAGGC TGAGACAGGA
218041 GAATCGCTTG AACCCAGGAG GTGGAGGTTG CATTGAGCCA AGATCATGCC ACTGCACTCC
218101 AGCCTGGGCG ACAGAGTAAG ACTCCGTTTC AAAAACAAAA AACCCAAGAA ATTAATATTG
218161 CTTTTATCTG GAGCCCAGAG TGATGCAGCT TCTGGCCCTC TTATCTGAGA CAGTGTTCTT
218221 TTAGTGTGAA AAAGGATGCT AATTTTCCCC CAAACAACCC ACAGTATCAT GGGGGTAAGT
218281 TAATGGCTGG TCTGTGTAAC TGACAAATTT TGGTGCTAAC GTATCTCTAT AACTACTCTG
218341 TATAAACTTC CTTCCTTCAG AGTGGAGTTC TGTCCTCCCT GCCTTTTATT GCTGCTGCAA
218401 GCTGTACAAT TTTAGGAGGT CAGCTGGCAG ATTTCCTTTT GTCCAGGAAT CTTCTCAGAT
218461 TGATCACTGT GCGAAAGCTC TTTTCATCTC TTGGTAAGGA TAAGCGTGTG GGCCCATTTA
218521 ACCAATCCCT TTTCTGCACA TGGTCTCAGA GGGTTCCCTG ACAGCATGTC CTCATTGCCC
218581 AGGGCTCCTC CTTCCATCAA TATGTGCTGT GGCCCTGCCC TTTGTGGCCT CCAGTTACGT
218641 GATAACCATT ATTTTGCTGA TACTTATTCC TGGGACCAGT AACCTATGTG ACTCAGGGTT
218701 TATCATCAAC ACCTTAGATA TCGCCCCCAG GTAAGAGCTC TACCTGTTTT TTCCCCTCCT
218761 CCAGACCCCT CCAGAGGTGT TAGACCTCAG TGGTCGCCGT GAAACTCTTT AATGTTACTG
218821 ACATTGCACT AATGGCAGAA TGACAAATAA CTACAAATAT CTGTCTGTGG CCATTTTTAG
218881 AACAACAAAT GTGGCATTTT TAGAACAACA ATTTCCAATC TTGGCCAGTA ATCATTTTGA
218941 CAAAAACCTT CCCAAGCTTC CCTAACAGAG ATTGAACTGT GTATGCTGGG AAAAGGCCCA
219001 CACACAGGTG ATTTGGAAAA GTTTCCATGG TGTTGTTCAT ATTAGCTACC ATATATATAT
219061 ATATATATAT ATATATATAT ATACAGTCAC AATAAGCCAG CTCCTGTGCC AAGACTTGCC
219121 ATATATCAAC ACATCTAATC CTCACAGTTA TATTAGGTAG GCCCTATTGT TATCCCCATT
219181 TTATAAGGGA GAAGGCTGAG GCACAAGGAG GTTAAATGGT GTGACTATGG TCACATAAAG
219241 GCAGAGCCAG GATTTGGACT GGGGGAGTCT GGCTTTGGAG TCTGTGTCCT GCCCGTTGCA
219301 CAAACTGGCT TCTCCACTGA GCAGCCGGGG TAAAGAAACG TGGTTCCCAG AGAGACTGCA
219361 TTGCTCCCTG GTTATTGACT TGGTAGATTG GTAATTTCAG GTTTGGCAAA TAGACATTGC
219421 CCTGAATGTC TTTAGGTGAA TGAAAACTG CATTAAGCAA AATGACTTTG CCATTAGAGC
219481 TGAATTGCAT TAAAGTTGAG TTGCTGCAGA AGCTGTAGGT GGCTTTCTAT ATAAAATCAT
219541 TTATAAAATC ATCTTCCCAC AGATATGCAA GTTTCCTCAT GGGAATCTCA AGGGGATTTG
219601 GGCTCATCGC AGGAATCATC TCTTCCACTG CCACTGGATT CCTCATCAGT CAGGTTGGGC
219661 CAGTTTATTG AACATCTTCA AGTGGCAGGT ATTGTTTTAG GTGTTGGAGA TACACACGGT
219721 GCTCTAAAGA TCTGGATGGC AACACAATTA CTCTATTTAC ATGAGCCTCT AAATCAGACT
219781 CTGGTAGGTC AGATTTCCCA GAGGAAGAAA AATATAAGCT TATTTTCTCA AGATGAATAG
219841 ATGTTAGATT GATTAAAATG AGCTGTTCCG GTGCAGAAGA CAGCACGTGT GACTTCCTAG
219901 AGGTACATGA GCATGAAACA GTTCTTAGTT ATGACCAGAA TGAAAGACAC ATGTCAAGGA
219961 ATAGCAAGAG ACGAAGACAG AGGGGCAAAA GAAGATCATG AAGAATATGT TCAGACTAAT
220021 CCAATTTTTA AAAAATCACA AAAGGGAAAC AAAGTGTCCT AGGCCAGTTT AAAGATAATT
220081 TAATGTCTGG AAACAGATCG GCTGTGAGAC ATTGCAAGGA GGCTTGCTCG GTGTTTGGAA
220141 ATGCAGGCTC ATGAGGAAGA TGAAAAGACA GACCCAGGCA GGGATGGAAG GACTGACGAG
```

Figure 1 (Page 68 of 73)

```
220201 AACCAACTTA CAAAGAGAAG TTTTGTTTTT ACTACATTTC TATGTGATCA AGTTCCCAGG
220261 TTAATATTTG ACTAAACTGC TAGGAATCCA CTGTGACTAT AATGCTGGAA ATGACTTAGT
220321 AGGGCTTTCT GAGGAGGGTC ACACAGAAGA CCAAAGAGAA CTCATGTTGA ATTGAGATGG
220381 GTTGTAGTGA TAGTTGTCAA CAGCCAATAC AGAAACAAAA AAAAACAAAA CAAACAGCAA
220441 CAACAACAAC AAAAAAAAAC AGAGAAGACA CAAACACAAT GCCACAATGC CATTTTAGGC
220501 ATAATTTTAA ATGAGTAATA TTATATGTTG AAATCCAAAT TTTCAGAAAA ACATTAGTGT
220561 ATTTTATTTT TGTTTAAAGA AATAACCATC TCAACTCAGA ACCCCATGTG CATTTTGGCC
220621 ATTTTGTTTC CAATAGTTTC ATAAACTTTC TTAAGTAACT ACTGCACATT GTTCCTTATA
220681 TTCCTTGTGA TCAACATTGC AATACACAAC TGGGAGGGCT ACTAGAACTG GTGTAGAAGG
220741 AACTTGTGAG ATTGATCATT TTCTCTGTTT TTTACATCTA GGATTTTGAG TCTGGTTGGA
220801 GGAATGTCTT TTTCCTGTCT GCTGCAGTCA ACATGTTTGG CCTGGTCTTT TACCTCACGT
220861 TTGGACAAGC AGAACTTCAA GACTGGGCCA AAGAGAGGAC CCTTACCCGC CTCTGAGGAC
220921 ATAAAGTTAC AAACTTAAAT GTGGTACTGA GCATGAACTT TTTAAACATT TTTTACTTCT
220981 CTCCATATTC CTGACCATAG ACTCAGCAGT TCTTAACTCT GGCTGTGTGT TAGTCTTCCC
221041 TGGGGAGCCT TTATAAGACA CTGATACTTG GACCCACTC CAGAGATTCT GAATGAATTG
221101 GTCTGGGGTG GAACCCAGAT ACTACTAATT TTTAGATACT CCTTAGAGGT TTCTAGCATG
221161 CGCCCGGGGT TGACAACAGC TGGACAAACT TGAAAAGTCA ATTCATGTGG CCTTTGAATT
221221 TTCCTCATTG GAAAGTACTA AATAAATAAA AATTCATGTG AAAATGATCA CTGATAAATA
221281 TCTTCATGGT GGGGCAGGTT ATTGGATGCA GAGAAGATCT GCTCGGAATT GTAGCCATAT
221341 GTTACAGATC TCAGCACCGA TCGGAACTGT AAAGCTATAA TCCCCAGAAT TAAAGTTTTT
221401 ATTATTTTTT ATACATTGTA AAACATAGAC GTTTATTTAT GTGATTAAAT TCTATTAAAA
221461 TTTACATGCT AAAATAAAAT AGACCATTTT CAAATTATTT AGATCCAGAT ATTTCCATCA
221521 GATTAAACAG ATATTTATTT ATCCTAGCCC AATTGCAAGA GATTAATGAT GAGAAAATGA
221581 CCAATACAAG ATTAAATAAA TGAGGTTAAC TTAGAAATCA AGGACAGAGA AGATAGAACT
221641 GGAAGGCTTG TATTGTGAGA AGAATGAATG TGAAGGAAGG CAATGTAGAC ACTTCCAGAA
221701 GGGATAGCAA TATAGTTTAG ACCATATAAT GAAAATTGGA GAGAGATGAC AGAGACACTT
221761 TCAAGTGAAA TGACAATTTA TATGGGGGAG AAAAATATTG AAGACATAAC AAGATGAGAA
221821 AAGGCATAGA AATGTATCAC ATACAAGGCA TAGAAGTGTA TCACATACAA GAGAAGTTCC
221881 TTTTGAGCGT AGAAAAAGAT AATTTAACCT TCTTCATATT TTTCTTACTT TCCCAAGATA
221941 CTCAGATAGG CAGCGTCAAC TCTAACAGGA ATTAATTTGG CTCCTAACAC TTAAGACATA
222001 TCCTTTAGTT TGTCTCCTCA CACAGAACTG ATTCTGGTTT TGCCACAACA TGTCTAGAGA
222061 AGAAGTTCCC ACCATATTTT AAATCCTATT AAAAAACTGC TTGGACAAGA ACCTTGGGTT
222121 AATTCAGCAG ATGAAGAGAA TCTCCTAATG CAAATCAATG GGTATTTTTG AGCAAGTTTT
222181 TCAGAAAAAC AGAGTGTCAG GCCCTGAGGG TGGTACTAAG ATGAGAACAT TGATTTTGCC
222241 TTCATGATAT TGACAACACA AAGAGGAAAG GGGGTTTGCA GAAAACTAAA AGAAGAAGTA
222301 GAAGAAAAAA GAAAGACATA GTATAATAGG TAGTCAAATT ATGTACAGAA AAAAGAGAAA
222361 AAAAAAACAA AAAAGGGTGG GGGACAGACA ACCCAACTAA AAAATGGGCC AATGACTTGA
222421 ACAGGGACTT CATAAAAGAG AAAATGTAAG TGGCTCCTTA ACATATAAAA AGATGTTCAA
222481 CTTCATTAGT CATTACAGAA ATGAAAATCA AAACTACAAT GAAATACCAC TATAAAATTA
222541 ACTAATGGAT AAAATGAAAG GAGATGGAAA ACAAAATGTT GCCAGACATG TGGAGCAACT
222601 GGAACTTTCA TACGTTACGA ATGTGAACTT TGGAAAGCTG CTCGGCAATA TCTCCTAAAG
222661 CTAAATGTAC AATTCCAGTG ACTCAAACAT TTTACTTAGA AATGCACATA TACATCCATA
222721 AAACATGTAC AACAATGTTC ATAGGAGCAC TATCTGTAAT AGCCTGAACA GGAAGTTGTC
222781 TGTTAAAAAA AGAATGAGTA AATAAACCAC GGTCTATTTG TATAGCAATG AGAATTAACA
222841 GACCCCAATA TATAATAGAT GAATGGGTCT CATAAGCACA ATATTGATTA AAGGAAGACA
222901 AAACGCACAT TCTTTTAAAG GTTTATAAAA TACTTTTTAA AAACAGCTAC AACCAATCTG
222961 TCCTGTTAAA AATCAGTGAG CGATTTCCCT TGTGCAGGGA TGGGGGTTGT GGCTGGATGG
223021 ATGGTACTTA AGAAGTGCTC CTGGGGTACT AGAAATATTT TATTTCTTGA CTTGGATGTG
223081 TGTTTACTTT GTGAATATTG TACATTTATG ATTTGTGCAC GTTTATGAAT GTAGAAAATA
223141 AAACAGAAAG CAAATTCAAA GTATCATCCT TTTGAGAGCT TCTGCTCTGA CTTCGTTTTG
223201 ACCAATGGAG CAGTTGGGAA GGGGTCTTGG TCCTTCGGTC CTTTGCTTTT TTTTTTTTTT
223261 TTTTTTTTTT TAGACAGAGT CTTACTCTGT CGCCCGGGCT GGAGTGCAGT GGCTCGATCT
223321 TAGCTCACTG AAAGCTTTGC CTCCCGGGTT CATGCCATTC TCCTGCCTCA GCCTCCCCAG
223381 TAGCTGGGAC TACAGGCACC TGCCACCATG CCCGGCTAAT TTTTTGTATT TTTTAGTAGA
```

Figure 1 (Page 69 of 73)

```
223441 GACGGGGTTT CACCATGTTA GCCAGGATGG TCTCGATCTC CTGACCTCGT GATCCGCCCA
223501 CCTGAGCCTC CCAAAGTGCT GGGATTACAG GTGTGAGCCA CCGCGCCCGG CCCCTGGTCC
223561 TCTGCTTTCA TGTTCTTCTT GGTCCTGTTC CTCCTCCTCT TTTGTTGGAA CTTCCAGTAT
223621 CAGAGCAGGA AGGAAGGCAA TGGGTCAATC GATGCTGTCA GCTTTTGGAT CAAACTGCAA
223681 GTTCTCAAAC AGCAAAATTA ATGAGCTCAG GCTTTGAAGA AACCATGACC CTGAAAGCAT
223741 CAGTTGCTTC CAATTGCATC AGTTGCCACG GGTGATAAGA ACAATGATGA CTCAGAATGC
223801 CTAGGTTTTC CCAGCAGCTT CTCTGAGGTT TTCCCAGCAG CTTCTCTGAT TGATTCCTGA
223861 CAGATGACTT CGGTGTGTCA GACTTTCAGG GTATCTTTCC TTATGTGATG GTTGAGGAA
223921 GAGTTACCAT TCACATTCCT AATGGCTTCA GAATAGATGC AATTGTGAAC TGATAGGAAA
223981 CATTTCTAAT TCATCTCCCC TCCCCATCCC TAAAGGATTG TTTCTAACAA TAGTCATGAA
224041 AATTAATTCA CTTTTCTCAA ATAGTTTATT GTCATCTACC TAATGATGAG ATGACTTACT
224101 TTTTCTCCTT GACTGTTAAA TATTATGAAT TATATTAATG TATTTCTTAA TGTTGAGCTT
224161 TCCCTTGAAT ATTCTTTTGA TGTACGACAG AATTTGATTC ACTAATAGTT TATTTAGGAC
224221 TTTGGCTGAT GTACTGATAT ATGAGATTGG CTCTGTATGC ATACATGTGT TTTGTGTATC
224281 TTTTTTGTGT CTGGATATGG AGCTTATGCT GATTTCAAAA ACAAGAAAGG AGAACTTTCC
224341 TTTTTCCCCA TTACTCTGAA AAAGATTGAC TAGAATGGAA TTTTTATAAT TGCTGTTGTT
224401 ATTTGAAAGC TTGAAAGCAT TGGTTTGTAA AAATCATGCA GGCTGAAAGC CATTTTGAGG
224461 AGACTTTGAT AACTTTCTCA ATTTCCTTCA GTTACTGGTC TTTTAAGGGG TTTTATATTT
224521 TTCTTTGATC AATTTTGACC ATTTATGTTA TCTTGGAGGA TCATCTATTT TACACACTAT
224581 TTAAAGTATA TTTGCAAAAA TTCAACTGTT TTATCAGGCT ATCTTTTTAA TAATATATTC
224641 ATTTTATCTA TATCTGAGGT TTTAGCTTCT TTGTACTTCT GACCCAATTG CATGTGTGCT
224701 TTCTTTCTCC TTCATTAGAC TACTTAGTCA TTTACTAATT TTAAGAATAG CTTGTCTTTT
224761 ATTTATTTAC TTATTTATTT TTGAGACGGA GTCTCACTCT GTCACCCAGG CTGGAGTGCA
224821 GTGGCGCGAT CTCGGCTCAC TGCAACCTCC GCCTCCCGGG TTCAAGTGAT TCTCCTGCCT
224881 CAGACTCCCG AGTAGCTGGG ATTACAGTCA TGCACCACCA TGTCTGGCTA ATTTCTGTAT
224941 TTTTAATAGA GATGGGGTTT TGCTATGTTG GCCAAGCTGG TCTCAAACTC CTGACCTTAG
225001 ATGATCTACC CACCTTGGCC TCCCAAAGTG CTGGGATTAC AGGCATGAGC CACTGCGCCC
225061 AGCCCTGCTT GTCTTTTTAT TTTATATTTG ATTAGCTTTA TCTTTTATCA AGCTTATGTC
225121 CTATTTCCCT TTGCTTTACT TCATATAAAT TTTGTTTTGG ATAGTTTATT TATTTTTCAT
225181 TTAATTATGA AACAGGTTAA AGCTTAGAGG AAAATTGCTC CTCTAAGTCC AATTTTGTGG
225241 GCAGATTACA TTTTGCTGTG TTGTGCTCCC AAATTCATTG TTCTTTTAAT GCTTTATTTC
225301 TCAAGTTAAT AACCTATATA GTAAAAAAGT GGCTGTTGAC TCTCAGCTTT TTTTTTTTTT
225361 TTTTTTTTTT GTAGATACAG GGATCTTGCT GTGTTGCTCA GGCTGGTCTG AAACTGCTGG
225421 CTTCAAGGGA TCCTCCTGCC TTGGTCTCAC AAAATGCTGG GATGACAGAC ATGAGACACC
225481 ATGCCTAGCC ATGTCTCTCT CCTTATATAT AATAAGAAAA CAGACACACT GAGGCATCCT
225541 ATCATCTCAC TCTTGGTTTC ACTACTGTTC TCTGGAAGTT TTGCTCTGAC CTTTTGCAGT
225601 TAATGTATTA ATTTTGCATT GAGTAGTTTC CATAGAAGAA TTATAGCATT TGCATTCTGT
225661 TGGGTATTAT ACTTTTCACT GTTATTTGAA CATAATTTGA GGGCTGAAAC CAAGATGAGG
225721 CAAGTGAGGT GCCCAGGAAG CAATATTTAA GGAGGCATCC TTTCTTAGGC TCATGCAAGA
225781 ACAGAATTGG CACATGAGAG TGAGTGCCTC CTTAATTTTG AGTGCTGGAC ACTTCTTGCT
225841 CACTTAGCAT ACCCCTGGAC AATGAAGTGT TTTTTGTTTT GTTTTTTCAT GTCCATCCTT
225901 TATCCTTCTT CATCTCAAAA CATTTCAATG GAGTATTTTT TTGGAGCAGT ACTTGGATGA
225961 GCCTCTGAGT CCCACAGTAG CTGAGAATTT ATTTCATAGT ACTCTTTATG ATCACTGTGG
226021 AGCCTTAAAA CATTGTAATA TTAACTTAGC TGGGAACAGA AATTTTGTTC CACAATTTGT
226081 CTTATTCAGA ACAGTATTGA CTTCCTGCTA GTCTCTTCTG ATGTCCAATA TGAGGAAGTC
226141 TAGTTAGCCA GCTACTTTTT GTAGGAGAGC TATGTTTAGG CTAGGTGCTA TAGGATTCTC
226201 TTTATCCTGG AATTCCTTCA CCAAGATGTG CCAAGGTGTT AATCATTTTC TCTTGCTTTT
226261 TGGCTGGTGG TCTTAGAGTT TCCTTCGATT TTGTTTTATT TAGTGATTGT CCTCAATTTG
226321 TTTTCTTTAC TAAGAATCTC TCTTCTATTT ATCTGTATGG TAAAACCTTG TTGCCCATCT
226381 TTCTGGTTTC TGCTGACTTT CATTTTGGA CCTTTTACTT TGCTTTCTCC ATGGACTTTT
226441 TGGTAGTGGA GGCAGGCAAA CACTTTCCAA AGTCTTTCTC AATTTCCATC AATTTCAACT
226501 TATTTCCTAA AATTGCCTCA GAATGTGCCT ATGTCCACAA TATCCCTCCT TCCACTTTAG
226561 AAAGGAAAGG CATCCACACT TTATTTAGGT GCAATGCCTG AAGTGTAAAC ACTTTCTGGT
226621 TGTCAACAAA GGAGTACTTC CAAATATTGG TTTGGGGATA ACCTGCTAAT GATTAACACA
```

```
226681 TTCACCTTGG CTCTTGGTTT GCCTGCTCCC TCTTCTTTTA TCTGCTGTGT GTATTTTTTT
226741 TAATCACTGA GAATATGCAC AGTATTGTAT GTTTTATTAT AAGAGAGGAC TGGCCAGAGT
226801 GGGAATGTTC TGAATTCAGA ATAACTGAAG CAGTACAGGA TAGGAACTCA TTCTTTCAAA
226861 TGAAGCTGGC ATATTTTCCC AGAGCACCAA ATTTCAATAT ATATTTAAAA AACTTGATAT
226921 GAATGATACA ATAAAGTGGT TAGAACTTTT ATTAAAATAA ACTTATGTCA TGAAATACTT
226981 ATTCTAATTA TAGTCACTCT TCATCTTATT TCATCTTATA ACATGTTTAA TGTTTTCTTT
227041 TATTTACAAA ACAATTTATT TTTTGATGAA AAGTTTTAGA AATCAAGTTA AAAATATTCA
227101 AAGGAATGCC TAAAGTTTTC AAAATTCTTT TACATGTTGT ACAATCAAAA GAGTCTGAAG
227161 ACCATTTAGC TATCCAAATT GTTTATTTTT AAGCAGTATC CCTTCTAATA TTTACTATTT
227221 ATAATCCTTA AAAATTTGCC TTAGCACAGG AGAATTGCTT GAACCCAGGA GACGGAGGTT
227281 GCAGTGAGCC AACACAGTGC CACTGCCCTC CAGCCTCGGC GACAGAGTGA GACTCTGTCT
227341 CAAAAAAAAA AAAAAAAAAA AAAAAAAAAG GCCAAAACA AATAAACAAA CAAAAAAATC
227401 CGCCTTAACA TTATTTGTTC ATTAAAAACT TTCTTTAATA CTACTAGTTT CCCTTTCCTC
227461 TCAGCCCATT GTCATATTTT GATTTTTATC ACTTGCTTTG TAGGACATAT GAGGTTTTG
227521 TTTTTTTTTT TTTTTGGAGA TGCAGTCTCC CTCTGTTGCC CGTGCTGGAG TGCAATGGCG
227581 CAATCTTGGC TCACTGCAAC CTCTGCCTCC TGGGTTCAAG CAATTCTCCT GCCTCAGCCT
227641 TCCAAGTAGC TGGGATTACA GGCACCCACT ACCACGCCTG GCTAATTTTT GTATTTCTGG
227701 TAGAGACGGG GTTTCACCAT GTTGGCCAGG CTGGTCTCGA ACTCCTGACC TCAAGTGATC
227761 CACAATCCTT GGCCTCCCAA AGTGCTATGA TTACAAGCAT GAGCCACCTG CCCAGCCAGA
227821 ATATATGTTC ATTTTGAGTC CTTTAACAAA GTCATAAGAA TTTTAGGAAT TCAGTTACTT
227881 TCTTGAGAAA ATCTCTGAAA AGATGCCAAT AATTTGTAGC CAATTATATT GATTTCTCTT
227941 TTTCATATTG AGAATTGTTT TTTAAAAAGT TTGTATGTGT GAAGATTTT GCACTGTAGT
228001 TAAAGAAACC ACCTGTGTGT TGGTTAAGCC ATAAGTACAT GTATTCAAAT AAATTGAGGT
228061 GGGGTTACTC TGAGAATCAA AGGAAAACCT GAAGAAACAG GCAGCCTCAA AAGGTCTTAG
228121 CTGTAGCAAC TTGCTCCATT GTTGAAATAA ATAGGCTTGA ACTTGTATTT TCCCTCTACT
228181 CAACATTTAA GGTCTCAGAA GATAATATAA TTGGTGAAAT TTAAGTAAAG TGCTCACTCT
228241 TTTGCTTTAA CAAACCCTAG AGAGCTGGTA GGCAGAGCCT CAACAGACCG TTTTAGCTTC
228301 CAAAGGGAGT TCAGGACACC ATGATTCACG ACCACAATAC ATCACACATA ATTGAGAAAA
228361 GATAGTTCCA CCAAATAAAG TTGAAATGCT GACAAGAAGG GGTAAGAAAT CTTGGAAATA
228421 AGTTTATATA AAATTTATTT TTTCCTTTTT TATTGTTATG GAATAGGACC AGTTCTACTT
228481 AAGCCACCCA TTTGCCAAAA TAAAGTGAGA ATCGTTTCTT TTGGGGACTC CTCTTTGTAG
228541 CTCCAAGTGC CACTAACAAT TCTTAGGACC TGAGCTATAA GCCAGGTGAT TTCAGTTAAT
228601 ATGATCAATT ATTTCATTTA AATGGCTCTA ATGTGCAGAG GAACGGAGC CCATCAGCAT
228661 TCCCTGCAGG GAACTGCAGT GGCTTTTATC AACTTGAACA GCTAGCTTTC AACTGTTTTG
228721 AAATCACTTT CAGGGTGGTC ATGTAGTTGC TTTTTTGAAA TCAGAAGATG ATTCTGCCTC
228781 TTTTAATATG TGACTCCTCA GATTCAGAAA GTGCTCGCTA GTCTTAAGAG TGAATTACCC
228841 TCAGTGGTCC AGCGCTTATG AACCCACATC TAACCCTATC CCCTGGGGGA ACTATCAGAG
228901 AAATTGGTGC CATGGACATA AGAGGAAGGC ACAGTGAAGC AGAGAGCCCC GCATGATGAA
228961 AATCAGTGGA CAGCATCATT ATTTACAACT TTGTAATCAC CCAGGAGCAT GAAAATCCAG
229021 GCCAATCTGG CACCATGAGC TCTAATTTTT GTTGGAGTTC TTGGAACCGA TTCTGATGAA
229081 TGACTGTTTA GCCATTTTAG AGTGTGGCAT ACGTGGCTGC TGGCATACAG AGGTTGGATG
229141 TAAACGGGCC TTTGCCCTCT CTTATGAACA TAGACAGGAA CTAAACTGTG TCACATAGGT
229201 TCCAAATGGT GGCCTGAATA CTATTTACAA CTAAGGTACA ATGAAATTGA GTAAGTCTTT
229261 TCCTCTTTTG CAGATACCAT CATTATTCAT ATATTTCTTC AAAGTTAACT ATTTGTATTT
229321 GGTAATTTTT AATAGAAATG TAATAATTGC TTCTCAAGTT TAGTCTTTAG TCTTAAGGTT
229381 GATGCTCTCC ATGTCCTTCC AAAAAAAGGT ATGTTGCTTT TATTATATCC TCGCCTTCAG
229441 ATGGGATTAT TCCATTTTGT TCTTTGTTAA TATATACTTT GAGCCACTTT TTTTGTGGCT
229501 CTGGGTGAGA TGCTATAGGT ACAATGACAA GTGATACGTG TGTTGTCCCT GTCACAAAAG
229561 TGGATAGCCT AAGTGGTGAC TTTTACCTCC ACTCCAAATA TATGTATCAC ACACCAGCCG
229621 TATGCCAGGC ACCACTCTAG GTGCTAGGGA TACAGCAGTA AACAGACAAA TGCAACCCCT
229681 GCCCATGTGA AAGAGAATAA GACAATAAAT AAGTAAAGTG CATGTTATAT GGAGGTGGCA
229741 AATGCTAAAA AGAAAAATTA AGCAGGCAAG AGGACTCATT GAAAGATGA CATTTGGGTA
229801 AAAGCCCATG TATATATGTT CTATTGGTTT TATTTCTCTG GAGAGCCCTG ACTAATACAC
229861 AATGACTTTG AGAAGTTACT GGCTTTTGAT TTATCACACT ATTCGGAGTG CTGAGAGCCT
```

Figure 1 (Page 71 of 73)

```
229921 TCTTAGTGTG TATTCAGTGT TTTAAGAGAG CTTGTGGATG AATAATAAAT AGGACAAAAT
229981 TTATCCAAAC TTAAGCCTTG CTTTAGGTAA AAGGGCTCCT CTTACAAGGT AGAAGGTTAT
230041 TATTTGGCAT TTAAATCCAA CTGAAGACTA ATAAGACTAA TTAATTAAAA GTTTTTAAAT
230101 CACAACTGGG TGCAAAATAA ATGGAACTGC CATGCTCGCC AAGTGTGCAT GAGTGGTGTG
230161 CATGGGAGAC AGCACGAAGC TAATCCCACT CATCTTGCAG GTTGCTCCAT TTTTCTCCTA
230221 AAATCAGTAA GACAGAAGCT GGTCAGATTA TCAAGAGCCC TAGTTAAACA CAGCAGTAGC
230281 ATTTGGAAGG GGTTGCTCTC ATTAGGCAGT GCCTGACCAC AACAAGAGAT GAACAAGCCC
230341 TGTATCTGAA GCCATCATGC CTAGTTATGG TCCCCCACTG TTCATGATGC CTGAAAGGGA
230401 GGCCCCCTGC ACCCTAGAAA GCTGGGTGGG TTCTACTGTC TGCTTTACTG CTAAAAACCC
230461 TCTTCTTTGG ATCTGGACTT TACCTCTATC TGATTTTTTT TTCTAATATA TGATTTGGCA
230521 CTGAGTCTGT CACTGCTGCT AACTCAGCAG TTCTAGGGTC ATTGCCCCAT TGCCTCACAG
230581 AAAGAATTTC ATAGCTTCCA GCATCCTCTC TCCTTCATTA TACTTTGATT TCAGCATTGC
230641 TATTTTTTCT CTTGGGTGTT GCAGCTCTCT CTCTCCTTCC CATGTCTTGT TGGTTTTCTG
230701 CTAACTCCTG CTTTTTTTCT TTTTTTTTTT TTGAGACGGA GTCTCGTTCT GTCACCCAGG
230761 CTGGAGTGCA GTGGCACAAT CTCGGCTCAC TGCAACCTCC GCCTCCCGGG TTCAAGCTAT
230821 TCTCCTGCCT CAGCCTCCCA AGTAGCTGGG ACTACAGGCG CTCACCACTA TGCCCCACTA
230881 ATTTTTGTAT TTTTAGTATT GCTGTCATCA ATCCACATGT CCAGAAGCAC CTAGAAACTC
230941 TAATTCTTTG TAGGTATCAA ACCCTAGGAC TCTTTCCTCT AATCACAATA TATAATCCCT
231001 GATTCCCAAA CACGGTCTTT TCATATACAT TTTCCACTGT ACATACTTTC TGACCTGGAA
231061 AGCTCTTACA CAAACACGCC CTCCCCTAGG AAGCCTTTAT AAATGTTCCC AGGAAGAATC
231121 AGTCACCCAA CAGTGTCCTT GTCACATCTT AGGTTCTACA CCTTTATTTG TTCTATCTGA
231181 ATGTAATCTC CCAGAGGGTG TTATCATCTT TTTTTTGAG ATGGAATCTT GCTTTGCTGC
231241 CCAGGCTGGA GTGCAGTGGC ATGATCTCGG CTCACAGCAA CCTCCACCTC CTGGGTTCAA
231301 GTGATTCTCC TGCCTCAGCC TCCTGAGTAG CTGGGATTAC AGACGTGTGT CACCACACCT
231361 GGCTAATTTT TGTATTTTTA GTAGAGACAG GGTTTCACCG TGTTGGCAAG GCTTTCCTCG
231421 AACTCCCAAA CTCAGGTGAT CCACCCGCCT CAGCCTCCCA AAGTGCTGGG ATTACAGGTG
231481 TGAGCCACCA TGTCCAGCCC CATCTTTTTC TTTTAGTTTA GTTCTTAACA AATAGTCTGA
231541 CACAAAGTGG ATATAACAAT ATTTGAATT ATGAATAACT AAATGAATAT TTCCAGATTT
231601 CCTGGTGCTC TCAAAGTTTT ATGTTACAAA AGAAAAACAA GTCTAAAATA CCTGCCTCAA
231661 GTTTTTATCT GTACTATGAT TTCAAACCAA ATAAAAAACA GGTGGGGTAA AAACTGAAAC
231721 AGGAAATACA TATAACTGAA AAATTTTGGT ATGTTAGTAT GATAATACTA GGTCATTTTT
231781 CCTGTTTCCC CAACTTCATT TTCTATAGCA ATAAAAAGAA ACAAGTAAAT GTATATTAAT
231841 TTAATTTAAA AGAAGTAGTC TACCATCTCT TCTGTTAAAA AGAAAAAAGT ATTTTAAAAA
231901 ATTATCTCTG GAAGGATACA CAGGGAACAT TGCTCTGGTT TCTTCCAAGA GAGAAATGAG
231961 GAACTAGAGA GCATGGCCAA GTGGGGTTTT GCTTTTGTTT TTGTTTGTCT ATCTGTTAGC
232021 TTTTTATTAT TTTCTTTTGT AGGTTTGAAT TCAAACCAC ATAAATCTGT TACATGCTCA
232081 TAATAATAAG TTTAAAATAA AACTTTTGGC TGGGTGCAAT GACTTACACC TGTAATCCCA
232141 GCGCTTTGGG AAGCAGAGGT GGGAGGATAC TTGAGGCCAG GAATTTGAGA TCAGCCTGGG
232201 CAACATAGTG AGACCCTGCC TCTGTAGAAA TAAACAAAAA TTAGCTGGAT ATGGTGGTGC
232261 ATGCTTGTAC TCCTAGCTAC TTGGGAGGTT GAGGCAGGAG GATCCTTTGA GTCCAGGAGT
232321 TTGAGGCTGC AGTGAGCTAT AATCACCCAC TGCACTATAG CATGGGCAAT AAGGTGAGAA
232381 CTTGTCTCAA AAAAAAAAAA AGGGGGGGGG AAACAAATAA ATAAATATAA ACAAAACTTT
232441 TGTTTCAAAA TATGTAATAT TTAGCACTAA AGAATTCTGA ATTGTAGAGC TAAAAAGTAC
232501 TTAAAAGTTA ATAATTATTG TCTCCTTTAA AAGAATTGTT ATCAAAGTAT AATTTTTATC
232561 CAGAAAATCA TCCATATCAG CAAGCTAAAC TTTCTCAAAA TGACATATCC ATGTAATTAG
232621 CTCCCAGGTA ATTAGCAGGC AGCCTCTACT CAGGTTGAGT ATTCCTAATC TAAAAATTGG
232681 AAATTCAAAA TGCTCCAAAA TCGGCAACTT TTTGAATGCT AACATGATTC TCAAAGGAGT
232741 GCTCATGGAA TATTTCAGAT TTTGGATTTT TGGATTTGAG ATACTCAGTA TAATGCAAAC
232801 ATTCCAAATC TGAAAAAATC TGAAATACTT CTGGTTCTAA GCATAAGGGA TACTCAACGT
232861 GTGTTAGCTA ATTAGACCCT TCATGGTCTC TTCTAGACCT CAGCTTCTTC AAGGTAACCT
232921 CTATCCTCAC TTCTAATAGC ATGAACTTTT CTGTTTTAGA ATAATTTGGA TTTTCAGGAA
232981 AGTTGCAAAG ATAGTACAAA GACAGTACAG GAGAGTTCCC ATATATCTTT CACCTAGCTT
233041 TCCCCCATTG TTAGGATTTT ACATTATTAT GATACATTTG TCAAATATAA GCAACTCACA
233101 TTGATACATG AAACTCTATT AACCAAACCC TAGACTTTAT GTGGATTTCA CCACTGTTTC
```

Figure 1 (Page 72 of 73)

```
233161 CACTAATGTT TTCTTTCTGT TCCAAGGTCC AATCTGGAAT ACCACACTGC ATTTTCTTGT
233221 CATATCTCCC TAGTCTTTTT TTGTCTGTGA CAATGTCTCA GTCTTTTCTT GCTTTTCATG
233281 ACCTTAACAG TCCTGAAGAT CATTTGCTTT TTTTTCATAA TTACACCGGA GTTATAGATT
233341 TTTTGAAATA ATACCACAAG GGCAAAGGGC CCTTCTTGTC ACATCATTTT AGGGAGAACA
233401 TGATATCCAC ATGACATCAC TGATATTAAC CTTCATCATG TGGTTTAGGT AATGTTTCAG
233461 GTTTCTCTAC TGCAAAGTGA TTTTTTTCCC TTAATTTAGC CCACCTGAAC TTATCAATTT
233521 TGTTTTCTTC CATGACTAAT ACTTTTGTTA TTATAGCTAA AACTTCATTG GGGCCAAATC
233581 TTAGATCATG TAAATTTTCT TCTATATTTT ATTCTAAAAG CTTGTAATGT TTGATACATT
233641 CTAAAAGATG TAATGTTTGA TACATTACAT CTAGTCCTTT GATTTATTTT TAGTTACTTT
233701 TGTATAAGGT GTGAGAGATG TCTCCAGTTT CACTTTATTA ACACATTGTG GTGTTCCAGT
233761 ACTATTTGTT GCTAAGACTA TCTTTTTTCC ATTGATTACC TTTGCCTTAG TTGGCAATAT
233821 TTTTGTTGGT TTATTTCTAG ACTGTTTATC TCATTCCACT GATTTGTGTC TATCTTTTTG
233881 ACAAAACTGT TGATTACAGT AAGCTTTGAA ATAGTTCATT TTTTGTGTCA ACTTGACTGA
233941 GTCAGGGGAT AACCAGCTAT CTGGTTAAAC ATTATTTCTG GCTGTGTTTG TGAGCGTGTT
234001 TCTGGATGAG ATTAGCCTTT GAATAGGTGA TCCTAGTAAA GTAAACTGTC TTTCCCAGTG
234061 TGGATGGCAT TATGCCACCT GATATTCAGG GTCTGAATAG AAGAAAAGGC AGAGGAAGGG
234121 GGAATTTGGG CCTTTTTTTC TGCCTCACTG CTTGAGCTGG GACATCTCAT CTGGTCTCCT
234181 GCTCTTGAAC TGGGATTTAC ATCATCAGTT CCTCTGGTTC TCAGGCCTTC AGATTCAGAC
234241 TGAATCATAC CACCAGCTTT CCTGGGTCTC CAGCTTGCAG ATTACAGATC ATGGGACTCC
234301 TCATCTTCCA TAAATGCATG AGCCAATTCA GTCTATGTCC TTGAAAACTG CCCCACTGCA
234361 GATTAAGGCT TTTTTCCACT AGGTGAAATA AAGAAGCTTG TTAGACAGAT TTCCCTTCAT
234421 CCAGTGCCCT CTCCTCTTTA AGTTACAACA CATTGGCTAC ACCTAAGTGC AGGGGTGGGG
234481 ATGAGGGTAT AGTCCTCTTG TTTGCTGAGA AGAGAACTGT ATTGGGAAAG CTCTAGAAGT
234541 GTTTGATACA TACATAAACA AGGCATGGTT TTTGCACTTA ATTTCACATT ACATTTTTCC
234601 CAGAAAAAAA GGAATGTATA GGCATCACGT AACTGTACTA GCTGGAGTCA TTCTTCCTGA
234661 TTATCAAAGG TAAACAGTTA TTAATCCTAT ACCAAGATGT CAAGGAGAAG TACTTTTGGA
234721 ACACAAGGAA TTCTCTGGGA GTCCTTACTA CTCTCAAGCC CAGTGAAAAA GTTAATGAAA
234781 AACTATAGTA CCTTCCTATA AGCTGGATGA CTAATTACCA GGCTCATTTA GGAATTTGCC
234841 TTACCAAGTA AAACATAAGG GCAGCTGAGG TGCTGACTGA AGACAAATGG AGCATAGAAT
234901 AAGAGTAGTA AAGAATGCCA AAAATGCTGT CATGTATCCA TTGACAAAAG GAGCTATAAA
234961 GCCTTTAGGT ATTTTCACAC TTGCTCTGTT ACGTAAATGT ATGTGTGTGT GTGTGTGTGT
235021 GTGTGTGTGT GTG
//
```

Figure 1 (Page 73 of 73)

```
   1 CACACACACA CACACACACA CACACACACA CACAAATGAG GTATATAAAG GGTCTCCTAA
  61 AATGTCATCT GATATTTGTT ATTTCATATT CTCAGATTTT TAATCCATTT AGGTAGGTCT
 121 ATTTTAGATA GCCTTGTCTG AAACAGAGCT GGGACCTGAT GAGTGAAAAT GAGCTCACCA
 181 GAAGAAAAAT CAAACAGGCA TTTCAGAGAT TGAGGCCAAG AAGTTAAATG TCTTAAATGG
 241 GCAGAGCTTA GCTGCTTGAT GTGAAAAGAG ACCAGCGTGG CTGGAACAGC AAAGGAGAAC
 301 AGCAGAAGAG GTGAACAGAG GCCAGAGATG GTCACTGAGT GGGCCCTTAA GTCATGGTAA
 361 GGAGTATGGA GAATGAATTA TTGCATGTAT TGAATATGTA GGTGACGTGA CTCACAGATA
 421 CTTTGGATTT GTAGAGATGA AGGAAATGTA GCAAGTGACA CTCTTAGAAT GTTGATTTGA
 481 GTAAATGGTA GTGTCAGTTA TTGAACTGGG GAGAACTGGA AGGGATAACA GGCTTAAGGA
 541 GCACGTTTAT TCCTGTGTCT TGGAAGTGTT TAGGGTGAAA GACCTATTAG AGTTCTAAAT
 601 GGAGATGTCA AGTGAAAATG TGGCTACACA CATTTGCATT TCAGAAAAAA GGTCAGGCTG
 661 GAGATGTAAA ATTGGAAGTT TACTGCATAT AGATAGTCTT TGGAACCGTA GTATTGATGA
 721 AGCCATTAAT GAGACAGAAC AAAGACTAGG GACCAGAGCC AAGCTCCAAG TTTCTAAAAT
 781 TTAGAGGATA GTATAGTCTG GTCATTTGA GGTGAATACT TAATAACAGA ACAATTTGCT
 841 GAAGTGTAAA TTTAGAGCCC TACACTTTTA GCTCTGACTA TTAACGAATA CAGGAAAGAA
 901 TGGATATGGT TATCTGCCTG GTGTCTGTGA AATAATTTAA GCCAGGAAGA GATCCTCACC
 961 AGAAACTGAC TATGCTGGCA ACTTGGATCT TAGATTTCCA GCCTGCAGAA TTGTTAGAAA
1021 ATAAATGTCT ATCGTTTAAG CCACCAGTCT GTAGTATTTT GTTATGGCAG TCCAAGCTGA
1081 CTAAGTTTTG GTACCCAGGC GTGGGATGCT GCAACAACAA ATACCTAAAC ATGGGGAAGT
1141 GGCTTTGGAA ATTGGTGATG GGTAAAGGCT GGAAGAGTTT GAGGTTCATA CTAGAAAAAG
1201 CCAATTGTGA AGGGACTATT GAAAGAAATA TGGACATTAA AGGCAATTCT GGCAAAGGCT
1261 CAGAAAGGAA GAGAGCTGGA CAGAAAGCTT CCATTTTCAT AGAAACTTAG ATTTATAACG
1321 ATCATGGATA GAATATTAAA TATGCTGGTT AAAATATGGA CTTTAGGCCA GGCGTGGTGG
1381 CTCACGCCTG TAATCTCAGC ACTTTGGGAG GCTGAGGGCA CAGATCACGA GGTCGGGAGT
1441 TTGAGACCAG CCTGGCCAAT ATGGCGAAAC CCTGTCTCTA CTAAAAATAC AAAAATTAGC
1501 TGGGCATGGT GATGTGCTTC TGTGGTCCCA GCTACTCGGG AGGCTGAGGC TGAAGAATCG
1561 CTTAAACCCG GGGGGTGGAG GTTGCAGTGA CCCAAGATCA CACCACTGCA CTCCAGCCTG
1621 GGATACAGAG CAGGACTCCA CTCCCCCGC CACACACACA CAAAAAATAT ATATATATGG
1681 ACATTAAAGT CAACTCTTGT GAGGTCTCAG ATGAAAATGA GGGACAGGTT ATTGGAAACT
1741 GTAGAAATCA CTGTTCTTGT TACAATGTGT CAAGAACTTG GCTGAATTAC GCTGTAGTGT
1801 TTACTGGAAA GAACTTATAA GCAGTAAAAC TGGATATTTA CCAGAAGAGA TGTCTAAGCA
1861 AAGTATTGAA GGTGTGATTT AGGTCCTCCT TACTGCTTAA AGTGAAATGT GAGAGGAAAG
1921 AGCCGAAATA AAGAAGGAAT TTTTAAGCAA AACACAATCA GAACTTGGAG ATTTGGGATA
1981 GATTTCTCAA TCTATATTGT AAAAATTGAG AAAGTTTTTC TTGAAGAGGT ATGGTTGAAC
2041 AATGTTTTCT TTTTCTTTTT TTTCTTGGT TTTATTTTTA TTTTTATGTT TTTTGAGACA
2101 GGGTCTGGCT ATGTCATCCA GGCTGGAGTG CAGTGGCACA ATCTCAGTTC AGTGCAACCT
2161 TTGCCTTCAG GCTCAAGCAA TCCTCCCACC TCAGCCTCCT AAGTAGCTGG GACTACATGT
2221 ATGCACCACC ACACCCTGGC TAATTTTTTG TTGTTGTTTA TAGAGATGGG GTTTTGACAT
2281 GTTGCCTAGG CTGGTCTCTA ACTCCTGAGC TCAAGTGATC TGCCCTCCTC AGTCTCCCAA
2341 AGTGTTGGGA TTACAGGCGT GAAACACTGA GCCTAGCCTG AACAACCATT TGATAAAGAG
2401 ATAATGGGTG TGACCCAAGG ATTTAATCAG CCATCTCAGC AGAAGCCAGG AAGAGAGATG
2461 GGATTATTCC AGCAGAGACA CTGCCAATTT AAACTAACGT AGGCAGAGAA AACAGAAAGG
2521 AACAAAGGAA GGTTGTCGAC TTTTTGAATT CTATAGAACA GGATCATAGA GCTACCTGGC
2581 TGTCAATGTG TACTATTCTT TAAGAAAAGG AAAGACTGAC CCACCAAAGG CAACTTACAA
2641 GATCACTAGG GCTGACTCTT TTTTGTTTTT TCTTGAGGCA GTCTCACTGT CACCCAGGCT
2701 GTAGGGCAAT GGTGTGATCT CAGCTCACTG CAATCTCCAC CTCCCAGGTT CAAGGGATTC
2761 TCTTGCCTTA GACTCCCAAG TAGCTGGGAT TACAGGCTCT AAATCTGTAC CCTCCCGAGT
2821 AGCGCTCCTG CCACCACTTG CCCAGCTAAT TTTTGTATTT TTAGTAGAGA TGGGGTTTCA
2881 CTATGTTGGC CAGGCTAGTT TGGAACTCCT GACCTCCAGT GATCCATTCT CATTGGCCTC
2941 CCAAAGTGCT GGGATTACAG GCAGGAGCCG CCAGGGCTGC CACTTTGATG TCAGACTCAG
3001 AGAGTACAGA TGGGATAGGG TGGGGTGGG AACATGTAGT CAAGGCTGAC TCTACCTGTT
3061 TCAAAGATGC CCTGCAGAAC TGTGTGGGAG TCTCTCACAG ATGGCTGCCT GGGTGGGACC
```

Figure 2 (Page 1 of 74)

```
3121 CCACCAAACT GAAAGACCGA GACTTCAGGC AGGGCAGATG GAGTAGGCCA ACTACAGAGC
3181 CAGAGGTGAC ACTGAGACAC CACTGGGCCT GGAAATCAGG GCATCAAGCC AAAGAGGGTT
3241 TTTCTTAAGA CCTAACAGAA TTTGCCTTGC CAGGTTTTGG ACTTGATTAG GACACATTAC
3301 ACCTTCCTTC TTTCCTATTT CTCCATTTTC TAATGGGAAT GTCTATTATG CCTGTTTCAC
3361 CATTGTACCT TAGAAGCATG TAACATTTCT GGTTTCACAC GTTCAAAGCT GGAAAGGAAT
3421 TTTGTCTCTG GATGAATCAC ACATTGAGCC TCACCCGTAA CCTGATTTAG ATGATTTTTT
3481 AGATGACACT TTGAACTTTA GAATTGATGC TAGAATGAGT TAAGACTTTC AGGGGGCTGT
3541 TGGGATGGAA TAATTTTTTT TTTTTTTTTG AGACGGAGTC TAGCTCTGTC GCCCAGGCTG
3601 GAGTGCAGTG GCACCATCTT GGCTCACTGC AAGCTCTGCC TCCCGGGTTT ATGCCATTCT
3661 CATGTCTCAG CCTCCAGAGT AGCTGGGACT ACAGGCGCCC GCCACCACGC CTGGCTAATT
3721 TTTTTTTTAT TTTAGTAGAG ATGGGGTTTC ACCGTGTTAG CCAGAACGGT CTCGATCTCT
3781 TGACCTTCTG ATCCGCCTGC CTTGGCTTCC CAAAGTGCTG GGATTACAGG TGTGAGCCAC
3841 CATGCCCGGC TGGGATGGAA TAAATTTATC TTGTATGGGA GAAGGACATA CATTTTGGCA
3901 GGTCAAGGAC AGAATGTTAT GGACTAAACT GTGTCCCCCA AAATTCATTT ATTAAAACCC
3961 TAAACCCCAG TGTGACTGCA TTTGGACATA GAGCCTTTAG GGGGTACATA AAACTAAAGA
4021 TCACAGGATA GGGCCCTAAT CCCATTGGGG CTGGTGTCCT TACAGAAGAT GAGACACTTA
4081 GAGCTCTCTC TCCACGCAGG CACCAAGGAA ACACCATACA AACACACAGT GAGATGGCAG
4141 CCATCTGTTA GCCAGGAACA GATTCTCACC ATAAACTATG TTGGCACCTT GATCTTAAAC
4201 TTCCAGGCTC CAAAACTGTG AGAAAATGAA TTTCTGTTCC AAGCCTCTTA GATATGGAAA
4261 AAAAGATTCT GTTGTTTAAG CCATCCAGTC TCTGGTATTT TGTTATGGCA GCCTGAGTAG
4321 GCTAAGACAA TGAAGGATGT GGTAAAACTT TACGTCCCAA CCACATACCA AAGAGGCTGG
4381 AATTTAGCAT GCTTTCTTCT TTCAACTGTA GGCAATGTGC ACAAGTTCTA AATCCTAAGA
4441 CATGTTGGCT CCTTTACTCT GCCCAAACTA CAACTCAAAC AAACAACTGT AATATAATAA
4501 CATCCAATGA AGTTCTGACA TTTCTTCAAC ATGAGTACAG TAATTCAATG CCAGAGAATT
4561 CATTTTATTT TGAAATCTAC ATGCCATATT CCAATTTCTG TTGAAGATGC AATGGTTATA
4621 TTTATTCTTT TTAATATAGA TTTATCAGAC TGGGCGCGGT GGCTCATACC TGTAATCCTA
4681 GCATTTGAGA GGCTGAGGTG GGCATATCAC CTGAGGTCAG GAGTTTGAGA CCAGGCTGGC
4741 CAACATGGTG AAACCCTGTC TCTACTATAA ATATAAAAAT TAGCTGGGTG TGGTGGTGCA
4801 TGCCTGTAGT CCCAGTTACT AGGGAGGCTG AGGTAGAATT GCTTGAACCT GGGAGCAGGA
4861 GGTTGCAATG AGTGGAAATC GCACCAGTAC ACTCCAGCCT GGATGACAGA GCAAAATAAT
4921 AAATACATAA AATAGATTTA TCAGTTTATC AATAATATAG TTTTCTTTTC TAGGTGTAAA
4981 TATAGGTAAT GACTGTCCTT TAGTACATTT TCTCATGATG CTCCTCTTAC TTGGTTTGGT
5041 ACAATATTAA GTATTGAAAT AAAATAGAGA ATCCTGTCGC TACACATGAG CACTTATTCC
5101 ATTTGCTCAT CTCCAATATG CACGGGAAAT TCTCAAATTG CTAATAATCT TGTAACACAC
5161 ATGCATTATA TTCAACAGGA ATATATAAAT TTATAATTAT AATTTAGGAT CAACAGATGA
5221 CAAACCTTTA GAAGGTTTGT ATTTAACCTT AAAATATAAT TTTTTAAAAA TTGGTTATAA
5281 AATTTCTAAT ACTTTCTTTT TTGTGACCTC AAGGGGAAAA TATAATTCTT ATAAAAGTTC
5341 AAATGATTTA CAGAATACAA AAAGTGAATA GAGATGATGA ATGAATTAAA GGAAAGGATA
5401 TTGCTACATA GATTTGGAAA TTTAAAAAGG GAAATTACGA TTGTTGATTT TGTGTTAAAC
5461 TGATCTGCTT TGTTCAAGAT ACCTTATGTA CCAAAAAATG ATTTTATCTC AGCCTCATAT
5521 CTCAGTAAAT TCCTGAGACA AACTTTAGTC CCTGGTGCCC AGGTGCCTTT GGTAATTGGG
5581 AGACCTCTAG GTTTAGCATC CTCATCCACT CGCCCCAATT TAAATAGTCC TCCCCAGGGC
5641 CATTCAGGCA AGGGAGATGA AAACTTGCTC AAGAGTTGGA ATCCAATTGA AGCTACCGAA
5701 ATTCATTGCT CAATAGATAA TTTTCCCTGG AAGTAACTAG GGCTTTTGAA TATAATAGTG
5761 GGCATTTCAA AGTAGAAGGT AAAGTATTTT GGAGATGAGG AGACAGGACA GAGCTACGAG
5821 GAATGTCCTT TGCTCAGGGA CTAGGCTCTT AGCAGTACCT CTTAGGTAAG AACTGGTTAA
5881 CTGGCACCTT CTGTGTTTCT CTGAAGCTCC CTTTGCTTAG GGACTAGGCT CTTAGCAGTA
5941 CCTCTTAGGT AAGAACTGGT TAACTGACAC CTTCTATGTG TCTGAAGCTC CCAGAACAAA
6001 CTGCCAATGA AATTTGGATT TTTGGAATAT AGTTTCTTTT TTGTTGTTAC TTTTTGTTTT
6061 GTTGTTTTTT TTTGAGAGTC TCACTCTCAC TGCAACCTCC CCTCCTATA TTCAAGTGAT
6121 TCTCTTGCCT CAGCCTCCCG AGTAGCTGGG ACTACAGGCG TGCACTAGCA TGCCCAGCTA
6181 ATTTTTGTAT TTTTTAGTAG AGATGGGGTT GGTTTTTTTT TGAGACAGAG TTTCACTTTG
6241 TCGCCCAGGC TGGAGTGCAG TGGCACGATC TTGGCTCACT ACAACCTCCA CCTCCCGGGG
6301 TTCAAGTGAT TCTTCTGCCT CAGTCTCCTG AGTAGCTGGG ACTACAGGCG CCTACAGGTG
```

```
6361 AACACCGCCA CACCTGACTA ATTTGTGTAG TTTTATTAGA GATGGGGTTT CGCCATGTTG
6421 GCCAGGCTGG TCTCAAACTC CTGACCTCAG GTGATCTACC CACCTCAGCC TCCCCAAGTG
6481 CTGGGATTAC AGATGTGAGA CACCAGATCA GCCTCAGAAG ACATTTTCTA TTGGAAAGAG
6541 AAAACACTAT TAGCAACCTA TTAGTCTAAT ATTTAATACT TAATGTCTTC CTTAGTAATA
6601 AACCAACTCT CTACAACAAA GTGCTTCCTG GCTGCCAGT CATTGATTCA TTCAGTTCAA
6661 CATTTTCTCA ATGCCCAACA GCCAAGTGTC TCCTGTATGC CAAGTTCTAT GCTGATTATC
6721 AGTATTTGAA TAAGAGGGGG TCTACATCTT AAGTACTGCT TAAGATGAAA GCCTCTAGGT
6781 TAACAAACTT AACACAATGT ATCATTCACT ACTAAATAGA CCGAATACAA AATCTTGTTA
6841 TTGGAGCCCA GAGAGAAGAA TTGAAATTCA AGTTTTCTCT CTCTCCTTTT CTCACTCACC
6901 ACAATAAGTC AGTTGCACCA AGTCTTGTAG CTCTTTACTG AGCCATGTTT TCACGTGTCC
6961 CTTTGTTTTA TTTGCCACAC CCTAAATAAA AATTGTACTG GCTTTTTTTC CCTGGGTTTA
7021 CAGTATTAAT ACATTGTCAA GATTTACCTC TTCGTGTAGA TTCCCTGGGG AAAATTACCT
7081 TTCCTCCTTC CCTTAAATTC TTCAGAGGTT AGAAAGCCAT TAGTAACATT CTGGTATGTG
7141 GACAAAGTTT ACCCATTATG TATGGATGTT TTACTCTTTC CATTTTTCTG ACAATAATCT
7201 CTTAAGGAGG TGTGGTTATA GAATAGTCAG CTGTTATAAG TACTGTTTTC CTGGCCTTAC
7261 AACTTAAATT CTTTAAGCTG TTTCTTAGTT TGCTCATCTC AAAATTCGGA ATAAGGATAA
7321 AACCTATCTC TTAGATTGTT GGATTAAATG AATTAACATA CTGGAAGCTC ATGAAATGTG
7381 CCTGGCACAC AGTAGTGCCT AATAAACCAT CTCTCTTATT CAGCCTGTTT TCTGATTTCA
7441 GAATCTACAC TTGCTGAGCC AGGTTCTTTT CATTTCAAGG TGAGCAAAAG CATACAAGGA
7501 AGAGATGGAG GTAGGAAGAG ATTAAGCCCT AGGCCAAGGG AGCTGGAATC AAAGGCAATT
7561 TGGTCAGTGA ATAAAAAGGA TTCCAAGGCC CATAAGGCAA TTCTAACCTT AGGATCGAAA
7621 TTCTCGGACA TACAGGAAAT GCTGGGGGGG GGAAAATCCG GTCTTCTCAG CCCAAGAGCC
7681 ATGTGAAACC AGACCTTCAA ATCTGATGAT TCTCAGCCCA GCTGCCCATT AGAATCGTTG
7741 TAATTTAAAA ATACCCTCGG AAAATTCTAA TATGTGGCTA TCAAAGGTGA TCATTTGCTT
7801 TTATGCCACT TTGTTTTCAC CCAAATGGGA CATCCAACCC TTTTCCTTTG AGAGTAGTTG
7861 TAGGGAAAGG AGGGGGTGGA GGGAGGGAAG AGCGGAAAAG GCTGGATCCG CCCCGAGCCG
7921 GTGTCAGTAT CTGGGAAGTG GGAGGCGCGT CAGCAGTAAA CAGCTTCTGC TAGGATTATT
7981 ATCTCCTGCC ACACACTCGG ATTTGAAGGC TCCAAACGAA ACAATGCAAA ACGCTTCAGT
8041 GGAGTTCCAG AAGCGTTAGA CTAAACGACT GGGTCTGTTT GGCCAGTCTG AGCAGCTGGG
8101 CGCAGATGCA TAGGCAAGAC TTAGCCCGCC TAGACTTTTC TGCCCACTTA ATTCCGATCA
8161 AAGCAGAAAC CGGCCGGGCG CGGTGGCTCA CGCCTGTAAT CCCAGCACTT TGGTAGGCAG
8221 AGGCTGGCGG ATCACCTGAG GTCAGGAGTT CGAGACCAGC CCGGCTAACC TGGTGAAACT
8281 CCGTTCTAC TGGTGGCGGG CGCTTGTAAT CCCATCTACT AGGGAGGCTG AGGCCGGAGA
8341 GTCGTCTGAA CCCGGGAGGC GGAGTTTGTA TGCAGTGAGC CGAGATCGCG CCACTGCATT
8401 CCAGCTTGGG CAACAGGAGC AAAACTCCGT TTCAAAAAAG CAAGCAAACA AACAAAAAAA
8461 TGCAGAAACC GAGATCCGGA AGAAACCTC GGCGAGATTC ACAGAATCCA GGAAAATAGG
8521 TCTCTAGAAA TTTGTCCATG GTCCCAGATC TCCATTTCTT GTGGGTGGGG CAGCTGTTAC
8581 CAGATCCCTA GAAGCAAAGG TTTTTTTGGG GGACCGTGTC TCACTGTTGC CCAGGCTGGA
8641 GGGCAGTGGC ACGATCTCGG CTTACTACAA CCTCCGCCTC CCAGGCTCAA GCGACTCTCC
8701 TGCGTCAGCT TCAAGAGTAG CTGGGAGTAC AAGGTATGTG CCACCACGCC CAACTTATTT
8761 TTTTATTTAT TATTTTTATT TAGTAGAGAG GTGTTTCACC ATGTTGGCCA GGTTAGTGTC
8821 GAAGTCGTGA CCTCAGGTGA TCAGCCCCCT CGGCCTCCCA AAGTGGTAGG ATTAGAGGGG
8881 TGAGCAGAAA GCAAAGGTTT TTGAGTGGCC ACAGGCCCCA CTCTATTTCC TTTTCTGCCT
8941 GTAATGGCAA CCTAGACGCT TGAGCTTCTT AAAATACAAG AGTAAGTTGC ATGTCAGGCA
9001 CCGTTCTACA TTAGGGACAT TAGTCTGTTT TACAGACACC TTTCAACTCC CTGGTTAACT
9061 TTTAGGTAAT ATACTCTGCA CTTTAGCAGG AATGGAACCT ATAACTCTCA CAGAATTAGG
9121 AAAGTGAGGC TGCCTACAGC CTAAATTGAG AAAAAAATAG ACGGGGGACT AGTCGGAGGA
9181 CCAAACAAGG TTACCAACAC GTTAGAGTTT TGCCTTCAAT TTACATTTTT AAAGTAATCA
9241 CAACGAAGTG TTTAGATCAC GAGGCATCCC TGCATGTAAA CTGTTAGGCA CTAACTATGG
9301 TCGATCTTAC AAAGCATTAA CTAGAATATT TCTTTAGAGT ATGATAGTAC GTAACTGACC
9361 TACTATTACA TACAAACAGA CCAACCTTTA GTAACAGCGC TCCCCAAAAA CCGAAAAGCA
9421 GTAATACGCT TTGCTCAAGG TTGGCATAAA ATTAACTTAC CTTAGTGCCT TTTTTCCTTC
9481 TACCTACAAG CAGTGAGGTT AGCTCTTCCT TTGAAACGGT AGGGGGGCTC TGAAAAGAGC
9541 CTTTGGGTTT GATAGCGTTT CCGGGAGCTC AGATACCTGT CAAATCACTT GCCCTTGGCC
```

Figure 2 (Page 3 of 74)

```
 9601 TTGTGGTGAC TCTCGGTCTT CTTAGGCAGA AGCACGGCCT GGATGTTAGG AAGGACGCCG
 9661 CCCTGAGCAA TGGTCACCCG GCCTAGCAGT TTGTTGAGCT CCTCGTCGTT GCGGATGGCC
 9721 AGCTGCAAGT GGCGCGGGAT GATGCGAGTC TTCTTGTTGT CGCGAGCCGC GTTGCCGGCC
 9781 AGCTCCAGGA TCTCGGCGGT CAGATACTCT AACACCGCCG CCAGGTACAC CGGCGCGCCT
 9841 GCCCCAACCC GCTCTGCGTA GTTGCCTTTA CGGAGCAGGC GGTGCACTCG GCCCACCGGG
 9901 AACTGGAGAC CAGCGCGAGA AGAGCGGGAT TTCGCTTTGG CGCGAGCTTT GCCTCCTTGC
 9961 TTACCACGTC CAGACATTGC AATCAGACAA AAATCACCAA AACCAGCAGC CTAAGCTCAC
10021 GAGAAAACAA ACAAAATCAA GAAATATGTA AAACATGGCC GCTTTTATAG GTAGTTCCTG
10081 GGGAGTAAAT CCGACTTTTT GATTGGTCGG TAGCAAATGC TAGTCAGATA GCCAATAGAA
10141 AAGCTGTACT TTCATACCTC ATTTGCATAG CTCTGCCCAC GGATGACAAC TGTGTAGTTT
10201 GTCTTCCAAT TAACTAAGAG GTACTCTCCA TCCCTCATTA GCATAAAAGC CCTATAAGTA
10261 GCAGAAATCC GCTCTTTACT TTCGACACAT TTCTGGTGTT TTAAGATGCC TGAGCCAGCC
10321 AAGTCTGCTC CCGCCCCGAA GAAGGGCTCC AAGAAGGCAG TGACCAAAGC GCAGAAGAAA
10381 GATGGCAAGA AGCGCAAGCG CAGCCGCAAG GAGAGTTACT CTGTGTACGT GTACAAGGTG
10441 CTGAAACAGG TCCATCCCGA CACTGGCATC TCTTCCAAGG CCATGGGCAT CATGAATTCT
10501 TTCGTTAACG ACATATTTGA GCGCATCGCG GGCGAGGCTT CCCGCCTGGC GCATTACAAC
10561 AAGCGCTCGA CCATCACCTC CAGGGAGATC CAGACGGCCG TGCGCCTGCT GCTTCCCGGA
10621 GAGCTGGCCA AGCACGCCGT GTCGGAGGGC ACCAAGGCCG TCACCAAGTA CACCAGCTCC
10681 AAGTAAACAT TCCAAGTAAG CGTCTTAACA CCTAACCCCA AAGGCTCTTT TAAGAGCCAC
10741 CCAGATACCC ACTAAAAGAG CTGTGGCCAG ACGCCAAATT TTATTTGGCG GCGGAGGGGT
10801 ATTAGAATGT AGGAACTGGA GAGGGGTGGG GACAAGTGTT GCAGCTTAGA GAGGGACAAA
10861 GGGTCCTGAA CCCGAAAGAA GCCAGCCATT AAAAATGGGT TTGGGGTCAA TTCGTTGTGC
10921 TTAAATTTAA AATGGGGACA AGCGGCCATT TTGCTAACTC GGCGTTCCCG GAAGAAACCG
10981 CAGGCTCGCT TAGGTTTCAG ACCCAGCTGT CTGTCCCTGT CTACGTCGCC AGGATCAACG
11041 GTTGCCGTAA TGTCATAATT TCGCCACCAG CTTCTAGCCA ATAGGCTGTC CTGTCATTTT
11101 AAATATTAAC CAATCGAGGG AAAGCTGTTT TGAGACTCTG ATTTACATAG CGGACCGGAG
11161 TGGGAACCTG GGCAGTAACT GCCTAAGGAA GGACTCCCCC TCTGTTTTCG TGGCGCACAC
11221 CTTCGTAGTA TACTGAAGGG TGTGTCTCCT GGGTTTCCAA CTGCCCCGGT AATAGTCTTT
11281 TAACCTAATA TGCGTCAGTT TTGATAACAA CACTAAGGCA GTACAGAACT AAAGATGTAA
11341 GCACTGCGCC AGATGTTGCT TCATACATCT TATTCTATTC AACTGGTTTA TTCAAGATTC
11401 AAATCAAATC AAATTTTGCT TGAATCCCAG TGCTCAGTCA GCCATAAATG GTGTGTTGCC
11461 TGATTGAAAC TTAAAATCTC CGTAGGGGGC TTGTAACATG CAGAAAAGTT TGAAAGTTGC
11521 TTTAGGAGAA GCCAACTCTT AACTGCTGGG TAAATTGACA AGCCTTCGAA CACTGAACTG
11581 AAGGCCAGTA AGGACTAGGC GCTGGGTGGG GGAGAATGAA GAGGAGACGT CATTAAACTT
11641 AGCACATACA CTGTGTCTCC TAGAGGACTC TCCCTTCCTA GACAACTGCA GGCCGCTTTG
11701 TGGCCTGGGA AATTCCACAT TCCCTTAAGT ATTTTACTCA TGGTCTTTTC CAGGTAAAGA
11761 TTTTAAGATG AAGGGTTAGA CGTAGTCTAC CTATCTTTTT ATTCAAGTCT AGAACACGTT
11821 TTTAGCACCT AGAAGTTTGC TTTCTCCATT AAAAACCGGG AATATACAAT AAATAAAATT
11881 AGTGTTAAAG CAGATTTTTA CAAACTTAAA TACCATGTAA TTTAGGTTAC AGTTACTTAA
11941 CATAAGGACT GTGTGATCTT AAATCTGCAA TTTCTTTCAC ACCTGGGAAA TAAACTAAGG
12001 CCTGTCTTTG GTGCCAGACA AGGCCTTATA CTTGAACACT GCTGTGCAAT CACAGGCTGC
12061 CTTGCCTAGA TAACTTATCT GAGAAATTCT GATGAGAAAT GAAATTTCCA GAGTCCCTCA
12121 CAAGTAAATT TTTTTTTCTT TTTTTTTTTT TTTGAGACGA AGTTTCTCTC TTGTTTCCCA
12181 GGCTGGAGTG CAATGGCGCG ATCTTGGCTC ACAGCAACCT CCGCCTCCCG GGTTCAAGCC
12241 ATTCTCCTGC CTCAGCCTCC GGAGTAGCTG GGATTACAGG CATGCGCCAC GACACCCTGG
12301 CTAATTTTGT ATTTTTAGTA GAGACGAGGT TTCTCCATGT CGGTCAGGCT GGTCTCGAAC
12361 TCCGGACATC AGGTGATCTG CCCGCCTTGG CCTCCCAAAG TCCTGGATTA CAGGCTTGAG
12421 CCACCGCGCC GGGCCTAAAT GGTTTTTTTT TTTTCTATGC CTCTAATGGA CCTGGTCACT
12481 TATTCCCATT CAGACTGACC GCTCTCCTAC CTGCCAACTA ACTAATCAGT GTAACCAAAA
12541 TCTGCAAACA AAATTCAGTA TTCTTTCCCC GCCTTTTCCC CTTTCTCTTA CATAGATTAT
12601 GTTTTTGCCT GTGTTAGATG AAATAATTCT ATTGCTTGTT CTCTCTTCTG TACAAGTACC
12661 CAGTAAGCAA ATTATTAACT TCTTGGTCAT TTATTTCTGA ATTTTCCACC AAGACAGTGT
12721 TTATGTGAGT CATACAATAA GAACCAACAG AAATGTGTGT CTTGGAAACA GGTTGTCTAT
12781 CCCTGGACCC TTTGAGTTTT CTGTTCACTT TCCTTTGGCT TTTGCATGCT AAAAGTTTAT
```

Figure 2 (Page 4 of 74)

```
12841 CGTCCGCGTT TGTTTGTTTT GGTTATTCTA ATTGGACTTG GCTGATTGGT TGCATATTGG
12901 TGGCAGTAGT AGAATTTGAA TTCTGGTTTT CTGGTCACAT CATTAAGTGA TTAGTCAGTG
12961 GAGAGGACAG GAAATCTGGT TTATTTATTA ACCTTTTTTT GGGGTGTTTT TGTTTGAAGA
13021 TGTTGATATT CTCTGTGAGG ACACAGGGTT AGAGTTGGTG TTTTTCTTTC TGACTTTACA
13081 TGGGATTTGA TGTTTTGTGC TTGTATGCCT CTTTCCACCT TCCAAAACTT GTCTTTTTTG
13141 AGTCCAAATA GTTGTCGATA TCTGCAAAAC CAGTATTCCT GTGTTAAGAT GATATGAATA
13201 TAAAATGGCT GCCCTGTTAT AACTTTTGAC TTTAAGAAAG TGTTAGGACT AACAGGAGAC
13261 AAAAAGGAAA TCAAGGAAAC CAAATGTCTG GTCTCAATAA CTGCTATGGC AGAGGCTCTA
13321 CAGCTTATTA TTAATTTTAG TAATTTCACA TTATTGCCCC TTCACGTTCT TTAAGTAAGG
13381 TTAGAGGACA GAAGAAACAT AATGTTGTTA CAAATTGGAC TATTGAGTCA GGAAAAAAAA
13441 AGAGTGCTTT CAATATCTGA ATAAAACAAA GATTTAATAT TTTCTAAACC TTAACGAGTT
13501 TATTGTAAGG GATGTGATGC TGGAAACTAG GAAACTAGAA TTTTCTTCTA AACTGAGAAT
13561 CAGAATTATT CATATTCTCA GCAGTGGTGC CACCTGAGGG ACTTCTGATC TTAATTACAT
13621 ACTTTTATTT CTTTAACTGA TCAACATGCT AAATAGATAA CCTATGGCTC TGTTTTTACC
13681 CACTTTAAAT TCTGTTCTAT TAGCACGGTT AGCTTTCCTA ATTGGCAATA AGATTGAGAC
13741 TATCTTTTTT TTTTTTTTGA GACAGAATTT TGCTCTGTGG CCCAGGCTGG GGTGCAGTGG
13801 CACAATCTCG GCTCACTGCA ACCTCTGCCT CCAGGGTTCT AGCAATTTTC CTGCCTCAGC
13861 CTCCCCAGTA GCTGGGATTA CAGGTGCACC ACCACGCCTG GCTAATTTGT GCATTTTTAG
13921 TAGAGATGGG GTTTCGCCAT GTTGGCCAAA CTGGTCTCGA ACTCAGGTGA TCCACCTCGG
13981 CCTCCCAAAG TGATGAGATT ACAGGCGTGA GCCACCGTGC CCAGAAAAGA CTATCTTATT
14041 TTATGAATTT AAATAATTGT GAAATTATCC ACTTAAGGGA ATTAATAAAT TATAATGTAA
14101 TCTTAAATTT TAGTTGGCTT ACATAAAGAC TTAAAATACA TCAATTTAAA TAAAAACTCA
14161 TTTGTCTAAA AAAAAATCAA AAATTTTCCT TGTGCTTTAA ATGTGCTACC TCTTTAAGTT
14221 CTAATTAAGA GAAAAAAAGT TTAACTGTGA GTTTCATTAG TGGTCTTAGT TAACAGCTTA
14281 AAGTATTTTG TAAAAAAAAT ACTTCACAAT TTTTAAATAA CTTAAAAATA TTAATACCTC
14341 TTTTATTAGG TTTTTTTAAT AAGGAAAATA TATAATACAT CTAATCAAGA TTATTTTTG
14401 GACAAATTGG CTTAATAATT TCATTTTAAA AATGGCTTCT TTATTCTTAT ACTGTAAAAA
14461 TAATATTAGC AGAATATTAT AGTATACACA AGTTTAGGGT TCATATTCTA AAAAACAAAA
14521 ACAAAAGCTA ATTTAACTTG CATTTACTAA ATTTCTTCCA CTAGTTGTAC TGGTTACATG
14581 AGTTAACATC ACTTTATTTA TTATTCTAAA ATTGTAAATT ATTCATTGAA CCAAATTAAA
14641 TGATAATAGA TAATGTCATT TTTAAAAATG GAATTAAATT TTATGTTACT AATTATAAGG
14701 ATTCAATGTG TGAGCTTAAG TACTGAGTTC ACAGTGTATG ATAACTTTAA GAATTTAGGT
14761 GAATATTATT AAATTGAGTA AATTAATTCT CAATCTTTGG ATACCTGGAC AATTTCTAAA
14821 TTGGAGGGTA CAAAATACAA ATCACAAGAA ACAGTGTAGT TTTATGCAAA TAACATTTTT
14881 ACACAGTTTA GAATAACCAT TGATAAACAG ATAAGAGAAC ATATGATTGC CTTAGAATAG
14941 ATACTGTTGC TTTCGCCACT TTAGATTTGT AAATCATGTA CTGTATACGT GTGGGCGTAG
15001 AGGACCATGC AGGTTTTGGA TGACTGCCTC TGTTTTCGTC ATGCCTATGC GGGAACACAA
15061 TTGCCTGCTT TGTTTAAGGG CTATGGTTAA TCCAAACAGC TCTGACTCTA TCAAGTACTA
15121 TAGCTACAGA GAAACACAAG TAAGCATTCG AGATAATGAC TACCTTGAGC CTTTACTTAT
15181 TTAAAAAGTT GTTACTGTTT GTTAATGTGG TACATTCAAT TTACTATGGA TTGTCACTCT
15241 AAAATAAGAC TTCAATCTTT TTCTTATTTT TATATAGCCA TGATTTATAT TCATATCTTA
15301 ATGTAATAAC CAATCTTCTC TGACAACATT ATAACAATGC TGGAACCTCC ATTTTCAGTA
15361 CTTCAAACAA CAAATACTGC TTTTATACTT CAGAGCAGAT GGATATGTGC TTCCCAGTGT
15421 AAACACATTT GGAATCTCAC TGAGAAATAC ACTATCACTA AAAATACAGT TCTGAGATTC
15481 ATTAAAAGAC CTCCAGAATT CTGGAAGTAG GAAGTTTCCT CTTCAAAGTC TACAGAGGAA
15541 GACGAGGTCT GAAATAGACA GCTTCTTCCT TCTTTTACCT GTGGTATTAT TCTGTTTTGT
15601 CCTTTTCTCC ATTATCTGTC TTTCCAGTGA TGAAATTTTG ATCTGGCCCT CCCAAGTATT
15661 AAAAAACAAG CAAATAAACA AATCTCAGTT ATATTTTACT AAGATATTGG CATGCTAACT
15721 TTTTGCAGGT TTGTAACAAG GACCTTTATA ACTTGACTAA AAGTTCCTAA ATAAGAATAT
15781 TTACTAGAAA ATTTATTTCT GCCTGTGGCC CACATTTGAG TCAAAATAAT CAATTAGGAA
15841 AAATGAACTT GTTTAACTAA AGTTGGCCAA ACTGATCTTT GAGACCTATT CATCTAAGAC
15901 AAGCCAATTA AATTCTTGGA GACAATTTGT ACTTTAAGGA ATTCTTATAA TATTTGTAAT
15961 TACCCTCATA ACTTTTTTTT TGCCCTACTT CTGTGCTTCT CTAATATGCA GATTATTAAA
16021 TGTTGTTACA AAGCCATTGT CAAAAAAACA AAAAACAAAA AACTAAACAA ACTCACATGG
```

Figure 2 (Page 5 of 74)

```
16081 TTAGACTTGC TCCTTTATGA GATATTTTTA CCAAAAATGG AGGAGTTGAA AAACTCTGGT
16141 GCCAGAAATC GTGAAGACAT GGCCTACCTA ACTTGGAAAT GTTGGTTGTC AGTGGAAAAT
16201 ACTACACAGA GATAGCCATA GTGCTGCACA GCCAATCTTA AGTGTTTCTA GAGAATCACT
16261 AATTGTTTCT AGAGAATCAC TAATTGTTTT CTTTTAACAT TCTTGGTTTA TACAAGAAGA
16321 GAGTATCCAT ACTAAACTCT TTTCTACTGA AAATAATGTG CAAACATAAC ATCCTATTCC
16381 TAGACAGTTT GTAGTTTTTT TCTCCCATTT CTATTTTATA AATCATCTTT TTAAAATACT
16441 TTGTTGAGTG AAATCAGTCC ATTGCTTGAT ATACCTTGAG CACAAGTAAA TAGTATGCCA
16501 AAAATTAAAT GTCTTTCAGT CACAGTTTGA CAAACTCAAC TACCCTGAGC CTATAGAGTG
16561 GTAATAATTG CCCTACTCAT AAAGATGGGG TGAAGATTAA ATGAAATAGC ACCTATAGAA
16621 CACTAGTTCC AGACGTGGTA TCATGCTAGT AAAATGGCTG CACAGCACTG CTCAATGATG
16681 ACAAAAGTG AAGCTTCTGG AGACAGACTC CAAGTTTGAC TCCCAGATCA CCACATATAA
16741 GATGTGGGAC TCTGAGGCAG GTCATTTAAT CTCTCTGTGC ATTAGTATCC TTCTCTATAC
16801 CTTTACAGTG ATGGTAATAG CACCTACCTT CTAGAAGTAT GTGAAGATTA AAGATCCTTA
16861 ATGCATATAA ACCACTGTGT TTACTGCTGT TTGACAAATT TTATTTATAA CCATCTTTAC
16921 GCTCCTAAAA GGACTTGAAG CAGCTTATGA CTGAAGACTT TGGTAGGAGT TGGCCTTCTA
16981 TAAATTATAA GAATTTCATA AATTATTTGA TATGAAAATG CCAGTTGATC ATAGTATGTT
17041 TACCGGGGTC CAACAGGTTG AGAAAAAATA CACTTTTTTT CCCTGAACAT ATGAAATTAG
17101 CTCTCTAGGC ATATTCCTAA GGACTTAAAG AATGATAACT ATCATTTCTC TTAAATCTTC
17161 CAGATTTGGA AGGATATATA TATTCAGCAC ATTGACAGAC AATCCCAGTA GTCCTAAATT
17221 AAAAGACATT AAAAATTAGT GAAACTTTTC CTACCTTTAG CCTGTGTAAT CCTGGATGAC
17281 CAAGCATAAA ATTAAATTGA GTAGAGTATA CCACTGTAAC ATTTCCTGAA AGGTATTCTA
17341 GGCTCTGAGT AATTTCTTTG GGGTCTGAAG ATCAGTTTGA CATATCCTCA AGTATCATGA
17401 GTTCATTATA ATTAAGAAAA AGGGAGTAAA TCTGGAGAAT GAGCCACTTT CTTACTACTC
17461 CTTGACCTCA GTTCTTTTTT TCAGAGACAG GGTCTCACTT TGTTGCCCAG GCTGCCAGGC
17521 TGGAGTGTAG TGGCGCAATC GCATCTCATT GTAACCTCCA CCTTCTGGGC TGAAGCCATC
17581 CTCCTGCCTC AGCATCCTGA GTATCTGGAA CCACAGCAGG TGCACACCAC CATGCCAAGC
17641 TAATTTTTTA AAAGTTTTT TGTAGAGATG GGGTCTTACT ATGTTGCCCA GGCTGGTCTC
17701 AAACTCCTGG GCTTAAGTGA TCCTCCTGCC TCAGCCTCCC AAATTGTTGG GATTACTAGT
17761 GTGAGTCACT GTACCCCGCC CCACTTCAGT TCTGAGGAGG AAAAAATATG TAATAATAAT
17821 GGGACTTTGG TTTGCTGATT TAAAGATTCA TGTAACCTTA TCATCCAATG CGCAATTTGT
17881 AGAATAATTA ATAGAGACAT CTGGTCTCAT GTTTCTACAG TTGCTCATGC CTTGATAGTA
17941 GATCTCCTTG CTGCTGGCTC AGAAGGGTAA AAGAGCAGAA ATGATGGGGC TTCTCTCATT
18001 CTATGAGGAA ATAGACCTAT GTAGAGGAGG CTACCTGTGG TAAAACCTTA TCCTCATCAC
18061 TTAAAATTCT AGGCTTATTC TCTGACCATA TCAAGTTTTC AAATGGTAAA AGAATTGGAT
18121 TCAAGAGAAA TATGAATAAA CTTTTGTTTT CACTTTTCTC CCTCCTCTCC CCCCATTCTC
18181 CCTTCCTTTA TTTTCTTGTC CTTAGTTTTC TTTTCACTTT TTTGTCTACT ATTATTTGCC
18241 CAAACTCAAC TGTAGGCTAG AACAAAAAAA AATTGAAAAT TAAAATGTGC CCCTTTTGTT
18301 GTTAGACTTG CTTAAACAAT TGGGGTAATG AACCTTGGAC ACTAGATTTT AAAACACACA
18361 CATTTGAGCT TCAGTGCACT GAAATAAATA TATTTTTAAC AATTAAAAAA TAAAATTGCA
18421 TGTTTAAAAA ATCTGCAGAG AACAATACAC GTTGTGAGAT CTTGAATGGA AGGAAAACTG
18481 CTAGCCTCAA GAGTGGATCA AAGATGCTCA GCAGGCAACA GAGTAAGAGC ATGTTGGAGG
18541 GTTAGAGAG TGTGCTCAGG GTTCTAGGCT CTAAAAATCA GACAGTCCCC ACGGCCTGGC
18601 CTTCGTCGCT GTATCTTCTT TATGAAAAAC ACTAAGTCTT TTTCCTCACT GGATAAATTT
18661 TTATCCTTCA AGTTTAGATC AAATGGAACT TTAGGACACT GACTAGGTTA CATTCATCTT
18721 TTAAGAGCGT ACAGACATTC AAGGGCTAGA GGATGTGGGT TTACTGCACA GGCTCATTAT
18781 CCAACAGCTG TGCTACCTGG GAAACTTAAC CTCTCTGTGC CTTAATTTCC TCATCTATAA
18841 CGCAGGGAGA ATGACAGTAG GTATCTCATA AGGTTGTTGG AACAACTAAA TGCATTGGTA
18901 TCTATTGTGT AAAGTGCTTA AAACACTGCC TGGCACAGAG CAAACATCCA GTGAACTTTA
18961 GCCATCATCA TTATCATTGT TCTCAGAGTC AAATACAATA TCTCTATATCT GATAAATTAC
19021 AGAAGTGAAT CAATCACTCT CTCTCTTTTC TCCAGGGGGA GACAACAGCT TTTAGACATA
19081 TCTTTTCCAA CAGTCGTCAC TGCTGGACAC TGTTTCATCT TGCAAATAAA CCAATGAAAA
19141 TGAGTGATCC TAGAAGAAGA TAAATGGAGG TATTTTGAAC AATCAAAGAA GGACAAATGA
19201 ACACCTGGCT GAGAAAAATT AGCTCTTTTT TCTATGCATA AAACTATTAA AATATTCTTC
19261 ATAGAAATTT ATGACACAGG AAACATAAAG ACAAAATTAA AATAACTCCT AGTATCTCCT
```

Figure 2 (Page 6 of 74)

```
19321 ATTCTTTTTA TATGTATATT ATATATACTC ATATTCATAT ATACATATAT CTCACATCAT
19381 GTATCATATA TAAAATAAAT TTAGGTGTCA TGATATATAT TTAGATAAAT ATACTTAGAA
19441 ACTTTTTTAT GGATGTATAA TTTATGGATA TATTGATAAT TATGTATTTG TTATTGACTA
19501 CTTCAATTGA TTCCCATTTT TATGCATTAT ATTATAGATT ATATAGCTCA CACATCTTTG
19561 TACATAAATC TTTGTTCAAA TATTATTTCC TAAGGATAGA CTTCATGAAG TGGAAATACT
19621 AAATCAAAAG TGAAAACAT TTTCTAAGGT TCTTAACATA TACATTGCCA AATTGCTATT
19681 CAGGATCATA CCAATTTATA ATCCCAAAAT AATATGAAAA TTCCTGTTTT ATAGCACTCA
19741 TATTTACAAT AAATTTTAAA AATCACTGTT AACCTAATAG TCCTTCAAAA GAAAAAAAAA
19801 TTGAAATTAC ATTATTTTAA TGACTCTATT AGTGAGGGTC ATTCTTCCCA TGTTTCTTGT
19861 TAGCCATGAC CCTATAAGAA ATAAACTGCA CTGCAAAATG ATAAACATGA TATCAATCAT
19921 TACATGGGAA GGCACTATAT AAAGAATAAT ACCTTAGGTT AAGGCCACAT AAATATTTAT
19981 CAGGTGCCTT TTCTGCGGAG GACTCTGAAG GGATACTAAA CTGCATTTAG CTGCATGCAA
20041 CTGAAATTAC TTTTACCTAC ATTGTCTCTT ATAAACATTA TAACTACTCT TTGAGAAAGT
20101 GTTTACTATG GACTGAATTG TCTCCCCATC CCCCCAAATT CATATATTGA AGCCATAAAC
20161 CCCAATATGA CTCTATTCCT AGACAGGACT TATAAGAGGT AATTAAGGTT AAATGAGGTC
20221 ATTAGGATGG GTTCCTAACT GGATAGGATT GGTGGCCTTA TAAGAAGAGG AAGATTCTGC
20281 ACTTGGTCTT CCAAATTAAA TAATTTATTT AAAAGAAAAA AAAAAAAGA GGAAGAGAGG
20341 GAGCTCTGCA CATATACTGA GGAAAGGCTA TGTGAGCTCT CACAGTGAGA AGGTAGCACT
20401 CTACAAGCCA GCAAGAGAGC CCTCACCAGA ATCCAGCCAT GCTATACCCT GCTCTGAGAC
20461 TTCCAGCCTC CAGAACTGTG ATAAAATTTT GTTGTTTAAA CCACACAATC TATGGTATTT
20521 TTTTATGGCA GCCCAAGCCA ACAAAGACAG CATCATTGCT GTCACTTACA GACAAGAAAA
20581 CTAAGACTAG GAGAGAGAAA AGTTAAACTT GTCCAAGGTC ACAAAAGCCA GAAACAAGTG
20641 AGGTGAGAAG TTGACCTTGT TCTCCTCAAT CCAAGGCCAG GACTCCTCCA CTCCACATGT
20701 AGATAGCCAC CTCACAGTCA ACAGCCAAAT GTCCACACCC CAGAGTCAGC ATTAGACCAA
20761 GATGTCTTAC CAGGAGACAA ATGCCTCATC TTGAATAAAT ATGTTCTAAC AACTTACCCA
20821 TGTAAAACAT TGAATCTCAT GAGAAACAAA AATGCAAAGT ATGTAGAAAA CTATGTTTAC
20881 CACTTAACTG ACAGTGATAA AAAGCTTAAT GATATCCTTA TAGTCTTGGA GGGGTTTGTA
20941 TATGTGGTGA AACAGGTGCT CACGCACTGC TGATAGACTG TAAATTGGTC CTAGAGAGAA
21001 AAATAAATAA ACTGGAAGGA GTTATGCTGT ATGTTTACTT TTTTTATGGA AACATATGAT
21061 ATACCTGGAA ATTCGATTGG CCATGCATCT ATTTCTTCAA TGGGTATGCA CAGTTGAGCT
21121 GTTCCCATGC ACCAGGCACT GTAATGGGAC AACTGCACAT GACAGTCAAA AATCTCAGTC
21181 TCATGAAGTC GACATGCTCA TGGAGAGGTG CTACCCACTA AACTAATATT TGTATATCAA
21241 TTATGGATAC ATTGGGCCAC ATTTACAGAA ATTCACTTAC AGTGGGTTAC CAGAAGGGAT
21301 TTTTTTTCTT GATTGGCAAG AAGGCTAGGC TGTTTTGTTG GGGGCTGGCA GGAGCTGTCT
21361 AGGCTGCCCA AGTATGCAGG TCTCTTCTAT CATCCTGTGT TAACCATCTT CCATGTATCT
21421 TTCAACCTCA TGGTCATCTG CAGCATGTCT AGGGGTCATA TCTATGTTCC ATGCAGGAAA
21481 AAAGGGTAAA GGGAAAGGGA AGTAGGCATG TACCATTTTA ATGCACACCT TGGTTTTCAG
21541 AAAATTTAAG AAGAAAGACT TTCTGCTTTT CTCTGACTAT TCTGTATTCT GGATTACAAC
21601 GCAACAGAAA CGTCACCTTA AATTCTAATG TTTTTCTCTC CTTGCTTTCA AAAACTGACT
21661 CATTAACCTC CACGTGGCTT GGAAAAATTA TTTCAGTCAT CCAGTAATGA GCTGTTCATA
21721 GAAATGTTTT GGACATCAAG TCTGTGTTGT TAGCATTATA CATGTTAAGC ATTGAATAAA
21781 AAACAACATG ATGTGGGTAC ATTTCTTTAC TTACATATAA GTACTTATAT ACTTATAGCT
21841 GAAAAGAGAG GTTGAAATGT CAGGTGGAAC AGAAATAAGA TTACCTAGAT GTTTCTCCTA
21901 TGGGTGATTT TCAGCTATGC TGATCTTTCT TCTGGGTCAG GTACTCCCAG AACTTCCTAA
21961 TTAAATGGTG GCCCTGATCT TAGTTCCTCT CTCCTCTTAG ACATTTTCCA GGACTACAGA
22021 AGATGTGCAG TTTATAAATG AGTAGCAGAA ACCTACTGAA CAAATTATTC AGGCTCATCT
22081 GAACAGAGAG GACACCTTCT CTGCTATACT CTCTCAGTGA TTTCCCTGCC TTGGGGTCAA
22141 TTATTGTCTT GGACATTGAT TTAAGCACAT AATAATTGTT GTCATTGCTT ATGTTTGGAT
22201 TTCATCTCCC AAAATAGATG GTAAATTCTT TAGTTTAGAG ACCAAGTAAT ACTTACAAAA
22261 AAATTTTGTG TGTGTGTGTG TGTTTTTTCT GTGTCTCTCA GCCCTGTAAT AGCATCGTAC
22321 TTACACTTGT TAGATTTTTA GAGACAACTT TTACAAAACA TGGAATTATC TACATACCCT
22381 TTCTACAAAA CAGACAAATT AAATACTCAG TAGTTGAACC AAAAAAAGCA GTTCAAATAA
22441 AATACTTGAA AATGAAGAAA TCATTTGAAC AGAGTTAAAG TTAATCGTAA AATAATGTCT
22501 GTAAAAATTA TTGCCAATCA AATATAAAGT TCAAAAATAG TGCTTGAAAA AGGAAGAATC
```

Figure 2 (Page 7 of 74)

```
22561 ATATGAAAAG GGACTACTCA TTTTAAAAAT GTTAGATATC AGGAAAAGCC AAGAAGTGAG
22621 TATGGTAAGA GTGCTGTCAA GTGAAACCCT GCTAATCTCA CTGAACATGT AAAAATCTGT
22681 AGATGCCTTT ATTTTATTCA CTCACACACA TATGTAGAAA GAGAAATATA TGGTAAACAT
22741 TAAAAAAAAC AAATTAGAAT GTAAATTAA TACTTTAAAA AATGGGCTGT ATACTTTTCT
22801 TATCACCGGA GATAAGAATT TATTATTTTT AAAATAAAGT TATTTCTCT GTGACTGTTT
22861 CCATGACTTT GCTACTTAGA AGTTAGAGAT GCCAAAGTTT ATCTAAGAAA ATGTTTATGG
22921 AAATATTATT TCAATAATGA ATGTTTAGAA GACTGAATTT CCTGACTGGG CACAGTGGCT
22981 CATGCCTGTA ATCCCAGCAC TTTGAGAGGC TGAAGAAGGA GGATCGCTTG AGTCCGGGAG
23041 TTCAAGAGCA TCCTGGGCAA CACAGCGAGA CCCTGCAGCA AAGTAAAAAG AAAAAAGAAT
23101 TGAAAAAGGA AGACTGAATT TCCTTTGGGC AAGTCATGTG ACATTCCTGT GCCTCAGTTT
23161 CTTCATCTAT AAAGTTAATT CCTACATTTT TGGGGAAGGG AGAGAAAAAC TTAGGATAGT
23221 GACTGGCACA GAAGAAGCAC TATATACTAT ATATATGTGG ATATCATTTG TTTTTATGGT
23281 ACCATTTTAG CTATCTAATG CAAAATATGA ATCTTTTTTT TCTGGGTCTT AAATTATGGA
23341 ATGTAAGAAT TTTCTAAATT CTCTAATTCT GTGTTAGTTT TAAAGCAATG GAGTAACGTA
23401 TCTGTCAACT TGTAAATATA AGGATCAACC TGATCCACAA TTTGACCCCT AGCCACTAAT
23461 ATTTAATAGT ACAACACTCA GAAATTATCA AAGGTCAGAG AAGCCAAACA AATGTAAAAA
23521 CATACAGGTG CTCAGAAAGA TGCACCTGTA ATCTCTCTAA GGAGAAATAT TTTCCAAACT
23581 GAGTGACACG GTGCTTTAGT GAGTTGTGGA ATCAATCTCA TGATTTCCAA CCTAGTGTTC
23641 TTTTAAAAAT GAACTAGTCC ACAGTAGAAT ATACTAAAGT GCTGGTGCTT AAGATAGTAT
23701 TGTTTTCTGG AAAAAAAAAA AAAATTTTTT TTTTTGAGA CAGGGTCTCG CTCTTGCCCA
23761 GGCTGAAGTG CAGTGGCACA ATCATGCTCA CTGCAGCCTT GACCTCCTGG GCCCAAGTGA
23821 TTCTCCCACC TCAGCCTTTT GAGTAACTGG GACCACAGGT ACGTGCCACC ACACCCGGGT
23881 AATTTTTTAA TTGTAGAGAC AGGGTCTTGC TATGTGCTTA GGCTGGCCTT GTGAACTCCT
23941 GGGCTCTAGT GATCCACTAG CCTCAGCCTC CCAAATTTAT GGGATTATAG CATGAGCCA
24001 CCCTACCTGG CCTGTTCCCT GAATTTTTTT TTCTTTCAGG TGTTTGTGCA TATGTGTGTG
24061 TGTATGGGTA TAACAGAGAG ACAGAGAGAA AGAAACTTTT CTATCACACT TTGCAATCAG
24121 AAGTTTGAAG TCTTATCTTT TGGCTTTTGT TTCAGAAATA TTTCAAATGT AGACTCTCTC
24181 CTTTACCACA CTGTCCCCTT AGGCAAGGTC TTTGCCATTC TTCTGAGACT ATTGCAACAG
24241 ACTCCCAACT TCTGACTGTG GGCCCTTCTC AAAAATGATT GTTTATGCAA TAAATCTAAA
24301 CCCAAGACAA CTACAACAAT ACAACAAATT CTCTGCTTAA AAACTTCCAA TGTCTGCCGG
24361 GCGCGGCGGC TCACGCATGT ATTCCCAGCA CTTTGGAGGC AGAGGCGGGC AGATCACTTG
24421 AGGTGGGGAG TTCGAGACTA GCCTGGCCAA CATGATGAAA CCCCATCTCT ACTAAAAATA
24481 CAAAAAATTA GCCAGGCATG GTGGTGGGCG CCTATAATCC CAGCTAATTG GGAGGCTGAG
24541 GCAGGAGAAT TGCCTGAACC TGGGAGGTGG AGGTTGCACT GAGCCAAGAT CACACCATTG
24601 CACTCCAGCC TGGGCAACAA GAGCAAAACT CTGTCTCAAA CCAAACCAAA ACAAAACTTC
24661 TAATATCTAC CAAATGTTTC ACACAAGTAT TTGGGGATCT TCACAAATGG CCCTTATGGA
24721 GTTTTCCTTT GCTGAGACCC TATGCTCTGG CCACACTAAA CTCATTCAGC ATCCCAGAAA
24781 GGCCTCAGCC TTTGTGAGCA AGCTCTTATC TCCAGGCCTC TCACAAAGAC CTGTTCCAGT
24841 AGAAGCTCAG GGGAGCACAC TGGACATTAT TCCAACAACC CTTTCCCCAC AGCTATGCAG
24901 CCAAATCTGC CAGCTCAGTT AATTAATTAA GCAATTCAGA GATGAGGGTC TGCCCAGGCT
24961 GGAGTGCAGT AGCTGCGACC TCAAGCTCCT GGGCTCTAAG TGATCCTCTT CAGTCTACCC
25021 AGAAGCTGGG ACTGCAGGCA TGTGCCACCA CACCCAGCTA ATTTTTTTTT TTTTCAGTAG
25081 GGACCAGGCC AACCTAGTCT TGAACTCCTG GCCTCCAGCC TTCCGAAGTG CTGTAATTAC
25141 AGGCATGAAT CACTGCGCCC AGCCAACCCG CCCAGTCTTG TTAGACATGG GGTCTGTAGT
25201 TTCTAGTAGG TTCTTGAGTC TAGGGTTCCT ACCTCATGTT TTATAGTTAA TTTAGGGGAG
25261 GGACTGTGTC TGTTTATCTG GGGATGTAGG GGTGGGCAGG GGGATAGAGG GGACTTCAAT
25321 TAATGAAACC AGAAGCAAAA CTCAGTTGAG GACACCGGTC ATGAGAGTGG CCTGATTATG
25381 GCCAATCTTA CATAATGTGT GAGATCTTGA TATTACCCCA TCCTTGAGAG TCCTCTATAA
25441 AGCTACAGGG ACTTGGGAGC ACCTTTAATT ACAGACAACC CATGTTCCTG TGGATTATGA
25501 TTTATTAGAT TGCACATGCC TAAATAAAGA CATCCTCTGC AGTCTTTTGA CAATTCTATA
25561 AGCATCTTCT GACTCCGCAA TTAGACAGCT AAGAGATCTG TGTTACTTCC CTCACATATA
25621 TAAATAATTT TAAATAAAAA TCATGGCGTG AATAATTTCT TTCCTCTACC GATTTGAAGC
25681 TATCCATTTG GAAGACCACT CTGAAGAGAT GAAATAAGTC TTCTGCCAAA GATTACTTAT
25741 TAATTTACAA GGAAAAGGGG AAGTTTTGTT CCTCTCCGTG AATTTGATTG AAAATCGAGG
```

Figure 2 (Page 8 of 74)

```
25801 GCTTTCTCGA ATAGTTTTGG CATCCAGGGT CATTTTTCAT TAAAAAGAGA AAAGTCATGT
25861 CAAATATGAA TTTCCGCAGA TTATTCAGCA CTAGACCCTG GGAGATTCTG TAAAGAGGGG
25921 TTTTGTTATA CTCAACTTTT CCGGGTAAAA CAAACACAAA TACTCCTCCT CCAAGGGGCG
25981 GGGGCGGTGC CTAGGTGATG CACCAATCAC AGCGCGCCCT ACCCTATATA AGGCCCCGAG
26041 GCCGCCCGGG TGTTTCATGC TTTTCGCTGG TTATTACATC TTGCGTTTCT CTGTTGTTAT
26101 GTCTGAAACC GTGCCTGCAG CTTCTGCCAG TGCTGGTCTA GCCGCTATGG AGAAACTTCC
26161 AACCAAGAAG CGAGGGAGGA AGCCGGCTGG CTTGATAAGT GCAAGTCGCA AAGTGCCGAA
26221 CCTCTCTGTG TCCAAGTTGA TCACCGAGGC CCTTTCAGTG TCACAGGAAC GAGTAGGTAT
26281 GTCTTTGGTT GCGCTCAAGA AGGCATTGGC CGCTGCTGGC TACGACGTAG AGAAGAATAA
26341 CAGCCGCATC AAACTGTCCC TCAAGAGCTT AGTGAACAAG GGAATCCTGG TGCAAACCAG
26401 GGGTACTGGT GCTTCCGGTT CCTTTAAGCT TAGTAAGAAG GTGATTCCTA AATCTACCAG
26461 AAGCAAGGCT AAAAAGTCAG TTTCTGCCAA GACCAAGAAG CTGGTTTTAT CCAGGGACTC
26521 CAAGTCACCA AAGACTGCTA AAACCAATAA GAGAGCCAAG AAGCCGAGAG CGACAACTCC
26581 TAAAACTGTT AGGAGCGGGA GAAAGGCTAA AGGAGCCAAG GGTAAGCAAA AGCAGAAGAG
26641 CCCAGTGAAG GCAAGGGCTT CGAAGTCAAA ATTGACCCAA CATCATGAAG TTAATGTTAG
26701 AAAGGCCACA TCTAAGAAGT AAAGAGCTTT CCGGGAGGCC AATTTGGAAA GAACCCAAAG
26761 GCTCTTTTAA GAGCCACCCA CATTATTTTA AGATGGCGTA ACACTGGAAA CAAGTTTCTG
26821 TGACAGTTAT CTATAGGTTT AAGTTGTGAT GCAGCTGAGT TGAAAAGGCT TGAGATTGGA
26881 GAATTAATTC AGGCCAGGCT TCAAGACCAT CCTGGGCAAC ATAGCCAGAC TACCATCTAT
26941 ACCAGGGGTC CTCATTCCCC CGGCCACCGA CCGGTAACCG GTCCCTGTCC ATGGCACGTT
27001 ATGAATTGAG CCGCACAGCT GAGGGGTGAG CGAACATTAA CCAACTGAGC TCCACCGCCT
27061 GTCAGGTTAG CTGCAGCATT AGATAGATTC TCATAAGCTC AAACTGTATT GTGAATGGCA
27121 CATGCAAGGG ATCTAGGTTT CAGGCTCCTT GTGACAATCT AATGCCTGAT GATCTGAGGT
27181 TGGAGCAGTT TTAGTCCGGA AATCATTGCT CCCAGCCCCT GCACCCCTG GTCCGTGGTA
27241 TAATTGTCTT ACACAAAACG GTCTCTTGTG TCAAAAAGGT TGGAGACTAC TGGTTTTACA
27301 AAAAAGTAAA TTAGTCAAGC ATGGTTGGCA CGCTCCCTTA GTCCCTGCAC CCAGGCGTTT
27361 AAGGATACAG TGAGCTATGA TGGTGCTACC TCACTCCAGC CTGGGTGACA GCGAGTCAGA
27421 CGTTGTCTCA AAACTTAAAA AAAAAAAAAG TTAAAACAGA AAAAGGGCTT CTTGTCAGAG
27481 ACTGCCGTAT ATCTAGAGGT CCAGGAACTA AAAAGTCTGA TGTCCAATCC TGAAAAGCTC
27541 GATGGTGCAC TAGAGGAGGC TTTTACATGT AAGAGCATCT AAGTTCTGGA AATGCCAGTG
27601 TCAGGGAAGG GAAGTGGAGA GCAATTTGGC ATCCAAACAT AACTTGCTGA TACTTTTTTT
27661 TTTTTTAACA CAAGTACTAC ATTCTAGTCT TTCTGTGGTG TCATTGTAAC TATTGTTTCT
27721 TAATATGCTA TCCACTGACT TCAAGGGATC AATAAATAGG AATCAAGGTG TCCCAGAATA
27781 TGGATTAGGG GAGTTTTTTT TTTGTTGTTG TTGTTGTTGT TTTCATCTAT TCATTATCCT
27841 GTAGCTGAAA TTTAGAATTT TCTTCCATTG TGTGTGACTG ATAGAAATAA CAAATTTGTA
27901 GGTTATAGTT GTTGCAAGAA TCTGGAAATC GTGCTTGCTT ATTTCCGAAG TACTATTAGG
27961 TATATCAACA AAAACACACA TATTACGGTC AAGTGGTTTG ATAATTATTT TAATATTATT
28021 GGTCTAATAC AATTGTAACC CTATGAATTA CTTTAAGTAT CTTATTTATG AAAAGAATCT
28081 GTAAGTTTCA TCAAACTACC AGAGCATACC GAAGACTGAA AAATTTTAAG AATCCAAACC
28141 TTAATGGAAA TGTTGGAGGC TGCCCAATTA GGTTCTGAAT TCCACCTTCC TGAATCACAA
28201 ACTTGTTTTA ACTCTCAGTC TGAGGTAAAC TACGTTTCTC TTTAAACAGA CATAGTTTAA
28261 TTTTCCTTTG ATTTTTGATT TAGTATTCTT ACTGATCATC ATAAATAACC AATGCTAATG
28321 TTAGTCTACT TTGGACCATG GTATTTCGAG AAACTTTGAA CAAAGTCCCC TGCAAAACTA
28381 TGCATTGCAT TATTTCACAT ACATTTATGT TTTCCAGACG GTTCAATAGT ACCTCACTTT
28441 TCTGAACTTA TTTGTATAGT TTGGCATCTT TTTAAAAATT GTGTCCTATA ATGAAAGGTT
28501 GTAAACATTA TGTTTTAAAT TTGTATAGAT AAAATCAACC ACAGACCTTT CCTTGCTTGG
28561 ATGTAATTGC CATTGTTTCC CAATGAGTTC GGAATTACTA GGATTGTGCA AAAATATGCC
28621 TCACTTGCCT GACATAGCAG AGAGCCATTT TGCCTAAATG CTGTGCCCAG CAATGGACTG
28681 TCACCAGATT CTCATCACAT ACAGTGAGGA TGAACAACTA GCCTCTCCCA GCAGCTGGCC
28741 GGTCTCTCAA TAATATGGGA CTCCCTCAAG ATGGCTTCCT GCACCTTTGC TCCTCTAGCC
28801 TTGTATGTAT ACAAGGCTAG CATGCCTGGC ATACATAAGG TTAAAAACAA AATCAATAAG
28861 TTATGGTTCT TCCTCCAGTT CTGGGGATTA TTAGACCACT TTTTGTTTT GTTTGTTTT
28921 GGATGGAGCC TCGCTCTGTC ACCCAGGCTA GAGTGCAGTG GCACAATCTC GGTTCACTGC
28981 AACCTCTGCC TCCTGGGTTC AAGCAGTTCT CTGGCTCAGC CTCCCACGTA GCTGGGATTA
```

Figure 2 (Page 9 of 74)

```
29041 CAGGTGCCCG CCACCACGCC CAGCTAATTT TTGTATTTTT AGTAGACGGG GTTTCACCAT
29101 CTTGGCCAGG CTGGTCTTGA ACGCCAGACC TCGTGATCCA CCCACCTTGG CCTACCAAAC
29161 TGCTGGGAAT ACAGGCGTGA GCCACCGCGC CCGGACTTAG ACCACTTTGT TTTGGCCAAT
29221 AGGACAACAG CCATAGAACC CTCCGCAAAT GAGAGCTTGT CCCTAAAGAT GCTTTATTTA
29281 CATAGCTGTG TGCCGCATGA GCCAAAAGGT GATAACCTTT GTTCAACACG CGCCTCCAGC
29341 CCTTCGGTTA AGTCCAAAGT ACCATTCTTA GAATGCTCTA AAATACATAA TTTTTTTTTT
29401 TTTTTTTTTT TTTTTGAGGA GTCTCTCTCT GTCTCCCAGG CTGGAGGGGA GTGGCGCGAT
29461 CTCGGCTCAC TGCAATCTCT GCTTCCGGGC TAGCTGGGCC TACAGGTGCA GACCACCACG
29521 CCCGGCTAAG TTTTGTATTT TTTTTGGTAG AGGGGGTTTC ACCATTTTGG CCAGGCTGGT
29581 CTCGGATTCT TGATCTCAAG TGATACACTA GCTTTGGCCT CCCAAAGTGC TGGGATTACA
29641 GTCGTGAGCC ACTGCGCCCA GCAAAATGCT TTTTGTGGAG CCAATCACTT TATTAGCGCT
29701 TACCTCTCTA TGCCTACTTT ATGCTTTGAA ATTTTGTCAC AGTGGGGCCG GTCATGGCAA
29761 ACACAATTCA TTCTTATGCA GGCTGTCACG GTTATTCTG TCATCCAAAC TCATTCTCGC
29821 AACGCATTTC AGCTCTTTAA ACGACTTTGT GAGCGGCCCT GAAAAGGGCC TTTGGGTTTT
29881 TTTGTTTTTG TTTTTTGAAG TTCTCAGGAG ACCGCGTATT CTTAGATTCA GCCGCCGAAG
29941 CCATACAGAG TGCGCCCCTG ACGTTTCAGG GCATATACTA CATCCATGGC TGTGACAGTT
30001 TTGCGCTTGG CGTGCTCCGT ATAGGTGACG GCGTCTCGAA TAACGTTCTC TAAGAAACC
30061 TTAAGCACAC CTCGAGTCTC CTCATAGATA AGACCGGAAA TGCGCTTGAC GCCACCGCGC
30121 CGAGCCAAAC GGCGGATAGC CGGTTTTGTA ATGCCCTGGA TGTTATCCCG GAGCACCTTA
30181 CGATGGCGCT TAGCACCACC CTTCCCCAAG CCTTTTCCGC CTTTGCCGCG ACCAGACATG
30241 ATTCCTATCG CAGTGGAAGG TATGAACTGA AACAGTTCCT TAAATACAAA CTTGGCGGAC
30301 CTGATTGAAA ACAACATGAG TTGGCGCGGT TTTTTTTTTT TTTCAAATTT GGTCACCGAG
30361 TGGGTGGAGC AAGAAAAACT GTTTCATTAT GGTTCATTGT TTTGATTGGC CAGTGACAGC
30421 TTGCTCTTTG TGGGAGTGGA AGGGTGTTTG CAAGTTGAAT GCGCTGTATT CCTGTCAGCT
30481 TAATGACGCT AAGCATAGCC CCATTCCACA TTTCTTTTTA TTTCCACTTG CTAACTAATA
30541 AATTACGAA TAGTTTATTG GGAACATAC AAATAATGTT TAAAGGAGGT CAGATTTATA
30601 GGTCAAGGGA TTTACCCTCC CAATCATTTT AATATTTTTA TTTAAACCAG GCATTTTGAT
30661 GGCCTTCTCT GTGCTGGACA AGGTATAAGT TTGGCTATGA AGTTTCACTC CTAAAGACCC
30721 TATGTTTTGG GAAGGCAAAA AGGTAGCCAA ATAATTGCAA ATTAAAACCT CATAAGTGCA
30781 AACTTCTTCC TCGTCACTTT CCCTATCTCG ATTCAAATAT TTGTTGAATG ACTCATTTTT
30841 CTGCAAAAGT CTGAGAGAGA CAGGGAATAT AAACTTAAGT CTGGATAATA TGTTTTCCCG
30901 GGACGCTCTT CCTGGTCTGC TGTGCCTGTT TGCTGTGCCT GAAATTCCAA ACACTCTTCC
30961 CTTCCCTCCG TTTTTAATCC CCTTTCAACT TGCTACAGCT TTAGAGAAAA GAACATACGT
31021 TTTGTACAGT TGGGGATTAA TTGAAGTGTA GGGCTAAATAC TTGATTAAGG TCATTACAAA
31081 ATCTACAGGG TCTTCCTCTG GGAGGTTTTT GTGATAAGAT TATTGGTGTT AAAATAAGGC
31141 TAATCCCCTT GAAAAATAAA TAGAATAGCA GAATTGGGTC TGAATGTGGT TTGAAGAAAG
31201 GGACTTCTCA ATTCAAAATT TTATTCTTAG CTTCCTGTGG GAGCTTTCCA GAATGCCCAT
31261 AAGATCCACT TTTGTTTAAA AAACAAAAAC AACCCCACCC ACCACTCTCT GGTTAATAAA
31321 TGAATTTCTA TTGGGAATAT TTAGAATGGG GCTGTGGCCT GTGAGAGACA TTATATAGTA
31381 ACCTCAGACT TGCTCACATG AAGAGAAGAA ATCCAGGAAT GGAGAAAAAA GACCCAGGAA
31441 AGGCCAGAAT GCTCTACATG TCATATTGTT TGTATCACTT CTGAAATAAT TGATTACATT
31501 CTTCTGCCCC AAATTGAGTT CTTAGGTTCT TCCACTCACT GTCCACATGC CACAACACAG
31561 ACCTTATAAC TAGAGACTTA GCTAGGAAGA AATGTCAAAC ATTACAGAGA AAAAATGCAG
31621 AGTCTGAGAT CATAAGTAAA ACTCTGAAAT CTCAACATGC CTTTTAATTC ATGAAAATAA
31681 AAAATATAGC AGCATATGCA ATATGATAAT TCTCTGAAAA CATACATCAT GTGAACTACC
31741 CTGGAACACA TCTCGCCAAG TGCCATCTTC ATTTTAACCA GAGGTCTAGG ATGCCTTTCC
31801 TTTATTTTGC CTATTATATC ATTTATAAAA CCCCATTTTT ATTTGATAT TTATTTACT
31861 TTCTATTTCC TGCTCCTAAT ATCTCCTTTC TAAACTTTTC TCAATGACAG TGACTCAAAA
31921 ACAATGAATG TCAGAACAAA TATTTAAAGG ATCTGTACAT GTAGATATAT ATATTTAAAA
31981 TGGATTCTTC CACTCTGGGA AGAATTCAGG CATACTCAAT CTTATGGTTA GGGAGAGATT
32041 AGGCTCACTC GCCTAATCTG TATGGCTTCT CGTTCGCTTT CCATTTCACC TTCCTCTCAC
32101 CCATCAGATC AAACTCATTC ATTGAACAAG AGACCTAAGC CCTTCAGATT AAAACTCTGC
32161 AAACAAGTTG TGGTTGAGAG GATACATGAA GCATTCAAAC AAATAAATCT ATGATATTAA
32221 TCAGAGGTTA ATCTATGATA TTAATCAGAG GTTAATGCAG TGGCTCACGG CTGTAATCCC
```

Figure 2 (Page 10 of 74)

```
32281 AGCACTTCAG GAGGCTGAGT TGGGAGAATC GCTTGAGCTC AGGAGTTCAA GACCATTTTG
32341 GGCAACATAG CAAGTCTTCA TCTCTACTTA AAAAAAAATA ACCAGAGGTG TTATGAAAAT
32401 ATAAATTGTC CAGAACTACC CTCCACAAAC TAACTCTCTC AGAATATTCG ATATGAGGAA
32461 TGAAATATGG TGTGTGTGTG TGTGTGTGTG TATGTGTGTG TGTGTGTGTG TGTATGCACC
32521 TATATATGGC ACCTATATAT TCAACAAACA ATTCTGATAA TTGGCCAGGG TTGAGAATGA
32581 CTAGCAGCCC AGCATACACT ATCAGTTTTA AGTATATAAT TGCGCTTTAG TAAAATGTAA
32641 AGAAATCCCA GAGTAGAAAT ACTTTTAAGC TATATTACAG GTGAGAAAAT GCATAAGTAT
32701 AGTCTCACCC AACTTAGACT ATGGGGCTT TATAATGTCA AACAGTTGT TTCCAGGCAT
32761 TTGGGACAT CACCACTGGT CTTGGGCAAG AAACTCCTCT AGCCAATGGC TGATTTATCT
32821 CACTCCCATC TAAGGCTTCA CTGCATTTCT CTTTTTCAGC AACCTAACTT ATTTAAAAAT
32881 ATCCATTTTC TGATTCATTT TTTTCTGAAT TAAACTGTCA GTACCATTGG CACACCTTTG
32941 GTTCCGTAGC ATACCTGTGT CTCTGCTGTG GTTTTTTTTA CCTCCACTCC TTACTTTTCT
33001 AGAAAAAAAT CTCTGCTTTT TCTTTTCAGT TTAAATTATT TCACAAAAAG TTTTCTTGAC
33061 TTGCACTTCC TAGGCTTGCT GTCCTTGTGT GGGCACGCTC CCATAAACAC TATTAATACA
33121 CTTCGATTTG TTAAAAATAA AGATATCTGG ACAGAAAATT TCTTTTCTTT TTTTAAGATT
33181 TTAAAATTTT TAATGTTTAT TTTTTTCCTA GACTGGAGTA CAGTGGCACC ATGATGGCTC
33241 ATGGTAGCCT ACACTTCCCC GGGCTCAAGT GATCCTCCCA CCTCAGCCTC CAAGTAGCT
33301 GGGACTACAG GTGTGCACAA CCACACCTGA CTAATTTTGT TTATTTGTTT GTTTTGTTTT
33361 TTGAGATGGA GTTTCGCTCT TGTTGCCCAG GCTGGAGTGC AATGGCGGGA TCTCGGCTCA
33421 CCGCAACCTC TACCTCCCAG GTTCAAGCAA TTCTCCTGCC TCAGCCTCCC GAGTAGCTGG
33481 GATTACAGGC ATGCATCACC ACGCCCAGCT AATTTTGTAT TTTTAGTAGA GACGGGGTTT
33541 CTCCATGTTG AGGCTGGTCT GGAACTCCTG ACCTCAGGTG ATCTGCCCGC CTCGGCCTCC
33601 CAAAGTGCTG GGATTACAGG CGTGAGCCAC CACGCTCGGC CACTAATTTT GTATATTTTG
33661 TAGAGATGGG CTTTCCCTGT GTTGTCCAGG CTGGTCTTGA ATTCCTGGGC TTAAGTGATC
33721 TGCCCACCTT GTCCTCCCAA AATGCTAGGA TTACTGGCGT GAGCCACCAG GTCTGGCTGG
33781 AAAGATAATT TCTAACATTA TCCTCTCTTA AACATTTGTT TCAAAAATTT TACAAACATG
33841 AGAGTAATTA AATTTGATTT TCAAAATTCC CTTGAATACT TTCTTAATAG CACACAGAAA
33901 GCACAAAGTA TTTTACATTT GTTTTAATGA TGAAATTGTG AACCCAAACT TACACAAAGA
33961 AAAACCGTAA CATTATACCC ATACTTAAAA CAGATGCCCT CATATACATA GTAAAACTCT
34021 TGGGGGCAGT AGTGAAGTTG GTTATTTACT GTTTTATGAA AGTGCCATTC AGCCGGGTGC
34081 AGTGGCTCAT GACTGTAATC CCAGCACTTT GGGAGGTCGA GGCAGGCTGA TCACGAGGTC
34141 AGGAGTTCAA GACCAGCCTG ACCAAAATGA TGAAACCCTG TCTCTACTAA AAATACAAAC
34201 ATTAGCTGGG CGTGGTGGTG TGTGCCTGTA GTCCCAGCTA CTCAGGAGGC TGGGGCAGGA
34261 GAATCGCTTG AACCTGGGAG GCGGAGATTG CAGTGAGCCG AGATCGCACC ACCGCACTCC
34321 AGCCTGGGAG ACAGGGCGAG CTCCGTCTCG AAAAAAAAAA ACAAAAAAGT GCCGTCATAG
34381 TGACTTAGTT TTAAGGAATA AATCAAGGAT ATTTAACTCA ATAGACTACA GTTAGCTAAC
34441 GTGACTTGCA CTGAAAGTTA TACGAATATT GGTACTTATT CCCCTGCCCC TGAAGTATGA
34501 ATTAAAGACT CCAAAATTCT TTTTAGAATC TTCAGAGTAA AAGCTAGAAT TTGATTTTTT
34561 TAAATAATAA AAAAATACTT TGTATCTAAA TCTGGTGTAT AAAATAACTT GGTGGATGAT
34621 GCTTCAAGGC TATCCATCCC CAAATTTCTC CCTGAATGAT AAAGAGAATA AATGAATATG
34681 TCAATTCAAA AGTTAGAAAT TTGGCCGGGC ACGGTGGCTC ACTCCTGATA ATCCTTTCGG
34741 ACGCTGAGGT GGGTGGATCG CATGAGCTCC GGAGTTCAAG ACCAACCTGG CAACATAGC
34801 CAGAACCCGT TTCAATAAAT AATAGAAAAA AATGAGCCAG GCGTGGTGGT CCCAGCTACT
34861 CAGTAGGCTG AGGTGGGAGG ATCACTTGAG CTCAGGAGGT CGAGACTGCA GTGAGCCGTG
34921 ATCGCAGTAC TGCACACCAG CCTTGGTGTC AGACTGAGAC CCTGTCTCAA CAACAACAAA
34981 ACAAGTTAGA AATTTGGCTG GGCGCGGTAG CTCACGCCTG TAATCCCAGC ACTTTGGGAG
35041 GCCAAAAGG GCGGATCATT TGAGGTCAGG AGTTCGAGAC CAGCCTGGCC AACATGGTGA
35101 AACTCCATCT CTACTAAAAA TACAAAAAAA CTTAGCCGTG CATGGTGGCA TGCGCCTGTA
35161 GTCTCAGCCA CTTGGGAGGC TGAGGCAGGA AAATTGCTTG AACCCAGGAG GCAGAGGTTG
35221 CAGTGAGCCG AGATCATGCC ACTGCATTCC AGCCTGGGT ATAGAGTGAG ACTCCATCTC
35281 GAGAAAAAAA AAAAATTCT GTATGAACTG AACAAATAT CCTTAAATTT TAAAATACAT
35341 CTGAAAGATA TTTCAAAATA TTTAGGAAAA AAATTATAGG GATCAGGCAA ATTCTGAGAT
35401 TCCTTTTTCC CTGCAGCAAA CATTAGGAGT GCTGCTGTTC CTAAAAACAT GGTAACTGTT
35461 GCCACACCGT ATGTTTCCTT GGCTCAGACA TAAGGTTGTG TAGTTGTTAT TCCAGAATAG
```

Figure 2 (Page 11 of 74)

```
35521 CTAGAATAAA AATCCAGCAC ATCATTTTCT TCAGCAAGTT AACTAACCTC TCTGTGCCTT
35581 GGTTTCATAA CAGCAACATA AGCATAACAG AATAGCAGCA ATAGCTCCTA CCTACCTCAT
35641 AAGATTCTTT GGAAGAATTA AATTAAGATT CAGAACACAG CCTAATATCT AGTAAGTAAT
35701 AATAATTGGC TAAAAAAATT TTCTTAAGAT TATATATATT CATGGGGTAC AAGTACAATT
35761 TTGCTACATT AATATATTGC ATTGTGGTGA AATCAGGGCC TTCAATCCAT CCCGGAAAAA
35821 AAAAGTTTTT GAAAGATTT CTGCCATGGA AAACTTTTAA TGTACAAATT CATCCATCCA
35881 AGAAATAGAA AATATATAAG TATCAACTCC AAATCCACCA TATCTATCTC TTCTGCACCT
35941 TAAACAATTA CTCAGAAATA GAATGCTTGA GATACCAGAA TGCATGCATA TCAAGTAATA
36001 AATGCATGCA GGATGTCAAC GCATCCTAGG CTTTCAAATA AAATTGTCAT ACAAAATACT
36061 TTAATATTGT AGTAACATTC TACATGTTAG AGTGTAGAAG TTAATCGCTG ATGCAAAAAA
36121 GGAAAAGAAC ACATTATACC CAAAGCCTAC AGAGAGAATC ACAATTACAA ATATCAGCCT
36181 GCATGTGAAA ATCTTTAATT TGAAAGTCAG AAATATTTAA ATGATAGTCA TTGTTAAATC
36241 AGATTGTGGT TTGAAAAAAA GTTAGTTTAA AACTGAGTTT ATGAAAAATT TGGGGATTTT
36301 AGAGACAGTG TTTTGTTTTT AAATGTGTGT GAGTTTGTGA AGAATGTTTT ATAAAATACT
36361 GACAGTATTA TAAGATGACA TTATTATAAT ACAACATAAG AATTTTGGCC TGTACCTCTC
36421 AGCAGTCCTC AATCACCTGC TGTACTTGAC TCAATGATTA TCAGAGTGGT TTGTTTTCCT
36481 TCTGTTGTGT TCCCAGTTCA GGCAGCTCAG CAATGGCCTG TGATTCCAGC AATTCAAATA
36541 GCTGGTAAGT AGTTTCTTGT TTGTTTTCTC AAATTTTCAG GGGCTTTTCT CTACAAGTGA
36601 TTTCCAGTGC ACGCCCCTCC ACCCATTCTT TATTCCTTTA CCTTCAGGAA AACCCTCAGC
36661 GCTGCATCTC TGGTCACCGG ACCACCGTGG TACATTTACC TATGGCCACC AGGTGTCACC
36721 CTTCTCTTTA CTACCATGGT TTGTGAATGG TTTTGCCAGA GGTGAATAAG AATTTAAAAT
36781 GCAGGTCTTT GATTTTTCAA ATGTAGTTGA CCTTAAGAAT TTATGAATAA AGCCAGAAAA
36841 ATTAAGCTTA AAAAACACCG AAAGAAAATG AGGACTTAAA ATTTCTATTA AAAAAATTAA
36901 CAGGCCACAG TTGCTGATGT TTAGTAAATG TGTTAGTGAA ATGTGTTACT GTGAAGACTG
36961 GGGTGTTTCT TGAAATCTCA GCCCAGGTGA AATAAAACCA ATATAAAACA AATGCTTACC
37021 TAATAAATTA ATTGTAACAT ATTCCTTATG AGGTAGAAGA GTAAGTGAAG CCTTATAGCA
37081 GTCTGCTTTC AGTATAGTAA GATATTAAGA GAGAAATAAT TTGTCATATG CTTTCAGAAT
37141 GGTTTGCTGG TAAAATAACC AATGTCTTAC AACTTAGACG ACAATGTCCC TAGAGTGAAG
37201 AAACACGATT AATTCGGCTA CCACAGTTGA ATGAAAATAT TCCGTAAGAC AAAATGTAAA
37261 GAAATTAGAA GCAAATAAA TGTCTCCAAA ATGACAAAGC GATTAAGTAT ATACACAAGA
37321 TGAACAAGAA CTTCAATAAA ATCATGCAGT ATACAATACA ATGTACATTT ATTAAAGTAT
37381 ATGCATTTTT AATGCAACAA TAATACTAAC AGGTAATAGA CAAGTTGTTA ATAGTTTTTC
37441 ACTGGCTAAT TAAATAACAG CTTTAATTGT ATTCATTTTA TAGCTTTTCT ACAATGAGCG
37501 TAAATCACAT TTACTTTTTT CTACATAACT TTTCTAACCA CAAAAAAAGA AAATGGTTTA
37561 AAAGAAGAGA TGAGATATCT TTGCTAAAAT TTAATGCCTA AGAAGAAAC TTCTGAGCTG
37621 TATATGGTAT CCTGAAGCAC CTGCCCTTCA AGACAGAATG CTTGTACCAC ATTTATGCAG
37681 CCAAGTGCAT GTAGTAACAT AAAGTAAACA CATGCCATCT GGATATATAT ATTAAGACTC
37741 TTTTGACGGC TGGGCAGGGT GGCTCACACC TGTAATCTCA GCACTTTGGG AGGCCGAGGC
37801 AGGCGGATCA CGAGGTCAGG AGAGTTCGAG ACCAGCCTGG CCAACATGGT GAAACCCTGT
37861 CTCTACTAAA AATACAAAAA TTAGCCGGGC ATGGTGGTGC ACGCCTGTAA TCCCAGCTAC
37921 TTGGGAGGCT GAGACAGGAG AATCGCTTGA ACCTGGGAGG CAGAGGTTAC AGTGAGCCGA
37981 GATCATGCCA TTGCACTCCA GCCTGGGCAA TAGAGTCTCA AAAAAAAAA AAAGACTCTT
38041 TTGAACATGG TGAACTGATT TCCAGAATC TAGCAATTCC TGAATGTCCT GGTTAGATTT
38101 TTTTTTTAAT GTGCACCGGA ACCCCAGTGG CTCCATGGAA GGACCTGGGC ATCCTCTAAG
38161 CCACTTGGTG GCTTCCATTA TACCATCTCA AAATGAGAGA GCTTACTCCA CTTCATTGAG
38221 GGAAATACCA CCAGAGTTCT GACTCCAGAG GCACTGGCCT AGGGAGGACA CCGTGTGTGA
38281 AGCCCAGCAG GGCCACTAGC TGTCCCCACC AATTACAGTC CTTGCGTAGG GTCCAAAGAA
38341 ATGAATGCCA AAGAGAGCAA CAGAGGAGCA AGGGAGTCAC ATTCCAGGAC CTTCCTTCAG
38401 GGACTTTTAA AGGAAACATG ACAGCTGAGG ATCAGTTGGT TGTTTCTGC TGTTCCCCTT
38461 CATGTGATTC AAGCTCATTC AGAAGAAACA CAATGAGACA AGAGAAGAGC CATCTCCTTC
38521 CTTCTCTATT TATTCTAGGC ATCTAAACTA CTGAATGTAG TGGTGTCTGA GATGTATCAA
38581 ACGGTCAGAT TGACTGAGTT TGAAACCTGT TTCTATCACT GACAAACTAT GAGATACTCT
38641 ATACTTCACT TTCTTTTTTT TTTCATTTTT TTATTTTTAT TTTTATTTTT TTGAGATGGA
38701 GTCTCACTCT GTCACCTAGG CTGGAGTGCA GTGGCGCAAA CTCGGCTCAC TGCAAGCTCT
```

```
38761 GCCTCCTGGG TTCATGCCAT TCTCCTGCCT CAGCCTTCCG AGTAGCTGGG ACTACAGGCG
38821 TCTGCCACCA CGCCCAGCTA ATTTTTTGTA TTTTTATTAG AGATGGGGTT TCACCATGTT
38881 AGCCAGGATG GTCTCGATCT CCTGACCTCG TGATCCACCC GCTTTGGCCT CCCAAAGTGC
38941 TGGGATTACA GGCGTGAGCC ACCGTGCCCG GCCTACTTCA CTTTCTTCAT TTAAAAAGA
39001 AATGGGGATA ATAGTACCTA TCTCATAGAA TTATTGTAAG AAGTGCATGC AGTAATGCAT
39061 GTAAGTAGGT GCTCAGAAGA GTCGGACACG AAGTAAGTGC TTTTATCATC CTTATCATAA
39121 TTTTCATTAT CAGAACAAGG AGAGACCAGG TAGAAAATTA TTGTGATTCT TCAGGTCTGG
39181 AATACTAGAG TAGCATCCCA AATGAAGGCA CCATTAAACT TTGCAAATCT GTATGACACC
39241 TTCATGCCAA TTAGAAAAAA CACCTCTTCA CAACCCCTTT CAAGATATTT GCCTCCTACC
39301 TGCTAAAAAC ACCCATCATA CTACCCACAG ATAGCCATGA TGCTTTTTCT GGGACAGGTG
39361 CCTCTTCCAT TCGTGCAGTG TACAGCCTTC ATAGCTGTGC AACTCACATC ACAATCAGAT
39421 GGAAGAATCC CCAAGGCTTG GTGACAGATG AGTTACTGGG TAACACAGAG AGAGGATTCA
39481 AAGGAAAAGT TGAACGGGTC CAGAAAATGC ATAGATACAT GTGTAAAAAT CTGGTAAGGT
39541 TATGACTAGC CACGTCCAG GGTTCAAAGC TTTTCTCAGA TGTTAAAATG AATCATGTAA
39601 GTCCCCCAAA TTTAAGGAGT CCTCTTCCAA AAATAGGAAA TGAAATGACA TAGGTGTATG
39661 TCTCTGAGGT GACGGAGGAA ATGAAGGAAG CCTCTAGATG CAGCTTGAGG TTCATGAGAG
39721 ACAGTTCCAG GGGAGAGGTC ACAGCTAGGG ATCACCGGCA TGCAGGAACT CAGAAACCTA
39781 AATGGGGAAA TCTTTTTGAG GAAATGAACA GAGAAGGCTA AAATCAAGGA GTTCGTCAGG
39841 CAATTTCTAT GTTTAGGTTC AACTCTCTCC TGAAACATGA AGAGCTCATA AATGCACTCC
39901 CTCTTTGAGT CTCTAGTTTT GTCTCCTTCC CACAGTGAGT CTGCAGGCTG CGTGTCACTC
39961 ACGTTCAGCT AAGACGTAGT GCCCCATGGC TCCTCCTGTG GAGACAAGAG ACCCAGGAAA
40021 GAGGCATCAC AAACCTAGGC ACCATCTTGC CTCTTCTCTC TTCCTTATTT TCCTCATTCA
40081 CCCATCTCAA TTTAGACCTG GCACTATTG GATTTCAAGA ACCATTATCT CTCATCTGGA
40141 AATGCTTATT GGCTTTCTAA CTGGTCTCCT CACCTCTCAT CTAACTTCTT AACAACACAT
40201 TCACCATATA AGGGAGATCG TGGTCCTCCT TTCTTAGGAT CCTTCAATGA CACCCCAGTG
40261 ATCATAACCC AATATCCCAA AAGACCCTTG GACTCTGTAT GAGCTGGCTT CTTTCTGATT
40321 CTCTTTTCCC TACACCACAG ATGTTCAGGG GGTAGAAATG CATAATTGGT GAGTGATAGC
40381 TAAGCAAACT CAGGGTTAAG GTACAGTAAT TATTTCTAAT CTCCCAGTAT GCCTTATACT
40441 CTCCTACTTG GCATGGTTGC TCCGTCTGTG TAGACCTCCC ATCATCTTCA ACCTCACCTA
40501 ATGGAATCCA GCTTCTCCTT CAAGATCCAG AAGGCTATCT TGATCCCCAG CTGAATGTGA
40561 TCATTCTTTC CTTTGACACC CTAAGCATTT GCTTCCTGCC TGCTTTAGGA CCTCATGGGG
40621 TCTTCTTTAA CTACATTTAC TTGCTATCAA TTTCATTCCC TACCAGATTT GGGTTCTGAG
40681 AATAGCCACA GTGACTTCTC AACCTCAAAG CCCCTGTACT ACCTTAAACA GCTCTTGCAA
40741 AATAGTAGGT GCTCTGAAGA TGTTTGTTGA ATTAGAGACT TTCATTCTGG GGAGAACCAT
40801 TATTTTCTGT CTCCCAGGGA GCTGCTGGTG TCCCCAAAGA ATATAAATGA GAAAAATGCT
40861 TCCCATGGAT GCCAGATCCC CTCTGCCCCT CTTCCCACTG TGCCCTGGGG CAGAGGTACT
40921 AAGAGACTTC CCCCTTGTTC CTACTCACTT GAACCCTGCC TCTTCCTTAA TATTATGAAC
40981 AAAATTCCAA TGAACAAGAT GACGACAAAA ACAGCAATTC CACTGATGAC TCCAATGACT
41041 AGGGTGCCAG ACGGTGAGGG CTCTAAAACA GAAAAAGCAA GTTAAAGCCT TTGATTGCCA
41101 CCCTCAGCCC ACCCCCTAAC AAAGAGCAGA TCCTCATCTC ACTGCCATAA TTACCTCCTC
41161 AGGCACTCCT CTCAACCCCC AATAGATTTT CTCAGCTCCT GGCTCTCATC AGTCACATAC
41221 CCCAGATCAC AATGAGGGGC TGATCCAGGC CTGGGTGCTC CACCTGGTAC GTATATCTCT
41281 GCTCTTCCCC AGGGGGTACA GCCAAGGTTA TCCAGCCCTG GTAGGTCCCA TCCCCATTGG
41341 GCAATACGTC TTTAGGTTCG AACTCCTTGG CATCCATTGG CTGCTTATCC TTCAGCCACT
41401 TCATGGTGAT GTTCTGGGGG TAGTAGTTCA AGGCCCGACA CCGTAGAGTG GTCACTGAAG
41461 AGGTCACATG ATGTGTCACC TTCACCAAAG GAGGCACTTG ACAGGAAAGA GGAAGGATGA
41521 GGAGAGGGGA TCTGTTTACC CTTGCCAGGA AGACTGGAAC TTTCACTTCC TTCTATAGGT
41581 TGGAGGAAGG AAATACCCTT TTCAGAAAAA AACAAGCTAC AGGAGAGACA CCATTTTGTG
41641 TCCTAAGATT GGACTCTAAC ACAGTGTCAC TTGGAGAGCA GTCAGATCAG CTTGTTCTCC
41701 TCACATGTAA ATATACATAT CTGTTACCCA TGTTCTTTGT TCTGATAGAT AAAATTGCCC
41761 TTTATGTGCA TTGAAAATGA TTGAATACAG ATGGTCAGTT TCACCTGGGT CAACCTAGGA
41821 GGCATTGTTA TAAGAAGCGG ACTTGTAAGA TAGGTAGCTT CAGTGATTAT TGCTATGTTC
41881 TATGAAAGAA ACTTTTAACC TAAAGGATTC TTCTACTCTG ATAAGTGGCC TCACTTGATA
41941 TTTTGTCCTG GTATTCATAT GATAGCTGAG ATCTCTGAAT TCTCTTTTTT TTTTTTTTTT
```

Figure 2 (Page 13 of 74)

```
42001 TTTTTAAGAT GGAGTCTCAC TCTGCTGCCT AGGCTGGAGT GCAGTGGCGC GATCTTGGCT
42061 CAGTGCAACT TCCGCTTCCC AGGTTCAAGC GATGCTCCTG CCTCAGCCTT CCAATTAGCT
42121 GGGACTACAG GTGCGCATGA CTGTGACCAG CTAATTTTTG TATTTTTTTA GAGACGGGTT
42181 TCACCATGTT GGTCAGGCTG GTCTCAAACT CCTGACCTTG TGACCACCCG CCTCGGCCTC
42241 CCAAAGTGCT GGGATTACAG GGGTGAGCCA CCGTGCCCGG CCTTGACATT TCTGAATTTT
42301 TAACAGGTAT AAATATACAA AAGATTATTG GTTAAATAAA AAGCAAGGGC CATAGACACT
42361 TCCCTTTGAG CCATATGCAT GGAGAAAAGA AATTAAACCC ATGACTTGTG GCTGTCTCAT
42421 ACATCTCAAT TATAAGGTAG AGACTCTAGG ATTGAGAAAG TCCCTTCCCA GAATTTGGAG
42481 AGGCACACAG CCTCAGCCAC CTCTGAAACT CCAACCAGGG ATTCCGTGCC CTGCAACCTC
42541 CTCCACTCTG CCACTAGAGT ATAGGGCAG AAGTGTGTTT CCACCATACC TTGTTGGTCC
42601 AAAACACCTC TCCCCAGCTC CAGCAACTGC TGCAGCTGTG CAGGGCAGTC CCTCTCCAGG
42661 TAGGCCCTGT TCTGCCTGGC CCGAATCTTG TGCCTTTCCC ACTCCAGCTT GGTGGGCCAG
42721 GCCCTGGGTT CTGCTGCTCT CCAATCCAGT GTGTCAGGGC AGAATTCAAG GTGGTCCTGC
42781 CCATCATACC CGTACTTCCA GTAGCCCTCG GTACTGTTGT CTTCTTGCAT TTCACAGCCC
42841 AGGATGACCT GCAGGGTGTG GGACTCTGGA AAAATCCCCA GCCTTGTTAA CTGCAACCAA
42901 AGGAATAGGT CCCTATTTCC ACCATCCCCA AGGACCAAAT GATCTCAGGA AGCAAATTCC
42961 TTCCCTCTTC CCTGCTCCCA CAAGACCTCA GACTTCCAGC TGTTTCCTTC AAGATGCATG
43021 AAAAGATGAA AAGCTCTGAC AACCTCAGGA AGGTGAGGCC CCCTCTCCAC ATACCCTTGC
43081 TGTGGTTGTG ATTTTCCATA ATAGTCCAGA AGTCAACAGT GAACATGTGA TCCCACCCTT
43141 TCAGACTCTG ACTCAGCTGC AGCCACATCT GGCTTGAAAT TCTACTGGAA ACCCATGGAG
43201 TTCGGGCTC CACACGGCGA CTCTCATGAT CATAGAACAC GAACAGCTGG TCATCCACGT
43261 AGCCCAAAGC TTCAAACAAG GAAAGACCAA GGTCCTGCTC TGAGGCACCC ATGAAGAGGT
43321 AGTGCAGAGA GTGTGAACCT GGAGACAGAG CAACAGGCCT TAACCATGTG TAGTAGGAGG
43381 GGAGCAGGAT GTTGAGGCTC CACACACCTG CATCAACTCA TACCATCAGC TGTGTCTGGT
43441 CCTCATTTTG TGAAGGGTGA GTTGCAGTCC TGTCTTTCTT CCATATGACA GTCCTGGGTG
43501 CTCTTTCCTT GTGTGCTTTT CTCTGCCACA CGTGGCTGCC ACCCCCTCAC TGCCCCCAGA
43561 TCCTATTCCA ATACTCATGA TTAGACAGAC TCCACTAAAG CTGGTGGATT CTAGAAAATG
43621 TTAAGGTGTG TCTAGCCATG GTAGTTGAAC TCAGGAGTTG GTGCTCAGGG CAAATTAGAC
43681 CCAAATCCTG AGGAATAATT CCTTCAGTTT TTTTTTTTTT TTTTTTTTTT TTTTTTTTTT
43741 GAGACAGAGT CTCACTCTAT CACCCAGGCT GGAGTGCAGT GGCACAATCT CAGCTCACTG
43801 CAACCTGCAC CTCCTGGGTT CAAGGGATTC TCCTACCTAA GCCTCCTGAA AACCTGGGAC
43861 TATAGGCGTG CGCCACCACA CCAGGCTAAT TTTTGTATTT TTAGTAGACA TGGGGTTTCA
43921 CCATGTTGGC CAAGCTTGTC TCAAACTCCT GACCTCAAAT GATCTACCTG CCTCAGCCAC
43981 CAAAGTGCTG GGATTACAGA AGTGAGCCAC CGTGCCCAGC CTTGGTCCTG AATTCTTACA
44041 CTGAACTGCC TATGTGGCCT CACCACTTGG AAGCCTGACT GGAATCTCAA ACTTAACATG
44101 TCCAAATGCA GATCCTTGAT TTACCCCAAA CTGCTCTTTC CTCTGCCTTC ACCATCTCAG
44161 AAATGGCATT GCCAATTACC CCACTGCTCA GGCCAATAAA ATTAAAATAA AGAACAAAGT
44221 CAACTTTAAC TCTTCTCTTT TTCAGGGGGT CAGGGGAGAC AGGGTCTTGC TCTGTCACCT
44281 AGGCTGAAGT ACAGTGGCAC AGTCATGGCT CACTGCAGCC TCAACTTCCT GGGCTCAAGC
44341 AATACCCTCC ACCTCAGCCT CCCGAGTAGC TAGGATCACA GGTGCATGCC ACCACACCCA
44401 GCTAATTTTT GTATTTTTTG TAGAGAAGGG GTTTTGCTGT GTTGCCCAGG CTGGTCTTGA
44461 ACTCCTGAGC TCAGGAATCT GCTCTCCTTG GCCTCCTCCT TGGCATGAGC TACTACACCC
44521 AGCCAATTCT TCTCTTTCTC TCACACAACA TAGAATCCTT CAGCAACTTC CTTCAGAATA
44581 TATTCAGGAG ACAATGGTTT GTCACTCCCT TTTCTGTTCC CACCCAGCCC ACTCCACTAC
44641 CTCTTGCCTG GACTGTGTAA CAGCTTCCTG GCTGGGCTCC CTGCTTTTAC TGTTGCTCCC
44701 TTCATTCTGC TTTCCACATA GCAGCCAGAG CAATCTTTTA AAAGCCTGTG ACAGATCACT
44761 GTTACTCCTT GGCTAGAATT CACACCACAG CCTACAGGCG CCTGCACAAC CTTGTTTGTG
44821 GCTCCTCTTC TGAGCCCATT ACCTACTTCT TGGCCTCTAC TCCCCAGCAC TACTTGTTTA
44881 TTTTTTTCAA CCCGAGCTTC TTAACCAGGA GTTTGTCTAC TAGGTGACAT GTGGCAAAGT
44941 TTAGAGACAT TTTTGGTTGT CAAGACTGGG GGAGTGCTCC TAGCACCTAG TGAGTAGGGA
45001 GGACAGGATA CTGCTAGACA TCCTACATGC AGATGGTAGT CCCCCTTCCC ACCCCACGC
45061 CGCCCCCCCC CCCACACACA CACACATGAG TAGTGCTGAG AAAACCCGCT TTTTAATCCA
45121 ACTTGCCAGG CCCACTCAGT TTGCCTGGGA AATACTGCTC CCAGTCAATA TCATTCTTAT
45181 TTCCTTCATG TCTCTGCTCA AGTGTCAGCC CCAGAGTGAC TTGCCCTGAC TTCTCTGCTT
```

Figure 2 (Page 14 of 74)

```
45241 CTCACAACAC CCATGATTTC CTGATGTTGT ATATCTTTCT GCTCATTTGC TTATTGTCAT
45301 CTCTCCCACT AGAATGCAAA ATATCAAAGG GTAAAGACTT GTTTCCCTGC TCTCTCCCTT
45361 GGGGCTTGAA CAGTGCAACA CATGGCTGGG ACTCATTTAC ACTTGTAAAC AATGAATATT
45421 TCTGCTCAAC ATGAAATTTT ATTATTCAAC CTCTAATGCA GTGTGATGTT TAAGAATCAT
45481 AGCTATGAAG TGGAGACATG AGCTCTGCCA CCAAAGCCCC GTGTACCATT GAATAAATTT
45541 GCCAGGAAGC AGGCCGTGCC ATGCCTCATT CTTGTCATGT GTAAAATGTG GATACACGTA
45601 GTACCAAAAC TCAAAGTGCT GTGCTGAGGC CGGCGTGTGA CCCACAGAAC ACTGTGCTAC
45661 ACTACAGGGC AAAATCACTG TCAACTAAGA TTAGAAGCAG CTGTAGTACT TGAAATAACA
45721 TCAGAAAACC AGATTATTTA TGTTCTTTGT AACCTGAAAA GAGTTATATA ATCTGAATTC
45781 CAGTTAACTT CTAGTAAAAT AAACGTATTA TTAGCTCCTA CCTCCCTATG CCTAGTGAAA
45841 ATCAAATAAG ATCAGATATG AATGTAACTT AGAAGTGAGT GCATTGCTTA CATGTTCATT
45901 ATCAGTACTT TGTAGAGAGG CCTCTTAATT ACACAGCACA TTGCAAATCA ATAAAGCCTA
45961 GCCGAAAAGA GAATTGTTCA GTTCAAACGT TCAAAACTAA CATATACTTA ATTTTCCAGG
46021 CAAAAGAACA ATTGCCAAGA GTGGGGAAAG GCCCGAGGTA GGCCTCTCTC AGGAGCCTCC
46081 CACCCTAGAG ACCTCCACCC CAGGTCTCAC CAAAAGTGGG TGGAATGGTG AAGAATTCAG
46141 ATCCCCAACG CCACTCTTTC GCGCCCCAC CGCCCAACGC ATTCGTTCTG AGGTGGAAAC
46201 CCCGTGCGGA TCCTGCTGTG GGTTTGCTCA GCCTTCTCGG CAAGCACTCA GGGAAGAACT
46261 TCCTGTTTGG AGATGACTGG GGAAAAACT GCACAGCTGA CATTGGAAAT AAACCCGAGT
46321 TCCAGGTTCA AGGAGCCCCA GGCTTAGCTC AGCTCAAGTG AGGAACTACG AGATTTATTT
46381 AAAAGCATTC TAGTTGGGGG AAGGGAGTGG GCGGTTCCAA AAGTCACTCC GCAGAGCCGG
46441 GACAGCCGGG GGAGGGGGCA GGTCCTGGGG CGAGGGACCC CTATCTGCAG TTCAGTGGTA
46501 GGCACTCCCT CACGGGGTCT GGACGCAGAA AGTAGGGAGA GGGGCTTGCG GATTGGGTTG
46561 AGCAGGTCCT CCAAAGTTAG CAAACTCCCA AGCGCAAAGA AAAAGCTAGT TTCGATTTTT
46621 CCACCCCCGC CGCGCCCCTA GTTCGCCCGC AGCCCTCGGA CTCACGCAGC AAGCGCCCCT
46681 GCAGGACCGC GGTCTGCAAA AGCATCAGGA GGAGAAGCGC CGGCCTGGCT CGCGGGCCCA
46741 TTTCCCCAGC TCTGGCCGCA CGTCCCCGTT AAATCTCCGC TTCTTTTGGG GGGCGGGGAA
46801 ACGGGGATGG CTCCAGAAGT CACCCTACAG CTATTGCCTA GGCTCAGGAG ATGCCCAGTA
46861 AAACTTCCTG GTGAAAAGCA ACAGGTCTTT CAGAACTTTA GTTCTCTCTC TCCTACAGCA
46921 GAAGGTACCT GCTTGTGAAA CACTAGGTGA TCCAGTGTCC CCCTTGGTTT TTAAATCCTG
46981 AAGGGGTGTT GTTGATTGGG GAAAGTAGCT TCGCAATGTT CTGATCTGAA CTTTAGATAT
47041 TTAAATATTT ATGATTTTCA AAATTCAATC ATACATTTAA AAATTTTATC TCAACCTTAG
47101 ACCAACTTAT GTCTTATTTG ACTTAGAAAT ATAAAGCTTT TTCATTTTGT TTTTTGATTC
47161 AAATTAATTA AGTCATAACA TTAACCAATT AGATCCTACT GAAACACGTT CCACAGCCTT
47221 CATAATTGAA TTATCTGACA AGTGTTTCAC AAACTTTACA GTATTGGGAT TATCTGGAGA
47281 ATGATTAAAC ATATTGAGGC CTGCTCCTAA CCCCAGACAC ACTGATTTAA TGGGTAATTG
47341 TTAGGTAGTT AGACATTAGC AGTTGGGAGG GGATGACAGA AGAGAGCGGA AAGGCTGTCA
47401 CTAAGACAGC CACTGGCCCA CCTAAATTCA GGCCCAAGAC TACCCTAATG CCACCCTAAG
47461 GGATGGAGTT TATGATAAAG TCTGTGGCCA AAATATCCTG GAGAAAGAGA AAGGAGGGTA
47521 CAGGTGGAAA TTCCCTAAGG TGGCACATGC CCAACAACAC AAAAGCCTGT CTTCAAGTTC
47581 ACCCCAAGTT CATCATGCCA TCATTATAAT AGAATTTACA TACAGTTTTG CCCCCCCATC
47641 CCTGGGAGGC TTTTCTTAAC AAATTATAGG TAAGACCATG CACAGTTTAA TTTTAGATTG
47701 TATAGCTATA AACTTCAATC AAATAACATC ATCCTGTCAC TCAGATACAG CCCAAACCTC
47761 AACTCCTCCC CACAAACCCC ATAAAAGCAC CTTGAGCTCT GTAAAGAAGT GCTGAGTTCA
47821 CTTCGCAGAA ATAAGCCCGC TGTCCCTCAG AGTGTATTAT TGTGCTTCAA TAAACTTTGC
47881 TTTAAGCTTG CATTTTGGTG TTAGTTTGTA GTTCTTTGCT CACTATCACA AGAACTGAGA
47941 TTGCTGCTTC AGAGCTCCGG CTATAATAAT CTCCTCGGTT AAAGGATCCA TCCCAATGCA
48001 TAATTCCCAG TAACAGTATG GGATGCCACC TGGGCAATGG GATTTTAAAA GCTTTCCTTC
48061 TCCCTCAACG AAGTTTGGGA ATTATTGCCT TAGACATTTC AAACAATATT AATAAATTTA
48121 ATACACCTGA TTTGCTCCAA ACCTTTACAT ATCTAGCAAA TTCAACAGGC ATTATTTTG
48181 TAAGCATGTA TGCAAATTTT GGCAATTCAA GAAAATCAAA CAGGATATCA GGGCCTCGAC
48241 TGTAGGCAAA CAGATACAAT AACATTGGAA ACATGTAGAA TATTGATGAT GGGCACATTG
48301 GGGCTGATAG TACTATTCCT TTTTTTCAAT TTTTGGTAAG ATATAATTAG CATACCATAT
48361 AATTCATCTA TGTAAAATGC AAAAATTGGC CCAGCTCAGT GGCTCACGCT TGTAATCCCA
48421 GCACTTTGGG CGGCCGAGGA AGGCAGATCA CCTGAGATCA GGGGTTCGAG ACCAGCCTGG
```

Figure 2 (Page 15 of 74)

```
48481 CCAACATGGT GAAACCCCGT CTTTACTAAA AATACAAAAA TTAGCCGGGC GTGATAGCAG
48541 GCAACTGTAA TCCCAGCTAC ATTAGAGGCT GAGGCAGGAG AATCGCTTGA ACCCGGGAGG
48601 CGGAGGTTGC AGTGAGCTAA GATCGTGCCA TCGCACTCCA GCATGGGAGA CAAGAGCAAG
48661 ACTTCATCTC AAAAAAAAAA AATTAGCTGG GTGTGGTGGC ATGCACCTGT AATTCCAGCT
48721 ACTCGGGAAG CTGAGACAGG AGAATCGCTT GAACCTGGGA GGCGGAGGTT GTGGTGAGCC
48781 GAGATCATGC CATTGCACTC CAGCCTGGGC AACAAGAGCG AAACTCCGTC TCAAAAATAA
48841 AATAAATAAA ATAAAATGCA AAAATTAATG GATTTTAGTA TATTTACAGA GATGTGCAAC
48901 CATTACCAAA ATTTTACATT TCTATCTCCC CAAAAAGAAA CCATGTTCCC CTAATTCAGT
48961 ACCCTTAATT CATCGCCTCC CAGATTCCTC CATTCTCCTC CTCCTCCCCT CCCAGCCCTA
49021 GACAATCTTT AATCTACTTT CTTTCTATTT GGAACATTTA GTATACATAG AGGCATATAA
49081 TATATTGCTT TGCCGTGACT GGCTTCTTTC ATTTAGCATA ATGTTTTTAT GTATGTTTTT
49141 CATGGACCAA TAATATCTAT TATAAGGACA TACCACAACA TATTTTATTT ATTCATTCAT
49201 CAGCCGATGG ACATTGGTTT GTTTCTACTT TATGGCTATT GGGAATAGTG CTGTTATAAA
49261 CATTTATGTA CAAGTTTTTT TGTAGACTTA TGTTTTGATT TCTTTTGGTT ATATATCTAG
49321 AAGTGGGTTT GCTGGGTCAT ATGGTAACAC TGTTTAACCT TTTGAGGAAT TGCCACATTC
49381 TTTTCCAAAG TAAGCATTTT ATCCTCCTAT CAGCAGTGTA TGAGAGTTCT GATTTCTCTC
49441 CATCTTTGCC TGGGTTTTTG AATCAGGGCC CCAGATAGAA CAAAAATGTG GTTATTCAGT
49501 TGTTCCACCA TCACTTGTTG AGAAGACTCT TTTTTCATTG AAGTGTTTTG GCACCCTTAT
49561 CAAAAATCAA TCTACCATAA ATGTGAGAGT TTATTTCTGG AGTCTCAATT TTATCCCATT
49621 ATGCTATAAT CTATAATCCT ATCTTTTTTT TTTTTTGACA GAGCCTCACT CTATTGCCCA
49681 GGTTGGAGTG CAGTGGCCCA ATCCCGGCCA CTGGCTCCTC CTCCCAGGTT CAAGCAATTC
49741 TCCTGCCTCA GCCTCCCAAG CAGCTGGGAT TACAGGTACC TGCCACCATG CCTGGTTAAT
49801 TTTTGTATTT TTAGTAGAGA CGGGGTTTCA CCATGTTGGT CAGGCTGGTC TGGAACTCCT
49861 GACCTCAGGT GATCTGCCCA CCTCAGCCTC CCAAAGTGCT GGGATTACAG GCATGAGCCA
49921 CCACACCCAG ACTATAATCC TATCTTTATG TCAGGACTAC ACTGTCTTGA TTACTATAGC
49981 TTTTTAGTAA ATTGAATTCA AGAAGTTTCT CAACTTCAAA TTTGATCTTT TTTTGGAAGA
50041 CTATATTAGC TATTCTCAGT CTGCTGAATT TCCCTAGGAA TTTTAGGATC TATTATCAAT
50101 GTCTATTCTA TTTTTGTATA TGTTTTAATA TTTTCATAAG AAACTTTTTT CATTTAAACT
50161 TTTTTTTTTA AGAAAAATAG TGAAAATCAG AATACTGGGG GTCAGGCGCA TTTAACAGGC
50221 AGAAGAAGAA TAAAAACTTG TCATATAAAC AAAAAAGAAA TGACCAATCA CATTGTGGAA
50281 GCCATGGAGT GGTTATAGGT GCCAAAGGCT GCAGAGAAAT GGTGTCAGAT ATACCTGAAA
50341 ATTGTCCATT GTATTTGGCC ATTAAGAGAC TTAGAAGACT TAAGCCATAG ATTGCTCAGT
50401 GAGACCCCGA GGGCAAATGG TCTGAAGGTG AATAGATCAT TTCACCTTTA AGAGAGCAGG
50461 TAGGAAGCTA TAAATCCAAG ATTAAAAAGT TGACTGAACT GTTAAAGAAG AAACTCTAAT
50521 CTTGAGCCAC CCTATCCTTG CTCCACCTTC TGCTGCAAGC AAACAGAAAT GCTGAAATTC
50581 AACACTCACA AAGGCTGGTA AGCTGGAAAT GACAAAAATT ACTCCTGGGA AAGTCAGATT
50641 TAGAATTAGG CCATATTTGT TGGGGTTCAG ATTTTCATGT ACACTTGGGA AAGGGTTTAG
50701 CTTATAGGCA CATGCATGAA GGGAACTGGT ATAGGCTGT GTTCATAAGG TCAAGAGTTG
50761 AAGGCCAGGC ATGGAGGCTC TTGCCTGTAA TCCCAGCACT TTGGGAGGCC GAGGCAGGAG
50821 GATGGCTTGA GCCCAGGAAT TCAAGACCAG CCTGGGAAAC ATAGGGAGAT GCTGTCTTCA
50881 CAAAACAATT AAAAAATAAA ATTAGTCAGG TGTGGTGGCA CACACTTGTG GTCCCAGCCA
50941 CTCAGGAGGT TGGGAAGATC ACTTAAGCCT GGGACATTGA GGCTGTAGTC AGCCATGATA
51001 GTGCTACTGC ACACCAGTCT AGGTGACAGA ATGAGACCCT GTCTCCAAAA AAAGAGCTGT
51061 ATCCACATCC CAGGAAAGTG GTTGAAGATC TACTTTTCTC TGTAAACCTA ATAAAGAATA
51121 GAGTGACAAA TGTGTGTTGT GGAAAGAAAT GGGGTGAGAG CTACGTAGAT GCAAACAAT
51181 ACATCCCCAC ATACCACTTG TTAATCATCC TTTTCCACCC ACTTATGGGA TGAATTGCAT
51241 CTCCCCAAAA GATACTCTGT CCTAACCCTC AGTACCTGTG AACCTGACCT TATCTGGAAT
51301 ACGGTGAGTT CACTGGTTAA GAAGAGATTA TAGTGGAATA GGGTGAGTCC TCCAACCAAT
51361 GACTGGGGTC CTCACAGACA CAGAGGGATG ATGGCCAGGT AGAGATGGAG GCAGAGATTG
51421 GAGTTATGCT GCCACAAACC AAACACAGGA AGCTGCTAGA AGTGGAAACA GGCAAGAAAG
51481 AATCCTTCCC CAGAGGCTAC AGAGGGATCT TGGCCCTGAT AATACCTTGA TCTCAACTGG
51541 CCTACGTAAC TGTGAGAGAA TAAATTTCTT TTGTTCTAAG CCACCCAGTT GATAGTACTT
51601 TGTTACGGCA GCCCTAAGGA ACTTGATATA CATTTCTTTT ACTGTCATAG AAGTTTTGAA
51661 TCTTTTAAGT AGGTCTGTAC CCTTCCTCCC AGTGTCAACG CATGGAATTC CTCTCCTTGT
```

```
51721 GCCTTGAAAA GTGAAAGGTG TTTGAACTGG TAATGAAAGA AATCTCAGCA TGAGGCCAGA
51781 TGCTGTACCT CACACCTGTA ATCTCAGCAC TTCGGGAGGA TGAGGCGGGC AGATCACTTG
51841 AGGTCAGGAG TTCTAGACTA CTCTGGCCAA CATGGTGAAA CCCCATCTCT ACTAAAAACA
51901 AAAAATGTTA TCCTAGCCGG GCATGGTGCC TGTAGTCCCA GCTACTCAGG AGGCTGAGGC
51961 AGGAGAATTG CTTGAACCCG GGAGGTGGAG GTTGCAGTGA ACTGAGATCA CGCCACTGCA
52021 CTCTAGCCTT GGTGAGAGAG CAAGACTTGG TCTTAAAAAA GAGAAAAGAA AAATGAAATT
52081 TCAGCATTAT AGAATAAAAA TGTTTCCCCT TCCCCCCAAA CTTTAAAAAA GCAGAAGTCT
52141 GCATCATAAA ATGGTCTTTG CCAATGTTAT TTTTATTATA ACAAAGGAAT CTTGCAAGGC
52201 TACCAGATCT CAGCAATTGT CACTATGTTC TGTAAAAATC ACTTCCTAAA ATGTCTGAAT
52261 TGACTGCTTG TCTCATTTAT TTGTTTCTCG TGTCATACTG CAATGGATAT CTGTCTTGTT
52321 AGTATAAATA TTTGTGCATT TTGTTGTTGT TAAAACAGCT TTTTTGGCCT GTCTTCTTCC
52381 ACCTATGAGG TAATATAAAA CTCATGTTTA ACACTTATTT TTGTAGGAGG ACAAGCTACA
52441 GACAAAACCC CTCAGACACT GAGTTAAAGA AGGAAGGGCT TTATTCAGCT GGGAGCTTTG
52501 GCAAGACTCA CATCTCCAAA AACCGAGCTC CCTGAGTGAG CAATTCCTGT CCCTTTTAAG
52561 GGCTTGCAAC TCTAAGGGGG TCTGTGTGAG AGGGTCATGA TCGACTGAGC AAGTGGGGGT
52621 ATGTGACTGG CAGCTGCATG CACCAGTAAT CAGAACAGAA CAGGGATTTT CACAGTGTTT
52681 TTCCATACAA TGTCTGGAAT CTATAGATAA CATAACCGGT TAGGTCGGGG GTCAATCTTT
52741 AACCAGACCC AGGGTGCAAC ACCAGGCTGT CTGCCTGTGG ATTTCATTTC TGCCTTTTAG
52801 CTTTTACTTT TTCTTTCTTT GGAGGCAAAA ATTGGGCATA AGACAATATG AGGGGTGGTC
52861 GCCTCACTTA TTCACCCCCT TTGAGAATCT CACTCATTAG TGGGAGTTCT CACTTTTATT
52921 CTCACTACCT ATGTCTTCTT GAAAGACAGA TTGATAATGA TTCATATAGT ACACTTGTGC
52981 TGAAGCATTT TGGTGAGCTA AGGTAGTGAT GAAGCTTTTT ATCATTTGGA GAAGTACAGG
53041 TAGCAAACAA GGAAGCAGTA AGCAGGTTTC TATTAATATT ATAACTCCTA TTATAAGAGT
53101 TTTAAATCTT CTTAGCACTC GGAACCATTT TTCAAACATG GCCCCAGAAA CAAATCCATA
53161 CCACACCTAC ATGGGCACAT GTGCCACTTT TGTCATATTT CTAACTATGT CTTCAACTAC
53221 TTGCCCTTAA TCATCTATGT GTAGACAGCA ATTAGTAAGG TTAAATTTCC TACAGACCCC
53281 TCCTTCAGTT GCTAGCAAGT AGTCGAGAGC CAATCCATTT TGATAGATAG CATTTGCAT
53341 CTGAGTTTCT TGCCAGGCCA CAGTAGTCAG GGCTCTGCTG GTCTTATTAG TAATTATTTC
53401 TAAGACAGCT TGTAACCGTA TGATTCAGTT GAGCATGTAA ATGGGGGTCC CATATCCCCA
53461 CAAGCCGTCT TGTGCCCAAG TAGCAGGCCC ATAATATTGT ATGATTCTCT CAGGGGGCCA
53521 TTCATTATTT TTCCAATTTT CTATAGCTAT GCTTTTTTTT TTTTTTTTT TTTTTTTTT
53581 TTGCGGGAAG CATATACAGG GAAGCCCAGG AGTTTGCCTG TCTTTATGGG CAGTAGGAAG
53641 AAAGATGGTT TAATAGTGTC AATAACACAA CTACCTGCCC ACTGGTCAGG TAATTTGGCA
53701 TAAGCTGTAT GCCCACATAT CCAGTATAAT CCAGTGGGGG CTGTCCAGTC CCGGTGGGAC
53761 TCTGGGTGGG TCCACACAGT TTGCAACTTT GGGAATTTAC TAAATAGATT TTTCTTAGTG
53821 TGGTTTGAAC TCCACTAGGT GGCTGTTTTT ATAGTACTAT TATACAGTTT TTGCCCAAGG
53881 CAGCTGAGTC TTCCCACAGG AAGGGTGAAG TCCTTCCCCA CTTTTGCTAT ACAGTATTGT
53941 CTAATGATTG AGGCTTTTAG GACCCAGAAG TTATCAGGGT GAGTCTTTTG AGCTGGGAAT
54001 TTATCAGGAA CTGGGTCTGT AGGTACTAAT TCTCGTGCTT CCCATGGCCA TTGATCTCCC
54061 ATTACAGTTC CTCCACATAC ATACATAACA TGAAGTGACA TTGAGAGACT GGGCTACATG
54121 CTCAGCTAAT TGCAAAAACA AATTTCTTGT TTTTCCTGGA ATTTCTAGTA CTGGCACATT
54181 CAGTTCATCA TAAGAAGGTT TGAAATACTG GCTCAGGGGA GCATTTATAA ACTTCTCCTC
54241 AAACCACCAT ATTTACTCAA GGATCCAGTC CAGCCCCAAC TATTTCTAAG GTTACACGAT
54301 CCCCTTTTTT CCAGTGAGAA TCAAGGGGGT TGGTTATTAC TAGTTCTAAG GGGTTACACT
54361 GACCACTGGT ACAGGAAGGG CCACTTTTCC CTTTCTGAAG GTGGACAGGA TTCTTTTTAT
54421 TTTTTAACCA AGTTGCCTAA ATGACACAAG ACCAGTATCT ACATTTATTT CCACGCAGTC
54481 TTAATTCATG ACAAGCGTAC TTATTTCTG CCATATAGCC TCTTTCCTAA TGAACAGAAC
54541 CACATCCTAT TTCTAACTTA TTACTATTAA TGACAGCACA GGCATCAAAT TTCAAGGTGA
54601 CTTGTTTGGG CATTCCTTTT TCTTCTGTTT TGGCTAACAC TTTACTCGTA TCGTTTATGA
54661 ACCCCCACCA GTCCTCAGTC CTCAATCTTA TTTCAAAAAC TGTGGTCGTG GGAGGCTCAG
54721 ATGGGTCATA ACACACATCA GGTTGGTCAT TTCTTGGGCT ACCTGCCTTG TATAGAATAG
54781 CATTATACAA ACAAGTTATT TTTAGAGTCT TTGTACACTT ATAATAACCA TAAAATAATA
54841 AGACTGTAGC AACTTTTTGT CCTACCTCAG TGACTTGATG TATACACTGG GAACAGCCCT
54901 CAGTCTGAGG AAGGTTAGTT GAAGTCTTTA CTGTGCAAGT CCAAATTTTA AGGAAAATGA
```

Figure 2 (Page 17 of 74)

```
54961 GTCCCTTGAT GAGTTTTCTC ATGTTTCGGC CATGCATGGA CCAGTCAGCT TCCGGGTGTG
55021 ACTGGAGCAG GGCTTGTTGT CTTCTTCAGT CACTTTGCAG GCGTTGGCGA AGCTGCCACG
55081 TACAGCTCAC AGTCTACTGA TGTTCAAGGA TGGTCTTGGA AGTTGGGCCC ACTAGAATTA
55141 ACTGAGTCCA ATACCTCTAC TCAGTCACTT TCAACTGGGC TTTCTGATAC CAGGAGCAAG
55201 GTGGCAGGTT TTAGGGTGTT GCAAATTTCA ATGGTTATGC AGGGATTTTC ACATAGCAAA
55261 CTTTGGTACT TGGTTAATCT AGCATTTGTT AGCCAATGAT GTATTTATTA AAGTCACCAC
55321 AGCATGGAGG GCCTTTAAGT TTAGGTTTTG TCCAAGAGTT AGCTTATCTG CCTCTTGTGC
55381 TAGCAGGGCT GTTGCTGCCA AGGCTCTTAA GCATGGAGGC CAACCCTTAG AAACTCCATC
55441 TAGTTGTTTG GAGGCCCAGC CTCGGCCAGG GCCCACAGT CTGGGTCAAA ACTCCAACCG
55501 CCATTTTTTC TCTTTCTGAC ACATAGAGTG TAAAGGGTTT TGTCAGGTCA GGTAGCCCCA
55561 GGGCTGGGGC CGACATGAGT TTTTCTTTTA ACTCATGAAA AACTCATTGC TGTTGGTTGT
55621 AATAGATGTA GTTTATCCAA TCTACATTTT TATTAACTGT CACCCACCAA AATATTGACT
55681 CAAATCCTGC AGCTATTTGA TTTTGGGATT TAAATTGATC TGCTATTCCC TGTGGGACTC
55741 CAATTGCATC TAAATAGATG TGAGAGTTGA AAGACACATA AGGGTCTTCT CTTGCTTTAC
55801 GATGTCTTAT TTTTCCTCCC TCTGGTTGAT GAAATGCTAG GGTGAAAGGG ATAGCCAACT
55861 GGACTAAAGT ACAAGTGCCG CTCCAGTTAT TTGGCAGAGT GCCCAGTAAA GGTCCACCAC
55921 AATACCACCA CACATCCGCT TGGGGATGAA CAAAGGCTGA CTGATTGAGA AGCTCCTGAA
55981 AATTCTTAAG CTCACTGCAT CCCTTCAGGT CTCCAAGGAA TGCTAAGTTT CCTCCCTGTC
56041 ATGAGAGACA AGAAGTGAAC TTAGTTTTGG GAGATGGAAG CTGGATGGCC CTCAGGGGTT
56101 GACCTGCAGG GTGCTGGACT TTGGGATATA GCAGAGAGAG CTTGGCACGA CTTATTACTC
56161 CAGGCTGTAG CATCCTGGAA AACAGTTACC ATGCAGCCCA TGCCTGGTCA ACAGGAGGAC
56221 CACCTTAGTG GAAAGGGGAT AATCTGGCCC TCTGGCCTGC CATGTGCACA AGCATAACAA
56281 TTGGTTTTGT TTAATGTGTG GACAGAATAT TTGATCCATT CCAACTGGGC ATTTGCATCT
56341 TGGTATCCTG CTTAATTATC AAAGTTTGTT TTAAGTCTTT AACTTCTATG ACCCTCTAGT
56401 AAAATGAATG TATGATTTTA GGAAATTACA AAAACCGGTT GGGGCAGTCC ATCCTCGCTC
56461 TTTAGTGGTC CACACAACAT TCGACCAACT ATGGCATAAA AGCTCTACAT CAGGGGGCAA
56521 GACTCCTCGT TGACACTGGG GTCTTTATTG AAATCTCTCT GGATTAAATG GTCTCAGTTT
56581 ACTAAGGCTC AGTCTGAGGA GAGTCAGGAG GGACAGAGGT ACTTTTCTGA AGTACAGAGA
56641 TGTCTTCGAC TTGGCAAGTC CCCACAGGGT ATAACAAGGC AAGCATTAAA TTCAATAGTT
56701 TGAGGCAAAA TTGACTTGGT TATGTTAATA ACTAGATGGT CAGAAATAGA GTGAGGGAAG
56761 AAGAAAGAGT AATAGAATAG ATGAAGGAGT TAAATTTTTC TTAGCTTTAG TTTGGTAGGG
56821 TTTTCCCCTG GGACTATGGC CCATGACTCT GGAGGGGGTG GCACTTTCTT GACTCGGGTG
56881 TGATGAGTCC ATCCCTTTTT CACCGTATGA ACAACAGTCT CGGTGGTTAG CAGCACAAGG
56941 TAGGGTCCTT CCTAGGCTGG CTCAAGTTTT CCTTCTTTCC ACCCTTTGAT GAGAACATGA
57001 TCTTCAGGCT GGTGCTGGTT TACAGAAAAT TCTAGGGGTG GTACATGTGC TAAAAGACTT
57061 TTAGTTTTGA GGGAAAGGAA AGTGGAAGAT AAACCAAGTA TATAACTTTT AAGAAGTTGA
57121 CCTTTTGTTT TAAATGTGGG GACATCAGCA GTGGACTTTA TAGTCCTTGG TGCCTTCTTA
57181 CTGAGAAATT TCCTTTAGCA CCTATTTTTA TTAGTTTTTA GACCAAAGAA AGTCAAATGC
57241 CATTTTATAT TTGACAACGC TTCTTGTATG TTTATACCAG ATAAGCTAGA TTTCACCTTT
57301 ATATTGGTGT GTTATTAATG TTAAACTTAG TTTTAATAAA ACTCTGTAGA CATATTTATT
57361 TGATTTTTAA TGTCTGACCA TAAGGTAAGA TTTTTATAGA CTTTTCTTTA ACCTTTTATA
57421 ATTTTTGTTA AAGAACAGGT TAGTGCTTTA AGAAAAACCC GTTGTGTTTT TATTTTAATG
57481 TTCAGTTCAC AGAAAAACTG TATGATACCC CTTAACTTTA GCCAATATGT TTAGACACAG
57541 AATTTCTTT ACAATTAAGG TTTCAAAACT TGCTTAAACC TTCAAAACAA TTTTTGTAAC
57601 CTTTTAATGT AGGTAAAAAT CCACATTCTT ATGCATCCTC ATAATCCTTT TACCAAAGGT
57661 ATATTTACT TTCCTTACAT ACCTTGCACA TAAACTGTTT ATTCAATAGT TTTACATTTA
57721 GAAGGAGGCC TAATTACTTT TAAATTATAC AACATTTCTT GCATAAATTT ATTTTTCTAA
57781 CACACATTTT TTTCATGACT TTCACAGACA ATTCTTCGAC ATGCCTCAAC TTTCTGACTT
57841 ATTGCAAACA TCCCTTTCTT TAAACAACTA GTTAATTTAT CTCAGGACAA GGATTTTCCA
57901 TACAACATTC TTTTTATAT AAATTCTGCC TCCTCTTTAT TTCCTTTTTT TTTTTCCGAG
57961 GATGATAACC ATTCTTTTCC AAAGCGAACT TCTTTTATGT CTGTGGACTA GACTGTCTAA
58021 GGCCACAAGA TTAGAAGTTA CTATAATACA TGTTACACTG TTAACTTTTA GCAAACTTTA
58081 CTTTTGTTGA AAACCTTGTA AGTTTGGGAT TCAATTATC CTTTGCTATT AATAAGACCT
58141 TATTTAGTCC AAATTAACTT AGAATTGGTA TAGATGGCTT TTTTTTTTTT TTAATTACC
```

Figure 2 (Page 18 of 74)

```
58201 TGGGAGGAAC CATCTATCCT CCTGTCCTGA AGGGAGTTCC TCCTAGGTCT GGTCAGAGCT
58261 TTGTATGGTA ATTAAGATTT AGATCCCCTG TTAGGAAACC TGCCGGGTTA AGAGAATTTT
58321 CAGTGGTTAA TGTTAAATCA TCTTCTTTTT TCTTTTTTCC TTAGGATACT TCTGAACCGG
58381 TGAGGTGTGC TCACAATGAG GTTCCTGTA AAAGTTATTT TTTTACTTTC TTCTGTTAGC
58441 AAAGCAGTTG CCGCTACAGA TTGAATGCAT TTGGGCCATC CGCGGGTTAC TGGGTTAAGG
58501 ATTTTTGATA GGAAGGCCTT AATGCTTTTG AATATGCCC TGACAACAAA GTGCCAGTTC
58561 CTTCCCGGTG TTCAGCCACT GCGTTGATCC TCCACGAGGG CCTGCCACGT GCTGCTCTGG
58621 TGAGGCGTTC CACCGGGGCA ATTGCCTACC TGGGAGCGCT CTCCAGATCT GTGTCGCTCA
58681 AACTGGCTGG AGTTCCCCGT AGGGATGCTC CACAGGGCAG GCCTAAGTCG CCTAAGGGGC
58741 TGCCTTGACC GTCCGTTAAT CACCTCTGTC TCCAAAAACC AGCTCCCTGA GTGAGCAATT
58801 CCTGTCCCTT TTAAGGGCTT ACAACTCTAA GGGGTCTGC ATGAGAGGGT CGTGATTGAT
58861 TGAGCAAGCA GGGGGTACGT GACTGGGGCT GCATGCATCA GTAATCAGAA CAGAACAGAA
58921 CAGCACAGGG ATTTTCACAA TGCTTTTCCA TACAATGTCT GGAATCTATA GATAACATAA
58981 CCTGTTAGGT CAAAGGTCGA TCTTTAACCA GACCCAGGGT GCGGTGCCGG GCTGTTTGCC
59041 TGTGGATTTC ATTTCTCCCT TTTAATTTTT ACTTTTTCTT TCTTTGGAGG CAGAAATTGG
59101 GCATAAGACA ATATGAGGGG TGGTCTCCTC CCTTAATTTA AACAAAATTT TCAAAGTCCT
59161 ACCCCAAGTA AATTGGCAAA TATTAATAAA GTTATGGCAT AGAAAATAAA AATGATTGTA
59221 AAAGGCGTAA AGATATTTCT GTGGGGAAAA CATTTGTTCA TTAGTTATCA GTTAAAATTC
59281 TGTGAAAAAT AACCACTAGA GACCCTAAAG TACCCAGGGG CTAATAATAA GAAGGGAGGA
59341 ACACCCTCTC AGTCCCCACC GTTACCTCCC CAGAAGGGAA GAGGAAGAGG GTGACTCCAG
59401 GAGAGCTGTG GTCTCCCCTC CCCATATGTC CACATATACC TGACCTCCCC TCCCCAAAAT
59461 ATATACCCAA TATCTCTCCC ATATATACAT ATTTATCTGA CCTCTCCACA TATGTATACC
59521 TAAACTTTCT CTATATATCC ACATATACCT AACCCTCTCA CACACATATA GCTGACCTCC
59581 AGTGGAGGAA AATGGGGAAG AGAGAAGAAG TTATCAAAGG ATAAATCTAG GTCATACTCA
59641 GAAATGTGAA AAACAAAAAC CACACACAGA AAAAAAAAC ACACACAAAA AAGAAATTGA
59701 TAAATTTGTT TGTGTCAAAA TTAAGAATTC CGGTTCAATG AAGGATCCCA TGGATAAAGT
59761 TAAGACACTG CTGTAAGGAT GGTAGAGAAT TAAATGTCTG AATCAGACGA AAGGATGAGT
59821 AATTAGAATG CACAAGGCCA AGAAGAACAA AACAGAAACT CCACATAAAA AATGTATGAG
59881 GCCGGGCGCG GTGGCTCATG CCAGTAATCC CAGCGCTTTG GGAGGCCAGG GCGGGCCGAT
59941 CAGGAGTTTG AGACCAGGCT GGCCAACATT GTGAAACCCC ATCTCTACAA AAAATACAAA
60001 AAATTAGCCG GGCGTGGTGG TGGGTGCCTA TAATCCCAGC TACTTGGGAG GCTGAGGCAG
60061 GAGAATCACT TAAACTCAGG AGGCAGAGGT TGCAGTGAGC TGAGATCACA CCATTGCACT
60121 CCAGCCTGGG TGACAGTGTG AGACTCTGTC TCAAAAAAAA AAAAAAATTA TATATATATA
60181 TATATATATA TATATATATA TATATATATA TGAAATAAAT GAACAAGAAA TTTAGATACA
60241 GGAAAATCCA AGCACTTGG TAATGAAAGA AAGGTAAAGT GATGTGTCCT TTTGCATTTA
60301 AAAGAGAGCA TTAACAAATT AGAGAGCTGA ATAATGCTCA GTATTGGTGT GGATATGGAG
60361 ACTCAGGAAT CCTCATACAC TGCTGATGGG AGTGCCCACT CCCTGGGAAT ATTTTCCAAA
60421 TATCATCTCA AACATATCCC ATAAAGGTGA CAGGAAAGTG TGGGCTGACT GATATCCTTC
60481 ACTGAGAGAG GTGGAGGTAA AATGAAGTCA CTGCACAATA TAGAGTTGGA AGCAATGGAT
60541 TAGATGTCCA CATAGTTACG TGGAAGAATC CGTAAGATAC ACACACACAC ACACACACAC
60601 ACCTTTGTGT ATATTGTTCC TGGCAGGTAG GCATGGAGGT TTAGAGGCTT TCTACATCAC
60661 ACCTACTGCA CACAGTAAAT GGCCAGGCTG AGCACTGACT TCCATGAAGG GAGATTGAAG
60721 GTAAGAGATT GAAGATTGTT CCCTGGTCTG GGACCCTGCA ACTGAATATG CAGAAAAAAG
60781 TACACCCCGC CACCCCGCTT CCCATCTTTC CTACCTGATT AGAATAGCTT TTTCAGAAAA
60841 CGTTGGCCAG GGGTTGTGGC TCACACCTGT AATCCCAGCA CTTTGGGAGG CTGAGGCGGG
60901 CAGATCATCT GAGGTCAGAA GTTCCAGACC AGCCTGGCCA ACATGGCGAA ACCCCATCTC
60961 TACTAAAAAT ATAAAAAATT AGCAGGGCAT GGTGGCACAC ACCTGTCATC CCAGCTACTC
61021 GGGAGCCTGA GGCAGGAGAC TCACTTGAAG CACAGTGATG GAGGTTGAAG TTAGCTGAGA
61081 TCTTGCCACT GCACTCCAGC CTGGACAACA GAGTGACACT TTGTCTCAAC AACAACAACA
61141 AAACCCACCA AAACTTTAAA TCTACCTATG GCCAAATGCC TGCTAAAATG AGCACCCAAG
61201 AAGCAGTGTT CAGGAAAGTC AGATGAATAC CCTAAAATTA GATGCAATGT TGGCTGGTCA
61261 CAGTGGCTCA GGCCCTGTAA TCCCAATCCT TCTTGGGAGG CCGAGGCGAC AGATCGCTTA
61321 AGCTCAGGAG ATCGAGACCA GTCTGGACAA CATGGTGAGA CCGTGTCTCT ACAAAAACGT
61381 ACAAAAATGA GCTGGGAGTG GTGGCGCACA CCTGTAGTCC CAGCTACTCA GGAAGCTGAG
```

Figure 2 (Page 19 of 74))

```
61441 GTGGGAGGAT CTCTTGAACC CAGAAGGCGG AGACTGCAGT GAGCAGAGAT CATGCCACTA
61501 CACCCCAGCC TGGATGATAG AGCCAGACCC CCATCTCCAG AAAAAAAAAT AAAGAGAGAG
61561 AGAGATGCAA TATTTAGGGT TCAACAAGAC TGAACTTCTG ACTCCTTTCC CTACCTCTCC
61621 AGCATGTTAG ATTCTGGGTC CTTCATCCTA ACCCCTGTT CATGCCATAG CCACCCTGTG
61681 GTACCAACTT TGGAAGCCTG GATCTTCATC CCTCATGAT AATGAGTGTC CCATTCAGGT
61741 CTCCATGCTC AGCTTGGCAA GAGTATCTGT CTTCTCCTCA TGGGACGGTC ACATTCACCC
61801 AGCACTGACA GGTTCCATTC CCACTAGGGT GGCACCCTAT ATGGTCTGAG TCCAGGCCTT
61861 CCTGGTCCCT CAGTAATCTC AGCATGGTAG CACAATCGAA AAGGGCTAGG CACGGCAGCA
61921 CCATTTCCCA CCAAGAGGTC TGATGGCTCA TCACATAGAC TGAAGGAGAT TCTGAAGAGC
61981 AGAGGTGGAA TGAAGAATGA ATCCTGGGCT CTGCTCTTCC TAGGCCTGTC TTCCTCTCTC
62041 CCGAGATGTT AGCTAACTCA TGAGAGCCAG AAACCAACTG CAGGCTGGCC TCAGGCACTT
62101 AGGTAGTGCT TCAGCCTCAG CAGTCCACAT TCTAGGAACC CTCATAATAT GGGTTGAAGT
62161 ATGCATTCCC ACAAAAATAA AGTTGTTGAA GTCCTAACCA CCAGTACTGA AATGGGAAAA
62221 GTTCCCTTGT CCCGCTCGCA TGGCATGTGA TAGGAGTGTG GCTAATTTCT TCAGTGCCTG
62281 GCTGCTCAAA CCTCTAGGGG AACAGTAAGA CGGGCAGGTT GTGGGTCTCC AACCCCATGA
62341 CCCCACCACA GTGTCTAGGG TTGAATGTTT ACAGCTCCTG AAGCCACAGT GGGTGTGTGT
62401 TACAGGGTGC TCTTTTAGTT TTGCCATTTA TAGGCAGCTG GTGTTAACCA ACTCAATTAG
62461 ACCGTCTACC TTGTCCCAAG GACAGAAGAA GGCTTTCTGT ATCCCAGGTT CTTGCCTTGG
62521 TGTACCGGAA TAAATCAGAC CACACCTGGG CTTAGAGAAA GAGTGCAAGG TTTTATTAAG
62581 TGGAGGTAGC TCTCAGCAGT TGGGCAAAGC CAAAAGTGGA TGGAGTGGGA AAGTTTTCCC
62641 TTGGAGTCAG CCACTCAGTG GCCCAGGCTC TCCTGCAACC ACCCCAGTCA AATTCCGCCT
62701 CATTTGCCA GGCAAACGTT TGTTGTGTGC TCTTCTGCCA GTGTGCTCCC CTGGACGTCC
62761 AGCTATTCGT GTCTTGTGGC AGGCCAGGGG AGGTCTTGGG AAATGCAACA TTTGGGCAGG
62821 AAAACAAAAA TGCCTGTCCT CACCGTGGTC CCTGGGCACA GGCCTGGGGG TGGAGCCCTA
62881 GCCGGGACC ACGCCCTTCC CTTCCCACT TCCATATCAT TTAAAGGGAC CATGCCCTTC
62941 CCTTCCCAGC ACTTTCCCCC TCCTGTATCA GGACCTGTGA ATGTGGCCTT ATTTGGAAAT
63001 AGGGTCTTTG CACTTCATCA GTTAAGATAA GAGTGGGCTC TAACCCAACA TAAAGGGTGT
63061 CCTTATAAAA AGGAGAAATG TCATACACAG AGACTGACAC CTATAGAGAG AAAATGTGGT
63121 GAGTAGACAC AGGGAGAATC ACCATTCAAG TCAAGCAATG AGTCTGGGA TACCAGAAGC
63181 TGGGAGAGAA ACCTGGAACA GATTATCCCT CATTGCCTTC AGAAGGAATC AAACCTGATG
63241 ATACTTTGAT TCAGACTTC CAGCTTCCAG GACTGTGTGA CGATAAATAT CTGTTGTTAA
63301 GCCAACAAGT TTGAGGTACT TTGTTACTGC AGCCCCAGAA AACTAATACA GTAGGTACTA
63361 TGGACTGAAT TGTGACTCCC CGTCGCAAAA TTCATATGTT GAAACCCTAA CCCCCAGTGT
63421 GATGGTACTT GGAGCTGGGG CGTTTGGGAA GTCATTATAT TTAGACAAAC TCATCAGGAT
63481 GTGTCTCTCA TGATGAAATT CATGCCCTTA TTAAAAGAGA CAACAGGCCA GGTGCAGTGG
63541 CTCATGCCTG TAATCCCAGC ACTTTGGGAG GCTGAGGTGG ATGGATCACC TGAGGTTGGG
63601 AGTTTGAGAC CAGCCTGGCC AACATGGTAA AACCCCATGT CTACTAAAAA TACAAAAATT
63661 GGCCAGGTGT GGTGGTGCAC GCTTGTACTC CCAGCTACTT GGGAGGCTGA GGCAGGAGAA
63721 TCCCTTGAAC CCAGGAGGTG GAAGTTGCAG TGAGATCACA CCACTGTACT CTAGCCTGGG
63781 TGATAGAGAC TCCATCTCAA AAAAAAAAAA AAAAAAAGAC AATAGAGCCA GGTGCTGCAG
63841 CTGATGCCTG TAATTCCAAC ACTATGAGAG CTGAAGCAG GAGGCTCGCT TTAGCCCAGG
63901 AGTTCAAGAC CAGCTTGGAC AAAATAGTGA GACCCCAAC TTCTAAAAAT TTAAAAAATG
63961 AACTGGGTGT GGTGGTACAC ATCTGAGGCT CCAGCTACTC TGGAGGCTGA GGTGGGAGGA
64021 TTGCTTGAGC CCAGGAGGAG CTGCAGTGA GCCATTGCTG TCCAGCCTGG GCTACACGAG
64081 AACCTGTCTC GGGAAAAGGA GAAACAGTG AGACCTCTTT TTCTCTCCTC CTTCTCTCCA
64141 CTGCCTAAGC CCTACAAGCA CAAAAAGGAC ACCACATGAG CACATAGTGA GAATGCTGCT
64201 GCCACCAACA AGTCAGGAAG AGAGCGTTCA CCTAGAAACT GAATTGGCCA GCACCTGGAT
64261 CTTGGACTTC TGAGCTTCCA GAACTGTGAG AAAGTTATTT TTTTTTTAGC GACTAAGTCT
64321 ATAGTATTTT ATTACAGCAG CTCAAGGTAA CTAACATAGT AGAAGGGATG AATTATGGAG
64381 ATCACAAGTC CACGCCTCCA GAAAAAGACT TCCCTAAAAA TTAGTCTGAG CAAAATTCGA
64441 ATGATGAATT ATTTTTAAGA ACTTTTAAGG GATCTGACAA GTTTGCAAGA GCTAGAGAAT
64501 GCTTTACAAC GTGATAATAG AATGCTCTGT GATGACAGAA ATCTTTCCAC ACTGTTCAAA
64561 ACTAGCTACT GGCCACTTGT GACTATTGTG CACTTGAAAT GTGACTGGTG TCTGAGGAGC
64621 AGAATGTTTA ATTTTACTTA ATTTTAATTC ATTACAATAG CTACATGTAG CTAGGGGCTA
```

```
64681 CTGGATTGAA CAGCACAGCT CGAGTCTTTT AGAGGGAGAC AGGACTCACC AAGGTGGATG
64741 CTGGTGGCCA AGCAGCAATG GCAGGTAGTA CACACACAAG AGGCAGATGA TACAACACAT
64801 CCTTCCCAAA CCTGGAGATA AGCTCACCCC ACAATCCCGC CGCTGAAATA GAGTTGATGT
64861 TACCAATGTG CATTTTTATG TCCTTTTCCA TACAGAAAGA TCATTCAACA AGTACTATGG
64921 TACTTAAAAA ACAACATTCA ATTCATTATT ATGACAAAAT TAAATTAATA GCTCTTCCTT
64981 AAACTTTTAA ATTCAATTTA CAATGCTTAC TATTGGCATT TATTAATCTA CCAATTTTTT
65041 CCCATAGAAC CCATAGAACA AATAATCTAC CAAATTTTTA ACATTCATTT TTGGCAAGGC
65101 TTTTGCAATT TGACGAACTT TAAGAAGAAA ACTTATAAAT TGCAATTTTT AAATCTGACA
65161 TACTGGACTT TTAAAGTATC CAATTGACTA ATGAACAAAA CTGCTCCAAA TTTTTCAATT
65221 CTTAAAAATC TTAAGACAAT ACTTAATATG GCAAATCTTA ACTTCTTAAA CTTTGTAAGA
65281 ATGCTAATCA ACTTAGATTG GTATAAAGTT GAGTTAAAAA TCACAGGATA CATCATCTCA
65341 GCTATAAGTT TTCATGAGTT GAGTTTTTAC AATCACTTGA AATGCTTAGA ATAGGAAATA
65401 CGTATAAATT ATTTAACATA AAATATTGTT ACAAAACCTC TGGAGTGTCA GTTTCTCTGG
65461 CCAGACTTTA TGCTGCAGCA CCTTTGCCTG AGTTCTTGTC CTGCATCCAG GAAGAATTAG
65521 GTACAGAGGC AAGAGTCAAG AAGATTAGTT TTCCAATAGT TCAGCTCACC TAGTTAACTC
65581 CTGTTCACAA TCTTCAAAGT TATCAGAAAC CTGCAATTGA GGGTTATAAT CCATTCTTTG
65641 CAGAGTTTCA AAACAAGACA ACATTTGTCT ATGAATGTTA AAATGTCCTA GGGTAGTCAC
65701 AGTCAAAAAC ACAATTGACA AAGAAATTTA GTCACCTCTG TGATTTACAA TAGCCTAACA
65761 CAATAACTCT AATTATAACT GATGACACAA ACTCAGATAT CAGAACTCTA GAAATCCCCT
65821 ATAATTTTGG AACACATATT CACAGTTTTC ACTGAAATAT GACCTGAAGA TCAAATATCA
65881 CCTTATTTCA ACAATCCTAT ATAACTAAAC GTGTCAAATG ATCCTGTTTA CCTCTCCTTT
65941 GGATACTCCA GGGGCCCTCT GTAGCATCCA AAAGTTAGGG GTTAGCAAAG ACAATTTTGA
66001 AGCTGTAAAG GCTCAAAACA CTTAATGAAC CTCTAGTCAT ATCTGTTCT TACTCACTAA
66061 ATGCTAGTAG CACCTCTCAG TTGTGGCTAA GCTGGGAGGA TCTCTTGAGC CTAGAAGTTT
66121 GGGGACGCAG TGAGCTATGA TTATGCCACT GCACTCCAGC CTGGGCAACA ATGCAAAATC
66181 CTGTCTCAAA AACAAAAACA AAAACAAAT TGCCTATGCT GTGGTTATCT CACAATTAAT
66241 AAAAAGGAAA AAAAAAGTAT GCAGTCTTTG TAGGTCCTTG GGGTTTGTTG GAACTCAGAA
66301 AACAATACCC CAAAATAAAG ACCGCAGAAG CCAAAGTTTT TCTCTGATCT TCTCCTGCCC
66361 TCCTGTCTCT GAGTCCCATT CTCCCCGGAG TCTAGCCATA GAAATGAGAA TTCCTCTTCC
66421 TCAAGTTAGG TCATAGAAAT CAAAACACCT TTTCCCAGA GCCCAGCCAT AAAACCTAAA
66481 AATATTACTC TAACTTTCCC TCTGTTTTTC TGTGTAAAAA CTGGCCATAA AGAAATTATC
66541 TGAACTACCT TATTTGATCA TAGATCACCA GACCGCATTC AGAGAGGAT CCAGAAGGAA
66601 GGAATGCTGC ACAGAGAGGC CAAGAAGAAT CTAGACAGAC AGGCCTTGCT GGGTTTCCCT
66661 ACTCTGTTTA TTAGCAATCC TATTTCTACA CGGCGGCCCA TACTTTGTTG AATCTAAAAA
66721 ATAAAAATGG ACAATTTCCC CTGTACATGT TAATACACAT TAATAAATTG GATATAAATT
66781 GGATAATTTA TTAATATACA CATTAATAAA TTGGATGCAG CCGGGTGCAA TGGCTCACGC
66841 CTGTAATCCC AGCACTTTGG GAGCTGAGGC GGGCAGACCA CGAGGTCAAG ACCACCCTAG
66901 CCGAAATGGT GAAACCCCGT CTCTATTAAA AATACAAAAG TTAGCTGGGC GTGGTGGCAC
66961 ATGCCTGTAG TCCCAGCTAC TGGGGAGGCT GAGGCAGGAG AATTGCTTGA ACTCGGGAGG
67021 CGGAGGTTGC AGTGAGCCGA GATTGCGCCA CTGCACTCCA GCCTGGTGAC AGAGTGAGAC
67081 TCCGTCTAAA AATAATAATA ATAATAATAA TAATAATAAT AATAATAATA ATAAATTGGA
67141 TGCATTTTAT CCTATTAATC TTCCTCTTGT CGGTGGTTTT CAGCGACTCT TCAGAGGCCA
67201 AAGAGTAAGT TTTCCCTTAG CCCCTACAGG TTCTTATGTT TAATTTGTTA CTCTCATTTA
67261 AGACATAATT AAAGTGGCTT CTCCATGAAG ATTATTTCTG CATCCATTAT TTGGTAAGAT
67321 TGGCCGTTTT CTCCTTTGAT CTCTACTTCA CACTGACCCA CATAAAACAT CACTGCCTGT
67381 TTTTTTGTTG TTGTTGTTTG GAGACGGAGT CTTGCTCTGT TGCCCAGGCT GGAGTGCAGT
67441 GGTGTGATCT CCGCTCACTG CAAGCTCCGC CTCCCGGATT CACGCCATTC TCCTGCCTCA
67501 GCCTCCTGAG CAGCTGGGAC TACAGGCACC CACCACCAAG CCCGGCTAAT TTTTGTATTT
67561 TTAGTAGATA CGGGGTTTCA CTTTGTTAAC CAGGATGGTC TCGATCTCCT GACCTCGTGA
67621 TCGGCCCGCC TCAGCCTCCC AAAGTGCTGG GATTACAGGA GTGAGCCACT GCGCCCGGCC
67681 CCGTTTTTTT TTTTTTGGTT TTTGCATGTC TTCTCCCTTT TACTGTAAAC TATTTCCACT
67741 ACCAGCGTAG TTATCATTTC TACTGCTTAA TAATTGTTTT GGGGAAGTGA ATGCATCAAC
67801 CCACATGAAT TTCTTGTCTA TTTGACAATT TATTCTCTTT AGGAATAGTA TTAACTCCTA
67861 AGGTCCTGGG AGCCAGTCTC TGTACTTGGC TGCTCCAGGG TCCTACTTCA GTTTCCCAGC
```

Figure 2 (Page 21 of 74)

```
67921 TTCTCAGTAC TGTCACTGTC AATTGTGGGT AATAATTATT TTTGTCCACC AAAAGACTCT
67981 GTATGTGAAT GAGTTTTGAA ATCTGCTGAG TAATACAGTG TCAACCCAGT TAATGATTTG
68041 CCGGGCGGCT TGATCAGGGG CTGTCCAACT ACCGGCATTT TGATTTGGAG CGTCATCTAG
68101 TGTCTGAAAG CACAAACAAC ATCCTACATT GTAAATGCCT TTGGCTACAG AGATTGAAAC
68161 CAAAGCAAAC CTATGTTTTG AATTGTTATT CTTCAGCAGT TCTGCTAGCC TTGAAAAATC
68221 TAAAAGTTAA AAAAAAGCTT TATATTTCAT TTTCTGCCTA AACTCTTTAA AATTGCTAGT
68281 TGACAATTAG ATATTTTCAA TTTAATGAAA TTTTTTTTTA GTTCACAGAT TAATACACAA
68341 TGGGGGAGGG TTCTTATTCT GTTGGACTTT TACATAACCT CCACTTTAGT GCAGTCTGCT
68401 TTATGGGGTC TTGTTTGAGG TGTGTGTGTG TTTAAGGGAA TGTGGTTTAC AATCAAAATA
68461 TTGGGTTGCT CTTAGGCACA TTGTAAAGTC ACACACCTGT ATTCTTATTG ATACATAATG
68521 ATTAATAACA TTATTATTAC AGCCTGATCA CCATCATTAT TGATATATCT AAATAATGAA
68581 TTTTATAATT TTGCTTCCTG TCAGGCAAGA GCCAATTTCA GTGCTACCAT GTTTGTATAG
68641 CAGTATTTAT GTCTGTCATC CTCAGTCATT TTACTTCACT TGTTCTTAGC CAAACGGCCG
68701 AGAAGCGATG GTCATTTTAC TTCAAAAATG AAAAGAATTA ATATTTTTAC GTTTCCCTTA
68761 AAGACCCTAT GTTTAACCTC CACTCCCGGG TAAAATGGTC TAGTCCCTCC TTTTCATATC
68821 ATCTCTGATA TCTTTTGCAC AGCCACTATT ACCTACCGTT TTCTAGATCC CTATTCTTCA
68881 AACACCACCA TGAAGGTAGA GCCTGTCTGA ATTATTTTCT TGTCCCGTGA ACTCAGTACA
68941 TTGTTAGGCT TCTTGAAGAT GTTGATCAGT TGTTTGTGGA GTGAATGAAT CAGCTAGCAT
69001 GATTTTTCTA GACCACTGAG ACAAGTGTCT AAGACACTTG TTCCTTCCCA TGTTCTTGCC
69061 TGCCTGTGCA ATCCATGCAG TCTCATGGCT TCCCAGTGCC TCAGAATTAT CCCCTGTCAA
69121 ACAGGCATTA TAATTTCTGT CCACTGAAAA GGACAAAAAA CTAAGTGTAT AGCTAGAAGT
69181 TAAAAATTAC CGGCCAGGTA CTGTGGCTCA CTCCTGTTAT TCCAACATTT GGGAGGCTG
69241 AGGCGGGCAG ATCACCTGAG GTCAGGAATT CGATACCAGG CTGGCTAACA TGGCGACCCC
69301 GTCTCTATCA AAAATGTAAA AGTTAGCCAG GTGTGGTGGC TCGCACCTGT GGCCCCAGCT
69361 ACTCAGGAGG CTGAGGCAGG AGGATCGTTT GAGCCCTGGA GGTTGAGGCT GCAGAAAAAT
69421 AGGAATATAC TCTCTTTCAA GAGTTCGTGG TTTTGACTGC CACCTAGCGT ACATCAGAAA
69481 AACCGCATGA CATAGGAAAT GCCTGTGACA GAGGGGTAAG GTGAGAGAGG TTGATGAAGA
69541 ATGTATTGAA GGAGTGAAAA CGCTTCCATC CCTCTACTTA CTAAATATAT TAGTTAAGTA
69601 GTTGGGGCAT ATTTTAATTC ATGCATTTTG TAGATAGAAA AACAAAAGTT TTATTCTGTT
69661 TGATTTAGTT GATACTTTAA TATGTGTGTG TTTAGGATGC ATGATTTATA ATCAGTCTGC
69721 AGCACTTCTT GGAGAAGTCT GAATTCTCAT TCTCCATTTC CTTATTGGCA ACGTGAGAAT
69781 GATTACAATG GTGGTTGTCT CATAGAATGC AGGGAGTCAG AATGAAAATA GTCCATATAA
69841 TGCCTGGTGC AGAGGAAGGG TTCAGTTAAC TGTCTGTATT AATATTACTG ATAACAGTCA
69901 TGACAAACAA AAGCTTAACA ACAACACCAC CAACAACAGT TGCAGAATTG AGCCACCAAT
69961 TTGCACACAA GATTGTAGGT AGGATGTTTT AGAAAGTTA TTATTTAATA TATGTATATA
70021 TTTTTGTACT TAAAATATGT CAGAGGTTGT TCTAAGAACT ATTTAAATGT TAACTCCTTA
70081 ATCCTCATAA TGACCCATGA AACAGGTAGG CTTATTATTG TCTCTTTACA TGTGAGAACA
70141 CTGAGACACG AAAAGGTTTA TTAACTCACC CAAAGTCACA CAGCTGGTAA AACGGCAAAA
70201 TTGAATTTGA ACTCAGACAT TCCAGGTTCC AAGACAGTCT AATTATTCTT TTGACTAATA
70261 TACTAAGCTG CCTCTGTATT TTTCCTTGAT TACTTTGTAA AAGTATGAGG AAAATATAAG
70321 TGCTTCAAGT AACCATGAAA AATATAAACA ATCTATGTAT CAACTGAAGC ATAATTACAA
70381 ATCCTTTGAT AAGCAAACAT AATAAAAATT TGATATCAAT CAAAACTTTC ATGTAATGTA
70441 AGCAGGTTGA GATGAATTCT ATAGTAAAAA AGTGCAGAGT GCTGGAATAC CATGCTCCTA
70501 ATATATTGGC TAGGCACACC TGCCTGCTAT CAAAGGTATG CACACACCTT GGATACAGAA
70561 AGTTGGGACT GGGTAGTTAT GTGAGTGTCA TCAGAATTCT TTCCCACTTG GGAAAGAATT
70621 GTCCATCATA AGCTTGGATG ATGGACAAGG AGTGAGCTCC CAGAACAGTG ATGTGGGGAT
70681 ACATCCTCAC ATCACAGTGA GAATGAGTGT TCTAGACTGT TTACACACCT ACCACTCCTA
70741 AATGCACACA TATAATTGCT TGCACACACA CACATACACA CTCATCTCTT CTCTGGTGGT
70801 CCAGCTCTAT CTCTTATCAT TAGGCTTCTT GGGGCTAGTA CCTAGGGCCT GTATCCTTTC
70861 AGAGGCAGCT AAGGGAAGCA CACATAATTA GAAAGAATGA ACCAGCTTGT TGGATTGGT
70921 CTCTTCGCAT CCAGCCCTCC AAGTTAAGGA GAGTACCATC TTTCTTAGGG TCACCAAAGG
70981 AAAAAAAAAA AAAAGAAAGA AACAGAAGGA TATCATACAG CAAGGATCTA ATGCAAATAT
71041 GCCTCAAATG AGAGGCTACT GTGTGCTGAT CCCAATCCCA GGAACTGTAT GCACATTATC
71101 TAATTTAATC CTCACTGTAT TTCTGGGAGT ATTATTCCCA TTTTACAGAG AAGGAACTTG
```

Figure 2 (Page 22 of 74)

```
71161 GCAGGGTAAC CAAGCTCATG AATGGAGAAA CTGGGATTAA ATATAAAGCT TCCTTGCTCC
71221 AGAACTGCTG TCTTTCTGCT CTTCCACACT ACCAGCTCAG CTGTGCTCTC TACATGCAGG
71281 CAGTTTTACA AGTTTCAGAT TAGCCTGGGA CTTCCAGGGT TTTGAATGGG TTAGGGAATG
71341 GGGAACTTTT GGGTTTACTT TCCATTTTTT CTTCATACAT ATGTAATATA TAACATAAAT
71401 CTATGGTATA TATGATAAAT ATATGGCTAC ATATGAACTA TATAATCACA TATATGCATT
71461 ATAAATAAAT ATTAATTTTA TAATATTTTA AAGGTTATCA AATAAATATT AATATAAATA
71521 ATTAAATAAT TAATACTCAG CTTTGTTTTC CAAAGTGATA AATGCCTATA TTTAGCAAAA
71581 TATTTTTTGG AGGCCTGATA GTTTTTAGGA GTGTAAAGAA GTCCTGATAT CTAAATGTTT
71641 AAGAACCACT ATTTTAGGCT GTTGTCTTCT GTCTTATTTT CCCAGCTAGA CTGGTAAATA
71701 CTTGAAGGCA AACGTTTAGC CAGCACATTA ACATTTTATG TTTTTATTCT TTTGTGCTCT
71761 CAGTGGCTGT GTCTTTTCTA TCGATTTCTC ACACTGTATG ATGGTTATAT TTGTCTGTAT
71821 CTGTCCCACC AGGTATAAGT TCTTGAGAGG ACACACTGCT AGGCTGATCT TAGTTTTTAT
71881 TATTTCTCCT GGTGTCCTGT GCTTAACAAG TGCTCATTAA GTGTGTAAAA ACACAGCACA
71941 GTAAAAAACT AGACATTAAA AAATAATGTC AACCAATCTA TTGAAATTTG CATTTCCATG
72001 TTTCTTCCAA TATAGTCATT GTGTCAGGTT ATGTACTTAT TCTGATGAAG ACTATTGCCT
72061 AATATACGTT TGCATCTTGT GCTTTATAAC TGCCTTCATA TAGACACAGA TTGAGAAGGT
72121 GTAAAAATGT GCATATCCTC ACAATTGACA AATTCTTATC CTTTGAGGGT AGGTTTGACT
72181 TTCTGAAATG CTTTGACATC ATTTGAAAGA AGCTTGAAGA ATAAGATAGC TGTTAATGAC
72241 CCAGTTTCCT ATGTCACTTA TACAATTATA ATGGCAATTT CAAAATGTTA GGTAAATATA
72301 TTTTGCAATA TATTGTTCCT TTTGTAATAC TCTCTATGTA TTTATTTATA TTTTTAAATT
72361 TTATATTTAT GTATTTATTT TTCTGGACAG AGTCTTGCTC TGTTGCCCAG GTTAGAGTGA
72421 AGTGTTGTGA TCATAGCTCT CTGCAACTTC AAACTGCTGG GCAAAAGTGA TCCTCCTGCC
72481 TCAGCCTCAT GAGTAGAGTA GCGGGAACTA CAGGCGCATG CCACTGCACC CAGCTAATCA
72541 CTATTTATTA TGCTCCTACT GTGTGCTTTA GTATATTTTC TGTTGTTTTC TGCAACCCAT
72601 TTTGAGGGCG TGTTAGGGAA TACAGATGCA GTAACTTTGG TCTCAGCCCT TGAGGTGAGG
72661 AAATATTTAG CCTCAGGTTT AATCTAATTG TTGGCCATTT GCCTTCAAAG ATTGAAATAT
72721 GAGCAAAACT GTGGCTCTGG GTTATATGTT AAAAAAAAGT TTATGGGGCT GAAGCCAGGC
72781 AACAGACAAG AGCCCCTACA ATCTTATTTA GGCTGAAAAT ATCCTGGAGT CCCTGTATTG
72841 TTGGTCTCAA GCAGATAGCA ACACTAACAC TTACTCTTTG AGGCAGGCAC TGCCAGTGGG
72901 GTGGCTGTTA TTATTAGCTT CATTAATTGG TGAGTCAGGA AAAAACAGCT TTAAATCATT
72961 CAAAGTTCTG GCCTATACAG GATTTAGTAA TATTAGGTTA GCTACATCCA AAAGATGACA
73021 GAACCCTACT CTAAGGCTGG GCTTGGTGGT TCACACCTAT AATCTCAAAA CTTTGGGAGG
73081 CTGAGGCAGG AGGATCACTT GGTGCCAAGA GTTTGAGACC AGCCTGAGCA ACATAGTGAG
73141 ACCCCTGTCT CTATCAAAAA CAAAGAACTC TAATTGGCAT AGTAGAAGGA AAAAGTGAAA
73201 GAAAAACCAG CTGTCACCCT CATTCCTTAC ACCTGTCCTA ACAACTCCTC TCACTATCCT
73261 TTGAATATAT CTTGGCTGTT TGAGTCTCTC TCTAGCCCCA TTACTGCTGT TTGGACTTGA
73321 CATTTGCTC TGCATTTTTA ACTTTCTAC CAGGGTTTCC AGACCCTGAA GAGTGTGGCA
73381 TGAAACAAAA CTAGTCAACC TATAATATTT ATGATGTGTG TGTAAATAAA AGAATACACA
73441 ATATATTGCA TTACAATATT TTAACTGTGT CCTCAATTTG TTTGTGGCTT TCTTGAGGAC
73501 ATCAGTTTTG GGTGGGACGA CCACATCCTT AATCTGAACT TTCCCTTGGA GGTCATTCTT
73561 TTTTTTTTGA AATAGAGTCT CGCTCTGTCA CCCAGGCTGG AGTGCAGTGG CGCAATCTCA
73621 GCTCACTGCA ACGTCCGCCT CCTGGGTTCA AGTGATTCTC CTGCCTCAGC CTTCCAAGTA
73681 GCTGGGATTA CAGATGCACG CCACCATGCC GAGCTAATTT TTGTATTTTT AGAAGAGACG
73741 GAATTTCACC ATGTTGGTCA GGCTGGTCTT AAACTCCTGA CCTCATGATC TGCCCACCTC
73801 AGCCTCCTAA AGTGCTGGGA TTACAGGCGT GAGCCACCCC GCCCGGCCAG AGGTCATTCT
73861 AATAGACTTT TTTTTGTTG TTGCTCACAG GCTTGTTCAA TCTTATTTCA AAATTTGAGA
73921 AATACAGTTT CCATGGAACA CCAACCAGAT ATCAGGTTGC TATGGAGTTG ATAGTCAAAA
73981 GCTTTGTATC TTCCAGTTTT TCAGAATGGC TTCTAAAGGT TCTGATTCAG AGCTCTTAGG
74041 CGAAATTGAA CAACCAAGTG TCAAAGTACA ACATTCAGGA AGTTAAAAAC ATGACTGACA
74101 TATATGTACT ATATATAGTG AGCTTGTGTA TGTGTCAATG AATGATTTAA TTCATTAATG
74161 AAGGAGGAAG CAGAATCACA ATTAGGTCAA AGGAAGATAC GGGAGAATAA AATATGTATT
74221 TGGTCAGGGA AAGGATGTAT ACTGGAAGAG GAAGGGAAAA TCAGATATAA AGTTGTTTAA
74281 TGACTTATTA GGCAATACAA TAATAACTTT TAGGGTCATT TTTTCTATAT TAAGAATTCA
74341 TTTCCATCTC TATGACAAAA TCCTTATTAA TTTATTAAAC TTCTACAAGT GAATGTTTAC
```

Figure 2 (Page 23 of 74)

```
74401 TTTTAGATAG TCTGGACCCA ATAAAATGTA AACATTAAGT CAGAGTTACT TTCACGTAGG
74461 ACAGTGTTGT CCAATAAGGT ACCACTAGCT ACACGTGATC ATTGACCATT TGGACTATAG
74521 CTAGACTGAT TTAAAATGTT CTAAAAGTGT AAAATACACA CCAGGTTCTG AAGATTTATC
74581 ATTTAAAAAA GAATGTCAAC TGTCTTTTTT TTTAGCTTAT TTATTATATG TTGAAGTGAT
74641 AATAGTTTAG ATATATTAAG TTAAATAAAA TATCTTAAAA TTAATTTTAC TTGTTTCTTT
74701 TCATTCTTTC AATGTGACCA CTAGAAATCT GGAAAGTATT TATGTGATTC ACATTCTATT
74761 TTACTGTCTA GTATTGCCTT ACATCATCAG GTACCCCATA AGTAGGCTTT TTAGATAATT
74821 CTCTAATATA GCTTGGAAGG ATATGGAGAA ATATTTTGC GTTGCTTTTA AGTTTTGCAT
74881 AACTTTTTCA ACACACTTTA TAAAGGATCT AGAAAAGGGT TGGTTACATG TTTCTCTGTC
74941 TTCTGGCCTC CACCATGTTG CCAGGAGGTT GGGGACAAGA TTCTGGGTGG CTGGATGTCC
75001 TAATGGCTTG AGGTCTGGAC TTGAGATTTG CATATAAAGA GATGTGATTA GATTGAGTCG
75061 ACTAGAAAAA TCATATTAGA GAACTGAATC ACAGCGATTA AATTTACATG TCGATTTATA
75121 AACCAGGACA CCAATTTATA GTGAAAGAAG GTCCAGTTAC CTGGTAATCA AGACGTTTCA
75181 TAGCTATTTT CATGATGGAT ATACTTAGCT GAGTTTTAAA TGAGAAGGGG GTTCATTGCA
75241 CATAGAATAA GATCTAAGTG AAATGTTTAT TTATTTTTT TTTTTTTGA CATGGAGTCT
75301 TGCTCTGTTG CCCAGGCTGG AGTGCAATGA GGCAATCTCG GCTTCTGGAG TGCAATGAGG
75361 CAATCTCGGC TTCTGGAGTG CAACGAGGCA ATCTCGGCTC ACTGCAACCT CCACCTCCCG
75421 GGTTCAAATG ATTCTCCTGC CTCAGTTTCC TGAGTAGCTG GGATTAGAGT TGCCTGCCAC
75481 CACGCCAGGC TAATTTTTGT ATTTTTTTTA GTAGAGATGG GGTTTCACCA TGCTGGCCAG
75541 GCTGGTCTCG AACTCCTGAC CTCAGGCGAT CTGCCCGCCT CAGCCTCCCA AAGTGCTAGG
75601 ATTACAGGCG TGAGCCACCA AGCCTGGCCT AAGTGACATG TTCTTATATT GTTCCTTTCT
75661 TTCTTTTTTT TTCGACTGAG TCTCACCCTG TTGCACAGGC TGGAGTGCAG TGGCGTCATT
75721 TCGGCTCATT GCAACCTCTG CTTCCCGGGT TCAAGCGATT CCCTTGCCTC AGCCTCCTGA
75781 GTGCCACCAC CCCCAGCTAA TTTTTGTACT TTTAGTAGAG ATGGTGTTTC ACCATGTCCG
75841 CTAGGCTGAT CTCAAACTCC TGGCCTCAGG TGATCCGCCC CCGAGTCTCC CAAAGTGCTA
75901 GGATTACAGG CGTGGGCCAC GGGGCCCAGC CTTATATTAT TTCTTTTACT ACAATATATT
75961 AGTATGATGC AGGTGCTTCA ATTGTTTATA CACTTTCCAT AATTTTGTAT AATTCTTATA
76021 CCCTGTCACT CTGAGGAATA GCCGGTCTAA GTGTTTTTCC ACCACTGCTA ATTCATCCAT
76081 CACTAATCTC ATTAGACTGT TAATTCCCAG AGGACATAAG CACACAAGCA GACAATGTTT
76141 ACAAATGTTG GACAAATGTT ATTTAATAAA ACAATGGGGT CACCCTTAGT CTAAAAGATG
76201 TTTCACTTTT CATTTGTCAT TGAACTCTTA TTTGTAGGTT CCCTTTTGAC TTTCCCACAA
76261 TCTAAGGCTG TTCTCTTTAA CACATATTTT CATGAAAACA TATATTTGAG CAGAAAATTGT
76321 TGGGGAGTTG TAATATTACC TTTGTCCCTA AATATGAATC TATAATTATA TCAAATATAT
76381 GGGCAGACAA TTTACTTTGC CTTTAATCTC AAGAAAAAAA TAGCAATTAC TTGGGGTCGG
76441 AGAGTAAAAT AAGAAGTAGT GAACCTTAAA GTAGCAAACT TTAGAACAGA ATAGTTTCAG
76501 AGGGGATGAG AAGAGGTGAT TTTTCAGCTC ATCAACAACA GATCTTATAA TAAATTACAT
76561 GTTCTGGTAC TTTTCTTGTC TTTCTGTGTT AAATTTTGCT ATTTAAAAAA ATAAATTTCA
76621 AATACATTGT TCATCTTAAA AGTCAAGAGT GTGTTTTATT AAAGTCAGTT GCTTTATTTG
76681 CAACTCAAAA GATATATTTG AGTTCCCAAC TGGAGATTGT CCTATATGGT AACTTGCGTA
76741 AGGTATGGTT ACTGAAAGTA ACCTACAATT TTCATGGGCT GAAATTCATT TCTATATTGC
76801 AGCGTACAAA AATAAATAAA TAAAAAATGC TTGTTTTCTT TGAAAACATA TTATCTCAGT
76861 GCCTCTAACT GCCAAATCTA TTGGCTTTTT TGCAGGCTTA AGGGCTCTCC CTTGTTCCTT
76921 TATGATCTCT ATCTTGAGGG CCAGACCTCC TGCCTTACAC AACTCAGAGG GGGACCTCAG
76981 AGCTCTTTAA AAAGAGCCCA ATTTCTCGCC TGTAGAGAAG TGAAAAGGAT GCCCCACCCC
77041 CATCTATGAA AAGAGGGATT TGATAGTTTC AATGTCTTCA AATCAAAGAT TTAAGTCTGT
77101 AGCCCCCCAC CACCCCGGAC CCTAGCAAGG CTCATGAACC CCCTCCCATC CCGCCCTAAT
77161 TGCTTTGGAC TGGCCGTGGA ATCCTTGTCC CAGTCCACAG TTCCTGTGCG ACTGCACGAA
77221 GAATTCACAG AGGACCTGTG TTACTTCCCT TGTGAAGAAA CAGAATTATC ATGAAAATTT
77281 AGGTGGAAAC CATTTCGCTT TTTTCTTCAA AAATAAGGGA AGCATGTGCC CAACCACCCC
77341 TGGAAAAAG AACCTTCAGG GGCAAGGAG CGAACAGGTA ATTTATAAGA AAAACAGAAA
77401 GTGGTCTCTG ACTGCCCCAG ACTTCCTTCG GAGTTGGGGG AATTGGGGAC GCCTGGACGC
77461 GTTGTTTTTG CGTTTGTGGA AAAAATAAAT GAAGAGCATG AAGCCCGAGG CTTCTGAGAT
77521 CCTTTCCTGA CCAAACCCAA GTGATTTGGT GCGGGGAATT TTAATATTTT TCCCCTTTTG
77581 TGAGGTGGAA CAAACACAAC TTGGGAGCAG CGCAGCGGCT CAGAGCCTGC CAGCCAGGCG
```

Figure 2 (Page 24 of 74)

```
77641 GGCGACCAGA GCACCAATCA GAGCGCGCCT GCGCTCTATA TATACAGCGG CCCTGCCCAG
77701 ACGCTGCTTC ATCGGCGCTT TGCCACTTGT ACCCGAGTTT TTGATTCTCA ACATGTCCGA
77761 GACTGCTCCT GCCGCTCCCG CTGCCGCGCC TCCTGCGGAG AAGGCCCCTG TAAAGAAGAA
77821 GGCGGCCAAA AAGGCTGGGG GTACGCCTCG TAAGGCGTCC GGTCCCCCGG TGTCAGAGCT
77881 CATCACCAAG GCTGTGGCCG CCTCTAAAGA GCGTAGCGGA GTTTCTCTGG CTGCTCTGAA
77941 AAAAGCGTTG GCTGCCGCCG GCTATGATGT GGAGAAAAAC AACAGCCGTA TCAAACTTGG
78001 TCTCAAGAGC CTGGTGAGCA AGGGCACTCT GGTGCAAACG AAAGGCACCG GTGCTTCTGG
78061 CTCCTTTAAA CTCAACAAGA AGGCAGCCTC CGGGGAAGCC AAGCCCAAGG TTAAAAAGGC
78121 GGGCGGAACC AAACCTAAGA AGCCAGTTGG GGCAGCCAAG AAGCCCAAGA AGGCGGCTGG
78181 CGGCGCAACT CCGAAGAAGA GCGCTAAGAA AACACCGAAG AAAGCGAAGA AGCCGGCCGC
78241 GGCCACTGTA ACCAAGAAAG TGGCTAAGAG CCCAAAGAAG GCCAAGGTTG CGAAGCCCAA
78301 GAAAGCTGCC AAAAGTGCTG CTAAGGCTGT GAAGCCGAAG GCCGCTAAGC CAAGGTTGT
78361 CAAGCCTAAG AAGGCGGCGC CCAAGAAGAA ATAGGCGAAC GCCTACTTCT AAAACCCAAA
78421 AGGCTCTTTT CAGAGCCACC ACTGATCTCA ATAAAAGAGC TGGATAATTT CTTTACTATC
78481 TGCCTTTTCT TGTTCTGCCC TGTTACTTAA GGTTAGTCGT ATGGGAGTTA CTGAGGTATC
78541 AGAGACGAAT TGGGTGACGG GGTTGGAGAG TGGCCGTGGT GAGGTTACAG CATTTAAACC
78601 TTTATTGCGG CTTCTAGGTC CCTGACCGGA GGCTTTTCTC GCTGGCGGAT GGTTTTGGGA
78661 TGGCAGTCCC GCCCCAGGCC TGTGAACGGC AGAAAAGACC GCAAAACAAG AGCCAGTTTC
78721 TTAGTCTAAA GGGATGTCCG GATTGGACTA AAAAATTTTC AAAAGTCCCG CCCTGCTCCC
78781 GGGTTGGTCC GTTCTTCTAG TACATGACTT TCATTCTGTA TTTAATTGGA TGGTGGAAGA
78841 CGTTGCTTAT TCTGTGTTTT TTGCTTTACT GTGACTTAAA AGTTTTGCCT CTTTTCTCTT
78901 TATATTAATG TCTGGGATTT CGGACGCTTT CCATGTTGTT GGTAGTCAAG TTGATGTCTC
78961 CTGGAGGTAG TGGCAACATC CAGCCCTGGG AGGAGAGTGC GTGCAGGTAC CTTTGTCCTA
79021 CATTCCTCTG CTGTTAATTT CTCATTCCTG TGGCAACGAA GGAATGCATT TAAAAAACAG
79081 CCACAACAGC GGCAATAGCC CTTCCTCCAC CCAAGGCAAT CGTGGACCTA GGGAGTTTTT
79141 TGTGCCACAT AACATGTAGC CTTCCGCTAA ACTGACAGGT TTGAGCGTAT CGATTTTGAG
79201 CGTATCGAAA GCACAACTTT TAGCCAGCCA TTTTGTCCTC GCATGACTAC GGTTGCTTAT
79261 CCTGTTTAGA CAGACAGCAA CATTTAAAAA TCGAAGTTCC TTTAAACGTA TTTTGTTTGG
79321 CAGTCCAAAT GTTTCTATGC AGAAAACAGT ATTTGTACTA TTAACTATGA AGAGTGTATG
79381 GATAAATGGG AGACATTTCT AATAAAGGCC TTCGTTAATG GTTCCCTCTG TTTGACATCC
79441 ATGGTGCTTC TGAATACAGA AAGCCTAGCG TCTTATATTC GCTTCTTTTA AAATCTGGTG
79501 GGCACATTTT GGTGAGACCT AAATTATGGG GACTGGGGCT TCTGGAGATA AGCTGCTCAA
79561 TTATTCTACC ATCTCCACAA TGATTAATAT AGTGAGTTGA TTTGTTAGTG ATAGTGACCA
79621 CGGATTCATC CCAAGAAAGA GAAAGGGGAG GGAGGCAAGC AGAGAGACAG GAAGACAGAG
79681 GCAGGGAAGA AGGAGAAAAC ATTCTCCCAT GGTTTAAGTA ATTTTGTGTT GTTAATTTTA
79741 CATTACAACA CGGTTTAACA TGGTGAACCC TCTATTTTGG TGTAAGGTTT AACATATGGA
79801 CATATTTTTC CCAAGACCAT TTATGAACTT TCATTTCTGC TTCCCCCTTC TTCCTCCCGT
79861 GCCACCCTCC ACGCTCCTAT CAATTTTGGC TGTTTTGTCA TAGGCTAATA CGCTATAATT
79921 TCATGGACAG TTGGACTGTC TTAGGTTTCT CAGGTTTCTA TTTTGTTCCT TTAGTCATTC
79981 CCACAATTCT TAAGGTAGAA TTGTATTGTT TTAAACATTG TGTTGTGTGC TATCCTCAAT
80041 GCTGAGATGA TTATGTGACA AATGGCAAGT GTTCAACTAA TACCTAAATC TGTAGTATCT
80101 TATCAAGCCT AATGCTACTT CACAATGCCT ACTCCATTCA CCGCACTTTA TCTCATTACT
80161 GGCATTCTGT CATCTCACAT CATCACAAGT AAAACGGTAA GCTATTTGA GAGAGATCAC
80221 AGTCATATAA TTATATTTAT ATTTATTTAT TTATTTATGA GACGGAGTTT CCCTCTGTCA
80281 CCCAGGCTGG AGTGCTGTGG CACGTTCTCG GCTCACTGCA ACCTCCGCCT CACGGGTTCA
80341 AGCGATTCTC CTGCCTCCGC CTCCCGAGTA GCTGAGATTA CAGGGCCTG CCACCATGCC
80401 CGGCTAATTT TTGTATTTTT AGTAGAGACG GGGTTTCACT AAGTTGGCCA GGCTGGTCTC
80461 GAACTCCTGA CCTCAGGTTA TCCGCCCACC TCATCCTGCC AAAGTGCTTA GATTACAGGC
80521 GTGAACCACC GTTCACAGAC TCAAATCATT TTTATTACAG TATATTGTTA TAATTGTTGT
80581 TTTATTATCA GTTATTGCTA ATCTCTTACA GTGCCTGATT TATAAATTAA ATTCATCATT
80641 GCCATGTGTA TATAGAAAAA AACAGTGTAT ATACGGTTCA GTACTATCTG TGGTTTCAGG
80701 CATCCACTGG GGGTGCAGTT TATTAAACAT GCATTTACAT TAGTCTCCCC TTTGGGAGAC
80761 TAATTAACTG AGATGTTGTA ACGTGACTTT AATAGCAGAT AGAGCTAATT TTCTCTCATT
80821 ACTCTTCTTT TTCAGAATTT TCCTGGTTAT TCCATTTTTT ATTTTTCCAT ATGTATATTA
```

Figure 2 (Page 25 of 74)

```
80881 AGATCTCTTC CACCTCCTCC TGTTTCTCCA TCTCAACATC AAACAATTAA AAAAAAAAAA
80941 AAAGGCTGGG CGCGGTGGCT CACGCCTATA ATCCCAGCTC TTTGGGAGGC CTAGGCGGGT
81001 GGATCACGAG GTCAGGAGTT CAAGACCAGC CTCGCCAAGA TGGTGAAATC CCGTCTCTAC
81061 TAAAAGTATA AAAATTAGCC AACCATGGTG GCAGGCGCCT GTAATCCCGG CTACTCGGGA
81121 GGCTGAGGCA GAGAATTGCT TGAACCCGGG AGGCGGAGGT TGCAGTGAGG CGAGACCTTG
81181 CACTCCAGCC TGGGTGACAC AGCGAGACTC CGTCATAAAA AAAAAAGCCG GAAGCAGTGG
81241 CTCACGCCTG TAATTCCAGC ACTTTGGGAG GCTGAGTCAG GCAGATTACC TGAGGTCAGG
81301 AGTTCAGGAC CAGCCTGGCC ATGAAAATAC AGCCTGGCCA TGAAAACACA CAATAAATTA
81361 GCTGGGCGTG GTGTCACACA CCTGTAATCC TAGCTACTCG GGAGGCTGAG ACAGGAGAAT
81421 CACTTGAACC CAGGAGGCAG AGGTTGCAGT GAGTTAAGAT GACGCCACTG CACTCCATCT
81481 GGGCGACAGA GCCAGACTCT CTCTCAAAAA ACTAAATAAA TAAAAATAAA GTTATGGTAC
81541 ATTGAACTTC TGTGTTCCTT TCTCCCTTAG ATACTTTCAT GGCTACCCAT TTAATTGATG
81601 TTCTTATCAT CTCCAAGAGT TAGTCAGGAG AGGAATCAAC CCAAGCAAAA ATAGCTGATT
81661 TTCTAATTTT CCTTCAATGC CCTTTGGGGT CTTAATCCAT TTGATTTATG TACTTTCAAT
81721 TAATCCTAAC CTCGAATGTC TTCTGCAAAC ATGTTTCCAC AGATGAAACT CGTCAAATGA
81781 AACACATTCC TTTAATTTAT AGAGTTAAAA ATTAGAAAAA TTTTCAATTC TATTTGGCCT
81841 TTAGATTCAG TCTTGCATAT GTTTTCTCAA TTTTGTTCAT GCTCTTTAGT TTTGTTTTAT
81901 TCCATCACAA TTGTTCACAT AGCTTACTGG CTTAGGTCTA ATGAACCATT CATTTGGAAA
81961 TTAAAATTGG CCATTTTAAG ATGAAAAGA TTCTTGCCTC AATTTTACTT AGTTTTTGAA
82021 ACTGTCAATG AGGACACATG TTTTTCTGTA CTCTTAGATT CACTAAGTAG TGTCTTGCAA
82081 ATTTAACTGA CAAAGGACAG ATTAACATGC GAAAAAAAAA GCATGCAATT TTATTAGTAT
82141 ATTACATGCA CAGAGTTCCC AAAGAAAAAA AAATTGAAAC CTTAAAAACG CGGTTAGACT
82201 CACAGACTTA TACACCATTC CAACAAAGGA AAGGGAGTTT GCACTTCATG GGATGACGAA
82261 TTTGGGAATG TGACAAGGAA ATAAATACAT GGGCAATAAA AACCATGGAA GATAAAATGA
82321 AAGATAGAAA TAATTGTAGT AAGGTTTGTT TTTGCAGAGT CATCTCAGTG CCAACCTTCC
82381 ATATCTAGTG ATAAGAATTG CTCTCTTTTT CCTGGTATAG CAGTTGGGGA CACTTTTACA
82441 AGGGAAATTT CTGTCACCTT CACAAAGGGA AATTTGGGTA AAGAGAAGAC AGAGACCTCT
82501 TCCTACACCT GTTGATTTTC AATTGCCTTC AGCTGAAAAT AACTTTTATG CCAAAGTAGA
82561 ATAATTTGGG GGTGACATCC TGATATTCTT CAAAACTTAT ATTTAATTTC ACATTAGTAA
82621 TTATATCATT TTTGATTTTT AAATTAGTTT TATAAAATAA TTTTGAAAAA CGGTAATAAT
82681 ATTCAAATAA TTCCAGAAAC ACTGCTGATA AGCCAAAAAC ATCAATGAAT ATTGCATAAA
82741 CAACTGATAA TTCAACCATG AAAATTTATG ACATTGTTCT TGTGTGATAA AACTATGAGT
82801 AACATAAAAA CTAGAGGCTA CTTGTAATGC ATTATTCCAA ACTTTCTGTT TTTTATTTAT
82861 TTATTTATTT ATTTTGAGAC ATAGTCTCTC TCTGTCACCC AGGTTGGAGT GCAATGGCGT
82921 GATCTTGGTT CACTGCAGCC TCCACTTCCC CGGTTCAAGC AATTCTCCTG CCTCAGCCTC
82981 CTGAGTAACT GGGATTACAG GCACCTGACA CCAAACCCGG CTAATTTTTT TGTATTTTTA
83041 GTAGAGACGG GGTTTCGCCA TGTTTGCCAG GCTAGTCTCG AACTCCTGAC CTCAGTGATC
83101 CACCTACCTC GGCCTCCCAA AGTGCTAGGA TTACAGGCGT GAGCCACCAT GCCCGGCGCA
83161 TTATTCCAAA CTTTCATACA CAGTGCTATC ATGGCTACAA ATTGAAGTAT CATATTATAC
83221 ACTCCTAGGC AAAGCTCTGG ATATTTGGC TATATAAGCC TGAGGGAAAT GTAGTAAGGA
83281 CATTGTGGTT GAAATTCATA CCAGAGATGA ACAGGCCCAG TGCAAGACAG AATTACATCA
83341 CTAAAGGATA TCAGAAGAGA ATAGGGATTT AGGGTACAGT GGCAACAACA GTTTTGGGAA
83401 CTAGCATTTT TTGAGCACTT ATTTACAATA TGCCAAGCAC TGTTGCTGAT TACTCTATAT
83461 TTATTTTCAA ACACATTCTT GTCACAGCAC TTTGAAGTAA GTGCCATTGT CATTCCCACT
83521 TCAGGGTGAA GGACTAAAGC TTGGTGTCAT TAAGGATGTA GCTAGTTAGC TGTGTGTGTG
83581 TGTGTGTGTG TGTGTGCATT TTTTTTTAAA TTTAAAGTCA ATAAATTTTT ATTTGAAGAA
83641 TTTCACATCA AGGTAAACTT TGTTCCTCTA AAGAGCTGGA GTCAAAATGT ATCTTCAAAA
83701 GATTCATCTT CAAGTTAGCC CTTCTTAATA GAACTGATGC TTAATCCACA GTTGTCAGCC
83761 CACAGTTCTT TTATTTTGAC TTTTTTTTTT TTTTTTTTTG AGACGGAGTC TCTCACTGTC
83821 ACCCAGGCTG CTGGGCAGTG GCGTGATCTC GGCTCGCTGC AACCTCTGCC TCCCGGGTTC
83881 AAGTGATTCT CCTGCCTCAG CCTCCTTAGT AGCTGGGACC ACAGGCGCAT GCCATCGTGC
83941 TCGGCTAATT TTTGTATTTT TATTAGAGAC AGGGTTTCAC TATGTTGGCC AGGCTGATCT
84001 CAAACTCCTG ACCTCATGAT CCGCCTGCCT TGGCCTCTCA AAGTGCTGGG ATTACAGGTG
84061 TGAGCCACTG CACCCGGCCT TATTTTGCCT TCTTTAATCT CCATTTGAAC ATGGACATAC
```

```
84121 TGATGAAAAC TACAACATTC TTCACCAAAA ATCTTTGGGA TTTAATTTCT TCAACCACTT
84181 TACTTTGGGG TCATTTTAAG ATTAGGTGTA TCTGCCTGGT TCTCAATTTG ACACCCTTTC
84241 TCTCTAAACA TGAATGAGTT CCAATCATAT TTATTCCTAA GCTATCACAC TCAAATATAC
84301 TACAGATCTG TGGAATATGC CAAAAGTTAA GGTGAAAAAT TAAATTATTA GGTATTTCAT
84361 AGTTTTGCTA GTTTTTGATC TGTGAGTGAA TATAACTATC CTCTATGTCC TGGCACTGTT
84421 CCTCAGAAAC ATAGGGTCCA CATATGTAAT TTTAAATTTT TTAATAGGCA CATTTTAAAA
84481 AGTGAAAAAA GAAATCTATT TTAATGATTT GAATCCAGTG TAACCAAAAA TTGTTTCAAC
84541 AAGGTATCTA ATATTAAAAT ATTGAGTTTT TACTTTGTTA TTTTACTAGG TCTTTGAAAT
84601 CTGGTGTGTA TTTTACACTT AAAGCACATC ACAGTTTGGA GTAGCCACAT TTCCAATGCT
84661 TAATACTCAC ATATGGTTAG TGGCAACTAT CTTGGACAGG ACAGCTTTTA TACTCTGGGA
84721 AGACACAAGC AAATACTTGC TCTGCAGCAG AATCCAGATG TTTTCCAAGA AAACACTTTT
84781 TCTGACCTGT TCGTGAAACC CAGGTAGTGT CTCTAATACT TTATATTTTA TTGGTTTGTC
84841 CTATTGTAAC CACCCAACGG GCTCTCCTTG TCCACTTCCT AGACAGAGCT GATTTATCAA
84901 GACAGGGGAA TTGCAATAAG GAGCCAGCGC TACAGGAGAC TAGAGTTTTA TTATTACTCA
84961 AATCAGTCTC CTTGAGAATT TGGGGACCAA AGTTTTTAAG GATAATTTGA TTGTAGGGGA
85021 CCAGTGAGTC GGGAGTGCTG CTTGGTTGGG TCAGAGATGA AATTATAGGG AGCCTAAGCT
85081 GTCCTCTTGT GCTAAATCAG TTCCTGGGAG TGGTGGGGTG GGGGACTCAA GACCAGATAA
85141 TCCAGTTTAT CTATATGGGT GGTGCCAGCT AATCCATTGT GTTCAGGGTC TGCAAAATAG
85201 CTCAAGCATT GATCTTAGGT TTTAAAATAG TGATTTTATC CCCAGGAGCA ATTTGAGGTT
85261 TAGAATCTTG TAGCTTCCAG CTGCATGACT CCTAAACCAT AATTTATAAT CTTGTGGCTA
85321 ATTTGTTAGT CCTGCAAAAG CAGTCTGGTC CCCAGGCAGG AAAGGGGTTT GTTTCTGAAA
85381 GGGCTGTTAT TGTTTTTGTT TAAAAGCAAA AGTATAAACT AAGCTCCTCC CAAAGTTAGT
85441 TAATCCCAAA CTCAGGAATG AAAAGGACAG CTTGGAGGTT AGACGTTAGA TGGAGTCGGT
85501 TAGGTAAGAT CTCTTTCACT GTAATAATTT TCTCAGTTAT GATTTTTGCA AAGGCAGTTT
85561 CACTGTCCAC TTCACCTCAC ATCAGGCCTC TGACTAGAGG ATTCCAACAA TACTTAGGCC
85621 AGGACACCAC CATGTCTCCT TATCCACCCT GAGGGATTCC AATTTCTGAA ACAAAGGAAA
85681 CTATATATGA TAGTATGAAA CTATATATGA GAAGGAAATT ATATATGATA ATCAATTTTA
85741 GGGTTATCTT ATTGATTAGA AGATATTAAA GTGTGACACT GCCTGGCAAT GATATCTGCT
85801 GGTAGTAAGA ATTTGGCGAA TTTAGTGAAA TTCCTGAGGC TGAACCTCCA CTTCTGTAAA
85861 ATGGAGACAG TGAGATAATT TGCCTTACAA TGCTGAAGTA AGAATTTTAC ACAATAATTC
85921 AGACCAACCA CTTCATGTGG TACTTGGCCC GTGGAAGACT ATCAATGACA GTTAGTTTAT
85981 AGTTTATACT ATTAATGAAT CCTTTGTTTC ATTGTTATTT CCTTCTACAC GTTGGCCTCT
86041 CTAAAAGAAG GTAATATTCA ATACAAATAA AGTTAAAACA GCTTGCAGAG TTGTCCCAGG
86101 GAACTCACTT AACCACTGAA GTGTTCAAAT TGCTTAAGGT TGACTTTATA TTCTCCTGAC
86161 TAACCTTTCT CCTTCTGGTA TTTCTTCTGA GAACAGCACC ACCATCCAAA GCATCATGCA
86221 AACAGTGGTC ATCCCAGACC AGTAATTCTC AACTCACAGG GTGCTCCTGC AGAGATGTAT
86281 TTGAATAGAG TGGTAGGATG CTGAAGAAGG CCACGTAAAA TTTGGCCAGT GATCTGGGGC
86341 AGATTTATCC TGAAGCTAAT GAAACACAAG TGTAAGGGCC TGTACTTCCA AGGTGCAGAG
86401 AGGGGCCCTA CAAATGTGTT AGTTTGTCTC TCTCTCTCTC TCTGATTTTA AAATTTGCAG
86461 TATTAAGGTA CTTTAATCAC GGATGGTTCA GGCTGCTATT TTCACTCAAT CCTCCTTTTT
86521 ATTAAAATCA CCATTGTCTG ATTATGTTAG AATCCTGATG AAAATATTTG GAATTTGAGT
86581 AAGAGAAAGT TTAGTTGAAG ATGTATCTAG TATGGGGATA ATAAGTTACG TGATTTGCAT
86641 ATGTGATCAT GTGTACTTCA TTCGTTGCCA GCCAATCTGA CGTAAGAATG GCTTCAAGGA
86701 GGCCGGGCGC GGTGGCTCAC GCCTGTAATC CTAGCACTTT GGGAGGCCGA GACGGGCGGA
86761 TCACGAGGTC AGGAGATCGA GACCATCTTG GCTAACACGG TGAAACCCCG TTTCTACTAA
86821 AAATACAAAA AATTAGCCGG GCGTGTTGGC GGGCGCCTGT AGTCCCAGCT ACTTGGGAGG
86881 CTGAGGCAGG AGAATGGCAT GAACCTGGGA GGCGGAGCTT GCAGTGAGCC GAGATCGCGC
86941 CACTGCACTC CAACCTGGGA GACACAGCGA GACTCCGTCT CAAAAAAAAA AAAAAAAGAA
87001 TGGCTTCAAG GAATGTTCCT ACTGCTCACT GGAATAACTC ACCTAAATTC CTGGCAAGAT
87061 GCAGGTCTAG ATAAAATGTT ATGACATCTA AGTATTCAAA ACACATTCCC AGCACTGAGA
87121 GTGAGTGTCT AGTGGAGAGT AGAAACGTAT AGAGCCAGAA GCTAGTCTGG AAAGAATTCT
87181 TACAAAGTTT ACAACTTACA TGTGAAAGGA GCTTAACAGA GGATTTTCCA AATTTGAAAA
87241 CAATCCTAAA AACTTACTTG ACATTACCAA TAATGTGTTT TGAAACTGAA ATACTTCTAA
87301 GTTATGAAGA AAACATATTA TCATCAGCCA CCCTGGAGGA AAGATTGAAT TCTATTTCCA
```

```
87361 TTACCTATAG ACAACATTAC AAAATAATTT CGATCTGAAG ATGGAATCAG AGTATTCAGT
87421 CAAAACTACA GGAAAATATA CTTGGTAGTG TCATATTCAG AAGTTAATAA AATATGCTAT
87481 TTTCTGAATT TTGTGATGGC TGTTGTTTTG TCAGCTTTTA TAAAATTGGA ATTTGATTTT
87541 ATTTTCCCAT TATAAATTTA TATTTACAGT CTGCAGTACT TTTGCATTTT TAATTTTACA
87601 TTATAGCTTT TAATAGTTAA CAAGTTGTAA AAGGTTTGAT CCCCAGAAAA CCTTGATCTA
87661 CCCCCTCAGT TAAGTATACT AATATATTTA GAAAATGGAT GAAATCAGCA TTTGAATATT
87721 TTTAAATATT TATTAAAAGA GGACATGGGT AAAAGAGCTT TGCAGTTGCC ACCCTTCATT
87781 CTCAAATTCC CTGGATAAGG ATGACCGCAT AATCTTTGGA TGGTCATACG CAAGTCTTGT
87841 GTATTTGTTA CATAAATCTA TTTAGTGGAC TTTTGGCAGT GTGTACTGAG GCCAGTTTCT
87901 TCCACCTGAG CTCTGACTCC ACCTCCAGCA GCCCAAAACC AATACTGAAT TTTGGGGTCA
87961 GCTATTGTTT TTGTGGACTT AGGTAACTAC ACACACATTG TCTTTATGAT AGCTTTAATA
88021 ATACTGCCAT CAGAACTAAA ATTGTCACGT GGATTAAAAG GAGTGACGGT GGTGTCCCCA
88081 GGAGCCTTTC AATATGTAAG TATTTACACA TATACATGCT AAAAAGACCC CTAGGAATTT
88141 TTTTAACAAG GGCAAAACAG TAACTCAGCT TGTTTTCTCG CAGTAAAACC GGTTGAAAAG
88201 GCCTGATAGA CTTGTCTGCA GTTACAAAAC TTGTGTGTAG TTATCACCTT TATATCTCCT
88261 GGAAACTAAC ATAGACAACC GAATGGGTTA CAACTGTTTT TAAGTGAAAT TGTGAGTGGC
88321 TCTGAAAAGA GCCTTTTCAA TGAGGAAGAA ACGGGCAGAC TTATGCCCTT TCCCCACGGA
88381 TGCGACGTGC CAGCTGGATA TCTTTGGGCA TGATGGTGAC GCGTTTAGCG TGAATAGCGC
88441 ACAGATTGGT GTCTTCGAAG AGTCCCACCA GGTAGGCCTC GCAAGCCTCC TGCAGCGCCA
88501 TCACCGCAGA GCTCTGGAAA CGCAGGTCGG TTTTGAAGTC CTGGGCGATT TCTCGCACCA
88561 GGCGCTGGAA CGGCAGCTTC CGGATCAGCA GCTCGGTGGA CTTCTGGTAG CGACGGATTT
88621 CGCGCAAGGC CACGGTGCCC GGGCGGTAGC GATGAGGTTT CTTCACGCCA CCGGTGGCCG
88681 GAGCGCTCTT ACGGGCTGCT TTAGTAGCAA GCTGCTTGCG CGGAGCTTTG CCGCCGGTAG
88741 ACTTGCGAGC TGTTTGCTTC GTACGAGCCA TTTGCAATGA GAGCACACAC AAAAGTGTAG
88801 TGAACTGAGA GCAAGTGGCC TTTAAATATA GTGAGAAACA TTCTGATTGG TCCTGTAATA
88861 TTTCAAAAGT CCCGCGCGAT AAAATCATTG GCTGAAGAGT GACCAGACTG ATTGGTTCAT
88921 TACTAGACAA TCTTATTGGA TGAGTTGCCC CACCGCCCAT CCTGTCCTTT TCGTTTCAGT
88981 TATCTGCAGC GACAAATTGT CTAAAATTCT AGTTCATCCA GTCCCAAAGA ACAGAGTGTA
89041 TAACAAGGTA TCTAAGGATT TTTAAAATGT AAATTCCGAT TCAGTAAGTT TGAGTGGGAC
89101 TTGAAATTCT GCATTCCTGA CAGTCTCGCA AGTTATCAAT GCTGGTGAAC ACTCACTAAA
89161 CCACCAGAAA CGTTCAGACT CATGTCGGGA AATAACGCTT ATATTCAGAG AATGAGATTC
89221 CATGCTATTT TGTTACTGGC GAACAGCAAG TTTCCTTGCC CTTTGTTTTC TAAGTCCAAG
89281 TCACATTCCC ACCCTGCCTG TTCTCAAAAT GTCTTATTTT GGTTGGCCTT AAGTTTCACT
89341 TTGTATACTC TAAAATGTAC TTTCTAAAGG AAGGTGTTAT TTTCTCGAAA CTTAACTTTT
89401 TAACACCATT AGGCTAGGGG GGCGGTGGCT CACGCCTGTA ATCCCAGCAT TTGGGAGGG
89461 CGAGATGGGA CGATCACTAG AGGCCAGGAG TTCAAGACAA CCCTGGCTAA AATGGTGAAA
89521 CCCCGTCTCG CATAAAAATA CAAAAACTAG CTGGGCGCGG TAGCAGACGC CTGTAATCCC
89581 AAGTACACAG GAGGCTGTGG CATGAGAACC GCGTGAAGCG GCGGGGTGGA GGTTGCAGTA
89641 AGCCGATATC GCGCCGCTGC ACTCCAGCCT GGGTGACAGA GCTAGACTGT CTCAAAACAA
89701 ACCAATCCAA ACGAAAAGCA AAAATACCC TAACAGAAGC AAGTTATCAT CCTTTCTTGT
89761 GTAACTATGG ACGGCTCTGA AAAATGCCGT TTCAAGTGTA AGCTACGTTT TCTGATTTGA
89821 GTGTTTACTT GACCTTGGCC TTATCGTGGC TCTGTTATTT TGGCAACAGG ACGGCCTGAA
89881 TATTGGACAG GACGCCTCCC TGAGCAATAG TGACGTTGCC CAGCTGCTTG TTGACCTCCT
89941 CGTCGTTTCG GATGGCCAGC TGCAGGTGGC GGGGGATGAT GCTGCGGGTC TTGTCACGTA
90001 TGGCGCTGCC CACCAGTTCT AAGATCTCGG CGGCCAGGTA CTGTAAGTAC ACTGGCGCAC
90061 CGGCTCCGAC CGGCTCAAAA TAATTGCCCT TTCGAAAAAG ATGACGGACT CTGCCCTATT
90121 GGGAACTGCA AGCCGGTAG CGACGAACAA GTTTTTGCTT TAGCTCCATT TTCCACGTCC
90181 GCAAATAGCG ACCTATGAAA GCAGCGGAAA ACTGTGAAAG ACAAGCAAGC TGGAATGGCG
90241 CCTGAACAAA TCCTTTTATA CAAACTGCAA GGCTGCAATA GGAAGCTATC CTATTGGTCA
90301 ATTATGTTTG GTGCTTTATC CAATAGAAAA AGATAACATA AATTCCATAT TTGCATAAAC
90361 CCCACCCCTC AGTGAAACCG TGTTTCTTTT GTCCAATCAG AAGTGAGGAA TCTTAAACCG
90421 TCATTTGAAT CTCAGGACTA TAAATACATG GGCTCTGAAC TGTTCTCTGT ACTACTCTGT
90481 AGTGGAGAGT GTTAGTAGCT TTTCTATTCT GTTTAGGAAT AGCAATGCCT GAACCCTCTA
90541 AGTCTGCTCC AGCCCCTAAA AAGGGTTCTA AGAAGGCTAT CACTAAGGCG CAGAAGAAGG
```

Figure 2 (Page 28 of 74)

```
90601 ATGGTAAGAA GCGTAAGCGC AGCCGCAAGG AGAGCTATTC TATCTATGTG TACAAGGTTC
90661 TGAAGCAGGT CCACCCCGAC ACCGGCATCT CATCCAAGGC CATGGGGATC ATGAATTCCT
90721 TCGTCAACGA CATCTTCGAG CGCATCGCGG GCGAGGCTTC TCGCCTGGCT CACTACAATA
90781 AGCGCTCGAC CATCACCTCC AGGGAGATTC AGACGGCTGT GCGCCTGCTG CTGCCTGGGG
90841 AGCTGGCTAA GCATGCTGTG TCCGAGGGCA CTAAGGCAGT TACCAAGTAC ACTAGCTCTA
90901 AATAAGTGCT TATGTAAGCA CTTCCAAACC CAAAGGCTCT TTTCAGAGCC ACCTACTTTG
90961 TCACAAGGAG AGCTATAACC ACAATTTCTT AAGGTGGTGC TGCTGCTATT CTGTTTCAGT
91021 TCTAGAGGAT CAACTGGAAT GTTAGCGAAG ACAAGTTTTA GAGCCAAGGT TAACTTGGAC
91081 GGGGCCGTGC GCGGTGCCTC TTGCCTTTAA TCCCGGCAAT TTGGGAGGCC GAGGCGGGCG
91141 GATCACTTGA GGTCGGGAGT TCGAGACTAG CCCGGCCAAC ATGGCGAAAG CCCGTCTCTA
91201 CTAAAATACA AATGATAGAC GGTCGTGATG GCGCTCTTTC TCATCTGTCT TAGCAAACTT
91261 CTTTGTTCCC CCTGGGTAAG CCTTCGGGTA CTATGTATAA TTCCTTTGAT AAGGTCACTA
91321 CTCCCTCCCT GGTCTAGTAC AGGAAACTTC CCTTTCTGGA TAATGAAGCA GGTAATGGAA
91381 TTCAGGGTAT AGTGTTCCTG TGGGGGTCAT TAGCCGTTAA CTTCTTGTGA GATGCGGGGG
91441 AGGGGAGCAG AAAAGTCTAA GCGACAAAAG GGCATGTAGG GATATTTGCT CCTGCAGCTT
91501 GCCTATGCTG TAAATTCTTA CTTCAAGTAT TGAGGAAACA ATAAGCGAAG TCTGATTTCC
91561 CGGGCGCCTT TATACGGAAT ATTTCCCGCT CCACAAAATG AAATCGCAGT AGTTTTGAGT
91621 TATAATTGTT TATCAATGAC AACAGCTATG TAGTTTACAT ATTTCATGCA TCCCAGAAAT
91681 CCAGATTCCC ATTTCCTAAG CCACTTAACG TTCTGATTTC CAGCTCTGCG AGATACAAAA
91741 GGGTTTGGAT TTTGTGCCCT TCCCATCTG GCGCCACTGC AAAGCTTACT AGGAGGGCCC
91801 CACTTGGAGA GGGAAATCTT TTTCGAGAAG TCCAGGACGC CAAAAACAAT ATAGCTAAAA
91861 AAAAAAAAAA AAAAAAGGCA GGAAGAGCAC TAGTTGAGGA GGAGGACTCA ATGGGCCAAT
91921 TCTGGGGCTG GGCTGGGGG AAGAAATGCA AGAAGAAAG ACACTTGTTG ACTGCACAGT
91981 AAGCAGGAGG GGGTGGGGGA ATCGGAGGGG AGTATTTTCA GCGAATTTAT GGGCATTATA
92041 TGTAGGTGAC ATACAGCAGT GTCTTTGGAT GAAGAAATAA AGTTTCTCAA ACAGTTCTTG
92101 TTTTTGTTTT GAGAAAGGGC CTTTCTCTGT CGGCCAGGCG CCATCATAGC TCACTGCAAC
92161 CTCGACTTCC CCAGCTCAAG CGATCCTCTT ACTTCAGCCC CTTGAGTGGC TGGGACTAGA
92221 GAAATGCACC ACCATACCCA GTTAATTTTT TAATTTTTTG TGGAGGCAAA GGGTCTTACT
92281 TTGTTGCCCA GGCTGGTCAA GCGAACTCCT GGGCTCAAAT GATCCTCCCG CCTTGGCCTC
92341 CCAAAGTCCT GGGATTATAG GAATGAGTCA CCGCGCCCGG CCCAGATTTA ATTTTTAAGA
92401 ATCTTTTAAA AGAGGTTCTG GCCGGGTGT GGTGCAGCTC ACGCCTGTAA TACCAGCATT
92461 TTGGGAGGCC AAGGTGGGAG GATCACTTGA GCCCAGGAGC TCAAGACCAG TCTGGGCAAC
92521 TTAGTGAGAC CTTTTGTCTC CACCAAAAAT TTAAAAAATT AACCAGGCCT GGTGGCACAT
92581 TTCTGTAGTC CCAAGTACTG GGGAGGCTGA AGTGGGAGGA TCATTTGAGC CTGGAAGGTG
92641 GAGGTTGCAG TAAGCTGTGA CGGCACAACT GCACTCCAGT CTGGGTGAGG ACAGACCCTG
92701 TCTCAAAAAT AAAAAATAAA AAAAAATCTG GATGCCACAC AAAATGTCAG TGAACAACTG
92761 TAAGTGAAGC ACTTCCCATC CTAGTACTGT ATATGCAAAC TGCCGTTGTG AAAGTGACGC
92821 TTGGCTTAAA AATCTACATT CTTTTTTTAA TTATAAAACT ACCACATCCC CCAAAAACAT
92881 TACTAAGGAA TTGAGGCTGC AGTTTAAGAA GCTGATATTT AGGATCTATC TCCGGAGAAG
92941 TGAGACCTGG TAATATAAGC ATTTTCAAAA TGAACTTTTG GGCCAGGTGA GGTGTGTCAT
93001 GCCTGTAATC CCAGCACTTT GGGAGACCTA GTCAGGCAGA TCACTTGAGC TCACAATTCG
93061 AGACCAGCCT GAGCAACATG GCGAAATCCA GTCTCTACAA AAAATTAGCA GGGCGTGGTG
93121 GCATATGCCT ATAGTTCCAG CTACTATAGA GGCTGAGGTG GGAGGATTAC TTGAGCCCGG
93181 GAGGCAGAGG TTGCAGCAAG CCAAGATCGC GCCGCCACAG CCTGAGCGAC AGAATGAGAT
93241 ATGCACCCAC GCCCTAAAAA AAAGCATGAC TCATTAAAAA AAAAAAATTT AGCCGGTCGC
93301 GGTGGCTCAC GCCTGTAATC CCAGCACTTT GGGAGGCCGA GGCGGGCGGA TCACGAGGTC
93361 AGGAGATGGA GACCATCCTG CTTAACACGA TGAAACCCCG TCTCTACTAA AAATACAAAA
93421 TAATTAGCTG GGCGTGATGG TGGGCGCCTG TAGTCCCAGC TACTCGGGAG GCTGAGGCAG
93481 GAGAATGGCG TGAACGCGGG AGGCGGAGCT TGCAGTGAGC CGAGATCGCG CCACGGCACT
93541 CCAGCCTGGG TGACAGAGCG AGACTCCGTC TCAAAAAAAA AAAAAAAAA AAAATTAAAA
93601 AAATATGAAG TTTTGAAGCA GAAATTATTT TGTCGTATGT TCTTTCATAA ATTTTTTGCC
93661 TGCCTGCCTT CTTCCTTTGT TACAGAACTC CAACACTTAC CCAAAGGTAG CTGTTGGGTC
93721 AGGGTTTCTG TACTATAGTC CCTTCTGTGG TGGCCAGAAA TATGTTACAG GAAAGAGGTC
93781 CCCATCCAGA CCCCAAGAGA GGGTTCTTGG ATCCCGCGCA AGAAAGAGTT CAGGGTGAGT
```

```
93841  CCGCAGTGCA AAGTAAATGC AAGTTTACTA AGAAAGTAAA GTGGTGAAAC GACAACTACT
93901  CCATAGACAG AGCAGGACAT TCCCGAAAGT AAGAGGAGGA AGGCATCCAC CCTAGGTACA
93961  ATACTTGTAT ATATGGGGAG ATGTGCTCTG CTACAAGTTT GTGATAAAGG ATTAATTTTC
94021  TTAGTTACTA TATTTTGCAA GAATCAACAT TATTATCTTT AAACAAAATT AAGAATGCCT
94081  TTGTTCTCCA GATATAGGGA TATCTGGACA CTCCTAAGTC TGAGTCTGTT TAGTAAACAT
94141  TATTTATTTG TTCCCTTAAC CGTAAACATC TAGAAGCTAG GAATGACTGA CTTTCTGGGA
94201  ATGCAGCCCA GAAAGTCTCA GCCTCATTTT CCTAGCCCTC ACTCAAAATG GAGTTACTCT
94261  GGTTCAAGTA ACTCTGACAC TTTTCTTCTC TTTTTTTCTT CTTTTTTCCT TCCTTTATTT
94321  TTTATTTTTT ATTTTTGAAA TAAGAAATCA AGAATACTTG ATGTTTCATC TAAAACAATA
94381  CCCATAATTG ATAAGCCAAA ACAAAAACCT AGGTCTTCTA ACTCAAAACT AGGATGTTTT
94441  GCTGTCTCTG CTGATACTCG GCTGATCGTT AATAGGTAAT TAACAAACAA GCCTTGCTAT
94501  GTCCCCCTCA GTTTATTACC ATTAGATCAT ATGCCTACTG TCAATCATAT TAATCCACAA
94561  CTATGCATTT CACAAAACTT GCCATAAAAA TTCACAGGTT TCCCGCTTCC CTCGAGTTTT
94621  CATTTCCGAA GGGTCCCATG TAATATAAAA CTTATATTAA ATACATTTGT ATGCTTTTCT
94681  CTTGCTAATC TTTTTTTTTG TTTTTGAGA CTGAGCCTTG CTCTGTCACC CAGGCTGGAG
94741  TGCAATGGCG CGATCTCGGC TCACTGCAAC CTCCGCTTCC CAGGTTCAAG CGATTCTACT
94801  GCCTCGCCCT CCCGAGTAGC TGGGACCACA GATACGTGCC ACCATGCCCC GCTAATTTTT
94861  GTATTTTTAG TAGAGACAGG GTTTCACCGT GTTGGCCAGG ATGTTCTCAA TCTCCTTACC
94921  TCGTGATCCG CCCGCCTCGT CCTGCCAAAG TGCTCGGATT ACAGACGTGA GCCACTGCAC
94981  CCGACCAATC TGTCTTTTTG TAGAGGGGCC TCAAGCATGA ACTTACTGAT GGGTGAGAAA
95041  AACAGAATTT TCTTTTCCCC TACAATATAA ACATTAATTG TAATGTTATC ATTCAGGACA
95101  TTTTGGTGAC CAATCTTACA GAAATTTTAT CTTGTGCAAG TCTATGCAAA CCAATATGTA
95161  AATCTTCTAT AAGTGAGATT GTATTTCACT TTTCTAGTAT CCTTTTAAAT TAATAAAAGA
95221  GATTCTAATG ATTATTTTCA TTACTGCATT TCATTGTAGG GAAGTAGATA ATTGCCCTTT
95281  ATTCACTGAC CTTCGCTTTT TAAAAATTTA AACCATGTTA CCATGAAAAT GCTTTTCAGT
95341  ATTTCTCTAC ACACAAGATT GCTGTAAGGG CAAAAATAGA GATAGGAATC ATGCATCCAT
95401  TGATATACAT ATTTTGATTT TTAATACATG TTACCAAGTT GCCTCCTGAA GGTCTGTTTA
95461  CACTCTCACC AACAGGGTGT TTTTTCCTGA CTTCCACAAA TGCTCTTGAA CAGTGGGTGT
95521  GTTAGTCTGT TCAAATTGCC GACATGAACA ATTAAATCTC ATTGTTGTTT TTATTTTTAA
95581  GACAATTATT GTTTGAGACT GCACATTTTG ATAATAACAT TTCTTCTATT ATGGTTTGAT
95641  TACTCATGAT TCTTGCCCAT TTTCTTTTGG GATGTTGCCT TATGTACATT ATTTTAAATA
95701  GATAGCTCCA TGTATTAAAA GATTATTAAG TTTGAGGGCT TATGATATGT CAGTTACATT
95761  TCTAAGATTT TTTTTTTTTT TTTTTTGAGA CGGAGTTTCA CACTTGTTGC CCAGGCTGGA
95821  GTGCAATGGT GCGATCTCGG CTCACCGCAA CCTCCGCCTC CAGGGTTCAA GCAATTCTCC
95881  TGCCTCAGCC TCCCCAGTAA TTGGGACTAC TGGCAAGCGC CACCACGCCT GGCTAATTTT
95941  GTATTTTTAT TAGAGATGAG GTTTCTCCAT GTTGGTCAGA CTGGTCTCGA ACTGCCGACC
96001  TCAGGTGATC CACCCGCCTC GGCCTCCCAA AGTGCTGGGA TTACAGGTAT GAGCCACTGG
96061  GCCCGGCCAC ATTTCTAAAT TCTTTATAAG TATAAATTCA TTCAATCTTC ACCAAAACTC
96121  AATGAAGTGT GAGTACTATT ATTATCATTG TTTTACAGAT CAAAACAAGT AATACAGTCA
96181  CTTACTGAGT TCTATACACC TGGTAATTTT TTTGTTTCGT TGTTCTATCA ATTATTGGGG
96241  AAGGGGTGTT GAAATCTCTA CCTTTAAATC ATGTATGTGT CTATTTCTCC TTTCGGTTCT
96301  ATCAGGTTTT GCTACACATA TTTTGCAGTT CTGTTATTTG GTGCATATAC ATTTAGAATT
96361  GCTTGTTTTT CGTATTGGAT TGACCCTGTT ATCATTATGT AATATCCCTG TCTGTTCCTA
96421  GTAATTTTCT TTGCTCTGAA ATATACTTAT CTGATATATC ATCCAAAAGA CCACCAGGAT
96481  GGCTAAAGAG TAGAAAGGAG AGATTTACTG GCAATACTAA TTTGCAAGCC AGGAAGAGAT
96541  GGTCCCAGAA CCTGCCAAAA TTACTCTCTC TTTGGGGAGA AGGAGCAGGT TGGTTATTTT
96601  TATGCCTCAT AGGCTATATA TTACACAATA GAGTCATACA TATTTAGCAC GTTTGGGGGG
96661  ACAGCTATAT ATATTATGAG GGGTGCCAAG TGCATTCACA ATGGATAAAC ACGTGTAATA
96721  TACCTCCCAT GTTCACTTCG AGGTTAAATT TTGGTTAAAA TGAGGTAGAA TTTAGGTCTT
96781  TACATCACAA GGTGAACTAT AGGAACAAAG TTTACGTGCT GCCTCTAGCA GCTGGCTGAA
96841  AATGGCTTAA GGTCTACAAT TACGTGTAAG AATAGAATGT GTGTCAAGGC GGTCCTCTGT
96901  CCAATCAGAG TTGTAGTGGA CTGGACTGTA AATCAGAGTT AGGAGGGCTT CTGATAGCTC
96961  CTATAGTTAA GGAATTTAGC AAGTGTGAGT TTTTTGGTAG TCTTTGGAAT TTAGGAATTT
97021  GCCATGCCAG CCAAGCCATG AATGCTCTAC CAGTAGGTAA CTTTGTTTGC TTAATCTTAG
```

Figure 2 (Page 30 of 74)

```
 97081 AGTCTGTCTT AGTTGGTATA GGGGCATCTA TTTTGGTCTT TCAGATCCCA GATATTATTA
 97141 ATACAGATAC TCTTGCAGTT TTGGGCTGAT GTTTATATGG CTTATCTTTT TTGCAGCCTT
 97201 TAATTTCAAC CTGCGTTATG TTTATATTTG AAGTGAGATT CTTGCAGACA GTGTACAGTT
 97261 GTTGTTTTTT TTTTTTTTGA GATGGAATTT CACTCTTGTT GTCCAGGCTG GGGTGCAGTG
 97321 GCACAGTCTC AGCTCACTGC AACCTCCGCC TCCTGGGTTC AAGGGATTCT CCTGCCTCAG
 97381 CCTCTTGAGC AGCTGGGATT GCAGCCATGC GCCACCACAC CCGGCTAATT TTTGTATTTT
 97441 TAGTAGAGAC AGGATTCACC ATGTTGCCCA GGCTGGTCTC GAACTCCTGA CCTCAAGTGA
 97501 TCCGCCAGCC TCGGCCTACC AAAGTGCTGG GATTACAGGT GTGAGACCTC GCGCCCAGCC
 97561 AAACTGTTTT TTTATGGGTG TATTTTATACC ACACACATTT AATGCAATTA TTGATATCTT
 97621 AGGGCTTAAG TTCATGAAGG GTAGTGTGGG AACCATAGTC TCTTGGCCCA CTAAATGTTT
 97681 GCCAGAAATC ACTGACAAGG CAGATTGATT AATAGGTGAA AAGGCATTTT ACCTATTGTT
 97741 TAACGTGTCT ATGTGGGAGC ATTCAGAATT AATTACCTAA CTTCCCAATG AGTTATAGAT
 97801 GCTTATATAC CATTTTTAGA TCACAGAAAG AATTGGGGCT TAGATTCTGG TAAAACAGGT
 97861 TATGGGAGGC AAAAGAGGTT TGGCTTGCAA AGGTGGCCTT GTTAGGTAGG TGAAGCCTCC
 97921 CTCAGAAAGA ACAGATGGTA AATGTTTCTT TTATGATTTT TAAGTGTCAG ACTCTCAGTC
 97981 TCTCCTGGAT CTGGGGAAAG GTATAGAAAG GTGAGGAGGC ATGGCTGCAT TAATGGAGAT
 98041 TCTCTACAGA TGTAAAATTT TTCCCATTTA AGGCAGCTTT GCAAGCCCAT TTCTGCCTGC
 98101 TGGCCAAGCA GCAGCCATTT CAAAATATGT CAAAGAAATA TATTTTGGGG TAAAATATTT
 98161 TGATTTCCTT TAGACTGGTG GCCTTATAAG AAAAGGAAGA GACACCTGAG CTGACACACA
 98221 TACCCTTGCT CTCTCAACAT GTTATGATGC AGTAAGAAGG CCCTCACCAG ATACTAATTC
 98281 CATGCCCTTA GCTTCCCAGG TTCTAGAACA GTAGGAAATA AATTTCTTTT CTTTAAAAGT
 98341 TAGCCAGTCT GTGGTATTCT GTTATAGTAT CACAAAATGG ACTAAGTAAC TATATTATGA
 98401 TCATCTTACA TGACTGATCC CTCCTACATC ATACACATAC ACAGGCCACA TTTGGAACAT
 98461 TGTTAGAGGT TCCTCTACCC AGTACAAATG TACTACAAAT TATATATGTA TTTTTAAATT
 98521 TTTGAGTATC TTCAATAGTA TATTTTCGTT AACTTTTGTA GTCAAAATGT CATTATAACA
 98581 TGTATTCAAT ATGCATAATT ATTAGTCAGA TGTTTTACAT TCTTTCTTCA TACTAAGTGA
 98641 TATGGTTTGG ATATTTGTCC CCTCTAAATC TCATGTTGAA ATGTAATCTC CAATGTTGGA
 98701 AGTGAAGCCT GGTGAAAGGT TTTTGGATCG TGAGGGTGAA CCCCTCATGA AGCGCACTCT
 98761 TCAGGGTAAT CAATGGGTTC TCACTTTGAG TTCACAAGAG ATCTGGTTCT TTAAAAGAGT
 98821 GTGACACCTC CCCCATCTCT CTCGCTCAGC TCTCACCATA TGATATGCCT ACTCCCTCTT
 98881 CACCTTCCAC CATGATTGGA AGTTTCCTGA GGACTTGCCA GTAGCAGATG CCTGCACCAC
 98941 ACCTCCTGTA CAGCCTGCAC AACCGTGAGC CAAAAAAAAT TACTTTTCTT TATAAATTAG
 99001 TCAGTTTCAG GGATTCCCTT ATAGTAATGC AAGAACGAAC TAACACACTA AGTCTATTTC
 99061 ATATTTACAG AATAGCTCAA TCTGAAGTAC CCTTTTTCAA CTTCACAGTA GCTACTTGTA
 99121 GCTAGTGGGC ACTGATTTGG AGCGTGTTCA AGGGTGAATT GTATTATGCA ATTAACAGAT
 99181 TTTTTTTATT GTTTTCGCAA ACCACGAGGC ATAGATTGTC TTACTTTCTC TGCTCCTGGT
 99241 GTTGGAGTTG TTATTGGGAA ACAACTTATT TTCCTCTTAT ATTTATATGG AATAAATAAC
 99301 CCCCAATATT TCCCTCCCCA ATATCTGCCT TTTGTATGTT TTTTGAAGGC AAGTGCCTAG
 99361 AATTTACTGT TTTTGAAGCA CTTACTGAAA GGATTGCCAT CAAGTTGTTT TGCTAATAGT
 99421 ACATGCCAGG CGCTTGTTGG TTTGCTTAAT TCAAGGTAAC TTGGATGAGA AGAAGAGTTT
 99481 TTCTCATCCA TGGCTCAGTG GAGTATAGAT TACTGATATT GTGACTGGAT GTACTCCTGC
 99541 TTTCTAGTCT GAGTTTTTGA AGCTACCCTT AATCTTGGTT TCAATTTTAT CTAGCCCTGT
 99601 ACATATCCAA GGCTCTTTCC AAAATGGTCT ACGATTTGTT TAGGAAGTTA GAATAGCTGT
 99661 ACTTTCTGAA CCACGGTTCC TGACATTTTC TGGACTTCAA ACACATCCAG CATTTTATCG
 99721 AAGTATTTAT CCTTCCTACT TGGCTGGCTT CTTCCTTGCC TTCAGGTCTG AATTCAAATG
 99781 ACATTCTCCT GATGAAACTT TCCATCCTTA TTTCTATTCT TTTTTCTTAT CCCCTTTCTT
 99841 TATTTTTCTC CACAGCACTC ATCACTTATC TCTACATTTT CATTATGTAT TTACCTTATT
 99901 GTGCACCTCC CACTACAAGA CAAGTAGCAC CGTAAGGAAA CAGGTTGTCT GCTTTTTCAC
 99961 TGCTATGCTC CCTGCACCTA GAACACTCTC TGGCACTTAG CAGGTTTTCA GTAAATATAT
100021 GCTGAACTAA TAATGCTGGA TATACATCTC CCTCATGAAC TCTCTAAATC CTTCTAATTT
100081 ACATTGATCA ATCTTCTTTT CCATGTGCTT TTGTATGATT TATTGCTCAA AATCTTTATT
100141 TTGTATGCAG AACGTGCACT GCTATTTAAT CTTCATGTAC GTAAGTCCTC CCTTCTCTGA
100201 GTATAATCTC TTCAGGGCAC TATCTGAGAT AACTTTTTAA CATCTCCATC ATGAATCTTG
100261 TACCTTTTCA AAGAAAATGA GCCAGTGATT ACTGATGTTT ACGGCTATTG TTGAGGGTGA
```

Figure 2 (Page 31 of 74)

```
100321 AGATCATTAT AATTTTGAAA AGGGAAGTTG AATATTGTGA AGGGAAAGAT AACACTAGAG
100381 TCAGAAGACT TGGGAGAAGG CAAAAAACAA ACTAAAAATG AGCACTTTTA GTCTCCTGAC
100441 AGTTTCTCTG AATCAAATCC ATAGTTCTGT GACAGCGTTG GCTTAGAAGC AGATTTTTTT
100501 TTTTTTTTTT TTGAAATGGA GTTTCGCTCT TGCCCAGGCT GGAGTGCAGT GGCACGATCT
100561 CGGCTCACTG CAACCTCTGT CTCCAGGGTT CAAGCGATTC TCCTGCTTCA GCCTATGGAG
100621 TAGCTGGGAT TACAGGCTCC CACAACCACG CCCAGCTAAT TTTTTGTATT TTTAGTGAAG
100681 ACTGGGGTTT CACCATGTTG GCCAGGCTGG TTACGAACTC CTGTTCTCAA GTGATCTGCC
100741 CGCCTTGGCC TCCCAAAGTG TTGGGATTAC AGGCATCAGC CACCGTGCCC AGCCAGGAGC
100801 AGATTTTTTT ACACTCATGT TTCTTTTTCC TTCTGTCATC CTGTTTCAGT ATAAGCAGAC
100861 CACAGATAGA AGTAGTAGAT ACCTCAGAAA TTCCTGGAAT AATTAATCCA CGTTCATCTG
100921 TACTCCATCT GCTCCTATCT CATGGAATAT AAAAGGAAAA ACACCAAGAT TTCCCTAGGC
100981 AATCTGTCTT GATTTTAGGT TCCTCAACAG GAGAGCCAGA CAATGGCTGT AATAATATTG
101041 TCCCGGCCAA GGAAAAACTT CCCCTTTGCC CTCCCAAGGT TTATGGAAAA TTACTGGCAA
101101 AACACAGATT AACTGGAGAA AAGGCATATA TATTTATTTC ATCACAATTT TACAGGAGAT
101161 TTTAGAATTA AGACTGAAAG ATACAGGGGA AATTGCCCAT TTTTATGCTT AGGTTCAACA
101221 AGATAAACAG CTGTATAGGG TACGATCTAA TGCTAACAGA CTGAGTGGGG AAGCCCGCA
101281 AGGCTTGTCT GTCAAGATTC TTCTTGACCT CTCAGTGCAG CATTTCTTCC TTCTGGTTAT
101341 AGGACAAGAC TCTCTTTTAG AATGGGGGGT CTTATGACCT ACAGGCAAAC AAGGTAGGTT
101401 AGAGTAATAT TTTTAGGTTT TATGGCTGGT TCTAGGGAAA AGGAGTTCTG GTTTGTATGG
101461 CCTACCTTGA GGAGGAATTC TGGTTTCTAT GGCTAGACTT TGGGGAGAAT GGGACTTACA
101521 GACAGGAAGG CAGAAGGTGG TCAGTGAAAC ACTTTTATAA TCATAATCCC ATTTTGAGTA
101581 TTTCTGTGTT ATGGAATGTT TGTTCTCTCA TTTCCTGAAA GATTCCAGAG ACTCCTCATT
101641 CAGTGTTGTG AAAAAGTTCA GGAAATGCAA CTCAAAAATG TGCCACTTTG TTACGCTGAT
101701 TTCTTTGAAC TGAGGGCACC TAGGAAACAG TAAATTCAAG GAAGGGCTTT CGCTGAACTC
101761 TAATCAAAAA TTTGAAAATT AAAAAAAAAT TCAAAAGGA ATTTAGTTGT TAAGATTCAC
101821 TTCCCTGGGG AATCTCATCA ACCAGAGAAG ATTAACTGTA TCACAGGAGA GGAGACTGGT
101881 GGTTAACACC ATCTAAACAG ACTTTGTCAC AGCTGTCACC TATTCTTTGA AACACCCATT
101941 TATTTTTCTC CAAAATCATA TACTCTCCCC TAAGTTGCCT ACATCCCCCT TCTTTCTCCC
102001 TTATGAATCA AGAGAGCTTA TAAGCTTCTA CAGTTCACTG GGATTTGGGG TATTCGCTTT
102061 TCTTCCCTCC CACTCCCCCT CCCCTTTTTT TGTCTTTGAG ACACAGTCTT CTGGCTCTGT
102121 CGCCCACGCT GGAGTGTGGT GGCTCTATGT GAACTCACTG CAACCTCCTC CTCTCGGGTT
102181 CAAGCGATCC TCCCACCTCA GCTTCTCGAG TAACTGGAAC TACAGGCGTG CACTACCAAG
102241 CCCGGCTTTT TTTTTTTCTT TTTCTCCCCC GTTTCTTTTT TGGTTATTTT ACTGGAGACA
102301 GGGTTTCTCC ATGTTGTCCA CGCTGGTCTC GAACGCCTGA CCCGCCGTCC TCGGCCTCCC
102361 AAAGTGCTGG TATTACGGGC ATGAGCCACT GCGCCCGATT TGAAGGACCT CTTAAATATC
102421 TATTTAGAAA TTGGTCGGAG TCCACTCCTT TCCAAAAACA TGAGTCACAA TCCGGGAAAA
102481 GCACGAGCGG CTGAAAGTCA AAATAACCAG AACAAAACCT CCACTCATGC TTAAAAAAGG
102541 TATTTTGACA AAATCCTAAT TCGGCCAATT ATTATTAGTA TTCAAGTCGA AGGCTCGTCA
102601 AGCCAGACTG GGGATTGGGT CAAACATAAA CCTTACACCA GACGGAAGGA TTACATGCAA
102661 ATGAAGGATG CAGATTCTGA TTTCCCATTG GGTATTTGAC ATTAGCCAAT GGGAGAATTC
102721 CTCACAGCCT ACCTCCAGTC AGTATAAATA CTTCTCTGCC TTGCGTTCTA ATGTAGTTTC
102781 ATTACATTTT CTTGTGGCGA TTTTCCCTTC TTATCAGAAG TAGTTATGTC TGGTCGCGGC
102841 AAACAAGGCG GTAAAGCTCG CGCCAAGGCT AAGACTCGGT CTTCTCGTGC AGGTTTGCAG
102901 TTTCCTGTGG GCCGAGTGCA CCGCCTGCTC CGCAAAGGCA ACTACTCCGA GCGCGTCGGG
102961 GCTGGCGCGC CGGTGTATCT CGCGGCGGTG CTTGAGTACC TGACCGCCGA GATCCTGGAG
103021 CTGGCGGGCA ATGCGGCCCG CGACAACAAG AAGACCCGCA TCATCCCGCG CCACCTGCAA
103081 TTGGCCATCC GCAATGACGA GGAGCTTAAT AAACTTTTGG GGCGTGTGAC CATCGCGCAG
103141 GGTGGCGTTT TGCCTAATAT TCAGGCGGTG CTGCTGCCTA AGAAAACTGA GAGCCATCAT
103201 AAGGCCAAGG GAAAGTGAAG AGTTAACGCT TCATGCACTG CTGTTTTTCT GTCAGCAGAC
103261 AAAATCAGCC TAACAGCAAA GGCTCTTTTC AGAGCCACCT ACGACTTCCA TTAAATGAGC
103321 TGTTGTGCTT TGGATTATGC CGCCCATAAA GATGTTTTTG AGGTGTTTTT AATGGCTTTG
103381 AGTGTGGCAC TTTTAGTAAT TTGTCCTGCA GAAATTAGAT CCATAGAAAC CTCAGGAATT
103441 CTAGGTATGT GGGAGAAGTG CCATGCAGCA CAAAACATGT TTACAGGGGT GATTCGCGTT
103501 AAGTTTCACA CACAGCAGTT ACTACATTTT AGAGGAAGGA AATTATACCC ATGAGTGCAT
```

Figure 2 (Page 32 of 74)

```
103561  TCCTAACTAT CTTGAATGGA AGTGTTAAAA CCCGCATGCC CCACACAAGT TTGAATATGT
103621  CATACCATTT GCTGTAGCAA TTAATGGCAT ACACAATTGA GAGCACACAC ATTACCACTG
103681  AACATTTGAG TATGTATTTC CCAAAATGAG CTTTTTTCCA GTTTGGGGAT GTTTTGCTTT
103741  GTTTTGGGGT GGAGTCTCCC TCTCGCCCAA GCTGGAGTGC AGCGGCGTGA TAACAGCTCA
103801  CTGTAACCTC GAACTCGGGC TCAAGCGATC CTCTTGACAG CCTTCTGAGT AGCTGGGATT
103861  ACAGGCGAGA GCCGCCACGC CCGGCTAAGA GCATTTTTCT AATTGCCCAC ACTTCTTATG
103921  CGACACCCAG AAAAATACAA TTTTAAATAA AGCGCATATG CAAATTTCCC TAATCGTCTC
103981  CAATATTCTC TGATTTCTTT TTTATATTTT AACTAGAAAC AATTGGAGGT TTCCGCGTTG
104041  CTTTGTGTGG TTGTAAATTT TAAGACTTCA GGAAACTTTT CCAGTACAAG ACTTGTCCAC
104101  AGTGGATATA GCAGCTAAGG GGTTAACAAA ATGACGTCAG AGTAGCTACG GTAATGGGCA
104161  GGAGCCTCTC TTAATCTGCA ACCAGGCACA GAGATGGACC AATCCAAGAA GGGCGCGGGG
104221  ATTTTTGAAT TTTCTTGGGT CCAATAGTTG GTGGTCTGAC TCTATAAAAG AAGAGTAGCT
104281  CTTTCCTTTC CTCCACAGAC GTCTCTGCAG GCAAGCTTTT CTGTGGTTTT GCCATGGCTC
104341  GTACTAAACA GACAGCTCGG AAATCCACCG GCGGTAAAGC GCCACGCAAG CAGCTGGCTA
104401  CCAAGGCTGC TCGCAAGAGC GCGCCGGCTA CCGGCGGCGT GAAAAAGCCT CACCGTTACC
104461  GCCCGGGCAC TGTGGCTCTG CGCGAGATCC GCCGCTACCA AAAGTCGACC GAGTTGCTGA
104521  TTCGGAAGCT GCCGTTCCAG CGCCTGGTGC GAGAAATCGC CAAGACTTC AAGACCGATC
104581  TTCGCTTCCA GAGCTCTGCG GTGATGGCGC TGCAGGAGGC TTGTGAGGCC TACTTGGTAG
104641  GGCTCTTTGA GGACACAAAC CTTTGCGCCA TCCATGCTAA GCGAGTGACT ATTATGCCCA
104701  AAGACATCCA GCTCGCTCGC CGCATTCGCG GAGAAAGAGC GTAAATGTAA AGTTACTTTT
104761  TCATCAGTCT TAAAACCCAA AGGCTCTTTT CAGAGCCACC CACTTATTCC AACGAAAGTA
104821  GCTGTGATAA TTTTTTGTTG TCTTAACAGA ACAAATTTCT AAGGACCCCC CCGGAAAGCA
104881  TTAGACTATG GTCTTAAAGT TGATTAACAG AAATAACGGT TTGGTCAGTC TTGCAGTGTA
104941  GGTTATTTCT GACCTTATTA AGGTGCTATT TGGAGAGAAG CTGTGTAAGT CCACTATCAT
105001  TCAGGCCTCT AGCTTGCTAT GATTAGCATT TGTTTAAACA ACTTTGTAAG AGTAAGGGAA
105061  AAATCTGGTA AGTAGTTAAC TGGCGCTTAC TAGGCATTTT TGCAAAGCTT TGAAAAGATT
105121  AGAAAATTGT GTCTTGCGAG TTCCAGTGTC TTCCTCAAAA TGCTTAGGAA GATTTTCTCA
105181  GCTCAATACA TAGTCCCCTA GGTTTTCTCA TATATTATAT ATATATATAT ATATATATAT
105241  ATATATATAT ATATACTGTT AAATTCATTT GGCTGTTAAC ATTAACCTGA AATTTATTCT
105301  GGTGCAAAAT GTGAGGCAGG GATCTAACTG GCTCTCATTT TATCCATAGC TAGCTACCCA
105361  CTTTAAATCT GTCAGTCTGT CGACCAAGCA TAATTTAATC CCTTATATAT GAATTTTTAT
105421  ATGTGTGGCT TTGCTTGTAA ATAGTCTATC TGGTTGCATT GCTTTGTCTC CTCTAGGACT
105481  ATGCACCATG ACATGCCACA TTCTTTTTTT CAGTACTTCT TGCCTGTAGT TATTAAAATC
105541  TAGAATTTAC AAGTTTTAAC CATTTTCTTT CTGTTGATCT TGCTTTTCGG TTTTGGAGGT
105601  TGGGGATTGA GTACTGGAAG AAAATTTAGA GGGATGGGAA TACTGTACGC AAACAAAAGT
105661  AATATTTACT TTAAAATTTT TATATTTTGT ATTTTTTTAT CATATAGCTT TTACATCACA
105721  TTTTACAGAC TAACTTTAGA ACAACCACAG AATGTCCAAC ATTAAAACTA CTAATTCCAA
105781  AGACCTTGCC TCACATTCTT TTTTACAATA AATATTTTTT ACACCTAACA TTCTTTCTTG
105841  GCCTACATCT AGAATGTAAA CTGATGTACC ATACTAAAAT CGCCTGACCA ACTGTCAACA
105901  ACAACAAATC ACACACACAA AAGATCAAAT TTGAATTGCA TCGTTTACTT AAATTCATTT
105961  GTGTTCCAGC TTTTAATAAG GCAGTTTTTG GTTTATAAAG TAATATTTGC ATTTTAAAAA
106021  TTATGAAAAT GAATATGTCA GTTTGTTTTA TGATTCGTTT TTCTTGACTC TTATACAAGC
106081  GACTCTAACT GGCATAGACA TTTGTTATCC ACAGACAGTA TAGATATGTT AGAGATGCCA
106141  ATGGACTTGG TCTATGCCAA GGTGACTACT CACAAGCTCT GGGCCCAGCT GAAGGTCAAG
106201  TATTTTTTTT CCAGTTATAG ATGTGCTGGA TCTGATGTAT AGCGCTTGAC TTTTTATATT
106261  TTCTTTATCT GTAGGAAACA AATGTGTTGG AGGTACTGGG TCTGACGAAT AGCATAAAAG
106321  AATAAAGTTA CATTACTGTC TGAGGATCAG ATGGACAGGG GGTGGTAGCT CAGTCCAGCT
106381  ATTTTCCACT CCCTCACTTA CATTCTTTGC CCCCTCCTCA ACAGAACAAG GATTCTGCTG
106441  TAACTCTTCA TTGACAGTTG ATATTTAAAA ATTAACGAAT GGATGAAATT CTCATTTGTG
106501  AAAGAAAATT TATTGAGCAT TTTGTATTTG TGAGTAGTGC AAACATTTTA ATATTATATT
106561  AAGAATCTAT TGTTTTGTAT TAGAGGAGTA ATTAAGGAGA GATTGGAGAC AAAAAGGGGG
106621  TGTTGTTTGC AGAATATACC ATCCAAAAAT AGACCACTGT GGGATCAGGA TTCTTTTGAG
106681  CTAAAGGCAC TTCAAAAACA GCATTCAAGA AGGGAATTCT TCTAAACTTT TCTTTCTGAA
106741  AACAGGAGAT AAAAGTTCCA ATGTGAAAAA TGCTCTGCTT GTACCAGGTG AAAAGACATA
```

Figure 2 (Page 33 of 74)

```
106801 TTCTTCAGCC CAGAGGCATA GATGAGATAA TTCTGCACAA ACACAGCAGG GAGTCATAGC
106861 CGAGAGACTT CTATACACAA ACAAACCTTG TTAAAATAAT CATATATTCC TTTAATCTCC
106921 TCATATGGTT TACTTTCCCA CAATTGCCTC TCTTTAACTT AATGTGAAAG CATTTAGCTT
106981 TTGCCATTTC TTTGGGCTT CACTTTTTA TGAGGGTTCT CCTGTCCCAT AAAATTTACA
107041 TTAAATACAT TTGTATGCTT TCATTCTGCT AATCTGTTTT ATGGCAAATG AATTATCAGG
107101 TCCAGCTGGA GACCCTAACA GAGTAGAGGT AAAATTTTGC CTCCCTACAA GATAGAGATT
107161 GTGTGCATTA AATGTTGTTT GTTCCCAGTT GTTCAGTTTG TCAGGCCTCT GAGCCGAAGC
107221 TAAGCCATCA TATCCCCTGT GAACTGCACG TATGCCTCTA GATGGCCTGA AGTAACTGAA
107281 GAAACACAAA AGAAGTGAAA ATGCCCTGTT CCTGCCTTAA CTGATGACAT TACCTTGTGA
107341 AATTCCTTCT CCTGGCTCAT CCTGACTCAA AAGCTCCCCC ACTGAGCACC TTGTGACCCC
107401 CACCCCTGCC AGCCAGAGAA CAACCCCCTT TGACTGTAAT TTTCCACTAT CTACCCAAAT
107461 CTTATAAAAC GGACCCACCC CATCTCCCTT CGCTGACTCT TTTCGGACTC AGCCCGCCTG
107521 CACCCAGGTA GAATAAACAG CCTTGTTGCT CACACAAACC CTGTTTGATG GTCTCTTCAC
107581 ACGGACGCGC TGAAACAGT TTAACAGGGT TTTTCCTGCC CAGTCACAAC AAAGTGATGT
107641 TATGCTGCAG GCTGAAGTTT ACAGCTAATG CTGTTGAAGT CTAAAATCAG TTTTGGTTTG
107701 TTAGATTTGG GTGAGATGGC TAAGATTCTC AGAGAAAGAA GTCAAGTTTG GGGTGCATTT
107761 TTCAGACTTA AAAATTTAGC AGTAGCCCTT GCAGTTTTTC CAATAGAAGT GATTTACGAA
107821 TGTTTTCAGG AAATTTAAAA CAACAGTGAG AAGCGTGTAT GGAGAGTTGA ACTACACTCC
107881 AGACTTGGCT ATAGGAAAGC ACGAATGCTG CTATTGTATT GCACCTTGGA AAAGAGAACA
107941 AAGGAATATT TTCGACAAT TTTAACATGT CACATATGAA AAGCTAAACG GAATCTGTCA
108001 ACACCTTGTA CGTTATTACA GGCTGTGATT TTAAAAAAAC AATCCTTACT AATACATACA
108061 TAGTTGCTGC TAGCAATATA GTGTTGGGAG TAAAAACACG AAAATGAGAG TTCAGGACAA
108121 TATCCCAACT CTGAGCAGAT TTTTTTAAGT AGTAACATCT AAAATTAAAC CATATTATGT
108181 AATATTTATT TCTTTTCCAC AGTCTCTTCT CATGCCTCGT TCACATTAGC TAATTAAAAG
108241 TCCCCTGAGT ATCATCATAA CCCGATTTAC AGATGAAGGC ACGGTTGCAA TGAGCTATCA
108301 CCCTCTTCTG AATGAGACAG TACAGTGTGA AGGATAGCAA AACTCCACTC CCATCCTCTT
108361 AGGGCTCTGG CTGGACCAGC AAATTAAATT AATGTAAAAT GGATTAACAG GAGAAAGGTA
108421 TATGCATTTA TTTAACACAG GTTTTACGTG ACACAGGTGC TCTCATAAGG TAATGAAAGC
108481 CCAAAAAAAG CAGTTAGCTA CTTATATAAT GAATTGGACA ATTAGTAAAA TGTAAAAATG
108541 CGCTAAAGCA AAGGGATTTA GGCTAGAATA TATAACTGTG TAGAGAAGCG CCCAGCAAGG
108601 GCTAGTGCAA GGTTTGTACA GAATTCTCTT GGCCTCAGCC TCCTATCCTT GAGAAGAATG
108661 TTGCTTTTTT TAAACTACAG TGAGAACATC TTTCATATGA GAATTTCACC TACTGCTTCT
108721 AAGAAACAGG TCAGCTTTCA AGAAAACATA AGGCCAGAGT GATCTTTTCA CGCCTGCTCT
108781 TTTAAGTACC TTTGAATAGT CAATATGTCT TCAAGCACTT GAAAGACTTA AAAAGTTTAC
108841 CACTCCGGCA TATTAGTGAA AGCCCTTAAT ATAAGCCCTT ATTAAAATTC TCAGTCGAGG
108901 GTATAAATTC AGATTCAAAT AGTAGTGTCG TAAACGGGAG GGAAAAACTA AAGGGATTAA
108961 AAAGTGAAAC TATTGTGTTC TCCCTCGCAG TCCTTAGGTC ACTGCCCCTC GAGGGGCGGA
109021 GCAAAAGTG AGGCAGCAAC GCCTCCTTAT CCTCGCTCCC GCTTTCAGTT CTCAATAAGG
109081 TCCGATGTTC GTGTATAAAT GCTCGTGGCT TGCTTTCTTT TCGCGTACCT GGTTTTTGTT
109141 GTCAGCTGGT TAGACATGTC TGGTCGCGGC AAAGGCGGTA AAGGTTGGG TAAGGGAGGT
109201 GCTAAGCGTC ACCGAAAAGT GCTGCGGGAT AACATCCAAG GCATCACCAA ACCGGCCATT
109261 CGGCGCCTTG CTAGGCGTGG TGGGGTTAAG CGAATTTCCG GTTTGATTTA TGAGGAGACT
109321 CGTGGCGTTC TCAAGGTGTT TCTGGAGAAC GTGATCCGGG ACGCCGTGAC CTACACGGAG
109381 CACGCCAAGC GCAAGACTGT CACTGCCATG GATGTGGTTT ACGCGCTCAA GCGTCAAGGA
109441 CGCACTCTGT ACGGCTTCGG CGGTTAATCT TTTCGTCAGT TTTCTTCCAA TGGCCCTTTT
109501 TAGGGCCGCC CACTCCCTCT CAGAAAGAGC TGTGATTGTA TTCTTTCGGA TGGTAACATC
109561 TCAATGGCTT TACTCGGCTA TTCTGCCTAG TATGTAGAAC TATTATAAAC CAGTTGGGAG
109621 AGACCAGGTT GTTTGGTCTG AGTGGCTGCT AAAGCAGAAA TCAGCTAAGT AAACGAGGTC
109681 TCCGAGATAA GTGAGCTATA AACTTCAATG CTATAGTTTT GACATGTCAA GCAACTTAAC
109741 GTGCAGCGCG AGTCCGATAA ATGAGTAGCT CAGCTTTTTA GTTTTAAAAA CGAGTTGTGC
109801 GTTATTTGTA CGAGAGCCTA AGATGCTAGC TGCCTGGAAC TGAGTAGGTG GATTAAAAATG
109861 GGTGTCAGGT CTGTTTCCC AGGCGTATCT GACTTAACGT CAGCAAAAGC TGTACTTTTA
109921 GCTTCCCTGG TAACACCTGC CGTCCTTAAC CGCCCCTGC CGGTAGCGCC AGAAGCCTTT
109981 ACTTCCATTT CTAGTTGAGC TTGGCGTCCT GCTGAGTGAC GTCACCTCCC CCTTCTGTGG
```

Figure 2 (Page 34 of 74)

```
110041 AGTAGGACTG GCGGTTAAAG CTGCTTTGCT ATTTTCAGTC CTCAGGCTGG AGGCTCCCCT
110101 AAGCAGGCTG CCTACGCAGT TCGTAAATTC CCACTTAGTA GACTAAGGGA GTCTGTTTTA
110161 TAAATAAGGA CTCAAATTTC TTCTGACTCC GAGGTCCGTG GCAGCAGCTA TAAGATGGAA
110221 GCCCCCTCTG ATGTAAGATT CTCAGATGAC TTGCATCTTC ACTGTACCTG TCAACCCAAT
110281 AGTCTTCTAT TCCTGCCTTA AATTGTAAAT TCCAAAACTG ATTTAATTGT GAAAGTTTCA
110341 AACTGTACGA CCTAGGAAGT GTCAAAGTTA GGTGACCAGA TTTTTAGAAG TCAGCCAAAT
110401 ATTCAGCATC TTTGATTTAG TAACAAATAT ATTGATGGCT ACTTCAGCAA AAAAAATCAA
110461 CTTTGTTTTC TGGTTACTTT GCTAACAAGC TTCTCCTGAC AGGAGGATAT AGTGAATAGG
110521 CAGTTGAATA AGTGAGTTCG GGTGAGAGGT CTGAGCTGGA GATAAAAATG TGTGAGTCAT
110581 CAGCAGATAA ATAAATGCTG AGACCAGATG AGATGGCTAA AAACTGAAAC ATAATGTAGT
110641 GCAGCATTGT TTGTAATAGT AAATGAGTGG CAACTGTAAA GTTTTCATCA GAAAGGACTA
110701 GAGTGATCTA TACATCCATA AAATAGAGTA TTTCTCTACA CAGCCCTACT AAAGAATGAG
110761 AAAGCTGTAC TCCACTACAT ACTCTGGTGT ACTCTGGCTC AGTTCTTGGA CTCCTCTTTT
110821 CTTGGCTAAC TCAACTGGCC TCACCACTTA CATGCTCTGT GCTCTGTCAA ATAGTTTGTT
110881 CAACAGAACA CCACGGCCTA GCTGTAAGTG CCACGTTAAC TTCTAGCAAT GCCAAAGCCT
110941 GTGATAGTGG CAGCTTCGGG CTGTTTCTCA TTCCCGGGAT GCCTAACCAC CTCTCCAAAT
111001 TCTATCAGTT TGCTTCCACC CACTTCAAGC TTCAGAACGA AACATAGAGC TTAAGAAATA
111061 TAGGCCCGGC AAGGTGGCTC ACGCCTGTAA TCCCGGCACT TTGGAAAGCT GAGCCGGTG
111121 GATCACCTGG GGTCAGGGGT TCGAGACCAG CCTGGCCAAT ATTGTGAAAC CCCGTCTCTA
111181 CTAAAAAAAA AAAAAAATTA GCTGGGCATG GTTGCGGGCG ACTGTAATCC AAGCTACTCG
111241 GGAGGGTGAG ACAGGAGAAT AGCTTGAACT CGGGAGGCAG AAGTTGCAGT GAGTTGAGAT
111301 CGCGCTATTA CACTTAGGCC TGGGAGACAA GAGTGAAACT GTGTCTCTAA ATAAGTGTTT
111361 GCAATTATAA ACCATCTCCC TGACCTTAAA TCTCTAGACT CATATACAAC TGCATATTTG
111421 ATGTATCTAA TTGAATAATG GGCATCTCGA ACTTGTCCAA AATATGTTTA TACGTAAACA
111481 CCAAGTCTGT TCTTCCTCTG ATATTTGTCA TGTCAATCAA TAGAACTCCA TTCTTCAAGC
111541 AGCTTGGGCC AGGAATTGTG CAATATTGTT TGTCCTGAGC TTCTTACAAC TTTCACCCAA
111601 TGCAGTCAGC TCTGTTGAAA ATCAATCAGA ATACCTTTCA TTGTTTTCTT TGCTGCTTCT
111661 CTAGGAGCAA GCTGCCATGG CGGTTTGTCT GAATGACCAC AGTGACCCCA AACTGGTCTT
111721 TGTTTTCACT TTTAATCCCC CTGTCATACA GTTTTTCTCT ATCCAGCATC AACAGTGATC
111781 CTTTTTGAAG GTATTATGTC CACTGTCTGC TGAAAAGATT CCACTGGCTT TCCATCACCT
111841 TCATAATAAA AACCAGCATC CTTATCATAG CCTACAAGTA AGATGACCAA CCATTACAGT
111901 TTGCCTGACT CTCAGGGGTT TCTCAGGGTG TAAGACTTAC AGTGCTGAAA CTTAGAAAGT
111961 TCCAAGCAAA CTAGGATGAG CTGCTCAACC TACTAGATCT GTACTCTGGC TACCCTCTGA
112021 CCTCATTCTC TTCGCAGTTC TTTCTCTTCA CTGACCTTGC TGTTTCTGGA ATGGACCAAG
112081 CATTTCCAGC ATCAGCACCT TTATATCTAT TCTTTCTCCC TAGAAGGGTC TTGTCCTGGA
112141 TATCTGAATG GCTCTAGATC TCATTTCATT CAAGCCTCTC CTCAAATACC AACCTTAAGA
112201 AAGAGACCTC CCATAATCAT CCCTTGTAAA ATAAGCTTTT CTGCTCATTT AGCATATATA
112261 TATATAGTTG ACTATCCTCA ATAGCATATA TATATAACAT TTCCCCACCT AGAATTATAT
112321 ATGTAATAAT ATATTTAACA AAAAATACAT ATAACTAGAT ATATTTATT TTGTGTTTGT
112381 TCTCTCTCCC CCAACTGGAA TATATTTTTT GAAGGTAGGG ACTTTGTTTT GTCCCAGAAG
112441 TATCCCTAGC ACCTTGAACA GGGCTGACGT TTAACAGGTA GTTTATGGAG GTTTGTTGAA
112501 TGAAAGGATG TGTGAATTTT CTATGTAAGT CTCCAGGCTC TCCACTAAGC CCACCAGAAT
112561 GCTAACACAA TCAATTCCCC ATCTCATTCC TTGACCTGCC ACTGCCTGAA GCAATCAGCG
112621 TGCAGTTTCT CTTTAGAAAA TCTGGGGGAT AGTCTAGGGG TTGCAAATTA AGCAACATTA
112681 TCTTTGTTCT GAACAAGGAC TGCATGAGTG TTAGGACTGA AGAAGGCCCA AGGTGGTGGT
112741 GGGTATGCCT AAGATGAGTA TGACATATCA GCAATGCTAT GAACATAGCA ATGCTATGAA
112801 AGGCCAGGCA AAACGTAACA GGAGCTAGTC GTGGCTTATT GTTACAACGA CTATACCTCC
112861 CATATGGGTA ATCGATATCC ACACACCCCT CTACATTGAC TCTGGAATTC AGGAAAGGGA
112921 ATTAAAATTT TCTAACTTAT GTACCCCAAT GATTTCAACA ATATCTGGCA TATGAGATCA
112981 ATAAATATCT TTAAAATACC AACTAAGAAA GACATAAAAT GACCCACCCT CCATACCAGG
113041 CTCATTTTTG CTCCTCTGAT TCCTGAAACT ATCCAGAATG CAGCTATGAA TTCTCTCCAT
113101 TGTCAGTTTT AAATTAAGCC AAGCTGGGTA CTTGTGTAAT TCCTCAAGAA ATCCTGGATG
113161 AAAACTGTCA GGTGGAAAAC AGGACCTCAA AATAAAGAGA CATCCATCAC TGAAGCTAAC
113221 ATCGTGAGGC TGAAATCAGT CCTATAACAA TGGTACCAAA AAGAGCACAA TGAGAGGCAT
```

Figure 2 (Page 35 of 74)

```
113281 TTGTGAATAT TTACTCAGAT GAGAGTAAGA TATTTCCCTA TCAGCTAACC TGAAGTTCAC
113341 ATCCCTTTTC CAGCTGAGTT CTGAAGCTAG ATGTACTTAA CTGGAACACA TAACTGCATC
113401 AGGAACATCC TTTAAAACTA TGGCTACAAT GGCTTGACTG GACAAACCCC AGGCTTCCAG
113461 GTTTAGCACA GGTGGCCCTT CACAGACCAA CATTGCCTAT GCTACCAACC TCATGTCCTA
113521 CCACCCTGCT TGCATCATTT CTCTCTCTGC ATATATAAAA ATATATGTGT ATGTATATAA
113581 TCAGCTTTAT TGATATTTAA TATACCACAA AATTTGCCCA CTTTAGGTAC AGTTCAATGA
113641 ATTTTACCGT GTTTTCTTAG TTGTACAACC ATCATCACAA TTTAATTTCG GAATATTTCT
113701 ATCACCCAAA TTTCCATTTC TGCGTAAAGG GGGAAAAAAA AAGGTTAACT GCTGAAGGCC
113761 GCGGTAACAC TGAAAAAGGT GCCTTTTCTC TCTAAAACAG ATTTTAATCT CCCCTGAATT
113821 TAGTGTCCTG GGTATTCCAG GAGTCTGAAT AGGGTTTCAA TTTTCAGGGT CTTTTTAATA
113881 GAGTAAAACT GTATTGGTGG CGATAAATTT AGTATTGCTC TCAGTACATG ATTGAGGGAT
113941 ACTTAAATGT CTCTGTGATT TTATTTCATA ATCGCTAAAA GATGGTTTTT TTTTTTCCTA
114001 AAACAGGGTT TTTGTTTTTT CTCAATAAGC TTCTTAGCTT CCCCTCCGGC TCCCTGGCTT
114061 GCCTCAGGAA ATATTAGCTC ATCAGTTCTG ATTGGTTGAC AGCTACGAAT GGCCCTCATT
114121 GATTGGGCAG CGCTTCTTTG TCCCTTGGAA ACTAATACAA ATTTTTAACA CTACTTTTTT
114181 TCCACTCTTT CTTCAGAGTT GGAATATCGT TGCTCCCCTA CCCATATGTA GTGAGTGGAG
114241 GGCAAACTTG GAGTTCCCCT AATCTTTCCT TTTTAGGATG TCAGCTCAGT ATCATTCATC
114301 TTAATTACAC ATTGAGCTTC TTGACTTAAT GGATACAGCT CTTCTTTTGT TTAGTTGGGC
114361 GGCCCTGAAA AGGGCCTTTG GTTCAGAAAT GCAAGCTGTG GAGAAATCAG CAACCTTAAC
114421 CGCCAAAGCC ATAAAGGGTG CGTCCCTGCC GCTTAAGCGC GTAGACCACG TCCATGGCAG
114481 TGACTGTCTT GCGCTTGGCG TGCTCCGTAT AGGTGACAGC GTCACGGATC ACGTTCTCCA
114541 AAAACACCTT GAGCACCCCG CGAGTCTCCT CGTAGATCAG ACCAGAGATC CGCTTCACAC
114601 CGCCACGCCG GGCCAGACGC CGGATGGCCG GCTTGGTGAT GCCCTGGATG TTGTCACGCA
114661 ACACCTTGCG GTGGCGCTTG GCACCCCCT TACCCAAACC CTTCCCGCCC TTACCACGTC
114721 CAGACATGAC TTCCCAAGAA GTGAACCAAG AGCAAGTGAG AGAATAGGAA ACCGATCTTT
114781 ATATATCTAC GTTACCCCTG CCCCCACCTC CAGCGGACAC AGAGACTGAA AAGCGCGCAG
114841 GCGGGAAATG TGACGCCTAC AGTCCGCTCC TTTAACCCCT CCTCCAAGCC CCAGGAAATG
114901 GCGGGAGCAG CGATTGGGGG AGGGTGGGGA GATGAGGGTG GGACCAAGCA GGCTTGACCA
114961 ATGGCCTTTA TTTTCTTAAC AGAGCTACAG GCTTTGAGGA ACTGGGTTAA GAATTAAATG
115021 TAAACCCATT CTGACTCCAG AATTATTTTA AGTCGAACTT TTTTTTTAAC CGAATCTCTC
115081 TGTCGCCCAG ACTGGAGTAC ATTAGAGCCA TCTCGATTCA CTGAAACCTC TGCCTCTCAG
115141 GTTCAAGTGT TTCTCCTGCC TCAGCCTTCA GAGTGTACCT GGGATTACAA GCGCTCGCCG
115201 TCGCGCCCGG CGTGTTTTTG TATTTTTCGT AGAGACGGGA TTCGGCCATG TTGGCCAGGC
115261 TGATCCCGAA CTCCTGATTT CTGGTAATCC GCCCGCCTCA GCCTCTTAAA GTGCTTGAAT
115321 TACAGGCGTG AGTCACCGCG ACCGGCCGAA ATCGATTGGT TTTGAAGCCT TCAGTAGCAT
115381 TAAAACGAAA AGTGCTCCCA ATGCATTCCC TTTTGTCTTA AATTGGTTTC TTACAGCTAC
115441 TTTACTTGAA AAGGTGGTGG CTCTGAAAAG AGCCTTTGCT TGGACCGTCA GAGAGACCAC
115501 AGTAATCACG CCCTCTCTCC GCGGATGCGG CGGGCGAGCT GGATGTCCTT GGGCATGATA
115561 GTGACGCGCT TGGCGTGGAT GGCGCACAGG TTAGTGTCCT CAAATAGCCC TACCAAGTAG
115621 GCCTCGCACG CCTCCTGCAG AGCCATCACA GCGGAGCTCT GGAAACGCAG GTCTGTTTTA
115681 AAGTCCTGCG CAATCTCGCG CACCAGGCGC TGGAAAGGTA GTTTACGAAT AAGCAGTTCA
115741 GTGGACTTCT GATAACGGCG GATCTCGCGC AGAGCCACGG TGCCCGGCCG GTAGCGGTGG
115801 GGCTTTTTCA CGCCGCCGGT GGCCGGAGCG CTTTTGCGGG CTGCCTTAGT GGCCAACTGT
115861 TTGCGTGGCG CCTTGCCACC AGTAGACTTC CGAGCAGTTT GCTTAGTGCG AGCCATGACG
115921 GAAAACAGC ACAGCGGAAC ACCCAACACT AGCGCAAATA CGCCCATGAG CTGCTCTATT
115981 TATAGTGTGT AAAGTGCAGT GATTGGATGA TAGAAGACGC TAAATATGAC GTTACACACT
116041 CTGATTGGTC TATCTTTAAG CCAGCAACAA TCGTGCAGTT TCACCGGCTA CTATATTCTA
116101 TTCCAACTCT ACAGATGATT ATTTAAGTGG TATTTTATTA CTACTATTAT TTTATTTTAC
116161 TTTTGCTTTG TTCCCCAAGC TGGTCTTAAA CTTGGGCTCA AAAGATCTTC CCGCCTCAGC
116221 ATCCAGAGTA GCTGGGATTA CAGGGGAGCC CCACTGCGCC GGCTTGGACT TTAATTTTTT
116281 AAACTTGTCC TCTTCTACAT CTGGTTTTCA TAACCTGAAG GCTGTGTTTA TTTTCCATAA
116341 AACAAGGCAT TGATTCCAAA GGTATTATAA TTCCCCAATT CCGTATAACC TTCAGCTCTT
116401 TAGGAAAAAA AAAAAAAAAA AAAAAGAGG GAATACTGCT CACCTCCTCT CCGGAAATGT
116461 ACCCTTTACG GGAATTTCTG AAACCTTTCA CAAGAATTGG ATTCCTTTGT AATGCTTTAA
```

Figure 2 (Page 36 of 74)

```
116521 TTGACTTAGG AGTGTTATTG AAATCTACAA AGCATCTCAA ACATAGTAGG ATTACACTAT
116581 TACTCAGAAA CATTTTCTAT GAGACGTCTT TCTCTTGATT ATGCTCTTTG AATCCTAAAC
116641 TTGCAGCGTT CTGCAGCTTT TGTTTTCTAA AGCCTAGGTG TACTCTGCCA GTCACAAAAT
116701 GGCGTTTCTC CAGCACTGCC GCCAGGTACC ACCAGCTGGG AGTTGTTCCT CTTGCGGAGC
116761 AGGAGGTGGA CTTGGCCCAA GAGAAACTGG ATAGTGGTTC GCAAGGAACA TAATTTAGCA
116821 TTGCCAAGAG CTAATGCAAT CATTTTGAAA ATCTCAAAAC ACTGAAAAGT GGATTGTGAC
116881 CTTTTTAAAT TCACAAGAGA CAGGCCACAT TCTATCTTTT GATTGGTTTA GGCTATTTTC
116941 TTGAACAGCC ATTTAGAAAG CAGATCTATC ATCCTTCATT TGCATGGAGC GTTCCATTT
117001 TATTTGAAAC CAGTTTAACC CAATAGAAAA AAGGGAGGCA GAACCCATTA TTTAAAGTGG
117061 AAACTCCTGA ATCAGATAAT TAGGAGTATT TCCTTTTCAA AAGTTGCGTT TTTTCAGATA
117121 CCTCGCTTAT TACACTAAGA AAGGTTTATA TCTTTCACAA AGGGTTTACT TACAAAAATC
117181 TTCCAATTTT GTATACCTGT GTTTCATAAC TGACTAGCCG TCAAACCAAG ATGTAGAGTT
117241 TCCAACCGTT ATTTTCCAAA TTTTTAGAAA TTACGTGAAA TATTTGAATG CATGCCTTCT
117301 CAATAAAATG GGACGTAGGA AGCACTGGTG CAGAAGATGG GTACAATACT TATCTGGGAC
117361 CACTCCATTA TTTGGTTGGC ACGTTGTTTG AAGAAAAAGG GGAAAAGCTC AGGTTACTTA
117421 GCATGGTTCG GACTTATTTG AAAACTACCA CAGCAGGAGC GGAAATAAGA CCGCATTACC
117481 TCACTCTCTG CTGTGCTGTG CTAGGGGGTT ATCCAGAATA GGATTGTAGA AGTGGATGTC
117541 GATTTAATAG TTTTTTATTC TCCCATTAGC TGAGTCTCTG ATTGGCAATG TGAGATCGTT
117601 TTAGCTTATT GATACTTTGA AATGCACTTA ACAGCCACAA ACAAGTTAAA GGGTTGTTAC
117661 CATAAAATCT TATCCCCAGG GTGTGCTTGC ATTTATCACC CGTGTTTGCT TTCACACTAA
117721 GTGGACTTAA CTCCCCAGCA GAATGCCTGT CAGGGAACCG GTTTCGTGGA CCCAGCATTT
117781 AACGCCTTTC GCAGGCTTGT GAGGCCCATA AATATTTGTT GAATAAAAGA ATGAGTTGAC
117841 CATGTCATGG TGCGCTGATT GCGTGTGCTG ACATGGAACA CAGGTTGTAA ACCTTAATAC
117901 CAATTTGGGG CATGTTGTAT GGATGAAAAG GGCATTGGAA ATTCCTGAAG TGCATCCCAC
117961 ATTGGACTGT GGAAATAAGT TGCAAGTGCA GAAACGTTTC CACACTTGCA GTTTGAGTAT
118021 TAATTGCAGC GTTTGTGAAT TCTGGTGTTG TCTACGATTC ATTCTTGTTT GACGTGAAAG
118081 GTATTCGCGA GACACATCGC TCTAAAACAT TGCCAGAAAA TGTAATAGAG TTGATGACAA
118141 CTGGCCCTAA CACGGCCTAA AACTCGCACT TTTCTCTCCC TCCGCAACTA TTCAAAACAC
118201 TGTATTTTAC ATTTCTTGCA AATTAAAAAC TAACATCTCT GGCAACGGAC CTCTAAAAAT
118261 TTCTAATAAA ACTCCTCGGA TGCTTGTGGC ACTGCATTTG TAAACCGCCC CCTCTCAACC
118321 TACTCCCTAA AAAAGAGCTG CTTTTTGAGA GAGAAGCGGT ACCCTCTGAT GTTACTGGGC
118381 GGCAGTCTGC CTACAATTTC CTTCACAATG AGGCAACCAG AGCGGCTTTT TCTGTGTGTT
118441 TGCTTGCGTT GAGGGGAGCA GGACCATAGG CCCTAGAGGC CCCCAGCTGC CTTCTGAGAC
118501 TGGGCGAAAC CCTCGGCAGC GCGCAGGGGG CGCTAGGGCG CGAGGGGCGG GCACTGACGG
118561 GCACCAATCA CGGCGCAGTC CCACCCTATA AATAGGCTGC GTTGGGGCCT TTTTTTCGCA
118621 TCCTGCTTCG TCAGGTTTAT ACCACTTTAT TTGGTGTGCT GTGTTAGTCA CCATGTCTGA
118681 AACAGTGCCT CCCGCCCCG CCGCTTCTGC TGCTCCTGAG AAACCTTTAG CTGGCAAGAA
118741 GGCAAAGAAA CCTGCTAAGG CTGCAGCAGC CTCCAAGAAA AAACCCGCTG GCCCTTCCGT
118801 GTCAGAGCTG ATCGTGCAGG CTGCTTCCTC CTCTAAGGAG CGTGGTGGTG TGTCGTTGGC
118861 AGCTCTTAAA AAGGCGCTGG CGGCCGCAGG CTACGACGTG GAGAAGAACA ACAGCCGCAT
118921 TAAGCTGGGC ATTAAGAGCC TGGTAAGCAA GGGAACGTTG GTGCAGACAA AGGGTACCGG
118981 AGCCTCGGGT TCCTTCAAGC TCAACAAGAA GGCGTCCTCC GTGGAAACCA AGCCCGGCGC
119041 CTCAAAGGTG GCTACAAAAA CTAAGGCAAC GGGTGCATCT AAAAAGCTCA AAAAGGCCAC
119101 GGGGGCTAGC AAAAAGAGCG TCAAGACTCC GAAAAAGGCT AAAAAGCCTG CGGCAACAAG
119161 GAAATCCTCC AAGAATCCAA AAAAACCCAA AACTGTAAAG CCCAAGAAAG TAGCTAAAAG
119221 CCCTGCTAAA GCTAAGGCTG TAAAACCCAA GGCGGCCAAG GCTAGGGTGA CGAAGCCAAA
119281 GACTGCCAAA CCCAAGAAAG CGGCACCCAA GAAAAAGTAA ATTCAGTTAG AAGTTTCTTC
119341 TAGTAACCCA ACGGCTCTTT TAAGAGCCAC CTACGCATTT CAGGAAAAGA GCTGTAGTAC
119401 ACAGATGAAA TCCCCAAGC AAATGCAACA CGCCCTCAAT TATATTAGAA TCACTTGGAG
119461 AGTCGATAGA ACTTTAACAT AGCCTCATCT AGTAAGAATT TACTACTCAA TCTATCAAAG
119521 ATAGCAAGGT GAATTCAAAT GCACCGAGTT AAAATCGAGT TTTAAAGTCA CCTGGGTTTC
119581 GGTAGCCGGA AGTCCCGCGT CTCACGACTC CAAGCTAATT AGTCATAACC GTATTGAACC
119641 AAGGTTGAAG CCCAGTCCCA GGCTTGAGGC TTTTTATTAT ACAAGGTTAA AGTGGGGATA
119701 TTGCGTTTTG GGGTCAATAT TGCTAAAGTA GCATTTTCCG AAATTGGGTG GTCCTAAGAA
```

Figure 2 (Page 37 of 74)

```
119761 ATGCTTCTGG GATAGTTGGC AAAATATATG GCTTAACCAC GCCCTCTCCA CAGGAGTGGC
119821 TAGCGAGCTG TCTGTCCTTG GGAAGGACGG TGACCCTGCT GGCGTGGCTG GCGCCCACGT
119881 TGGCGTCCTC TGAAAGCCCC GCCAGGTAGG CCTAGCTCGC TTGCTTTCTG CAGCGCCATC
119941 ATGACAAAGC TTTGAAACGC AAAATGCTTT CTTTGTGCAG CGCCTTACCA TGGGTGCACT
120001 TACGGGCTGT CGACTTGGTT TAGGCCCTTG TCAGGACAAA GGAGCTTAGT TTGTTGGAGT
120061 TTTAGAGCTG CAACCCAAAA TCCCTTGCTC GGTTTCTCTG TTTTTAGAAA CGGAAGCGCC
120121 CTGATTGGAT ATTTGAAAAT TACTGTGCTT AACTGGATCG TGTTTCATCA ATCGTGCAGG
120181 ATTTTCAACC CTGGTGGAGC CCACACATTC AAAACTGAAG ATCCTTTTCT CAGAACTGCC
120241 CCTTTAAGCT TTTGCAATTT TAATTCTGGG GGTCAGATTT TAATAATTGG ACTTTTTTGT
120301 TTACATCTGA CAAGAGTATA TGATGAGCCA AGTTTACTCA CTTTTACTTA GTGCAGTTCA
120361 ATTCTAAAAG TTTATTTTTG CGTGTGTGCA TATGAGTTAA TAATCAGTTG TATTTTTCAA
120421 ACGGTCTTTT TTCAATTGTT TTGCTTAGCT CCTTCCATCG TCTAAAGTCA GGGATACAGG
120481 CACATCACAT CCCTGTTCCC CCTTCCTCAA ACTAATATGT AGCTACCTAG GTTTATCCTT
120541 TAAAACAAAA ATTCTCACCT ATTTTGTGA GAAATATACA TGTTTTTCTT TGAACTAAGT
120601 ATTTTACATA CACCTATCTA TATACATGCA TACTTGTGGT TTTGTTTTTT TAAAAAAAAA
120661 AAAAAAAAAA CACGTTATCT TTTGAGACTG GGTCTCAGTC TGTTGCCCAG ACTGGACTGC
120721 AGTGGCATAA TCACAGCACA CTGTAACCTC CAACTCCTGG GCTCAGGCTA TCCTGCAGCC
120781 TCAGCATCCG GAGTAGCTGG GATTGCATGC ACGCACCACC AAGCCGGGCT TTTTGTTTTT
120841 ATTTTTTGTG GAGACAGTCA CACCATGTTG TCCAAGCTGG TCTAGAAATG GCCTCAAGTG
120901 ATCATCGACC TCCCAAAGTG TTGGATTAC GGTCACTGTG CCTGGCCTTG TATGCATAAT
120961 TGTTTTGTCT TTTGATTAGG GTTATTAATT TAAAAAACAA AGCCTGGACG CAGTGGCTCA
121021 CATCTGTAAT CCCAGCACTT TAGGAAGCCG GATGGGCAGA TTACTTGAGC TCAGGAGTTC
121081 AAGACCAGCC TGGGCAACAT GGTGAAATCC CATCTTGACA AAAAATACAA AAAATTAGCA
121141 AGGCCCAGTG GCACGCACTT ATAGTCCCAG CTACTTGGGA GGCTGGGGTG GGAAGATGAC
121201 TGGAACCTGG GAGGTAGAGG CTGCAGTGAG CAGAGATCGT GCCACTGCAC TCAAGCCTAG
121261 GTGACAGAAT GAGACCCAGT CTCAAAACAA AAATAATAAA AATTTTTTAC AACGATGTTA
121321 TATACACTTC TGCATGTTGC TTTTCTCTTA ACCAAACTTT TCTAAAACCC TGTCATGAAA
121381 AAAGAAATCC TTCACATGGA ATAGCATAAG TTATTCATCC ATTTCTTATT GATAAGCATT
121441 GATGTTTCCA GTTACCACTG CTGAACATGG TGCAATTGAA TAGAATTCCA GGGCTGAGAT
121501 TGCTAGGTTT TAGGTTGTAT TTTATTATTT TATTTATTTA TTTATTTATT TAGACAGAGT
121561 CTTACTCTGT CACCCATGGT GGAGTACAGT GCCATGACCT CAGTTGCAAC CTTTGCCTCC
121621 TGAGTTCAAG CGATTCTCAT GCCTCCGGTC TCCCGAGTAG CTGGGATTAC AGGCACCTGC
121681 CACCAGGCCT GGCTAATTTT TGTATTTTTA GGAGAGATGG GGTTTCACCA TGTTGGCCAG
121741 ACTGGTCTCA AACTCCTGGC CTCAAGTGAT CTGGCCACCT CGGCCTCCCG AAGTGCTGGG
121801 ATTACAGGTG TGAGCCATGG CTCCAGACCT GGACTTTGTC TTCTGTTTCA TCAGTCCTTC
121861 TGTTGGTTCA AGCACAGTAT CACACTGAAG ACTGATGATT CTATATAAAT ATGGTAAAGA
121921 CTGTACACCC TAACTGTTCT TATTTTTTAA TTTTAAGGCA ATTTTAGATT CCAGCTTTCC
121981 AAAGAATTGT GGAATGCTTA GAGCTAGAGA AGCCTTGGAA GTCATTTAGT TTTTGTTTTG
122041 TCAGAGAAAA TTCTGTAGAG ACTCTGTCCT GCTCTCACTG AATACCATCC CATAGTACCC
122101 CCCAACAGCT TTAAAGGGCA ATAATACCTT ATGGACAGTA TGCTTTTCCT CAAATATATT
122161 CTAAGCCATG GTCAATGCAA AAGAGTGAGA AGGAAAGTAG AATAAGTTAT CTAAGAATCA
122221 GTGGGTGCTC TCTTTAAACT GATTTATCAC TCCCCCTTCC AAACTCTCTT GAAGGTCACT
122281 CTGCCTCCCT TTCTACATAA GAACTCCTAA CTCCAAGGGA GGAAGGTAAG TTATTCTTAT
122341 TCCTTGCTTA GAAAAGAGA AAATAGGTTT GGTAAGCATC CGCTTTCTGC TACCATTCTC
122401 TGTGTTTCTG TGTTTTTTAT AGGATCATTC AATTATTGGT TGGCTCTTGA GAGGGAATGC
122461 AAGGTTCAAG GACACAAGCC TAGATCTTGC CTGTATAGAA CCTCATGATG TTATGCTTCT
122521 CTAAAATGAG GCCTGGAGGA GACATGTTGA AAGTGACCCA TAAATCTGCA GTATCTCATG
122581 TCTCTCAATG GGGACAAGGA GTACCATGGG AAATAGCATT AGGTCAATGA CAGTAACAAC
122641 TCCCAGGTGA GTTGATTTAT TCTTTTATTT ATAAAGTTGT TAATATGCTA CATAGTCCCT
122701 AATTTTGCCA CAAATAGTCA TTATTTTAAT TTCATATTTC ACTATTGATA AATGAAGGAA
122761 AAAATGAGTA GCAGTTAAGC AGTCCATAAA CCTACATATA AAGCAAATTG GAGATTTTAA
122821 AATTGATTCT GGATGCTTAA AATCCTTCTC ATTGAAAAAA AATTTCGTAT TAGAAGATTT
122881 CAACATTCTT TAAACTGAGA AGCATAACAT ATAAACAGAA AACCACAGCA AAACAAAAAT
122941 GCAAAGCTCA ATAAATGAAC ACAAAGTGAA CACCATAATA ATTGCCACAC AAGTAAAAAA
```

Figure 2 (Page 38 of 74)

```
123001 ACAGAAAATC AGCCAACCCT CCCAGAGCTG CCTGATGCTT GCTTCCAGTC ACATTATCAC
123061 TCCATCTGCC CTAAACATAA CCCCTATTTT GATTTCCAAT GCTGTAATTT AGTATGCCTG
123121 TTTTTGAAAC ATATAAAATG GAAATAAAAC AAATGTAATC CTATGTACCT GACATATTTC
123181 ACTCCAGAAC ATTAGGTTTG AATAGATTCA TCTGTGTTGC TGTGTATAAC TTTAATTCAT
123241 TTTTATTGTT ATGTAATATT CCATGTTATG AGTGCAACAA TTTAGGTGTC TACTGTTGAT
123301 GCATATTTGC TTCCCTTTTT CAGCTAATAT AAACAATACC GTGAATATTC CTGTGTATGT
123361 GTCTTGGTAT ATATAGGAAT ACATATTTTG TTTGTATACC TAGGAGAGGA ATTGTTGGGT
123421 CAAATGCTAA ACTCTTTTTG AAAGTGGTGA TATTAGGTTT ACATGCGATG AAATGAAAAT
123481 TAAAACCACA GTTATAAACA GCATGGATGA ACCTCACAAA CCTAATGTTG ATGGAATCTA
123541 GCTGGGAATT CCTGTTCTTC CATATACTTC CCAATATTTT TTTCCAATTA AAATTGTTAA
123601 TCTTTTGAAG ATGTTATCCA TTGTGGCAGA TGTGCAGTAT TATCTCATTA TGGTTTTATT
123661 TTACATCTTT TGCCCATTTT TTCTTAATTG GATTGTATAT CAGTCGACTT GGGCTGCCAT
123721 AACAAAAATA CTAGACTAGG TAGCTTGAAC AAAAGGAATT TATTACCTCA CAGTTCTAAA
123781 GGCCAGGCCA GAAATCCTAA ATTGAGGTGC CAAGAGATTC AGTTTCTAGT GAGGGCTCTC
123841 TTATTGACCT GAAGATAGTT GCTGTCTTAG ATTGTTTGGT GCTGAACAGA ATACCAGAGA
123901 CCAAATAATT TATAAAGAAT ACAGATTTAT TTCTTACAAT TCTGGTGGCT ATAAAGCCTA
123961 TGGTCGAGGG GCCCACCTCT GGCAAGGGCC TTCTTACTGT TATGGCAGAT GTGAGATGTC
124021 ATCTCATATT CAAACCACAG CAGTCGCCTT TTGTGTCCTC ATGTGGCCTC TTCATATGCC
124081 CATAAAATGA CCTCATGTCT CTTCCTTTTC TTATAAGGAC ACCAGATCTA TCAGACTACT
124141 GGCCTACTCT TATGACCTCA TTTAACCTTA AATATCTCCA TAAAGTCCCA AAATCCCTAT
124201 CTCCAAATAT AGGCACATTG GGTGTTAGAG TTTCAACATC AATTTGGGG GAACACAATT
124261 TAGGCCAAAA AGATTGTGTT TTTTCTTGTT GGTTTAAGAT AGCTGTCTTT TTGTCCTTTT
124321 TGTCCTTTCT TTTTTTTTGA GGTGGACTCT TGCTGTGTCA CCCGGGTTGG AGTGCAGTGG
124381 CGCTGTCTCA GCTCACTGCA ACCTCCACCT CCTGGGTTCA AGAAATTCTC CTCCTCCCAA
124441 GTAGCTGGGA CTACAGGTGC ATACCACCGC GCCCTGCTAA TTTTTGTATT TTTGATAGAG
124501 ACGGGGTTTC ACCATGTTGG CCAGGCTGGT CTCAAACTCC TGACCTCAGG TGATCCACCT
124561 GCCTCGGCCT CCCAAAATGC TGAGATTACA GGTGTGAGCC ACCAAACCTG GCCTGTCTTT
124621 TCTGTTTTAA GTTTTTAAAT TTTGCTCACG AACCCTTTAT CCATTTTATG TGTTGCAGGT
124681 ATTTCCTCTG TAACTTGTCT TCACTCTGTC AGAGGCTGGA GTGCAGTGGC ACAATCACAG
124741 CTCACTGCAG CCTCCACCTC CAGGATCAA GCGATCCTCC CATCTTATCC TCCTTAGTAG
124801 GTGGGACTAC ATGTGCAGGC CACCATGCCC AGCTAATCTT TGTATTTTTT TGTAGAGATG
124861 GTGCTGTTGC CCAAGTTGGT CTCAAACTCC TGAGCTCAAG CAATCCATCA ACCTTGGCCT
124921 CCCAAAGTGT TGGGACTAGA GGTGTGAGCC ACCACTGCAC CCAGCCAATG ATATCTCATG
124981 ATGCATTAAA GTCATTAATT TAGTGTACTC AAATTAAGCA CACTGCCCTT TTATGCACAA
125041 CCTTTTTTGT ATCTTATTTA AAAAATCATT TTCTATTTCA AGGTCATGAA GATCTTATTT
125101 TATAATACCT TCTTGTGAAA TTAGTTCTCA AGACTACCCT CACTTCTAAC ACCAATTATA
125161 AGTTGGGAGG TCTGTGGTTC CCAATCAACC TTAGGTTAGT AATTTGCTAA AAGGACTCAC
125221 AGAACTTGCT GAAGCTGTTA GCCTCATGGT TACAATTTAT TATAGGATAT ATAGCTTATT
125281 ATGTCATTCC AATGCAATGT AAAATTATAC AACTACTTTT AAAAAGATTT TAGCATTTGA
125341 CCCAACAATT TCACTCTGAG GTATACAAAC AGCAGATATG TGTGCACATA TATACCAAGA
125401 CACATACACA GCAAAATTCA TTGTTTGTAA TAGTTGAAAA GGGGAAACAA CTCAAGGAAT
125461 AAAGATTAAA ATCAGCTGAG AAAAGAAACA CACAAGGCAG TATTATGGAT CGAATTGTAT
125521 GCAGATCTCC CTTGCCCCCA GAAGATATGT TTAAAGTCCC AACTCCCAGT ACCTCAGAAT
125581 TGTGGCCTTA TTTGGAAATA GGATAGTTGC AGATATAATT AGTTAAGATG AGGTTATAGT
125641 ACAGTATGAT GGGCTGGTGA CTTAGAAGAA GTAGTATATA TATATTTTTT AATAGAACTA
125701 GTATTCTTCT AAGGTGGTCA CGTGAAGACA GACACACACA GGCAGAGACT GCGGTTATGC
125761 AGCTGCAGGT CAAGGAATGT CAAAGGTTGC CAGCAAGTAC GAGAAGCTAG AAGAGTCAA
125821 GGAAGGATTT TCCTACAGGC TTCAGTGGAA GCATAGATCT AATGATACCT TCATGTCAGA
125881 TTTCTAGCTT CCAGAACTAC AAGAGAATAT ATTTGTTGTT TTAAGCCACC CTAGCTTCTA
125941 GCTCTTTGTT ACAGCAGCCC TAGGAAACTA ATATAGGCAC AATCCAGGCA AGTTCCAAAT
126001 ATGAGCTTCC AGTTGTCCTC TCCCAGTAAT ATGAACAGTA TTACTTTCCC AGCATTAATG
126061 TGTGACAATA CACATGACGT ACAGAGCAGT CCCCACTTAT GCACAAAACA TATGTTCCAG
126121 GACCTCCAGT GGATGTCTGA AACCATGGAT AGTACTGAAC TCTATATAGC TGTTTTTTCC
126181 TATACAGACA CAGCTATGAT AAGGCTTAAT TTATAAATTA GGCACAGTAA GAGATTAATA
```

```
126241 ACAATAAATT AGAATAATTG TTAAGAATAT ACTGTATAAA AGTTAGGTGA ATGTTTATTT
126301 CTGAAATTTA CCGTTTATTA TTTTTGGACT GCAGTAGACC ACAGGAACTA AAACCATGTA
126361 GAAACCGTAT ACAAGAGAAC TGTATTTCAC CCGAGCCTCA GTGTGCAGTT TTAATGGCCT
126421 GCCATGGTTG ACTGCTCACA TGGCCGATCT TTTAGTCTAC CTCCACAGGT AGAGCTGATA
126481 CTGTGTGGCT CAAAGTTCCT ATTATAAATC ACATTGTTGA CTGTGTGGTG GTCAAAACCT
126541 CCAGGTAAAC AAAGACACAC TTATCAGTGA GAACATTTCA AGGGTCTAAA ATTCATCTCC
126601 CAGTAGCTGA GGGCAAAGGC TAGACCTCTT TTTGGGTAAG ATAAATTTTT TACCATATAC
126661 TTTATTTTGC TTTTCATGTT TAACTTTATT TTGCTTTTCA TGTTAGTTCC CCTGGAATTG
126721 TTTTTTGTGT ATAGTGTGAA GTAGGGGGTC AAGTTTCTTT TTTTTTCCTT TTTGTTCTTT
126781 TTCTGTTTAA AAGGCTATAC AATTGTCCCA TGCCATTTAT TTACAAGAGT CCTTTCACCA
126841 TTGTTGTATG GTGCCACTTT AGATGTAAAT CAATGTCCAT ATTTGTTTGA GCCTGTTCCA
126901 TTCGTTTGTC TATTTTTGGA CAACACTGCC CTGATTATTG TCATTTTATC AGTTTTGATA
126961 TTTAATAAAG CAACAGATTT GTTTATTTTG GGCCCTTGGA TTTGTGTATT AAATTTGAAC
127021 CCTGTTTGTC AATTTCTATA ATAAAGCTTA TTGGGAATCT GATTAGGATT ACAATGGTTT
127081 TGTAGATCAG TTTGGGGACA ATTAATACCT TTAAAATATT GACCGCTTCA ACTGTAAATA
127141 TACTCCTCCA TTATTTAGTT TTCCTGTTTA ATTTATCTGA GTAATACATT ATAGTTTTCT
127201 TCGTAGAAGT CAGATACGTA GAAAATTCAA AGCCCAAGTG CAATAGCTCA TGTCTGTAAT
127261 ACCAGCACTT TGGGAGGCCG ATGTGGGTGG ATCACCTGAG GTCAGGAGTT TGAGACCAGA
127321 CTGGCCAACA TGGTGAAACC TCATCTCTAG TAAAAATACA AAAATTAGCT GGGTGTGGTG
127381 GCGGGCACCT GTAATCCCAG CTAATCAGGA GACTGAGGCA GGAGAATCGC TTGAACCCAG
127441 GAGGCAGAGG TTGCAGTGAG CCAAGTTCCT GTCACTGCAC CCCACCCTGG GCGACAGAGC
127501 GAGACTTCGT CTCAAAAAAA CAAAAAAAAG AACATTCAAA TAATCAATGT AGATAATTCA
127561 AATAACTAAA AAATGAACAG TTATTAAAAT ATCAGGATAT AAAAGCAAAA AAATCAATAA
127621 CCTCCATATA TACAAAATGG CCAGTTAGAG AAAAAAAAAA GAATAGGCGA GACTTAAAAA
127681 GGCTGGGAAT CTCCCTGAAA ATCTTTGAGA GCCTTGGCCC TGCCCTCAGG GATTTCTCTG
127741 GCTTCATGCC CAGATATGGG TACAGTTCCT TGTTTAAAAA AATTTTGCTC CATCAATCAA
127801 CAAGGGGCTC CTTCCTCAGA GCACAAGGAC CTCCATAACA CCGGACACTA GATGTCTAAG
127861 GGACACCTCT TAAGGAAGTT AGACTTCCAA AGAATGGTGT TTCCTCTGTC CCCAAACTCT
127921 GGAACTCACA GCACAACTGC TCCTGGAGT TCGGTTTCAA ATCTACAAGG CTGTCATGGA
127981 GGTTGCAGAC CAAGTCCGTG GCCTCAGTGT CCGGATGTAC GGTGGCCTTG CACCTGAAT
128041 GTGAGAACAT GACCTCCCTG AAACCACCAC AAGTATTGTT TCATGTTATG TATGTTTTT
128101 CTTATCTGAA ATTCCTTTTC TTTAAAAATT CAAATTACAT ATTTTCAAG CCCCTGAACA
128161 AGCTTCATGA GCATTTATTG AACCCACAGC TTTTAAAACC TACTGAACAC TTTGCTCTAT
128221 GTTGTCATTC ACTATCCACC AATTATTTAA TTATTGATCA ATATTGTTTC CTTAGTGTTG
128281 GGATCATTTA TGCATGTATT TCTTTTATAT TGCATATTTT ATATTCTGC ATTACAGTTA
128341 TTACATATTA CTTTTGCTAC AGTAATAGTT CAGAAGTGTA CATCCAAAAT TTAGCTGTGA
128401 AGTGGATGGA CTGAGGCAGA ACTGGAGGCA AGAAAATGTC ACAGTAATTC TAAAAAAGAT
128461 GATGTACAAT TAGAGCAAGA GAGTAGCACT GAAATTGAAG AAAAATAGAT GCGTTTGAGA
128521 GAAAATTAGG AGGTAGAATC AACAGATTAG ATGTAGGGAT GAGAAGGGTC AAAGATGACA
128581 CTAGGGTTTT TAACTGGAGC AAGTAGGTAG ACAGAACATT TCTTCCTGAA AGGGCAGGTC
128641 AGATCATGTG TTGTCTCAAA GGGCATGAAG AGTAGAAAGC CTGGGACAGA TCCTGAGATG
128701 ACCAATACCC ATGGTGCAGG GAGAGGGAGG GAGATCTGCT AAAAAGACTG CAAATGTCAG
128761 GATAGTAGAA AATCATGAGT GTGTGATGTC CTGGAAGTTG AGACAGTATC ACATTTGAGA
128821 ACATTTAAAT TGGTAACTCT GACAAAACCT GGAGGCCAAC TGTGAATGCC CATGAGAGTG
128881 AGAAGCTCCC ACACTTTTGT GGGCATCAGA AAGCCCACCA GGTTCCTGCA GTGAAGATCT
128941 GAGAAGGATC CTCTTGTGGC TTTGGCAGGG AGAGAAGAAT TATTATGAAA TACACCCCAG
129001 AACCTTCTTC AAAACAAAGG CCTACTCTCA AGGGGAAAAC ATTTTGCCAG AGTCTTATCC
129061 CAGCTGGGAG AAGGTAATTC TTCCCACTGC AGCCTCATCT AGGCTTTCTG TCTCACTTAA
129121 GGGAAGAAAA TTAGTCAACA GGGATCAGAG CTTCATGAAA ATAAATTGGA AATGGTGCAG
129181 CCAGGAAAGG AGCAAAGGTC TGAGGAGGAG GAGAAGGAGG AAGAGGAGTT GTATCATTAT
129241 AAATACTTGA GGAAGAGGAG GAGAAGGAGG AGGAGGAGGA GTTGTATCAT TATAAACACT
129301 TGAGGAAGAG GAGGAGGAGA AGGAGGAGGA GGAGTTGTAT CATTATAAAC ACTTGAGGAA
129361 GAGGAGGAGG AGAAGGAGGA GGAGGAGGAG TTGTATCATT ATAAACACTT GTGACGGTCC
129421 CAGCCCCAAG ATATAGGCAT GCTAATAAAC TGAGGCTTAA CACTTTGACT ACAGAATGCT
```

Figure 2 (Page 40 of 74)

```
129481 GCTTCTCCCT AACACCATCA AGGCTCCAAC TGAATAACAA TGAATTATGA ATGAAAGAGC
129541 TGTAAGGAGA GACAAAAGTT AGAATGAGAC AAGTATTGTT ATCTAGAGAT GCCAAGAAGG
129601 CAAGGAAGAT AACTAAAAAG GCACTCTGGA TTTAGAAATA GGAAGTCATT AGTGACCTTG
129661 TAAATAATGG AGCCAGAGGA ATACCAAGGG CAGAAGCCTC ACTATAGTGT GTTGCACCTG
129721 TCAGAGGTCA GGAGGTGTAA CTGACTCTCC CACAGTGTGG CTTTGGAAGA GAGAAGTCAG
129781 CAGCTGCATG GAGATTTGGG AGAGGGAAAG CTTTTTTTTT TTTTTTTTAA TTGGAAAAGA
129841 CTGAGCTATG TGTAAATAGA ATAAGACAGG AAGAGTGTAG ACACAGGAAA GAGGGCAGAC
129901 AAAAACAAGT GCACAGTTAT CTAAGGGAAA CAATGGGATC AAGCTGCAAG TATATAAACT
129961 TGTCTTGATA GAAGAATCCT TGATCTGGTT TATTCAGTGT TTGGTCCAAA CCCACATCCC
130021 TGTTCTGCCT GTCTCTGACT TGCTCTGTGC CCCAGAAGCC CAGCTTCTAC AGATAGCATT
130081 AGCTGGGCAG CCCTGCCCTC TTGCAACAGC TGGATTTGGC CAGTGATCAG CCCAGCAGGA
130141 ATGTAGATGG CAAAGGAGAG AGAGGTTAGT GTACTTATTC CCTGCATCAC CCCCCTGCTT
130201 GGTGGGCAGC TCTTCCTCCA CAGTCCCAGC TCTGGCCTAG CTCTGGTTAC AGGTTCCCTC
130261 CCATTGCCTC TTCAGATTTA AAGGTGTGTC TGTCAGGGTA TAACTGGGAG CTAGAAATTG
130321 CACTGAAATT GAACAAAGAA TTTTATGGGA ATGGTTGTTA ACTAGTTATA AGAGGACTGA
130381 AAATGGAAAA GTGGAACAAA CGTATCAGAG ATAGTAATGA CAGAAAGCAA CTACCACCTC
130441 CAGGTTTAGG AGAACAAGGA AAAGATTCTT TGAAGAGATC CCCAGAACTG GGACCTCTGA
130501 GGAGTGTATG CTGGACCACT GATGATGATA TGTCTGTAGA TAGAGGCATG ATGAGGCTGA
130561 TTTTAGGAGC ATGGAAGATC TCCAAACTGA AGCCAACTGC TGTTACTGGA TTCAACTGCC
130621 ACTGCCAGGT TGAAGAACCC ATTCTGTGAG GATGTCAACA AACAAGTGG GAAATCTTTT
130681 CACATCCTTC CAGCCCTCTA GTCTTCCTCC AGTGCTTTCT ATTGGTAGGG TTTGGGGAGG
130741 TGGCTAGCAA AGCGGTATTG GAAAGATAG AAGAGACTAA ATCTTCATAA CCAGCACAGG
130801 GTGACACTGG ATCACTACTG TTGCTGATCT TGGGCTGCCT CATATCCCCT GTTCTTCCCA
130861 TTAGCCCTGT CACAACTTTG TAGATATCCC TTCATTATAT GCCCTTCATA TATTCTTTTG
130921 GTTTAACTTT TTCTGTTGGA ATCCTAATAT GGCACTCCTC CATTTTTCAG GACCAAAAGA
130981 GTATAAAAGA TTATCTTTTA CCAAAAAAAA GACAAAAAAC TGATCTAATT CCTGATTTGA
131041 TCATTACACA ATCTATACAT GTATCAAAAT ATCACATAGT ACCCCATAAA TATATACAAC
131101 TGTGTCCATT AAAAATAAAA ATTAAAGAAA AGATGGTAAA TATAGCTCTG TCAGGCAGTG
131161 GAGGTTTTAC CACGATGGCT GTTATTTCCC CCATGAAGGG GGGAGTGAGG GAGCAGCTGA
131221 AAGTAGGTGC TTATAGGGGT ATAGAGGGGC TCAAAGCTTT GAGAGAGGAG AATGTCTGAA
131281 AGAGCTGCCA AATAGCATGC AGGTCCCATG GGGGCAGAGC CTCTGCTCAT TCACCAGTGC
131341 CTCTTCAATA TCTACACTTA AGCCTAACAC AAAGTGTGTG CTTAATAAGT ATTTGCTGAG
131401 TATGTAAAGT GGAAACAGAA CCAATCTGGC AAACTTTGTA GGACTGGTGG GCAATGAAGA
131461 TCAGTCAGGT AAAATCTGTG GATATAAATT TATATTGATC AAAAAATTCA AGGTTAGGTG
131521 TTTTTCTTCA GTCATGCTCA ACGATGCTTC AGCCATGCTC AACTCTTCTG TAGCCACAGA
131581 AAAAAGTTTA CCCATAATCG AGCTGTGTCT GTGTCTGAAT AATGAAAAGA CCATGATGCA
131641 AGGGAGTTGG AGACACAGAA ACAGTGTTTG AAGTAATGGG TAATGGAAGC ATGCTACCAG
131701 GGAAAGGAAA GAAGTGGCAA TAGGAAGGAA CAGAGATCTG TGGTCCTATG TCCCCTGAGC
131761 ATATTCACAT GTTAAAGCTA ATTCAGTTTT CAATCATCAT TAAAATTTTG TTCCTAAATA
131821 TATGGCCATT ATTTTCCACA ACCACACTAA AACTTTATTA CCTCTGGCAA GTGACTATGC
131881 AAGTAACTAA GAGCAAAAAT ATCCACAACT ACCATTTGAG CTATCAATTT AGGGAAAGTC
131941 ATCTGGCTAT AATCTAAGTG ACCCTCCACT GAATGTCAGT ATCTTTGCAT ATGTGATTTA
132001 AATCTGGGCC TTCGCAACAC CATGAACTGT TCTTGTCTTG AATATCCAGA TTGAAGGAAA
132061 TAATCTGAGT AGTTACGAGT CCTGAAGCTA GAAAGATGGA AACCCCATTT GCTCATCAGA
132121 AAGCCTTAGA GCTTGGGCGC TGGCGGGTCC TGTCTCACCG GGACAGAGGG GCTCTTTCCT
132181 CCCCATCTGA TAGTCTGATA ACTAGAGAAG CCGGCCAACT TATTCTCCAA GAAGGAGCCA
132241 TCTTAGTTCC TCCTGAAATG TTCATATTTA GAAATTATTG TTTGTCAGTA ATTTAACCCC
132301 TTAATGGGCT TGCCTTGTGG TCCATACCAC TGAGTGCAGA GCTTGCCTGG AAGAATTGTG
132361 AGGGCCATTC CATCTTCCAG GCAGTAGAGT TCAGTACTTC TTTAAAATTG CTGCTGAACT
132421 CTGTATTTGA AAAGAAAGAA TCATTTGGGT GTGGTAGCTC ACACCTGTAA TCCTAGCGCT
132481 TTGGGAGGCT GAGGTGGGAG GATCATTTGA TGCCAGGAGG ACCACTTGAG ACCACCCTGG
132541 GTAACATAGC AAGACCCTGT CTTTAGAAAA AAAAAATACA ATAAAATAAA TACAATAAAA
132601 ATAAAAGCAA AAAGAAAGAG TCCATCTTAG GGACAGACTG TAACTACTCA CTGGAGCTTA
132661 CCTTTACATA GTTCAGGATC AATTATAATA AAACACTTTT GTGCAGATTC AATAGGATTA
```

Figure 2 (Page 41 of 74)

```
132721 TTTTAATCCC CATCATCTCT CTGAGTTTCC AGTCAGTTTC TCTGCATGTA GACACCCTTC
132781 TCCAGCCCAC CATTGTCTCT CCTCCTATAG CTCCACCAAC AAATCAGAAC TTTTTCTAAC
132841 TGCACCTAGT GCACCTAGAG TCTACTCCAG AATGCTCATG GAGAAAGTTT CTGAAAGGTA
132901 AAACTCTGAA TGATATTTGT AGCTAAAGGG AGACTTGCTA GAGACAATAA GCTAATAGTT
132961 GTAGACTTCA GTAGAAGAGG AATGACACTG CAATGTCAGG GTGCAGGACT TCAAGAGGGC
133021 AGAGTATGGA AACCCAATGG GAAAAATGCT CACCAGGAAC ATGAAGAGAA GGAATTACGT
133081 GTAAGGATTT CTCAATGTGT TCCCAAATTT GCCCAGCAGA GGGAGGCCTC GGGTTGATGG
133141 CAGGCTGACC ACACAATTAA AGAAGGCTGA ACCTGGGGGC TTTTAACAAC CATCGTGGGC
133201 TCTACTGTAA GCATTTAGAA AAAGAAAGTT ATCCATTCAA AAATATATAT ATTTTTAAAC
133261 TTCAGAACAA AATTATGAAG AGCTATATTT ACTTTCTAC ATTCTAATTT TTATAAATCT
133321 GAGTATATTT TGCATATATT GTTATAGTAC ATATTCAATT TTGTATTTTG CTGTTTTCAC
133381 TTAACCATTT TTACTAGATT ACTCTGTGTT CATAATAATC ACTTTTTAA AACTTTTATT
133441 TTTATTTATT TATTTTTTTT TTGAGTCAGA GTCACACTCT GTCGCCCAGG CTGGAGTGCA
133501 GTGGCGTGAT CTTGGCTTAC TGCAACTTCC ACCTCCTGGA TTCAAGCAGT TCTCCTGCCT
133561 TAGCCTCCTG AGCAGCTGGG ATTACAGGTG TGCACCACCA AGCCCGGCTA ATTTTTGTAT
133621 TTTTAGTAAA GACGGGGTTT CACCATGTTG GTCAGGCTGG TCTCCAACTC CTGACCTCAT
133681 GATCTGCCCA CCTTGGCCTC CCAAAGTGCT GGGATAATCA CTTTTTATGC TGCATAATTC
133741 TTCAGATTTG TCAGTACGAC TGTATTTACA CTCATTTGTT TTATTAGAAA GAATTCCAGA
133801 ATATTTTGGC TGCCCTAATT AATTTTACAA TTAATATGAT TTGAAATTG GGTATTGGCT
133861 CCTTCTGAAT TGGTTTATTA AAATATATTC TAATGTAATT TATGACATTT TCATCATATT
133921 AGCATATTTA TTCTGTTAGA ATTTCATAAT TTATAAAGCT ACAAACTGTA TGTGATATAG
133981 CTTGTAACTT TATCTCATAA CTTTATGCAG TTACAAGTAG AAATAAAATG TTCCCCTCAA
134041 GATTGCTTAA AATTTTATTA TAAACAAGTG TAAAAACAA AATCACTAAA ACACTCCCTC
134101 TTTTTTCCCC CAAAATGCAT GTTTCCATTT TAACAGAACC CGTATTTAAT CAGCAGATTT
134161 CTATGGTGGC TAGATTTGTA GACTAAATAT TAAAAGTCCC AAAGCAAATG CATTTTTCTC
134221 TTAAATTTTA CTGACTTTTT TTTTTTTTCT TTTTCTGAGA CGGAGTCTTG CTCTGTCGCC
134281 CAGGCTGGAA TGCAGTGGCA CAATCTCGGC TCACTGCAAC CTCCGCCTCC CGGATTCACG
134341 CCATTCTCCT GCCTCAACCT CCCGAGTAGC TGGGACCACA GGCGCCCGCC ACCACGCCCA
134401 GCTAATTTTT TGTATTTTTA GTAGAGACAG GGTTTCACCG TGTTAGCCGG GATGGTCTCG
134461 ATCTCCTGAC CTCATGATCT GCCCACCTCA GCCTCCCAAA GTGCTAGGAT CACAGGCATG
134521 AGCCACCGCG CCCCGCCTAC TGACTTTTAT CCAAAGAAAA TATAAGAGCT CTTCATCATA
134581 ACGTATGTTT CTTGCTCTTG TTATTAAATA TGACACATTT AGACTTAAAC TGATTTGAAG
134641 GTTTATGACA TTGTTAAGT TATTACATAA TTAATTCATA AAGATAATGA CTAGTTTGAA
134701 CTACTGACAG CTCACACATC ATCAGTTGAA CAGCAGAAAG CTTATTAAGC TACTTTCTTA
134761 TGTTTCTGTC TCCCAGCTAC TAAAAGAAAC GAAACCCTTC CAGGTGTTAA GGCAAAACTT
134821 TCCTCCCCCT TTCTTCTATA AATCTGATTC CATGTTAGTG AAATTTCTAC TGATGGCTTT
134881 GGTTTCCTCT ATAGTAGAAT AGAGATCCTA TGGCAAAAGT CATGTCTGAC ATGGTAGCAA
134941 ATAGAAATGG GGAAAAGGAA GGTCTGCAAG AGCCAATGTG GGAAATGGGG AGAGGACTGA
135001 CTACAAAAAC CCAGCAGGAA TTCCAGAAGA AAACTCCTCA GGACGGGCAC ATTGGCTCAT
135061 GCCTGTAATC CCAGTACTTT GGGAGGCCGA GGTGGGCAGA TCACTTGAGT CCAGGAGTTT
135121 GAGACCAGCC TGGTCAACAT GGCGAAACCT CATCTCTACA AAAAATAAAA AAATTTGTCA
135181 GGCGTGGTGG CATGCACCTG TAGTCCCAGC TACTCAAGAG ACTTAAGTGG GAGAATCACT
135241 CGAGCCTTGG AGGTGGAGGT TGGTGAGCCG AGATCACGCC ACTGCATTCC AGCCTGGGCG
135301 ACAAAGTGAG ACGCCATCTC AATCAATCAG TCTCCTCGAA AAGCAACATT ATGGAGAGAC
135361 AGGATTCCGT CAAGGCCTGG GGCACACAGG AAAATATTAA GGCAGAAGAG AGTTTCCTCC
135421 CCACACCACA CCGTATCCCA CAGGCACTGC GGATGTGCAT ATGCAAGAGG GGTTGATCCT
135481 AAGAATTTAG AGTCACAGAG GAGGAGGCAC CAAGCAGACT GTGGAGAAAG TCATGACCAG
135541 AAAGGGACAG AATGTAAAGC TTCAGCTGAT TATCTGGCCT CAGGGATTCC AGAGGAACTG
135601 GTCCCAATGG TCTCCTGGTG ATGTAGGTTC TTAGGTTTCT TTTACAGGGG TTTTCTGGGA
135661 GATCGTTGAC CCAGTTAGCA TTCAAGCAAC TTCCACCCTG CACTTTTATT CTTTCCCCTT
135721 CACCTGCTTA GGTTTTATCT GTCCAGGCAA TAATAATAAA ATTATTGAGC CCTGGACATG
135781 TACCTGTAAA GCTCCTTAAA GATGATGCCT TCTAACTCCT CATTCAACAG ATACAAAAAC
135841 ATTACAATAA AATGACTCAT GCAAGACACC CAGGTAGTTT ATAGCAGCTA ATAAAAACAG
135901 AATAACTATA AAATATGGTA AGTTTATAAA AGTTACATTG AGTATACTTT ATAAGAACTG
```

Figure 2 (Page 42 of 74)

```
135961  CTTATTGAGT  TTGCCTAATA  ACCACACAGC  ACAATAATAA  TATGTATATA  TTTTTAAATA
136021  TGTGTAAATA  TGTGTAACAC  AAACTTGTAG  AAGGTATATC  TGAGTACAAC  CCTATTCTGT
136081  TTGGTTACCT  TTTCTAGTTC  ATTATGTAAG  TGGCATAGCT  ACCTAAGGAC  TTATGCTTAT
136141  AAATGTTACT  CAAAAAAATA  CAGAGGACAT  ATGTGGATAG  ATAATGGAAG  AGATAAGATA
136201  GGTAGGTTGA  AGGGTTGGGC  TGCCCCTCCA  CACCTGTGGG  TGTTTCTCGT  TAGGTGGAAT
136261  GAGAGACTTG  GAAAAGAAAG  AGACACAGAG  ACAAAGTATA  GAGAAAGAAA  AAAAGGGGTC
136321  CAGGGGACCG  GTGTTCAGCA  TACGGAGGAT  CCCACCGGCC  TCTGAGTTCC  CTTAGTATTT
136381  ATTGATCATT  ATTGGGTGTT  TCTCGGAGAG  GGGGATGTGG  CAGGGTCAAA  GGATAATAGT
136441  GGAGAGAAGG  TCAGCAGGTA  AACACGTGAA  CAAAGGTCTC  TGCATCATAA  ACAAGGTAAA
136501  GAATTAAGTG  CTGTGCTTTA  GATATGCATA  CACATAAACA  TCTCAATGAC  TTGAAGAGCA
136561  GTATTGCTGC  CAGCATGTCC  CACCTCCAGC  CCTAAGGCAG  TTTTCCCCTA  TCTCAGTAGA
136621  TGGAATATAC  AATCGGGTTT  TACACTGAGA  CATTCCATTG  CCCAGGGACG  AGCAGGAGAC
136681  AGATGCCTTC  CTCTTGTCTC  AACTGCAAAG  AGGCGTTCCT  TCCTCTTTTA  CTAATCCTCC
136741  TCAGCACAGA  CCCTTTACGG  GTGTCGGGCT  GGGGGACGGT  CAGGTCTTTC  CCTTCCCACG
136801  AGGCCACATT  TCAGACTATC  ACATGGGGAG  AAACCTTGGA  CAATACCTGG  CTTTCCTAGG
136861  CAGAGGTCCC  TGTGGCCTTC  CTCAGTGTTT  TGTGTCCCTG  AGTACTTGAG  ATTAGGGAGT
136921  GGAGATGACT  CTTAACGAGC  ATGCTGCCTT  CAAGCATTTC  TTTAACAAAG  CACATCTTGC
136981  ACAGCCCTTA  ATCCATTTAA  CCCTGAGTTG  ACACAGCATA  TGTCTCAGGG  AGCACAGGGT
137041  TGGGCTAGG   GTTAGATTAA  CAGCATCTCA  AGGCAGAAGA  ATTTTTCTTA  GTACAGAACA
137101  AAATGGAGTC  TCCTATGTCT  ACTTCTTTCT  ACACAGACAC  AGTAACAATG  TGATCTCTCT
137161  CTCTTTTCCC  CACAGGAGGT  GATGGCCGGA  AGAACATGGC  AGAGGGCAAA  ACAAAACAGC
137221  ATTGGGAACA  AGCTCTGTTT  AAAAGGAGAC  TTGTGAACAG  CAAAGAGTAG  AAAGGGTTCT
137281  CTTACAACTG  AAGCCCATGG  AAGACAAATG  TGTACTGCGT  GAGTTTTAAG  GCAATAGGAG
137341  TAGTGGGACC  TAGGGCACAC  CAGAGAGCAT  ATTAACTCTC  AAACTTTTAA  AAACATTATA
137401  TCTGCTGGAC  ACAGTGGCTC  ACACCTTAAT  CCTACAACTT  TGGGAGGCCG  AGGCGGGCGG
137461  GTGTAGCTTG  AGCCCAGGAG  TTCGAGACCA  ACCTGGGCAA  CATGGCAAAA  TCCCGTCCCT
137521  ACAAAACAAA  CAAACAAAAA  ACAAAATTAG  CCAGGCACGG  TGATGCGTAC  CTGTGGTCCC
137581  AGCTACTCAG  AGGCTGAGGT  GGGAGGATCG  CTTGAGCCCC  GGGAGGTTAA  GGCTGCAGTG
137641  AGCCATGATA  ATGCCACTGC  ATCTCAGCCT  GGGCAACAGA  GGGAGAACCT  GTCTCAAAAC
137701  AAAAACAAAA  ACACACCATA  CCCAACCACA  ATGCATCTGT  CTTAAGTACC  AGTACCACAC
137761  CCCTCTACTC  ACTACTAAAT  AGGTGAGTTC  CCAATCCCTG  GTAGCAGGTT  TAAGCATGTT
137821  ATATTAAAGG  TCTTAGGCTA  GTGACTCATT  CACTCATTAA  ACAAATACTT  ATTGTGCATC
137881  TACTATAAAC  TAAGTACTGT  GCTAGGTACA  AAAGCAAATA  ATCTAAGCTC  TATAAACTTT
137941  ACTTTCTTCA  TCAACAAAAT  GGAGATGTTT  TAGGCATCTA  CTCATCATTC  TGAGCTCCAT
138001  CTTTTGTGAC  TGTAGTTGGC  AGAGCTTTTT  ATCAGTTTCT  CTAAATAGCT  CTACCAGTCC
138061  CTGGTGGATG  CTGGCATGCC  CAAAGGATCC  ATCCTGATGG  CCCTGTCTGC  TTACCTTACC
138121  TGCCTGCCTT  TGCAGCACCG  CTCTGCTCTT  CTGCAGGACT  TCCCTTATCC  TTTGGGTCT
138181  TGCTGCTCTT  AGGCTGCTCT  GCTTGTTTTG  ATCTGCTTTG  CATCACATGT  ATGTAAAGGT
138241  CCTTTCCTTA  TTTACCCATG  ACCAAGGTAT  TATGAGATTC  TGGAATTTCC  CCAAACCACA
138301  TTGATTGCTG  GGAGAATAGA  AGAAGTGGAT  TACAAGTGGA  ACTTAGAAGG  GGAGTATTCG
138361  AGAAGACGTC  TCTGCAAATC  CATTTAGAGA  GACCTTTCTC  CAGTGGTGAC  TCAAAGATGC
138421  AGCTCCTTTC  ATCCTGTGGC  TTGGCCATCT  TCAGCACATG  GCTCCCAAGG  ATGTCCTCAG
138481  GATGGTCTCT  AATCCAAGGA  GCCTGAAGAG  AAAAAAAGGC  ATGGAGTATT  GTGAGTGGTA
138541  GGTGGTTATG  GACCAGTTAT  GGAAGAATAC  ACATCACTTT  TGCCCACCTT  CTACTAACCA
138601  GAACTCACAC  AGCCATAGAC  ACTGACAAGT  AGGACTTAAC  AAGAATCTAA  TTTTGAGTCT
138661  AGGAATACGA  CTGTAGCAAA  TATTTAACAG  CTTCAAACAC  AGGTGCATTG  CTATCACTAT
138721  GCTTGGCCCA  GGCCTGTCTC  CCTTTCCTGC  CATGTCACAG  GGCCAGCAT   TTATGTCTAG
138781  ATTGGGTTGG  TTGGGATATT  AAGACAATAA  TGAACCAATA  CAACATCTTG  AGCATAAAAC
138841  CAACTGATAC  AATGATGTAC  AAGTCAGATG  ATTCTGATGA  TTATGAATTA  TGTCAATAAA
138901  AGAAATGTGA  TAACTAAGGT  AATTTTTGTT  TTGGCAAATT  TTTGTTTGTT  CATGACAGGA
138961  TGAAATCCTG  TCATTTGTAG  CAACATGGAT  GGAATTGCAG  GATACTACAT  TAAGTGAAAT
139021  AAGCCAGAAA  CAGAAAGTTA  AACACCACAT  GTTCTCACTT  ATATGCAGAA  GCTAGCTAAC
139081  TAAGTAAATA  AGTTTATCTC  ATTGAAGTAA  AAAGTACAAC  AGAGATTACT  AGAGGCTGGG
139141  AATGGTAGGG  GAAAGAGATG  ATAAAGAGAG  ATTCATTAAA  ATAAGTTACA  GCTAGATAAG
```

Figure 2 (Page 43 of 74)

```
139201 AGCAATCAGT TCTAGTGTTC TATTTGTACT ACAGAATGGC AATAGTTAAC AGTAATAAAT
139261 AATTTCAAAG AGCTAGAAAA GAGGACATTG AATGTTTCCA ACACAAAGAA ATGAGAAATG
139321 CTTGAAATAA TGGATATTCT AATTAATTAC CCTGATCTGA TCACTATACA CAGTATGTAT
139381 AAAAATAACA CTATGGGCTG GGCGCAGTGG CTCACACCTG TAATCCCAGC ACTTTGGGAG
139441 GCCAAGGTAA GCAGATCACT TGAGGTCAGG AGTTAGAGAC CAGTCTGGCC AACATAGTGA
139501 AACTCCATCC CTACTAAAAA TACAAAAATC AGCCAGGCGT GGTGGCATGT GCCTGTAATC
139561 CCAGCTACTC AGGAGGCTGA GGCAAGAGAA TTGCTTGAAC CCAGGAGGCG GAGGTTGCAG
139621 TGAGCCGAAA TCGCGCCACT GCACTCCAGC CTGGGTAACA GAGCAAGGCT CTGTTTCAAA
139681 AATAAATAAA TACATAAATA AATATTTTTT AAAAAAAGAA CATCACTATG CACCCCATAT
139741 ATACATATAA TTATTATGTC AATTTGAAAC ATAATTTTGA AAAATGAAAA AATGAAACAC
139801 AAATATGAAT CAATCCTCTC CAAGTTGATA TACTTAAAAG GAAAAAAGTC CGAGGGCTTA
139861 AACTATTCAA TCAAAATTTT ATTAAAATGC TATAGTAATC TGGAAAGTAT TTCAGAATGA
139921 ATTGGTATAA GGTTAGACAC AAAGATCAGT GAAACAAAAT AGAGAACCCA GAAATAGATT
139981 CACACATCTA TGGACAACTG GTTTTGACAA AGGTGTCAAG GCTATTTAAT AAGTAAAAAA
140041 ATCGTCTTTT CAGTAAATGT TTCTTGAACA AGTAGACATC CGGTGTGGGG GAGAGGAGCA
140101 GGAGCCTTAC CTCAAACTTT ATGCAAAAAT TAACTCAAAA TAGACCATAG ACTTAAATGT
140161 AAAAGCTAAA ATTATAAAAC TTCTTTAAAA AATAGGAGAA AATCATCAAC ACCCTAGGAT
140221 TAGCAAAGAT TTCTTTAAAA CAAAACAACA GGTTTATAGT TTATAAAACA TAAATAACAA
140281 AATGATAAAT TTCATCAAAA GTGAAAATTT GCTTTTCAAA AAACATTATA AAATGAAAAG
140341 CAGGAGGCTG AGGCATGAGA ATCACTGGAA CCCGGGAGCT ACAGGTTGCA GTGAGCCAAG
140401 ATGGTGCCAC TGCACTCCAG CCTGGGTGAC AAAGTGAGAC TCTTCCTAAA AATAAATAA
140461 ATAAATAAAT AAATAGAAAA GAAAAAGAAA AATCACAGGC TGAGAGAAAA TATTTATAAT
140521 ACATGTATCT GACAAAGGAC TCGCACCTGG AAAATATAAG GAACCTTATA ACTTAGTAAG
140581 ATGACAAGCC AAAACAAAGA GTAAAAGTTT TCAACAGACA TTTCACAAAA GAAAACATAC
140641 AAATGGCCAG TATGCACATG AAAAGATTTT AAACATCATT AGTTACTAGG GAAATGCAAG
140701 TCAAAACCAC AATGAGATAC TTCACATTCA ACAGAATAGC TAATGTTAAA AGGACTGACA
140761 ATCCCCAGGG TGAGCAAGGG TGTGGAGGAA ACTACTCTCA TATATTGTGA ATGTAAGAGG
140821 ACAATGTTAC AACTACTTTG AAAAAGTTT GGCTGTTTCT AACATAAAAT TAAACACTTA
140881 TACAGCCCAG CAATATTTCT GGGTCATTTC TCCCAGATAA ATGAACACAT GTCCATACTA
140941 TGACATGTAC AAATGTTCAT ACTGGCTTTG TTTCACAATG CTATAAACTG GAAACAACCC
141001 ACGTGTCCAT CAACAGGTGA ATGGGTAAAT AAATTGTAAT ATATCGGCCA GACGCAGTGG
141061 TTCATGCCTG TAATCCCAAA ACTTTGGGAG GCCAAGATGT ACGGATCACC TGAGATCAGG
141121 AGTTTGAGAC CAGCCCATCC AACATGGTGA AACCCCATCT CTACTAAAAA ATTAGCTGGG
141181 CATGGTCACG GGCGCCTGTA ATCCCAGCTA CTCGGAAGGC TGAGGCAAGA GAATCACTTG
141241 AACCGAAGAG GCGGAGGTTG CAGTGAGCCA AGACCATGCC ATTGCACTTC AGCCTGGGCA
141301 ACAAGATGGA AACTCCATCT CAAAAAAAAA AAAAAATTGC AATATATCTA TATCTTGGAA
141361 TATTATAAAG CAATAAAAGG GAATAAACTA CTGATATATA CACAAAATGG ATGAATCTCA
141421 AAAATGTGAA GGAAATAAAA AATACATAT GATATAAATT CCATTCATAT GAAATTTTAG
141481 GAATGGGAAA ACTAAGCTGT AATTATGGAA AGTACATCAG TGGCTGCCTG GGGCCAAGAG
141541 GATGGAAGAG GCGGCACAGG TGATACTACA AATGAAACT ATCTAGGTTG ACGGAAGTGT
141601 TCTGTAACTT GATTACAGTA GTAACTGTTT GGGTATATAA AACGCATCAA ATTGTATAAT
141661 TAATACAGGT GTATTTACT GTGTATAAAT TATTCCTCAA TAAAGTTGAT TTTTCATTAA
141721 ATATATTATT TGCTAAAATG AGGAGAGACA ACTATTATCT TAAAATAGTT AAGCACAATA
141781 AAAATACTAC AATCAACTCA TTATATATGG AAATTAAAGG AGAAAAATAG TGGTATGATT
141841 AATTAAAATA AAAAGAAAAC CTTCTAAATT TTATCTTAGC TCATAGTTGT AAAAGCTGCC
141901 ATCCCTAACC AAGGCCACCC TTGACCCTTT CTCATGTTCC ATCTTTCTGT TTGTTTCATA
141961 GTTTATGTCT CACCAAAATC TATCAGATAA ACGTATTCAT ATGAAGATTT AAATATATTA
142021 CATGTTAAGC CTTAGCGAAT ACTTCAATAT CTAAAGAAGG TACAAACAAA ACAAAAATCA
142081 ACACTTAGTT ATAAGAGATT ACATACTCTC CAGGGAAGAC CTGAAGACTA GCCCCTTTCT
142141 GGATCCCACT AGCCCCTCAT CCCACTCCAA GCCCTCCCCT CCAATCCCAT ATGCACTGGG
142201 CATTCATACA AATAAGACCA TCAGCTCTGG ATATCTGTAC TGATTGATGC TCCTGCTAAC
142261 TACCTGAATG ATTGCGATGT AAGGACAGCA CTGCCTGAAT CCTATTTATC TCTCGCTATG
142321 CCATAGCGGC CTTCCATGCT GATGGCGTGT TTGAGGATCC AGAGGGTCT TTGGTTGGCA
142381 GGATTGTTTT ATTTCCCCAA GAGGAGAGCC TTGATGCAAA AATAGGTGAA GAAATCAGTA
```

Figure 2 (Page 44 of 74)

```
142441 CAACAAAACA GAAAGCCTAG AAACTACTAT GAACACAATA GAGCAGAAGT AGCCTTAAGA
142501 GTTGGTGGAG AAAGGATGGT CTATTCAATT ACCTGAGCTG AGAAACTGGC TTTCATATGG
142561 AATAAAAATA AAATTATAGC TATACCCCAT ATCATACACA AAAGTTTCTA CATCTAACAA
142621 AGACACAGAT AGAAAATGTT TTAAAATTTT AGAAGAAAAT AGTGCAGAAT TTTAGTGCAG
142681 AATTTCTTAG ACTAGATGCA AAAACAAAAA TGATTAAAGT GGCCAGGCAC GGTGGCTTAT
142741 GCCTGTAATC TCAGCACTCT GGGAGGCCGA GGTAGGTGGA TTAGTGGAGG TCATGATTTC
142801 GAGACCAGCC TGGACAACAT AGTGAAACCC CATCTCTACT AAAATACAAA AATTGGTAGG
142861 GTGTGGTGGC TCACGCTTTT AATCCCAGCT ACTTGGGAGT CTGAGGCAGG AGAATCACTT
142921 GAACCTGGGA GGCAGAGGTT GCAGTGAGGG GAGATGGCGC CACTGCACTC CAGCCTGAGC
142981 AACACAGCGA GACTCTGTCT CAAAAAAATC TAAAAATAAA AAGATTATTT TTAAAAGACT
143041 ATTTTAAACA AAAAAAATCG TTTAAATGAT ATGATACACT ACATCTAATA TTTGGAAAAG
143101 TACTTCTTAA TACTTTTAAT AAAAAGAGGC GCTGAGAGCA TACAACCTAT CCTCAGAAGA
143161 GTGTTTGACC TCTAGGAGGG ACGCAAGCGC GTTCTTCCTT CATTTTAACT GGTCATTTTC
143221 ATTTATTTCA GGAACATCTG AAGTAAACAC AGTCACACGT TAACCTTTAA AAATCTAGGA
143281 GGTGCGTACG CATAGTTCCA TTACTTCAAT TTTTGTACTT TTGCATTTTA AAATATCACA
143341 GGGAAGCTCG GTACAGCTTC AAGGCTAGGA GGGGTGGCTC TCTCTTAAGC CCTGTCCCCG
143401 CCAGCCCCAG ACCTCTCGTC CCGCCCCCAT TGCCCAGTCC CCACCCTCAC TTCCCCATTT
143461 CCCCACTCCC GCGGTCTCTT AACGCACCTG TTTTTCGTCC AGTGGACTCA GACCTGTACT
143521 CTTCCACCAG GATCGGCTCC TTTCCCGGAG CTCTCGCTCT TAGAGGAAAT TGAGAGAAGC
143581 ATCAGCGGAG ACCCATCTGT GGCTCTCCAG AGGGCGCGGC ATTCAGACCC CAGATCCAGC
143641 TGTGAGAACG GACCCCAGGC TCACACCAGG CCTGCGGGAG GCGGCCCACC AGAGGCGCTA
143701 GAAAACAAGC CTCGCGGGGA GGCGCGCAGG GCGACTGCAA GCTGTAGGGG GCGCTGGCGC
143761 CCTCACAGGC CAGGGGCAGG GCCGGCGCTG CGGGCGGGGC TCCTGCGGCG TGAGGGCGG
143821 CCCCAGGCCA GCAGCTGCGC CCTGGCTGGG AGCCGGGGAG CATTTGCTGC TCTGCTGGAC
143881 CCTGAGTCTG GCGGCGGGCG GCCTCCTCTC CGCTCCCCGC CCGCCATCCC CCAACTCCCG
143941 ATCTCTCTGC TGCGTCTGGC CTCAGGCTGA GACCCCAACG AATCATTCCC CGCATGGGAA
144001 CATTTTATGA TATAACTGAA TTCAGTTTTA TGTATAACTG AATTACGGAT ATGAGAATCT
144061 CAAATGAGGA CGAATGGTTT TTACGCACAA AACATGAGAC ACAAATCTGT AAGAAATATA
144121 AAGTCGTGAC CACGTCCTTT CAGAACTTTA ACCTGTTTGC TGAAGTACGT CAGTAACAAT
144181 GGCAGGGAAA GGGTATCTTA AATTTCACCA CAGCCTCAAA GAGGCCATTT CGTGGATCCG
144241 CTGAGGCTTG GAGTCGGCCT TCTGACCACG AGTCCTGCGG CTATGAAAGA GGAAGCCGCG
144301 GTTCAGGGCG TCCTCGCGAG TCGCGCAGCC CGCCCTGCTC CAGCTGGGGA CACAGGTGGT
144361 CACGGCGCTT TCCAGCTGCA GATCCAGGCG GCAGCCCAAG ATTTGGTCCA GCCGCCAAGG
144421 GGTGGCTCGA GTGACTGACG GGCCTTGAAC GCTCCCAGGA CCCACATCTG GAGAGGGAGG
144481 TGGGGGTGGG GTGCTGAAGT CATTCTTGGG GCCCCTGGGG GCGGGCATGG ACCTGGGTAA
144541 GGCCAGAGAA ATTGACACCT CGTGACATCC CTGGAAGAGA AGTACGTTCA GTGTCACTCC
144601 AGAGCTGAAA GATACCGCCT TCTGGCTGGT CCCTCCTCAC CTACATACTT TTCTAATTTG
144661 TCTGGAGCAG GCCGGCATC TGTATTATCT GGTTATTTAA ATATCTGGTT ATTTAAAAGC
144721 TCTCCATTAA ATTCACATAC ACGAAAATAA AAATTAAAAA AAATTTTAAA AAAAAGAAAC
144781 AAAAGCTCTC TAATGACCAA GTCCTACACG ATAGTGAATA AATTTTTTTG TGTGGTCCCT
144841 AAAATTGAGT TCATGCCTTT TCTGAAGTAA TAGACGCCCA GAGAAGGGAT CGACTTACCC
144901 ATCATGCCAC AGAGATTAAT TGGCCCCAGA ATTCTTTAGC AGACCGTGTA TATGAACGTC
144961 CTTTGCAATC ATATAAATTA ACTGGGAAAA CCTCATTTAG TATGTTACAT GCCTAGCGTT
145021 TTGTGCCTGA ACACCTTACA AGAACCAGGG ACTATTGCCC CAATATTATA TTTCAGGAAA
145081 GGAAGGCCCA GACAAATGGT GTCACTGGTC CACTTTCACC CAGTTGGTAA ATGAAACCAG
145141 AAATTATAGC TGTACCACAG AAAGGTGAAA ACGTTTCTTT TATAATTTCA CATACAATCT
145201 TTAATGGACC CAGTGTCCAA CACATTAAAG CAAGTGCTCA GGAGTGACAT CAAGATGTAA
145261 AAAATAGTCC TGTCCTCAGG GAGTTTAGGT CTTGGAGAAA AGAGACCCAA GGAGACACAA
145321 GACAAAGGGG AAAGAGAAGG AGCGCTGAAG ACTGAGGACC CTGCCTGTGG ACTGAAGTGA
145381 GGATGGGGAC ACCCGATGCC CGGAATATGA CAGTTTGGAG GGGCCTGAAG GACTCTTCTA
145441 TTCTCTATCA GAAAACAGA ATTACTCTCC TAACCAGAAA AGGTATTTCA ATTTATATTT
145501 TCCATCACAG CACTTTTCTG GTGATAATTT AATGTGTTTT AAAAAATGTA TCACAGTGAT
145561 GGCCTGGTGT GAAATAAATA ATAAAATTTT AAGAATTAAA AAATATAAAA ATCTTTTATA
145621 TAGACATTAG GAGTTACAAG GATAACTGTG AATTATAATT AGTAATTAAA TTGAAATACT
```

```
145681 GATTATTTTC ATTTTTATTT AATTATTTAA TAAAACCTAT TTAACATTTA ATATTTATCA
145741 GTAATTAAAT CTAATTGTTA ATATTTATTA TTATAAATTA TTTTAGAATT AAAAATAAGT
145801 GTAGAAGCGA GGCATGGTGG CTCAAGCCTG TAATCCCAAC ACTTTGGGAG GCTAAGGTGG
145861 GAGGATTGCT TGAGCCCAGT AGTTCAAGAC CAGCCTGGGC AACATGGAGA AACCCTGTCT
145921 CAATACAAAA AAATGAGCCA TGTGTGGTGG TGCGTGCCTG TATTCCCAGC CATTCTGGAG
145981 GCTGAGGTGG GAGGATGACT TGAGCCTAGG CAGTCAAGGC TGCAGTGAGC CCTGATCTTG
146041 CCACTGCACT CCAGTCTGGG CAACAGAGCA AGACCCTGTG TCAATATACA TATGGACAAA
146101 CTTAAAATTT AAAATGAAAG CATACTACTG ATACAGAATT GAGTAGAGAT GCAAAGCTAG
146161 TCCTATAACC AGAACAATAA AGATAAAAAG GAGAGTGGAA GAAGGTATGT CATGAATTTC
146221 ATGATAAATG GCAATTGCAA ATATCCTGTA GCAGAACAAA ACAACAAAAT TGTAGATAAA
146281 ACATATCCAA CCCTTTGGAA GGCCAAGGAG GGAGGATTGT TTGAGCCCAG AAGTTGGAGA
146341 CCAGCCTGGG CAACATAGTG AGACCCTGTA TCTAAAAAGG AAGAAAGAAA AAAAAAAAAA
146401 AGGATGATAA AGTAGACAAT ATTGAAAGCC ATTTTCTGCA AATACATAGT GAATTTGATC
146461 AGTAATTTTC TTCCAACAGT GCAAAAATGA ATAGATATTA GTTGCCTGAA ATAAAAATCA
146521 AATATCCAAC AAAAAATATT GACTATCTAA TAGTATCTAA GCTAGTAAAT TTGGCCAGTT
146581 ATAAAATGTC TTAAATTTTT ATTTAAAAAA AGAAAACCAT ATTTATAAGA AGAGGTGATA
146641 AAGAGAAATT ATTTCAGTTA TGAAGATTTT GTTAGAAAAC TATGAGAAAA AAACTATTTT
146701 TTGTTTTCAA AAAGTGAAAG ATTAAGTTAC CAAACAGTTG CTAAAGAATA CCAGATGGCT
146761 GAGCGTGGTG ACTTATGCCT GTAATCCCAG TACTTTGGAA GGCCAAGGCA GGAGGATCAT
146821 TTTAGGCCTG GAGTTCGAGA CCAGCCTGGG CACTGTAGCA AGACCCGTCT CTATTAAAAA
146881 AAAAAAAAAA AAAAAAAAAG AATACCAGAC CTTGCTAACA ATAGCAAAGA TCAATTAATT
146941 CAAAATTTGA AAAACTGTAA TTTATTTAGC TTTAGAGTAC TCTCGTGATA TGAGATTGCC
147001 AAATTAATAC TTTGGGTGCA TTTCTTTTCT CAAAGGACTT GCAAATTTAC AAAGAAGTGT
147061 TGAAGAAAAG CCACACATTG GCAGGTAATG TTTGCAAAAG ACAGATCTGA TGAAGAACAA
147121 TATTTTTAGA ATATACAAAG AATACTTAAA ACTCAACAGT AAGAAAATAA CCTGATTTAA
147181 AGCAGGCCAA TGACCTGAAC ATCTGTTCAC CAAAGAAGAT ACACAGATGC AAGTATGCAT
147241 ATGAAAAGAT GCTTGACATC ATGTCATTAG GGAACTGCAA ATTAAAACAA GTAGATACCA
147301 CTGCATACCT AGTAGAATGA CCAAAATTTA GAACACTGTC AGCACCAAAG GTTGCAAAGA
147361 TATGTAGCAA TAGTAACTTG TTCATTACTG GTGAGAATGC AAAATGTGCA ATCACTTTGG
147421 AAGACAGTTT GGTGGTTTCT TACAAAAGTA ACCATACTTT TACCATAAGA TTCACCAATC
147481 ACACTCCTTA GTATTTATCC AAAGGAATTG AAAACTTATC TCCACACAAA AACCTGCACA
147541 TAGATGTTTA TAGCAGCTTT ATTCATAATT TATCCAAAAC TTGGAAACAA GATGTCTTTC
147601 AGTAGGTAAG TGGATAACTG TGGTACTTCT GAATAATGGA ATGTTATTTA GAGTTAAAAA
147661 GAAATGCATT CACTTTGGGA GGCCGAAGTG GGTGGATTGC TTGAGGCCAG GAGTTTGAGA
147721 CCAGCCTGGT CAACATGGGA AAACCCCAAT TAGCCGGGCA TAGTGGCGTG AGCCTGTAAT
147781 CCCAGCTACT CGGGAGGCTG AGATATGAGA ATCGTTTGAA CCTGGGAGAT GGAGGTTGCA
147841 GTGAGCCAGT GCCACTGCAC TTCAGCCTGG GCAACAGAGC AAGACTCCTC TGTCTCAAAA
147901 AAAAAAAAAA AAAAAAAAAA AAAAAAAGAA AGAAAAGAAA AAGAAAAAG AAAAAGAAAA
147961 GAAACGATCA AGCCATGAAA ACACATGAAG GAAACTTAAA TGTATGTTAC TAAAAAGCCA
148021 ACCTGAAAAG ACTGCATACT ATATGACTCC AACTGATGCA GGGCAAGCAA GCCAAAAATT
148081 AGGGCTTAGC CCGGGAAGAA TTCAAGGGTG AAGTGGTGGT GTTAGCAACT TTTACTGAAG
148141 CAGCAGTGTA CAACAGCAGA ACAGGTACTG CTCCTTGCTG AGCAGGGCTA ACCCATAAGT
148201 AATGTGCCCA GAGTAGCAGC TCAGGGGCAG TTCTGCAGTA ATATACCTGC TTTTAGTTAA
148261 GTGCATGTTA AGGGGATTA TGCAGAAATT TCTAGAAAAA GAGTGGTAAC TTCGGAGTAG
148321 GTACAGAGGA AAGAAGTCGA TAATGTCCTG TTGTTGCCAT GGCAACGAAA AACTGACATG
148381 GCGCTGGTGG GCGTGTCTTA TGGAGAGGTG CTTTAACCTC GTCCCTGTTT CGGCTAGTCT
148441 TCAATCTGGT CCGGAGTAAA GTCCTGCCT CCGGAGTTCA CTCCTGCTTC CTGCTTCACA
148501 ACTGTATGAC ACTCTAGAAA AGACAGTAAC TATGGACACA GTCAAAGAT TAGTTGATAG
148561 AAATTGGGTG ACAGGAAGTG TTGAAAGGC AGAACACAGG ATTTTTAGGG CAGTGAAACT
148621 TCTGTGATAC TATAATGGTG AATACATGAC ATTATACATT TGTCAAAACC CATAGAAAGC
148681 ACAACACCAA GAATAAACCC TAATGTAAAT TACAGACTTT CGTTGATAAT GACGTGTCAA
148741 TGTAAGTTCA ATTGTAATAA ATGTACTACT GTGGTGCTGG ATGTCTATGG TGGGGGGACA
148801 TTTTTGCTTC AATAGTTACA GTTGAAGTAA ATGTTTGTGT TTCCCACAAT GCATATGTAG
148861 AAACTCTCAC ATTCAATGTG ATGGTCTTTG GAGGTGGGCT CTTTGGGTGA TAGTTAGGTT
```

Figure 2 (Page 46 of 74)

```
148921  TAGTTGAGAT  CCTAGCAGAT  CGAGTCTTCA  TGATGGGCAT  GATGGGACTG  GTCCCTTATA
148981  AGAAAAGACC  AGAAAGCTAG  CTCTCTCTTT  GCCATGTGAA  GACATAGCAG  GAAGGTAGCC
149041  ATCTGCAAGC  TAGGAAAGGG  CCTTCACAAA  GAATCAACTC  AGACCTCAGA  ACAGTGAGAG
149101  ATAAATTGTC  GTTGTTTAAG  TCACTCAGGC  TGTGGTATTT  TGTTTCAGCA  GCCCAACCTA
149161  AGACTGTTAA  TTGGATTAGA  AATTTCCTTT  TGGGGATGGT  GTGTGGCGGG  GGGTGCGGGG
149221  AGTACCTTTG  TTAAGCTTTT  ATATCAATGA  GTTTGTAGGC  TTTTCTTTTT  TGGTCATTGA
149281  CTAGGACAGT  TTAAATAGTA  TGAGTGTGAA  GGAGATTGTT  GGTCATCTAT  TCGATGTCCC
149341  TTCTCTGTTT  TTTAATATGA  GAACTCCTGA  TTTTCAGCCA  ACTACCCTGG  AAAAAAAGCT
149401  AATCTTTCTG  ACTTCTTAAG  TGTGGCCATG  TACTAAATTC  TGGCTAATGC  AAGGCAAGCC
149461  AAAGGTTTTA  TGATAGGTTT  TAGGACACTA  GAGTAAAAGA  GAGCTGTTGC  ACACATGCTC
149521  TTCACCCTAC  TTTTGTGTCC  TTTTTTCCAT  CCTACAACTT  GGGTTGTGAG  TATGATGGCT
149581  GGAACTTTAG  TGGCTCTCTT  GGATCCCAGG  GGTAATTGAG  GGGTGGCTGG  AAGGAATCTG
149641  TGATTTTCTG  GAGTTTCCAT  ACACAAACAA  GACCTGGATT  TTCTGGGCTT  CCCAGACTTC
149701  CACATCTAGA  CTTGCTTTAA  ATGGGAGAGA  AATAAACTTG  TTTCAGCCAC  TGTCATTTTG
149761  GGCTATTTTA  TAGAACTTAA  TCTAATCTTC  AAGGGTACAT  GAATTGCTTT  TCCTTAAAAA
149821  AAAAATCAGC  CATAAAATCA  TCTTCTTTTT  TCTTTTGTTC  CCCACATTAT  TTAGTTGGAG
149881  CTCTGTAACT  TTTTTTTTTT  TTTTTTTTGA  GACAAGGTCT  TGCTCTGTCA  CTTAGGCTGG
149941  AATTCAGTGG  CATGACCATG  GCTCACTGCA  GCCTTGCCCT  CCTAGGCTCA  AGCAATCCTC
150001  GTCTCAGCCT  CCTGAGTAGC  TGAAACTAAG  GCACATGCCA  CCATGCCCAG  CTAATTTCTT
150061  TTCTTTTAGA  GATGGGAGCC  TTGCCCAGGC  TAGTCTCAAA  CTCCTAGCCT  CAAGTGATCC
150121  TCCCATCTCA  GCCTCCCAAA  GTGACAGGAT  TACAGGTGTG  AGCCACCATG  CCTGGCTGCT
150181  CTGTAAGTGT  CTGAATTTCA  TTTTGTATTT  ATCAGTCTGT  TTAGATTTTC  TTTCCCTTCT
150241  TGGGTCAGTT  AGGCCATTGG  TTTCTTTTTA  AAGGTTTTCA  AATTTATTTG  CATCTAATTC
150301  TTCAAATTAC  TCTCAAAATT  ATTCCAGTAT  ATATTCTTTT  GTTCCTATTT  TCTTCTGTAT
150361  TCTTTATTAA  AATAGCTAAT  GATTTATCTA  GCAGGACTTA  TATTCTTTCC  ATAACTTTCC
150421  TGCACCCCAA  TTAATCTCCA  ATTTTATATT  TCTTCTGGCC  TTCCTTATAG  TTTCCACAGG
150481  TTTATTTTAT  TCATTTTTTA  AAACTTTTAT  TTAATTGTTT  ATTTTATTAT  CATTCTTTCT
150541  TATTCAGCAA  TCTAAGTGCT  TAGGGATATA  GAATTTCCTC  TAAGCAGCAT  ATGCTAGGCT
150601  TTAACAATGT  TAGGGAGGCC  TCCCCTTTCT  GGGGAAGACC  ACACTTACAT  TAACACAGGA
150661  CTGTGGGATG  CCAAGAGGTA  GAGAAGAGCT  TATGAATATC  CAGATTACAT  CTTCACTGAT
150721  CCTGCACAAA  GGTGGGGTTC  CTCGGTTACC  CACTGGGTCC  TATTACCCAA  GTCTGGGTCA
150781  GCATACCGAG  ACTACGGGTA  TATAGAACAA  GTGCAACTGG  CGATAATCCT  TCTGTTGGGG
150841  AGAAAAATCT  TTTTTTTCTA  TTCATCTTAG  GTTCTCCATC  TGTGGCCCTA  TCAAGTAGAC
150901  TAACAAAAGA  CAGATTGACA  AGACAGAAAC  AAAGCATGTG  CATTGTACAA  ACACAGGGGA
150961  GTACTGAGAT  GAATACTCAA  AAGAGGATTT  AGAACTTGGG  CTTATATAGC  ATTTTAAGAA
151021  AAGAATACAT  TTTTTAAGTG  ACAAGGAAGA  CGAAAAGGAC  TTTGAGTTTC  TAGTGCAGTA
151081  AATTGTGGGA  AGGCAACTTT  TTCTTTCCCT  TTTTTTTTTT  TTTTTTTTTA  AAAAAAAGAC
151141  TTCTCTGGTG  CTATGTCCAG  GCTGATAAGA  GTCTAAAGTC  TCTGGTGACT  AACTTTTGTT
151201  CTTCCCCGAG  TAAGAAGACA  CCTTCACAAT  TTCATATCCT  GCTTTTAGGC  AAACAGGGAG
151261  AGGGCAGAGG  TGTTTGTTTG  TTTTTAATCT  ATTTTTTTTC  TCAATTGTCT  TCAACTCAAA
151321  ATACTTCTTA  TGCCAAAGAT  GGCATATTCT  GCTACCCTTC  ACTTACTACT  TACAACCCAG
151381  CCTCTATCAT  CATAATTAGA  ACTTCTGACC  CTGGGGAACA  TGGGCAATAG  TTTGAACTCT
151441  TTTATATCTC  CCTTAGGCAG  AGATGGAGGC  CCAGCCATGC  CTCTGACATC  TAGACACAAC
151501  TGTTGCTTCA  TTTCTCCTAT  TCTCAGAGGT  GATGTTGTAG  GACTTCAACA  AATATCAGTA
151561  AACATTAATT  TTTTTTTTCC  TTGAGGCACA  GCATGATCTT  GGCTTACTGC  AGCTGCTGCA
151621  GGCTCAAGCA  ATTCTCCTGC  CTTGGCCTCA  CGAGTAGCTG  GGTTACAGGC  CCTACCACC
151681  ATGCCCGGCT  AATTTTTGTA  TTTTTAGTAG  AGACAGGGTT  TCACCATGTT  GGCCAGGCTG
151741  GTGTTGAACT  CCTGACCTCA  AGTGATCCAC  CTGCCTCAGC  CTCACATAGT  TCTGGGATTA
151801  CAGGCGTGAG  CCACCATGCC  TGGCCATCAA  TTTTTATGTC  AACTCTAAAT  TATAACATTT
151861  AGCAATTTTG  TGACTTTTTA  TGGTCATCAT  TAATGTTGTT  TATGTTTTAG  TTGTAGTCCT
151921  GTCATTACTC  ACTCGGGTAT  GGTAATTTGG  TCTTTTTCAA  AATGAAGTTA  AGGTCTATTT
151981  GCTCTTCTCT  GAATCATAAT  AAGAACTGCC  AACAGCCATT  TCAGCAATAA  CTATTTACTG
152041  AGATTTTAAA  ATATTTCAAG  GTAATTGGTC  CTAGCAGACT  GGAAAATACC  AAATTCTTTT
152101  CCAGAACTGA  ATCCCCCATC  AAAGTTCAAT  TTTACTCATA  ATTCCCTTTT  CATTTGAAGC
```

Figure 2 (Page 47 of 74)

```
152161 ATCTCATTGT AAGCCAGTCT TAACCCTTCT CTCACACTTT GCTTGGCTGT TTCTCAGGTA
152221 GAACTCAGTA AGTCTGGTAG CCTCCAGGAC TGCCGCTTAG ATTATTAAAC AACATGTCAG
152281 TGGTTGGAAG AGTCAATGTT ATTTTGATTT TTCTGTTTTG TTTTGTTTTA AATGCAGTTG
152341 GCGGATAATT GCAGCTTTCT TTCATTCCCT ACATGAGTTC AAATGGCAGC AAACAAACTA
152401 GGAGAACGCA GACCTTCTGA CTTGTGGGTA CCCCTACTCA TCACCTGAAG ACCCTTGGAA
152461 ATCAAAGCCC TGACCCATTA AAGACGGATG GAGACAGCAA CATACGATCA TCACTATTAT
152521 CTTGCTTTGC CCCAGTCCAG GTTAACCATC TGTGGTATTT TTAGTTGCTA AGTCCATATA
152581 TTCAACATAA ATCAATTATA TATCCACTAA AATCTCAGCA CTAGTCTAAC TACTAAGGAA
152641 ATGACAGCGA AGAAAACAGA CCAAACGTCT GCCCTTATGG GATTTATATT ATTTTCTCTG
152701 TGCTGGTTAA ACCAAGGAGC TTCTGCTCTT TTCCTTAGTC ACCTGGGGGA GGCAGAAACA
152761 AAGGAGAATA TTGATAAACC TGGAAATAGG GCCGGAGAGT ATCAGAGAAG GAAGCCTTCG
152821 GGAAAGTAAA GATGTGGCAG CCAGTATTCC CGTTATAAAA GGATACAACT CCGGCCTCAT
152881 AGTCCAGAAA AATTCCCACA AGCAGGGGCT GCTCATGCAG ATGAAGGGAA GTTGGGGGAG
152941 AAGTAAGTGC TACATAGCCT TTCTTTTTGC ACAGCCTGAG GGTCCAGAAT CCAGACTGAG
153001 GCTCTTGCTT CATGCCAGTG CCCCTCTGCA CATTTTCCAT ACAAACTCCT AAATCCCATC
153061 CGGTTCCTTC GCCAACATCC ACTTCAAAGT AACGTCTTCC TGAGGTGAAG CCTTCACAAC
153121 CCAAGACACA GGGGAAGGCA GTAAATCTCC TGGAAGATGT GTCCTGATTC TCCTGGGTGT
153181 ATCCACGAGT CACTTGTCTC CGATCCTCAG AGAGAATTAG TTCGTGATGA GCTGTATCTG
153241 GATCCAGAGT CACACTAACT GCAAAACAAA ACAAAACAAA CAAAATAAT TTTGTTGCTG
153301 TGAAGAACAC AGGTTATTTT ATTTTATTTT ATTTTGAGAT GGAGTGTTGC TGTCACCCAG
153361 GCTGGAGTGC ACTGGCACTA TCTCAACTCA CTGCAACCTC CACCTCCTGG ATTCAGGCAA
153421 TTCTCCTGCC TCAGCCTCCG GAGTAACTGC GACTACAGGT GCGCACCACC ACAAGTGGCT
153481 AATTTTTTTA AATTTTCTGT AGAGATGGGG TTTCGCCATG TTGGCCAGGC TGGTCTCAAA
153541 CTCCTGACCT GAAGTGTTCC ACCCACCTCG GCCTCCCAAA GTGCTGGATT ACACAGGTGT
153601 GAGCCACCAT GCCCAGCCAC AAGTTATTTT CAATAAAACC AGCCTGTGTT CAAACCCAAC
153661 TATTGTTTCT TATAAACTGG GTGAGCTTAG GCAAATCATT TAACTTTCTG AGCCTCAGTT
153721 TGTTAACTAT AAAGTGGAAA TTACCGTATT TGTTGCAGAG AATGGTGGGT AGGATTGAAT
153781 AAGCTTATGT TTGCTTAATG CTTGGTAAAA TTCCTGGTAC ATGGTAACCA CCTAATAAGT
153841 GGTAGTTGTT GGGGTGATCA GGCCCAACAC CAGGCCGTGG GGGCTACAAA GTCCGGCGGG
153901 GTCAAGGAA TGAGAAAAGA CAAGTTAAGA GTGCATAAAG TGGGTCCAGG GTGCCAGCAC
153961 TAGATTGGAG GCTGCAAAGG CCCTAAGCTC TGGGAGCCCA CACTATTTAT TGGTGATCAA
154021 ACAAAGAAGC AGGTGGTGAG GACGTGAGGG TAAACAGGTG AGGGCATGAG GACATGGGGG
154081 TAGAAAGGTA GTGGTGCATT AAGCGTAGCT GTGACAGTTT AGCATTTTCT TTGACACATG
154141 TAGAATATAC TCTGCTGCTT GAGATAGTAG AGGACACGTT TATGAGTGAA AAGCAAGGAA
154201 CCAACAAGTC TGTGCACTTT CCAGAGGCTA TGAGGGGTTT TATGCCCTGA GCCCTGGGTT
154261 CCATCCAAGC CACAAGGGGT TTTATGCCCT AGGCTTAGAT TTGTGGTGCG GCAGGGCAGC
154321 CTTCCACCAT TTGGCACAGA GCTTGGTGTT CCAAAGGCCA CGAGGGGTTT TGGACCCTGG
154381 ACCCCGGACA TCTTCCAAGA CTCTTTTACA TTATGACAGA CAAGCCAGTC CTGCTTCAGC
154441 TCTTCTAACA ACATGTAGTA ATAATGATAT CATCAACATC ATCTTCGTCT TAATTATTCA
154501 AGGATGCCAA GGTACAGAAC TAACCTGTTA ATATGGTTAC CATCCTGTCC AAAGTTCTTC
154561 TCCCATGCAG GACTTCCAGG AATCATGAGA CAGTTGAGCA GAAAGATACC TTTTCCCTTC
154621 TCTACTGAAT AACCACCAAC ATTGAGAATC AGAGAGGGAA AATGACTCAG CTAATGTCTT
154681 AGCTTGTTAT TGGAAGACCC AGGTCTCATG ACACATGCCT AGTCCCATGA CTTTTAATTG
154741 TAAGCTCTTC TCTTTCCCCT CAGATAATGT TCCATAAGCA TTAGTATGAG ATAATAATAC
154801 ACTGAGGACC AATATACATG AAAAATATCA GACTAGAATC AAACAAGACA GAAAAAAGAT
154861 CTGATAACCT AAAGTGAGAT ACTGAACAGT ATGCAGTTTT AAAAATAAAA AATGGTAATA
154921 GGATGTTCTA ACAAGAGAGT TAAGAAACCA CTGTGCTACT GAGTTAAATG TTGATCAGTT
154981 GGTCTGTGAC AATTAAGGAA TTCAAGTATT CAGAAACACT TCCTGTGCTG GATGCTCTCT
155041 GTTTGTTCTT CCAAATAATC CCTCACTTTT CCCTGTCTTG CTCTGTGCCC AGGAAGGCTG
155101 ACATGGACAG ATTAACCAGG CTTTCCGCCC TCTGGCTTGG TTCAGCCAAT GGGAAGCACC
155161 AGAGGAGACC ATAGGGCACA AGAAGCAGC CTTGGGAGTA TTCAGTACCC CAGTCCCACG
155221 CTATGATTTG GAGGGTCTGC ATTCCTCTGC CTCTGGGCAC ACTCTAGTAT AGTTACAGCT
155281 CCCTACACCT GCCACTTGAG GCCCAGAGGA GGTGATGGCT CTCTAACTGT TCCTAGTTCT
155341 GGGTGCTTCC TGTTCCTTGT GGATTTCCCA ACTCCTCACC TTTGTAAATA CCCTCCTTTT
```

```
155401 TCAAACTCTA TTCAGTTAGC TTTTATCAGC CTGACTCACA GAAGTTTGGG GTTTCAATTC
155461 ATATTACCTG AATGACCCAG GAAAACCCAT GTTGAGAAAT TAAAATGTTT ACGGGGTGGT
155521 AATACCACTT AAGAGAAAAA ATATCAATTG GATTTTTAAA ATTCCACCTA TCTATTGGTG
155581 TGACACATCA ACAAAAACAT ATAGAAAGAT TGGAAGCTAA AAGATAGATA ATATAGTCAT
155641 ATACTGTTAT AGTATTATAT CAAAAGATAT TAAGTCAGAG CATTATTAAG AATGGAAGAA
155701 GGGCCAGGTG TGGTGGCTCA TGCCTGTAAT CCCAGCACTT TGGGAGGCCA AGGCAGGCGG
155761 ATCACTTGAA GCCAGGAGTT CAAGACCAGC CTGCCCAACA TGGCAAAACC CTGGCTCTAC
155821 CAAAAATACA ACAATTAGCT GGGCATTGTG GCACATGCCT GTAATCCCAG CTACTTGGGA
155881 GGCTGAAGCA CAAGAATCAC TTGAACCGGG GAGGCAGAGG TTGCAGTGAG CTGAGATTTC
155941 GCCACTACAC TACAGCCTGG GTGACAGAGA GAGATTCTGT CTCAAAAAAA AAAAAAAAGA
156001 AAGAATGAAA GGAGTCACCT AAAAAAGATA ACACAATTTT AAACATAAAT GTACTACATT
156061 ATTAGTGAAT TCATGTTTAG AATTGTGTTA ATATACAAAG CAAAAATTGT AGAATTATAG
156121 GAGAAATGGA CAAATCTACA ATCATCATGG GATGTTTTAA CATTCTTCTT TCCATAATTG
156181 ATAGATCAGG CAGACCAAAA GAAAGAAATA AGGGAAGATA CGGAAGGTCT GAACAATCTA
156241 AGAAGCGCAA TCTCATAGTC AATACATAAA GCTCAGCAAT TGTTTAATAA TAGTAAGCAG
156301 AGAATATGCA GTTTTCTCAG GTATAGATGG AACATGCACT AACTGAGTAA ATACTAGGCA
156361 GAAAACAGTC TGAACAAGTT TCAATAAATC TGTATTACAC AGATCATTTT CTCTAGCCTC
156421 AATATAAGAT TATAAACCAA TAATAAAAAG ATGACTAAAA AGATTCTAAA TATTAGGAAA
156481 TGTAAACTAC TAATAAGTCA TTAGAAGATG TATAGAATGG AACAATAATA AAATGTTATT
156541 TATAAAAATA TACAATGAAG CTAAAGCAGA ATTTTAAGGA AAATTTGTAG GCTTTAAATG
156601 CTTATCTTAG AAAAATTAAA AAGCTGAACA TTAATGAGCC AAGCATCTAA TTTAAATTTT
156661 AAAAAGAACA TAGAAAGCCA AATATAATTT TTTAAAAAGA AAAAATAGAT ATTAAACAAT
156721 ATAACAGTGA AGTTAAAGAA AACAAGAATG CAATAAAGAG GAAAAACAAA CAAAAAAAAA
156781 AGTAGCTTCT TTTAAAAGAA ATTTAATAAA ATAGACATAC CTCCAATGAG ATTTATCAAA
156841 GTAAGACAGA AGGCACAAAT GGAATGAATA CAGAAACTTT TTAAATATTA CAGAACTTTA
156901 TAATAAATCT TATGCTACTA ATAAAATTGA AAGTACTGAT AAAATTATTA CTTCCTAGAA
156961 AAAATATTTC TGAGTAAAAC TCACTCAAAA AACAAATAAA GCATGGGCAG ACCTAACATT
157021 AAAGAAATGA AATCACTACT TTAAATTTTA CCGACAGATA ATAAAACGTG CATCTTTATC
157081 AAGCAAAAAT GGAACTTGTC AGTTTTATAG GAAATTTAGA AGTCAAGGCA TGAGTAATGC
157141 CAATCTCATA CCAAATCCTA CAAAGAATAG AAAATTATGG CTCCCGCTTA TAGACATAGA
157201 TATAGAACTC CTGCACAAAA TAATATAAAT AACAAACCAA ATTTTATATT TGCAACTATA
157261 CATATTATAT GTGTATGTAT TATATATGTT AACATATACA TATATAATAT GTATAGCATA
157321 TGTTCTACAT ATTATATATG TATAGTGTAT GTATTTTACA ATATATAAAT GAAAACCCAA
157381 TCTTTAATAT ATTCATCTAG ATTGTCATAT ATGACATATA TAATACATTA CATCAAAAAT
157441 GTGTACAATA ATCAGGCCAG GCACAGTGAC TCATGCCTGT AATCCCAGCA CGTTGGGAGG
157501 CTGAGGCGGG TCAATCACTT GAGTCCAAGA GTTTGAGACC AGCCTGGTCA ATATGGCCAA
157561 ATTCCATCTC TACAAAAAAT ATGAAAATT ATCCAGGCAT TGTGGTGCAC ACCAATAGTC
157621 CCAGCTACTC GGGAAGCTGA GGTGAGAGGA TCACTTAAGC CTGGGAGGTG GAGATTGCAG
157681 TGAGTCGAGA TTGCGCCAGT GCACTCCAGC CTGGGTGGCA AAGGGAGACC CTGTCTCAAA
157741 AAAAAATTAA AAAATTAGCC AGGTATGGTG GCCTGTTCCT GTAGTCCCAG CAACTGGGGA
157801 GGCTGAGGTG AGAAGATCAC TTTAGCTCAG GTGGTGGAGC CATGATCGCA CCACTGTACC
157861 ACTCGGCTTG GGCAACAGAG TGAGAGCCTG TCTCGAAAAA ACAAATATAT ACACACAGTA
157921 ATCAATATAT ATATTATATG TACCAATCAA TGCTTCACTT TTATATATAA TATAGATTAC
157981 ATCTTATTAG ATATATAGTA TTCCTTCTCC ATAGATAGAT AGATACAGAT ATAGACATAG
158041 TATCCTCTAT CCATATTAGA GAGAGGATAC TATATATATC TATAGCATAT AGAGATGCTG
158101 TCTCAAAAAA ATTTAAACAT CAGCCAGATG TGGTGGCCCA TGCCTGTAGT CCCAGCTACT
158161 GGGGAGGCTG AAATGAGAGG ATTGCCATTG ATCCTCTCAT TGGTTGAGCC ATAATCGCAC
158221 TACTGCACCA CTCAGCCTGG GAGACAGAGG GAGACCTGAG GTGGAAGGAT ATAGATATAG
158281 ATATATAAAT AAATATGTAT AGAGAGAATA TAATATATGT GTGTATGTGT ATATATATAT
158341 ATTATGAAGA CACTGGGAGA GAATACTATA TATATATGTG TGTGTGTATA TATATATTAT
158401 GAAGACACTG GTGGGATGGT TTCATTACCA ATTGGACCAA GAGTCCAGGT ATGGAGCCAA
158461 CATGCAATGT TGTTGTTGAC TGAGCTGGCA GAGCACTGGT CATAGTTACG GGAAAAGAAG
158521 GTCTCCAATG AGACATACTT AACAAATATAT ATGAACTTGC CATATACGTG GAGAGTTCTG
158581 GTGTGTATAT AGCCTTCTCT CACCAACCTA GCAATTGTCT TCATCATCAT TATAATGCTA
```

Figure 2 (Page 49 of 74)

```
158641 TCAGAGCAAA GATGACAGCT AAATTTTTTT GTCCCTTTCT TCTTCTTTCT CTTCCTTCCC
158701 CTCCCCCACC TCTTTCTCTT CCTCCTCCTC CTTCATCTCT CTTCTTTTTT TTTTTGAGAT
158761 GGAGTCTTAC TCTGTCGCTC AAGCTGGAGT GCAGTGGCAC AATCTCAGCT CACTGCAACC
158821 TCTGCCTTCT GGGTTCAAGC AATTCTGCCT AAGCCTCCAG AGTAGCTAGG ACTGCAAGTG
158881 CACACCACCA CACCTGGCTA ATTTTTGTAT TTTTAGTAGA GATAGGGTTT CACAATGCTG
158941 GCCAGGCTGG TCTCAAACTC CTGCCCTCAA GTGATCCTCC TGCCTCGGCC TCCCAATGTG
159001 CTGGGATTAC AGGCGTAAGC CACTGTACCC GGCCTCCTCC TTTAATAGAC AGGGTCTAGC
159061 TCTGTTGCCC AGGCTGGGTA CAGTGGCGTG ATCATAGCTT ACTGCAGCCT CGAACTCCTG
159121 GGCTCAGGAG ATCCTCCTGC CCTAGTCTCC CCAGTAGCTG AACTACAGG CATAGCACAC
159181 GGGGCTAATA AAATTAATTA GGTGATAAAA TTCACTGCCC ACTGATGACT AAGCTCTTTG
159241 GACATAAAAG ACACAGACCT TGAAGGAAAA TGTGTCTACT TAATTTTGAA ACCCTATTTA
159301 TCAAAAAACA GGATGAAAAT GCAAAATGCC ATCCACATGC CAGAAGATAT CAGCTATAAT
159361 AAGTTCCCAT AAATCAATAA GGAAAAGAAC CCAATAAAAA TTATTAAACC ACAGTAAATC
159421 ATGGGTAAAT CACAGAGGCC TGAAGGGCTA ATGGACATAC AAAAAGAATC TCAATCTCAC
159481 TAGTGAAATC AGAAAAGCAC AAATTAAGTA CACAATTAGG TACCATTTTA AATCTGTAAG
159541 ACTGTCAAAA TCATAAATTA TATAAGTAAA GACTCAGGGA GTTTTGGAGG AGTGAGAGCT
159601 CTTATATTGC TTGTGGGGTA GAATTGGAAC AATTTCAAGA TCTGTAGTAT CTGGTAAAAT
159661 TATGATATGC ATCCCTCACA CCAGCATGTC ACTCCAAGGT ATCTCCCTGG AGGGAACATT
159721 TACGGGACAC AAGGAAGCAT GGATAAGAAT GTTCACAGTA GTATTGTCTG CAACAGCAAC
159781 AACAACAAAA AAACCCAACT ACACACAACT TCAATGCCCA GTCCACAAGG CAATGGATTA
159841 AATAAACTTC AGGCCGGAGA TGGTGGTTCA TGCCTGTAAT CCCAACACTT TAGAAGGCCG
159901 AGGCGAGAGG ACTGCTTGAG CCCAGGAGTT CAAGACCAGC CTGAACAAAA TAAAGAGATA
159961 GTGTTTCTAC AAAAAATTTT TAAAAAATTA GCCAGACGTG GCAGTGCTTG CCTGTGGTCC
160021 CAGCTACTGG GGAAGCTGAC GTGGGAGGAT TGCTTAAGCC CAGGAATTTA AGGCTGCAGG
160081 GAGCCATGAT GGGGCCATTG CACTCCAGCC TGGGTGACAG AGTGAGACCC TGTCTAAAAG
160141 AGATAAGTAA ATAACAACTT TGCATTTTCT GCCACATTGC AAAATGGTGA GAGAGTGGTT
160201 TCTAGACTCT AGACTCTTTC TATGACTACC TTCTAGTTAT GAGATCCTAC AACACTCACC
160261 TAACCTCTCT GTGTCATATT TCCTCCTCTA TAAAGCAAAA ATGCCCCATA TAGAGAGGAC
160321 TGTGATATAA AACAAGAACC AAGAAAGTA AAGCTTTTCT AATCTGTCAC AGACTAAAGA
160381 GTGCTCAGTA TATGTGAGTC ATTATTCCTG GTGCTGGTAG GAGTGTATGT TACAACTTTG
160441 AGTCAAGTAA TATGGTACCA TATATTAAGA TTAACAACAA CCTCGGCAAT CCCAGTTTGG
160501 GGTATGTTCC CAAAAGAAAT GAAAGCACCA GGATATAAGG ATGCATGGAC TAGAAAGTTA
160561 TTGTAGCAAC ATTGTAATAA CTAAGTTCTA AAAACAGCCT GAAGCTCCAT CAGTAGGGAT
160621 ATGGTTACAT ATATTTATTA TATTCTTATG GAATATTAGA CATAAAAAGT AACGAGTAAC
160681 ATAGAAGAGA CAGTGTATAT ATGTTACGTT TGTACAAACT TAGGGAAAGA TATAGATCAC
160741 CCTACCTAGA GAAGTCAGAT TGGAGAGGGG TGGGAAAAAC CTTGAACTTT CTCCTTATAT
160801 CCTTTATATT GTTTGACTGA TTAAAATGTA TTTGTTGCAT CTGCTTGAAG GCAATGTAAA
160861 ATAAAATAAA CATACATTTA AAAATAAAAA TAAAATTTAT TCCTATCACT TTTGTAATAA
160921 AGCTGGGCAC AGTGACTAAC ACTTGTAATC CTAGCACTTT GGGAGGCAGA GACAGGCAGA
160981 TCACCTGAGG TCAGGGGTTT GAGACCAGCC TGGCCAACAT TGTGAAACCC CATCTCTACT
161041 AAAAATACAA AAATCAGCCA GGCATAGTGG TGCGTACCTG TAATCCCACG CTACCCGGGA
161101 GGCTGAGGCG CTGGAACCCA GGAGGCAGAG GCTGCAGTGA GCTGAGATTG CGGCACTGCA
161161 AGCCAGCCTG GGTAACAGCG AGACTCCATC TCAAAAAAAA ATTTGAAAAA AGAAAAATTT
161221 TAATAAACAG TGTTTAAGAG GGGAGAAATA TTTAGTTAAA AGATAAGCCC ATTTAAGAAA
161281 TAGTTTCACT TGACCCGGAA GGCGGAGCTT GCAGTGAGCC GAGATCGCAC CACTGCACTC
161341 CAGCCTGGGC GACAGAGCGA GACTCTGTCT CAAAAAAAAA AAAAAGAAA GAAAGAAAGA
161401 AAGAAATAGT TTCACTTGAA CCATATTATG ATTCCTTCTG TAAAAGATGA GAGTAGGCAA
161461 ATTGACTCAG TGAAATCCCA GCAAAACTTA CACAAAGTCT TGTTCTTCCT TCCTGTCATC
161521 TGTATAGGAT GAAATACAGA GTGCTTTTGG GTTTTGTTGT TGTTTGTTGT TGTGTATTTG
161581 AGGGGAACAC AGGTCTATAA TTCCTTTTCT GAAATCCCTG GAACAAAATG GGCTTTGCCA
161641 TTCAAATTAG TTTAGAAGTT ATAAAGGCAA AAAAATGCAT ATACTCTAAA GTTCAACCCC
161701 ATCATGGCCT AAGGCAGAGC CCTGTAATCA AATTCATCAA TATATCTGCA GCAAAACATT
161761 TATTCAAATT AAGTGGGATA AATAAAGACT TTTAAATAGT CTCATCTCAG TGCCGTTCAG
161821 GGTTGGCCAC TGTGGAAGAC AGACTCAAGG GTGGCCTTCT ATGATTCCTG CCTCTTGGTG
```

Figure 2 (Page 50 of 74)

```
161881 TTCACACCCT CGTAAAATTC CTTGTCTTTG AGTGTGAGCA GGGCTTATGA ATTGCTTCTG
161941 ACCAATAGGA TATGGCAAAG ATGATGGGAT ATAATTTCTA TGATTACGTT TCATTATGTA
162001 AGACTCCATC TTGCTGGCAG ATTTTCTCTA AAGAGTCTGT CTCCTGAGCT CTCTCTGAAG
162061 AAATAACTGG CCATGTTAGA AGCCCATGTG CAAAGAGCTG AGGGGTGGCC TGTAGAAGCT
162121 GTGGGCAACC TCCAGCCAAC AGCCAGAAAT AACCAGGGCC AAAGTCCTGC AACCATCAGG
162181 AAAGAAATTC TGCCTGCTAT CTCAGTGAGC TTGGAAGTGG ATTCTTCCTT AGCCTAGCCT
162241 CCAGATAAGA ACACAGCCTG ACCAACACCT TAACTGCAGC CTTATCAGAC CCTAAGCAGC
162301 AGGCCCAACT AAGCTGTGCC CAGATTCCTG AACCACAAAA ATTGAGATAA CATATCAGTG
162361 TTGTATTAAG GTTCTAAATT ATGGTAATTT GTTTGTACTA ATAGATAACT AATATAACCA
162421 CCAAATCATT TCAGGTTAGG CCAGATTTTT GTAGCCAAAT GAATCATGAT AAAACTTTCC
162481 ATTTTCAGGG GTTTTTTTGA TTTTGTACTT ACGGATACAA ATTTGTAAA GTATAGTCAG
162541 CACTGATTTA AAAAATCAAG GGAGCAGGAA ACTCAGTAAA TGGTTCTAAC ATTTTGGAAT
162601 CTGTAAATTG GTTGTAACAT TTGTCATCTG TGTTATCTAA GTCAAGTTCC TAAAATATGT
162661 GAATGATAGG TTATCATACT CACCTACTTT TCTTGCATTG CTCTAAGAGT TGGCTGAGCT
162721 ATTGATAATA AACACTATGA TCAGATCTAA TACCATGATG TGCTATTATG ATCATGTGTC
162781 AGTCACAGGG CTAAGCACTT TGTACATGTT GATGCATTTA ATTTTGATGA TAACTCAATG
162841 AAGTAGGAGC TGTTAATATT TTCATTTTTC AGAGGGGGAA ACCAAGTCAC TTGGAGTAAC
162901 ATGGCTAATA AGTGAAAGAA TAAGAATTTG AAAGGTTTGC ACAGATAACC AGAATGCAAT
162961 GCTCATCACA TTCACTGAGC AGTGAATCAT ACTAACTAGA GAAAGTATGA AAGCTCTACT
163021 GAAATTAACT AAACAACCTC TCTGGCTGTG AGCCTGCCAA GGGACAGGTG GTAAACTTGG
163081 TTACTGCATA AGGCCCCTTC TATCCACAGT ATTCAGGAAT TCTTTAGTGA ACATACCTTG
163141 ATGACTCCTT AACATTTTCT TCACATCGAA GTAAAGCTTG AAACATTGC ACATAGTATG
163201 AAGTTCCAAG GAGACAGCCT CTGATGTTTC CAGCTTCACA GCCCAACTCC TAGAATAAGC
163261 AGAGGCGAGA GATTTCTTCA GAGGTGCATT CCATTCATTT CTATATACGC ACACCCCTCC
163321 CCTCCTGCAT TCAAACAGGA CTTACCTGCT CAAAGTGTCA TTCACATTCT ATAAAGAAAC
163381 AAAAAGAAAA GGTGAGCATG GAACATCGG TATTTCATGG GGCTTGTCAT GCAGGGCTAT
163441 TCTTCTTTGC TTTACCCGAA GAAGTAAAGA GAGTTACCCT AGTCTTAGTC TTAGATATTG
163501 ATGGATACTC AAACAAAGTA ATTCCCACCA GTCTTAGGTA TTGATGGATA CCCAGATGGA
163561 ATAATTCCTA CCAGCTTCTG GGAGATTCAG CATGGCAGGA TGTTTATCAA CATTTGCATC
163621 TATTCTCATC CTTGCTGAAG TCTGAGGGCC AGGAGCTTTG TCCATGCTCC CTCTGTAAGG
163681 ACTAGCTTTT GGTGATCGGA TTTCCTTCAC AGTGAGCCCA GATTAGAGAA CACTTATCAT
163741 AAAGGTCCTT AGTGGTGAAT CTGTGCACAG CCCTGAGACT GGGCCACTGC CACTAAGATG
163801 GTGGTAGCAG GTATCACACA GTGGTAAAGC AATCATGCTA TACACTCAGC CTTACAGTAT
163861 AGTCACCAAT CCTGTTAGTT AGAACCAGAA TTAATGGCTC CAGATGTTTA TCTTCCTACA
163921 GATAAAGCTG TAGATTGTAC CATAACAGCT CTGGAGCAAG GGTTCTACAA GCAAATCAGG
163981 GAAAAGGTTA TCACTCATTT TGGCTGCCCC ACTTCATCAC CCATCAGTCA CCTAGTGGAG
164041 TATTTCAGGA GAGAGTCAAC AACCAGGGTT CTCTGCACAT GGGCCAAGGA GGCAAACAGT
164101 GGTAAATGTT ATCCCGTGGT TTCATTTGGC CAAGCTGTGT TCCCTCAGAA GTTTATTTTT
164161 CTAATTGACA TAAAGGTACC CTATAAATTA GTGAAGGCCA GCCTGATGGC ACTGATGTAC
164221 ATCTAAAAGA AACATTACTT TATCTTCCCA TGCTTCCTTA CCATTCTCCT TTAATAGCAC
164281 TATAACATAC CTTTTTTCCC TACTCCAAGT ACACAGCCTC ACCTGCAGCA ATTTCTGGGC
164341 TGAGCCCTGA CATTTTTCCT CCAGTTCCAG GATGTGGCTC TTGAGTTCAT TGCTCTTCAG
164401 CCCCAGACCA GCCTCATAGT CCCTCAGTCT ACTCAGAGTC TGTTGTTCTT CTTTCTCCAG
164461 CCTCCAGAGA TAAGACTTCT CTTCCTCATG TAGGAAACAC TGGAGATTCT TAAAGTCAGA
164521 CCGGATTTTT TGTCTCTGAA TCTGTACCTT CTCCTGGAGT CAAGAAAGTA TGGTCAAAAG
164581 GTGGAAGTAA ACCAAATGTC CATCTATGGA TGAATGGATA ACAAGAATG AAAGTCTGAC
164641 ACACGCTACT ACATGACAAG CCTTGAAGAC ATTCAAGCAA AATAAGCCAG AAACAAAAGG
164701 GCAAATATTG TAAGACTTTG CTTATACAAG GCATCTGGAG TAGTTAAGTT CATAGAGACA
164761 GAAAGTAAAA TAGTGGTTAC AAGGTGTTGG CAAGACCAGA AAATGGACAG TTATTGTTTA
164821 ATGGGTAGTG AGTTTCAGTT TAGAAGATGA AAGATGAAAC TGAGTTGCAG TTTGGAGATG
164881 GGAATGGTGA TGGTTGCACA ACAATGTAAC AATGTAAAAG CACTTAATTC TACTGAACTA
164941 TATACTTAAA AGTGGTTAAA TGCTTAAGTG TTATATATAT TTTCACACAA ACACACACAC
165001 ACACACAATC AGCCACTGGG ACATTATTTT CTCATGAGTC ACTGAAGCTG GAAGAATGTC
165061 CCCAGTTTCC TGCTGCAGAG TCATGTGTGG GAGGCAGGCA CTCAGATGTG GAAGAGGTTG
```

Figure 2 (Page 51 of 74)

```
165121 CCTCAGATTC CTTATAGTCA CCCAATTAAT TTTCTTGTTC TTCAGCCAAG ACACAGGAGA
165181 AAGCTGGGTT AGGAGTGCTA GATAATTTAA TTGTGAAACT AGGGCCAAGT TCAAACACTT
165241 TATCAGTTAC AAGGATAAAA AGAGGTTTTT ACTTATGATT TAAGAAGTTA GATTTCTGAG
165301 TTGGAGCGAT TTTCTTGAAG TAAAAGCTTA TAATGAACAT CACCCAGACT GGATTTTAAG
165361 ACAACCAGGC TGGTAAGAGG GTCCATAATT CTTGGCAGGG GGAGCTTTGA GTGTGACAGG
165421 CATTTATTAT GGTTAACTGA GAAATACTGT TCTACTACCC TAGGGTCATC TTAAGCATTC
165481 CTATGTGTAA GACTGACAGA AATCAAGTGA AACTCTCATC TGAGGAGATG TAAAGTTGCA
165541 ATTTCCATTA GTGCTGTCTA AATTAATGCA GTGGGAGTGT GTATTCAGGG CAATTTGAAT
165601 CTATGTTCTT GGATTGCAGT CTTCAAACTT GGCCCAAATA AACTCTCTAC TTATCTTAAA
165661 AAAATAAAAA TTAAAAAATA AAAATAAATT CATACAGTGT TTTGATGACT ATGATATAGA
165721 AGAAGGGTCT TTGACTTAGG ATGAGGTGGA ATTTTTGTGT AGGAGACAGG TGCAGCTTTA
165781 ACTCTTGTAT AGACGGGTTT TCATATATGT TAGTTACAAT CAAGGTCTTC CCCATTGCCC
165841 AAGATCCTAG AAATGGGGGA AGTAAGAGTG TACTCAGGAG CTCAAGAGCA ACATCCACAA
165901 ACAAAGATCA GGGTAGAGGT TAGAGAGGAC TCCTGAAAGA GAGAAAATTG GTAATCAGCT
165961 TGTGGGATTT TACTGCAAGC TAGTGAATTA TATAAATATA AAGATTGGTG CAAAAGTAAT
166021 TGTGGTTTTT GCCTTTACTT TAATGGCAAA GACCGCAATT ACTTTTGCAC AAACCTAAAT
166081 ATTTCCATAA AAGAATGTGG CTCTGATAAT GTGGAGGTTA GTCAGCCACG GAAATAATCT
166141 GAAAGTTTGT AGTTGCAAGT GTGTAGGTTG TTGCATTACT TGTGATGTAC TTATAAATCA
166201 AGTATAGGCC GGGTGCAGTG GCTCACGCCT GTAATCCCAG CACTTTGGGA GGCTGAGGTG
166261 GGTGAATCAC GAGGTCAGGA GATCAAGACC ATCCTGGCCA ACATGGTGAA ACCCCGTCTC
166321 TACTAAAATA CAAAAAATTA GCCAGGCATG GTAGCACATG CCTGTAATCC CAGCTACTCA
166381 AGAGGCTGAG GCAGGGGAAT TGCTTGAACC CGGGAGGTGG ACATTGCAGT GAGCTGAGAT
166441 CGCACCACTA CACTCCAGCA AGACTCCATC TCAAAAAATA GTAATAATTT AAAAATAAAT
166501 AAATAAATAA AGTATATTTC TTTCATCAGC TTCATGAGCT TGAGTAGTAT GAATTTCAAT
166561 CTGGAGTGAT CCTGTTTTCT AAGTGTTCAC AAAGCTTGGT TTCTGTACCT GTAAAGTTGA
166621 GAGCCAGATG CTCCACTGTG GTAAAAGTGC CAGGGTAATG AGTTGAGGCC TGCAAACCAG
166681 GTTTATTTTG AGGTATTTAA AGTTGAGAC CCACTCGATG CTTTTTCTAG GTAAATAGTC
166741 ATACTAATTC TGCTTCTTCT GACTGAAGTA TCAGGAATCC CAGCCAACTA CAGTTTAAAG
166801 ATGGAAAGAT TGGTGCTAAA TACTCATGGA TGTAAACCTG GAACCAGGGG CATAAGTACA
166861 AATAATGGTT TCTTCCTTGG GTTTCATTTT TTCAATCTGG TTTAGTGAGA ATAAATCCTC
166921 ATTGTGCTTT TCCTCAATCA TCCCCTATGC CTAAGCTCTA GAATGGAAAA TAGCTTGAGA
166981 TCAATGAAGT CAGATTCTTA CTTTCCATTT AGTTATTCGC ATTGCTGTGG ACAGCTTCTG
167041 CTCCGTACAT CTGTCTTCAA GTTGCTTCAG TTTTGTCACA GCTTTCTGGA GCTTTTCCTG
167101 AAGGAAAAAT TTGATAAGTG AAGCCTATTC AATTTGACTC TTCATTAGGG ACCTAGGGGG
167161 AATCCCAATC TTCTAAGATA TATTTGAATA ATAGTGAATA TTTATAGAGT CCTCATTGTT
167221 TTTTGCTAGA GAGCATGCTA AAGGCTATAT GTGCAGGAAC ATACTGATCC CCTTGGCAAC
167281 CCTGAATAGT TGGTAGGATT TTAAACTTCA TTTCTGTGCT GTAGAAAATG AGACTAAGAA
167341 AGGGGTAAAA TAACTTGCCC AAAGGGCTAT GACTGCCAGG TGGTGGAGCA ACAATTGCAA
167401 TCTCATCTGC TGACCCAGAG CCTGAGCTAT GTCCACCACT AGAGTCCTGC CAGGAAAAAG
167461 TTGGATATAG AACAAGGTAA TCATCATCTA AAAGATTTTG TAAAACAACA TGCTGAACCA
167521 AGCAAAACCA ATACCAGTGT TTGGCACACA TGAAATTTTG TGTCTTATGA GTCAGGAAAA
167581 ATCAGGATGC CAGCTGGTTA TTAGAAACAG TTCATGGAAG AGGGGAATTC TGGTATCTTT
167641 TGAACAATGG TATCATGAAT CCAATTTAAA ATGATTTAGT ATTCATGTCA AGCTTTTAGC
167701 TTATTCTTCA AAACAGTTTC TCATATTTCT ATTGAAAGTG ATTTGAAGCT GACCCAAATT
167761 GCTAATTGTA GTCAATGCTG AAAGAATTGT CTCCTGTCCT CTGTAAACCC AACAAGTATA
167821 CTCATTCATT CTCGAGTGTT CTCAGGAAAA GGTTCTATGT AACTGTTTTA GCAAAAGATG
167881 ACATTGTCCT TACTATATGC CAAGTGCTAT TCTATGCATT CTATATTTTA ATGTCCTCAA
167941 AGCTTATAAC CACCTCCTGT GTATGTGTTT TAGGGAGGGA GGACACTGCT ATTATCCCCA
168001 TTTACAGATG GAGAAACCAA GGTGTGAAGA CATTAAGTAA CGTGCCCAAA ATTGCCCATC
168061 TAGTAAGTGA CAAAACTCAA TTTCAACATA AGCTGGTTCC TTTTCTTACT ACTTGGTGGA
168121 AAAGTAATTC AAATGGGAAT ATGATCATCG CAGTTATTAG CTGCTCCATG GAGTTTAAGG
168181 AAGAGCTGCC ATGAGCTGAG TGGTGGTCAT GATTGACATG TCCTTAGAAG GACTTAGAGC
168241 CTTCATACAA GACCACCTCT GCCTCATGGA GGACAGAATA AGGAGCCTGA CACTGGAGAC
168301 AACATTTTCC TCAAATTTAG GCAGGACAGA GAAGGAAAAA GGACATCAGG ACTATGCCCA
```

Figure 2 (Page 52 of 74)

```
168361 TTCCTCCATG CTGCCAACAG CAAAGTCCCA CCTTCCTTAA TATGCTTTCT GGCAAGAAAT
168421 CTGGATGGTA CACAAAACCT CTCCCTCTGC TTCACCTTCC ACAACCAAGC ATTTCCAAAT
168481 CTTTGACTCT TCTTCCTGAA TCGTGCTTAA AATCTGCCCT CTCCTCCCTT TCTTATACGG
168541 ATAGTTTGAA TTTTACTCCT TGATATTCCT TTTATCATAG ACATGCCACA GTAGCTGGGC
168601 ACAGTGGTTC ATGCCTCTAA TCCCAGCATT TTGGGAGGCT GAGATGGGAG GGAGACCAGG
168661 GGTTTGAGGC CAGTATAAGC AAGAAAGGCA GACCATGTCT CTACAAAAAA TAAAAAAATT
168721 ATCCAGGTAT GGTGGGGCAT CCCTGTAGTC CTAGCTACTT GGGAGGCTGA GGTGGGAGGA
168781 TTGCTTGAGC CCCAGAAGGT TGAGGCTGCA GTGAGCCGAG ATTGCACCAT TGTACTCCAA
168841 CCTGGGATAC AGAGCAAGAC CCTACCTCAG AAAAAAAAAA AAAAAAAAAA AAAGTAGAGG
168901 TACCAGAGTG ATATTTTCAA TGTCACTGAC CCTTCATTCC CCAAATGAAA ATCCCCCAAT
168961 AGGTGTTCAA TTTTTACGTG TCCTTCAGGA GTTACTTCTA AGATGAACCA CTCTCTACCC
169021 TAAATGTCCC TCCCCACCAC CAAAACCAGG GACCTCCAGG CAGACATTTT TGATGGTTTG
169081 TTTTCTTTAC TAGACTGTAG ATACCTAAAA GGTGATGGGT CTTTCTTCCC TGTTTTCAGG
169141 CCCTACTGCA TGGCTTTACA TATTGTGGTT TTTCAAATGA TATTCATGGT GTGAAACAAG
169201 AAAAAATGCG GGTGTTTGGT TTGAGAACAA CCTGTTCTAA AGCAAAAAGA AATTCATCAT
169261 AACACAAATG GATAGAGATA AGAGTCCAAC CATCCCATTG AAGGTCAGGA TGGACAGTCT
169321 AGATAATTGA GCAAGAAATC ATCATAAACT ATTTTTCAGA AGAATGACAT GATGAAAGCT
169381 GTATTTCCAA GTCATAATGT TAGGTTTCAA GTTAAATCAT CTCAGCTCCT GGGGAGCAGG
169441 ATAAGACTTG GTACTTACCA AAGCTCCCGG GCCCACACAC TCACCTTGTA GCCCTGGCAT
169501 ACGTCTTCAA CAAGAGCTGT GGTGTGCCCT TTGTGCTGTG GTGCCCGCTC ACAGCGCCAG
169561 CAGATGAGCT GCCCCTCATC TTCGCAGAAC AGGTGGAACT GCTCTCCGTG TTCCTCACAT
169621 GACATTTCTT GATCCGTCTC TTTGAGGGCT TCAATGAGGC TTCCCAGCTG CTTGTTGGGT
169681 CGGAGGCTAT CCATATGAAA TGGAGCCCGA CACTGGGGAC AGCAGAATGT CTCCTGCCTC
169741 AGTTGCTTTT GGCTTGGGTT TTTAAAGAAG TCTGTTATAC ACAAGTGGCA GTAGCTGTGT
169801 CCACAGTTGA TGCTTACTGG GTTCGTCATC AGGCTCAGGC AGATGGAGCA GGTGGCTTCC
169861 TCCATCATCT TCTTGGTGCT GGTGGTTGAG GCCATAGCTT TTATTGAAAA GCTCCAATAT
169921 TGGCTCTAGA GATGGAGATG AAGCAGCCAG AATTTTCCAC CGTGATGAAA ATACACCTCA
169981 CCTGCACCTC TATGTGATGA GCTGGCTGCA ACTGACTTCC ATAGGTCTTG AAGGTTTTCC
170041 TTCCAACCCC TATTATCTCA TTTTGTATTG AAGAAAAGAG GACCTAAAAG GAAGAAGTTG
170101 AGGCTGAGGT TGTTTGGGCC ACGTTTGAGA ACTGCAACCC AAGTGCAGAG TTTCAAGTTG
170161 CCCTCATTAG CAAGCAGTTA CAAGTGGTTG TTTAGAGGAA AAAAAGCAGT TTTAAAGCAG
170221 TTTTAAAGTT GTTTGCCAAG AATTTACATT AAAAATAGCAT AAGCTTTTGA CTGGCTATAC
170281 ATTGTTCTTT GTATTACAAA TCTCGGGAAT ATGTAGGTAA TAGATGAGGC AGCCAGTCAG
170341 GAACAAAATG CTTTTAAACA TGGGGTCTTA ACTGAAGACC TATACTCCTG CCTCACTTGT
170401 CCTGATAAAT TTTGCATACC TCACATAGCT CAGACTGCTC TAAATTATTT CATTATTTTT
170461 CTTTTCTCAG TCTTCTAACT TTTTTTTTTT TTTTAATGA GACGGAGTCT CACTCTGTCA
170521 CCCAGGCTGG AGTGCAGTGA CGCTATCTCG GCTCACTGCA CCTCCGCCTC CCGGGTTCAA
170581 GCGATTCTCC TGCCTCAGCC TCCGAGTAG TAGCTGGGTC TACAGGTGTG CACCACTACG
170641 CCCAGCTAAT TTTTGTATTT TTAGTAGAGA TGGGGTTTCA CCATGTTGGT TGGCTAGGAT
170701 GGTCTCGATC TCTCGACCTT GTGATCCACC CGCCTCAGCC TCCCAAAGTG CCAGGATTAC
170761 AGGCATGAGC CACCGTGCCC AGCCTCTTTT TCTTTTCTTA TAAGACAAGT TCTCGCTCTC
170821 TTGCCCAGGC TGTAGTGGAG GGCAGTGGCA TGACCACAGC TCACTGCAGC CTCGACCTCC
170881 TGGGTTTAAG CAATCCTCCT GCCTCACCCT GGCAGAGTGG CTGGGACTAC AGGTATGTGC
170941 CACCATGTCC AGCTAAAGTC TTCTCTCCAG AAAGAAGAAA TGCATTGGAA TTTAGAGGAT
171001 ACACAAACAT CTAGCTGTAT AGCTAATACA GTAGCCACTA TCATGAGTAG GAATTTAAAT
171061 TTAACTTAAT AAAAATTAAA ATGAAAAAAT TCAGTTTTTC TGTTCCAGTT GCCACATTTT
171121 GATTGCTTAA TAGTTGCATG TGACTAGTGG CTACATAACA GCCTCAATAT ACAACATTCT
171181 GTTATACAG AAAGTTACCT TGGACCAAGT GCTGGAGAA GCAATGCAGG CTTCCTCACA
171241 AAAGCTGTAA AAGAGAGAAC TCAGGGAGTG TGAAACTCTT TCCTATTCTA GTTAACTTCA
171301 AGAATAATTG TTACCAGGCC AGCACGGTGG CTCACGCCTG TAATCCTAGC ACTTTGGGAA
171361 GCCGAGGCGG GCAGATCACC TGAGGTCAGG AGTTTGAGAC CAGCCTGACC AACATGGCAA
171421 AACCTCATCT CTACTAAAAA TACAAAAAGT TAGCTAGATG TGGTGGTGCA CACCTGTAAT
171481 CCCAGCTGCT CAGGAGGCTG AGGAAGGAGA ATGACTTGAG CTCCGGAGGG GGAGGTTGCA
171541 GTGAGCCCAG ATTACACCAC TGCACTCCAG CCTGGGTGAA AGAGCGAGAA TCTGTCTTAA
```

Figure 2 (Page 53 of 74)

```
171601 AAAAAAAAAA AAAAGAATAA TTGGTACCAG AATTACTCTT TGTAATTAGT AGTAACACTT
171661 ATGCAATTGG GTGATCTGTG ACAGATTCCA TTGAAGGAGT ATGGGGAGCT TCACCCCAAT
171721 ATATGACTCC CTGGTATAAT GAGTATTTTG AATTAAAGGC CCTTAGAGAT CAGCAGATGC
171781 TGGAAGAGAC TTTTCCCCTA TCTACATAAA GACCAGTCAC ACTAGACAAG AAGAACAATT
171841 GTTTTTCCTT CCAACCCCTA TTATCTCATT TTGTACTGAA GAAAAGAGGA CTAAGAATGT
171901 AACCAGACCT AATCAGACAC TTTCACAAAA TAATGTCTGT CTCTCAGGCT CATTCATTTT
171961 CCAAAGAGAA CCATTTACAA GTTAAACTCT GTTCCTCCAT TCATTCATCC TCCCAAATAT
172021 TCATTTATTC TCCCTAGTAA TCATTTACTG CCCCTCAAAG AATTACCTAT ATTCTCCTGA
172081 TATCACCCTT CCCCTCTGAA ATAAATATGT ATACATGTAT AAACGTTATA CATACATATT
172141 TATACAGTAT ACATACATAT TTATACATAC ATACATATGC ATACATATTT ATATTTATGT
172201 ATTTATACAT AAGTATTTAT AAATAAGGCT ATATAAGTAT CTACCCCCAT TGGCAGAGGG
172261 GGTAATCACT CTGTGATTCT AGCCCATGTA CTTGTTAATA AATTTGTATG CCTTTTCTCC
172321 AATTAGCCTG CCTTTTGTGA GTCGATTTTT CAGTGAACTT CAGAAGGCAA AGGGGAAGTG
172381 TTCCCTTGGC TCCTACACCA TCATGACAAT AAAATTTGAC TCCACCTCGA CCCCCCCCAT
172441 CCCCCACAAA GAACAACAAC CAACACTGGT TAATAAGGTC GGTTGTTTTT TGTTTGTGTT
172501 TTTGTTGTTG TTGTTGTTGT TGTTGTTTTT GCTTTCAGGA GCAGAGGTAT AATAGGCAAA
172561 AGAAAGAGAA AGGAGAATAG TGAATACCTC TTCTGCAGAG AGGGGTGCCT AAGTGGGACT
172621 TCCCTGGCTA ATAACGTCTT GCTAGAGACC CAACCAGGAG GATAATGGAA GCAATCAAGG
172681 CAACCAGAAC AACCAGAAGA ACCAGTTTAT CCTTTTTGTG CCCTCTCCCT AAACTGAGGG
172741 AATAAGAATT GGAAAGAAGG CTGCAGAGCA GAGGGTTTGC TCCTGAGGAG CAGTTATTTC
172801 TATGGGATCA GAGCTCCTGC AGAACTGGGG AGTTTACTTT TACTATCTCT TCTCCAGGAC
172861 AGGACCTATC TCAAGAGACA TGTTCAGAGT GATTGCAACA TAAAGAGTTT GCAGACCCAA
172921 GGAGGTAGGG AAGGCAGAAA GAAGATGGGG GAGGCCAGGG ATAGGCAACA GAGGAGTGAC
172981 CAGGAGCGAA AAAGCCTGCC TCTTCTGAGA ACCTAGCTGG GCTCTCCCTG TACCCCCGAT
173041 CCCTCCCCCC CGCCCGCCCC CACACCCCTA CTCCTGGGAG CTCCTCTAGG ACAGGGGCAG
173101 AGTCAGGAGG AAGTTTGAAG AGTGCCTAGA ATAAAAAACA GTAATTTAAC TACAATTACC
173161 GGGTAGGCTG TTTTCCTCTC ACAATTTGAT CAGTCTCTTG AAGCCACACA GAATTTCTTC
173221 TGAAGACGTG TATTCCTTGG CAGGCTATTT CCTCCAGTGA TACACCAGGC CCCTCTCTGC
173281 TGGGGTCACT GCTCTTCTGG GGAGATGGGG CTCCCCTCCT TCCAAGGCTC CAGGGTTCCT
173341 GTCCTGGGCC CCACTCATCT AAGTTCTGAA TCTTCTGAGA TTTGGTGTAA AGTCTGGTGA
173401 AAGAAAGAGC AGGAAAGAGG TGAGAGCTGT AAAACAAAGA AAGTCCTGAC CATTTTCAGA
173461 GTTGGAGGGG CCCTGCTGTC ACGAAATATA TTCCCCACCC CACTTGCCAT CAGTACACAC
173521 TCACATATCC ACTGAGAAAA CCTTAGCCTG GACCTTTTCC GTAACCTTCA CTGCTCAGAC
173581 ACTTACATAT TCGCTGCTAG TCCCCTCTGT TGCTGCCACT TCCTGGGTCA GGAAGTTAAC
173641 TCAGACCGGA TTAAACTGAG AAGTGAAACT ACTGTGGGAG GCGGGGCTCA TAAGATTTAG
173701 GAGAAAACTA GTGACGTTGT TCATATCATT TGCACTCCGC CTCTCCGGTA AAGGAGGGGG
173761 AAACGTAGGA AGAAAATATC CTTCTTTTAC AGCAATAAAA AGAAGGAACC AATTAATAAC
173821 CCTGTAAACT ATCATGTGAC CCCAACACAG AGTATCTAAA AACAGGAAGC CTGCAGAGGT
173881 TCAGTTCACA GACTCTGATT TGAGATCTTT CTACTTTTGC CACCAACTCC CTTGGGAGTC
173941 CTTAAGCCTT CCTAGCTGAT GTTACTTCTT TTGCTATTTA TGGGTTGCTT GTGGTTCTAT
174001 AACTGCTCTG AAGGGTGTGG TGGAAAAAGG GGTGGTAACA GCAGTAGGAC TCATTGGCAT
174061 CACAAAATTC ATCTGAGTCA GCTTTCTATT CTTCTCTGTC CCGTTCTGTG TCTTGTTTTT
174121 CTCCTTGCTG TCCTTCTGCA GGACTCAGAT CTTCTTCAAT AGCGAGGGTC AGCCAGGATA
174181 GAAAATGGGA GTCACTAGTG GCCCAGCAGT GAGTGCCCCC AGCTTAGAGC TGTGTGGGAT
174241 CCCTGGGACC ATCACTCTGC TTTGTGCTTT GTGGAGAAAA GGCTGTGGGG TCCAGGGTCA
174301 AGTCCTTAAT GACTTAGCTC CAGCTTCTCC ACTTCAAAAT GAAAGGAAAA GTACTATCAC
174361 CACCCGTTAG AATTATTATT TCATGGGGAA AAAAGATGGA TTACTATCTC ACAATAAGAG
174421 CTTGTCACAT TTATAAGTCT CAGGTGTAAG AGGCATTTAT GATAACAACA TAATAAATGC
174481 TGGCTTAAGT AGATGCAGTG GTCCAAGGGA ACCAGTAAGG GGAGCTCAGG ACACAGGTGG
174541 GAGGAGAAAT TAAACTTGAA TTCTGGGAGC CACTGGCCTG TCTGGGCCCC TGGCCTGCCT
174601 GCTGACCCTG ATAGCCAATG GAACATGGAG TTTGGCCCAG CTGCAATCCC TCTGGTCCAA
174661 CTACTCAAAA TAAAGGCAAG ATTGGGAAAC ACGTTCCTTT CTTCCTATAC CAAGCAGAAG
174721 ACTCTTCAGC ACTGCACCCT CCTGGGTGCT CACAGAGCCT TCTGTTGTTT TGCCACCTAC
174781 GATTCATCAT GCCCTGGCAT GATGGTTGCA GACCCCATGC ATAGCATGGG ACATTCTACT
```

Figure 2 (Page 54 of 74)

```
174841  CCTGAGGCAA CCAGCACACA GAGAGAGGAG AAAGAATGAG CCCCTGAATC CTTGGTCCCA
174901  CGATGAGTCC TTGCAGATAT CTACAACTTT CATTGTTGTG GATGTGACTC TGTACCCAGG
174961  CATGGCTCAT TCCAGATCTG TCCTATTGTC AGAGGTGTTC AAACCAGAAT GACTCCATTT
175021  TGAATGGGGG CTAGGTAAAA TAAGGCTGAG ACCTACTGGG CTGCATTCCC AGGAAGTTAG
175081  GCATTGTAAG TCACAGGATG AAATAGGCAG TTGGCACAAG ACACAGGTCA TAAAGATCTT
175141  GCTGATAAAA CAGGTTGCAG TAAAGAAGCT GACCAAAACC CACCAAAATC AAGATGGCAA
175201  CAAGAGTGGC CTCTAGTCAT TCTCATTGCT CATTATACAC GAATTATAAT GTGTTAGCAA
175261  GTTAGAAGGC ATTCCCACCA GCTCCATAGT GGTTTATAAA TACCATGGCG ATGTCAGGAA
175321  GCTACCCTAT ATAGTCTAAA AAGGGGAGGA ACGCTTGGTT CTGGGAATTG CCCACATCTT
175381  TCCCAGAAAA CATATGAATA ATCCACTCCT TGTTTAGTAC ATAATCAAGA AATAACTGTA
175441  AGTATCTGTA TTAGTCCATT TTCACACTGC TGATCCAGAC ATACCTGAGA CTGAGTAATT
175501  TATACCAGGA AAAAATGTTT CATGCTCTTA CAGTCCCACG TGTCTGGGGA GACCTCACAA
175561  CCACAGCAGA AGGCAAGGAG GAGCAAGTCA GGTCTTACAT GGATGGCAGC AGGCAAAGAG
175621  CTTGTGCAGG GAAATTCCTT CCTATAAAAC CATCAGGTCT CATGAAACTT ATTGACTATC
175681  ATGAGAACAG CAGTATAAAT TACTCAGGGA AAGACCTGCC CCCATGATTC AATTACCTCC
175741  CACCAGGTCC CTCCCACAAT ATGTGGGAAT TTAAGATGAG AGTTAGGTGG GGACACAGCC
175801  AAACCATATC AGTATCCTTA GTCCAGAAGC TGATGCTCTG CCTGTAGAGT AGCCATTCTT
175861  TTATTCCTTT ACTTTCTTGC TTTCACTTTA CTGTGTAGAC TTGCCCCAAA TTCTTTCTCA
175921  CACGAGATCT AAGAACCTTC TCTTAGGGTC TGGGTTGGGA CCCCCTTTCT GGTAACACTA
175981  TCAAAGGATC AGGAAAAGGA AGCTAGTGAA TGCTAAAAAG GAAACAAACT ACCATTACCA
176041  ATAATAACAG CAAGACAAAA GCAAACGGA TTGTGACAGC TGTCCCATCT CACACCTGTT
176101  TCCCATTGCA GGAAGGAGGG GCTGGTCAT GCACAGAGTG GCCAATATTA GAAGCAGAGA
176161  GGGGGTGCAG ATGAGACTTC AGGAATATGT TGACAAAGGC AGGCCTAGGG AGAAATCAAC
176221  CTGAACTATC CCCAAGGAGG AATGCATTAT CTCTAATATG TAAAGTTAGG CTTGATCCTG
176281  TGATTATGGG ATATAGGAGT CCAAAGACTC ACAATGGGAA GTAGGTCACT AGAGTCTCCT
176341  TCAGAAGCTC TGTACTGTGT GTTCCCACTG TGGGCAAGAG TCAGCACTCA GCTATTCCTA
176401  GAATGCCTTT CCTCAACTCC TTCAGATTTT GCCTCTCAAC TAACCCTATC CTGACCACTT
176461  GTTAGCAAGT GTACCCCTCT CTCCCTCCCA AACATTTTCA AATCTATTTT GTTCCCATGG
176521  CACTTATCAC TGAATATTTT ACTAATTTAT TTTGTTTAGT GTTTGCTTCC CTCATGAGAA
176581  TGCAAAGGGA TGGATTTTTT TCAATATTGT TCACTGATGA ATCCCAGTAA CTAGAATATT
176641  TCTAAGCATA GTGATGTGCA TTAAATCAAA GAGTAACTTT CTGAATTGCA CTAAACACAC
176701  ATCACAAGAG GTGTGTGCAC ATATGTGCAT GATGCACGTA GTGTGGTGTG GGTGTTGTGT
176761  GGGGTATGTG GTACTGTGTG TGCTGTGTGT GGTATGTGAT ACATAGTTTG TGTTAGTGTG
176821  ATGCATGTGA TGTGGTATGT GTGTGCGTGT CCATACATAT TAGGGGTGGC GGGGATGTTA
176881  ATATGTCAAA TGGTACTAGA AAGTATCAGA ACTCATGGTG CTTACTGGTT TCCCAGAGAG
176941  CTGCTTCTCT CCCACCTGTA GGATATACTG ATGGTTTGGA CAGAGAAGAA ATAAAAAGAA
177001  GGCTGTGACC TACTGGGCTG AGGAAATAAA AACGAAAGTA AAGAAGAGC TGGGAAAAGA
177061  GAGTGGAGGG GCCAAGGGAA ATTTCCCCTT TGGCTTCTGG GAAACTTTG CTGAAAAATC
177121  AACTCACAAA TTTATTAACA TGTACACAGG GAGAACCATA GAATGATTAT CCACTTCCCA
177181  AGAGGGCTTA AAAGCTTATA TATTATCCTG GCAAAACAGA TTATGGGAGG GGAAGAAGAG
177241  AAACTCTGTT GATGGGATTA CTGTTGCGGA TTTTTGCTCC TTCGCTCAGC TAGGTCCGGG
177301  TTTTTGTCTC ACAGCCAGGA AGAATTAGGC ATGCAGCCAT CAAAGAATGA GTGGAGTAGA
177361  ATTTATTAAG TGAAAGGAAA GCTCTCAGCA AAGACAAGGG TCCTGAAAGC AGATTTCTGG
177421  TTTGCTCTTC ACAGTTGAAT ACTAGGGCTT AAGACTCAAA TTCCTGACAA CTCCACCCTG
177481  TCCTACCAGT GCATGCAGGC CTTTAGACTG AGCTACTCCA TATTGATTAA TTTCCTGAAC
177541  TGCGCATGTG TTAAGGAAAG GAATCATCCA CTGCAGGCAT GTTAGGCAA GCCCCTGTG
177601  CAAGTTCCCT TATCTGCACA AAACATCCGG TGTAAGCACT TGTGGGGCAG GTCAGAGGTT
177661  CTCTGGGTAC CATTCCCTTA CTGTCTGCCT AAAGCAAGCT GGCCAACTCC TTTCATTACT
177721  AGGGAGAGTA AGTAGATCAG GGAACAGAGA TTAACTTGAA CATTATCTTG TGAAAGTCCG
177781  TTCGGGCATG GTTACATTCT TGGTCTTACA GGAAGGGTAA ATAAAATAA TTGCTCTTTT
177841  TGGTGGGTCT GGATCTTAGG TAGATAAAGA AACTTTAATT CCACGATGTG TTTTGGTAGG
177901  GATAGTTGGT GGCAGGGATG TCAGAGAGAC TTTGAGGCTT CTTCAGTTCA ATATGACCAA
177961  GGGCCATATA TTAGGGTATC AATTTCTGAG CCCCAACAAG AGCTTAGGAG AGATGTGATA
178021  GCATCACAGT GTGAAAGCAA TTTTTTGTCT GTTTTAGAG ACAGGCTCTT GCACTGTCAC
```

Figure 2 (Page 55 of 74)

```
178081 CCTGGCTGAA GTACAATGGT ACGATCACAG CTCACTGTAA TCTTGAACTG GGTTCAAATG
178141 ATCCTCCCAT CTAAGCATTT CAAAGTGTTG GGATTACAGG CATGAGCCAC GGTACCCAGC
178201 CTGAAACTGC ACCCACTTTC TGATAAACTT TTCAAATGAC TAAAGGGGAG AGAGTAAGCA
178261 CTACTCAGAG GTAGGAAGAA AGGACACAGG ATTATAGGAT TAAAACAACA ACCACCAAAA
178321 AAAACCAGAC CGGTGTGGTG GCTCACACCT GTAATCACAG CACTTGGGGA GGCTGAGGTG
178381 GGGGGAGTCA CTGGAGGCCA GGAGTTCGAG ACCAGCCTGG CCAACATAGC AAGACGCTGT
178441 CTCTATTAAA AAAAAAAAAT ACCTGCCTTG AGCTAATCAG AATCATGGAC CTGACAAAG
178501 GATGTCCCAA AGTAAGTCTT AGCATTTTTT TTTTTTTTTT GAGACAGTCT CGCTGTGTTG
178561 CCCAGGCTGA AGTTCAGTGG CGTGATCTCG GCTCACTGCA ACAGCTGCCT CCCAGGCTCA
178621 AGCAATTCTC CCTGCCTTCA GCCTCCCAAG TAGCTGGGAT TACAGATGCC CACCACCACG
178681 CCTGGCTAAT TTTTGTTTTT TTTAATAGAG ATGGGGTTTT GCCATGTTAA CCAGGCTGGT
178741 CTTGAACTCC TGACCTCAAG TGATCTGCCC ACCTTGGCCC CTCCATAGTG CTGGGATTAC
178801 AGGCGTGAGT CACTGCACCC GGCAAAGTCT TAGCATTCTT TACAAACAGT TTGTACCCGT
178861 ATCTCTAAAA GGGAGTAGTG AATTTCACCC CAAAATATGG CTTCCTGATA TAATGAGTAT
178921 TTTGAATGAA AAACTCTTAG AGATCAACAG ACACTAAAGA GACTTTTCCC TAGGTACATA
178981 AAAATAGGAT GGCCCCACCA GCGAGAACAA TTGTTCTTTT CTCCCTCCCT GTTATCTCAT
179041 TGTGCATTAT AGGAAAGACC AAGAATGTAA CCACACCTGA ACAGACCCTT TTATAAGATA
179101 ATCAGTCTCT AAGCATCATT TAAATTCCAA GGAGAACTAT TTACAAATTT ATCTGTTCTT
179161 TGATCCAATT AGTCTCTCCT GGTAGTTACA TATTGCCCCT CAACAGAATT CCTCTTCTTC
179221 TGTTTCCCAT AACCTATTTT GCAAGGATCA AGCCCCTGTT ACTTCTTCAA CTTCAAGTTG
179281 GCATATAAGC TTCTAAATTC CACTGGGATA TTGGTACTAT GTGCATGAGG AGAACCACAG
179341 AGTAATTAAA TTGTAAAGCC TTTTATCTTA TGAATCTGCC TTTTTTGTG TTCATTTTTC
179401 AGCAAAACTT CCAAGGGCAA AGGTATAAAA CAAAAATAAA ATTCTAAAGC CCCCCAACCA
179461 TCTGAATAGA CTTTCTCTTC AGTCAGGCTT CTTAAAATGT AACCTGAAAG ACTGGCTCAG
179521 GCCATTAAGG GAAGTGGGGG TTGAACATGC CTCATTATTC CTCTCTGGCA TTAACATCAA
179581 CACAGCTTTT AAGTCTGATA AGAAACATTT TACAACCTAT TCTCTCTGAA GCCTGCTAGC
179641 TAAAAACTTC ATCCCATAGT ACAACTTTGG TCTTCACAAC CTGTTATCAC AACCTAGTGC
179701 TCCTTTCTAT TAATCCCAAA TCTTTATACA AACTCAACCA ATTGTCATCA CCTCCACCCC
179761 ACTCCTCCGC TGCTTCCAGT TGTCCGCCT CTCTGGACCA AACCAGTGTA CATTTCTTAA
179821 ACGTATTTGA TTGATGTCCC ATGCCTCCCT AAAATGTATA AAGCCAAGGT GCATCCCAAC
179881 CACCTTGAGC GCTTGTTCTC AGGACCTCCT GAGGGCTGTG TCATGGGCCA TGGTCACTCA
179941 AATTTGGCTC AGAATAAATC TCTTCAAATG TTTTACAGAG TTTGGCTCTT GTCATGACAC
180001 AGATGACTGC TTCACTGAAG CCTGCTCTGG AAGTGAGTGG GGGTTTTGCA AGGATAATTT
180061 TCCCCGGATA GCCCAGAAG CAGCTAGTAA TAATACACTT AAAGGTAGCT AAAATGCATT
180121 GAACACTTGT TTTGTGCCAG ACCTATGTCA ACATTTGCTT TGTGCCAGGC TTATGCCAGT
180181 ACTCCTGATT TGTTAATACA TTCTAAATAA AAATTCTGGA GTTTCAAATA TAATAACTGA
180241 AAAACAGAAA ATAAATAAAA ATATATAATA ACTGAAATAA AAATTTACTA AGGCTGGGGA
180301 TGGTGGCTCA CTCACACCTG TAATCCTGTT ACCGGAAAGG GGTCCGTCCA GATCCAGACC
180361 CCAAGAGAGG GTTCTTGGAT CTCACACAAG AAAGAATTCG GGCGAGTCTG TAAAGTGAAA
180421 GCAAGTTTAT TAAGAAAGTA GAGGAATAAA AGAACGGCTA CTCCATAGGC AGAGCAGCTC
180481 TGAGGGCTGC TGGTCGCCCA TTTTTATGGT TATTTCTTGA TTATGTGCTA AACAAGGGGT
180541 GGATAATTCA TGCCTCCATT TTTTAGACCA TATAAAGTAA CTTCCTGACG TTGCCATGGC
180601 ATTCGTAAAC TGTCGTGGCG CTGGTATGAG CATAGCAGTG AGGACGACCA GAGGTCACTC
180661 TCATCGCCAT CTTGGATTTG GTGGGAGCA GTGAGGATGA CCAGAGGTCA CTCTCATCGC
180721 CATCTTGGAT TTGGTGGGGT TTAGCCAGCT TCTTTACTTT TTTCCTTTTT TTTTTTTTTT
180781 TTTTTTTTTT GCCCAGGCTG GAGTGCAGTG GCACGATCTC AGCTCACTGA AACCTCCAAT
180841 TTCTGAGTTC AAGCGATTCT CGTGCCTCAG CCTCCCAAGT AGCTGGGATT ACAGGCATGT
180901 GCCACCACAC CCAGCTAATT TTTTATATTT TTAATAGAGA CCGGGTTTCG CCATGTTGCC
180961 TACGCTGATC TCCAACTCCT GCGCTCAAGC CATCCAGCCA CCTTAGCCTC CCAAAGTGCT
181021 GGGCTTATAG GTGTGAGCCA CCCCACCTGG CCTAGCCGGC TTCTTTACTG CAACCTGTTT
181081 TATCAGCAAG GTCTTTATGA CCTGTATTTT GTGCCCACTG CCTGCCTCAT CCTGTGGCTT
181141 ACAATGCCTA ACTTACAGGG AATGCAGCCC AGCAGGACTC AGCCTTATTT CACCCAGCTC
181201 CTATTCAAGA TGGAGTCTTT CTTGTTCAAA TACCTCTGAC AAGCCCAACA CTTTGGGAGG
181261 ATGACACAGG AGGATTGCTT TAGCCTAGGA GCTCAAGACC AGCCTGGGCA ACACAGTGAG
```

Figure 2 (Page 56 of 74)

```
181321 ACCCCATCTC TAAAAAAAAA AAATACAAAA AAATTAGCCA GGCATGATGG TGTGTGCCTG
181381 TAGTCCCTGC TACTCAGGAG GCTGAAGTGG GAAGATGGCT TCAGCCCAGG AATTCAAGGC
181441 TGCATTGTCA GAGGCATTTG AACCAGAATG ACTCTATCTT GAATAGGGGC TGGATAAAAT
181501 AAGGCTGAGA CCTGCTAGGC TGCATTTCCA GTATGTTAGG CATTCTTAGT CACAGGATGA
181561 GATAGGAAGT CAGCACAAGG TACACATCAC AAAGACCTTG CTGATAAAAT AGGTTGTGGT
181621 AAAGAAGTTG GCCAAACCC ATCAAACCA ACATGGCCAC CAAAGGGACC TCTGGTTGTC
181681 TTCACTGCTC ATTATATGTT AATTATAATG TATTAACATG CTAAAAGACA CTCCTACCAG
181741 CATCATGACA GCTTACAAAT ACTGCGGCAA TATCTGGACT TTACCTTATA TGGTCTAAAA
181801 GGTGGAGGAA CCCTCAATTT TGGGAATTGT CCACCCCTTT TTTGGAATGC TCATGAATAA
181861 TCCACCCCTT GTTAGCACA TAATCCAGAA ATAACTATAA GTATGCTTAT TTGAGCAGAC
181921 CACGCTGCTG TTCTGCCTAC AGAGTAGCCA TTCTTTTATT TCCTTACTTT CTTAATAAAC
181981 CTGCTTTCAC TTTACTGTAT GGACTTGCCC TAAATTCTTT CTTGTGTGAG ATCCAAGAAC
182041 CCTCTCTTGG GGTCTGGATC AAGACCCCTT TCTGGTAACA TCTTTCTGGT GACCACGAAG
182101 GGACAATACT GAGGAGACTC TGAAGCCAAA GGAAACAGAC TACAGCACCA ACTGGCTGAC
182161 TTTGGGTAAG TGGTGGAGTC CCCGGGTAAA GGATAGGATT GGGTTAGAGG TGCAACTTAG
182221 GGGAGATAGG GTCTCTCCTA AGACAGAGAG CGTTTCAGTC CGCTCTTAAT AAAGGGCAAG
182281 AATGCTTGAC CGAACTTGGG TTTGAGACCC AACTTAGGAA GGCTACAGTC CTTAAGATTT
182341 AAGGGGTTAG AGGCCCTCT CAGTAAAGTC TCTCTTGGTT AAAAACGGAT TTAGCATTAG
182401 GGGATGTTAA CTGCTATTCT GTTTGTATTA ATCTTCCCTG TGCTCTTTGC TGACAGCTAT
182461 GGGTGACAGG ATTAGGCATG TACAGGATCA CGGGACATTG GAACTTTTC TTCTCTCCAA
182521 AAGGGGAAGC TTGACAGCTG ATAGGACTGT TGGAAAAGAT CCCTTTGCTA TGACAAGCAG
182581 CCGCCTGAAC TTTTGATTCA GTGTTGCTGC AATGGGTGGG TCTTTCTCTG GCCTCTGTGA
182641 ACTCCTCACC TTCCCCACCT CACCACAGGG AATGCTTTTC TCCCTTTCTC TCTTTTCTCT
182701 TTTCTGTCTT TTCTGTTACT TGAGACAACC ATCTTGCCCA GAGACCATAT GTTGAAACTC
182761 CTGGTCAGAA GTTTGATTAA AGATGAAAGG GCCTATCTGG GGGCAAGTTT GAGCCTTCCC
182821 AGTTAGATAT TGGGTGCTAA GTGGAGTGGC CAATGTCTAT GTTTTGTCAC ATGTATATTG
182881 CTCTGGCTGA AATGGAAAAC GTTAATTTGG TTACTTTATG TGGCCATTGG GCAGCATCTT
182941 ACAAAAGTGA GAGACATTTA TTTGCCTGTG GTTCCATGAA ACAGAAAAAA GTTGGTTTTC
183001 CTTTGTGTCG TAGCTTGGAC CCAAGGGCTT TGCAGTGAGC AAGGTTGCTA GCGCTGCTCA
183061 GTGAAAGAGA ACCCAGAAAC CTGGCATGCC AGCAAAAGGG TAAAGATTTC TTACCAGTCA
183121 GGCTTCTGGC CTCTCTCTCT TAGTGAAAAC TGAATGAATG GTAAAAATCA CTGTTTATCA
183181 CCTCTGTAAA GTTTTGATTA ATGGGAACAA GGATTTGTGG GGCTAGTCTT AAGCTGTAAT
183241 GAATCTGGTA TACTTTGTGA TATCAATTTG TCTTTCTGTA TTACTCTGTC ATAAAGAGGA
183301 ATATGGTAGG ATAGAACATG GGCTTAGGAC TCCATAAGCC TGCTGTTCAA GCCAGCCCAG
183361 TAAACTGGTC CGTTGCAAAG TTTATTACAG GTCCCTGGAA AAAAAAAAA TTAAAAACTG
183421 GATGAAGTTT CCTTCTCATC TTGTTTTATG TCCTTTGGAG CTTCACCTTG TAACCACGTG
183481 GCGGTACTTT CTCTTGGTCT CTGCCATCCA GGGAACAGGA ATTTGGGGT TTATGTAATA
183541 GTTAACTCTA AAAATTATCT CAAGCCATTG CAAGCTCAAA ATTGGCTGCT CTGGACCCCT
183601 TCTGGGAAGG GCAATGGAAA CTAACCAGTG TTGTAGCTCA GCAGCTAAGG ATTTGTCATT
183661 TTATAATGGC GGCCAAGGTT CAATCCTGGC TTAGGGAATG AGTACTTTCT GATTGATATC
183721 TGTGTGACCT TTACCATTTG TTGATTCTGT TCTCTTCCCC TCCACACACT GTCTTGAGTT
183781 TTCCTCTCTC TGAGAACCTG GGAGATTATC TTTGGTAAAG TTCAAAAGCC AGAAATAATG
183841 GCCGTGTGGG ATGGCTAAAG TTGAGTAATA AGAAACTTAA AAGGACTCCT TTTTTTTTTG
183901 CTTTAGAGTG CTATGGTTTA TGGTTAAAAG CTTAATTAAA AGTGGATATT CAATCTCTAA
183961 AAGCCTGGGA CTCCTTGGGA AAAGCAGAGG AGGCACCACA GACCCCATTT TGGGAAAACC
184021 TCTGTTTTCC TCATGAAACC CCAGGAACTG GAAGTGGATA GATCCTTCGC AAAATCTAAG
184081 GCTCTGTTTG GCTTTGCATT ATGTTATCTG ATGTTTTTGA CTTTTGGGGG TATCAGAAAT
184141 TACTTTGCAT TATGAGGGAG ATCTGGTGTG TAATAACCAG GTAGGAAATA TACTTCTGGG
184201 GATAGCTAAA GGCAAATATA GGTGAATACT TGGCTATTTG CACTTTTGGA TCACAAGAAG
184261 CATTCTCTTG ACTACCTAGA AGGTATGGAA ATGTCTCCAT CCCCACCGAG AGATAAGATT
184321 CCCAGGGGAG ATGGCTGATC CCCCAAAAGA GGGCTGATTC CCTCTTTTGG GATCCAGGAT
184381 CTGGTATAAA AATGGGACCC TGGCCAGGCA CAGTGGCTCA CGCCTGTAAT CTCAACACTT
184441 TGGAAGCCT CAGAGTTATG AATGTCTCAC CATACTGACA CTTTGTGACT GAGCTCCTCT
184501 CTACCCTGGA CACAAGAGAC CCTAATAATT AGACAGGAAT ATCATTGCCC CTATTTAGTC
```

Figure 2 (Page 57 of 74)

```
184561 TGAAGAAGTT ATAGAAGATG GATCTTTATC CCACTGCAAT CCTTAGGATT AAGGGTTCCC
184621 TGGTAAAAGG GAGTGGGAAA ATATGTCAGA GGCATTTGAA TCAGAGTGAC TCCATCTTGA
184681 ATAGGGGCTG GGTAAAATAA GGCTGAGGCC TGCTGGGTTA GGTTAGGCAT TCTAACCAGG
184741 AGTTTAGTCA CAGGATGAGA TAGAAGGTTG CACAAGGTAC CCGTCACAAA GACCTTGCTG
184801 ATAAAATAGG TAACGGTAAA GAAGCCAGCT AAAGCCCACC AAAACCAACA TGGCCACAAA
184861 AGTGACCTCT TGTCATCCTC ACTGCTCATA TACACTAATT ATACTGCATT AGCATGCTAC
184921 AAGACACTCC CACCAGTGCC ACGACAGTTT ACAAATACCA TGACAACATC TGGACGTTAC
184981 CTTATATGGT CTAAAACGGG GAAGAACCCT TAGTTCTGGG AATTGTCCAC CTCTTTCCTG
185041 AAAAATTCTT GAATAATCCA TTAGTTTAGC ACATAATCCA GAAATAACTA TACGTCTGCT
185101 TATTTGAGCA GTCCATACTG CTGCTCTGCC TATGGAGTAG CCATTCTTTT CTTTTATTTT
185161 TATTTTTTAG ATAAAGACTC GCTCTGTCAC TCAGGCTGGA GTCTGGAGTG CAGTGACGTG
185221 TTTTGGCTCA CTGCAACCTT CACCTCCCGG GTTCAAGCAA TTCTCCTGCC TCAGCCTCCC
185281 AACTAGCTGG GACCACAGGT GGGTGCCACC ATGCCTGGCT AATTTTTGTA TTATTAGTAG
185341 AGATGGGGTT TCGCCATGTT GGCCAGGCTG GTCTCGAACT CCTGGCCTCA AGCGATCCAC
185401 TTGCCTTGGC CTCCCAAAGT GCTAAGATTA CAGGCATTAC CCACTATGCA TGACCCATTC
185461 TTTTATTTCT TAACTTTTTT TTGTTTTTTT GAGACAGAGT CTCACTCTGT CACCCAGGCT
185521 AGAGGCTGGA GTGCAGTGGT GCGATCTTGG TTCACTGCAA CCTCTGCCTC CTGGGTTCAA
185581 GCGATTCTTC TGCCTCAGTC TCCTGAGGAG CTGGGACTAC AGACATGTGC CACTACACCC
185641 AGCTAATTTT GTATTTTTAG TAGAGACAGT GTCTTGCCAT GTTTGTCAGG CTTGTCTCGA
185701 ACTCCTAACC TCAAGTGGTC TGCCTGCCTC AGCCTCCCAA AGTGCTGTGA TTACAGGCAT
185761 AAATCACTGC GCTCGGCCCT TCTTTACTTT CTTAATAAAC TTGTTTTCAC TTTACTGTAT
185821 GGACTAGCCC CAAATTCCTT CTTGTGTGAG TTCCAATAAC CCTTTTGTGT GTGAAAGAAT
185881 TTATGGCTGC TGTTCAGGCT GGAGCAAGCT GGAGCTCATG CTGCTGCTCA GACTGGAGCA
185941 TGCGTGATCT GTGATCCCAG TAAGAGGATC ATGGTCACTC CAGCCTGAAC GACAGCATGA
186001 TATCTCATCT GTAAGAAAAA AAAAATTACT AGAGGGCTTT AACAGCAAAT TTGAGCAGCA
186061 AAAAGAAGTA ATCAGTGAAC TCAAAGATAG GTCAATTGAA ATGATCTACT CTGAAAAACA
186121 GAAAGAAGAC AGAATGAAGA AAAAGAAATA GAGCCTTAGA GACAGGGGAT ACCATCAAGC
186181 ATACTAATAT ATGCATAATG GGACTCCTAG AAGGAGAAAA GTGAGAGGAC AGGGAGAGAG
186241 AATGTTTGGA GAAATAATTT CTCAAAGCTT CCCATGTTTG GCAAAAAAAC ATTAACTTGC
186301 ATACATATTT TAGGAGCTCA ATGAATTCCA AGTAGGATAC ACTCAAAGAG ATCCATACCT
186361 AGACACATCA TAATCAGATT ATCAAAAGAT GAAGAAGATG AATCTTGAGA GCAGAAAGAA
186421 AGGAACAATT CATCACATAC AAATAGTACT CAAAAGATGT CTGGAGTAGG TATACTAATA
186481 TCAGACAAAA TAAACTTTAA GATAAGCATT GTTATAATAA ATAAAGAAAG GTATTTGTA
186541 ATGATAAAAG TGTCAATTCA TCAAGAAAAC ATAACATTAT AAACATACAT GCACCTAACA
186601 ACAGAGCCCT AATATTCATG AAACAAAACT GACAGAATTG AAGGGAGAAA TAGAAAATTC
186661 GACAATAATA GTTGGAGACA TCAATACCTC ACTAGTTAGA CAAGATCAAC AAAAAAATAG
186721 AAGACTTAAC ACTTGAAAAC ACCTAACCTG ACCCTAACAT AAATCTATAG GTCACTACAC
186781 CCCAAAACAG CAGAATAAAC ATCCTTCTGA AGCTCACATG AAACATTTTT CAGGATAGAC
186841 TGTATATTAC TTCATGAAAT AAGTCTCAAT AAATGTAAAA GGACTATAAT AATAGAGTAT
186901 ATATTCTCTG ACCAAAGTGG AATGAAGATA GAAATCAATA ACTAGGCTGG GCGTGATGGC
186961 TCACGCCTGT AATCCCAGCA CTTTGGGAGG CCAAGGCGGA CAGATCACGA GGTCAGGAGT
187021 TTGAGACCAG CCTGACCAAC ATGGTGAAAC CCTGTCTCTA CTAACAAAAT ACAAAATTA
187081 GCCAGGCCTG GTGGCATCTG CCTGTAGTCC CAGCTACTCG GGACACTGAG GCAGGAGAAT
187141 CACTTGAACC CAGGAGGCAG AGATTGCAGT GAGCTGAGAT CGCGCCACTG CATTCCAGCC
187201 TGGGAGACAG AGCGAGACTC CATCTCAAAA TTAAAAAAAA AAAGAAACT AGAAAATAA
187261 GAACAAATCA AACCCAAAGC AAGCAAGAGG AAAATGAAAA ATTTCAAAGC AGCCAAGAAC
187321 AAAAGGCACA TTATGTACAG AAGAACAAGT GTATAGATCA CATATTTCTC ATAGACACAA
187381 TATAAGCAAA AAGACAGTGG AGCAAAATTT TTTAGATTAA TGAAAGACCT ACAATTCTGT
187441 ACCAAGCAAA AAAACTCCCC CCAAATGAGG GTGAAATAAG ACAATTTAAT ACAGAGAAAA
187501 GAGGAAGGAA TTTATCTAGT CATATGTGAG AGTTTTATGA TACATTTTGT ACTGTATATG
187561 TGGATGTTTT CTATTTCATT TAAAAAATCA ACCGTGCAAT TAAATGGTAG ATTGTCTTGC
187621 TTCTTTTTGA TTGACACAGT CATTAACTAA AATATTGTAG TATTTTTTA TCTCCCTGCC
187681 TAAAGGCAAT AAACATCTAA TCAGCAGACT AGAACAATAA AAAATATTTT TTAAAAGTCC
187741 TTTAGGCAGA ATGATAAAAG TCCCTTAGGC ATATTGAAAT TCCTATTTAT ACAAAGGAAT
```

Figure 2 (Page 58 of 74)

```
187801  AAACAGTACT AGAAATTGTA ACTATGTGAG TAAACAGATA ATATTTTTC TCCATAAAAT
187861  GTGGTTGACT ATTTTCACAA AAATAGTTAA CAATGTAATG TGTGATTTAT AGCATTTAAA
187921  AGTAAAACAG GCCGGGCACA AAGGTTCGTG CCTGTAATCC CAGCACTTTT GGAGGCCGAG
187981  GCGTGCAGAT CACTTGAGGA CAGGAGTTCA AGACCAGCCT GGCTAACATG GCAAAACCCC
188041  ATCTCTACTA AAAATACAAA AATTAACCAG GCGTGGTGGT GCACGCCTGT AATCCCAGCT
188101  ACTCTGGAGG CTGAGGCACA AGAATCACTT GAATCCAGGA GGTGGAGGTT GCAGTGAGGC
188161  AAAATTATAC CACTGTGCTC CAGCCTAGGC AACAGAGCTA GACTCTGTCA CACACACACA
188221  CACACACAAA AGAAAGTGT ATGACAACAA CAGTGCAAAA GAAGCGGAAA TGAAAATAAT
188281  GTTATTTTAT ATAAGTGGTA TACTTTTAGA TGAACTACGA TAAATTAATG ATGTATACTA
188341  TAAACTCTAA GGCAACCACT GAAATAATGA AACGAAGAAT TATGGCTAAC AAGCCACAAA
188401  AAGAAATAAA ATAGAATGAG AAAAAATATT TAAGTTGTTC AACAGATGGG AAAAAAAAGA
188461  GGAAAAAGAG AACAAAGAAC AGATGGGACA AATGGGAAAG TAATAGCAAG ATGATAGACT
188521  TAACTCTACC CATATAGATT ATCACACTTA AGGTAAATGA TCTAAATACT CTAATACAAA
188581  AGCAGAGGTT GTCAGATTGA ATTAAAAAAA CAGACAACAA CAAAAAAAG CAAAAAAAGA
188641  GCCACAACAT GCTGCCTACA AAAAATTCAC TTTAATATAA AGACACAAAT AGTCTAGAAC
188701  ACCATCACTT TTAACCTTAT TTACTCAAAC CTCCTAACTG ATCCCTATTT ATTTATTTAT
188761  TTATTTATTT ATTTATTTAT TTATTTTTGA GACAGAGTCT GACTCTGTTG CCCAGGCTGG
188821  AGTGCAGTGG CACCATCTAG GCTCACTGCA GCCTCTACCT CTCGGGTTCA AGCGATTCTC
188881  CTGCCTCAGG CCTCCCAAGT AGCTGGGACT ATAGCACATG CCACCATGCC CAGCTAATTA
188941  TTATATTTTT AGTAGAGACG GGGTTTTGCC ATGTAGGCCA GGTTGGTCTC AAACGCCTGA
189001  CCTCAGCCTC CCAAAGTGCT GGGATTACAG GCGTGAGCCA CAGCACCCAG CTCCTCTTCA
189061  TTTATTCTTG CTACGCTTCC TCCAATCCAT TTTGTGCATT TGATGATTTT GCCAGTAACT
189121  TCTTTATTTT TCTGGTAAAA TTACTTATGG GTCACTGAGG ACTGGGATGT TCTTTCTTCT
189181  AGAGGGGGTT TGTGTCTGCT TTTGCCAGGA AGCTGGGGTA CCACCAGTCA AGTATTACTT
189241  TAAACTCAAT TCATGAATTG AGACTTTTTT TTTTTTTTT TTTTTTACGC AGAGTCCTAC
189301  TCTGTCACCC AGGCTGGAGT GCAGCGGTGT GAACATGGCT CACTGCAGCC TCAACCTACT
189361  GAGCTCAAGC AATCCTTCTG CCTCACCATT CTGTATAGCT AGGACTACAG GTGTGTGCCA
189421  CCATGCCTGA CTAATTTTTT AAATGTTTTT TTTAGAGATG GGGCTCACTT TGTTGCCCAG
189481  GCCGGTCTCG AGCTCCTGGG CTCAAGTGAT CCTCCCACCT TGGTCTCCCA AAGTGCTGGG
189541  GTTACAGGCA TGAGCCTCTG TGGCTAGCCA AGACTTTTTA TTTTTAGCC TAAATGTGTA
189601  TAAAAGTTGG CTTGTGGTTA CAACTTATCA GGATTGATGA TCTCTCTCTC TCTCTCTCTC
189661  TCTGTCTCTC CCCACCTCTC TCACATCCCT TGCTCTGCTG AGAAGCAGAG CAAACATTCT
189721  AGCAGTTTCC AGAGAGTAGG ATGGGATTAC TTCTAGTTTA CTTTTATCAT CCTTTGGGAT
189781  CGCAGTATTA CTGGGAGAAC ACAAGTATCT CTTATTAGAC ATACCACCTT TGTAGAATCT
189841  GGACTTTCAT TTTAGACTTT ATTTGTTTTC TACTATAAGC AATTTAAGTT ACAGATCTCT
189901  CTACACACTG TTTAAGTTGC ATCCCATGAA TTTTGATGTG CTTTATTGTC ATTATTATAT
189961  AGTACAATGT ATTTTGTAAT TTTTTGTGAT TGTTTGGAG AGATTGATTA ATTAGAATGA
190021  TGTTTAATTT CCAAATATGT GTGTTTTTTT CCTACATTTC TTATTTTAT TGATTTCAAA
190081  TTTATTTCTA CTGTAGTCAG ATTTAATAAT TCATTTATTT TTATTATTTT CATTTTTTTA
190141  GAGACAGGGC CTTTCTGTGT TGCCCAGGTT TGTCCCAAAC TCCTAGTCCC AAGCAGTTCT
190201  CCTGCCTCAG CCACCCAAAG TGCTGGGATT ATAGGCACGA GCCACCCGTG CACAACCAAC
190261  AATTCATTTA AAAAGTGGGC AAGTGAACTG AACAGACATT TCTCAAAAGA AGGCATACAA
190321  TTGGCCAACA AATATATGAA AGAATGCTCA ACATCACTGT ATTAGTCTGT TTTCATGCTG
190381  CTAATAAAGA CTTAACCTGA GACTGGGGAA TTTACAAGAG AAAGAGGTTT AATGGACTTA
190441  CAGTTCCACA TGGCTGGAGA GATCTCACAA TCATGGTGGA AGGCAAGGAG GAGCAAGTCA
190501  CATCTTACAT GGATGGCAGC AGGCAAAGAG AGAGCTTGTG CAGGGAAACT CCCGTTTTTA
190561  AAACCATCAG ATCTCGTGAG ACTCATTCAC TATCATAAGA ACAGCATAGG AAAGACCCGG
190621  CCCATAATTC AGTCACCTCC CACTGGGTTC CTCCCAGGAC ACATGGGAAT TGTGGGAGTT
190681  ACAATTCAAG ATGAGATTTG GTAGGGACA CAGCCAAACC ATATAAATAA CTAATCATCA
190741  GGGAAATGCA AATCAAAACC ACAATAAGGT ATCATCTCAC CCCAGTTAGA ATGGCTATTG
190801  TCAAAAAAAC AAAAAATAAC AAATGCTGGT GAGGATGTAC AGAAGAGGGG ACTCTTATAT
190861  CCTACTGGTG GAAATGTCAA TTAGCATAGC CATTATGCAA AATAGTATGG AAGTGAGGTA
190921  GGTTACATAG GGTGGTCACA GCCTCCCTTG AAAGGAAACA AGAAACTTGT CAAATTGATG
190981  GAGAGAACAA ATCTCTTGAC ATTACACAAA CTGCATCTGG GGCTAGTGGT TAGAATATCC
```

Figure 2 (Page 59 of 74)

```
191041 TCAGTCAAGG AGGTAGAAGA GCAGGAGGGA AAATCCCTAA GTTCGTGCAA GTGCAGAAAC
191101 CCACAAGCTG TGTTCTCAGG TTGACATATA CTCATTTTAA TAGTAAGAAA CACACCCTTG
191161 GGTAGAGAAT TAAAATGCTA ATAATACATG TGATGTATGT ACTAGCGTGT ATGGCAATAT
191221 TGCATGCACA TTCAAGAGAC CACCCAAAAC ATATTTAACA ACAATGCCCA TTCCCACCCC
191281 CTCATGGATA ATCACGTAGG ACTCCCATAA CGGGAGTTTC TTCAGTGTCA ATTGGTGCTG
191341 AAGTAGCCGA CCCTGACTCT GCTATCAGCG TGTACTTTCA CCTTGCAATA AACTCCTTTG
191401 CCTACTTTTA CTTTGGACTG GCTTTCAAAT TCTTTTGTGC AGGGAATTCA AGAATCTGAA
191461 CCAGCCCACT GACAACAGAG GTTTCTCAGA AACCTAAAAA TAGATCTACC AGATGAGGCT
191521 GAAAATCTGC TACTGGCTAT TTATCCAAAG GGAAGGAAAT CAGTATACAA AGAGACACCT
191581 ACATCCCCAT GTTTATTGCG TCACTCTTCA CAAGAGCTGA TATATAGAGT CAACCCTAAA
191641 TGTTCATTAA CAGACAAATG GATAGAAAAT GTGGCATATA TACACAATGA AATACTATTT
191701 GGCCATGAGA AGAATGCAAT CTTGTCATTT GTGGCAACGT AGATGAAACT GGAGAACATT
191761 ATGTTAAGTA AGATAAGCTA GGATTGGAAA GATAAATACT ACATGTTATC ACTCATATGT
191821 GAAAGTAGAG AAAAATTTTT AGCTCATGGA TTTAGAGAAC AGAACTGTGG GTACCGGAAG
191881 CTGGGAAGGG TAGCAAGGAG GGGAGGATAG GGAGAGGTTG GTTAATGGTG ACAAAATTAC
191941 AGCTAGATTG TAGAAATGAG TTCCGGTGTT CTGCACCATT GTAGGGTGCA TATGGTTAAC
192001 TCTCATTTAT TGTATATTTT CAAAAAGCTA GAAAAGAATT TTGAATACTC ACAACAAAAT
192061 AAATGATAAA TGTTTAAGGT GATGGATATA CTAATTACTC TGATTTGATT ATTACACATT
192121 GTGTACACAT ATAAAAATAT CACTCTTTAT CCCGTATATA TGTACAGTTA TTATATGTCA
192181 ACTAAAAATA AAAGAAAAAA AGAATATGAT CTATCATGAT GTATATATCA TGTGTACTTG
192241 AGCAAAATGT GCATGCAGAT ATTGTGTATA ATGTTCTATA AATCAATTAG CTCAAGATAA
192301 TAGATAGGAT TGTTCAGATC TTCTGTGTCT TTACTGATAT TTTGTCTAGT TATTGCATCA
192361 TTACCAAAAA AAGGGTGTTA AACTCTCCAA ATGTGATTGT AGAATTGTCT ATTTTGTCTT
192421 TTCTTTTCCA TTTTTACTTT ATGTATTTTG AAACTCTGTT ATGACATTTT GCTATGTATT
192481 TTAAAACTTC GTTATGTATT TTGAAACTCT GTTGTTAGAA TCATACATTT ATGATTATTA
192541 TGTTTTCTTG ATGAAATGAC CCTTTTCTAT TGTCGTTGTT TTTGTTTTTT CTGAAATGGA
192601 GTCTCACTCT GTTGCCCAGG CTGGAGTACA GTGGCACAAT CTTGGTTCAC TGCAACCTCC
192661 ACCTCCTGGG TTCAAGCGAG TCTCCTGACT CAGCCTCCAA GTAGCTGGGA TTACAGGCAT
192721 GTGCCAGCAT GCCAAACTAA TTTTGTATTT TTATTAGAGA CAGAGTTTCA CCACGTTGGC
192781 CAGGCTGGTC TCGAACCTCT GACCTCAGGT GATCGCCCA CCTCGGCATT TTTATTTTAT
192841 TTTATTTTTT TGAGACAGAG TCTCACTCTG TCACCCAGGG TAGAATGCGG TGGTGTGATC
192901 TTGGCTCACT GCAACCTCCG CCTCCTGGGT TCAAGCAATT CCCATGCCTC AGCCTCCCGA
192961 GTAGCTGGGA TTACAGGCAC ATGCCACCAT GACTGGCTAA TTTTTGTATT TTTAGTAGAG
193021 ATGGGGTTTT TCTATGTTGG CCAGGCTGGC AACTGACTCC TTTAACAATA CAAAATATCA
193081 CTCTGTCTCT GGTAACACTC TCTGTCTTAA ACTCTATTTT AGCTGTTATT ATTATAGCCA
193141 TTTTAGTCTT TTTATGCTTT CTGTTTGCAT AGTGTATATA TTTTAATATG TTTATTCTCA
193201 AGTTATCTGT GTTTTTATAT TTAAGATGTT TCTCTTCTAG CCAACGTGTT TGGTTCTTGC
193261 ATTTTTAAGT CGATTCTAAC AATCTTTGCC TTTCAATTGA AATATTTACA CCATTAACAT
193321 CTAACATTAA CATTTATTTT TCTTTCCACA GTACACTGGC TAGCATCTCC CATATAATAT
193381 TGAACATAAA GTGTGATAAC TGACATCCTT ATTTCATTCC TACTCTGAGT GGAAAGGGCA
193441 GGGGTGGAGA AAGCATTCAA CAATTTGCCA TAATTATAAT TCTTTTTGTT ACACTGTTTT
193501 CTTCTGCATT AAAAAATATC ATTACATTTT GCATGAATTA TTAGGAGAAA ATATTTTCCA
193561 ATTTTCCTGG AAAATGCCAT AACCACGTCT CTCAATTTTG TTTCCATCTT TCTTCCACAT
193621 TTTACATAAC CTACATAAGA GACACATTAT CAAGTATATT TTACATGGCT TCTCAGTGTC
193681 TTCTCTGTCT GCTAACAGGT TTACCAAGAG ATGGCACTCT TGTATTTCTG GTGGCTATGT
193741 CCATATCGTT TTGCCTTTAA GACAGCGTAA CTACTTCTTT CACCAGTATT AAAGACATGT
193801 ACATTTGATC TGGTTCTTGT GGATGATTTT AAATGACTCA AGCTAATAAT CCTAATTTTA
193861 CCTAAACACT CCATTATTTT AAAATGTATT CCTTTATGCC CACAATAAAC ATTTATTGAC
193921 ATTAGGCTGG ACATTAGGCT TCTCTATGGC AGACATTAGG CTGGACCCTA GCCATATATC
193981 TATTGAGGGA AAAAAAATTA TTTTCTATAT AAGTTTCCAG AAAGCCAAGA TGTGTTTTAA
194041 AAACAAAACA AAACATTACA TTCTAAATGC TGTAACAAGA TAAGAAAAAG TGTTGAGGCT
194101 GAGAGAAGAA CAAAGCAGCA AGCAACTCCT GGAAGGACCA CTGCTGCAGA GGTAATAACT
194161 GGTGAACCAT GTTTTGGAGA AGGAAAAGGT CACCAAGAGA AGGAGGGGGT CCAGGGTGTT
194221 CAGAAAGATT GCATGCATAA AGATCAAGGG TAATAAAAAA AATTCCGTAT TATGTAAATG
```

Figure 2 (Page 60 of 74)

```
194281 TGAAGTTCCA GGACCATGAG CTTGGAGAGC ATGAAGTACA GGAGGAGGGT TGGTTTCAAA
194341 TAAATCTGGG AATGAAACAG TGAAGCCTCT GGCAGAACTC ACATCTCTTT CCTCCCCTCT
194401 TCCTTGCACA TTCCCTTTAT GGAGTAATTG CAGGGATGGG AAAAGTTCAA AACCACCACT
194461 GAGCCTAGGA AGTGCTAGGG TAAAGTGGAG AATGAACCTG CGTGATTTGC TCATCCTAAA
194521 CTAGGTTCTT CTAGGAGAGC CCTTCCCCAT AAAATCTGCC CTCCTCGAAG GGGCCCAGAC
194581 AGCCTAAGCT CACCTCCCAA AGACCCCTTA CTTGCTGACT GAATCTGATT CCACCCAGAC
194641 ATGGCCTAAA ACCCTTCCAT AACTCTATAG CCAAATTCAA TTTTAGACAG GCCTCATACC
194701 AACCTTTCTT CCTCTAAGTC TGCCACCCTA GGCAATTCTC AACATTCTCT ACACACTTTG
194761 GGGCCATAGA CGTGCTACCA AGTCTCCAGA CCTAGACCTG ATGGAGCAGT GCTGTAATGA
194821 GACGACCACT GGCCTTTGAA CCAGACCCTT CTCTGTGGCT CCTATGCATC TCCAACCTGT
194881 TTTGAGCACT GCTGCCAAGA CATCTTTGGC ACTTTGTTGT GAAGTTTTAA AACTGAACTA
194941 ATCTACAAAA CACCTAACCT TTAAAAATTC ATTGTCATTT CATATCATGA AAGATAAAGA
195001 AAGGCCAGGA AACTGTTCCA GGTTAATAGA GACTAAAGAG ATAGCAACCA AATGCAATTT
195061 GTGATCCTGG ATTGAGGGGA AAAAGTGTTG TCAGAGACAT GATTGGGACA GCTGGTAAAA
195121 TTTGAATTTG AATTTAAAGA TAAAGTATTG AGTAATATAG AAGATGATT ATCTGCAACT
195181 TTCAAATGTT TCAGTAAGTA TATATATATA TAAAGAGATA TAAAGACATA TAAATAAATA
195241 GATGGATAGG TAGAGAAAAA GCAAATGTAT AATATTAACA ATCTAGGTAA AAAGTATATG
195301 AGTGTTCTTT GTACTGTTTT TCTGATTTTT CTATATGTTT GAAATCATTT TAAAATAAGA
195361 AGGTTTTTGG GGTTTTTTTG TTTGTTTTTT GTTTTAGAG ACAGCATCTT ATTCTGTCAC
195421 CCAGGCTGTA GCTCAGTGGC CCAATCATTG CTCACTGCAG CCTCAACTTC CTGGGCTCCA
195481 GTAATTCCCC CTACCTCAGG CTCATGAGTA GCTGGTACTT CAGGTGTGCA CCACTGCACT
195541 CAGCTAATTT TTATTTTTA AATTTTTGTA GAGATGGCAT GTTGCTATGT CACCCAGGCT
195601 AGTCTCAAAC TCCTGCCCCC AAGTGATCCT CCCACTTTGG CCTCCCAAAG TGCTAGAATT
195661 ATAGGCATGA GCCACTGCAC CCAGCCCAA ATAAAAAGT ATTTTATTTT AATTAACTAA
195721 TTAATTTTGA GTCAGAGTTT CACCCTTGTC ACCCAGGCTG GAGTGCAATG GCATGATGTT
195781 GGCTCACTGC AAACTCTGCC TCCTGTGTTT AAGCGATTCT CTTGCCTCAG ACTCCTGAGT
195841 AGCTGAGATT ACAGGTGCCT GCCACCATGC CCAGCTAATT TTTATATTTT TAGTAGAGAC
195901 GGGGTTTCAG CATGTTGGTC AAGCTTGTCT CAAACTCCTG ACCTCAGGTG ATCCACCCAC
195961 CTCGGCCTCC GAAAGTGTTG ATGAGCCACC ACACCCGGTC TAAAAGTAT TTTAAAACCA
196021 CAGTCCCACT CTACCTTGTC CTACACTACC AGGGGCTAGG ATCACCCCAT GTCTTCTAGG
196081 CTATGAGATA GAGGAATCCA AGGAAGAAGA TAAGCTACTT GGTTCCTCTA TAGGGTCTTG
196141 TGTGTGCTCT CATGTGCTCT CTCTCTCTCT CTCTCTCTCA CACACACACA CACACACACA
196201 CACACACACA CACACACATG AATACCAGAG CTATCACTTT CCCAGTCTAG TACTCATCTC
196261 ATCCCAAGGG TTTTGTGTTG TAGTGGTTTG CTCATTTGTT TGTTTTGTTT GTTTGCTTGG
196321 ATTATTCTTT TTCTCTTTTT GCAGCTGAAG GGAGAATTTC CAGGCCAGCC CTTTGGCCAT
196381 TAGAGTTACA GTGCCTCTAT TCAGGCTTCA TAGAGAGACC TGGGATTCAG TAGTGGGGGG
196441 CTTTTATCCA GTTCAAAATA ATGCATTCTC ACCAAGATGT ACTTTGAAAT AAAACAATAC
196501 TAAAACACAA AATTTTATTT ATGCTGAACA TTGAATCACT TTTTTCTGTA TTTTGTGTAG
196561 AAAGTTATAC ACACACAAAC ACATTTGCTC CTGCTTTGTT TATTGGCCCA GGGGTATGTT
196621 TGGTAATACT TCATCAGGCA TGAGTAGTAC GTCTTGGAAG GTGTGGTCTA AAGCCTAGAC
196681 TCCTATCTGC TTCCTTCAGC ATTCTCCAGT GTATCTGTCA TCTGTCTACC TTAGGATGGG
196741 GTCTCCAGAA CTTCCATTCA CATTTAGAAG AGGGCAGCGG CTTTCTATGG AAAATATGAA
196801 CTCTCATTCA TCTCTATTCC TTCTTCTAGC TATGGTCCAG CTCAGCTGTT TGGAATAAAG
196861 TATCTATATG AAGTCTGCGA ATGGTTCTCA GACTGGTTGA ACATTAGAAT CACCTGAGTA
196921 CCTTCTAAAA TTCTTATTAC CCAGGGCATA TCTCAGAATG AGTACCACAG GGTAGGGATA
196981 GGATTAGGGA TCATGATCTC TGGAGTCTGG TTTAGGCACT AGTGCTGTTT AAAACTACGT
197041 TCATGAGGTG GAGGTTGCAG TGAGCCGAGA TGGCGCCACT GCACTCCAAC CTGGGCGACA
197101 GAGTGAGAGT CTGTCTCAAC AACACAAAAC AAAAAAAACC AACTACCCTT GTGATTTGAA
197161 TGTCCATCCA AAATTGAGAA CCATTAGGTA AGGCCAAGCT GTATAATTAA AGAGCAGTTT
197221 TCATTTGTCT GGTGTGGTGG CAGCTTTTTG ATAAGGGAAG TATTGTTGCC ATCCACATAC
197281 CTGAGCCTCA CTCCTGAGAA CACTGGTGTG TATGTTGCTA AAATTCCCCA GGTGATTCTG
197341 AGGTTCCTTC CTGGATAAAA ACCACTGACC CTGGGAATGT ACCCACTGCC AATCTCCTGC
197401 GTAAACCTTG GATACTGGGA AGCCTACAGT TGAAAATATT GGGCTTGAGA TCCTGAAACA
197461 AATCTTGTAT TTCATTAAGA CTAATATTTG GTACAGTGCA GCAAATCAAG GGAATTTTGG
```

Figure 2 (Page 61 of 74)

```
197521 TGGCTGAGTT CTTTTAGAAC TTTTGCATTG AAATAGGTTC AAGCAGCAAT AAGTTAAAAC
197581 TACAACCTCA GCTAAAGGAT TAAAAGACAC GTGAGCTGGG TAGGATGAGG TCTAAGATTG
197641 GGTGTGGCGG CTCATACCTG TAATCCCAGC ACTTTGGGAG ACTGAGGTGG GTGGATCACT
197701 TGAGGTCAGG AGTTCAAAAC CAGCCTGGCC AACATGGTGA AAACCCATCT CTACTAAGAA
197761 TACAAAAAAA TTAGCTGGGC GAGGTGCCAG GCACCTGTAA TCCCAGCTAC TGGGGAGGCT
197821 GAGGGAGGAC AATCACTTGA ACTCAGGAGG CAGAGGTTGT AGTGAGCTGA GATCGCACCA
197881 CTGCACTCCA GCCTGGGTGA CAGAGCAAGA CTCCATTTAA AAAAATAATA ATAATAATAA
197941 CAATAATAAT AATTCAGACA TATCCAGGCA TCAAACAGAT ACCTGGGGCA GATGAATAGT
198001 CTTGAGATTC AAGTCACACA TGAAATTTAG GTGGAAAATG ACATTGGAGA AATTTGAGAT
198061 TATGATGAAT GGAAATTTTT CAAAGAGGAA TTTCAGGCTC TGTTCTTGAG GGGATAGATG
198121 GACTTCCAAC AGCAATAACA CAGGATTAAT GAGGACTTGG GATGTTACAT AAATTAGAGA
198181 TGTTAGATGG ATAAAGAGAT AAAAGTACTC TCTCTAAGAA CATGGGACCA GAGATAGGCT
198241 CACTTCTAAC CATCAGATAT AACTAGCAGA CTAAACGGTC TAAAAATAAA AATCATGCCC
198301 CACTCCTGCT TAAGACATTT TAATTACTCT CAGTAACTCT TCAGTTTTTC TACTGTGTTA
198361 TCTTTAACTA CAGGGTTGGT CTGGGTGTGC AACACAAGAA AGCCTGGCAT ATACATGGAT
198421 TCAAGTGTAT GCCATGTACA GGTATTCTTT CATGTACTAT TTCATGTATT CTTTTTCACA
198481 TCTGTTTTTT CCTTCATTGA AGTCAATGGC TGATATTAGA TTCTACTATT CATGTGTACT
198541 AGTTATATAT AATTGTTACA AAACAAATTA GCAAAAACTT AGTGGCTTAA AGCAACACAC
198601 ATTTATTATT ACCTAAGGTC TGTGGATAGA AGTTCTGACA TGGCTTAACT GGGTTCCCTG
198661 CTTCAAGCCT CATGTGGCTG CAATCCAGGT GTTGGCTGAG TCTGAATTCT CATCAGAGGC
198721 TTGATTGTGG AAATTTCCAC TTCCAAGCTC CCTCAGGTTT GTTGAAAAAT TCAGTTCTTT
198781 GCACCGGTAG AAGCTTCTTG GTAGAGGCTG ATTCAACTTC TAGAGGCTGT CTGCAGTTCC
198841 TGTCACCCAG GGTGGAGTGC AGTGGAGCAA TCATAGCTCA CTGCAGCCTT GACCTCCCAG
198901 AATCAATCTG TTCTCCCACC TCAGCATCCT GAGTAGCTGG GACCACAAGT GTGTGCCATC
198961 ACACCTGCCT AAAAAACAAA CAAACGAAAA AAAACCCCCA GAGAACTTTG TAGAGACAAG
199021 CTGGTCTGGA ACTCCTGCGC TCAAGCAATT CTCCTGCCTT AGCCTAAAAG TTCTGGGATT
199081 ATAGGTATAA GCCACCATAC CTGGCATATG GCAAGTCTTG AGCAGGACAA ATACAGATGA
199141 TTTATGTCTG TCTTCCATGG TATTCTAGGT TATTGTTGAG ATGGTCCTCT ATTGTCTTGT
199201 TCCATCTATT GATTAGATAA AACGTTGTTC CTTCTGTTAT TTTTCAACAG TAGCTTTTAT
199261 GTGTCTCTCT TTATCTTAAA ATTCTAACCA AAGAGCTGCT CTTTTCTTGG TGTACTTTAC
199321 CTTTGGTTGA TCCTTCTTAA CCTCTTCTTG CCCTCTGGGG CCTAAGATGA GGGCTGTTAT
199381 CAGATGTGAG TCTATGGAA AGCAAGCAAG AGGTTCTTCA GCCTCCGTTC AGCCTTAAAT
199441 GTCTAGGTAG AAATCAGTCA TGGCCCTTCC AATGTGGTAC AGACCAGATC ACAGAGACAG
199501 GGGTCTCAGC CAAGGTCTTG TGGCCTAAGC CTTATAGAAA TAATGAGTGT TTACTTACTT
199561 GGAGAACTCC CTTGGAATAT CTTTTTTTGT GAACCTGAGG CAACTTTTGG TGATTTCTTG
199621 ATGTCTTGGG AATCTTGGTC TAGAGCCATT TCAACCTGAT TTCTTTTCAT GTCAGTGGCA
199681 TTTTGTGACC AGATAGTAAA TAAGTTCTAT GATGTTCACT CAGAGAAATA CAATGACTTA
199741 TGATGTGAAG CTTCTGTGGT TCAGCCCTTA CTTCATCTTC ATTCCCTCTT ATCTGCATCT
199801 GTCTCCTGCT TGGGAACAAA AGTCTGGCTT CATTCTATGA CCCCCACGTT GAGTTTCTTA
199861 GTAGCACTTA CTTTTCAATT AGGAGTGTCC TCACTTCTAT CCATCAGACA TAACTAGCCG
199921 ACTAAACAGT CTAAATATAA AAATCATGTC CTACTCCTGC TGAAAACATT TTAATTACTC
199981 CCCATCATTT AATTTTTTCT ACTGGGTTAT CTTTAACTTC AGAGTTGGTC TTGTGTGCAA
200041 CACAAGAAAA CCTGGCATAT ACATGGATTC AAGTGTATGC CACGTGCATG TATTCCTTCA
200101 TGTACTATTT CATGTATTCT TTTTCACATC TGTTTTTTCC TCTAAAATTT ATTTCCTTTT
200161 AAAAATGAAA ATTTTGCATT TGACTAAATT TGTCAAATTT AGTCAAATTT GTTAAAACC
200221 ATTTTTAAAA TGTTTCCCGA AGTTTTGAGT GAAGTTAGTA CTTCAGAAAA ACTGTTTTGT
200281 ATTTTTCATG TGACCTCAGT GCACTGCTGT GCATTTCCAT TTCTGCGTCC ACACACATTT
200341 GTTTTGAGGA AATATAGGAA CGACAAGATA AAGTTCAAGC TCCTGGACAT TGCATAAAAG
200401 ACCGTCATGA CCTGGTCCTG TTGACTTCCC TAGATTTCCC GCTATTTCCT AAGTTGAGAT
200461 TTTTGGTTTG GATGCTTTGT GTTTTCCTAA AATCAAAATA GGTTTTTGCC TTTTATGATT
200521 ATACAGTAAA TAAATGCTAT TTGTGTGAAA CTTTAAACAA TACAAAAAAA ACCTAAGGAA
200581 GAAAGTCAGA TTCATCTAAA AATCCTTGTG GCCAGAATTA ACTACCTTAG TTATTATTTT
200641 CTCTATCTCT CTCTCTCAAT GTATATTTGG TGTAGGTATA GGGGTGTGTG TAGTGTGTGT
200701 GTATGTATAT ATCTGTTTCT ATTCCTGTAT GTGGATGTGC ACAACGCATC CTGCTTTGTA
```

Figure 2 (Page 62 of 74)

```
200761 CACTACAGTA CTAGCATTTT TCTAATGTAA TTCAATATTG TTGAAAACAT TTTAAAAAAG
200821 CTTGTATATA TACACACACA TACACATACA TGCATGTATG TACATATACA CATACAGACA
200881 AAAATGTATC CTATGTATAT TCACACATGT ATACACACTC ACACGTACAT AGAGTTTTAC
200941 ATCCATAGTT TATAAATGTT GCTTTTTTTT GGTCACCTTT TTGCTAAGTC TTACACTTTT
201001 TTTTTTTTTT TTGAGACGGA GTTTTGTTGT CATTGCCCAG GCTTAGTGCA GTAGCGCGAT
201061 CTCACCTCAC TGCAACCTCG ACCTCCCGGG TTCAAGCGGT TCTCCTGCCT TAGCCTCCTG
201121 AGTAGCTGGT ACTACAGGTG TGCGCCACCA TGCCTGGCTA ATTTTTGTAG TTTTTTTATA
201181 GAGACGAGGT TTCACCATGT TGGCCAAGCT GGTCTGGAAC TCCTGACCTC AAGTGATCTG
201241 CCTGCCTCAG ATTCCCAAAG TGCTGGGATT ACAGATGTGA GCCACTGCAC CCGGCCAAGT
201301 CTTACACATC TTTTTTTTAC CACTAAACTG TTTACCCAAA CCTGATAACC CAAGTCAACA
201361 GCTATTATGG CTCACACAAT CTTATGTAAA CAAAGATACA GATATATAGA ATTTTCTTGA
201421 TTAATATTCA GAAAAAAATG GAGTCCCTTT ATACGTCCTT AGTATCTGCT TTACTCATTT
201481 AAAAATGTAT TACATTATAT GAAAGTATTC AGGTCAAATG TTATAGATGT GATTCATTCT
201541 TTTTAACTGT GTTATTTTTC TGCAATGACT ATGTATCACA AAGTACTCAG TCTTCCACTG
201601 ATGAAAATTT GGGCTATTTC CAGTTTGTCT TCCATTTTTC TTTCTTCCTC TTGGATTTTC
201661 ACTCAATGTG TTTACTAATT TAGGAAGAAT CAATAGTTTT TATGGTATTA CTTCTCCCAT
201721 TCAAGAATAT AGCATATGGT ATAGTATAGT AGAGTACTTA GTTAATTTA GCCAGATCCT
201781 GTTTTCTGCC CTTTAATAAA ATTCTATCAT TTTCTGCCTT TGAGTCACAT TTTCCTTGTT
201841 CATATAATTC TTAAAAAATG TATAGTTTTC ATTCTAAGGG AACATAAAAA CTTCTTTCCA
201901 TTTCTATTCC TGTCTAGTTA ATTCTACTAT TGGGAAAAGT AACTGTTAAA AAAAATTCTT
201961 ATCTTTCCAG TCAGTTCACC ACATTTCCTT TATACCTTTG TACTTTAATC CCCAGTCATG
202021 TTGAACACTT CTTATTCCTC ACACCAAGCC TCAACGGGTT TGCTCTTTCT GGAAGGTGCT
202081 TCCCCTGTAT TACTGACTTA TTCATACCAC ACATGGAGAC TGGCGCAGCC CTGTTCTGCC
202141 TGGGAAGCCT TCCCCTGATA CCCCTAGTTG GCAGGAGTCT TCATTTGTTC TTTTCTAGTC
202201 ACCTGTGCAA GTTTGTATTG TTCATGTTTA TCATCCTTCA TTCTAGTTGT CTGTCTCTAT
202261 GTGTGGTCTC ATTCAGTGGA CTCTGAACTC TTATGAAGTC ATGTCATGGG TCAGATCTTA
202321 ATAAATTAAT ATTGTCGGAA GCTAATGTCA TGTCTAGAAT ACAGAAAATT TATCAAAAAA
202381 AAATATAGTA TGTTGGCTGG GCGCAGTGGA TCAAGCCCGT AATCCCAGCA CTTTGGGAGG
202441 CCGAGGCAGG AGGATCACAT GAGGTCAGAA ATTCAAGACC AGCCTGGCCA AAATGGTGAA
202501 ACCTCATCTC TACTAAAAAT ACAAAAAGTA GCCAGGCGTG GTGGTGCCCA CCTGTAATCC
202561 CAGCTACTCA GGAGGCTGAA GCGGGAGGAT CACTTGAACC TGGGAGGCAG AGATTGCAAT
202621 GAGCTGAGAT CATGCCACTG CACTCCAGCC TGGGCGACAG TGAGACTCCA ACTCAAAATA
202681 ATAGTAATAA TAATAATAAT AATTGTATGG AATTGAACTG CTCTGATTGG AAATAGCTGT
202741 TTTTTAAAAA ATTATTATTT TTTAAGTTCC TGGGTACATG TACAGGATGT GCAGGTTTGT
202801 TACATAGGTA AACGTGTGCC ATGGTGATTT GCTGCACCTA TCAACCCATC ACCTAGGTAT
202861 TAAGTACAGC ATGCATTAGC TCTTTTACCT AATGTTCTCC CACACCCCCA CCCCATCCTC
202921 CCCCAACAGG CCCCAGTGAG TGTTGTTCCC CTCCCTGTGT CCACGTGTTC TCATTGTTCA
202981 GCTCCCACTC ATAAGTGAGA ACATGAGGTG TTTGGTTTTC TGTTCCTGCC TTAGCTGTTA
203041 ATGTCAGGCC AGAGAGGCTT AAATTTTTAA GGATCTCTGG ACTTTTCTTC TACATTACTC
203101 TTGATGTTTA TAAATGTTAC AACTTCTTTA ATTTCATTAA ATGTATACCT TATTGAGTTG
203161 ATTTAACTGA GTTAACTTTG TTATATGAAA ATCATGATTG GGAGTGAGGG GGTTAAACCA
203221 GCTACAGAGA TCTTGATTGT TGGTGGTGAA GCAATGCAAG AATTCATTCA TTCAGTAAAC
203281 TAATGTTTAT TAAGCGTGTA CTGTCTTAGT CTGTTCAGAC TGCTGTAACA AAATATCATA
203341 AACTGGGTGA CTTATAAACA ACAAAAAATT TATTTCTTAC AGTTCTGGAG GTGGGAAGTC
203401 TAAGATTAAG GCCCTGGCAA ATTTAGTGTC TGGTGAGGAC AGGTAGCCAT CTTTTTGCTG
203461 AGTCCTAACA TGGCAGAAGG GTTGAATAAA CTTCCTTGGG TTTCTTTTAT AAGGACACTA
203521 ATCCTAGTGA TGAGGTTTCT GCCCTCATGG TATAACTACT GCCCAAAGAC CCCTCCTTCT
203581 AATATTATCA CTTTGTGGGT TAGGATTTCA ACATGAGTTT TGAGAGGATA CAGACATTTG
203641 GATCATAGCA CACACCATAG GACAGACACT GTGCCAAGAA TTGTGGATAT AGTGATTCTC
203701 AAAATGAACA AGATCCCCTC AGAGAGCTTG CAAAATCCAG CTATAAAATT ATGCTTTTTA
203761 AACAAATTAT GCAGTTTGAA AAATCTACTC TGAATCTTAC TTGTGGCATT GAATACTTTC
203821 GGCCACTCTT TCCTTATTAT ATTAAATATT TACTCTTGTT TGGGGGATCC AGTCTCACCT
203881 ACTTTTTCTA CCAGAACTGG TATCAGCTCA TGCTCTGCCT TATGCAAATT AAGAAAATAT
203941 CATACCTTTT GGGTAAATTA AGCCAAGAAA GTTCTCCTTT CTTCTCTTTC TCTCTTTCTT
```

Figure 2 (Page 63 of 74)

```
204001 TCTTTCTCTC TTTCTCTTTC TTTCTTTCTC TCTCTTTCTT TCTTTCTTTC TTTCTTTCTT
204061 TCTTTCTTTC TTTCTTTCTT TCTTTCTTTC TTTTTCTTTC TTTCTTTCTT TCTTTCTTTC
204121 TTTTTCTTTC TGACAGGGTC TTGCTCTATT GCCTAGGCTG GAGTGCAGTG GTGCAATCTC
204181 AGCTCACTGC AGCCTTGAAC TCCAGGGCTC AAGCAATCCT CCTGAGTAGC TGGGACTATA
204241 GGCATGTGCC ACAACATCAA GCTAATTTTT GCATTTTTTT GTGGAGACGG GATCTCCCTA
204301 TGTTGCTAAG GCTGGTCTTG GATTCCTGGG CTTATGCGAT TCTCCTGCCT CAGCCTCCCA
204361 AAGTCCTGGG ATTACAGGCA TGAGCCACTG CCCCTGGCCA TTATAACTAT TTTCATTGGC
204421 TTATCAGGCA CATGATAACT ATAATAAATC AATAACCAGA ATTTTTAAAT AAAGAAAGGA
204481 AGGAATTGTT TCAACTCTTC CTGCTACCCC TCTATCCCTC AAAAGGGTAG GCTGAATGTT
204541 GTCCTCCAAA GATATCCATG TCCTAATCCC CAGAACCTGT AAATATATTA CCTTATATGA
204601 CAAAAGGGAC TTTACATGTT TAATAAGTTA AGAATTTTGA GATGGGCAGA TTTTCCTGAA
204661 TTTTGCAGAT GGGCCCTAGT GTAATCACAA GGGTCCTTAT AAGAGACAGG CAGAAGAGTC
204721 AGAATAAGAG AAAAATACTT CAAGATGTTA CACTGCTGGC TTTAAGGTGG AGGAAAGGCC
204781 AAGAGCCAAA AAATGCAGTG GTCACTACAA GCTGAAAAGA AAAGAAATG GATTTTCCCC
204841 TAAAGCCTCT GGAGGGGGCA CAACCTTGCC AATACCTTGA TTTTGGCTCA GTGAAACCCA
204901 TTTTGGACTT CTGACCTTTA GAACTGTAAA TAAATAAATA ATTTTGTGTT GTTTCAAGCC
204961 ATCACAGTTG TGGTAATTTA CTACAACAGC AATAAAATAG AATTAAATAC AGAGATCTGA
205021 GGAGTTGAGT AGGATAAGCC TACTCCAGCA GGTTATTTCG GGAGTATGGT GAGACTCACT
205081 AGGATGGCGG AACTCAATTA AGGAAGTCTG AAGCTGATAA GCCAGAGAGG GAAGGCTCTC
205141 ACTTCATTTT ATAAGGGTTG CGTCACACTA GGAAGATCCA ATAGCAACCA CAGTCTCAAA
205201 ATTAATGATT ACAAATAGGA CACAATTCCA AGAGTCGGGA GCCAAGCAGA AAATGGATTA
205261 GGGAAGACAT GGATGATATG AAACAGGAAG GAGGGGTACA AGGCAGCTTC CTGGGAAGTT
205321 GCCAGGGCAG TCACAGTTCA CATTCATTAG GCTGTGGGCA CCAAATGCAT ATGGAAAATC
205381 TAGCTGACTT AACTGAACTC CTGAAGAGGA ATGAACACCT CATTTATTGA GGAGCTACTA
205441 CCAATTAGAA TATGTATTTC ATTTGTTCAA TAACCCCATG AGTACAGTAA CACAATCCTT
205501 GCTTTACTAA AGCGGAAGCC AATTCAAAGA GGTTCAGTGA CTTGTCCAAG CTCAGGGAAA
205561 ACACTAGGAA GTGAATATGG GTCTGACTCC ATCACTGATT TCAGGAGCCC TGCCCTTTCC
205621 TCCACACCAT GCCCCCTTGC TTTCAGAAAA AAAGGCTTGT TGACTGAATG GTTGTATGCA
205681 CAGTTCAAAG CAGAAACACA CGATGACATC TTTTGAGATA CTCTAACAGT GAGAACTTGA
205741 AAATGAAGTT AAAAATTAAG CGGCAAAACC AAGCCGAGGC TTTCTGAGAA AGTGGGCCA
205801 AACCTGTTGC CGTCTGACTG CCACGTGGCT CACTATTTAT CCCTGTAAAA ATCTGCAAAA
205861 GTATTTGAAA GGGAAGAAGG GACAGAAAAC TCCCTCCTTT TCCAAGTTAG CCTTATAGTC
205921 TAGGGCTTAA AATACTGGTT TAATGGTGAA GGTAAGTGCT TTTCTTCTTT TTGGGTAGAA
205981 GGATTATTAC TAACTTACCA AAGGTCCATT AAGGGGAGGG AACAGTTTTA GGAGAAGTCA
206041 GAGAAAAGAC ATTAACAGCA ACATAAGGAT CTCCATCTGG TAATATTGCC TAATTCCAAA
206101 ATGAAGAGAC TCTCTGAAAA AGATAACTGA TTCAATGAAG ACCCTAGGGC AAGGCTTGAG
206161 AAGCCACTGG TACCAATGGA CACTGTGGAC AATGGTCATT TCTCCAAGGA CGCTGTGAGT
206221 ATTAACTGTG ATGCTGTGAT TAGTCAGACT GGGATTGGCT GTGGAATGAA ATACTGATCA
206281 GAACTGACAA GATTTGTGTT TGGGACTGTG GCTAACGAGT CTTTTCAGAC TTCTATATGA
206341 ATTTGAAATG GTCTCTCAGG AAAAGGAGAA CATGGCCGGG CCTGGTGGCT CACGCCTGTA
206401 ATCCCAGCAC TTTGGCAGGC TGAGGCGGGC AGATCACTTG AGGTCAGGAG TTTGAGACCA
206461 GCCTGGCCAA CATGGTGAAA CCCTGTCTCC ACTAAAAATA CAAAAATTAG CAGGGCGTAG
206521 CGGCGCGTGC ACCTATGCGC ATGCATAGTG CGCGTGCCAG CTATTCAGAA GGCTGAGGCA
206581 GGAGAATTGC TTGAACCCAG GATGTAGAGG TTGCAGTAGT TGAGATCATA CCACTGCACT
206641 CCAGCCTAGG TGACAGAGTA AGACTCTGTC TCAAAAAAAT AATAATAATA AAAGAAAAGG
206701 AGAACATGAC CAAAGTTATG AATAAGACTG AAGGCAAGAA AATTGTACGC TTGTAGAGAT
206761 CACCTAGCTT GTTGCCCTCA TTGTACAGCT AAGAAAAGGC ACCCAGGGAC ATTGTGGTCA
206821 GCACCAATTT CTCAGAAAGA TAGGCAGATG ATGAGAGGGC CCTCAGTTTT CTAACACTG
206881 AAGGAATTGC TTCTATGTTT TCTGGTGAAC TCCTCCCCAC TCATCTTGAG GATTCCAGGC
206941 CAGAAGAATC CACTTTAAAA AAGAAACATT TAAAACCAAT TAACAACCA ATCAAAGGCA
207001 CTTTTATAGA AATACATTTC ATTTGCTGTT GGCCTGTATT TATGGATCTG AGAGGGCTAG
207061 ACTGCCAATA TTGTGACTGT TTATTATTAT TGCTGTTGCT AGTATCTAGA ATATTATACA
207121 ACATATAACA CTTTGCAATT TACGAGGCAT GTCTCATACT TTGTTTTCA CTCCAAACTG
207181 CCCAGTGAAG TAACATTATC CCAATTCTTC CTATGAAACA GTGAAAGCCC TAAGAGTTTT
```

Figure 2 (Page 64 of 74)

```
207241 TGAAACTTTA CCTGGTTTAC TCAATTTGGG AATGGCAGAG CAGAATTCAG TCCTTGAATA
207301 TCCTCCCACT GCAGGTTCAT GCTCTTTGAT CTAGGTGTAA CATTTACTCT GAGTAAACTA
207361 GGACTCTGGG CTAACAGAGA TGAAGCAAGA CAGGCTGGAT ATTAGGAGAA TCTAAGAGCA
207421 ATCTAACGAC CATTATAATA AAATCATGAG TTCTAGACTT AAAAAAAGGG AAAAACCTGT
207481 TTTTTTGCTT ATGCGTATAC CATAATATTT ACATTATTTA TTTTTTTCTC AAATTCAACC
207541 TATACGGTGT CAAGTAATTT TTTTTAATAT AACATTTTCC TTTAACTTAA TTTCAATTCA
207601 TTTTTCTGTG TCTACTTACA ACTTTGGCAC TAGAATTCAC AATTTTTTTT TAGAGGTATA
207661 TCTCCTTAAA GGGAAGGGTT CTGACACTGT TACATGTTCT CAATTGTTTG CAAATAGGTT
207721 AATAATTATT CCAGTGTCTC TAAGTACATA TCAACCATGC CAGTGTTCAG CCTCCATAAT
207781 TTTATTAGCT TCTGTGCTTA TTTTGGAAAA ACATTTCCCA TTACCATGAA AGACCTCAGT
207841 TTAGGATGGT TTGGTATGTT AGCCTGATTT CTGCATTCGT CTCATGCAAA GGAAAATAGG
207901 AAACGAAGAA CTGAAATTAC CTATTGATAC AAAATCAAAG TAGCATTTGA AACCATAAAA
207961 CTTAAGTAGG GCTTTTCATC CTTTCTCGTT AGACAGCAAC AGAGAATGGG AAGAAAAACT
208021 AAAGTGATGG GTTTGTGATA CAATTCCAGT AACATAAAGA GCAAGGAGAA GTAGTTTTGT
208081 TGTGTTTATG TTTAATATTC AAAGCTCAAC CTAAAAGTAT TTTTCATTAT CAAACTTCCT
208141 TCTAGAATAA ATGATTAAAA CTTGATTTAA AATATACAAA TTCTCCTTTA TAATACCTCA
208201 AAATGGAGCT ACCCCATTGA GTTTTAAGCT TGTGATTAAA ATATTACGAA AACAAAGGGG
208261 AAGTTGTAAT AGGTAGAACA AGCAGTAGTC TAGGCATTAG GGGATCTGGT GCTGGCTCTG
208321 TGCATCATGT GGTTTCAGGC AACTTTTCAA ATTTTCTACG CAAATTTTCT TATCAATAAA
208381 ATAAACAGTT GGGCCAGAGG ATCTCTGAGT CTCTTTCAGC TTTCAGTGTT TATAAGATTG
208441 GAGAAGTTGG TGGGAAAGCT TTAAGTGGAG TGTAAGTAAT TGCAGCTGCA TGTACAGTTA
208501 AAGAGTTGCC TTCAGCCAAG CCACGGGATC TTGCATAAAA AGTGAAATCA AATAGAAAAT
208561 GGTCCAAACT CTGGGTTTGA CCACAGATGA CTTCAGCTAG GATCTGAGTG TAGAGCAATG
208621 AGCTGAACTC CTGATATCCA GATGTTAGCA AGACTTGGAG GCCTTCTAAG GCAGAGCAAC
208681 AACCAGTATC TGTCCTGGTG CTGACCTGAT CTTACTAGCA ATTGGGCCTC CATTTGGGTC
208741 CATTGTACAA AACAACAACA ACAACAACAA TAAAATCTCC AAACACCCAA AATTCAAAAT
208801 TTAGATGGAG AGATACTATT CCCAGAATTC TAGAGATATT TGGAAAGCAG AAAACTATAC
208861 TTGCCATGCT GATGAAGTCC AATTATTGCT CTTTTAAATA CATTTAGCTA CTTCTGAATA
208921 TAAAATGAGT ATCTACTAAT TATTTACAAA ATCACTTGGT AAATATAGAA AGTCACAAAG
208981 AATGAAGTGA TCATCCTGTT TTGTAACCCA GAAATAGTCA TTACTGGCAC TTGTGTGAAT
209041 CAGTTTCTAT TCCTGTATGT GGATGTGCAC AGCGTATCCT GCTTTGTACA CTAGAGTACT
209101 AGCATTTTTC TAATGTAATT CAATATTGTC GAAAACATTT TAAAATAGCT TCCATCACAA
209161 TAATCTATCA AATTGACTTG CCAGACTCTC ATTATTAGGT TAATTTATCT CTAACATTAT
209221 GCAGTCATGA GTAATACTAC AAAGGATATT TTTGGACACA ATTTTTCATC TATGCCTTTC
209281 TTTATAATCC TTCATCCTAA GGTCACAGAT TATGAATATC TTTAAAGTAC GGACAAGTCT
209341 TTTAAATTTT GTGTGCAAAA ACAGTGCAAA GCCTTGAATG ATAAAATAGA GGTTTGATAT
209401 ATGTGTTTTT TTGTTTGTTT GTTTTGAGAC GGATTCCTGC TCTGTCCCCC AAGCTGTAGT
209461 GCAGTGGCAC GATCTTGGCT CACTGCAACC TTTGCCTCTT GGGTTCAAGC AATTATCCTG
209521 CCTCAGCCTC CTTAGTAGCA GGGTCTACAG GCATGTGCCA CCACACCCGG CTGTTTTTGT
209581 ATTTTTAGTA GAGATGGGGT TTCACCATGT TGGCCAGGAT GATCTCGAAC ACCTGACCTC
209641 AAGTGATCCA CCCACCTCAG TATCCCAAAG TGCTGGGATT ACAGGTGTGA GCCACTGCAC
209701 CCGGCCGATA CATGTGTTTT TAAAGTCACA GAAATTTCAG ATGTCTTGAA GGATTTTAAG
209761 CAATTTAAAA AATAAAGTCA TAGAAGCTTC AATTTAGGAA TGAATGGAAA ATTGATGATA
209821 TTCTTAGGAT ATGGATTTTT CCTAAAAGAA ACAAATGTAT GCATCCCAA AGATAATTTG
209881 ATTAGTATAC AAATATTAAA TTAAACATGT CCATATTTAG AGCCATGAAT TCTCTTTGCC
209941 TGTCACAATA GCTGGATTTA TTCACAATTG TAGTAATTAG TCCCTGTTCA TTATAATTTT
210001 CTAGGTGATA TGAAGACTTT GTCAGTCCAA GCAAGTGTCC ACATTGTGTG TAGCAAACAT
210061 GAGAATAAAC ATTTTAAACT TTTAAATGTA ATACATATTA GTGTTATGTA ATGTCATCCT
210121 TCATGTTCGA AGGCACATGG AACATTGTTC TGGTGGTACA GAGGGGAGAG AAACACCATC
210181 AGAATGAAAG GAAAGACCGC TCTGGAACCT TCCTCCTTAG CTCTTGAGCT TAGTTTAATT
210241 GTCCTGTCTT ATGGTCTGCT ACAAGCAATA CCACTCTTCA CCTTCGCATG CTTCTCTGTG
210301 GTTTGATAAA GTACATGCAA TTTTTCATTT AATTCTTCCA GCTGCACTAA GAAAGGAGCC
210361 TTATCTTTAT TGAACAGATG AGGAAATGAA TGATTAGAGA ATTTAAATGA CTAGCTCTAG
210421 GTCACACAGC TGGAACTTAC AGCCAGATTT CCTTTTAACA ATCCTGTAAC CAAAAGCATA
```

Figure 2 (Page 65 of 74)

```
210481 CCAGTAGTGC CCCATAAAAT GTAAGTTATA GAGCTGTGTT GGGTCAAAAC TTTTACTGAT
210541 GCTAAGAGGA GGCAACATTA ACAAGGGGAA ATTATTTGTG TATTATGTTT TGGATTATGT
210601 TCTCTCCATA GATAAAAGAC TGTCGTAGTA AAAGAGATTC AGGGCACAGG GAAACTCCAC
210661 CACAAAGCGT GGTACCATTT CCCACAGAAG CTAAATGGAC GGGAAGCCTG CCACCAGGAA
210721 AGGTAAAGCC ACTGCTCTTG TTTGCAGGCT ATGTTAATAA GCTGAAGCTT ATTCCGACAC
210781 ATTTACACAT CTCTGCATCA CACTGACCCT TCGTAAAGAT ACTCCCAGTG TAACATTGGA
210841 GCCAGCTCCA GCCCTGATC CTGTTGCTTT TTCCTTAGCC CCATGAAATC ATCTGCGAGA
210901 AATTAAGCCA AATAAGCAAT AAATCCTGGG ATCTAGGGAG TGGAATAAGT TTTGGGAAAG
210961 TCTTTTTTTT TTTTTTTTG ACTGAGTCTT GCTCTGTCTC ACAGGCTGGA GTGCAGTGGT
211021 GCGATCTCGG CTCACTGCAA CCTCTGCCTC CCGGGTTCAA GTGATTCTCC TGCCTCAGCC
211081 TCCCGAGTAG CTTGGACTAC AGGCACACAC CACCATGCCC AGCTGAATTT TTGTATTTTT
211141 AGTAGAGATG GAGTTTCGCC GTGTTAGCCA GGATGGTCTC GATCTCCTGA CCTCGTGATC
211201 CACCGGCCTC GGCCTCCCAA AGTGCTGGGA TTACAGGCAT GGGCCACCAC GCCTGGCCCG
211261 GGAAAGTCAT TTTAAACCAA CCTATGTATG AATCCCTACT ATAATATTCT CACCAAGCGG
211321 CTGGCTCTTT CTCCTGAGCT TGGAAACCTC CAGTAAAATG GAAATAATTA TTTCCCAGAC
211381 CACCACTCTT ATCTGTGAGC TTTTTTGGCC ATTAAAAATT ATTTCTTCCA TTATATTTTT
211441 ATCTGTGTCT TCACAGGTTT TCTCTTTCTT TCACTTTAGT GCTTTTCTTC AAATAAGCAG
211501 GAAAAATCCA ATCTATCATG CACATGGAA CCCTTTCAAT ATTGGTCTGT GGTTGTTCCA
211561 TTTTATGGGG ATGCTTTTAA AGAAAAAATT TGTCCTTTCA ATATATTGAA TATCTTCCAG
211621 CACCACATCA CCTGCAAGCT TTGTAAAAAT AGTTCTACAT ATTAATTTTT TTTTTTTTG
211681 AGATTGAGTC TCATTCTGTC ACCCAGGCTG GAGTACAGTG ACATGATCTT GGCTCATTGC
211741 AACCTCTGCC TCCTGGGTTC AAGTGATTCT CCTGACTCAG CCTCCCGAGT AGCTGGGATT
211801 ACAGGCATGC ATCACCATGC CTGGGTAATT TTTGTATTTT TAGTAGAGAT GGGGTTTCAC
211861 CATGTTGACC AGGCTGGTCT CAAACTCCTG ACCTCAAGTG ATCCACCTGC CTTAGCCTCC
211921 CAAAATGCTG GGACTACAGG CGTGAGCCAC TGCACCCAC GTAGTTTTTT TTTTTTTTA
211981 AGTTGAACAT ATGTGAAGGC AGGACCTAGT GACACATAGC AATAACATTT CCAAGTAGAC
212041 ATTACACTAG GGAATTAGTC AAAGTGCTCA TTTAAAGTAC CATCTCTCAA ATGTATTAAA
212101 AGAGAATCCT TGGATGTGCA ATACCTTAAT TCAAAGGCAG CTCGTTATGT ATAAACTCTC
212161 AAGCTTTGTG ATAAACAAAT GTGCATAACA GATGGGACTA TTGACTTACA GCCCAGGGAA
212221 TTTTATTGAC GCTGAGAAGG TTATGTGACT GGCTCTGCCA CTGTCATCCC CATTCACTTC
212281 ATTTTGGAGC AATATGACAT AAATGCCTTA CATGTGGGTT TTCTCTATTT ATCATGTGTT
212341 TCCTATCCCC TTGAAAGATG GCCATATTTG CTTTACTTGG TTATAAGATC CCATATTCGC
212401 TGTCTTGAAG CCAACCAAAT AATTTGACAA AGTGGGTTTG TAGTGCTGGC TATTTTGGTG
212461 AAAAAAAGAC AATGAGACTT CATGTGTCAT CCAAAGTTCT ATCAGATCGA GCTGTGAGAG
212521 AAAGGAAAAG AAAGGGGTCT CAGTCAGGAT GCTCACTGCA TACATCTGTG TTGTTGTCTA
212581 GGTCCAGATT TCTGTTCATT ACGCTATGGG CTGGCTCTTA TCATGCACTT CTCAAACTTC
212641 ACCATGATAA CGCAGCGTGT GAGTCTGAGC ATTGCGATCA TCGCCATGGT GAACACCACT
212701 CAGCAGCAAG GTCTATCTAA TGCCTCCACT GAGGGGCCTG TTGCAGATGC CTTCAATAAC
212761 TCCAGCATAT CCATCAAGGA ATTTGATACA AAGGTAAGTA TGATGGAAAA TAGGGCTCTT
212821 TGTTGAGAGA AAAAACTTTG AAAGGAAGGC ATAGATCTTG ATTCTGTGGA GTATGGAAGT
212881 ATACATTTCC AATGACAAAT TAAAACTGAC TGGAACTATT TTTCTTTGAG ACATTGCTTA
212941 CTTCAATAAT AAAAATAAGA TTTCATTGAG GTTATTATGA TTATAAGGTG GGGGAACTGT
213001 AGAGTTAAAT GTGAAAAATT TAAAAATGGA ACAGTTTATG TGATGTCTTC AATGAAAAAC
213061 TAGGTATTAC CTGGGCACAT TCTTATAGGT TACTCAATCC TATTCAGTTC TCTGCCTGTT
213121 TTATTGTTTC TGAGCAATTT TATATCCCTG TAAATTCTAT ATAACCAATA GAAATGCAAA
213181 CGATTCTTGT CCATAGCTTT GCAAATAAAT TTGCCAAGA GAAAAATCAG TTAAAACTTT
213241 TCTCCACTCA CCTCCCAGTT GAATTAGCCA ATTTTGCTGT TTGTTTGTTT GTTTGTTTTT
213301 TGAGATAGAG TCTTCCTCTG TCATTCAGGC TGGAGTGCAG TGGCATGATC TCAGCTCACT
213361 GCAGCCTCCG CCTCCCGGGT TCAAGAGATT TCCTGTCTC AGCCTCCCAA GTAGCTGGGA
213421 GTAAGGGGGC ATGCCACCGC GGCTGGCTAA TTTTTGTATT TTTAGTAGAG ACAGGGTTTC
213481 ACTAGGCTGG TCTCGAACTC CTGACCTCAG GTGATCCACC CGCCTCGGCC TCCCAAAGTG
213541 TTGGGATTAC AGGTGTGAGC CACTGTGCCA GGCTCTGCTG TATATTTAAA GTCTATTTCA
213601 GCATTGCTTC CTGCTTGTGT TATGCGTGAT TCTTTGAGTT TTCCTTTGAA CCAGTTATAA
213661 CATCTTACTT ACTTCCTCCA TTAATCAATG AGTTAAATAA AATCTTTGTT GTATGTTTAT
```

```
213721 TTTACATTTA TATGAAAACC ATGAATTTAC CCAATTAAAA AAATTATCCT TTAAATTATC
213781 TTGTACTGTA CATTTCCCAT GTCATCCCTA TAATTCATGA TTAATGATTT TATTACATTG
213841 GACCTAGCTT ATTTACAATG AGTACATAAA TTTATTGTCT CCAGTCTTTC CTCCATTATC
213901 CCGTCTACAT ATCCACACTG AGTAGATTCA CTACTCAGGA ATCTTGGACA CCTTCAAGTT
213961 GCCAAACATG CAGTGTTCAC TGGACATGCT GTGTTCCTTC AGAATTTGGG CCTGCTTCTC
214021 AGCACACTCA CATCTGCTAT CAATGACCCA TGGAAAGTTT TTGCCCTGAG CAAGCCAGAG
214081 TCCCTGTTAG TTTCTTCCAA ATGCTACAAG TTCACTTTTG CTATTTTTTC CGATGAGATA
214141 AAATTTTCCT TTTTGACTTT CTACAAATCA TAGTCATTTT TCAAGGGATA GTTCAAGTAT
214201 TGCTTCCTTT CTGGGACCTT CCCAAATTAT TATTTTCTCC TCTCAAAGTC TCTGTTTTAT
214261 TTATGTTCAT CCTCAAATCT TGATTCTCAC ATGAATCATA TACCTTGTAT TATTTATAGT
214321 TTTTTTGAGT AGGTAAAATA TTTCATATTT TATATTCTTT GGCTCTCTAC TTTATAGCAT
214381 GATGCCAGAT ATTTAGGGGC CTTACTGCAT TTATTTTTTA TTTTATTTTA AAATCTATTT
214441 TATTTTTTAT TTATTTATTT TAAAATCTAT TTATTTTTAG GTAAATATTC AGGTAATATA
214501 ATTTATGTAA TTATTTAGGA ATTTTAGGTA GTTATTTTAA AATAATTCAA ATTATTTATT
214561 GAGTTATATC AGAAGAATGT GATCTTATTC ATTTGTAATA TGTGTTTTAG GAACTCAGTT
214621 CAGCCAGGGC AGACCATAAT TCCCAAACTT GACTTTTCTT TTTAATTAGG CACTGATTTT
214681 GGTTAAGAGT TCAGTAAAGT TTTGTGTGTG TGTTTTAAAA AATTCTTTGA TATAAGAGTC
214741 AAGATGTTAC TCAACTTTTA CTAGAAGCAA AATAGAGGAA GTGCTTTCAC AGATGAAATA
214801 TCTCTCAATG TTTTCTTCCA TTTACTTCTT CCTATTATTC ATCTATATAA TCATTTTCTT
214861 TACCTCTTTT CTTCATTTCT TCTGTTTTTC TCTCCTACTA AGACAAGCAA ATTAGGGGTA
214921 TAATTGGTTA TTTGGGAAGG TAGGAAGAAT ACAGAGAGAA ACAAAAATCA ATATTTTATA
214981 CTAGGGTCTC ACTAACCTCA AGCAACTCTG ACTGTAAAGT AGATTTTCAT AATAGGACTT
215041 CTTGACAAAG AGTTTTCCTA TTTTTCCCCC AGGCCTCTGT GTATCAATGG AGCCCAGAAA
215101 CTCAGGGTAT CATCTTTAGC TCCATCAACT ATGGGATAAT ACTGACTCTG ATCCCAAGTG
215161 GATATTTAGC AGGGATATTT GGAGCAAAAA AAATGCTTGG TGCTGGTTTG CTGATCTCTT
215221 CCCTTCTCAC CCTCTTTACA CCACTGGCTG CTGACTTCGG AGTGATTTTG GTCATCATGG
215281 TTCGACAGT CCAGGGCATG GCCCAGGTAT CCAGATACTT TCTCATTCTT GGTGGGATCC
215341 AGATTTCTGA ATTCTACAAA ATATCAAAGG TCTTAATGAT TTTCATTTCA GGGAATGGCA
215401 TGGACAGGTC AGTTTACTAT TTGGGCAAAG TGGGCTCCTC CACTTGAACG AAGCAAGCTC
215461 ACCACCATTG CAGGATCAGG TAAGTGTGCA CAGATGGGTC ATAGCTTTGT CATCTGTTCC
215521 ATCCCACTGT GTCTTATCTT CTATGAATCA AATGGTTTGG GGAAGAGAGA GAAAAAGTAC
215581 TGCTGAAAAA TTCAACAATA TAAGACACTT GCATCACAAA TAGGAAAGAT GCATCTGTGC
215641 AGTAAAGACA TTGAAGCTTA GAAGTAGAAA AAACCATTGT GAGCTAGGTT TCAGCTCAGA
215701 AAAGCCTTAG TAGTCAGAAA AGCCTTAGTA GTCAGAAAAG CCTTGTCGGA AAAAGTTTAA
215761 ACCTTTAAGA ATTGCACACA TGGAAAAAGA TCAAGTAAGC TATATATACA CCATCTTAGC
215821 AATGATTTTG AAGTGAGAAT TAAGGCTACC ACAGCTCCAG GTGGTAAGGA GAGAAATCAG
215881 GCTGGAAGAG TTTGAAGTTT CTGTATTATT CTAAGCTCTT TACTATTCTA TTATGAGCTC
215941 ATTAATTCTC ACAACAACCC TCTCATATAA GTACCATTTT AAATTCTTAT TTTACAGAGA
216001 AGGGAGTTAA GGAAGGTGGA GATTAAGAAA ATTGCCCAAA TACAAATAGC CAGCAGGTGG
216061 TAGGTCTGAG ATTTAAGCCC ATGCAGATTT TAGCCCCAGA GCAGACATTC TCAATCACTA
216121 TGCTAGACTG CCTTTCCATG GTATGTGATC CTACTCAGGC CTCTACAGCT TTATCATTGC
216181 TGTTCTCCCC AGCCTGTCGT GCTGAGAGTA TATACTCGAA GAGCAGAACT AAAATTCCAT
216241 CCAGCTTCTC ACTCCTAGGT CCACTACACA GCTGCATCCT GCAGACTTTT ACCTCAAGCA
216301 ACCCTCCTGC GTTCTTGCTT CCTTCCATCA TAGTTGTAAC CATCTCCTCT ATTTGCAAAT
216361 ACTATCTGCT GATCTCTCTC TTCTAGACTG GTTTCTTTCA ACCTTCTTCC CACCAAAACC
216421 AAGTTAGCTT GCTAAAATAA AGATGGCGCA TTTTTACTCA CCCGCTTGAG AATTTTCAAT
216481 GTGTTCCTTC ATGCTTACAG AGTAAAGCCT GACCTCTTTA TTGCATGAAT ACAAAAGTTC
216541 TTAGCCATCT GGCCCCAACC TTGTTCCACT CAACTCCCCT GTGCAAGCAT GGCTCCAGTG
216601 GCACTGGACA TTGGCTGCTC TCCACATAGA TCTGCACTGC ACTTCCCTCT GGCTCTGCTC
216661 CCGTTAGTTT ATATGCCTGG AAAGTTCTTT GCCCCTGTTC CTTGTGCCAA AATTCCATCT
216721 ATCCTATTGC ATAGCTTATG TAAAAACTTC CTAAACCTTT TTTTTTTTTT TTTTTTTTTT
216781 TTTTTTTTTT TTTTTTGAGA CGGTGTCTCA CTCTTCCGCC CAGGCCGGAC TGCAGTAGCG
216841 CTATCTCGGC TCACTGCAAG CTCCGCCTCC CGGGTTCACG CCATTTTCCT GCCTCAGCCT
216901 CCCGAGTAGC TGGGACTACA GGCGCCTGCC ACCATGACCG CTAATTTTTT TGTATTTTTA
```

```
216961 GTAGAGACGG GGTTTCAAGC CAGGATGGTC TCAATCTCCT GACCTCGTGA TCCGCCCGCC
217021 TCGGCCTCCC AAAGTGCTGG GATTACAGGC GTGAGCCACC GTGCCCGGCC AAAACTTCCT
217081 AAATCTTATA ATTATTATCA ATTTATCCTC AGATATACTT CCACGTACAT TGTAGTTTTA
217141 TTATATTTAT ATTTTACATC TTTTTTTTCA AATTGCAGTT TGGGACCCAT TAGTGAGTCA
217201 TAAAATCCAT TGAGCGGGTT AAAATCATTA TTTTAAAAAA TGAGTAGAAT AGAATAGAAA
217261 TTGTTGGAGT GCATTGGACA TGGTAAAGTT AAATATCGAT TCATGAAACC ATCGTTTGAG
217321 GCATATGTGT GTGGTTGTAT GTACAAGTGT TTATGCATAT TGGTGTGTGT GTTATGTTAC
217381 CCTGTAAAAT GCATTTCTTA CTATAGGTCT CTGTGAAATA TGTGTCTTGT TGTTTTTTAA
217441 TGTAGACTTC CAAAGCCTAC ATGGCATTTC ACTAGTGACA ATCAATTTTA TTCACATTTT
217501 TCTCTCCAAT TGGACCAGAA GCTCTTTGAG GGCAGGGGCT GTATCTTACC GATTTTTGTA
217561 AGTCTTTCAT TTCCTGCCCC TAGCCTCATA TTAGATCATG CAAGAATGCA ACTGTAATCA
217621 CAAGAAAATG CTAATGGGCT GTGATAGCAG AGAGTTACTG TGACAAACTA AGGGATTTAG
217681 ATTTGGTCAC ATTGGTGTTG AGGAGCCATT GAAGAATCAG AGAGTGTGTT ACTATTATTT
217741 GTTAATTTTA ATTATATCAT ATTACTTTAC TGGGGAAAAT CTGTGAGCTA TTTTAGAAAT
217801 AAATACTCTC ATTGCCCAAT AATTCTAAGT CTGCCACCTC ACTGTTGGGA CATTGTTTAG
217861 GGAGGCCACG AAGTCTCAGC CTTTGATATT TTCATAAGTG TTTTTCTCCC TTTTTCCTTT
217921 AGGGTCAGCA TTTGGATCCT TCATCATCCT CTGTGTGGGG GGACTAATCT CACAGGCCTT
217981 GAGCTGGCCT TTTATCTTCT ACATCTTTGG TGAGTCACTT TCTCTTAAAT CCTAATGCCT
218041 CCATTTCCTG AGCATCCATT TTGGCACCTA CACCACCCAC ATTCTTCCTA TATGAAAGAA
218101 AATGTCCTTT ATCAAATGGA AGATGATAAA AAATGTCAAC GGTTGGTATC ATTTTTAATC
218161 TAGTCACACA ACCTGATTAA CACCTTCCTG GTGGTTCTGG GAAGCCACAC GCAAAAGGTA
218221 GAGGAGTTGA CTATTCACAT GGCACCCACC GACTTGTGAT GCAGTCTTGT CCTTCCATAT
218281 CAAGCACCTT CTGCAGAATC TCTACCACCA CATCTGAAGT GCCTGCTATA TGCAGTTAAG
218341 ATGTCAAAGA TAGTGAAGTA CATTTTCAAT GTGTCTTCAT ATTTCATTAT AATTATTATT
218401 TCTGTCCAAG ATGCCTTTCA CCTGTTCTCT ACCAAGTTAA TCTTGCAAAG TTCAATTCAA
218461 ATGTTCCCTT CCCCATGGGC CCTTCCAGGG CTTACCCTGT CAGATTCTGG CATTCTCTCC
218521 TTTATGATAT TTCCTCTCTA GGTTATGTTG GTGTGTAATT ATTTATTTCT CCTTTTCTTT
218581 CCACTAGACT GTGAAATGCT TGAGGCAAGG AATCCATTCT ATGTTTTCAT CACTTGGGTG
218641 TCATCATGGT GCCTGATTTT TAGCTTTAAA ATAAAAGAAT CAGTGAATCC AGTAATTAGA
218701 GGGGATTTAA AGAAAACTAG TCCTCAGAAT CTTTTAACAT AGAATGTTCT TCAAATAAGG
218761 AATTCCAATA ATAAGACAAT TTTCTACACT TGATTTGTT TTTATAGCCA AATGGTGTCA
218821 TTAAATATAG TCCTGGCCTG AATGGCTTTC TCATTAATGA TGCTAATTAT TTTGGTTTGT
218881 ACATGTTAAC CAGGTATTGT ACAAAAATAT TTCTTTTGGG AATCCATAAT GGATGTATGG
218941 CTTGAATACA AATAATACTG TCTCTTGTAA GTGCATTGGA AATTTTTCCC TGCCACATGA
219001 TTTCATGGAA GGTTGTTTCG TGTATGTATG ACTGCAAACC TGACTATTCA GATCTTCCGC
219061 AACAAGACAA CTTATGTGTG CATTAAGAAG TTGCTGCCTA AAATACATAA CACTGTAATC
219121 ATTGGAGACT TTAAAGTAAT TAATCAGCTA TGCAATGCCA CGCTCCTGTT ATCTCCAGAG
219181 GGCTCTGACA TTGACAAATG GTGGCTTTCT ATTTGAGACG TAATATCTAA AAAGCTTTAA
219241 CAGGTTTGTA GAAGGATTGA AAGAAAGAAT GGGAACATTT AGGTCCTTAT GGTAGAATAA
219301 GCATTAATTG ATTAGTGTGT AGAAGGGAGA GGCATGCCAC TTCAGAGGAA ACTTCCTTCC
219361 CCCAGTAAAC AAATCTACCT AAAAACTAAT TTTATCCCTT CTTCCCAGGT AGCACTGGCT
219421 GTGTCTGCTG TCTCCTATGG TTCACAGTGA TTTATGATGA CCCCATGCAT CACCCGTGCA
219481 TAAGTGTTAG GGAAAAGGAG CACATCCTGT CCTCACTGGC TCAACAGGTA CAGTGCACAC
219541 CTTGTACCTG TGGCCCATGC AGAGGTCTCT AGGGCAGGGT GTGGATCTCC TCTGAGAGGC
219601 ACCATCTTGG CTGCTCTAAT ACTCATGCTG ATTAGATCTT TCTTTTCAGC CCAGTTCTCC
219661 TGGACGAGCT GTCCCCATAA AGGCGATGGT CACATGCCTA CCACTTTGGG CCATTTTCCT
219721 GGGTTTTTTC AGCCATTTCT GGTTATGCAC CATCATCCTA ACATACCTAC CAACGTATAT
219781 CAGTACTCTG CTCCATGTTA ACATCAGAGA TGTGAGTTTA CTTCCTATAC TTCTACGAAA
219841 ATGATAATGG TAATAAGGAG AAACAGTTCT GTGTTACCTA TTACATTCTG GCTTTACATA
219901 TAACCATTAA TTTAACCTTC ACAATGACCT TGAGAGAGGC ATTGTTATAA TTCCCTTTTC
219961 ACAGATGTGG AAACAGGACA CTTAGAGGTG AGATAACTTG CCCCAGGTTG CACAATACTA
220021 AGTGATAGAG CTGCTGCAGC ATCCATATTC TTAACCACTA TGCTATACTA CCACACCAGC
220081 TGATTCCAAA GCTTCTTTTA GAAATAATAT TGCTGGGCCA GGCATGGTGG CTCATGCCTG
220141 TAATTCCAGC ACTTTGGGAG GCCGAGGCAG GCAGATCATG AGGTCAGGAA TGCAAGACCA
```

Figure 2 (Page 68 of 74)

```
220201 GCCTGACCAA TATGGTTTAC TAAATATCAT CTACTAAAAA TACAAAAATT AGCCAGGTGT
220261 GGTGGCAGGC ACCTGTAATC CCAGCTATTC AGGAGGCTGA GACAGGAGAA TCGCTTGAAC
220321 CCAGGAGGTG GAGGTTGCAT TGAGCCAAGA TCATGCCACT GCACTCCAGC CTGGGCGACA
220381 GAGTAAGACT CCGTTTCAAA AACAAAAAAC CAAGAAATT AATATTGCTT TTATCTGGAG
220441 CCCAGAGTGA TGCAGCTTCT GGCCCTCTTA TCTGAGACAG TGTTCTTTTA GTGTGAAAAA
220501 GGATGCTAAT TTTCCCCCAA ACAACCCACA GTATCATGGG GGTAAGTTAA TGGCTGGTCT
220561 GTGTAACTGA CAAATTTTGG TGCTAACGTA TCTCTATAAC TACTCTGTAT AAACTTCCTT
220621 CCTTCAGAGT GGAGTTCTGT CCTCCCTGCC TTTTATTGCT GCTGCAAGCT GTACAATTTT
220681 AGGAGGTCAG CTGGCAGATT TCCTTTTGTC CAGGAATCTT CTCAGATTGA TCACTGTGCG
220741 AAAGCTCTTT TCATCTCTTG GTAAGGATAA GCGTGTGGGC CCATTTAACC AATCCCTTTT
220801 CTGCACATGG TCTCAGAGGG TTCCCTGACA GCATGTCCTC ATTGCCCAGG GCTCCTCCTT
220861 CCATCAATAT GTGCTGTGGC CCTGCCCTTT GTGGCCTCCA GTTACGTGAT AACCATTATT
220921 TTGCTGATAC TTATTCCTGG GACCAGTAAC CTATGTGACT CAGGGTTTAT CATCAACACC
220981 TTAGATATCG CCCCCAGGTA AGAGCTCTAC CTGTTTTTTC CCCTCCTCCA GACCCCTCCA
221041 GAGGTGTTAG ACCTCAGTGG TCGCCGTGAA ACTCTTTAAT GTTACTGACA TTGCACTAAT
221101 GGCAGAATGA CAAATAACTA CAAATATCTG TCTGTGGCCA TTTTTAGAAC AACAAATGTG
221161 GCATTTTTAG AACAACAATT TCCAATCTTG GCCAGTAATC ATTTTGACAA AAACCTTCCC
221221 AAGCTTCCCT AACAGAGATT GAACTGTGTA TGCTGGGAAA AGGCCCACAC ACAGGTGATT
221281 TGGAAAAGTT TCCATGGTGT TGTTCATATT AGCTACCACA TATATATATA TATATATATA
221341 TATATATATA TATATATATA TATATATATA TACAGTCACA ATAAGCCAGC TCCTGTGCCA
221401 AGACTTGCCA TATATCAACA CATCTAATCC TCACAGTTAT ATTAGGTAGG CCCTATTGTT
221461 ATCCCCATTT TATAAGGGAG AAGGCTGAGG CACAAGGAGG TTAAATGGTG TGACTATGGT
221521 CACATAAAGG CAGAGCCAGG ATTTGGACTG GGGGAGTCTG GCTTTGGAGT CTGTGTCCTG
221581 CCCGTTGCAC AAACTGGCTT CTACACTGAG CAGCCAGGGT AAAGAAACGT GGTTCCCAGA
221641 GAGACTGCAT TGCTCCCTGG TTATTGACTT GGTAGATTGG TAATTTCAGG TTTGGCAAAT
221701 AGACATTGCC CTGAATGTCT TTAGGTGAAT GAAAACTGC ATTAAGCAAA ATGACTTTGC
221761 CATTAGAGCT GAATTGCATT AAAGTTGAGT TGCTGCAGAA GCTGTAGGTG GCTTTCTATA
221821 TAAAATCATT TATAAAATCA TCTTCCCATA GATATGCAAG TTTCCTCATG GAATCTCAA
221881 GGGGATTTGG GCTCATCGCA GGAATCATCT CTTCCACTGC CACTGGATTC CTCATCAGTC
221941 AGGTTGGGTC AGTTTATTGA ACATCTTCAA GTGGCAGGTA TTGTTTTAGG TGTTGGAGAT
222001 ACACACGGTG CTCTAAAGAT CTGGATGGCA ACACAATTAC TCTATTTACA TGAGCCTCTA
222061 AATCAGACTC TGGTAGGTCA GATTTCCCAG AGGAAGAAAA ATATAAGCTT ATTTTCTCAA
222121 GATGAATAGA TGTTAGATTG ATTAAAATGA GCTGTTCCGG TGCAGAAGAC AGCACGTATG
222181 ACTTCCTAGA GGTACATGAG CATGAAACAG TTCTTAGTTA TGACCAGAAT GAAAGACACA
222241 TGTCAAGGAA TAGCAAGAGA CGAAGACAGA GGGGCAAAAG AAGATCATGA AGAATATGTT
222301 CAGACTAATC CAATTTTTAA AAAATCACAA AAGGGAAACA AAGTGTCCTA GGCCAGTTTA
222361 AAGATAATTT AATGTCTGGA AACAGATCGG CTGTGAGACA TTGCAAGGAG GCTTGCTCGG
222421 TGTTTGGAAA TGCAGGCTCA TGAGGAAGAT GAAAAGACAG ACCCAGGCAG GGATGGAAGG
222481 ACTGACTAGA ACCAACTTAC AAAGAGAAGT TTTGTTTTTA CTACATTTCT ATGTGATCAA
222541 GTTCCCAGGT TAATATTTGA CTAAACTGCT AGGAATCCAC TGTGACTATA ATGCTGGAAA
222601 TGACTTAGTA GGGCTTTCTG AGGAGGGTCA CACAGAAGAC CAAAGAGAAC TCATGTTGAA
222661 TTGAGATGGG TTATAGTGAT AGTTGTCAAC AGCCAATACA GAAACAAAAA AAAACAAAAC
222721 AAACAGCAAC AACAACAACA ACAAAAAAAA AAAACAGAGA AGACACAAAC ACAATGCCAC
222781 AATGCCATTT TAGGCATAAT TTTAAATGAG TAATATTATA TGTTGAAATC CAAATTTTCA
222841 GAAAAACATT AGTGTATTTT ATTTTTGTTT AAAGAAATAA CCATCTCAAC TCAGAACCCC
222901 ATGTGCATTT TGGCCATTTT GTTTCCAATA GTTTCATAAA CTTTCTTAAG TAACTACTGC
222961 ACATTGTTCC TTATATTCCT TGTGATCAAC ATTGCAATAC ACAACTGGGA GGGCTACTAG
223021 AACTGGTGTA GAAGGAACTT GTGAGATTGA TCATTTCTC TGTTTTTTAC ATCTAGGATT
223081 TTGAGTCTGG TTGAGGAAT GTCTTTTCC TGTCTGCTGC AGTCAACATG TTTGGCCTGG
223141 TCTTTTACCT CACGTTTGGA CAAGCAGAAC TTCAAGACTG GCCAAAGAG AGGACCCTTA
223201 CCCGCCTCTG AGGACATAAA GTTACAAACT TAAATGTGGT ACTGAGCATG AACTTTTTAA
223261 ACATTTTTTA CTTCTCTCCA TATTCCTGAC CATAGACTCA GCAGTTCTTA ACTCTGGCTG
223321 TGTGTTAGTC TTCCCTGGGG AGCCTTTATA AGACACTGAT ACTTGGGACC CACTCCAGAG
223381 ATTCTGAATG AATTGGTCTG GGTGGAACC CAGATACTAC TAATTTTTAG ATACTCCTTA
```

Figure 2 (Page 69 of 74)

```
223441 GAGGTTTCTA GCATGCGCCC GGGGTTGACA ACAGCTGGAC AAACTTGAAA AGTCAATTCA
223501 TGTGGCCTTT GAATTTTCCT CATTGGAAAG TACTAAATAA ATAAAAATTC ATGTGAAAAT
223561 GATCACTGAT AAATATCTTC ATGGTGGGGC AGGTTATTGG ATGCAGAGAA GATCTGCTCG
223621 GAATTGTAGC CATATGTTAC AGATCTCAGC ACCGATCAGA ACTGTAAAGC TATAATCCCC
223681 AGAATTAAAG TTTTTATTAT TTTTTATACA TTGTAAAACA TAGACGTTTA TTTATGTGAT
223741 TAAATTCTAT TAAAATTTAC ATGCTAAAAT AAAATAGACC ATTTTCAAAT TATTTAGATC
223801 CAGATATTTC CATCAGATTA AACAGATATT TATTTATCCT AGCCCAATTG CAAGAGATTA
223861 ATGATGAGAA AATGACCAAT ACAAGATTAA ATAAATGAGG TTAACTTAGA AATCAAGGAC
223921 AGAGAAGATA GAACTGGAAA GCTTGTATTG TGAGAAGAAT GAATGTGAAG GAAGGCAATG
223981 TAGACACTTC CAGAAGGGAT AGCAATATAG TTTAGACCAT ATAATGAAAA TTGGAGAGAG
224041 ATGACAGAGA CACTTTCAAG TGAAATGACA ATTTATATGG GGGAGAAAAA TATTGAAGAC
224101 ATAACAAGAT GAGAAAAGGC ATAGAAATGT ATCACATACA AGGCATAGAA GTGTATCACA
224161 TACAAGAGAA GTTCCTTTTG AGCGTAGAAA AAGATAATTT AACCTTCTTC ATATTTTTCT
224221 TACTTTCCCA AGATACTCAG ATAGGCAGCG TCAACTCTAA CAGGAATTAA TTTGGCTCCT
224281 AACACTTAAG ACATATCCTT TAGTTTGTCT CCTCACACAG AACTGATTCT GGTTTTGCCA
224341 CAACATGTCT AGAGAAGAAG TTCCCACCAT ATTTTAAATC CTATTAAAAA ACTGCTTGGA
224401 CAAGAACCTT GGGCTAATTC AGCAGATGAA GAGAATCTCC TAATGCAAAT CAATGGGTAT
224461 TTTTGAGCAA GTTTTTCAGA AAAACAGAGT GTCAGGCCCT GAGGGTGGTA CTAAGATGAG
224521 AACATTGATT TTGCCTTCAT GATATTGACA ACACAAAGAG GAAAGGGGGT TTGCAGAAAA
224581 CTAAAAGAAG AAGTAGAAGA AAAAAGAAAG ACATAGTATA ATAGGTAGTC AAATTATGTA
224641 CAGAAAAAAG AGGAAAAAAA ACCAAAAAAG GGTGGGGGAC AGACAACCCA ACTAAAAAAT
224701 GGGCCAATGA CTTGAACAGG GACTTCATAA AAGAGAAAAT GTAAGTGGCT CCTTAACATA
224761 TAAAAGATG TTCAACTTCA TTAGTCATTA CAGAAATGAA AATCAAAACT ACAATGAAAT
224821 ACCACTATAA AATTAACTAA TGGATAAAAT GAAAGGAGAT GGAAAACAAA ATGTTGCCAG
224881 ACATGTGGAG CAACTGGAAC TTTCATACGT TACGAATGTG AACTTTGGAA AGCTGCTCGG
224941 CAATATCTCC TAAAGCTAAA TGTACAATTC CAGTGACTCA GACATTTTAC TTAGAAATGC
225001 ACATATACAT CCATAAAACA TGTACAACAA TGTTCATAGG AGCACTATCT GTAATAGCCT
225061 GAACAGGAAG TTGTCTGTTA AAAAAAGAAT GAGTAAATAA ACCACGGTCT ATTTGTATAG
225121 CAATGAGAAT TAACAGACCC AATATATAA TAGATGAATG GGTCTCATAA GCACAATATT
225181 GATTAAAGGA AGACAAAACG CACATTCTTT TAAAGGTTTA TAAAATACTT TTTAAAAACA
225241 GCTACAACCA ATCCGTCCTG TTAAAAATCA GTGAGCGATT TCCCTTGTGC AGGGATGGGG
225301 GTTGTGGCTG GATGGATGGT ACTTAAGAAG TGCTCCTGGG GTACTAGAAA TATTTTATTT
225361 CTTGACTTGG ATGTGTGTTT ACTTTGTGAA TATTGTACAT TTATGATTTG TGCACGTTTA
225421 TGAATGTAGA AAATAAAACA GAAAGCAAAT TCAAAGTATC ATCCTTTTGA GAGCTTCTGC
225481 TCTGACTTCG TTTTGACCAA TGGAGCAGTT GGGAAGGGGT CTTGGTCCTT CGGTCCTTTG
225541 CTTTTTTTTT TTTTTTTTTT TTTTAGACAG AGTCTCACTC TGTCGCCCGG GCTGGAGTGC
225601 AGTGGCTCGA TCTTAGCTCA CTGAAAGCTT TGCCTCCCGG GTTCATGCCA TTCTCCTGCC
225661 TCAGCCTCCC CAGTAGCTGG GACTACAGGC ACCTGCCACC ATGCCCGGCT AATTTTTTGT
225721 ATTTTTTAGT AGAGACGGGG TTTCACCATG TTAGCCAGGA TGGTCTCGAT CTCCTGACCT
225781 CGTGATCCGC CCACCTGAGC CTCCCAAAGT GCTGGGATTA CAGGTGTGAG CCACCGCGCC
225841 CGGCCCCTGG TCCTCTGCTT TCATGTTCTT CTTGGTCCTG TTCCTCCTCC TCTTTTGTTG
225901 GAACTTCCAG TATCAGAGCA GGAAGGAAGG CAATGGGTCA ATCGATGCTG TCAGCTTTTG
225961 GATCAAACTG CAAGTTCTCA AACAGCAAAA TTAATGAGCT CAGGCTTTGA AGAAACCATG
226021 ACCCTGAAAG CATCAGTTGC TTCCAATTGC ATCAGTTGCC ACGGGTGATA AGAACAATGA
226081 TGACTCAGAA TGCCTAGGTT TTCCCAGCAG CTTCTCTGAG GTTTTCCCAG CAGCTTCTCT
226141 GATTGATTCC TGACAGATGA CTTCGGTGTG TCAGACTTTC AGGGTATCTT TCCTTATGTG
226201 ATGGTTTGAG GAAGAGTTAC CATTCACATT CCTAATGGCT TCAGAATAGA TGCAATTGTG
226261 AACTGATAGG AAACATTTCT AATTCATCTC CCCTCCCCAT CCCTAAAGGA TTGTTTCTAA
226321 CAATAGTCAT GAAAATTAAT TCACTTTTCT CAAATAGTTT ATTGTCATCT ACCTAATGAT
226381 GAGATGACTT ACTTTTCTC CTTGACTGTT AAATATTATG AATTATATTA ATGTATTTCT
226441 TAATGTTGAG CTTTCCCTTG AATATTCTTT TGATGTACGA CAGAATTTGA TTCACTAATA
226501 GTTTATTTAG GACTTTGGCT GATGTACTGA TATATGAGAT TGGCTCTGTA TGCATACATG
226561 TGTTTTGTGT ATCTTTTTTG TGTCTGGATA TGGAGCTTAT GCTGATTTCA AAAACAAGAA
226621 AGGAGAACTT TCCTTTTTCC CCATTACTCT GAAAAGATT GACTAGAATG GAATTTTTAT
```

Figure 2 (Page 70 of 74)

```
226681 AATTGCTGTT GTTATTTGAA AGCTTGAAAG CATTGGTTTG TAAAAATCAT GCAGGCTGAA
226741 AGCCATTTTG AGGAGACTTT GATAACTTTC TCAATTTCCT TCAGTTACTG GTCTTTTAAG
226801 GGGTTTTATA TTTTTCTTTG ATCAATTTTG ACCATTTATG TTATCTTGGA GGATCATCTA
226861 TTTTACACAC TATTTAAAGT ATATTTGCAA AAATTCAACT GTTTTATCAG GCTATCTTTT
226921 TAATAATATA TTCATTTTAT CTATATCTGA GGTTTTAGCT TCTTTGTACT TCTGACCCAA
226981 TTGCATGTGT GCTTTCTTTC TCCTTCATTA GACTACTTAG TCATTTACTA ATTTTAAGAA
227041 TAGCTTGTCT TTTATTTATT TACTTATTTA TTTTTGAGAC GGAGTCTCAC TCTGTCACCC
227101 AGGCTGGAGT GCAGTGGCGC GATCTCGGCT CACTGCAACC TCCGCCTCCC GGGTTCAAGT
227161 GATTCTCCTG CCTCAGACTC CCGAGTAGCT GGGATTACAG TCATGCACCA CCATGTCTGG
227221 CTAATTTCTG TATTTTTAAT AGAGATGGGG TTTTGCCATG TTGGCCAAGC TGGTCTCAAA
227281 CTCCTGACCT TAGATGATCT ACCCACCTTG GCCTCCCAAA GTGCTGGGAT TACAGGCATG
227341 AGCCACTGCG CCCAGCCCTG CTTGTCTTTT TATTTTATAT TTGATTAGCT TTATCTTTTA
227401 TCAAGCTTAT GTCCTATTTC CCTTTGCTTT ACTTCATATA AATTTTGTTT TGGATAGTTT
227461 ATTTATTTTT CATTTAATTA TGAAACAGGT TAAAGCTTAG AGGAAAATTG CTCCTCTAAG
227521 TCCACTTTTG TGGGCAGATT ACATTTTGCT GTGTTGTGCT CCCAAATTCA TTGTTCTTTT
227581 AATGCTTTAT TTCTCAAGTT AATAACCTAT ATAGTAAAAA AGTGGCTGTT GACTCTCAGC
227641 TTTTTTTTTT TTTTTTTTTT TTTTTTGTA GATACAGGGA TCTTGCTGTG TTGCTCAGGC
227701 TGGTCTGAAA CTCCTGGCTT CAAGGGATCC TCCTGCCTTG GTCTCACAAA ATGCTGGGAT
227761 GACAGACATG AGACACCATG CCCAGCCATG TCTCTCTCCT TATATATAAT AAGAAAACAG
227821 ACACACTGAG GCATCCTATC ATCTCACTCT TGGTTTCACT ACTGTTCTCT GGAAGTTTTG
227881 CTCTGACCTT TTGCAGTTAA TGTATTAATT TTGCATTGAG TAGTTTCCAT AGAAGAATTA
227941 TAGCATTTGC ATTCTGTTGG GTATTATACT TTTCACTGTT ATTTGAACAT AATTTGAGGG
228001 CTGAAACCAA GATGAGGCAA GTGAGGTGCC CAGGAAGCAA TATTTAAGGA GGCATCCTTT
228061 CTTAGGCTCA TGCAAGAACA GAATTGGCAC ATGAGAGTGA GTGCCTCCTT AATTTTGAGT
228121 GCTGGACACT TCTTGCTCAC TTAGCATACC CCTGGACAAT GAAGTGTTTT TTGTTTTGTT
228181 TTTTCATGTC CATCCTTTAT CCTTCTTCAT CTCAAAACAT TTCAATGGAG TATTTTTTG
228241 GAGCAGTACT TGGATGAGCC TCTGAGTCCC ACAGTAGCTG AGAATTTATT TCATAGTACT
228301 CTTTATGATC ACTGTGGAGC CTTAAAACAT TGTAATATTA ACTTAGCTGG GAACAGAAAT
228361 TTTGTTCCAC AATTTGTCTT ATTCAGAACA GTATTGACTT CCTGCTAGTC TCTTCTGATG
228421 TCCAATATGA GGAAGTCTAG TTAGCCAGCT ACTTTTGTA GGAGAGCTAT GTTAGGCTA
228481 GGTGCTATAG GATTCTCTTT ATCCTGGAAT TCCTTCACCA AGATGTGCCA AGGTGTTAAT
228541 CATTTTCTCT TGCTTTTGG CTGGTGGTCT TAGAGTTTCC TTCGATTTTG TTTTATTTAG
228601 TGATTGTCCT CAATTTGTTT TCTTTACTAA GAATCTCTCT TCTATTTATC TGTATGGTAA
228661 AACCTTGTTG CCCATCTTTC TGGTTTCTGC TGACTTTCAT TTTTGGACCT TTTACTTTGC
228721 TTTCTCCATG GACTTTTGG TAGTGGAGGC AGGCAAACAC TTTCCAAAGT CTTTCTCAAT
228781 TTCCATCAAT TTCAACTTAT TTCCTAAAAT TGCCTCAGAA TGTGCCTATG TCCACAATAT
228841 CCCTCCTTCC ACTTTAGAAA GGAAAGGCAT CCACACTTTA TTTAGGTGCA ATGCCTGAAG
228901 TGTAAACACT TTCTGGTTGT CAACAAAGGA GTACTTCCAA ATATTGGTTT GGGGATAACC
228961 TGCTAATGAT TAACACATTC ACCTTGGCTC TTGGTTTGCC TGCTCCCTCT TCTTTTATCT
229021 GCTGTGTGTA TTTTTTTAA TCACTGAGAA TATGCACAGT ATTGTATGTT TTATTATAAG
229081 AGAGGACTGG CCAGAGTGGG AATGTTCTGA ATTCAGAATA ACTGAAGCAG TACAGGATAG
229141 GAACTCATTC TTTCAAATGA AGCTGGCATA TTTTCCCAGA GCACCAAATT TCAATATATA
229201 TTTAAAAAAC TTGATATGAA TGATACAATA AAGTGGTTAG AACTTTTATT AAAATAAACT
229261 TATGTCATGA AATACTTATT CTAATTATAG TCACTCTTCA TCTTATTTCA TCTTATAACA
229321 TGTTTAATGT TTTCTTTTAT TTACAAAACA ATTTATTTTT TGATGAAAAG TTTTAGAAAT
229381 CAAGTTAAAA ATATTCAAAG GAATGCCTAA AGTTTTCAAA ATTCTTTTAC ATGTTGTACA
229441 ATCAAAAGAG TCTGAAGACC ATTTAGCTAT CCAAATTGTT TATTTTTAAG CAGTATCCCT
229501 TCTAATATTT ACTATTTATA ATCCTAAAAA ATTTGCCTTA GCACAGGAGA ATTGCTTGAA
229561 CCCAGGAGAC GGAGGTTGCA GTGAGCCAAC ACAGTGCCAC TGCCCTCCAG CCTCGGCGAC
229621 AGAGTGAGAC TCTGTCTCAA AAAAAAAAA AAAAAAAAA AAAAAGGCC AAAAACAAAT
229681 AAACAAACAA AAAATCCGC CTTAACATTA TTTGTTCATT AAAAACTTTC TTTAATACTA
229741 CTAGTTTCCC TTTCCTCTCA GCCCATTGTC ATATTTTGAT TTTTATCACT TGCTTTGTAG
229801 GACATATGAG GTTTTTGTTT TTTTTTTTT TTGGAGATGC AGTCTCCCTC TGTTGCCCGT
229861 GCTGGAGTGC AATGGCGCAA TCTTGGCTCA CTGCAACCTC TGCCTCCTGG GTTCAAGCAA
```

Figure 2 (Page 71 of 74)

```
229921 TTCTCCTGCC TCAGCCTTCC AAGTAGCTGG GATTACAGGC ACCCACTACC ACGCCTGGCT
229981 AATTTTTGTA TTTCTGGTAG AGACGGGGTT TCACCATGTT GGCCAGGCTG GTCTCGAACT
230041 CCTGACCTCA AGTGATCCAC AATCCTTGGC CTCCCAAAGT GCTATGATTA CAAGCATGAG
230101 CCACCTGCCC AGCCAGAATA TATGTTCATT TTGAGTCCTT TAACAAAGTC ATAAGAATTT
230161 TAGGAATTCA GTTACTTTCT TGAGAAAATC TCTGAAAAGA TGCCAATAAT TTGTAGCCAA
230221 TTATATTGAT TTCTCTTTTT CATATTGAGA ATTGTTTTTT AAAAAGTTTG TATGTGTGAA
230281 GATTTTTGCA CTGTAGTTAA AGAAACCACC TGTGTGTTGG TTAAGCCATA AGTACATGTA
230341 TTCAAATAAA TTGAGGTGGG GTTACTCTGA GAATCAAAGG AAAACCTGAA GAAACAGGCA
230401 GCCTCAAAAG GTCTTAGCTG TAGCAACTTG CTCCATTGTT GAAATAAATA GGCTTGAACT
230461 TGTATTTTCC CTCTACTCAA CATTTAAGGT CTCAGAAGAT AATATAATTG GTGAAATTTA
230521 AGTAAAGTGC TCACTCTTTT GCTTTAACAA ACCCTAGAGA GCTGGTAGGC AGAGCCTCAA
230581 CAGACCGTTT TAGCTTCCAA AGGGAGTTCA GGACACCATG ATTCACGACC ACAATACATC
230641 ACACATAATT GAGAAAAGAT AGTTCCACCA AATAAAGTTG AAATGCTGAC AAGAAGGGGT
230701 AAGAAATCTT GGAAATAGGT TTATATAAAA TTTATTTTTT CCTTTTTTAT TGTTATGGAA
230761 TAGGACCAGT TCTACTTAAG CCACCCATTT GCCAAAATAA AGTGAGAATC GTTTCTTTTG
230821 GGGACTCCTC TTTGTAGCTC CAAGTGCCAC TAACAATTCT TAGGACCTGA GCTATAAGCC
230881 AGGTGATTTC AGTTAATATG ATCAATTATT TCATTTAAAT GGCTCTAATG TGCAGAGGGA
230941 ACGGAGCCCA TCAGCATTCC CTGCAGGGAA CTGCAGTGGC TTTTATCAAC TTGAACAGCT
231001 AGCTTTCAAC TGTTTTGAAA TCACTTTCAG GGTGGTCATG TAGTTGCTTT TTTGAAATCA
231061 GAAGATGATT CTGCCTCTTT TAATATGTGA CTCCTCAGAT TCAGAAAGTG CTCGCTAGTC
231121 TTAAGAGTGA ATTACCCTCA GTGGTCCAGC GCTTATGAAC CCACATCTAA CCCTATCCCC
231181 TGGGGAACT ATCAGAGAAA TTGGTGCCAT GGACATAAGA GGAAGGCACA GTGAAGCAGA
231241 GAGCCCCGCA TGATGAAAAT CAGTGGACAG CATCATTATT TACAACTTTG TAATCACCCA
231301 GGAGCATGAA AATCCAGGCC AATCTGGCAC CATGAGCTCT AATTTTGTT GGAGTTCTTG
231361 GAACCGATTC TGATGAATGA CTGTTTAGCC ATTTTAGAGT GTGGCATACG TGGCTGCTGG
231421 CATACAGAGG TTGGATGTAA ACGGCCTTT GCCCTCTCTT ATGAACATAG ACAGGAACTA
231481 AACTGTGTCA CATAGGTTCC AAATGGTGGC CTGAATACTA TTTACAACTA AGGTACAATG
231541 AAATTGAGTA AGTCTTTTCC TCTTTTGCAG ATACCATCAT TATTCATATA TTTCTTCAAA
231601 GTTAACTATT TGTATTTGGT AATTTTTAAT AGAAATGTAA TAATTGCTTC TCAAGTTTAG
231661 TCTTTAGTCT TAAGGTTGAT GCTCTCCATG TCCTTCCAAA AAAAGGTATG TTGCTTTTAT
231721 TATATCCTCG CCTTCAGATG GGATTATTCC ATTTGTTCT TTGTTAATAT ATACTTTGAG
231781 CCACTTTTTT TGTGGCTCTG GGTGAGATGC TATAGGTACA ATGACAAGTG ATACGTGTGT
231841 TGTCCCTGTC ACAAAAGTGG ATAGCCTAAG TGGTGACTTT TACCTCCACT CCAAATATAT
231901 GTATCACACA CCAGCCGTAT GCCAGGCACC ACTCTAGGTG CTAGGGATAC AGCAGTAAAC
231961 AGACAAATGC AACCCCTGCC CATGTGAAAG AGAATAAGAC AATAAATAAG TAAAGTGCAT
232021 GTTATATGGA GGTGGCAAAT GCTAAAAAGA AAAATTAAGC AGGCAAGAGG ACTCATTGAA
232081 AAGATGACAT TTGGGTAAAA GCCCATGTAT ATATGTTCTA TTGGTTTTAT TTCTCTGGAG
232141 AGCCCTGACT AATACACAAT GACTTTGAGA AGTTACTGGC TTTTGATTTA TCACACTATT
232201 CGGAGTGCTG AGAGCCTTCT TAGTGTGTAT TCAGTGTTTT AAGAGAGCTT GTGGATGAAT
232261 AATAAATAGG ACAAAATTTA TCCAAACTTA AGCCTTGCTT TAGGTAAAAG GGCTCCTCTT
232321 ACAAGGTAGA AGGTTATTAT TTGACATTTA AATCCAACTG AAGACTAATA AGACTAATTA
232381 ATTAAAAGTT TTTAAATCAC AACTGCGTGC AAAATAAATG GAACTGCCAT GCTCGCCAAG
232441 TGTGCATGAG TGGTGTGCAT GGGAGACAGC ACGAAGCTAA TCCCACTCAT CTTGCAGGTT
232501 GCTCCATTTT TCTCCTAAAA TCAGTAAGAC AGAAGCTGGT CAGATTATCA AGAGCCCTAG
232561 TTAAACACAG CAGTAGCATT TGGAAGGGGT TGCTCTCATT AGGCAGTGCC TGACCACAAC
232621 AAGAGATGAA CAAGCCCTGT ATCTGAAGCC ATCATGCCTA GTTATGGTCC CCGACTGTTC
232681 ATGATGCCTG GAAGGGAGGC CCCCTGCACC CTAGAAAGCT GGGTGGGTTC TACTGTCTGC
232741 TTTACTGCTA AAAACCCTCT TCTTTGGATC TGGACTTTAC CTCTATCTGA TTTTTTTTTC
232801 TAATATATGA TTTGGCACTG AGTCTGTCAC TGCTGCTAAC TCAGCAGTTC TAGGGTCATT
232861 GCCCCATTGC CTCACAGAAA GAATTTCATA GCTTCCAGCA TCCTCTCTCC TTCATTATAC
232921 TTTGATTTCA GCATTGCTAT TTTTTCTCTT GGGTGTTGCA GCTCTCTCTC TCCTTCCCAT
232981 GTCTTGTTGG TTTTCTGCTA ACTCCTGCTT TTTTTCTTTT TTTTTTTTG AGACGGAGTC
233041 TCGTTCTGTC ACCCAGGCTG GAGTGCAGTG GCACAATCTC GGCTCACTGC AACCTCCGCC
233101 TCCCGGGTTC AAGCTATTCT CCTGCCTCAG CCTCCCAAGT AGCTGGGACT ACAGGCGCTC
```

Figure 2 (Page 72 of 74)

```
233161  ACCACTATGC CCCACTAATT TTTGTATTTT TAGTATTGCT GTCATCAATC CACATGTCCA
233221  GAAGCACCTA GAAACTCTAA TTCTTTGTAG GTATCAAACC CTAGGACTCT TTCCTCTAAT
233281  CACAATATAT AATCCCTGAT TCCCAAACAC GGTCTTTTCA TATACATTTT CCACTGTACA
233341  TACTTTCTGA CCTGGAAAGC TCTTACACAA ACACGCCCTC CCCTAGGAAG CCTTTATAAA
233401  TGTTCCCAGG AAGAATCAGT CACCCAACAG TGTCCTTGTC ACATCTTAGG TTCTACACCT
233461  TTATTTGTTC TATCTGAATG TAATCTCCCA GAGGGTGTTA TCATCTTTTT TTTTGAGATG
233521  GAGTCTTGCT TTGCTGCCCA GGCTGGAGTG CAGTGGCATG ATCTCGGCTC ACAGCAACCT
233581  CCACCTCCTG GGTTCAAGTG ATTCTCCTGC CTCAGCCTCC TGAGTAGCTG GGATTACAGA
233641  CGTGTGTCAC CACACCTGGC TAATTTTTGT ATTTTTAGTA GAGACAGGGT TTCACCGTGT
233701  TGGCAAGGCT TTCCTCGAAC TCCCAAACTC AGGTGATCCA CCCACCTCAG CCTCCCAAAG
233761  TGCTGGGATT ACAGGTGTGA GCCACCATGT CCAGCCCCAT CTTTTTCTTT TAGTTTAGTT
233821  CTTAACAAAT AGTCTGACAC AAAGTGGATA TAACAATATT TTGAATTATG AATAACTAAA
233881  TGAATATTTC CAGATTTCCT GGTGCTCTCA AAGTTTTATG TTACAAAAGA AAAACAAGTC
233941  TAAAATACCT GCCTCAAGTT TTTATCTGTA CTATGATTTC AAACCAAATA AAAAACAGGT
234001  GGGGTAAAAA CTGAAACAGG AAATACATAT AACTGAAAAA TTTTGGTATG TTAGTATGAT
234061  AATACTAGGT CATTTTTCCT GTTTCCCCAA CTTCATTTTC TATAGCAATA AAAAGAAACA
234121  AGTAAATGTA TGTTAATTTA ATTTAAAAGA AGTAGTCTAC CATCTCTTCT GTTAAAAGA
234181  AAAAAGTATT TTAAAAAATT ATCTCTGGAA GGATACACAG GAACATTGC TCTGGTTTCT
234241  TCCAAGAGAG AAATGAGGAA CTAGAGAGCA TGGCCAAGTG GGGTTTGCT TTTGTTTTTG
234301  TTTGTCTATC TGTTAGCTTT TTATTATTTT CTTTTGTAGG TTTGAATTTC AAACCACATA
234361  AATCTGTTAC ATGCTCATAA TAATAAGTTT AAAATAAAAC TTTTGGCTGG GTGCAATGAC
234421  TTACACCTGT AATCCCAGCG CTTTGGGAAG CAGAGGTGGG AGGATACTTG AGGCCAGGAA
234481  TTTGAGATCA GCCTGGGCAA CATAGTGAGA CCCTGCCTCT GTAGAAATAA ACAAAAATTA
234541  GCTGGATATG GTGGTGCATG CTTGTACTCC TAGCTACTTG GGAGGTTGAG GCAGGAGGAT
234601  CCTTTGAGTC CAGGAGTTTG AGGCTGCAGT GAGCTATAAT CACCCACTGC ACTATAGCAT
234661  GGGCAATAAG GTGAGAACTT GTCTCAAAAA AAAAAGGGGG GGGGGAAACA AATAAATAAA
234721  TATAAACAAA ACTTTTGTTT CAAAATATGT AATATTTAGC ACTAAAGAAT TCTGAATTGT
234781  AGAGCTAAAA AGTACTTAAA AGTTAATAAC TATTGTCTCC TTTAAAAGAA TTGTTATCAA
234841  AGTATAATTT TTATCCAGAA AATCATCCAT ATCAGCAAGC TAAACTTTCT CAAAATGACA
234901  TATCCATGTA ATTAGCTCCC AGGTAATTAG CAGGCAGCCT CTACTCAGGT TGAGTATTCC
234961  TAATCTAAAA ATTGGAAATT CAAAATGCTC CAAAATCTGC AACTTTTGA ATGCTAACAT
235021  GATTCTCAAA GGAGTGCTCA TGGAGTATTT CAGATTTTGG ATTTTTGGAT TTGAGATACT
235081  CAGTATAATG CAAACATTCC AAATCTGAAA AAATCTGAAA TACTTCTGGT TCTAAGCATA
235141  AGGGATACTC AACGTGTGTT AGCTAATTAG ACCCTTCATG GTCTCTTCTA GACCTCAGCT
235201  TCTTCAAGGT AACCTCTATC CTCACTTCTA ATAGCATGAA CTTTTCTGTT TTAGAATAAT
235261  TTGGATTTTC AGGAAAGTTG CAAAGATAGT ACAAAGACAG TACAGGAGAG TTCCCATATA
235321  TCTTTCACCT AGCTTTCCCC CATTGTTAGG ATTTTACATT ATTATGATAC ATTTGTCAAA
235381  TATAAGCAAC TCACATTGAT ACATGAAACT CTATTAACCA AACCCTAGAC TTTATGTGGA
235441  TTTCACCACT GTTTCCACTA ATGTTTTCTT TCTGTTCCAA GGTCCAATCT GGAATACCAC
235501  ACTGCATTTT CTTGTCATAT CTCCCTAGTC TTTTTTTGTC TGTGACAATG TCTCAGTCTT
235561  TTCTTGCTTT TCATGACCTT AACAGTCCTG AAGATCATTT GCTTTTTTTT CATAATTACA
235621  CCGGAGTTAT AGATTTTTG AAATAATACC ACAAGGGCAA AGGGCCCTTC TTGTCACATC
235681  ATTTTAGGGA GAACATGATA TCCACATGAC ATCACTGATA TTAACCTTCA TCATGTGGTT
235741  TAGGTAATGT TTCAGGTTTC TCTACTGCAA AGTGATTTTT TTCCCTTAAT TTAGCCCACC
235801  TGAACTTATC AATTTTGTTT TCTTCCATGA CTAATACTTT TGTTATTATA GCTAAAACTT
235861  CATTGGGGCC AAATCTTAGA TCATGTAAAT TTTCTTCTAT ATTTTATTCT AAAAGCTTGT
235921  AATGTTTGAT ACATTCTAAA AGATGTAATG TTTGATACAT TACATCTAGT CCTTTGATTT
235981  ATTTTTAGTT ACTTTTGTAT AAGGTGTGAG AGATGTCTCC AGTTTCACTT TATTAACACA
236041  TTGTGGTGTT CCAGTACTAT TTGTTGCTAA GACTATCTTT TTTCCATTGA TTACCTTTGC
236101  CTTAGTTGGC AATATTTTTG TTGGTTTATT TCTAGACTGT TTATCTCATT CCACTGATTT
236161  GTGTCTATCT TTTTGACAAA ACTGTTGATT ACAGTAAGCT TTGAAATAGT TCATTTTTTG
236221  TGTCAACTTG ACTGAGTCAG GGGATAACCA GCTATCTGGT TAAACATTAT TTCTGGCTGT
236281  GTTTGTGAGC GTGTTTCTGG ATGAGATTAG CCTTTGAATA GGTGATCCTA GTAAAGTAAA
236341  CTGTCTTTCC CAGTGTGGAT GGCATTATGC CACCTGATAT TCAGGGTCTG AATAGAAGAA
```

Figure 2 (Page 73 of 74)

```
236401 AAGGCAGAGG AAGGGGGAAT TTGGGCCTTT TTTTCTGCCT CACTGCTTGA GCTGGGACAT
236461 CTCATCTGGT CTCCTGCTCT TGAACTGGGA TTTACATCAT CAGTTCCTCT GGTTCTCAGG
236521 CCTTCAGATT CAGACTGAAT CATACCACCA GCTTTCCTGG GTCTCCAGCT TGCAGATTAC
236581 AGATCATGGG ACTCCTCATC TTCCATAAAT GCATGAGCCA ATTCAGTCTA TGTCCTTGAA
236641 AACTGCCCCA CTGCAGATTA AGGCTTTTTT CCACTAGGTG AAATAAAGAA GCTTGTTAGA
236701 CAGATTTCCC TTCATCCAGT GCCCTCTCCT CTTTAAGTTA CAACACATTG GCTACACCTA
236761 AGTGCAGGGG TGGGGATGAG GGTATAGTCC TCTTGTTTGC TGAGAAGAGA ACTGTATTGG
236821 GAAAGCTCTA GAAGTGTTTG ATACATACAT AAACAAGGCA TGGTTTTTGC ACTTAATTTC
236881 ACATTACATT TTTCCCAGAA AAAAAGGAAT GTATAGGCAT CACGTAACTG TACTAGCTGG
236941 AGTCATTCTT CCTGATTATC AAAGGTAAAC AGTTATTAAT CCTATACCAA GATGTCAAGG
237001 AGAAGTACTT TTGGAACACA AGGAATTCTC TGGGAGTCCT TACTACTCTC AAGCCCAGTG
237061 AAAAAGTTAA TGAAAAACTA TAGTACCTTC CTATAAGCTG GATGACTAAT TACCAGGCTC
237121 ATTTAGGAAT TTGCCTTACC AAGTAAAACA TAAGGGCAGC TGAGGTGCTG ACTGAAGACA
237181 AATGGAGCAT AGAATAAGAG TAGTAAAGAA TGCCAAAAAT GCTGTCATGT ATCCATTGAC
237241 AAAAGGAGCT ATAAAGCCTT TAGGTATTTT CACACTTGCT CTGTTACGTA AATGTATGTG
237301 TGTGTGTGTG TGTGTGTGTG TGTGTG
//
```

Figure 2 (Page 74 of 74)

POLYMORPHISMS IN THE REGION OF THE HUMAN HEMOCHROMATOSIS GENE

This application is a continuation of U.S. application Ser. No. 10/301,844, filed Nov. 20, 2002 now U.S. Pat. No. 7,052, 845, which is a divisional of U.S. application Ser. No. 08/852, 495, filed May 7, 1997 now U.S. Pat. No. 7,026,116, which is a continuation-in-part of U.S. patent application Ser. No. 08/724,394, filed Oct. 1, 1996, now U.S. Pat. No. 5,872,237, which is a continuation-in-part of U.S. patent application Ser. No. 08/652,265, filed May 23, 1996, now U.S. Pat. No. 6,025, 130, which is a continuation-in-part of Ser. No. 08/632,673, filed Apr. 16, 1996, now U.S. Pat. No. 5,712,098, which is a continuation-in-part of Ser. No. 08/630,912, filed Apr. 4, 1996, now abandoned, which are herein incorporated by reference in their entirety for all purposes.

BACKGROUND OF THE INVENTION

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. The gene which is defective in this disease was disclosed in copending U.S. Ser. No. 08/652,265.

HH is typically inherited as a recessive trait; in the current state of knowledge, homozygotes carrying two defective copies of the gene are most frequently affected by the disease. In addition, heterozygotes for the HH gene are more susceptible to sporadic porphyria cutanea tarda and potentially other disorders (Roberts et al., *Lancet* 349:321-323 (1997). It is estimated that approximately 10-15% of individuals of Northern European descent carry one copy of the HH gene mutation and that there are about one million homozygotes in the United States. HH, thus, represents one of the most common genetic disease mutations in individuals of Northern European descent. Although ultimately HH produces debilitating symptoms, the majority of homozygotes and heterozygotes have not been diagnosed.

The need for such diagnostics is documented, for example, in Barton, J. C. et al. *Nature Medicine* 2:394-395 (1996); Finch, C. A. *West J Med* 153:323-325 (1990); McCusick, V. *Mendelian Inheritance in Man* pp. 1882-1887, 11th ed., (Johns Hopkins University Press, Baltimore (1994)); *Report of a Joint World Health Organization/Hemochromatosis Foundation/French Hemochromatosis Association Meeting on the Prevention and Control of Hemochromatosis* (1993); Edwards, C. Q. et al. *New Engl J Med* 328:1616-1620 (1993); Bacon, B. R. *New Engl J Med* 326:126-127 (1992); Balan, V. et al. *Gastroenterology* 107:453-459 (1994); Phatak, P. D. et al. *Arch Int Med* 154:769-776 (1994).

A single mutation in the HH gene, designated 24d1 in copending U.S. Ser. No. 08/630,912, gave rise to the majority of disease-causing chromosomes present in the population today. This is referred to herein as the "common" or "ancestral" or "common ancestral" mutation. These terms are used interchangeably. It appears that about 80% to 90% of all HH patients carry at least one copy of the common ancestral mutation which is closely linked to specific alleles of certain genetic markers close to this ancestral HH gene defect. These markers are, as a first approximation, in the allelic form in which they were present at the time the ancestral HH mutation occurred. See, for example, Simon, M. et al. *Am J Hum Genet* 41:89-105 (1987); Jazwinska, E. C. et al. *Am J Hum Genet* 53:242-257 (1993); Jazwinska, E. C. et al. *Am J Hum Genet* 56:428-433 (1995); Worwood, M. et al. *Brit J Hematol* 86:863-866 (1994); Summers, K. M. et al. *Am J Hum Genet* 45:41-48 (1989).

Several polymorphic markers in the HH region have been described and shown to have alleles that are associated with HH disease. These markers include the published microsatellite markers D6S258, D6S306 (Gyapay, G. et al. *Nature Genetics* 7:246-339 (1994)), D6S265 (Worwood, M. et al. *Brit J Hematol* 86:833-846 (1994)), D6S105 (Jazwinska, E. C. et al. *Am J Hum Genet* 53:242-257 (1993); Jazwinska, E. C. et al. *Am J Hum Genet* 56:428-433 (1995)), D6S1001 (Stone, C. et al. *Hum Molec Genet* 3:2043-2046 (1994)), D6S1260 (Raha-Chowdhury et al. *Hum Molec Genet* 4:1869-1874 (1995)) as well as additional microsatellite and single-nucleotide-polymorphism markers disclosed in co-pending PCT application WO 96/06583, the disclosure of which is hereby incorporated by reference in its entirety. Additionally, copending U.S. Ser. No. 08/630,912 disclosed additional markers 24d2 and 24d7.

The symptoms of HH are often similar to those of other conditions, and the severe effects of the disease often do not appear immediately. Accordingly, it would be desirable to provide a method to identify persons who may be destined to become symptomatic in order to intervene in time to prevent excessive tissue damage associated with iron overload. One reason for the lack of early diagnosis is the inadequacy of presently available diagnostic methods to ascertain which individuals are at risk, especially while such individuals are presymptomatic.

Although blood iron parameters can be used as a screening tool, a confirmed diagnosis often employs liver biopsy which is undesirably invasive, costly, and carries a risk of mortality. Thus, there is a clear need for the development of an inexpensive and noninvasive diagnostic test for detection of homozygotes and heterozygotes in order to facilitate diagnosis in symptomatic individuals, provide presymptomatic detection to guide intervention in order to prevent organ damage, and for identification of heterozygote carriers.

SUMMARY OF THE INVENTION

One aspect of the invention is an oligonucleotide comprising at least 8 to about 100 consecutive based from the sequence of FIG. 1 SEQ ID NO:1 or FIG. 2 SEQ ID NO:2, or the complement of the sequence, wherein the at least 8 to about 100 consecutive based includes at least one polymorphic site of Table 1.

Another aspect of the invention is an oligonucleotide pair selected from the sequence of FIG. 1 or FIG. 2 or its complement for amplification of a polymorphic site of Table 1.

Another aspect of the invention is an isolated nucleic acid molecule comprising about 100 consecutive bases to about 235 KB substantially identical to the sequence of FIG. 1 or FIG. 2, wherein the DNA molecule comprises at least one polymorphic site of Table 1.

Another aspect of the invention is a method to determine the presence or absence of the common hereditary hemochromatosis (HH) gene mutation in an individual comprising:

providing DNA or RNA from the individual; and assessing the DNA or RNA for the presence or absence of a haplotype of Table 1, wherein, as a result, the absence of a haplotype of Table 1 indicates the likely absence of the HH gene mutation in the genome of the individual and the presence of the haplotype indicates the likely presence of the HH gene mutation in the genome of the individual.

Another aspect of the invention is a method to determine the presence or absence of the common hereditary hemochromatosis (HH) gene mutation in an individual comprising:
providing DNA or RNA from the individual; and
assessing the DNA or RNA for the presence or absence of a genotype defined by a polymorphic allele of Table 1, wherein, as a result, the absence of a genotype defined by a polymorphic allele of Table 1 indicates the likely absence of the HH gene mutation in the genome of the individual and the presence of the genotype indicates the likely presence of the HH gene mutation in the genome of the individual.

Another aspect of the invention is a culture of lymphoblastoid cells having the designation HC14.

BRIEF DESCRIPTION OF THE DRAWINGS

FIG. 1 depicts the nucleotide sequence of approximately 235 KB in the HH subregion from an unaffected individual.
FIG. 2 depicts the nucleotide sequence of approximately 235 KB in the HH subregion from an affected individual.

DETAILED DESCRIPTION

A. Definitions

Abbreviations for the twenty naturally occurring amino acids follow conventional usage. In the polypeptide notation used herein, the left-hand direction is the amino terminal direction and the right-hand direction is the carboxyl-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA. The complement of any nucleic acid sequence of the invention is understood to be included in the definition of that sequence.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859-1862 (1981), or by the triester method according to Matteucci, et al., *J. Am. Chem. Soc.* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: a Laboratory Manual* (2nd ed.), Vols. 1-3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

The phrase "isolated" or "substantially pure" refers to nucleic acid preparations that lack at least one protein or nucleic acid normally associated with the nucleic acid in a host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome (s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. U.S.A.* 85:2444 (1988), or by computerized implementations of these algorithms (for example, GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologies. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, a Laboratory Manual*, Cold Spring Harbor Publications, New York, for a description of immunoassay formats and conditions that can be used to determine specific immunoreactivity.

As used herein, "EST" or "Expressed Sequence Tag" refers to a partial DNA or cDNA sequence of about 150 to 500, more preferably about 300, sequential nucleotides of a longer sequence obtained from a genomic or cDNA library prepared from a selected cell, cell type, tissue or tissue type, or organisms which longer sequence corresponds to an mRNA or a gene found in that library. An EST is generally DNA. One or more libraries made from a single tissue type typically provide at least 3000 different (i.e. unique) EST's and potentially the full complement of all possible EST's representing all possible cDNAs, e.g., 50,000-100,000 in an animal such as a human. (See, for example, Adams et al. *Science* 252:1651-1656 (1991)).

"Stringent" as used herein refers to hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

B. Polymorphic Markers

The invention provides 397 new polymorphic sites in the region of the HH gene. These polymorphisms are listed in Table 1. As described below, these polymorphisms were identified by comparison of the DNA sequence of an affected individual homozygous for the common ancestral HH mutation with that of an unaffected individual disclosed in copending U.S. Ser. No. 08/724,394.

These polymorphisms provide surrogate markers for use in diagnostic assays to detect the likely presence of the mutations 24d1 and/or 24d2, in preferably 24d1, in homozygotes or heterozygotes. Thus, for example, DNA or RNA from an individual is assessed for the presence or absence of a genotype defined by a polymorphic allele of Table 1, wherein, as a result, the absence of a genotype defined by a polymorphic allele of Table 1 indicates the likely absence of the HH gene mutation in the genome of the individual and the presence of the genotype indicates the likely presence of the HH gene mutation in the genome of the individual.

These markers may be used singly, in combination with each other, or with other polymorphic markers (such as those disclosed in co-pending PCT application WO 96/06583) in diagnostic assays for the likely presence of the HH gene mutation in an individual. For example, any of the markers defined by the polymorphic sites of Table 1 can be used in diagnostic assays in combination with 24d1 or 24d2, or at least one of polymorphisms HHP-1, HHP-19, or HHP-29, or microsatellite repeat alleles 19D9:205; 18B4:235; 1A2:239; 1E4:271; 24E2:245; 2B8:206; 3321-1:98; 4073-1:182; 4440-1:180; 4440-2:139; 731-1:177; 5091-1:148; 3216-1:221; 4072-2:170; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124; D6S306:238; D6S464:206; and D6S1001:180.

Table 2 lists the frequency of about 100 of the alleles defined by the polymorphic sites of the invention in the general population. As is evident from the Table, certain of these alleles are present rarely in the general population. These polymorphisms are thus preferred as surrogate markers in diagnostic assays for the presence of a mutant HH allele ("gene mutation") such as 24d1 or 24d2. Preferably, the frequency of the polymorphic allele used in the diagnostic assay in the general population is less than about 50%, more preferably less than about 25%, and most preferably less than about 5%. Thus, of the genotypes defined by the alleles listed in Table II, polymorphisms occurring at base 35983 and base 61465 of FIG. 1 are preferred.

It will be understood by those of skill in the art that because they were identified in an ancestral HH homozygote, the haplotypes defined by the polymorphic sites of Table 1 are predictive of the likely presence of the HH gene mutation 24d1. Thus, for example, the likelihood of any affected individual having at least two or more of any of the polymorphic alleles defined by Table 1 is greater than that for any unaffected individual. Similarly, the likelihood of any affected individual having at least three or more of any of the polymorphic alleles defined by Table 1 is greater than that for any unaffected individual.

Thus, for example, in a diagnostic assay for the likely presence of the HH gene mutation in the genome of the individual, DNA or RNA from the individual is assessed for the presence or absence of a haplotype of Table 1, wherein, as a result, the absence of a haplotype of Table 1 indicates the likely absence of the HH gene mutation in the genome of the individual and the presence of the haplotype indicates the likely presence of the HH gene mutation in the genome of the individual.

The markers defined by the polymorphic sites of Table 1 are additionally useful as markers for genetic analysis of the inheritance of certain HH alleles and other genes which occur within the chromosomal region corresponding to the sequence of FIG. 1 which include, for example, those disclosed in copending U.S. Ser. No. 08/724,394.

As the entire nucleotide sequence of the region is provided in FIG. 1, it will be evident to those of ordinary skill in the art which sequences to use as primers or probes for detecting each polymorphism of interest. Thus, in some embodiments of the invention, the nucleotide sequences of the invention include at least one oligonucleotide pair selected from the sequence of FIG. 1 or FIG. 2 or its complement for amplification of a polymorphic site of Table 1. Furthermore, in some embodiments of the invention a preferred hybridization probe is an oligonucleotide comprising at least 8 to about 100 consecutive bases from the sequence of FIG. 1 or FIG. 2, or the complement of the sequence, wherein the at least 8 to about 100 consecutive bases includes at least one polymorphic site of Table 1. In some embodiments the polymorphic site is at base 35983 or base 61465 of FIG. 1.

It will also be appreciated that the nucleic acid sequences of the invention include isolated nucleic acid molecules comprising about 100 consecutive bases to about 235 KB substantially identical to the sequence of FIG. 1 or FIG. 2, wherein the DNA molecule comprises at least one polymorphic site of Table 1. Such isolated DNA sequences are useful as primers, probes, or as the component of a kit in diagnostic assays for detecting the likely presence of the HH gene mutation in an individual.

C. Nucleic Acid Based Screening

Individuals carrying polymorphic alleles of the invention may be detected at either the DNA, the RNA, or the protein level using a variety of techniques that are well known in the art. The genomic DNA used for the diagnosis may be obtained from body cells, such as those present in peripheral blood, urine, saliva, bucca, surgical specimen, and autopsy specimens. The DNA may be used directly or may be amplified enzymatically in vitro through use of PCR (Saiki et al. *Science* 239:487-491 (1988)) or other in vitro amplification methods such as the ligase chain reaction (LCR) (Wu and Wallace *Genomics* 4:560-569 (1989)), strand displacement amplification (SDA) (Walker et al. *Proc. Natl. Acad. Sci. U.S.A.* 89:392-396 (1992)), self-sustained sequence replication (3SR) (Fahy et al. *PCR Methods Appl.* 1:25-33 (1992)), prior to mutation analysis. The methodology for preparing nucleic acids in a form that is suitable for mutation detection is well known in the art.

The detection of polymorphisms in specific DNA sequences, such as in the region of the HH gene, can be accomplished by a variety of methods including, but not limited to, restriction-fragment-length-polymorphism detection based on allele-specific restriction-endonuclease cleavage (Kan and Dozy *Lancet* ii:910-912 (1978)), hybridization with allele-specific oligonucleotide probes (Wallace et al. *Nucl Acids Res* 6:3543-3557 (1978)), including immobilized oligonucleotides (Saiki et al. *Proc. Natl. Acad. Sci. U.S.A.* 86:6230-6234 (1989)) or oligonucleotide arrays (Maskos and Southern *Nucl Acids Res* 21:2269-2270 (1993)), allele-specific PCR (Newton et al. *Nucl Acids Res* 17:2503-2516 (1989)), mismatch-repair detection (MRD) (Faham and Cox *Genome Res* 5:474-482 (1995)), binding of MutS protein (Wagner et al. *Nucl Acids Res* 23:3944-3948 (1995), denaturing-gradient gel electrophoresis (DGGE) (Fisher and Lerman et al. *Proc. Natl. Acad. Sci. U.S.A.* 80:1579-1583 (1983)), single-strand-conformation-polymorphism detection (Orita et al. *Genomics* 5:874-879 (1983)), RNAase cleavage at mismatched base-pairs (Myers et al. *Science* 230:1242 (1985)), chemical (Cotton et al. *Proc. Natl. Acad. Sci. U.S.A.* 85:4397-4401 (1988)) or enzymatic (Youil et al. *Proc. Natl. Acad. Sci. U.S.A.* 92:87-91 (1995)) cleavage of heteroduplex DNA, methods based on allele specific primer extension (Syvänen et al. *Genomics* 8:684-692 (1990)), genetic bit analysis (GBA) (Nikiforov et al. *Nucl Acids Res* 22:4167-4175 (1994)), the oligonucleotide-ligation assay (OLA) (Landegren et al. *Science* 241:1077 (1988)), the allele-specific ligation chain reaction (LCR) (Barrany *Proc. Natl. Acad. Sci. U.S.A.* 88:189-193 (1991)), gap-LCR (Abravaya et al. *Nucl Acids Res* 23:675-682 (1995)), radioactive and/or fluorescent DNA sequencing using standard procedures well known in the art, and peptide nucleic acid (PNA) assays (Orum et al., *Nucl. Acids Res.* 21:5332-5356 (1993); Thiede et al., *Nucl. Acids Res.* 24:983-984 (1996)).

In addition to the genotypes defined by the polymorphisms of the invention, as described in co-pending PCT application WO 96/35802 published Nov. 14, 1996, genotypes characterized by the presence of the alleles 19D9:205; 18B4:235; 1A2:239; 1E4:271; 24E2:245; 2B8:206; 3321-1:98 (denoted 3321-1:197 therein); 4073-1:182; 4440-1:180; 4440-2:139; 731-1:177; 5091-1:148; 3216-1:221; 4072-2:170 (denoted 4072-2:148 therein); 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, alleles D6S258:199, D6S265:122, D6S105:124, D6S306:238, D6S464:206; and D6S1001:180, and/or alleles associates with the HHP-1, the HHP-19 or HHP-29 single base-pair polymorphisms can also be used to assist in the identification of an individual whose genome contains 24d1 and/or 24d2. For example, the assessing step can be performed by a process which comprises subjecting the DNA or RNA to amplification using oligonucleotide primers flanking a polymorphism of Table 1, and oligonucleotides flanking 24d1 and/or 24d2, oligonucleotide primers flanking at least one of the base-pair polymorphisms HHP-1, HHP-19, and HHP-29, oligonucleotide primers flanking at least one of the microsatellite repeat alleles, or oligonucleotide primers for any combination of polymorphisms or microsatellite repeat alleles thereof.

Oligonucleotides useful in diagnostic assays are typically at least 8 consecutive nucleotides in length, and may range upwards of 18 nucleotides in length to greater than 100 or more consecutive nucleotides. Such oligonucleotides can be derived from either the genomic DNA of FIG. 1 or 2, or cDNA sequences derived therefrom, or may be synthesized.

Additionally, the proteins encoded by such cDNAs are useful in the generation of antibodies for analysis of gene expression and in diagnostic assays, and in the purification of related proteins.

D. General Methods

The nucleic acid compositions of this invention, whether RNA, cDNA, genomic DNA, or a hybrid of the various combinations, may be isolated from natural sources, including cloned DNA, or may be synthesized in vitro. The nucleic acids claimed may be present in transformed or transfected whole cells, in a transformed or transfected cell lysate, or in a partially purified or substantially pure form.

Techniques for nucleic acid manipulation of the nucleic acid sequences of the invention such as subcloning nucleic acid sequences encoding polypeptides into expression vectors, labeling probes, DNA hybridization, and the like are described generally in Sambrook et al., *Molecular Cloning—a Laboratory Manual* (2nd Ed.), Vol. 1-3, Cold Spring Harbor Laboratory, Cold Spring Harbor, N.Y., (1989), which is incorporated herein by reference. This manual is hereinafter referred to as "Sambrook et al."

There are various methods of isolating the nucleic acid sequences of the invention. For example, DNA is isolated from a genomic or cDNA library using labeled oligonucleotide probes having sequences complementary to the sequences disclosed herein. Such probes can be used directly in hybridization assays. Alternatively probes can be designed for use in amplification techniques such as PCR.

To prepare a cDNA library, mRNA is isolated from tissue such as heart or pancreas, preferably a tissue wherein expression of the gene or gene family is likely to occur. cDNA is prepared from the mRNA and ligated into a recombinant vector. The vector is transfected into a recombinant host for propagation, screening and cloning. Methods for making and screening cDNA libraries are well known. See Gubler, U. and Hoffman, B. J. *Gene* 25:263-269 (1983) and Sambrook et al.

For a genomic library, for example, the DNA is extracted from tissue and either mechanically sheared or enzymatically digested to yield fragments of about 12-20 KB. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science* 196:180-182 (1977). Colony hybridization is carried out as generally described in M. Grunstein et al. *Proc. Natl. Acad. Sci. USA.* 72:3961-3965 (1975).

DNA of interest is identified in either cDNA or genomic libraries by its ability to hybridize with nucleic acid probes, for example on Southern blots, and these DNA regions are isolated by standard methods familiar to those of skill in the art. See Sambrook, et al.

In PCR techniques, oligonucleotide primers complementary to the two 3' borders of the DNA region to be amplified are synthesized. The polymerase chain reaction is then carried out using the two primers. See *PCR Protocols: a Guide to Methods and Applications* (Innis, M, Gelfand, D., Sninsky, J. and White, T., eds.), Academic Press, San Diego (1990). Primers can be selected to amplify the entire regions encoding a full-length sequence of interest or to amplify smaller DNA segments as desired.

PCR can be used in a variety of protocols to isolate cDNA's encoding a sequence of interest. In these protocols, appropriate primers and probes for amplifying DNA encoding a sequence of interest are generated from analysis of the DNA sequences listed herein. Once such regions are PCR-amplified, they can be sequenced and oligonucleotide probes can be prepared from sequence obtained.

Oligonucleotides for use as primers or probes are chemically synthesized according to the solid phase phosphoramidite triester method first described by Beaucage, S. L. and Carruthers, M. H., *Tetrahedron Lett.*, 22(20):1859-1862 (1981) using an automated synthesizer, as described in Needham-VanDevanter, D. R., et al., *Nucleic Acids Res.* 12:6159-6168 (1984). Purification of oligonucleotides is by either native acrylamide gel electrophoresis or by anion-exchange HPLC as described in Pearson, J. D. and Regnier, F. E., *J. Chrom.*, 255:137-149 (1983). The sequence of the synthetic oligonucleotide can be verified using the chemical degradation method of Maxam, A. M. and Gilbert, W., in Grossman, L. and Moldave, D., eds. Academic Press, New York, *Methods in Enzymology* 65:499-560 (1980).

E. Expression

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding a sequence of interest. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al. Examples of expression of ATP-sensitive potassium channel proteins in both prokaryotic and eukaryotic systems are described below.

1. Expression in Prokaryotes

A variety of procaryotic expression systems may be used to express the proteins of the invention. Examples include *E. coli, Bacillus, Streptomyces*, and the like.

It is preferred to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.* 158:1018-1024 (1984) and the leftward promoter of phage lambda (PX) as described by Herskowitz, I. and Hagen, D., *Ann. Rev. Genet.* 14:399-445 (1980). The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

To enhance proper folding of the expressed recombinant protein, during purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from *E. coli* can be achieved following procedures such as those described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, a sequence of interest may be expressed in these eukaryotic systems.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8:17-24 (1979); Broach, et al., *Gene* 8:121-133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London) 275:104-109 (1978); and Hinnen, a., et al., *Proc. Natl. Acad. Sci. U.S.A.* 75:1929-1933 (1978). The second procedure does not involve removal of the cell wall. Instead the cells are treated with lithium chloride or acetate and PEG and put on selective plates (Ito, H., et al., *J. Bact.* 153:163-168 (1983)).

The proteins of the invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding the proteins of the invention can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. *Immunol. Rev.* 89:49 (1986)), and necessary processing information sites, such as ribosome binding sites, RNA splice sites, polyadenylation sites (e.g., an SV40 large T Ag poly a addition site), and transcriptional terminator sequences. Other animal cells useful for production of ATP-sensitive potassium channel proteins are available, for instance, from the American Type Culture Collection Catalogue of Cell Lines and Hybridomas (7th edition, (1992)).

Appropriate vectors for expressing the proteins of the invention in insect cells are usually derived from the SF9 baculovirus. Suitable insect cell lines include mosquito larvae, silkworm, armyworm, moth and *Drosophila* cell lines such as a Schneider cell line (See Schneider *J. Embryol. Exp. Morphol.* 27:353-365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773-781 (1983)).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213-238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known in the art. *Biochemical Methods in Cell Culture and Virology*, Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

D. Purification

The proteins produced by recombinant DNA technology may be purified by standard techniques well known to those of skill in the art. Recombinantly produced proteins can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference. For example, antibodies may be raised to the proteins of the invention as described herein. Cell membranes are isolated from a cell line expressing the recombinant protein, the protein is extracted from the membranes and immunoprecipitated. The proteins may then be further purified by standard protein chemistry techniques as described above.

F. Antibodies

As mentioned above, antibodies can also be used for the screening of polypeptide products encoded by the polymorphic nucleic acids of the invention. In addition, antibodies are useful in a variety of other contexts in accordance with the present invention. Such antibodies can be utilized for the diagnosis of HH and, in certain applications, targeting of affected tissues.

Thus, in accordance with another aspect of the present invention a kit is provided that is suitable for use in screening and assaying for the presence of polypeptide products encoded by the polymorphic nucleic acids of the invention by an immunoassay through use of an antibody which specifically binds to polypeptide products encoded by the polymorphic nucleic acids of the invention in combination with a reagent for detecting the binding of the antibody to the gene product.

Once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

This invention also embraces diagnostic kits for detecting DNA or RNA comprising a polymorphism of Table 1 in tissue or blood samples which comprise nucleic acid probes as described herein and instructional material. The kit may also contain additional components such as labeled compounds, as described herein, for identification of duplexed nucleic acids.

The following examples are provided to illustrate the invention but not to limit its scope. Other variants of the invention will be readily apparent to one of ordinary skill in the art and are encompassed by the appended claims.

EXPERIMENTAL EXAMPLES

I. Sequencing of 235 KB from a Homozygous Ancestral (Affected) Individual

In these studies the entire genomic sequence was determined from an HH affected individual for a region corresponding to a 235,033 bp region surrounding the HH gene between the flanking markers D6S2238 and D6S2241. The sequence was derived from a human lymphoblastoid cell line, HC14, that is homozygous for the ancestral HH mutation and region. The sequence from the ancestral chromosome (FIG. 2) was compared to the sequence of the region in an unaffected individual disclosed in copending U.S. Ser. No. 08/724,394 (a portion of which is provided in FIG. 1) to identify polymorphic sites. A subset of the polymorphic alleles so defined were further studied to determine their frequency in a collection of random individuals.

A. Cosmid Library Screening

The strategy and methodology for sequencing the genomic DNA for the affected individual was essentially as described in copending U.S. Ser. No. 08/724,394, hereby incorporated by reference in its entirety. Basically, a cosmid library was constructed using high molecular weight DNA from HC14 cells. The library was constructed in the supercos vector (Stratagene, La Jolla, Calif.). Colonies were replicated onto Biotrans nylon filters (ICN) using standard techniques. Probes from genomic subclones used in the generation of the sequence of the unaffected sequence disclosed in Ser. No. 08/724,394 were isolated by gel electrophoresis and electroporation. Subclones were chosen at a spacing of approximately 20 KB throughout the 235 KB region. The DNA was labeled by incorporation of 32P dCTP by the random primer labeling approach. Positively hybridizing clones were isolated to purity by a secondary screening step. Cosmid insert ends were sequenced to determine whether full coverage had been obtained, and which clones formed a minimal path of cosmids through the 235 KB region.

B. Sample Sequencing

A minimal set of cosmid clones chosen to cover the 235 KB region were prepped with the Qiagen Maxi-Prep system. Ten micrograms of DNA from each cosmid preparation were sonicated in a Heat Systems Sonicator XL and end-repaired with Klenow (USB) and T4 polymerase (USB). The sheared fragments were size selected between three to four kilobases on a 0.7% agarose gel and then ligated to BstXI linkers (Invitrogen). The ligations were gel purified on a 0.7% agarose gel and cloned into a pSP72 derivative plasmid vector. The resulting plasmids were transformed into electrocompetent DH5a cells and plated on LB-carbenicillin plates. A sufficient number of colonies was picked to achieve 15-fold clone coverage. The appropriate number of colonies was calculated by the following equation to generate a single-fold sequence coverage: Number of colonies=size of bacterial clone (in KB)/average sequence read length (0.4 KB). These colonies were prepped in the 96-well Qiagen REAL, and the 5' to 3' DNA Prep Kit, and AGCT end-sequenced with oligo MAP1 using standard ABI Dye Terminator protocols. MAP1 was CGTTAGAACGCGGCTACAAT (SEQ ID NO:3).

C. Genomic Sequencing

The MAP1 sequences from the cosmid clones HC182, HC187, HC189, HC195, HC199, HC200, HC201, HC206, HC207, and HC212 were assembled into contigs with the Staden package (available from Roger Staden, MRC). A minimal set of 3 KB clones was selected for sequencing with oligo labeled MAP2 that sits on the opposite end of the plasmid vector. The sequence of MAP2 was GCCGATTCATTAATGCAGGT (SEQ ID NO:4). The MAP2 sequences were entered into the Staden database in conjunction with the MAP1 sequences to generate a tiling path of 3 KB clones across the region. The plasmid 3 KB libraries were concurrently transformed in 96 well format into pox38UR (available from C. Martin, Lawrence Berkeley Laboratories). The transformants were subsequently mated with JGM (Strathman et al. P.N.A.S. 88:1247-1250 (1991) in 96 well format. All matings of the 3 KB clones within the tiling path were streaked on LB-carbenicillin-kanamycin plates and a random selection of 12 colonies per 3 KB clone was prepped in the AGCT system. The oligos –21: CTGTAAAACGACGGCCAGTC (SEQ ID NO:5), and REV: GCAGGAAACAGCTATGACC (SEQ ID NO:6) were used to sequence off both ends of the transposon. Each 3 KB clone was assembled in conjunction with the end sequence information from all cosmid clones in the region.

In some regions, the coverage of the genomic sequence by cosmids was incomplete. Any gaps in the sequence were filled by using standard PCR techniques to amplify genomic DNA in those regions and standard ABI dye terminator chemistry to sequence the amplification products.

D. Identification of Polymorphic Sites

The assembled sequence of the cosmid clones in connection with the PCR amplified genomic DNA (FIG. 2) was compared to the genomic sequence of the unaffected individual (FIG. 1) using the FASTA algorithm. Numeric values were assigned to the sequenced regions of 1 to 235,303, wherein base 1 refers to the first C in the CA repeat of D6S2238 and base 235,303 is the last T in the GT repeat of D6S2241 of the unaffected sequence (FIG. 1). Table 1 lists the differences between the two compared sequences. Note that previously disclosed (Feder et al., *Nature Genetics* 13:399-408 (1996)) polymorphic sites D6S2238 (base 1), D6S2241 (base 235,032), 24d1 (base 41316), and D6S2239 (base 84841) are not included in the list of new polymorphisms, although they are provided for reference in a footnote to the Table and were observed in the ancestral sequence. In the Table, a single base change such as C-T refers to a C in the unaffected sequence at the indicated base position that occurred as a T in the corresponding position in the affected sequence. Similarly, an insertion of one or more bases, such as TTT in the affected sequence, is represented as "TTT INS" between the indicated bases of the unaffected sequence. A deletion of one or more bases occurring in the affected sequence, such as AAA DEL, is represented as the deletion of the indicated bases in the unaffected sequence.

II. Characterization of Rare Polymorphisms

In this study about 100 of the polymorphisms of Table 1 were arbitrarily chosen for further characterization. Allele frequencies in the general population were estimated by OLA analysis using a population of random DNAs (the "CEPH" collection, J. Dausset et al., *Genomics* 6(3):575-577 (1990)). These results are provided in Table 2.

One single base pair difference, occurring at base 35983 and designated C182.1G7T/C (an A to G change on the opposite strand) was present in the ancestral chromosome and rare in the random DNAs. This change occurred in a noncoding region of the hemochromatosis gene near exon 7 approximately 5.3 KB from the 24d1 (Cys282Tyr) mutation. OLA was used to genotype 90 hemochromatosis patients for the C182.1G7T/C base pair change. The frequency for C occurring at this position in the patients was 79.4% as compared to 50% in the random DNAs. Eighty-five of the 90 patients assayed contained identical 24d1 and C182.1G7T/C genotypes. Four of the remaining 5 patients were homozygous at 24d1 and heterozygous at C182.1G7T/C; one was heterozygous at 24d1 and homozygous at C182.1G7T/C. The primers used for this analysis were as follows.

PCR primers for detection:

```
182.1G7.F    5'-GCATCAGCGATTAACTTCTAC-3'
             (SEQ ID NO:7)

182.1G7.R    5'-TTGCATTGTGGTGAAATCAGGG-3'
             (SEQ ID NO:8)
```

For the detection assay, the biotinylated primers used were as follows.

```
182.1G7.C    5' (b) CTGAGTAATTGTTTAAGGTGC-3'
             (SEQ ID NO:9)

182.1G7.T    5' (b) CTGAGTAATTGTTTAAGGTGT-3'
             (SEQ ID NO:10)
```

The phosphorylated digoxigenin-labeled primer used was:

```
182.1G7.D    5' (p) AGAAGAGATAGATATGGTGG-3'
             (SEQ ID NO:11)
```

A further rare single base pair change was detected at 61,465 bp. The inheritance pattern of this polymorphism, C195.1; H5C/T (a G to A change on the opposite strand), is identical to that of 24d1. The frequency of T occurring at that position (C195.1; H5T) observed in a set of 76 patients was 78.5% as compared to 5% in random individuals.

PCR primers for detection:

```
1951H5.3F   5'-GAATGTGACCGTCCCATGAG-3'
            (SEQ ID NO:12)
1951H5.3R   5'-CAACTGAATATGCAGAAAAAAGTACACC-3'
            (SEQ ID NO:13)
```

For the detection assay, the biotinylated primers used were:

```
1951H5.3.4   5' (b) AGTAGCTGGGACTCACGGTGT-3'
             (SEQ ID NO:14)
1957H5.3.5   5' (b) AGTAGCTGGGACTCACGGTGC-3'
             (SEQ ID NO:15)
```

The phosphorylated digoxigenin-labeled primer used was:

```
1951H5.3.6   5' (p) GCGCCACCACTCCCAGCTCAT-3'
             (SEQ ID NO:16)
```

These rare alleles are thus preferred surrogate markers for 24d1 and are especially useful in screening assays for the likely presence of 24d1 and/or 24d2.

All publications, patents, and patent applications cited herein are hereby incorporated by reference in their entirety.

TABLE 1

Polymorphic Sites in the HH Region *

| BASE LOCATION | DIFFERENCE |
|---|---|
| 35-36 | CA DEL |
| 841 | T - C |
| 2662-2663 | TT DEL |
| 3767 | T - C |
| 3829 | C - G |
| 4925-4928 | TAAA DEL |
| 5691 | C - T |
| 5839 | T - C |
| 6011 | G - A |
| 6047 | C - G |
| 6231 | G - A |
| 6643 | A DEL |
| 6698 | T - C |
| 7186 | T - C |
| 7273 | G - A |
| 7545-7558 | TCACACACCGATTGG DEL (SEQ ID NO:17) |
| 7672 | G DEL |
| 7933 | T - C |
| 8746 | T - G |
| 9115 | G - A |
| 9823 | G - A |
| 10027 | G - A |
| 10214 | C - T |
| 10828 | A - G |
| 10918 | C - G |
| 10955 | A - G |
| 11524 | C - A |
| 11674 | A - G |
| 11955 | T - C |
| 12173-12175 | TTT DEL |
| 13304 | G - A |
| 13455 | G - A |
| 14416-14417 | A INS |
| 14998 | C - T |
| 15564 | T - C |
| 15887 | A - G |
| 15904-15919 | CCAAACTGATCTTTGA DEL (SEQ ID NO:18) |
| 16019 | T DEL |
| 16211 | A - T |
| 17461 | A - G |

TABLE 1-continued

Polymorphic Sites in the HH Region *

| BASE LOCATION | DIFFERENCE |
|---|---|
| 19755 | G - A |
| 19949 | C - T |
| 20085 | C - T |
| 20366-20367 | A INS |
| 20463 | C - A |
| 20841 | A - T |
| 21059 | A - T |
| 21117 | A - G |
| 21837 | A - C |
| 22293 | A - C |
| 22786 | C - A |
| 23009 | G - A |
| 24143 | T - A |
| 26175 | G - C |
| 26667 | C - A |
| 26994 | T - C |
| 27838 | G - T |
| 27861 | T DEL |
| 28132 | G - A |
| 29100 | G - A |
| 29454-29457 | TTTT DEL |
| 29787 | T - G |
| 29825 | A - C |
| 30009 | T - C |
| 30177 | A - G |
| 30400 | A - G |
| 31059 | T - A |
| 31280 | C - T |
| 31749 | C - T |
| 32040 | C - G |
| 32534-32537 | GTGT DEL |
| 33017 | T - G |
| 33026 | T DEL |
| 34434 | C - T |
| 35179 | A - C |
| 35695 | G - A |
| 35702 | G - A |
| 35983 | A - G |
| 37411 | A - G |
| 38526 | C - T |
| 40431 | C - A |
| 42054-42055 | TT DEL |
| 43783-43784 | TTTT INS |
| 45120 | C DEL |
| 45567 | A - C |
| 46601 | A - T |
| 47255 | C - G |
| 47758 | C - A |
| 47994 | G - C |
| 48440 | G - A |
| 48650 | T - G |
| 48680 | A - G |
| 50240 | C - T |
| 50553 | G - A |
| 50586 | G - T |
| 51322 | G - C |
| 51747 | A - G |
| 52474 | C - G |
| 52733 | C - A |
| 52875 | G - A |
| 53631-53637 | TTTTTTT DEL |
| 53707 | G - A |
| 54819 | A - G |
| 55913 | T - C |
| 56225 | A - C |
| 56510 | T - C |
| 56566 | G - A |
| 56618 | A - T |
| 57815 | A - G |
| 58011 | T DEL |
| 58247-58248 | T INS |
| 58926 | C - G |
| 59406 | C - G |
| 59422 | G - C |
| 60221-60222 | A INS |

TABLE 1-continued

Polymorphic Sites in the HH Region *

| BASE LOCATION | DIFFERENCE |
|---|---|
| 60656-60657 | CA DEL |
| 61162 | G – A |
| 61465 | G – A |
| 61607 | A DEL |
| 61653 | T – C |
| 61794-61795 | T INS |
| 62061 | G – C |
| 62362 | T – G |
| 62732 | C – G |
| 63364 | G – A |
| 63430-63431 | GT INS |
| 63754 | C – T |
| 63785 | A – C |
| 63870-63871 | A INS |
| 64788 | A – G |
| 64962 | G – A |
| 65891 | C – T |
| 66675 | G – C |
| 67186-67187 | ATT INS |
| 67746-67747 | TT INS |
| 68259 | T – C |
| 68836 | T – C |
| 68976 | C – G |
| 72508 | T – G |
| 72688 | C – G |
| 75323-75324 | T INS |
| 75887 | G – C |
| 77519 | T – C |
| 77749 | G – A |
| 77908 | T – C |
| 78385 | C – G |
| 78592-78593 | AG INS |
| 80189 | T – G |
| 80279 | T DEL |
| 80989-80990 | A INS |
| 81193 | T – C |
| 81273 | A DEL |
| 82166 | G – A |
| 83847 | T DEL |
| 84161-84162 | CA – GG |
| 84533 | A – G |
| 84638 | T – G |
| 85526 | T – G |
| 85705 | G – T |
| 86984 | T – C |
| 87655 | T – C |
| 87713 | A – C |
| 87892 | C – T |
| 88192 | T DEL |
| 88528 | A – G |
| 89645 | A – T |
| 89728 | A – G |
| 90088 | T – C |
| 91193-91194 | 2209bp INS |
| 91373 | T – C |
| 91433-91434 | A INS |
| 91747 | G – A |
| 93625 | T DEL |
| 95116-95117 | T INS |
| 96315 | G – A |
| 97981 | A – G |
| 98351 | T DEL |
| 99249 | C – T |
| 100094-100095 | T INS |
| 100647-100648 | TTC INS |
| 100951 | C – T |
| 101610 | C – G |
| 102589 | C – T |
| 103076-103077 | TATATATATATATA INS (SEQ ID NO:19) |
| 103747 | T – C |
| 105638 | A – C |
| 107024 | C – T |
| 107322 | C – T |
| 107858 | C – G |

TABLE 1-continued

Polymorphic Sites in the HH Region *

| BASE LOCATION | DIFFERENCE |
|---|---|
| 109019 | A DEL |
| 109579 | T DEL |
| 110021 | C – A |
| 111251 | C – A |
| 111425 | G – A |
| 112644 | T – A |
| 113001 | G – C |
| 113130 | C – T |
| 114026 | G – A |
| 114250 | A DEL |
| 115217 | C – G |
| 117995 | G – A |
| 118874 | A – G |
| 119470 | T – C |
| 119646 | G – T |
| 120853 | C – T |
| 121582 | G – A |
| 123576 | A – C |
| 125581 | C – T |
| 125970 | G – T |
| 126197 | A – G |
| 126672 | A DEL |
| 126672 | G – C |
| 128220-128221 | A INS |
| 132569 | C – T |
| 133572 | A – C |
| 134064 | T – G |
| 136999 | G – A |
| 137784 | C – T |
| 138903 | G – A |
| 139159-139160 | A INS |
| 140359 | G – A |
| 140898 | C – T |
| 141313 | C DEL |
| 141343 | T – C |
| 142148 | T – C |
| 142178 | C – A |
| 142433-142434 | ATAGA INS |
| 143783 | C – T |
| 144090 | C – T |
| 144220-144221 | A INS |
| 144725 | A – C |
| 145732-145733 | AAAAAAAAAAAAAA INS (SEQ ID NO:20) |
| 147016-147017 | CG DEL |
| 147021 | G – T |
| 147536 | T – G |
| 148936 | T – A |
| 149061 | T – C |
| 154341 | A – T |
| 154588 | G – A |
| 155464 | G – A |
| 158574 | C – G |
| 160007 | C – T |
| 164348 | A – T |
| 164499 | C – G |
| 166677-166678 | AAAG INS |
| 167389 | G – A |
| 168506-168507 | AGGATGGTCT INS (SEQ ID NO:21) |
| 168515 | T – C |
| 169413-169414 | AA INS |
| 170300-170301 | TTGTTGTTGTTG INS (SEQ ID NO:22) |
| 170491 | G – A |
| 173428 | T – C |
| 173642 | G – A |
| 173948 | T – G |
| 175330 | T – C |
| 175836 | T – C |
| 176200 | G – C |
| 176222 | T – C |
| 176524 | A – T |
| 176684 | G – A |
| 176815 | T – C |

TABLE 1-continued

Polymorphic Sites in the HH Region *

| BASE LOCATION | DIFFERENCE |
|---|---|
| 177049 | T – C |
| 177065 | G – T |
| 178285 | T – C |
| 178551-178552 | CTTTTTTTTTTTTT INS (SEQ ID NO:23) |
| 179114-179115 | A INS |
| 179260 | C – G |
| 179281 | C – G |
| 180023 | G – C |
| 180430 | T – C |
| 180773 | T – C |
| 180824 | T – C |
| 181097 | C – T |
| 181183 | A – T |
| 182351 | C – T |
| 183197 | G – A |
| 183623 | A – T |
| 183653 | G – T |
| 183657 | T – G |
| 183795-183796 | A INS |
| 184060 | G – A |
| 184993 | G – A |
| 185918 | A – G |
| 186036 | T – C |
| 186506-186507 | TAAC INS |
| 186561-186568 | TATTTATT DEL |
| 186690 | G DEL |
| 186751 | T – A |
| 187221 | A – G |
| 187260 | A – G |
| 187444-187447 | CTCT DEL |
| 187831-187832 | C INS |
| 188638 | G – A |
| 188642 | C – T |
| 189246 | T – C |
| 190340 | A – C |
| 190354 | A – G |
| 190762 | A – G |
| 191260 | G – T |
| 193018-193019 | AGAT INS |
| 193147 | T – G |
| 193196-193197 | C INS |
| 193499 | C – T |
| 193738 | C – G |
| 193984-193985 | ACACACAC INS |
| 194064 | C – G |
| 194504 | A DEL |
| 194734 | G – A |
| 194890 | A – C |
| 195404 | G – A |
| 195693 | A – T |
| 196205 | G – A |
| 197424 | C – T |
| 197513 | C – T |
| 197670 | G – A |
| 198055 | C – A |
| 198401 | C – T |
| 198692 | A – G |
| 198780 | T DEL |
| 199030 | T – G |
| 199933 | C – T |
| 200027 | G – A |
| 200439 | T – A |
| 200452 | A – G |
| 200472-200483 | AATAATAATAAT DEL (SEQ ID NO:24) |
| 200559 | A – T |
| 200745 | A – G |
| 200919 | T – A |
| 201816 | C – T |
| 201861-201862 | 42bp INS |
| 202662 | T – C |
| 202880 | T – C |
| 204341 | C – T |
| 204768 | A – T |
| 205284 | T – G |
| 207400 | C – A |
| 208634 | T – C |
| 208718 | T DEL |
| 208862 | A – C |
| 209419-209420 | TT DEL |
| 209802 | G – A |
| 209944 | C – G |
| 210299 | A – G |
| 211142 | G – A |
| 212072 | G – A |
| 212146 | T – C |
| 212379 | G – A |
| 212637-212639 | TCT DEL |
| 212696 | T – C |
| 213042 | T – A |
| 214192 | A – G |
| 214529-214530 | TTTTTTTTTTT INS (SEQ ID NO:25) |
| 214549 | T – C |
| 214795 | C – T |
| 214908 | T – G |
| 214977 | A – G |
| 215769 | C – T |
| 215947 | C – A |
| 216232 | A – G |
| 217478 | G – A |
| 219052 | T – C |
| 219082-219083 | ATATATATATATATATAT INS (SEQ ID NO:26) |
| 219314 | C – A |
| 219327 | G – A |
| 219560 | C – T |
| 219660 | C – T |
| 219889 | G – A |
| 220198 | G – T |
| 220384 | G – A |
| 220451-220452 | CAAAAA INS |
| 221363 | G – A |
| 221645 | G – A |
| 222119 | T – C |
| 222358 | A – G |
| 222367 | A – C |
| 222686 | A – G |
| 222959 | T – C |
| 223270-223271 | TT DEL |
| 223283 | T – C |
| 224964 | T – C |
| 225232 | A – C |
| 225366-225367 | TTTT INS |
| 225416 | G – C |
| 225486 | T – C |
| 226088 | A – G |
| 228421 | A – G |
| 230047 | G – A |
| 230109 | G – C |
| 230376 | C – G |
| 230394 | A – C |
| 231226 | A – G |
| 231447 | G – A |
| 231835 | A – G |
| 232400-232402 | AAA DEL |
| 232402-232403 | G INS |
| 232515 | G – C |
| 232703 | G – T |
| 232750 | A – G |

* D6S2238 occurs at base 1. 24d1 occurs at base 41316. D6S2239 occurs at base 84841. D6S2241 occurs at base 235032

TABLE 2

Polymorphic Allele Frequencies

| Location | Frequency of ancestral variant in random chromosomes | Frequency of unaffected variant in random chromosomes |
|---|---|---|
| 232703 | 53% | 47% |
| 231835 | 53% | 47% |
| 230394 | 85% | 15% |
| 230376 | 25% | 75% |
| 230109 | 53% | 47% |
| 225486 | 45% | 55% |
| 225416 | 75% | 25% |
| 220198 | 43% | 57% |
| 219660 | 58% | 42% |
| 219560 | 53% | 47% |
| 214977 | 65% | 35% |
| 214908 | 50% | 50% |
| 214795 | 24% | 76% |
| 214549 | 53% | 47% |
| 214192 | 65% | 35% |
| 210299 | 53% | 47% |
| 208862 | 80% | 20% |
| 208634 | 48% | 52% |
| 207400 | 25% | 75% |
| 205284 | 50% | 50% |
| 204341 | 53% | 47% |
| 202880 | 58% | 42% |
| 202662 | 98% | 2% |
| 200027 | 25% | 75% |
| 199030 | 58% | 42% |
| 198692 | 55% | 45% |
| 198401 | 55% | 45% |
| 198055 | 55% | 45% |
| 195693 | 60% | 40% |
| 195404 | 25% | 75% |
| 194890 | 55% | 45% |
| 175330 | 53% | 47% |
| 173948 | 83% | 17% |
| 173642 | 55% | 45% |
| 173428 | 80% | 20% |
| 168515 | 80% | 20% |
| 160007 | 18% | 82% |
| 149061 | 58% | 42% |
| 148936 | 82% | 18% |
| 147536 | 100% | 0% |
| 147021 | 46% | 54% |
| 141343 | 55% | 45% |
| 140359 | 55% | 45% |
| 138903 | 55% | 45% |
| 132569 | 81% | 19% |
| 125581 | 18% | 82% |
| 121582 | 80% | 20% |
| 120853 | 18% | 82% |
| 118874 | 85% | 15% |
| 115217 | 50% | 50% |
| 113130 | 40% | 60% |
| 113001 | 48% | 52% |
| 107858 | 48% | 52% |
| 103747 | 50% | 50% |
| 96315 | 25% | 75% |
| 91194 | 80% | 20% |
| 90088 | 75% | 25% |
| 89728 | 50% | 50% |
| 89645 | 50% | 50% |
| 88528 | 63% | 37% |
| 87892 | 75% | 25% |
| 87713 | 60% | 40% |
| 87655 | 50% | 50% |
| 86984 | 79% | 21% |
| 85705 | 50% | 50% |
| 85526 | 50% | 50% |
| 84638 | 50% | 50% |
| 84533 | 50% | 50% |
| 82166 | 78% | 22% |
| 81193 | 58% | 42% |
| 80189 | 50% | 50% |
| 78385 | 80% | 20% |
| 77908 | 88% | 12% |
| 68976 | 50% | 50% |
| 68259 | 51% | 49% |
| 66675 | 80% | 20% |
| 62732 | 50% | 50% |
| 62362 | 40% | 60% |
| 61653 | 48% | 52% |
| 61465 | 5% | 95% |
| 61162 | 60% | 40% |
| 53707 | 100% | 0% |
| 52875 | 50% | 50% |
| 52733 | 74% | 26% |
| 52474 | 47% | 53% |
| 50586 | 50% | 50% |
| 50553 | 50% | 50% |
| 50240 | 50% | 50% |
| 48680 | 53% | 47% |
| 48650 | 63% | 37% |
| 48440 | 50% | 50% |
| 47255 | 50% | 50% |
| 46601 | 53% | 47% |
| 45567 | 49% | 51% |
| 41316 | 5% | 95% |
| 40431 | 20% | 80% |
| 38526 | 23% | 77% |
| 37411 | 70% | 30% |
| 35983 | 5% | 95% |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07595385B2). An electronic copy of the "Sequence Listing" will also be available from the USPTO upon request and payment of the fee set forth in 37 CFR 1.19(b)(3).

What is claimed is:

1. A composition comprising primers wherein the primers consist of
   a) a first sequence from SEQ ID NO: 2 and
   b) a second sequence from the complement of SEQ ID NO: 2
   wherein the primers amplify under PCR conditions a polynucleotide consisting of a sequence from SEQ ID NO: 2 that includes a single nucleotide polymorphism at position 35983 of SEQ ID NO: 1,
   wherein the primers are at least 8 nucleotides in length.

2. The composition of claim 1, wherein the first sequence from SEQ ID NO:2 consists of SEQ ID NO:8 and the sequence from the reverse complement to SEQ ID NO:2 consists of SEQ ID NO:7 and wherein the amplified polynucleotide includes the SNP at base 35983 of SEQ ID NO:1.

* * * * *